US010648004B2

(12) United States Patent
Cervin et al.

(10) Patent No.: US 10,648,004 B2
(45) Date of Patent: May 12, 2020

(54) RECOMBINANT MICROORGANISMS FOR THE ENHANCED PRODUCTION OF MEVALONATE, ISOPRENE, ISOPRENOID PRECURSORS, ISOPRENOIDS, AND ACETYL-COA-DERIVED PRODUCTS

(71) Applicants: Danisco US Inc., Palo Alto, CA (US); The Goodyear Tire & Rubber Company, Akron, OH (US)

(72) Inventors: Marguerite A. Cervin, Redwood City, CA (US); Michael C. Miller, San Francisco, CA (US); Derek H. Wells, Palo Alto, CA (US); Alan J. Wolfe, Buffalo Grove, IL (US); Madhukar S. Dasika, Ellicott City, MD (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 699 days.

(21) Appl. No.: 15/120,037

(22) PCT Filed: Feb. 20, 2015

(86) PCT No.: PCT/US2015/016954
§ 371 (c)(1),
(2) Date: Jan. 30, 2017

(87) PCT Pub. No.: WO2015/127305
PCT Pub. Date: Aug. 27, 2015

(65) Prior Publication Data
US 2017/0159074 A1 Jun. 8, 2017

Related U.S. Application Data

(60) Provisional application No. 61/942,546, filed on Feb. 20, 2014.

(51) Int. Cl.
| C12P 5/00 | (2006.01) |
| C12N 9/10 | (2006.01) |
| C12N 9/88 | (2006.01) |
| C12N 15/52 | (2006.01) |
| C12P 7/42 | (2006.01) |

(52) U.S. Cl.
CPC ............ *C12P 5/007* (2013.01); *C12N 9/1025* (2013.01); *C12N 9/88* (2013.01); *C12N 15/52* (2013.01); *C12P 7/42* (2013.01)

(58) Field of Classification Search
None
See application file for complete search history.

(56) References Cited

U.S. PATENT DOCUMENTS

| 7,659,097 B2 | 2/2010 | Renninger et al. |
| 7,915,026 B2 | 3/2011 | Keasling et al. |
| 8,288,148 B2 | 10/2012 | Cervin et al. |
| 8,455,236 B2 | 6/2013 | Beck et al. |
| 2003/0232782 A1* | 12/2003 | Escalante-Semerena ..................... C12N 9/0069 514/44 R |
| 2005/0287655 A1 | 12/2005 | Tabata et al. |
| 2009/0053797 A1 | 2/2009 | Shiba et al. |
| 2009/0203102 A1 | 8/2009 | Cervin et al. |
| 2009/0253174 A1* | 10/2009 | Serber .................... C12N 15/81 435/69.1 |
| 2009/0282545 A1 | 11/2009 | Eichelberger et al. |
| 2010/0003716 A1 | 1/2010 | Cervin et al. |
| 2010/0048964 A1 | 2/2010 | Calabria et al. |
| 2010/0086978 A1 | 4/2010 | Beck et al. |
| 2010/0196977 A1 | 8/2010 | Chotani et al. |
| 2010/0285549 A1 | 11/2010 | Muramatsu et al. |
| 2010/0297749 A1 | 11/2010 | Aravanis et al. |
| 2011/0045563 A1 | 2/2011 | Melis |
| 2011/0178261 A1 | 7/2011 | Feher et al. |

FOREIGN PATENT DOCUMENTS

| JP | 2008-61506 A | 3/2008 |
| WO | WO-98/02550 A2 | 1/1998 |
| WO | WO-98/02550 A3 | 1/1998 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2010/003007 A2 | 1/2010 |
| WO | WO-2010/003007 A3 | 1/2010 |
| WO | WO-2010/031062 A1 | 3/2010 |
| WO | WO-2010/031068 A1 | 3/2010 |
| WO | WO-2010/031076 A2 | 3/2010 |

(Continued)

OTHER PUBLICATIONS

Ausubel, F. M., et al., "Introduction of DNA into Mammalian Cells," *Current Protocols in Molecular Biology* (eds.) Chapter 9, 1987.

Baba, T. et al. (2006, e-published Feb. 21, 2006). "Construction of *Escherichia coli* K-12 in-frame, single-gene knockout mutants: the Keio collection," *Mol Syst Biol* 2:20006.008.

Berka & Barnett, "The Development of Gene Expression Systems for Filamentous Fungi," Iotechnology Advances, 1989, 7(2):127-154.

Bhayana, et al., "Amino Acid Sequence of *Escherichia coli* Citrate Synthase," Biochemistry, 1984, 23: 2900-2905 (Figure 5).

Bologna, et al., "*Escherichia coli* Malic Enzymes: Two Isoforms with Substantial Differences in Kinetic Properties, Metabolic Regulation, and Structure," Journal of Bacteriology, 2007, 189:5937-5946.

(Continued)

*Primary Examiner* — Iqbal H Chowdhury
(74) *Attorney, Agent, or Firm* — Mintz Levin Cohn Ferris Glovsky and Popeo PC

(57) ABSTRACT

The invention features compositions and methods for the increased production of mevalonate, isoprene, isoprenoid precursor molecules, isoprenoids, and/or acetyl-CoA-derived products in recombinant microorganisms by engineering the microorganisms to comprise one or more acetylating proteins such that the expression and/or activity of the one or more acetylating proteins is modulated.

20 Claims, 42 Drawing Sheets

Specification includes a Sequence Listing.

(56) References Cited

FOREIGN PATENT DOCUMENTS

| | | |
|---|---|---|
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/124146 A2 | 10/2010 |
| WO | WO-2010/124146 A3 | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO-2013/020118 A1 | 2/2013 |
| WO | WO-2013/066568 A1 | 5/2013 |
| WO | WO-2013/166320 A1 | 11/2013 |
| WO | WO-2014/015210 A2 | 1/2014 |
| WO | WO-2014/015210 A3 | 1/2014 |

OTHER PUBLICATIONS

Bunch, et al., "The IdhA Gene Encoding the Fermentative Lactate Dehydrogenase of *Escherichia coli*," Microbiology, 1997, 143:187-195.

Campbell, et al., "Improved Transformation Efficiency of Aspergillus *niger* Using the Homologus niaD Gene for Nitrate Reductase," Current Genetics, 1989, 16:53-56.

Castano-Cerezo, S. et al. (Dec. 2011, e-published Nov. 7, 2011). "cAMP-CRP co-ordinates the expression of the protein acetylation pathway with central metabolism in *Escherichia coli*," *Mol Microbiol* 82(5):1110-1128.

Danner, et al., "Four Terpene Synthases Produce Major Compounds of the Gypsy Moth Feeding-Induced Volatile Bend of Populus Trichocarpa," Pytochemistry, Jun. 2011, vol. 72, Issue 9, pp. 897-908.

Dawes, et al., "The Route to Ethanol Formation in Zymomonas Mobilies," Biochem. J., 1966, 98:795-803.

Duckworth, et al., "Structural Basis for Regulation in Gram-Negative Bacterial Citrate Synthases," *Biochem Soc Symp.*, 1987, 54:83-92.

Egan, et al., "Molecular Characterization of the Entner-Doudoroff Pathway in *Escherichia coli*: Sequence Analysis and Localization of Promoters for fhe Edd-Eda Operon," *J. Bact.*, 1992, 174:4638-4646.

Fowler, Z.L. et al. (Sep. 2009, e-published Jul. 24, 2009). "Increased malonyl coenzyme A biosynthesis by tuning the *Escherichia coli* metabolic network and its application to flavanone production," *Appl Environ Mocrobiol* 75(18):5831-5839.

Garms, Köllner, and Boland, "A Multiproduct Terpine Synthase from *Medicago truncatula* Generates Cadalane Sesquiterpenes via Two Different Mechanisms," *J Org Chem.*, Aug. 2010, 20;75(16):5590-5600.

GenBank NC 001416.1, (Aug. 13, 2018). 41 pages.

Han, K. et al. (Mar. 15, 1992). "Acetic acid formation in *Escherichia coli* fermentation," Biotechnol Bioeng 39(6):663-671.

Hedl, et al. "Enterococcus Faecalis Acetoacetyl-Coenzyme a Thiolase/ 3-Hydroxy-3-Methyglutaryl-Coenzyme a Reductase, a Dual-Function Protein of Isopentenyl Diphosphate Biosynthesis," *Journal of Bacteriology*, Apr. 2002, 184(8):2116-2122.

Hsieh, et al., "Structure and Mechanism of an *Arabidopsis* Medium/ Long-Chain-Length Prenyl Pyrophosphate Synthase," *Plant Physiology*, Mar. 2011, 155(3):1079-1090.

International Search Report dated Oct. 14, 2015, for PCT Application No. PCT/US2015/016954, filed Feb. 20, 2015, 6 pages.

Jones, et al., *J Biol Chem.* Mar. 24, 2011 ("Sandalwood Fragrance Biosynthesis Involves Sesquiterpene Synthases of Both the Terpene Synthase (TPS)-a and TPS-b Subfamilies, including Santalene Synthases," J. Biol. Chem. 2011 286: 17445-17454.

Kakuda, et al., "Identification and Characterization of the ackA (Acetate Kinase A)-pta (Phosphotransacetylase) Operon and Complementation Analysis of Acetate Utilization by an ackA-pta Deletion Mutant of *Escherichia coli*,". J. Biochem., 1994, 11:916-922.

Keeling, et al., "Transcriptome Mining, Functional Characterization, and Phylogeny of a Large Terpene Synthase Gene Family in Spruce (*Picea* spp.)," BMC Plant Biol., Mar. 2011, 7;11:43.

Kotlarz, et al., "Regulation of the Amount and of the Activity of Phosphofructokinases and Pyruvate Kinases in *Escherichia coli*," Biochim. Biophys. Acta, 1975, 381:257-268.

Kumeta & Ito, "Characterization of d-Guaiene Synthases from Cultured Cells of Aquilaria, Responsible for the Formation of the Sesquiterpenes in Agarwood," *Plant Physiol.*, Dec. 2010;154(4):1998-2007.

Lindberg, et al., "Engineering a Platform for Photosynthetic Isoprene Production in Cyanobacteria, Using Synechocystis as the Model Organism," *Metab. Eng.*, 2010, 12(1):70-79).

Luli, G.W. et al. (Apr. 1990). "Comparison of growth, acetate production, and acetate inhibition of *Escherichia coli* strains in batch and fed-batch fermentations," *Appl Environ Microbiol* 56(4):1004-1011.

Majewski, R.A. et al. (Mar. 25, 1990). "Simple constrained-optimization view of acetate overflow in *E. coli*," *Biotechnol Bioeng* 35(7):732-738.

Martin, et al., "Functional Annotation, Genome Organization and Phylogeny of the Grapevine (*Vitis vinifera*) Terpene Synthase Gene Family Based on Genome Assembly, FLcDNA Cloning, and Enzyme Assays," BMC Plant Biol.,Oct. 21, 2010;10:226.

Maurus, et al., "Insights into the Evolution of Allosteric Properties. The NADH Binding Site of Hexameric Type II Citrate Synthases," *Biochemistry*, 2003, 42:5555-5565.

Meile, et al., "Characterization of the D-Xylulose 5-Phosphate/D-Fructose 6-Phosphate Phosphoketolase Gene (xfP) from Bifidobacterium Lactis," *J. Bact.*, 2001, 183:2929-2936.

Miller, et al., "First Isolation of an Isoprene Synthase Gene from Poplar and Successful Expression of the Gene in *Escherichia coli*," Planta, (e-pub. May 10, 2001) 213:483-487.

Ner, et al., "Complete Sequence of the glt A Gene Encoding Citrate Synthase in *Escherichia coli*," *Biochemistry*, 1983, 22: 5243-5249.

Ogasawara, H. et al., PdhR (Pyruvate Dehydrogenase Complex Regulator) Controls the Respiratory Electron Transport System in *Escherichia coli*, J. Bact., 2007, 189:5534-5541.

Oh, M.K.et al. (Apr. 12, 2002, e-published Jan. 28, 2002). "Global expression profiling of acetate-grown *Escherichia coli*," *J Biol Chem* 277(15):13175-13183.

Okamura, et al., "Unprecedented Acetoacetyl-coenzyme a Synthesizing Enzyme of the Thiolase Superfamily Involved in the Mevalonate Pathway," *PNAS*, 2010, vol. 107, No. 25:11265-11270.

Peekhaus and Conway, "What's for Dinner?: Entner-Doudoroff Metabolism in *Escherichia coli*," J. Bact., 1998, 180:3495-3502.

Quant, P.A. et al. (Aug. 1989). "Treatment of rats with glucagon or mannoheptulose increases mitochondrial 3-hydroxy-3-methylglutaryl-CoA synthase activity and decreases succinyl-CoA content in liver," *Biochem J* 262(1):159-164.

Romanos, et al., "Foreign Gene Expression in Yeast: a Review," Yeast, 1992, 8(6):423-488.

Sanchez, et al., "Novel Pathway Engineering Design of The Anaerobic Central Metabolic Pathway in *Escherichia coli* to Increase Succinate Yield and Productivity," Metab. Eng., 2005, 7:229-239.

Sharkey, et al., "Evolution of the Isoprene Biosynthetic Pathway in Kudzu," *Plant Physiology*, 2005, 137: 700-712.

Shimizu, et al., "Phosphotransacetylase of *Escherichia coli* B, Purification and Properties," Biochim. Biophys., Acta, 1969, 191: 550-558.

Silver, G.M. et al. (Jun. 1995). "Characterization of aspen isoprene synthase, an enzyme responsible for leaf isoprene emission to the atmosphere." *J Biol Chem* 270(22):13010-13016.

Sprenger, Genetics of Pentose-Phosphate Pathway Enzymes of *Scherichia coli* K-12, *Arch. Microbiol.*, 1995, 164:324-330.

Stokell, D. et al., "Probing the roles of key residues in the unique regulatory NADH binding site of type II citrate synthase of *Escherichia coli*," J. Biol. Chem., 2003, 278: 35435-43.

Stulke and Hillen, "Regulation of Carbon Catabolism in Bacillus Species," *Annu. Rev. Microbiol.*, 2000, 54, 849-880.

Tabata, K. and Hashimoto, S. I., "Production of Mevalonate by a Metabolically-Engineered *Escherichia coli*," Biotechnology Letters, 2004, 26: 1487-1491.

(56) References Cited

OTHER PUBLICATIONS

Underwood, et al., Flux through Citrate Synthase Limits the Growth of Ethanologenic *Scherichia coli* KO11 during Xylose Fermentation, *Appl. Environ. Microbiol.,* 2002, 68:1071-1081.
Wiegand, et al., "Citrate Synthase: Structure, Control, and Mechanism," *Annual Rev. Biophysics Biophys. Chem.,* 1986, 15: 97-117.
Written Opinion dated Oct. 14, 2015, for PCT Application No. PCT/US2015/016954, filed Feb. 20, 2015, 6 pages.
Zhao, K. et al. (Mar. 26, 2004). "Structure and substrate binding properties of cobB, a Sir2 homolog protein deacetylase from *Escherichia coli,*" *J Mol Biol* 337(3):731-741.
Starai, V. et al. (Dec. 20, 2002). "Sir2-dependent activation of acetyl-CoA synthetase by deacetylation of active lysine," *Science* 298(5602):2390-2392.

\* cited by examiner

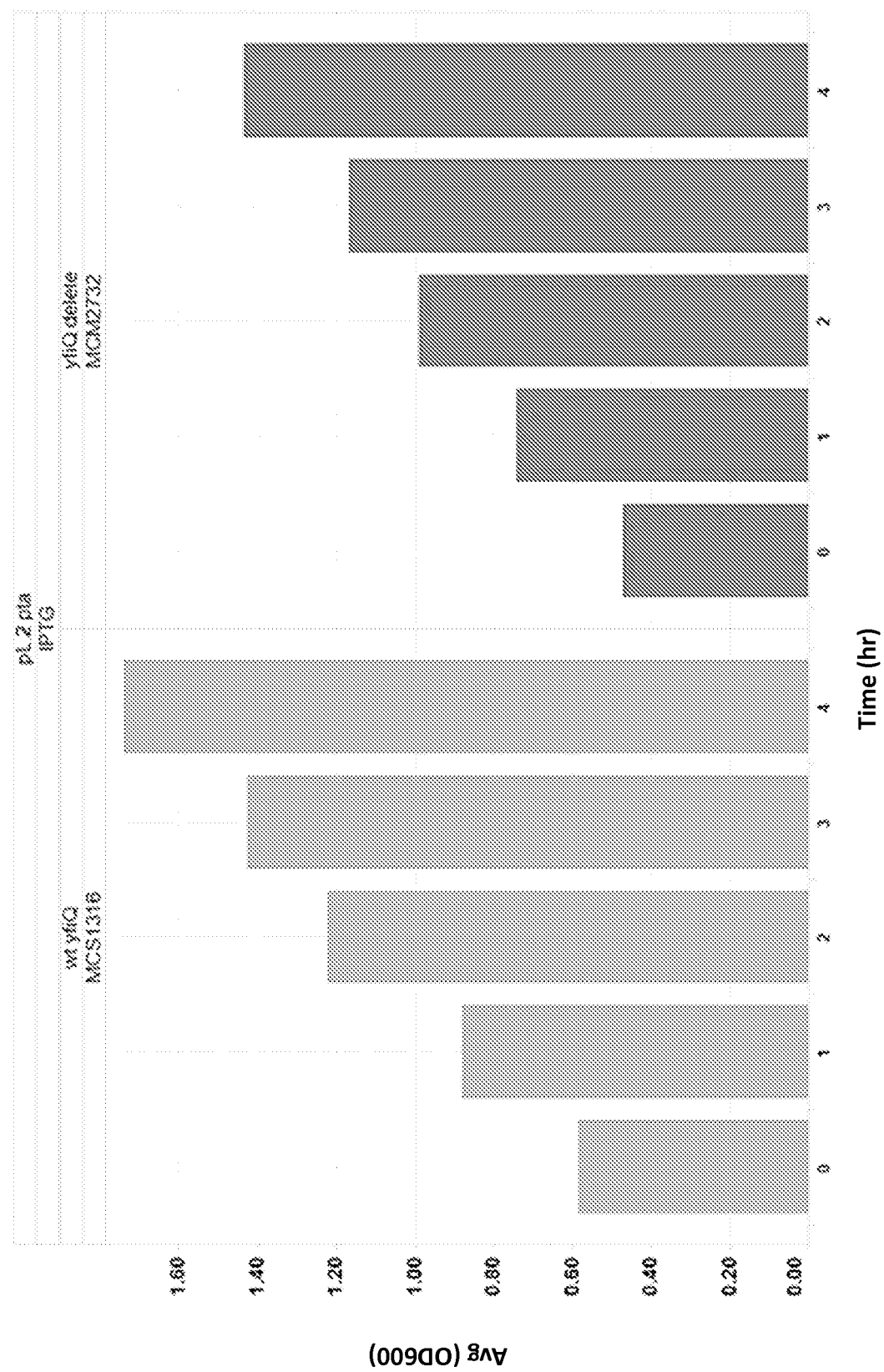

RECOMBINANT MICROORGANISMS FOR THE ENHANCED PRODUCTION OF MEVALONATE, ISOPRENE, ISOPRENOID PRECURSORS, ISOPRENOIDS, AND ACETYL-COA-DERIVED PRODUCTS

CROSS-REFERENCE TO RELATED PATENT APPLICATIONS

This application is a U.S. National Phase patent application, filed under 35 U.S.C. § 371, of International Application No. PCT/US2015/016954, filed Feb. 20, 2015, which claims the priority benefit of U.S. Provisional Application Ser. No. 61/942,546, filed Feb. 20, 2014, the contents of which are incorporated herein by reference in their entirety.

INCORPORATION BY REFERENCE

The content of the following submission on ASCII text file is incorporated herein by reference in its entirety: a computer readable form (CRF) of the Sequence Listing (file name: 48768-506NO1USSEQLIST.txt, date recorded: Aug. 18, 2016, size: 204,800 bytes).

FIELD OF THE INVENTION

This disclosure relates to compositions and methods for the increased production of mevalonate, isoprene, isoprenoids, isoprenoid precursors, and/or acetyl-CoA-derived products in recombinant microorganisms, as well as methods for producing and using the same.

BACKGROUND OF THE INVENTION

Mevalonate is an intermediate of the mevalonate-dependent biosynthetic pathway that converts acetyl-CoA to isopentenyl diphosphate and dimethylallyl diphosphate. The conversion of acetyl-CoA to mevalonate can be catalyzed by the thiolase, HMG-CoA synthase and the HMG-CoA reductase activities of the upper mevalonate-dependent biosynthetic pathway (MVA pathway).

Commercially, mevalonate has been used as an additive in cosmetics, for the production of biodegradable polymers, and can have value as a chiral building block for the synthesis of other chemicals.

The products of the mevalonate-dependent pathway are isopentenyl pyrophosphate (IPP) and dimethylallyl diphosphate (DMAPP). IPP and DMAPP are precursors to isoprene as well as isoprenoids. Isoprene (2-methyl-1,3-butadiene) is the monomer of natural rubber and also a common structural motif to an immense variety of other naturally occurring compounds, collectively termed the isoprenoids. Isoprene is additionally the critical starting material for a variety of synthetic polymers, most notably synthetic rubbers.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Conventional means for obtaining mevalonate and isoprenoids include extraction from biological materials (e.g., plants, microbes, and animals) and partial or total organic synthesis in the laboratory. Such means, however, have generally proven to be unsatisfactory. In particular for isoprenoids, given the often times complex nature of their molecular structure, organic synthesis is impractical given that several steps are usually required to obtain the desired product. Additionally, these chemical synthesis steps can involve the use of toxic solvents as can extraction of isoprenoids from biological materials. Moreover, these extraction and purification methods usually result in a relatively low yield of the desired isoprenoid, as biological materials typically contain only minute amounts of these molecules. Unfortunately, the difficulty involved in obtaining relatively large amounts of isoprenoids has limited their practical use.

Recent developments in the production of isoprene, isoprenoid precursor molecules, and isoprenoids disclose methods for the production of isoprene and isoprenoids at rates, titers, and purities that can be sufficient to meet the demands of robust commercial processes (see, for example, International Patent Application Publication No. WO 2009/076676 A2 and U.S. Pat. No. 7,915,026); however, improvements to increase the production of isoprene and isoprenoids and to increase yields of the same are still needed.

Such improvements are provided herein by the disclosure of compositions and methods to increase production of mevalonate as an intermediate of the mevalonate-dependent biosynthetic pathway; to increase production of molecules derived from mevalonate, such as isoprene, isoprenoid precursors, and/or isoprenoids; and to increase production of acetyl-CoA-derived products.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions and methods for the increased production of mevalonate, isoprene, isoprenoid precursors, isoprenoids, and/or an acetyl-CoA-derived products in a microorganism by using one or more specific gene manipulations in recombinant microorganisms/recombinant cells such that the expression and/or activity of one or more acetylating proteins in the recombinant microorganisms is modulated. Such modulation can result in increased production of mevalonate, isoprene, isoprenoid precursor molecules, isoprenoids, and/or acetyl-CoA-derived products.

Accordingly, in one aspect, provided herein are recombinant cells capable of producing isoprene, wherein the cells comprise: (i) either one or more nucleic acids encoding one or more acetylating proteins, wherein the cells have been modified or engineered such that the expression of the nucleic acids and/or activity of the acetylating protein(s) is modulated or one or more acetylating proteins wherein the proteins are engineered such that their activity is modulated; (ii) one or more nucleic acids encoding one or more polypeptides of the MVA pathway; and (iii) a heterologous nucleic acid encoding an isoprene synthase polypeptide or a polypeptide having isoprene synthase activity, wherein culturing of the recombinant cells in a suitable media provides for the production of isoprene.

In some embodiments of any of the embodiments disclosed herein, the activity of the one or more acetylating proteins is modulated such that the activity of the one or more acetylating proteins is attenuated, deleted or increased.

In some embodiments of any of the embodiments disclosed herein, the acetylating protein is an acetyltransferase. In some embodiments of any of the embodiments disclosed herein, the acetyltransferase is chosen from the group consisting of YfiQ, Pat, and AcuA. In some embodiments of any of the embodiments disclosed herein, the acetyltransferase is a YfiQ polypeptide.

In some embodiments of any of the embodiments disclosed herein, the acetylating protein is a deacetylase. In some embodiments of any of the embodiments disclosed herein, the deacetylase is chosen from the group consisting of CobB and SrtN. In some embodiments of any of the embodiments disclosed herein, the deacetylase is a CobB polypeptide.

In some embodiments of any of the embodiments disclosed herein, the one or more acetylating proteins is selected from the group consisting of a YfiQ polypeptide and a CobB polypeptide.

In some embodiments of any of the embodiments disclosed herein, the acetylating protein is a YfiQ polypeptide. In some embodiments of any of the embodiments disclosed herein, the activity of the YfiQ polypeptide is modulated by decreasing, attenuating, or deleting the expression of the nucleic acid encoding the YfiQ polypeptide.

In some embodiments of any of the embodiments disclosed herein, the acetylating protein is a CobB polypeptide. In some embodiments of any of the embodiments disclosed herein, the activity of the CobB polypeptide is modulated by increasing the expression of the nucleic acid encoding the CobB polypeptide.

In some embodiments of any of the embodiments disclosed herein, one or more polypeptides of the MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate.

In some embodiments of any of the embodiments disclosed herein, the heterologous nucleic acid encoding an isoprene synthase polypeptide or a polypeptide having isoprene synthase activity is a plant isoprene synthase polypeptide. In some embodiments of any of the embodiments disclosed herein, the isoprene synthase polypeptide or the polypeptide having isoprene synthase activity is a polypeptide from *Pueraria* or *Populus* or a hybrid, *Populus alba*× *Populus tremula*. In some embodiments of any of the embodiments disclosed herein, the isoprene synthase polypeptide or the polypeptide having isoprene synthase activity is from the organism selected from the group consisting of *Pueraria montana, Pueraria lobata, Populus tremuloides, Populus alba, Populus nigra*, and *Populus trichocarpa*.

In some embodiments, the recombinant cells described herein further comprise one or more heterologous nucleic acids encoding a polypeptide having phosphoketolase activity. In some embodiments of any of the embodiments disclosed herein, the one or more heterologous nucleic acids encoding a polypeptide having phosphoketolase activity is capable of synthesizing glyceraldehyde 3-phosphate and acetyl phosphate (referred to herein interchangeably as acetylphosphate, acetyl-phosphate, acetyl-P, Ac-P) from xylulose 5-phosphate. In some embodiments of any of the embodiments disclosed herein, the one or more heterologous nucleic acids encoding a polypeptide having phosphoketolase activity is capable of synthesizing erythrose 4-phosphate and acetyl phosphate from fructose 6-phosphate. In some embodiments of any of the embodiments disclosed herein, the recombinant cells further comprise one or more nucleic acids encoding one or more 1-deoxy-D-xylulose 5-phosphate (DXP) pathway polypeptides.

In some embodiments, the recombinant cells described herein further comprise one or more nucleic acids encoding one or more pentose phosphate pathway proteins, wherein the cells have been modified such that the expression of the nucleic acids encoding the pentose phosphate pathway proteins and/or the activity of the pentose phosphate pathway proteins is modulated. In some embodiments, the activity of the one or more pentose phosphate pathway proteins is increased.

In certain embodiments, the activity of the one or more pentose phosphate pathway proteins is increased by increasing the expression of one or more nucleic acids encoding the pentose phosphate pathway proteins. In such embodiments, the one or more nucleic acids encoding the pentose phosphate pathway proteins is selected from the group consisting of transketolase (tktA), transaldolase (talB), ribulose-5-phosphate-epimerase (rpe), and ribose-5-phosphate epimerase (rpiA).

In other embodiments, the activity of the one or more pentose phosphate pathway proteins is decreased. In certain embodiments, the activity of the one or more pentose phosphate pathway proteins is decreased by decreasing, attenuating, or deleting the expression of one or more nucleic acids encoding the pentose phosphate pathway proteins. In such embodiments, the one or more nucleic acids encoding the pentose phosphate pathway proteins comprises phosphofructokinase (pfkA).

In some embodiments, the recombinant cells described herein further comprise one or more nucleic acids encoding one or more acetate cycling proteins, wherein the cells have been modified such that the expression of the nucleic acids encoding the acetate cycling proteins and/or activity of the acetate cycling proteins is modulated.

In some embodiments, the activity of the one or more acetate cycling proteins is increased. In some embodiments, the activity of the one or more acetate cycling proteins is increased by increasing the expression of one or more nucleic acids encoding the acetate cycling proteins. In such embodiments, the one or more nucleic acids encoding the acetate cycling proteins can be selected from the group consisting of acetyl-coenzyme A synthetase (acs), acetate kinase (ackA) and phosphotransacetylate (pta).

In some embodiments, the activity of the one or more acetate cycling proteins is decreased. In some embodiments, the activity of the one or more acetate cycling proteins is decreased by decreasing, attenuating, or deleting the expression of one or more nucleic acids encoding the acetate cycling proteins. In such embodiments, the one or more nucleic acids encoding the acetate cycling proteins can be selected from the group consisting of phosphotransacetylate (pta), acetate kinase (ackA), and acetate transporter/acetate pump (actP).

In some embodiments, the recombinant cells described herein further comprise one or more nucleic acids encoding one or more proteins selected from the group consisting of: sfcA, maeB, pdhR, aceE, aceF, lpdA, glta, acs, pta, ackA, actP, pfkA, rpe, rpiA, tkta, talB, pgl, edd, and eda, and wherein the cells have been modified such that the expression of the nucleic acids and/or activity of the proteins is modulated. In some embodiments, the activity of the one or more of these proteins is increased by increasing the expression of one or more nucleic acids encoding the one or more proteins. In specific embodiments, the one or more nucleic acids encoding the one or more proteins to be increased is selected from the group consisting of: ackA, pta, sfcA, maeB, aceE, aceF, lpdA, acs, rpe, rpiA, tkta, talB, and pgl. In some embodiments, the activity of the one or more of these proteins is decreased by decreasing, attenuating, or deleting the expression of one or more nucleic acids encoding the one or more proteins. In specific embodiments, the one or more nucleic acids encoding one or more proteins to be decreased is selected from the group consisting of: pdhR, glta, pta, ackA, actP, pfkA, pgl, edd, and eda.

In any one of the recombinant cells described herein, the one or more nucleic acids encoding one or more acetylating proteins, the one or more nucleic acids encoding one or more polypeptides of the MVA pathway, the nucleic acid encoding a polypeptide having isoprene synthase activity, the nucleic acid encoding a polypeptide having phosphoketolase activity, the one or more nucleic acids encoding one or more pentose phosphate pathway proteins, or the one or more nucleic acids encoding one or more acetate cycling proteins, is placed under an inducible promoter or a constitutive promoter.

In any one of the recombinant cells described herein, the one or more nucleic acids encoding one or more acetylating proteins, the one or more nucleic acids encoding one or more polypeptides of the MVA pathway, the nucleic acid encoding a polypeptide having isoprene synthase activity, the nucleic acid encoding a polypeptide having phosphoketolase activity, the one or more nucleic acids encoding one or more pentose phosphate pathway proteins, or the one or more nucleic acids encoding one or more acetate cycling proteins, is cloned into one or more multicopy plasmids.

In any one of the recombinant cells described herein, the one or more nucleic acids encoding one or more acetylating proteins, the one or more nucleic acids encoding one or more polypeptides of the MVA pathway, the nucleic acid encoding a polypeptide having isoprene synthase activity, the nucleic acid encoding a polypeptide having phosphoketolase activity, the one or more nucleic acids encoding one or more pentose phosphate pathway proteins, or the one or more nucleic acids encoding one or more acetate cycling proteins, is integrated into a chromosome of the cells.

In some embodiments of any of the embodiments disclosed herein, the recombinant cells are gram-positive bacterial cells or gram-negative bacterial cells. In other embodiments of any of the embodiments disclosed herein, the recombinant cells are fungal cells, filamentous fungal cells, algal cells or yeast cells. In some embodiments of any of the embodiments disclosed herein, the recombinant cells are selected from the group consisting of *Bacillus subtilis, Streptomyces lividans, Streptomyces coelicolor, Streptomyces griseus, Escherichia coli,* and *Pantoea citrea*. In some embodiments of any of the embodiments disclosed herein, the recombinant cells are selected from the group consisting of *Trichoderma reesei, Aspergillus oryzae, Aspergillus niger, Saccharomyces cerevisieae* and *Yarrowia lipolytica*.

In any of the embodiments described herein, the isoprene production is increased relative to recombinant cells that have not been modified such that the expression of the nucleic acids encoding the acetylating proteins and/or the activity of the acetylating proteins is modulated.

In any of the embodiments described herein, the isoprene production is increased by at least 5%, wherein the increased production of isoprene comprises an increase in: (i) titer, (ii) instantaneous yield, (iii) cumulative yield, (iv) ratio of isoprene to carbon dioxide, (v) specific productivity, or (vi) cell productivity index.

In other aspects, also provided herein are methods for producing isoprene comprising: (a) culturing the recombinant cell of any of the embodiments disclosed herein under conditions suitable for producing isoprene and (b) producing isoprene. In some embodiments, the method further comprises (c) recovering the isoprene.

In another aspect, provided herein are recombinant cells capable of producing an isoprenoid precursor, wherein the cells comprise: (i) either one or more nucleic acids encoding one or more acetylating proteins, wherein the cells have been modified or engineered such that the expression of the nucleic acids and/or activity of the acetylating protein(s) is modulated or one or more acetylating proteins wherein the proteins are engineered such that their activity is modulated; and (ii) one or more nucleic acids encoding one or more polypeptides of the MVA pathway, wherein culturing of the recombinant cells in a suitable media provides for production of the isoprenoid precursor.

In some embodiments of any of the embodiments disclosed herein, the activity of the one or more acetylating proteins is modulated such that the activity of the one or more acetylating proteins is attenuated, deleted or increased.

In some embodiments of any of the embodiments disclosed herein, the acetylating protein is an acetyltransferase. In some embodiments of any of the embodiments disclosed herein, the acetyltransferase is chosen from the group consisting of YfiQ, Pat, and AcuA. In some embodiments of any of the embodiments disclosed herein, the acetyltransferase is a YfiQ polypeptide.

In some embodiments of any of the embodiments disclosed herein, the acetylating protein is a deacetylase. In some embodiments of any of the embodiments disclosed herein, the deacetylase is chosen from the group consisting of CobB and SrtN. In some embodiments of any of the embodiments disclosed herein, the deacetylase is a CobB polypeptide.

In some embodiments of any of the embodiments disclosed herein, the one or more acetylating proteins is selected from the group consisting of a YfiQ polypeptide and a CobB polypeptide.

In some embodiments of any of the embodiments disclosed herein, the acetylating protein is a YfiQ polypeptide. In some embodiments of any of the embodiments disclosed herein, the activity of the YfiQ polypeptide is modulated by decreasing, attenuating, or deleting the expression of the nucleic acid encoding the YfiQ polypeptide.

In some embodiments of any of the embodiments disclosed herein, the acetylating protein is a CobB polypeptide. In some embodiments of any of the embodiments disclosed herein, the activity of the CobB polypeptide is modulated by increasing the expression of the nucleic acid encoding the CobB polypeptide.

In some embodiments of any of the embodiments disclosed herein, one or more polypeptides of the MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate.

In certain embodiments, the recombinant cells further comprise one or more heterologous nucleic acids encoding a polypeptide having phosphoketolase activity. In some embodiments of any of the embodiments disclosed herein, the one or more heterologous nucleic acids encoding a polypeptide having phosphoketolase activity is capable of synthesizing glyceraldehyde 3-phosphate and acetyl phosphate from xylulose 5-phosphate. In some embodiments of any of the embodiments disclosed herein, the one or more heterologous nucleic acids encoding a polypeptide having phosphoketolase activity is capable of synthesizing erythrose 4-phosphate and acetyl phosphate from fructose 6-phosphate.

In some embodiments, the recombinant cells described herein further comprise one or more nucleic acids encoding one or more pentose phosphate pathway proteins, wherein the cells have been modified such that the expression of the nucleic acids encoding the pentose phosphate pathway proteins and/or the activity of the pentose phosphate pathway proteins is modulated. In some embodiments, the activity of the one or more pentose phosphate pathway proteins is increased.

In certain embodiments, the activity of the one or more pentose phosphate pathway proteins is increased by increasing the expression of one or more nucleic acids encoding the pentose phosphate pathway proteins. In such embodiments, the one or more nucleic acids encoding the pentose phosphate pathway proteins is selected from the group consisting of transketolase (tktA), transaldolase (talB), ribulose-5-phosphate-epimerase (rpe), and ribose-5-phosphate epimerase (rpiA).

In other embodiments, the activity of the one or more pentose phosphate pathway proteins is decreased. In certain embodiments, the activity of the one or more pentose phosphate pathway proteins is decreased by decreasing, attenuating, or deleting the expression of one or more nucleic acids encoding the pentose phosphate pathway proteins. In such embodiments, the one or more nucleic acids encoding the pentose phosphate pathway proteins comprises phosphofructokinase (pfkA).

In some embodiments, the recombinant cells described herein further comprise one or more nucleic acids encoding one or more acetate cycling proteins, wherein the cells have been modified such that the expression of the nucleic acids encoding the acetate cycling proteins and/or activity of the acetate cycling proteins is modulated.

In some embodiments, the activity of the one or more acetate cycling proteins is increased. In some embodiments, the activity of the one or more acetate cycling proteins is increased by increasing the expression of one or more nucleic acids encoding the acetate cycling proteins. In such embodiments, the one or more nucleic acids encoding the acetate cycling proteins can be selected from the group consisting of acetyl-coenzyme A synthetase (acs), acetate kinase (ackA) and phosphotransacetylate (pta).

In some embodiments, the activity of the one or more acetate cycling proteins is decreased. In some embodiments, the activity of the one or more acetate cycling proteins is decreased by decreasing, attenuating, or deleting the expression of one or more nucleic acids encoding the acetate cycling proteins. In such embodiments, the one or more nucleic acids encoding the acetate cycling proteins can be selected from the group consisting of phosphotransacetylate (pta), acetate kinase (ackA), and acetate transporter/acetate pump (actP).

In some embodiments, the recombinant cells described herein further comprise one or more nucleic acids encoding one or more proteins selected from the group consisting of: sfcA, maeB, pdhR, aceE, aceF, lpdA, glta, acs, pta, ackA, actP, pfkA, rpe, rpiA, tkta, talB, pgl, edd, and eda, and wherein the cells have been modified such that the expression of the nucleic acids and/or activity of the proteins is modulated. In some embodiments, the activity of the one or more of these proteins is increased by increasing the expression of one or more nucleic acids encoding the one or more proteins. In specific embodiments, the one or more nucleic acids encoding the one or more proteins to be increased is selected from the group consisting of: ackA, pta, sfcA, maeB, aceE, aceF, lpdA, acs, rpe, rpiA, tkta, talB, and pgl. In some embodiments, the activity of the one or more of these proteins is decreased by decreasing, attenuating, or deleting the expression of one or more nucleic acids encoding the one or more proteins. In specific embodiments, the one or more nucleic acids encoding one or more proteins to be decreased is selected from the group consisting of: pdhR, glta, pta, ackA, actP, pfkA, pgl, edd, and eda.

In any one of the recombinant cells described herein, the one or more nucleic acids encoding one or more acetylating proteins, the one or more nucleic acids encoding one or more polypeptides of the MVA pathway, the nucleic acid encoding a polypeptide having phosphoketolase activity, the one or more nucleic acids encoding one or more pentose phosphate pathway proteins, or the one or more nucleic acids encoding one or more acetate cycling proteins, is placed under an inducible promoter or a constitutive promoter.

In any one of the recombinant cells described herein, the one or more nucleic acids encoding one or more acetylating proteins, the one or more nucleic acids encoding one or more polypeptides of the MVA pathway, the nucleic acid encoding a polypeptide having phosphoketolase activity, the one or more nucleic acids encoding one or more pentose phosphate pathway proteins, or the one or more nucleic acids encoding one or more acetate cycling proteins, is cloned into one or more multicopy plasmids.

In any one of the recombinant cells described herein, the one or more nucleic acids encoding one or more acetylating proteins, the one or more nucleic acids encoding one or more polypeptides of the MVA pathway, the nucleic acid encoding a polypeptide having phosphoketolase activity, the one or more nucleic acids encoding one or more pentose phosphate pathway proteins, or the one or more nucleic acids encoding one or more acetate cycling proteins, is integrated into a chromosome of the cells.

In some embodiments of any of the embodiments disclosed herein, the recombinant cells are gram-positive bacterial cells or gram-negative bacterial cells. In other embodiments of any of the embodiments disclosed herein, the recombinant cells are fungal cells, filamentous fungal cells, algal cells or yeast cells. In some embodiments of any of the embodiments disclosed herein, the recombinant cells are selected from the group consisting of *Bacillus subtilis, Streptomyces lividans, Streptomyces coelicolor, Streptomyces griseus, Escherichia coli,* and *Pantoea citrea*. In some embodiments of any of the embodiments disclosed herein, the recombinant cells are selected from the group consisting of *Trichoderma reesei*, *Aspergillus oryzae*, *Aspergillus niger*, *Saccharomyces* cerevisieae and *Yarrowia lipolytica*.

In some embodiments of any of the embodiments disclosed herein, the isoprenoid precursor is selected from the group consisting of mevalonate (MVA), dimethylallyl diphosphate (DMAPP) and isopentenyl pyrophosphate (IPP).

In any of the embodiments described herein, the isoprenoid precursor production is increased relative to recombinant cells that have not been modified such that the expression of the nucleic acids encoding the acetylating proteins and/or the activity of the acetylating proteins is modulated.

In any of the embodiments described herein, the isoprenoid precursor production is increased by at least 5%, wherein the increased production of isoprenoid precursor comprises an increase in: (i) titer, (ii) instantaneous yield, (iii) cumulative yield, (iv) specific productivity, or (v) cell productivity index.

In further aspects, provided herein are methods for producing an isoprenoid precursor comprising: (a) culturing the recombinant cell of any of the embodiments disclosed herein under conditions suitable for producing an isoprenoid precursor and (b) producing the isoprenoid precursor. In some embodiments, the method further comprises (c) recovering the isoprenoid precursor.

In yet another aspect, provided herein are recombinant cells capable of producing an isoprenoid, wherein the cells comprise: (i) either one or more nucleic acids encoding one or more acetylating proteins, wherein the cells have been modified or engineered such that the expression of the nucleic acids and/or activity of the acetylating protein(s) is modulated or one or more acetylating proteins wherein the proteins are engineered such that their activity is modulated; (ii) one or more nucleic acids encoding one or more polypeptides of the MVA pathway; and (iii) one or more nucleic acids encoding a polyprenyl pyrophosphate synthase, wherein culturing of the recombinant cells in a suitable media provides for production of the isoprenoid.

In some embodiments of any of the embodiments disclosed herein, the activity of the one or more acetylating proteins is modulated such that the activity of the one or more acetylating proteins is attenuated, deleted or increased.

In some embodiments of any of the embodiments disclosed herein, the acetylating protein is an acetyltransferase. In some embodiments of any of the embodiments disclosed herein, the acetyltransferase is chosen from the group consisting of YfiQ, Pat, and AcuA. In some embodiments of any of the embodiments disclosed herein, the acetyltransferase is a YfiQ polypeptide.

In some embodiments of any of the embodiments disclosed herein, the acetylating protein is a deacetylase. In some embodiments of any of the embodiments disclosed herein, the deacetylase is chosen from the group consisting of CobB and SrtN. In some embodiments of any of the embodiments disclosed herein, the deacetylase is a CobB polypeptide.

In some embodiments of any of the embodiments disclosed herein, the one or more acetylating proteins is selected from the group consisting of a YfiQ polypeptide and a CobB polypeptide.

In some embodiments of any of the embodiments disclosed herein, the acetylating protein is a YfiQ polypeptide. In some embodiments of any of the embodiments disclosed herein, the activity of the YfiQ polypeptide is modulated by decreasing, attenuating, or deleting the expression of the nucleic acid encoding the YfiQ polypeptide.

In some embodiments of any of the embodiments disclosed herein, the acetylating protein is a CobB polypeptide. In some embodiments of any of the embodiments disclosed herein, the activity of the CobB polypeptide is modulated by increasing the expression of the nucleic acid encoding the CobB polypeptide.

In some embodiments of any of the embodiments disclosed herein, one or more polypeptides of the MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate.

In certain embodiments, the recombinant cells further comprise one or more heterologous nucleic acids encoding a polypeptide having phosphoketolase activity. In some embodiments of any of the embodiments disclosed herein, the one or more heterologous nucleic acids encoding a polypeptide having phosphoketolase activity is capable of synthesizing glyceraldehyde 3-phosphate and acetyl phosphate from xylulose 5-phosphate. In some embodiments of any of the embodiments disclosed herein, the one or more heterologous nucleic acids encoding a polypeptide having phosphoketolase activity is capable of synthesizing erythrose 4-phosphate and acetyl phosphate from fructose 6-phosphate.

In some embodiments, the recombinant cells described herein further comprise one or more nucleic acids encoding one or more pentose phosphate pathway proteins, wherein the cells have been modified such that the expression of the nucleic acids encoding the pentose phosphate pathway proteins and/or the activity of the pentose phosphate pathway proteins is modulated. In some embodiments, the activity of the one or more pentose phosphate pathway proteins is increased.

In certain embodiments, the activity of the one or more pentose phosphate pathway proteins is increased by increasing the expression of one or more nucleic acids encoding the pentose phosphate pathway proteins. In such embodiments, the one or more nucleic acids encoding the pentose phosphate pathway proteins is selected from the group consisting of transketolase (tktA), transaldolase (talB), ribulose-5-phosphate-epimerase (rpe), and ribose-5-phosphate epimerase (rpiA).

In other embodiments, the activity of the one or more pentose phosphate pathway proteins is decreased. In certain embodiments, the activity of the one or more pentose phosphate pathway proteins is decreased by decreasing, attenuating, or deleting the expression of one or more nucleic acids encoding the pentose phosphate pathway proteins. In such embodiments, the one or more nucleic acids encoding the pentose phosphate pathway proteins comprises phosphofructokinase (pfkA).

In some embodiments, the recombinant cells described herein further comprise one or more nucleic acids encoding one or more acetate cycling proteins, wherein the cells have been modified such that the expression of the nucleic acids encoding the acetate cycling proteins and/or activity of the acetate cycling proteins is modulated.

In some embodiments, the activity of the one or more acetate cycling proteins is increased. In some embodiments, the activity of the one or more acetate cycling proteins is increased by increasing the expression of one or more nucleic acids encoding the acetate cycling proteins. In such embodiments, the one or more nucleic acids encoding the acetate cycling proteins can be selected from the group consisting of acetyl-coenzyme A synthetase (acs), acetate kinase (ackA) and phosphotransacetylate (pta).

In some embodiments, the activity of the one or more acetate cycling proteins is decreased. In some embodiments, the activity of the one or more acetate cycling proteins is decreased by decreasing, attenuating, or deleting the expression of one or more nucleic acids encoding the acetate cycling proteins. In such embodiments, the one or more nucleic acids encoding the acetate cycling proteins can be selected from the group consisting of phosphotransacetylate (pta), acetate kinase (ackA), and acetate transporter/acetate pump (actP).

In some embodiments, the recombinant cells described herein further comprise one or more nucleic acids encoding one or more proteins selected from the group consisting of: sfcA, maeB, pdhR, aceE, aceF, lpdA, glta, acs, pta, ackA, actP, pfkA, rpe, rpiA, tkta, talB, pgl, edd, and eda, and wherein the cells have been modified such that the expression of the nucleic acids and/or activity of the proteins is modulated. In some embodiments, the activity of the one or more of these proteins is increased by increasing the expression of one or more nucleic acids encoding the one or more proteins. In specific embodiments, the one or more nucleic acids encoding the one or more proteins to be increased is selected from the group consisting of: ackA, pta, sfcA, maeB, aceE, aceF, lpdA, acs, rpe, rpiA, tkta, talB, and pgl. In some embodiments, the activity of the one or more of these proteins is decreased by decreasing, attenuating, or deleting the expression of one or more nucleic acids encoding the one or more proteins. In specific embodiments, the one or more nucleic acids encoding one or more proteins to be decreased is selected from the group consisting of: pdhR, glta, pta, ackA, actP, pfkA, pgl, edd, and eda.

In any one of the recombinant cells described herein, the one or more nucleic acids encoding one or more acetylating proteins, the one or more nucleic acids encoding one or more polypeptides of the MVA pathway, the one or more nucleic acids encoding one or more pentose phosphate pathway proteins, or the one or more nucleic acids encoding one or more acetate cycling proteins, is placed under an inducible promoter or a constitutive promoter.

In any one of the recombinant cells described herein, the one or more nucleic acids encoding one or more acetylating proteins, the one or more nucleic acids encoding one or more polypeptides of the MVA pathway, the nucleic acid encoding a polypeptide having phosphoketolase activity, the one or more nucleic acids encoding one or more pentose phosphate pathway proteins, or the one or more nucleic acids encoding one or more acetate cycling proteins, is cloned into one or more multicopy plasmids.

In any one of the recombinant cells described herein, the one or more nucleic acids encoding one or more acetylating proteins, the one or more nucleic acids encoding one or more polypeptides of the MVA pathway, the nucleic acid encoding a polypeptide having phosphoketolase activity, the one or more nucleic acids encoding one or more pentose phosphate pathway proteins, or the one or more nucleic acids encoding one or more acetate cycling proteins, is integrated into a chromosome of the cells.

In some embodiments of any of the embodiments disclosed herein, the recombinant cells are gram-positive bacterial cells or gram-negative bacterial cells. In other embodiments of any of the embodiments disclosed herein, the recombinant cells are fungal cells, filamentous fungal cells, algal cells or yeast cells. In some embodiments of any of the embodiments disclosed herein, the recombinant cells are selected from the group consisting of *Bacillus subtilis, Streptomyces lividans, Streptomyces coelicolor, Streptomyces griseus, Escherichia coli,* and *Pantoea citrea*. In some embodiments of any of the embodiments disclosed herein, the recombinant cells are selected from the group consisting of *Trichoderma reesei, Aspergillus oryzae, Aspergillus niger, Saccharomyces* cerevisieae and *Yarrowia lipolytica*. In some embodiments of any of the embodiments disclosed herein, the isoprenoid is selected from the group consisting of monoterpenoids, sesquiterpenoids, diterpenoids, sesterterpenoids, triterpenoids, and tetraterpenoids. In some embodiments of any of the embodiments disclosed herein, the isoprenoid is selected from the group consisting of abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In any of the embodiments described herein, the isoprenoid production is increased relative to recombinant cells that have not been modified such that the expression of the nucleic acids encoding the acetylating proteins and/or the activity of the acetylating proteins is modulated.

In any of the embodiments described herein, the isoprenoid production is increased by at least 5%, wherein the increased production of the isoprenoid comprises an increase in: (i) titer, (ii) instantaneous yield, (iii) cumulative yield, (iv) specific productivity, or (v) cell productivity index.

In further aspects, provided herein are methods for producing an isoprenoid comprising: (a) culturing the recombinant cell of any of the embodiments disclosed herein under conditions suitable for producing an isoprenoid and (b) producing the isoprenoid. In some embodiments, the method further comprises (c) recovering the isoprenoid.

In yet other aspects, provided herein are recombinant cells capable of producing an acetyl-CoA derived product, wherein the cells comprise: (i) either one or more nucleic acids encoding one or more acetylating proteins, wherein the cells have been modified or engineered such that the expression of the nucleic acids and/or activity of the acetylating protein(s) is modulated or one or more acetylating proteins wherein the proteins are engineered such that their activity is modulated; and (ii) one or more heterologous nucleic acids encoding a polypeptide having phosphoketolase activity, wherein the cells produce the acetyl-CoA derived product. In some embodiments, the cells produce increased amounts of the acetyl-CoA derived product compared to a cell capable of producing the acetyl-CoA derived product that does not comprise (i).

In some embodiments, the acetyl-Co-A derived product is selected from the group consisting of fatty acids, phenols, prostaglandins, macrolide antibiotics, isoprene, and isoprenoids.

In some embodiments of any of the embodiments disclosed herein, the activity of the one or more acetylating proteins is modulated such that the activity of the one or more acetylating proteins is attenuated, deleted or increased.

In some embodiments of any of the embodiments disclosed herein, the acetylating protein is an acetyltransferase. In some embodiments of any of the embodiments disclosed herein, the acetyltransferase is chosen from the group consisting of YfiQ, Pat, and AcuA. In some embodiments of any of the embodiments disclosed herein, the acetyltransferase is a YfiQ polypeptide.

In some embodiments of any of the embodiments disclosed herein, the acetylating protein is a deacetylase. In some embodiments of any of the embodiments disclosed herein, the deacetylase is chosen from the group consisting of CobB and SrtN. In some embodiments of any of the embodiments disclosed herein, the deacetylase is a CobB polypeptide.

In some embodiments of any of the embodiments disclosed herein, the one or more acetylating proteins is selected from the group consisting of a YfiQ polypeptide and a CobB polypeptide.

In some embodiments of any of the embodiments disclosed herein, the acetylating protein is a YfiQ polypeptide. In some embodiments of any of the embodiments disclosed herein, the activity of the YfiQ polypeptide is modulated by decreasing, attenuating, or deleting the expression of the nucleic acid encoding the YfiQ polypeptide.

In some embodiments of any of the embodiments disclosed herein, the acetylating protein is a CobB polypeptide. In some embodiments of any of the embodiments disclosed herein, the activity of the CobB polypeptide is modulated by increasing the expression of the nucleic acid encoding the CobB polypeptide.

In some embodiments of any of the embodiments disclosed herein, the one or more heterologous nucleic acids encoding a polypeptide having phosphoketolase activity is capable of synthesizing glyceraldehyde 3-phosphate and acetyl phosphate from xylulose 5-phosphate. In some embodiments of any of the embodiments disclosed herein, the one or more heterologous nucleic acids encoding a polypeptide having phosphoketolase activity is capable of synthesizing erythrose 4-phosphate and acetyl phosphate from fructose 6-phosphate.

In some embodiments, the recombinant cells described herein further comprise one or more nucleic acids encoding one or more pentose phosphate pathway proteins, wherein the cells have been modified such that the expression of the nucleic acids encoding the pentose phosphate pathway proteins and/or the activity of the pentose phosphate pathway proteins is modulated. In some embodiments, the activity of the one or more pentose phosphate pathway proteins is increased.

In certain embodiments, the activity of the one or more pentose phosphate pathway proteins is increased by increasing the expression of one or more nucleic acids encoding the pentose phosphate pathway proteins. In such embodiments, the one or more nucleic acids encoding the pentose phosphate pathway proteins is selected from the group consisting of transketolase (tktA), transaldolase (talB), ribulose-5-phosphate-epimerase (rpe), and ribose-5-phosphate epimerase (rpiA).

In other embodiments, the activity of the one or more pentose phosphate pathway proteins is decreased. In certain embodiments, the activity of the one or more pentose phosphate pathway proteins is decreased by decreasing, attenuating, or deleting the expression of one or more nucleic acids encoding the pentose phosphate pathway proteins. In such embodiments, the one or more nucleic acids encoding the pentose phosphate pathway proteins comprises phosphofructokinase (pfkA).

In some embodiments, the recombinant cells described herein further comprise one or more nucleic acids encoding one or more acetate cycling proteins, wherein the cells have been modified such that the expression of the nucleic acids encoding the acetate cycling proteins and/or activity of the acetate cycling proteins is modulated.

In some embodiments, the activity of the one or more acetate cycling proteins is increased. In some embodiments, the activity of the one or more acetate cycling proteins is increased by increasing the expression of one or more nucleic acids encoding the acetate cycling proteins. In such embodiments, the one or more nucleic acids encoding the acetate cycling proteins can be selected from the group consisting of acetyl-coenzyme A synthetase (acs), acetate kinase (ackA) and phosphotransacetylate (pta).

In some embodiments, the activity of the one or more acetate cycling proteins is decreased. In some embodiments, the activity of the one or more acetate cycling proteins is decreased by decreasing, attenuating, or deleting the expression of one or more nucleic acids encoding the acetate cycling proteins. In such embodiments, the one or more nucleic acids encoding the acetate cycling proteins can be selected from the group consisting of phosphotransacetylate (pta), acetate kinase (ackA), and acetate transporter/acetate pump (actP).

In some embodiments, the recombinant cells described herein further comprise one or more nucleic acids encoding one or more proteins selected from the group consisting of: sfcA, maeB, pdhR, aceE, aceF, lpdA, glta, acs, pta, ackA, actP, pfkA, rpe, rpiA, tkta, talB, pgl, edd, and eda, and wherein the cells have been modified such that the expression of the nucleic acids and/or activity of the proteins is modulated. In some embodiments, the activity of the one or more of these proteins is increased by increasing the expression of one or more nucleic acids encoding the one or more proteins. In specific embodiments, the one or more nucleic acids encoding the one or more proteins to be increased is selected from the group consisting of: ackA, pta, sfcA, maeB, aceE, aceF, lpdA, acs, rpe, rpiA, tkta, talB, and pgl. In some embodiments, the activity of the one or more of these proteins is decreased by decreasing, attenuating, or deleting the expression of one or more nucleic acids encoding the one or more proteins. In specific embodiments, the one or more nucleic acids encoding one or more proteins to be decreased is selected from the group consisting of: pdhR, glta, pta, ackA, actP, pfkA, pgl, edd, and eda.

In any one of the recombinant cells described herein, the one or more nucleic acids encoding one or more acetylating proteins, the one or more nucleic acids encoding one or more polypeptides of the MVA pathway, the nucleic acid encoding a polypeptide having isoprene synthase activity, the nucleic acid encoding a polypeptide having phosphoketolase activity, the one or more nucleic acids encoding one or more pentose phosphate pathway proteins, or the one or more nucleic acids encoding one or more acetate cycling proteins, is placed under an inducible promoter or a constitutive promoter.

In any one of the recombinant cells described herein, the one or more nucleic acids encoding one or more acetylating proteins, the one or more nucleic acids encoding one or more polypeptides of the MVA pathway, the nucleic acid encoding a polypeptide having isoprene synthase activity, the nucleic acid encoding a polypeptide having phosphoketolase activity, the one or more nucleic acids encoding one or more pentose phosphate pathway proteins, or the one or more nucleic acids encoding one or more acetate cycling proteins, is cloned into one or more multicopy plasmids.

In any one of the recombinant cells described herein, the one or more nucleic acids encoding one or more acetylating proteins, the one or more nucleic acids encoding one or more polypeptides of the MVA pathway, the nucleic acid encoding a polypeptide having isoprene synthase activity, the nucleic acid encoding a polypeptide having phosphoketolase activity, the one or more nucleic acids encoding one or more pentose phosphate pathway proteins, or the one or more nucleic acids encoding one or more acetate cycling proteins, is integrated into a chromosome of the cells.

In some embodiments of any of the embodiments disclosed herein, the recombinant cells are gram-positive bacterial cells or gram-negative bacterial cells. In other embodiments of any of the embodiments disclosed herein, the recombinant cells are fungal cells, filamentous fungal cells, algal cells or yeast cells. In some embodiments of any of the embodiments disclosed herein, the recombinant cells are selected from the group consisting of *Bacillus subtilis*, *Streptomyces lividans*, *Streptomyces coelicolor*, *Streptomyces griseus*, *Escherichia coli*, and *Pantoea citrea*. In some embodiments of any of the embodiments disclosed herein, the recombinant cells are selected from the group consisting of *Trichoderma reesei*, *Aspergillus oryzae*, *Aspergillus niger*, *Saccharomyces* cerevisieae and *Yarrowia lipolytica*.

In any of the embodiments described herein, the acetyl-CoA derived product production is increased relative to recombinant cells that have not been modified such that the expression of the nucleic acids encoding the acetylating proteins and/or the activity of the acetylating proteins is modulated.

In another aspect, provided herein are methods for producing an acetyl-CoA derived product comprising: (a) culturing the recombinant cells of any one of the embodiments disclosed herein under conditions suitable for producing the acetyl-CoA derived product and (b) producing the acetyl-CoA derived product. In some embodiments, the method further comprises (c) recovering the acetyl-CoA derived product.

BRIEF DESCRIPTION OF THE DRAWINGS

FIG. 1A depicts growth (OD600) for control wild type YfiQ cells versus cells carrying a deletion in the YfiQ gene over four hours.

DETAILED DESCRIPTION

Figure 1B:
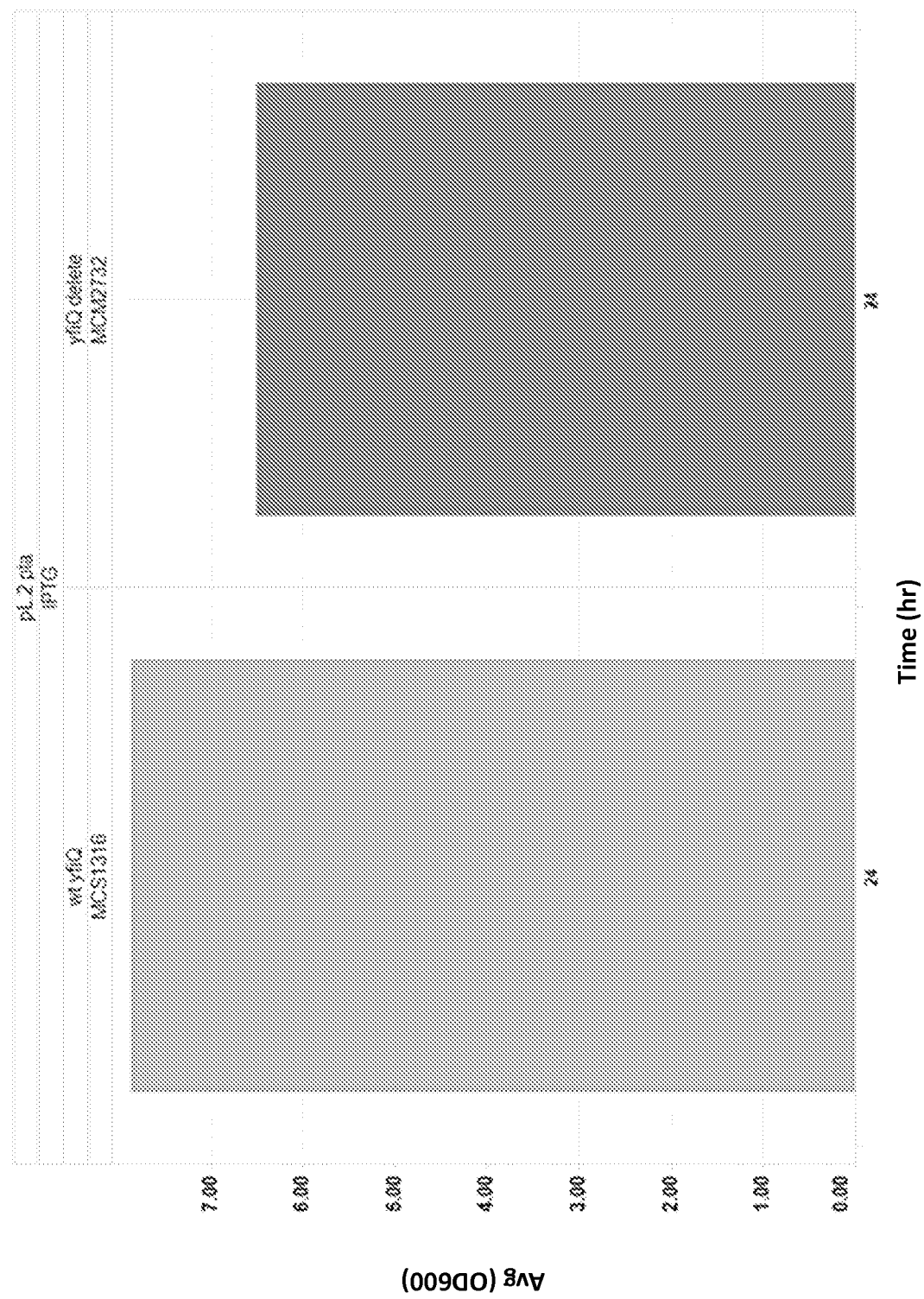
FIG. 1B depicts overnight growth for the same cells.

The invention provides, inter alia, compositions and methods for the increased production of mevalonate, isoprene, isoprenoid precursor molecules, isoprenoids, and/or acetyl-CoA-derived products in recombinant microorganisms that have been engineered for modulated expression of genes encoding polypeptides involved in protein acetylation ("acetylating proteins" or "acetylation proteins"). More specifically, the invention provides, inter alia, recombinant microorganisms, or progeny thereof, comprising cells wherein the activity of one or more acetylating proteins is modulated. These acetylating proteins can include, without limitation, acetyl transferase polypeptides (acetyltransferases) and/or deacetylase polypeptides. In some embodiments, the activity of said one or more acetylating proteins is modulated such that the activity of said one or more acetylating proteins is decreased, attenuated, deleted or increased. In some embodiments of any of the embodiments disclosed herein, the one or more acetylating proteins is selected from the group consisting of a YfiQ polypeptide, a Pat polypeptide, an AcuA polypeptide, a *Salmonella enterica* acetyltransferase (gi|16503810|emb|CAD05835.1| SEQ ID NO:51), a *Rhodopseudomonas palustris* GCN5 family N-acetyltransferase (gi|499473135|ref|WP_011159775.1| SEQ ID NO:52), a *Streptomyces lividans* protein acetyl transferase (EFD66247 SEQ ID NO:53), a *Mycobacterium tuberculosis* acetyltransferase (gi|15608138|ref|NP_215513.1| SEQ ID NO:54), and a *Mycobacterium smegmatis* acetyl transferase (gi|118468187|ref|YP_889697.1| SEQ ID NO:55). In some embodiments of any of the embodiments disclosed herein, the one or more acetylating proteins is selected from the group consisting of a CobB polypeptide, a SrtN polypeptide, a *Salmonella enterica* NAD-dependent deacylase (gi|16764576|ref|NP_460191.1| SEQ ID NO:56), a *Rhodopseudomonas palustris* NAD-dependent deacylase (gi|499471434|ref|WP_011158074.1| SEQ ID NO:57), and a *Mycobacterium tuberculosis* NAD-dependent protein deacylase (gi|614103494|sp|P9WGG3.1|NPD_MYCTU SEQ ID NO:58). In some embodiments of any of the embodiments disclosed herein, the one or more acetylating proteins is selected from the group consisting of a YfiQ polypeptide and a CobB polypeptide. In some embodiments of any of the embodiments disclosed herein, the acetylating protein is a YfiQ polypeptide. In some embodiments of any of the embodiments disclosed herein, the activity of the YfiQ polypeptide is modulated by decreasing, attenuating, or deleting the expression of the gene/nucleic acid encoding the YfiQ polypeptide. In some embodiments of any of the embodiments disclosed herein, the activity of the YfiQ polypeptide is modulated by increasing the expression of the gene encoding the YfiQ polypeptide. In some embodiments of any of the embodiments disclosed herein, the acetylating protein is a CobB polypeptide. In some embodiments of any of the embodiments disclosed herein, the activity of the CobB polypeptide is modulated by decreasing, attenuating, or deleting the expression of the gene encoding the CobB polypeptide. In some embodiments of any of the embodiments disclosed herein, the activity of the CobB polypeptide is modulated by increasing the expression of the gene encoding the CobB polypeptide.

As detailed herein, acetylation is a post-translational modification used by cells to control the activity of proteins as well as to regulate gene expression in response to rapidly changing conditions (Cerezo et al., 2011, *Molec. Microb.*, 82(5):1110-28). Acetylation of cellular proteins is controlled by enzymes known as acetyltransferases, which transfer the acetyl group of intracellularly available acetyl-CoA onto a target protein, and deacetylases, which remove acetyl groups from amino acids in proteins. As disclosed herein, the inventors have discovered, inter alia, that modulation of genes responsible for regulating intracellular acetylation results in substantial and surprising improvements in the production of molecules derived from mevalonate, including isoprene, isoprenoid precursors, and isoprenoids, as well as the production of molecules derived from acetyl-CoA.

In one aspect, the recombinant microorganisms disclosed herein are cells (such as bacterial, fungal, or algal cells) that have been further engineered or modified to heterologously express nucleic acids encoding one or more mevalonate (MVA) pathway polypeptides. The mevalonate-dependent biosynthetic pathway is particularly important for the production of the isoprenoid precursor molecules dimethylallyl diphosphate (DMAPP) and isopentenyl pyrophosphate (IPP). The enzymes of the upper mevalonate pathway convert acetyl-CoA into mevalonate via three enzymatic reactions. Without being bound to theory, it is believed that increasing the amount of acetyl-CoA intracellularly available for entrance into the upper mevalonate-dependent biosynthetic pathway will substantially increase intracellular concentrations of mevalonate and, consequently, of downstream isoprenoid precursor molecules such as DMAPP and IPP. The increased yield of mevalonate production by these strains is therefore advantageous for commercial applications. Any progeny of the recombinant microorganism is contemplated to be within the scope of the invention as well.

Furthermore, modulation of additional genes involved in the utilization of carbon during cellular metabolism or that are implicated with respect to the available intracellular supply of acetyl-CoA may also be modulated to improve production of mevalonate, isoprene, isoprenoid precursors, and/or isoprenoids. These include, but are not limited to, genes encoding phosphoketolase, citrate synthase, phosphotransacetylase, acetate kinase, lactate dehydrogenase, malic enzyme and/or pyruvate dehydrogenase which can be modulated to increase or decrease the activity of enzymes in metabolic pathways such that more carbon flux is directed toward mevalonate production. Other factors, the modulation of which can increase carbon flux towards mevalonate in cells, can include 6-phosphogluconolactonase, phosphoenolpyruvate carboxylase, the inhibitor of RssB activity during magnesium starvation protein, the AcrA component of the multidrug efflux pump AcrAB-TolC, and the fumarate and nitrate reduction sRNA. This, in turn, can lead to more substrate for the production of isoprene, isoprenoid precursors, and isoprenoids. The compositions and methods of the present application, therefore, represent an improvement over what has previously been practiced in the art, both in the number of strains of microorganisms available for increased production of mevalonate, isoprene, isoprenoid precursor molecules, isoprenoids, and acetyl-coA-derived products as well as in the amount of these compounds (e.g., mevalonate) produced by those cells (such as bacterial, fungal, or algal cells).

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Definitions

The terms "complete mevalonate (MVA) pathway" or "entire mevalonate (MVA) pathway" refer to the cellular metabolic pathway which converts acetyl-CoA into dimethylallyl pyrophosphate (DMAPP) and isopentenyl pyrophosphate (IPP) and which is catalyzed by the enzymes acetoacetyl-Coenzyme A synthase (e.g., thiolase), 3-hydroxy-3-methylglutaryl-Coenzyme A synthase, 3-hydroxy-3-methylglutaryl-Coenzyme A reductase, mevalonate kinase (MVK), phosphomevalonate kinase (PMK), diphosphomevalonate decarboxylase (MVD), and isopentenyl diphosphate isomerase (IDI).

As used herein, the terms "upper mevalonate pathway" or "upper MVA pathway" refer to the series of reactions in cells catalyzed by the enzymes acetoacetyl-Coenzyme A synthase (e.g., thiolase), 3-hydroxy-3-methylglutaryl-Coenzyme A synthase, and 3-hydroxy-3-methylglutaryl-Coenzyme A reductase.

The terms "lower mevalonate pathway" or "lower MVA pathway" refer to the series of reactions in cells catalyzed by the enzymes mevalonate kinase (MVK), phosphomevalonate kinase (PMK), diphosphomevalonate decarboxylase (MVD), and isopentenyl diphosphate isomerase (IDI).

The term "isoprene" refers to 2-methyl-1,3-butadiene (CAS #78-79-5). It can be the direct and final volatile C5 hydrocarbon product from the elimination of pyrophosphate from 3,3-dimethylallyl diphosphate (DMAPP). It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the mvaE and mvaS genes transformed in or integrated into the chromosome of *E. coli* is a heterologous nucleic acid.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth medium containing the minimum nutrients possible for cell growth, generally without the presence of amino acids. Minimal medium typically contains: (1) a carbon source for microorganism (e.g., such as bacterial, fungal, or algal cells) growth; (2) various salts, which can vary among microorganism (e.g., bacterial) species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., isopentenyl pyrophosphate (IPP) and dimethylallyl diphosphate (DMAPP).

As used herein, the term "mass yield" refers to the mass of the product produced by the cells (such as bacterial, fungal, or algal cells) divided by the mass of the glucose consumed by the cells (such as bacterial, fungal, or algal cells) multiplied by 100.

By "specific productivity," it is meant the mass of the product produced by the cells (such as bacterial, fungal, or algal cells) divided by the product of the time for production, the cell density, and the volume of the culture.

By "titer," it is meant the mass of the product produced by the cells (such as bacterial, fungal, or algal cells) divided by the volume of the culture.

As used herein, the term "cell productivity index (CPI)" refers to the mass of the product produced by the cells (such as bacterial, fungal, or algal cells) divided by the mass of the cells (such as bacterial, fungal, or algal cells) produced in the culture.

As used herein, the term "acetyl-CoA-derived products" refer to secondary metabolites derived from acetyl-CoA. Examples of secondary metabolites include, but are not limited to, fatty acids, phenols, prostaglandins, macrolide antibiotics, isoprene, and isoprenoids.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Modulation of Cellular Acetylation Machinery

Acetylation of residues in proteins is a post-translational modification seen throughout prokaryotic and eukaryotic cells. Acetylation of lysine residue is a common post-translational modification that is observed. As a post-translational modification, acetylation can be used by cells to control the activity of proteins as well as to regulate gene expression in response to rapidly changing conditions (Cerezo et al., 2011, *Molec. Microb.*, 82(5):1110-28). Acetylation of cellular proteins is controlled by enzymes known as acetyltransferases (such as, acetyl-CoA-dependent acetyl transferases or Gen5-like protein N-acetyltransferases, e.g., YfiQ) which transfer the acetyl group of a molecule of acetyl-CoA onto a target protein. As used herein, the term "YfiQ" refers to an acetyltransferase polypeptide encoded by the yfiQ which can be used interchangeably with the terms "protein lysine acetylase" or "pka." In contrast, deacetylation of intracellular proteins is controlled by enzymes known as deacetylases, such as $NAD^+$-dependent (Sir2-like) protein deacetylases (otherwise known as sirtuins, for example, CobB).

One important target for protein acetylation in microorganisms is AMP-forming acetyl-coenzyme A synthetase (Acs), which is a ubiquitous enzyme responsible for the conversion of acetate to the high energy intermediate acetyl-CoA, a keystone molecule of central metabolism (Cerezo et al., 2011, *Molec. Microb.*, 82(5):1110-28). The deacetylase activity of CobB has been demonstrated on Acs in vitro (Zhao et al., 2004, *J. Mol. Biol.*, 337:731-41). Without being bound to theory, since acetylation of Acs results in its enzymatic inactivation, cells engineered to decrease the amount of Acs acetylation could be expected to produce higher amounts of acetyl-CoA.

By manipulating the pathways that involves intracellular protein acetylation, the recombinant microorganism can produce decreased amounts of acetate in comparison to microorganisms that do not have modulated endogenous acetyltransferase and/or deacetylase gene expression or protein activity. Decreases in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% as compared to cells comprising one or more nucleic acids encoding one or more acetylating proteins, wherein said cells have been engineered such that the expression of the nucleic acids and/or activity of the acetylating protein(s) is modulated.

The activity of acetyltransferases (such as, but not limited to YfiQ (pka), Pat, or AcuA) or deacetylases (such as, but not limited to CobB and SrtN) can also be decreased by molecular manipulation of protein activity or gene expression. The decrease in protein activity or gene expression can be any amount of reduction of gene expression, specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99% or 100%.

The activity of acetyltransferases (such as, but not limited to YfiQ (pka), Pat, or AcuA) or deacetylases (such as, but not limited to CobB and SrtN) can also be increased by molecular manipulation of protein activity or gene expression. The increase in protein activity or gene expression can be any amount of increase in gene expression, specific activity or total activity as compared to when no manipulation has been effectuated. In some instances, the increase of enzyme activity is increased by at least about 1%, 5%, 10%, 20%, 30%, 40%, 50%, 60%, 70%, 80%, 90%, 100%, 125%, 150%, 200%, 250%, 300%, 350%, 400%, 450%, 500%, 750%, 1000% or more.

In some embodiments, the activity of said one or more acetylating proteins is modulated such that the activity of said one or more acetylating proteins is attenuated, deleted or increased. In some embodiments of any of the embodiments disclosed herein, the one or more acetylating proteins is selected from the group consisting of a YfiQ polypeptide and a CobB polypeptide. In some embodiments of any of the embodiments disclosed herein, the acetylating protein is a YfiQ polypeptide. In some embodiments of any of the embodiments disclosed herein, the activity of the YfiQ polypeptide is modulated by decreasing, attenuating, or deleting the expression of the gene encoding the YfiQ polypeptide. In some embodiments of any of the embodiments disclosed herein, the activity of the YfiQ polypeptide is modulated by increasing the expression of the gene encoding the YfiQ polypeptide. In some embodiments of any of the embodiments disclosed herein, the acetylating protein is a CobB polypeptide. In some embodiments of any of the embodiments disclosed herein, the activity of the CobB polypeptide is modulated by decreasing, attenuating, or deleting the expression of the gene encoding the CobB polypeptide. In some embodiments of any of the embodiments disclosed herein, the activity of the CobB polypeptide is modulated by increasing the expression of the gene encoding the CobB polypeptide.

In some cases, modulating the activity of an acetyltransferase and/or a deacetylase gene (either at the transcriptional (i.e., gene expression) and/or translational level (i.e., protein activity) results in more carbon flux into the mevalonate dependent biosynthetic pathway in comparison to cells that do not have modulated acetyltransferase and/or a deacetylase activity.

Recombinant Cells Capable of Production of Mevalonate

The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of the isoprenoid precursor molecules DMAPP and IPP, which serve as the basis for the biosynthesis of terpenes, terpenoids, isoprenoids, and isoprene.

In the upper portion of the MVA pathway, acetyl-CoA produced during cellular metabolism is converted to mevalonate via the actions of polypeptides having thiolase, HMG-CoA reductase, and HMG-CoA synthase enzymatic activity. First, acetyl-CoA is converted to acetoacetyl-CoA via the action of a thiolase. Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. Mevalonate is then converted into mevalonate-5-phosphate via the action of mevalonate kinase which is subsequently transformed into mevalonate-5-pyrophosphate by the enzymatic activity of phosphomevalonate kinase. Finally, IPP is formed from mevalonate-5-pyrophosphate by the activity of the enzyme mevalonate-5-pyrophosphate decarboxylase.

In some aspects, modulation of the any of the enzymes referred to herein can affect the expression (e.g., transcription or translation), production, post-translational modification or any other function of the enzyme. In some embodiments, the function of the enzyme (e.g., catalytic ability) in recombinant cells is increased or decreased as compared to a cell that has not been engineered for such modulation. In one embodiment, the function of the enzyme (e.g. activity) is increased as compared to a cell that has not been engineered. In another embodiment, the function of the enzyme (e.g. activity) is decreased as compared to a cell that has not been engineered.

Any of the enzymes from the upper and lower MVA pathway may be used in combination with the engineered host cells described herein. Non-limiting examples of MVA pathway polypeptides include acetyl-CoA acetyltransferase (AA-CoA thiolase) polypeptides, acetoacetyl-CoA synthase (nphT7), 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. MVA pathway polypeptides can include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein.

Non-limiting examples of MVA pathway polypeptides which can be used are described in International Patent Application Publication No. WO2009/076676; WO2010/003007 and WO2010/148150.

Genes Encoding MvaE and MvaS Polypeptides

In some microorganisms (such as, but not limited to, *L. grayi, E. faecium, E. gallinarum, E. casseliflavus*, and *E. faecalis*), the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., *J Bacteriol.* 2002 April; 184(8): 2116-2122). The mvaS gene, on the other hand, encodes a polypeptide having an HMG-CoA synthase activity. The mvaE and mvaS genes of a different bacterial species, *E. faecalis*, have been incorporated into *E. coli* strains previously to produce mevalonate (see US 2005/0287655 A1, the disclosure of which is incorporated by reference herein; Tabata, K. and Hashimoto, S.-I. *Biotechnology Letters* 26: 1487-1491, 2004).

Accordingly, cells (such as bacterial cells, e.g., *E. coli*) can be engineered to express one or more mvaE and mvaS genes (such as, but not limited to, mvaE and mvaS genes from *L. grayi, E. faecium, E. gallinarum, E. casseliflavus,* and/or *E. faecalis*), to increase production, peak titer, and cell productivity of mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Any genes encoding an upper MVA pathway polypeptide can be used in the present invention. In certain embodiments, various options of mvaE and mvaS genes (such as, but not limited to, mvaE and mvaS genes from *L. grayi, E. faecium, E. gallinarum, E. casseliflavus,* and/or *E. faecalis*) alone or in combination with one or more other mvaE and mvaS genes encoding proteins from the upper MVA pathway are contemplated within the scope of the invention. Thus, in certain aspects, any of the combinations of genes contemplated in Table 1 can be expressed in cells (such as bacterial, fungal, or algal cells) in any of the ways described above.

source organisms described herein that have at least one activity of a MvaE polypeptide.

Mutant MvaE polypeptides include those in which one or more amino acid residues have undergone an amino acid substitution while retaining MvaE polypeptide activity (i.e., the ability to convert acetyl-CoA to acetoacetyl-CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

TABLE 1

Options For Expression of MvaE And MvaS Genes In Host Cells Contemplated

|  | *L. grayi*, mvaE | *E. faecium*, mvaE | *E. gallinarum*, mvaE | *E. casseliflavus*, mvaE | *E. faecalis*, mvaE |
| --- | --- | --- | --- | --- | --- |
| *L. grayi*, mvaS | *L. grayi*, mvaE *L. grayi*, mvaS | *E. faecium*, mvaE *L. grayi*, mvaS | *E. gallinarum*, mvaE *L. grayi*, mvaS | *E. casseliflavus*, mvaE *L. grayi*, mvaS | *E. faecalis*, mvaE *L. grayi*, mvaS |
| *E. faecium*, mvaS | *L. grayi*, mvaE *E. faecium*, mvaS | *E. faecium*, mvaE *E. faecium*, mvaS | *E. gallinarum*, mvaE *E. faecium*, mvaS | *E. casseliflavus*, mvaE *E. faecium*, mvaS | *E. faecalis*, mvaE *E. faecium*, mvaS |
| *E. gallinarum*, mvaS | *L. grayi*, mvaE *E. gallinarum*, mvaS | *E. faecium*, mvaE *E. gallinarum*, mvaS | *E. gallinarum*, mvaE *E. gallinarum*, mvaS | *E. casseliflavus*, mvaE *E. gallinarum*, mvaS | *E. faecalis*, mvaE *E. gallinarum*, mvaS |
| *E. casseliflavus*, mvaS | *L. grayi*, mvaE *E. casseliflavus*, mvaS | *E. faecium*, mvaE *E. casseliflavus*, mvaS | *E. gallinarum*, mvaE *E. casseliflavus*, mvaS | *E. casseliflavus*, mvaE *E. casseliflavus*, mvaS | *E. faecalis*, mvaE *E. casseliflavus*, mvaS |
| *E. faecalis*, mvaS | *L. grayi*, mvaE *E. faecalis*, mvaS | *E. faecium*, mvaE *E. faecalis*, mvaS | *E. gallinarum*, mvaE *E. faecalis*, mvaS | *E. casseliflavus*, mvaE *E. faecalis*, mvaS | *E. faecalis*, mvaE *E. faecalis*, mvaS |

Exemplary MvaE Polypeptides and Nucleic Acids

The mvaE gene encodes a polypeptide that possesses both thiolase and HMG-CoA reductase activities. The thiolase activity of the polypeptide encoded by the mvaE gene converts acetyl-CoA to acetoacetyl-CoA whereas the HMG-CoA reductase enzymatic activity of the polypeptide converts 3-hydroxy-3-methylglutaryl-CoA to mevalonate. Exemplary MvaE polypeptides and nucleic acids include naturally-occurring polypeptides and nucleic acids from any of the source organisms described herein as well as mutant polypeptides and nucleic acids derived from any of the Amino acid substitutions in the MvaE polypeptide can be introduced to improve the functionality of the molecule. For example, amino acid substitutions that increase the binding affinity of the MvaE polypeptide for its substrate, or that improve its ability to convert acetyl-CoA to acetoacetyl-CoA and/or the ability to convert 3-hydroxy-3-methylglutaryl-CoA to mevalonate can be introduced into the MvaE polypeptide. In some aspects, the mutant MvaE polypeptides contain one or more conservative amino acid substitutions.

In one aspect, mvaE proteins that are not degraded or less prone to degradation can be used for the production of mevalonate, isoprene, isoprenoid precursors, and/or isoprenoids. Examples of gene products of mvaE genes that are not degraded or less prone to degradation which can be used include, but are not limited to, those from the organisms *E. faecium, E. gallinarum, E. casseliflavus, E. faecalis*, and *L. grayi*. One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (*J Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA are 1 mM acetyl-CoA, 10 mM $MgCl_2$, 50 mM Tris, pH 10.5 and the reaction is initiated by addition of enzyme. Assays can employ a final volume of 200 µL. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 µL. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Alternatively, production of mevalonate in cells (such as bacterial, fungal, or algal cells) can be measured by, without limitation, gas chromatography (see U.S. Patent Application Publication No.: US 2005/0287655 A1) or HPLC (See U.S. patent application Ser. No. 12/978,324). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaE nucleic acids include nucleic acids that encode a polypeptide, fragment of a polypeptide, peptide, or fusion polypeptide that has at least one activity of an MvaE polypeptide. Exemplary MvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi* DSM 20601, *Enterococcus faecium*, *Enterococcus gallinarum* EG2, *Enterococcus casseliflavus* and/or *Enterococcus faecalis*. The mvaE nucleic acid encoded by the *Listeria grayi* DSM 20601 mvaE gene can have at least about 99%, 98%, 97%, 96%, 95%, 95%, 93%, 92%, 91%, 90%, 89%, 88%, 87%, 86%, 85% sequence identity to SEQ ID NO:1. In another aspect, the mvaE nucleic acid encoded by the *Listeria grayi* DSM 20601 mvaE gene can have at least about 84%, 83%, 82%, 81%, or 80% sequence identity to SEQ ID NO:1. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:3. In another aspect, the mvaE nucleic acid encoded by the *Enterococcus faecium* mvaE gene can have at least about 84%, 83%, 82%, 81%, or 80% sequence identity to SEQ ID NO:3. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:5. In another aspect, the mvaE nucleic acid encoded by the *Enterococcus gallinarum* EG2 mvaE gene can have at least about 84%, 83%, 82%, 81%, or 80% sequence identity to SEQ ID NO:5. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:7. In another aspect, the mvaE nucleic acid encoded by the *Enterococcus casseliflavus* mvaE gene can have at least about 84%, 83%, 82%, 81%, or 80% sequence identity to SEQ ID NO:7. The mvaE nucleic acid encoded by the *Enterococcus faecalis* mvaE gene can have at least about 99%, 98%, 97%, 96%, 95%, 95%, 93%, 92%, 91%, 90%, 89%, 88%, 87%, 86%, or 85% sequence identity to SEQ ID NO:18. In any of the aspects herein, the upper MVA pathway polypeptides may be encoded by a nucleic acid with at least about 99%, 98%, 97%, 96%, 95%, 95%, 93%, 92%, 91%, 90%, 89%, 88%, 87%, 86%, 85%, 84%, 83%, 82%, 81%, or 80% sequence identity to any one of SEQ ID NOs:1-8 and 18-19. In any of the aspects herein, the upper MVA pathway polypeptides may be encoded by a nucleic acid with of any one of SEQ ID NOs: 1-8 and 18-19.

Exemplary MvaE polypeptides include fragments of a polypeptide, peptide, or fusion polypeptide that has at least one activity of an MvaE polypeptide. Exemplary MvaE polypeptides and include naturally-occurring polypeptides from any of the source organisms described herein as well as mutant polypeptides derived from any of the source organisms described herein. Exemplary MvaE polypeptides include, for example, MvaE polypeptides isolated from *Listeria grayi* DSM 20601, *Enterococcus faecium*, *Enterococcus gallinarum* EG2, and/or *Enterococcus casseliflavus*. The MvaE polypeptide encoded by the *Listeria grayi* DSM 20601 mvaE gene can have at least about 99%, 98%, 97%, 96%, 95%, 95%, 93%, 92%, 91%, 90%, 89%, 88%, 87%, 86%, 85% sequence identity to SEQ ID NO:11. In another aspect, the MvaE polypeptide encoded by the *Listeria grayi* DSM 20601 mvaE gene can have at least about 84%, 83%, 82%, 81%, or 80% sequence identity to SEQ ID NO:11. The MvaE polypeptide encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:13. In another aspect, the MvaE polypeptide encoded by the *Enterococcus faecium* mvaE gene can have at least about 84%, 83%, 82%, 81%, or 80% sequence identity to SEQ ID NO:13. The MvaE polypeptide encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:9. In another aspect, the MvaE polypeptide encoded by the *Enterococcus gallinarum* EG2 mvaE gene can have at least about 84%, 83%, 82%, 81%, or 80% sequence identity to SEQ ID NO:9. The MvaE polypeptide encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:15. In another aspect, the MvaE polypeptide encoded by the *Enterococcus casseliflavus* mvaE gene can have at least about 84%, 83%, 82%, 81%, or 80% sequence identity to SEQ ID NO:15. In any of the aspects herein, the upper MVA pathway polypeptides may be encoded by a polypeptide with at least about 99%, 98%, 97%, 96%, 95%, 95%, 93%, 92%, 91%, 90%, 89%, 88%, 87%, 86%, 85%, 84%, 83%, 82%, 81%, or 80% sequence identity to any one of SEQ ID NOs:9-16 and 20-21. In any of the aspects herein, the upper MVA pathway polypeptides may be encoded by a polypeptide with any one of SEQ ID NOs:9-16 and 20-21.

The mvaE nucleic acid can be expressed in a cell (such as a bacterial cell) on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

Exemplary MvaS Polypeptides and Nucleic Acids

The mvaS gene encodes a polypeptide that possesses HMG-CoA synthase activity. This polypeptide can convert acetoacetyl-CoA to 3-hydroxy-3-methylglutaryl-CoA (HMG-CoA). Exemplary MvaS polypeptides and nucleic acids include naturally-occurring polypeptides and nucleic acids from any of the source organisms described herein as well as mutant polypeptides and nucleic acids derived from any of the source organisms described herein that have at least one activity of a MvaS polypeptide.

Mutant MvaS polypeptides include those in which one or more amino acid residues have undergone an amino acid substitution while retaining MvaS polypeptide activity (i.e., the ability to convert acetoacetyl-CoA to 3-hydroxy-3-methylglutaryl-CoA). Amino acid substitutions in the MvaS polypeptide can be introduced to improve the functionality of the molecule. For example, amino acid substitutions that increase the binding affinity of the MvaS polypeptide for its substrate, or that improve its ability to convert acetoacetyl-CoA to 3-hydroxy-3-methylglutaryl-CoA can be introduced into the MvaS polypeptide. In some aspects, the mutant MvaS polypeptides contain one or more conservative amino acid substitutions.

Standard methods, such as those described in Quant et al. (*Biochem J.*, 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 mL assay system containing 50 mm-Tris/HCl, pH 8.0, 10 mM-MgCl$_2$ and 0.2 mM dithiothreitol at 30° C.; 5 mM-acetyl phosphate, 10,M-acetoacetyl-CoA and 5 ul samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl$_2$), is 12.2×10$^3$ M$^{-1}$ cm$^{-1}$. By definition, 1 unit of enzyme activity causes 1 µmol of acetoacetyl-CoA to be transformed per minute.

Alternatively, production of mevalonate in cells (such as bacterial, fungal, or algal cells) can be measured by, without limitation, gas chromatography (see U.S. Patent Application Publication No.: US 2005/0287655 A1) or HPLC (See U.S. patent application Ser. No. 12/978,324). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaS nucleic acids include nucleic acids that encode a polypeptide, fragment of a polypeptide, peptide, or fusion polypeptide that has at least one activity of an MvaS polypeptide. Exemplary MvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi* DSM 20601, *Enterococcus faecium*, *Enterococcus gallinarum* EG2, and/or *Enterococcus casseliflavus*. The mvaS nucleic acid encoded by the *Listeria grayi* DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:2. The mvaS nucleic acid encoded by the *Listeria grayi* DSM 20601 mvaS gene can also have at least about 84%, 83%, 82%, 81%, or 80% sequence identity to SEQ ID NO:2. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:4. The mvaS nucleic acid encoded by the *Enterococcus faecium* mvaS gene can have at least about 84%, 83%, 82%, 81%, or 80% sequence identity to SEQ ID NO:4. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:6. The mvaS nucleic acid encoded by the *Enterococcus gallinarum* EG2 mvaS gene can have at least about 84%, 83%, 82%, 81%, or 80% sequence identity to SEQ ID NO:6. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:8. The mvaS nucleic acid encoded by the *Enterococcus casseliflavus* mvaS gene can have at least about 84%, 83%, 82%, 81%, or 80% sequence identity to SEQ ID NO:8.

Exemplary MvaS polypeptides include fragments of a polypeptide, peptide, or fusion polypeptide that has at least one activity of an MvaS polypeptide. Exemplary MvaS polypeptides include naturally-occurring polypeptides and polypeptides from any of the source organisms described herein as well as mutant polypeptides derived from any of the source organisms described herein. Exemplary MvaS polypeptides include, for example, MvaS polypeptides isolated from *Listeria grayi* DSM 20601, *Enterococcus faecium*, *Enterococcus gallinarum* EG2, and/or *Enterococcus casseliflavus*. The MvaS polypeptide encoded by the *Listeria grayi* DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:12. The MvaS polypeptide encoded by the *Listeria grayi* DSM 20601 mvaS gene can also have at least about 84%, 83%, 82%, 81%, or 80% sequence identity to SEQ ID NO:12. The MvaS polypeptide encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:14. The MvaS polypeptide encoded by the *Enterococcus faecium* mvaS gene can have at least about 84%, 83%, 82%, 81%, or 80% sequence identity to SEQ ID NO:14. The MvaS polypeptide encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:10. The MvaS polypeptide encoded by the *Enterococcus gallinarum* EG2 mvaS gene can have at least about 84%, 83%, 82%, 81%, or 80% sequence identity to SEQ ID NO:10. The MvaS polypeptide encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:16. The MvaS polypeptide encoded by the *Enterococcus casseliflavus* mvaS gene can have at least about 84%, 83%, 82%, 81%, or 80% sequence identity to SEQ ID NO:16.

The mvaS nucleic acid can be expressed in a cell (such as a bacterial cell) on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Nucleic Acids Encoding Acetoacetyl-CoA Synthase Polypeptides

In one aspect, any of the cells (such as bacterial, fungal, or algal cells) described herein can contain one or more heterologous nucleic acid(s) encoding an acetoacetyl-CoA synthase polypeptide. The acetoacetyl-CoA synthase gene (also known as nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in Japanese Patent Publication (Kokai) No. 2008-61506 A and U.S. Patent Application Publication No. 2010/0285549, the disclosure of each of which are incorporated by reference herein. Acetoacetyl-CoA synthase can also be referred to as acetyl-CoA:malonyl CoA acyltransferase. A representative acetoacetyl-CoA synthase (or acetyl-CoA:malonyl CoA acyltransferase) that can be used is Genbank AB540131.1.

In one aspect, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl-CoA via decarboxylation of the malonyl CoA. Thus, stores of starting substrate are not limited by the starting amounts of acetyl-CoA. The synthesis of acetoacetyl-CoA by acetoacetyl-CoA synthase can still occur when the starting substrate is only malonyl-CoA. In one aspect, the pool of starting malonyl-CoA is increased by using host strains that have more malonyl-CoA. Such increased pools can be naturally occurring or be engineered by molecular manipulation. See, for example Fowler, et al., *Applied and Environmental Microbiology*, Vol. 75, No. 18, pp. 5831-5839 (2009).

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used.

An example of such an acetoacetyl-CoA synthase gene is the gene encoding a protein having the amino acid sequence of SEQ ID NO: 17. Such a protein having the amino acid sequence of SEQ ID NO: 17 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO: 17 can be obtained by a nucleic acid amplification method (e.g., PCR) with the use of genomic DNA obtained from an actinomycete of the *Streptomyces* sp. CL190 strain as a template and a pair of primers that can be designed with reference to Japanese Patent Publication (Kokai) No. 2008-61506 A.

As described herein, an acetoacetyl-CoA synthase gene for use in the present invention is not limited to a gene encoding a protein having the amino acid sequence of SEQ ID NO: 17 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO: 17 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO: 17, which is calculated by performing alignment of the amino acid sequence of SEQ ID NO: 17 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO: 17 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO: 17 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. 2×SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO: 17 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO: 17 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO: 17 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Recombinant Microorganisms Capable of Increased Production of Mevalonate

The recombinant microorganisms (e.g., recombinant bacterial, fungal, or algal cells) described herein have the ability to produce mevalonate at an amount and/or concentration greater than that of the same cells without any manipulation to the various genes or enzymatic pathways described herein. The recombinant microorganisms (e.g., bacterial cells) that have been engineered for modulation in the various pathways described herein to increase carbon flux to mevalonate can be used to produce mevalonate. In some aspects, the cells contain one or more nucleic acids encoding one or more acetylating proteins, wherein said cells have been engineered such that the expression of the nucleic acids and/or activity of the acetylating protein(s) is modulated. The acetylating proteins can be acetyltransferases (such as, but not limited to, YfiQ) and/or deacetylases (such as, but not limited to CobB). In some embodiments, the activity of the YfiQ polypeptide is modulated by decreasing, attenuating, or deleting the expression of the gene encoding the YfiQ polypeptide (such as, but not limited to, deletion of an endogenous yfiQ gene). In other embodiments, the activity of the CobB polypeptide is modulated by increasing the expression of the gene encoding the CobB protein (such as, but not limited to, increasing the expression of an endogenous cobB gene or heterologous expression of a nucleic acid encoding cobB). In other aspects, culturing the recombinant cells described herein in a suitable media results in improved production of mevalonate compared to a cell capable of producing mevalonate that does not comprise one or more acetylating proteins wherein said proteins are engineered such that their expression and/or activity is modulated. In other embodiments, improved production of mevalonate is characterized by one or more of an increase in mevalonate specific productivity, an increase in mevalonate titer, an increase in mevalonate yield, an increase in cell viability, and/or a decrease in acetate production.

In one aspect, the recombinant cells (such as bacterial, fungal, or algal cells) described herein which have been engineered such that the expression of the nucleic acids and/or activity of the acetylating protein(s) is modulated to have the ability to produce mevalonate at a concentration greater than that of the same cells which have not been engineered such that the expression of the nucleic acids and/or activity of the acetylating protein(s) is modulated. The cells (such as bacterial, fungal, or algal cells) can produce greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of mevalonate, inclusive, as well as any numerical value in between these numbers. In one exemplary embodiment, the cells can produce greater than about 85 mg/L/hr/OD of mevalonate.

The host cells (such as bacterial, fungal, or algal cells) described herein which have been engineered such that the expression of the nucleic acids and/or activity of the acetylating protein(s) is modulated to have the ability to produce higher peak titers of mevalonate in comparison to that of the same cells which have not been engineered such that the expression of the nucleic acids and/or activity of the acetylating protein(s) is modulated. In another aspect, the cells (such as bacterial, fungal, or algal cells) described herein produce mevalonate at a higher peak titer than that of the same cells that have not been modified to contain one or more acetylating proteins wherein said proteins are engineered such that their expression and/or activity is modulated when cultured in a suitable medium. The cells (such as bacterial, fungal, or algal cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers. In one exemplary embodiment, the cells produce greater than about 105 g/L peak titer of mevalonate after 48 hours of fermentation.

The host cells (such as bacterial, fungal, or algal cells) described herein which have been engineered such that the expression of the nucleic acids and/or activity of the acetylating protein(s) is modulated to have the ability to produce a higher cell productivity index (CPI) in comparison to that of the same cells which have not been engineered such that the expression of the nucleic acids and/or activity of the acetylating protein(s) is modulated. In some aspects, the cells (such as bacterial, fungal, or algal cells) described herein have a higher CPI than that of the same cells that have not been modified to contain one or more acetylating proteins wherein said proteins are engineered such that their expression and/or activity is modulated. In one aspect, the cells can be cultured in minimal medium. The cells (such as bacterial, fungal, or algal cells) can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In one exemplary embodiment, the cells have a CPI for mevalonate of at least about 4.5 (g/g).

The host cells (such as bacterial, fungal, or algal cells) described herein which have been engineered such that the expression of the nucleic acids and/or activity of the acetylating protein(s) is modulated to have the ability to produce higher mass yield of mevalonate in comparison to that of the same cells which have not been engineered such that the expression of the nucleic acids and/or activity of the acetylating protein(s) is modulated. In some aspects, the cells (such as bacterial, fungal, or algal cells) described herein have a higher mass yield of mevalonate from glucose than that of the same cells that have not been modified to contain one or more acetylating proteins wherein said proteins are engineered such that their expression and/or activity is modulated. In one aspect, the cells can be cultured in minimal medium. The cells (such as bacterial, fungal, or algal cells) can produce a mass yield of mevalonate from glucose of at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 55%, inclusive, as well as any numerical value in between these numbers. In one exemplary embodiment, the cells produce a mass yield of mevalonate from glucose of at least about 38%.

Methods of Using Recombinant Cells to Produce High Amounts of Mevalonate

Also provided herein are methods for the production of mevalonate. In some aspects, the method for producing mevalonate comprises: (a) culturing a composition comprising recombinant cells (such as bacterial, fungal, or algal cells) which have been modified to comprise one or more acetylating proteins wherein said proteins are engineered such that their expression and/or activity is modulated as described herein (including any of the cells, such as the bacterial cells described above), or progeny thereof, capable of producing mevalonate; and (b) producing mevalonate. In some aspects, the method of producing mevalonate comprises the steps of culturing any of the recombinant cells described herein under conditions suitable for the production of mevalonate and allowing the recombinant cells to produce mevalonate. In some aspects, the method of producing mevalonate further comprises a step of recovering the mevalonate.

The method of producing mevalonate can also comprise the steps of: (a) culturing cells heterologously expressing one or more acetylating proteins wherein said proteins are engineered such that their expression and/or activity is modulated; and (b) producing mevalonate. Additionally, the cells can produce mevalonate in concentrations greater than that of the same cells lacking one or more acetylating proteins wherein said proteins are not engineered such that their expression and/or activity is modulated.

Mevalonate can be produced in amounts greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of mevalonate, inclusive, as well as any numerical value in between these numbers. In some aspects, the method of producing mevalonate further comprises a step of recovering the mevalonate. In one exemplary embodiment, the instant methods for the production of mevalonate can produce greater than about 85 mg/L/hr/OD of mevalonate.

The method of producing mevalonate can similarly comprise the steps of: (a) culturing cells which have been engineered for increased carbon flux to mevalonate as described herein, wherein the cells heterologously express one or more acetylating proteins wherein said proteins are engineered such that their expression and/or activity is modulated.; and (b) producing mevalonate, wherein the cells produce mevalonate with a higher peak titer after hours of fermentation than that of the same cells lacking one or more acetylating proteins wherein said proteins are engineered such that their expression and/or activity is modulated.

The cells provided herein (such as bacterial, fungal, or algal cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, or 200 g/L peak titer of mevalonate after 48 hours of fermentation, inclusive, as well as any numerical value in between these numbers. In some aspects, the method of producing mevalonate further comprises a step of recovering the mevalonate. In one exemplary embodiment, the instant methods for the production of mevalonate can produce greater than about 105 g/L peak titer of mevalonate after 48 hours of fermentation.

The method of producing mevalonate can similarly comprise the steps of: (a) culturing cells which have been engineered for increased carbon flux to mevalonate as described herein, wherein the cells comprise one or more acetylating proteins wherein said proteins are engineered such that their expression and/or activity is modulated; and (b) producing mevalonate, wherein the cells have a CPI for mevalonate higher than that of the same cells lacking one or more copies of an upper MVA pathway gene encoding one or more upper MVA pathway polypeptides, and which have not been engineered for increased carbon flux to mevalonate production. In one exemplary embodiment, the instant methods for the production of mevalonate can produce mevalonate using cells with a CPI for mevalonate of at least 4.5 (g/g). Alternatively, the cells (such as bacterial, fungal, or algal cells) can have a CPI of at least 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing mevalonate further comprises a step of recovering the mevalonate.

Provided herein are methods of using any of the cells described above for enhanced mevalonate production. The production of mevalonate by the cells can be enhanced by the expression of one or more acetylating proteins wherein said proteins are engineered such that their expression and/or activity is modulated. The production of mevalonate can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate by cells without the expression of one or more acetylating proteins wherein said proteins are engineered such that their expression and/or activity is modulated.

Recombinant Cells Capable of Production of Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of mevalonate in cells (such as bacterial, fungal, or algal cells) by any of the compositions and methods described above will similarly result in the production of higher amounts of isoprene. Increasing the molar yield of mevalonate production from glucose translates into higher molar yields of isoprenoid precursors and isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production.

Production of isoprene can be made by using any of the recombinant host cells described here where one or more of the enzymatic pathways have been manipulated such that enzyme activity is modulated to increase carbon flow towards isoprene production. The recombinant microorganisms described herein that have various enzymatic pathways manipulated for increased carbon flow to mevalonate production can be used to produce isoprene. Any of the recombinant host cells expressing one or more acetylating proteins (wherein said proteins are engineered such that their expression and/or activity is modulated) capable of increased production of mevalonate described above can also be capable of increased production of isoprene. In some aspects, these cells further comprise one or more heterologous nucleic acids encoding polypeptides of the entire MVA pathway and a heterologous nucleic acid encoding an isoprene synthase polypeptide or a polypeptide having isoprene synthase activity. In other aspects, these cells further comprise one or more heterologous nucleic acids encoding a phosphoketolase polypeptide.

Nucleic Acids Encoding Polypeptides of the Lower MVA Pathway

In some aspects of the invention, the cells described in any of the cells or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase polypeptide, *Lactobacillus* mevalonate kinase polypeptide, *M. burtonii* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. In other aspects, the lower MVK polypeptide can be from *M. burtonii*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, *M. burtonii* mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Nucleic Acids Encoding Isoprene Synthase Polypeptides

In some aspects of the invention, the cells described in any of the compositions or methods described herein (including host cells that have been engineered for increased carbon flux as described herein) further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide or a polypeptide having isoprene synthase activity is operably linked to a constitutive promoter. In some aspects, the endogenous nucleic acid encoding an isoprene synthase polypeptide or a polypeptide having isoprene synthase activity is operably linked to an inducible promoter. In some aspects, the endogenous nucleic acid encoding an isoprene synthase polypeptide or a polypeptide having isoprene synthase activity is operably linked to a strong promoter. In a particular aspect, the cells are engineered to over-express the endogenous isoprene synthase pathway polypeptide relative to wild-type cells. In some aspects, the endogenous nucleic acid encoding an isoprene synthase polypeptide or a polypeptide having isoprene synthase activity is operably linked to a weak promoter. In some aspects, the isoprene synthase polypeptide or a polypeptide having isoprene synthase activity is a polypeptide from *Pueraria* or *Populus* or a hybrid such as *Populus alba×Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/mL) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 mL Headspace vial with a metal screw cap and teflon coated silicon septum (Agilent Technologies) and cultured at 37° C. for 15 minutes with shaking. The reaction can be quenched by adding 200 µL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba×Populus tremula*, or a variant thereof.

In some aspects, the isoprene synthase polypeptide, the polypeptide having isoprene synthase activity or the corresponding nucleic acid is from the family Fabaceae, such as the Faboideae subfamily. In some aspects, the isoprene synthase polypeptide, the polypeptide having isoprene synthase activity or the corresponding nucleic acid is from *Pueraria montana* (kudzu) (Sharkey et al., *Plant Physiology* 137: 700-712, 2005), *Pueraria lobata*, poplar (such as *Populus alba, Populus nigra, Populus trichocarpa,* or *Populus alba×tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide, the polypeptide having isoprene synthase activity or the corresponding nucleic acid is from *Pueraria montana, Pueraria lobata, Populus tremuloides, Populus alba, Populus nigra,* or *Populus trichocarpa* or a variant thereof. In some aspects, the isoprene synthase polypeptide, the polypeptide having isoprene synthase activity or the corresponding nucleic acid is from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, or at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed). In other aspects, the variant of isoprene synthase from *Populus alba* has at least one amino acid substitution, at least one amino acid insertion, and/or at least one amino acid deletion at the amino acid residue shown in Table 2. In another aspect, the variant of isoprene synthase comprises at least one amino acid substitution, at least one amino acid deletion, or at least one amino acid insertion at any of the amino acid residues shown in Table 2, wherein the amino acid residue numbering corresponds to the amino acid residue number of MEA *P. alba* isoprene synthase (SEQ ID NO:24). In one aspect, the *P. alba* isoprene synthase is a truncated isoprene synthase, for example, MEA isoprene synthase which is 16 amino acids shorter than full-length isoprene synthase.

TABLE 2

Isoprene Synthase Variants of *P. Alba* (MEA)

| | | | | |
|---|---|---|---|---|
| A118E | E472R | S510C | D323Y | W392S |
| S22K | K463F | S510V | D323D | W392T |
| S21R | K463T | I342I | G99D | W392V |
| S22K | R71K | K348F | K161K | A118P |
| S22R | R71L | K348Y | W392A | A118Q |
| E58L | R71M | K348K | W392C | A118A |
| T481T | R71V | C437L | W392F | E41M |
| T481Y | R71R | T240C | S288Y | G111S |
| T502F | K393L | M460M | M228Y | S74Q |
| T381L | F542L | R461A | A3T | S74S |
| T381M | P538K | H424P | W392Y | K36D |
| T381Y | P538R | H424H | W392W | S282H |
| T383H | P538P | A448L | F89D | S282I |
| T383L | A503A | A448Q | F89E | S282W |
| E480I | L436I | A448V | F89F | S282Y |
| E480R | L436Y | G389D | E41Y | S282S |
| K393V | L436F | S444E | E41E | K36S |
| K393I | E488L | S444S | R43E | K36T |
| E415H | E488M | H511Y | R43L | K36W |
| E415V | E488T | H511H | K36E | K36Y |
| E415Y | E488W | R071I | K36H | K36K |
| R71H | E488E | R071K | K36N | |
| R71I | I342Y | R071L | K36P | |
| E58Y | C437M | K374Y | K36Q | |

TABLE 2-continued

Isoprene Synthase Variants of *P. Alba* (MEA)

| | | | |
|---|---|---|---|
| E135G | C437W | K374K | A453I |
| A363L | C437Y | L526E | A453V |
| K374Y | C437C | L526Q | A453A |
| T381I | M460A | L526L | V409I |
| L436L | I447T | R242G | V409T |
| H254R | I447V | R242R | K161C |
| H254C | I447Y | A443G | K161E |
| E488C | S444D | A443Q | K161N |
| E488F | G389E | A443R | K161Q |
| T383Y | L376I | A443S | G99E |
| K414I | L376M | S13S | G99G |
| K414R | L376L | V268I | S288A |
| K414S | I504F | V268V | S288C |
| K414W | I504I | K161A | S288T |
| E472C | E467H | V409V | W392I |
| E472L | E467W | D323F | W392M |

In one embodiment, the MEA *P. alba* isoprene synthase is truncated so that it is 16 amino acids shorter than full length *P. alba* isoprene synthase.

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, WO2010/148256, and WO 2013/166320.

Nucleic Acids Encoding DXP Pathway Polypeptides

In some aspects of the invention, the cells described in any of the compositions or methods described herein (including host cells that have been engineered for increased carbon flux as described herein) further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2, 4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2, 4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

Source Organisms for MVA Pathway, Isoprene Synthase, IDI, and DXP Pathway Polypeptides Isoprene synthase, IDI, DXP pathway, and/or MVA pathway nucleic acids (and their encoded polypeptides) can be obtained from any organism that naturally contains isoprene synthase, IDI, DXP pathway, and/or MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

Recombinant Cells Capable of Increased Production of Isoprene

The recombinant cells described herein that have been engineered for increased carbon flux to isoprene have the ability to produce isoprene at a concentration greater than that of the same cells that have not been engineered for increased carbon flux to isoprene. In one aspect, the recombinant cells (such as bacterial, fungal, or algal cells) described herein comprising one or more acetylating proteins, wherein said proteins are engineered such that their expression and/or activity is modulated, have the ability to produce isoprene at a concentration greater than that of the same cells lacking one or more acetylating proteins, wherein said proteins are engineered such that their expression and/or activity is modulated. The acetylating proteins can be acetyltransferases (such as, but not limited to, YfiQ) and/or deacetylases (such as, but not limited to CobB). In some embodiments, the activity of the YfiQ polypeptide is modulated by decreasing, attenuating, or deleting the expression of the gene encoding the YfiQ polypeptide (such as, but not limited to, deletion of an endogenous yfiQ gene). In other embodiments, the activity of the CobB polypeptide is modulated by increasing the expression of the gene encoding the CobB protein (such as, but not limited to, increasing the expression of an endogenous cobB gene or heterologous expression of a nucleic acid encoding cobB). In other embodiments, culturing these cells in a suitable media provides for improved production of isoprene compared to a cell producing isoprene that does not comprise one or more acetylating proteins wherein said proteins are engineered such that their expression and/or activity is modulated. In some aspects, the cells further comprise one or more heterologous nucleic acids encoding an isoprene synthase polypeptide. In certain aspects, these cells can further comprise one or more copies of a heterologous nucleic acid encoding polypeptides of the entire MVA pathway, one or more heterologous nucleic acids encoding a phosphoketolase polypeptide, and/or one or more heterologous nucleic acids encoding an isoprene synthase polypeptide. The one or more heterologous nucleic acids can be integrated into the host cell's chromosome, in any aspect of the cells disclosed herein. In other aspects, improved production of isoprene is characterized by one or more of an increase in isoprene specific productivity, an increase in isoprene titer, an increase in isoprene yield, an increase in cell viability, and/or a decrease in acetate production.

In one exemplary embodiment, the cells disclosed herein can produce at least 5% greater amounts of isoprene compared to isoprene-producing cells that have not been engineered to increase carbon flux to isoprene. In other aspects, the cells (such as bacterial, fungal, or algal cells) can produce at least 5% greater amounts of isoprene compared to isoprene-producing cells (such as bacterial, fungal, or algal cells) that do not comprise one or more acetylating proteins wherein said proteins are engineered such that their expression and/or activity is modulated. Alternatively, the cells (such as bacterial, fungal, or algal cells) can produce greater than about 1%, 2%, 3%, 4%, 5%, 6%, 7%, 8%, 9%, 10%, 11%, 12%, 13%, 14%, or 15% of isoprene, inclusive, as well as any numerical value in between these numbers.

In one aspect of the invention, there are provided cells that have been engineered for increased carbon flux to isoprene wherein the cells comprise one or more acetylating proteins, wherein said proteins are engineered such that their expression and/or activity is modulated, one or more heterologous nucleic acids encoding polypeptides of the entire MVA pathway, one or more heterologous nucleic acids encoding a phosphoketolase polypeptide, and one or more heterologous nucleic acids encoding an isoprene synthase polypeptide. In some aspects, the cells can further comprise one or more heterologous nucleic acids encoding a DXP pathway polypeptide(s). The cells can further comprise one or more heterologous nucleic acids encoding an IDI polypeptide. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids can be integrated into a genome of the host cells or can be stably expressed in the cells. The one or more heterologous nucleic acids can additionally be on a vector.

The production of isoprene by cells that have been engineered for increased carbon flux to isoprene according to any of the compositions or methods described herein can be enhanced (e.g., enhanced by the expression of one or more acetylating proteins, wherein said proteins are engineered such that their expression and/or activity is modulated). In other aspects, the production of isoprene by the cells according to any of the compositions or methods described herein can be enhanced/increased/improved (e.g., enhanced by the expression of one or more acetylating proteins, wherein said proteins are engineered such that their expression and/or activity is modulated, one or more heterologous nucleic acids encoding an isoprene synthase polypeptide, polypeptides of the entire MVA pathway, a DXP pathway polypeptide(s), and/or an IDI polypeptide). As used herein, "enhanced"/"improved"/"increased" isoprene production refers to an increased cell productivity index (CPI) for isoprene, an increased titer of isoprene, an increased mass yield of isoprene, increase in the cumulative isoprene yield, an increase in late fermentation isoprene production, an increase in cell viability, a decrease in acetate production, and/or an increased specific productivity of isoprene by the cells described by any of the compositions and methods described herein compared to cells which do not express one or more acetylating proteins, wherein said proteins are engineered such that their expression and/or activity is modulated, and which have not been engineered for increased carbon flux to isoprene production. The production of isoprene can be enhanced by about 5% to about 1,000,000 folds. The production of isoprene can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by cells that do not express one or more acetylating proteins, wherein said proteins are engineered such that their expression and/or activity is modulated.

The production of isoprene can also be enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds.

Methods of Using the Recombinant Cells to Produce Isoprene

Also provided herein are methods of producing isoprene comprising culturing any of the recombinant microorganisms that have been engineered for increased carbon flux to isoprene as described herein. In one aspect, isoprene can be produced by culturing recombinant cells (such as bacterial, fungal, or algal cells) comprising one or more nucleic acids encoding one or more acetylating proteins, wherein said cells have been engineered such that the expression of the nucleic acids and/or activity of the acetylating protein(s) is modulated, one or more heterologous nucleic acids encoding polypeptides of the entire MVA pathway, and an isoprene synthase polypeptide. In certain embodiments, the recombinant cells can further comprise one or more nucleic acids encoding a phosphoketolase polypeptide. The isoprene can be produced from any of the cells described herein and according to any of the methods described herein. Any of the cells can be used for the purpose of producing isoprene from carbohydrates, such as, but not limited to, glucose or from other carbon sources, such as, but not limited to, acetate.

Thus, also provided herein are methods of producing isoprene comprising (a) culturing cells which comprise one or more acetylating proteins wherein the cells have been engineered such that the expression and/or activity of the acetylating proteins is modulated; and (b) producing isoprene. In other aspects, provided herein are methods of producing isoprene comprising (a) culturing cells (such as bacterial, fungal, or algal cells) comprising one or more acetylating proteins, wherein said proteins are engineered such that their activity is modulated, in a suitable media for producing isoprene and (b) producing isoprene. The cells can comprise one or more nucleic acid molecules encoding polypeptides of the entire MVA pathway as described above, one or more nucleic acid molecules encoding a phosphoketolase polypeptide, and any of the isoprene synthase polypeptide(s) described above. In some aspects, the cells (such as bacterial, fungal, or algal cells) can be any of the cells described herein. Any of the isoprene synthases or variants thereof described herein, any of the microorganism (e.g., bacterial) or plant strains described herein, any of the promoters described herein, and/or any of the vectors described herein can also be used to produce isoprene using any of the energy sources (e.g. glucose or any other six carbon sugar) described herein. In some aspects, the method of producing isoprene further comprises a step of recovering the isoprene.

In some aspects, the amount of isoprene produced is measured at the peak absolute productivity time point. In some aspects, the peak absolute productivity for the cells is about any of the amounts of isoprene disclosed herein. In some aspects, the amount of isoprene produced is measured at the peak specific productivity time point. In some aspects, the peak specific productivity for the cells is about any of the amounts of isoprene per cell disclosed herein. In some aspects, the cumulative, total amount of isoprene produced is measured. In some aspects, the cumulative total productivity for the cells is about any of the amounts of isoprene disclosed herein.

In some aspects, any of the cells described herein that have been engineered such that the expression and/or activity of the acetylating proteins are modulated (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells that have been engineered such that the expression and/or activity of the acetylating proteins are modulated produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells that have been engineered such that the expression and/or activity of the acetylating proteins are modulated produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the cells that have been engineered such that the expression and/or activity of the acetylating proteins are modulated comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

The production of isoprene by recombinant cells described herein which have been engineered such that the expression and/or activity of the acetylating proteins in these cells is modulated can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the cells that express wild type levels of one or more acetylating proteins, one or more heterologous nucleic acids encoding an isoprene synthase polypeptide, one or more heterologous nucleic acids encoding polypeptide of the entire MVA pathway, a DXP pathway polypeptide(s), and/or an IDI polypeptide and which have not been engineered for increased carbon flux to isoprene production.

The production of isoprene can also be enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprene by naturally-occurring cells or by cells that do not express one or more acetylating proteins, wherein said proteins are engineered such that their activity is modulated, one or more heterologous nucleic acids encoding an isoprene synthase polypeptide, one or more heterologous nucleic acids encoding polypeptide of the entire MVA pathway, a DXP pathway polypeptide(s), and/or an IDI polypeptide and which have not been engineered for increased carbon flux to isoprene production.

Recombinant Cells Capable of Production of Isoprenoid Precursors and/or Isoprenoids Isoprenoids can be produced in many organisms from the synthesis of the isoprenoid precursor molecules which are the end products of the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., Plant Physiol. 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate ($C_{10}$-GPP), farnesyl pyrophosphate ($C_{15}$-FPP), geranylgeranyl pyrophosphate ($C_{20}$-GGPP)) with corresponding number of isopentenyl pyrophosphates ($C_{15}$-FPP) (Hsieh et al., Plant Physiol. 2011 March; 155(3):1079-90). Examples of polyprenyl pyrophosphate synthases include, but are not limited to, farnesyl pyrophosphate (FPP) synthase (e.g. farnesene synthase codon-optimized for E. coli (SEQ ID NO:26) or amorphadiene synthase codon-optimized for E. coli (SEQ ID NO:25)); geranyl pyrophosphate synthase; or geranylgeranyl pyrophosphate synthase.

Production of isoprenoid precursors and/or isoprenoids can be made by using any of the recombinant host cells described here where one or more of the enzymatic pathways have been manipulated such that enzyme activity is modulated to increase carbon flow towards isoprenoid production. In addition, these cells can express one or more nucleic acids encoding one or more acetylating proteins, wherein said cells have been engineered such that the expression of the nucleic acids and/or activity of the acetylating protein(s) is modulated, one or more heterologous nucleic acids encoding polypeptides of the entire MVA pathway, and/or one or more heterologous nucleic acids encoding a phosphoketolase polypeptide, and/or one or more heterologous nucleic acids encoding an isoprene synthase polypeptide. In some aspects, these cells further comprise one or more heterologous nucleic acids encoding IDI and/or the DXP pathway polypeptides, as described above, and/or a heterologous nucleic acid encoding a polyprenyl pyrophosphate synthase polypeptide. Without being bound to theory, it is thought that increasing the cellular production of acetyl-CoA or mevalonate in cells by any of the compositions and methods described above will similarly result in the production of higher amounts of isoprenoid precursor molecules and/or isoprenoids. Increasing the molar yield of acetyl-CoA and/or mevalonate production from glucose translates into higher molar yields of isoprenoid precursor molecules and/or isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production.

Types of Isoprenoids

The cells of the present invention that have been engineered for increased carbon flux to mevalonate are capable of increased production of isoprenoids and the isoprenoid precursor molecules DMAPP and IPP. Examples of isoprenoids include, without limitation, hemiterpenes, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

Heterologous Nucleic Acids Encoding Polyprenyl Pyrophosphate Synthases Polypeptides In some aspects of the invention, the cells that have been engineered for increased carbon flux to isoprenoids described in any of the compositions or methods herein further comprise one or more nucleic acids encoding a lower mevalonate (MVA) pathway polypeptide(s), as described above, as well as one or more nucleic acids encoding a polyprenyl pyrophosphate synthase polypeptide(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to over-express the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells that have been engineered for increased carbon flux to isoprenoids described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in E. coli (e.g. SEQ ID NO:23). The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3):1079-90; Danner et al., *Phytochemistry.* 2011 Apr. 12 [Epub ahead of print]; Jones et al., *J Biol Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köllner & Boland, *J Org Chem.* 2010 Aug. 20; 75(16):5590-600.

Recombinant Cells Capable of Increased Production of Isoprenoid Precursors and/or Isoprenoids The recombinant microorganisms (e.g., recombinant bacterial, fungal, or algal cells) described herein have the ability to produce isoprenoid precursors and/or isoprenoids at an amount and/or concentration greater than that of the same cells without any manipulation to the various enzymatic pathways described herein. In addition, the cells described herein have the ability to produce isoprenoid precursors and/or isoprenoids at an amount and/or concentration greater than that of the same cells that have not been engineered for increased carbon flux to isoprenoids and which lack one or more nucleic acids encoding one or more acetylating proteins, wherein the cells have been engineered such that the expression of the nucleic acids and/or activity of the acetylating protein(s) is modulated, and one or more heterologous nucleic acids encoding a polyprenyl pyrophosphate synthase polypeptide. The acetylating proteins can be acetyltransferases (such as, but not limited to, YfiQ) and/or deacetylases (such as, but not limited to CobB). In some embodiments, the activity of the YfiQ polypeptide is modulated by decreasing, attenuating, or deleting the expression of the gene encoding the YfiQ polypeptide (such as, but not limited to, deletion of an endogenous yfiQ gene). In other embodiments, the activity of the CobB polypeptide is modulated by increasing the activity of the CobB protein (such as, but not limited to, increasing the expression of an endogenous cobB gene or heterologous expression of a nucleic acid encoding cobB). In other embodiments, culturing these cells in a suitable media provides for improved production of isoprenoid precursors and/or isoprenoids compared to a cell producing isoprenoid precursors and/or isoprenoids that does not comprise one or more acetylating proteins, wherein said proteins are engineered such that their activity is modulated. In certain aspects, these cells can further comprise one or more copies of a heterologous nucleic acid encoding polypeptides of the entire MVA pathway and/or one or more heterologous nucleic acids encoding a phosphoketolase polypeptide. The one or more heterologous nucleic acids can be integrated into the host cell's chromosome, in any aspect of the cells disclosed herein. In other aspects, improved production of isoprenoid precursors and/or isoprenoid is characterized by one or more of an increase in isoprenoid precursor and/or isoprenoid specific productivity, an increase in isoprenoid precursor and/or isoprenoid titer, an increase in isoprenoid precursor and/or isoprenoid yield, an increase in cell viability, and/or a decrease in acetate production.

In one aspect of the invention, there are provided cells that have been engineered for increased carbon flux to isoprenoids and/or isoprenoid precursors comprising one or more nucleic acids encoding one or more acetylating proteins, wherein said cells have been engineered such that the expression of the nucleic acids and/or activity of the acetylating protein(s) is modulated, one or more heterologous nucleic acids encoding polypeptides of the entire MVA pathway, and/or one or more heterologous nucleic acids encoding a phosphoketolase polypeptide, and/or one or more heterologous nucleic acids encoding a DXP pathway polypeptide(s), and/or one or more heterologous nucleic acids encoding polyprenyl pyrophosphate synthase. The cells can further comprise one or more heterologous nucleic acids encoding an IDI polypeptide. Additionally, the polyprenyl pyrophosphate synthase polypeptide can be an FPP synthase polypeptide. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids encoding one or more acetylating proteins, wherein said proteins are engineered such that their activity is modulated, one or more heterologous nucleic acids encoding polypeptides of the entire MVA pathway, one or more heterologous nucleic acids encoding a phosphoketolase polypeptide, one or more heterologous nucleic acids encoding a DXP pathway polypeptide(s), and/or one or more heterologous nucleic acids encoding polyprenyl pyrophosphate synthase can be integrated into a genome of the host cells or can be stably expressed in the cells. The one or more heterologous nucleic acids can additionally be on a vector.

Provided herein are methods of using any of the cells that have been engineered for increased carbon flux to isoprenoids and/or isoprenoid precursor described above for enhanced, improved, or increased isoprenoid precursor and/or isoprenoid production. As used herein, "enhanced"/"improved"/"increased" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, an increase in isoprenoid precursor and/or isoprenoid specific productivity, an increase in cell viability, and/or a decrease in acetate production by the cells described by any of the compositions and methods described herein compared to cells which do not comprise one or more nucleic acids encoding one or more acetylating proteins, wherein said cells have been engineered such that the expression of the nucleic acids and/or activity of the acetylating protein(s) is modulated. The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid and/or isoprenoid precursors by cells without the expression of one or more acetylating proteins, wherein said proteins are engineered such that their activity is modulated.

The production of isoprenoid precursors and/or isoprenoids can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursors and/or isoprenoids by naturally-occurring cells or by cells without the expression of one or more acetylating proteins, wherein said proteins are engineered such that their activity is modulated and which have not been engineered for increased carbon flux to isoprenoids and/or isoprenoid precursor production.

Methods of Using the Recombinant Cells to Produce Isoprenoids and/or Isoprenoid Precursor Molecules Also provided herein are methods of producing isoprenoid precursor molecules and/or isoprenoids comprising culturing recombinant microorganisms (e.g., recombinant bacterial, fungal, or algal cells) that have been engineered in various enzymatic pathways described herein and/or comprising one or more nucleic acids encoding one or more acetylating proteins, wherein said cells have been engineered such that the expression of the nucleic acids and/or activity of the acetylating protein(s) is modulated, one or more heterologous nucleic acids encoding polypeptides of the entire MVA pathway, and a polyprenyl pyrophosphate synthase polypeptide. In certain embodiments, the recombinant cells further comprise one or more nucleic acids encoding a phosphoketolase polypeptide. The isoprenoid precursor molecules and/or isoprenoids can be produced from any of the cells described herein and according to any of the methods described herein. Any of the cells can be used for the purpose of producing isoprenoid precursor molecules and/or isoprenoids from carbohydrates, such as, but not limited to, glucose or from other carbon sources, such as, but not limited to, acetate.

Thus, provided herein are methods of making isoprenoid precursor molecules and/or isoprenoids comprising (a) culturing cells that have been engineered for increased carbon flux to isoprenoids and/or isoprenoid precursors; and (b)

producing isoprenoid precursor molecules and/or isoprenoids. In other aspects, provided herein are methods of making isoprenoid precursor molecules and/or isoprenoids comprising (a) culturing cells (such as bacterial, fungal, or algal cells) comprising one or more nucleic acids encoding one or more acetylating proteins, wherein said cells have been engineered such that the expression of the nucleic acids and/or activity of the acetylating protein(s) is modulated, in a suitable media for producing isoprene and (b) producing isoprenoid precursor molecules and/or isoprenoids. The cells can further comprise one or more nucleic acid molecules encoding polypeptides of the entire MVA pathway as described above and/or one or more nucleic acid molecules encoding a phosphoketolase polypeptide. In some aspects, the cells (such as bacterial, fungal, or algal cells) can be any of the cells described herein. In some aspects, the method of producing isoprenoid precursor molecules and/or isoprenoids further comprises a step of recovering the isoprenoid precursor molecules and/or isoprenoids.

In one exemplary embodiment, the instant methods for the production of isoprenoid precursor molecules and/or isoprenoids can produce at least 5% greater amounts of isoprenoid precursors and/or isoprenoids when compared to isoprenoids and/or isoprenoid precursor-producing cells that have not been engineered for increased carbon flux to isoprenoids and/or isoprenoid precursors and that do not comprise one or more nucleic acids encoding one or more acetylating proteins, wherein said cells have been engineered such that the expression of the nucleic acids and/or activity of the acetylating protein(s) is modulated. In other aspects, provided herein are methods for the production of isoprenoid precursor molecules and/or isoprenoids that in one exemplary embodiment can produce at least 5% greater amounts of isoprenoid precursors and/or isoprenoids when compared to isoprenoids and/or isoprenoid precursor-producing cells (such as bacterial, fungal, or algal cells) that do not comprise one or more nucleic acids encoding one or more acetylating proteins, wherein said cells have been engineered such that the expression of the nucleic acids and/or activity of the acetylating protein(s) is modulated, and which have not been engineered for increased carbon flux to isoprenoids and/or isoprenoid precursor production. Alternatively, the cells (such as bacterial, fungal, or algal cells) can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive. In some aspects, the method of producing isoprenoid precursor molecules and/or isoprenoids further comprises a step of recovering the isoprenoid precursor molecules and/or isoprenoids.

Provided herein are methods of using any of the cells that have been engineered for increased carbon flux to isoprenoids and/or isoprenoid precursors described above for enhanced isoprenoid and/or isoprenoid precursor molecule production. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, an increased specific productivity of isoprenoid precursors and/or isoprenoids, increased cumulative yield isoprenoid precursors and/or isoprenoids, an increase in late fermentation of isoprenoid precursors and/or isoprenoids, and increase in cell viability, and/or a decrease in acetate production by the cells described by any of the compositions and methods described herein compared to cells which do not comprise one or more nucleic acids encoding one or more acetylating proteins, wherein said cells have been engineered such that the expression of the nucleic acids and/or activity of the acetylating protein(s) is modulated. The production of isoprenoid precursor molecules and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursor molecules and/or isoprenoids by cells that do not comprise one or more nucleic acids encoding one or more acetylating proteins, wherein said cells have been engineered such that the expression of the nucleic acids and/or activity of the acetylating protein(s) is modulated. In one exemplary embodiment, the production of isoprenoid precursor molecules and/or isoprenoids can be enhanced by about 5% to about 1,000,000 folds.

The production of isoprenoid precursor molecules and/or isoprenoids can also be enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursor molecules and/or isoprenoids by cells that do not comprise one or more nucleic acids encoding one or more acetylating proteins, wherein said cells have been engineered such that the expression of the nucleic acids and/or activity of the acetylating protein(s) is modulated.

Modulation of Additional Enzymatic Pathways for the Improved Production of Mevalonate, Isoprene, Isoprenoids, Isoprenoid Precursors, and Acetyl-CoA-Derived Products In some aspects of the invention, the recombinant cells described in any of the compositions or methods described herein further comprise one or more nucleic acids encoding one or more proteins, where the cells have been modified such that the expression of the nucleic acids and/or activity of the proteins is modulated. Such further modulation of additional genes involved in the utilization of carbon during cellular metabolism or that are implicated with respect to the available intracellular supply of acetyl-CoA may also be modulated to improve production of mevalonate, isoprene, isoprenoid precursors, and/or isoprenoids. These include, but are not limited to the modulations of pathways involving phosphofructokinase, modulations of pathways involving phosphoketolase, modulations of the pentose phosphate pathway enzymes, modulations of enzymes involved in acetate production, acetate cycling, and acetyl-CoA production, modulations of pathways involving the Entner-Doudoroff pathway, modulations of pathways Involving the Oxidative Branch of the Pentose Phosphate Pathway, and the like.

Nucleic Acids Encoding Phosphoketolase Polypeptides

In some aspects of the invention, the recombinant cells described in any of the compositions or methods described herein can further comprise one or more nucleic acids encoding a phosphoketolase polypeptide or a polypeptide having phosphoketolase activity. In some aspects, the phosphoketolase polypeptide is a heterologous polypeptide. In some aspects, the heterologous nucleic acid encoding a phosphoketolase polypeptide is operably linked to a constitutive promoter. In some aspects, the heterologous nucleic acid encoding a phosphoketolase polypeptide is operably linked to an inducible promoter. In some aspects, the heterologous nucleic acid encoding a phosphoketolase polypeptide is operably linked to a strong promoter. In some aspects, more than one heterologous nucleic acid encoding a phosphoketolase polypeptide is used (e.g., 2, 3, 4, or more copies of a heterologous nucleic acid encoding a phosphoketolase polypeptide). In some aspects, the heterologous nucleic acid encoding a phosphoketolase polypeptide is operably linked to a weak promoter. In a particular aspect, the cells are engineered to overexpress the endogenous phosphoketolase polypeptide relative to wild-type cells.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., *J. Bact.* 183:2929-2936, 2001). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri, Bifidobacterium longum, Ferrimonas balearica, Pedobactor saltans, Streptomyces griseus, Mycoplasma hominis,* and/or *Nocardiopsis dassonvillei.* Additional examples of phosphoketolase enzymes which can be used herein are described in U.S. Pat. No. 7,785,858, which is incorporated by reference herein.

Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. *Biochem. J.* 98:795-803).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. *J. Bact.* 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or a 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene, isoprenoid precursor molecules, isoprenoids, and/or acetyl-CoA derived products.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. 1995. *Arch. Microbiol.* 164:324-330).

In order to direct carbon towards the phosphoketolase enzyme, expression and/or activity of proteins of the non-oxidative branch of the pentose phosphate pathway (transketolase, transaldolase, ribulose-5-phosphate-epimerase and (or) ribose-5-phosphate epimerase) can be modulated (e.g., increase enzyme activity) to allow more carbon to flux towards fructose 6-phosphate and xylulose 5-phosphate, thereby increasing the eventual production of mevalonate, isoprene, isoprenoid precursor molecules, isoprenoids, and/or acetyl-CoA derived products. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. 1975, *Biochim. Biophys. Acta*, 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene, isoprenoid precursor molecules, isoprenoids, and/or acetyl-CoA derived products. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

Modulation of Genes Involved in Acetate Production, Acetate Cycling, and Acetyl-CoA Production In order to produce useful industrial fermentation products, microorganisms (such as *E. coli* and yeasts) have been widely used as host strains for high-cell-density fermentations. A substantial amount of glucose is added into the growth medium for high-density growth of host cells as well as for expression of heterologously expressed recombinant genes, since glucose is a relatively inexpensive and readily utilizable carbon and energy source. One major problem that can occur during high-cell-density fermentation is the production of fermentative acidic by-products, of which acetate is the most predominant, that can be a major factor in the limitation of cellular growth and production (Han et al., *Biotechnol. Bioeng.*, 39, 663 (1992); Luli et al., *Appl. Environ. Microbiol.*, 56, 1004 (1990)).

In the embodiments provided herein, acetate cycling proteins, acetate production proteins, or Acetyl-CoA production-related proteins include, but are not limited to Phosphotransacetylase (Pta), acetate kinase (AckA), AMP-forming acetyl-coenzyme A synthetase (Acs), and acetate transporter/acetate pump/(actP). In any one of the embodiments described herein, mutations to one or more genes encoding these proteins increase or decrease/attenuate/delete expression, or changes to the activities of these proteins can be made either singly, or in combination, to further enhance the production of mevalonate, isoprene, isoprenoids, isoprenoid precursors, and/or acetyl-CoA-derived products. Changes to the expression and/or activity of these acetate cycling proteins can be made singly or in combination with modulation of the activity of one or more acetylating proteins (such as, but not limited to YfiQ and/or CobB, as described above). In some embodiments, the activity of an acetyltransferase is modulated by deleting or attenuating the expression of the acetyltransferase polypeptide or the acetyltransferase gene along with modulation of one or more acetate cycling genes/proteins. In exemplary embodiments, the activity of YfiQ is modulated by deleting or attenuating the expression of the YfiQ polypeptide or the yfiQ gene. In other embodiments, the activity of a deacetylase is modulated by increasing the expression or activity of the deacetylase polypeptide or the deacetylase gene along with modulation of one or more acetate cycling genes/proteins. In exemplary embodiments, the activity of CobB is modulated by increasing the expression or activity of the CobB polypeptide or the cobB gene.

For glucose metabolism in microorganisms under aerobic conditions, carbon flow exceeding the capacity of the Kreb's cycle (the TCA cycle), is converted to acetic acid/acetate which is ultimately excreted outside the cell (Majewski & Domach, *Biotechnol. Bioeng.*, 35, 732 (1990)). The excreted acetic acid/acetate can inhibit the growth of the host strain and the production of the desired fermentation product.

Phosphotransacetylase (Pta) (Shimizu et al. 1969. *Biochim. Biophys. Acta* 191: 550-558) catalyzes the reversible conversion between acetyl-CoA and acetyl phosphate (referred to interchangeably herein as acetylphosphate, acetyl-phosphate, acetyl-P, or Ac-P), while acetate kinase (AckA) (Kakuda, H. et al. 1994. *J. Biochem.* 11:916-922) uses acetyl phosphate to form acetate. The genes encoding these proteins can be transcribed as an operon in *E. coli*. Together, they catalyze the dissimilation of acetate, with the release of ATP. Thus, one of skill in the art can increase the amount of available acetyl-CoA by modulating the activity of phosphotransacetylase gene (e.g., the endogenous phosphotransacetylase gene) and/or an acetate kinase gene (e.g., the endogenous acetate kinase gene). For example, such modulation can be achieved by increasing the expression of a phosphotransacetylase gene. Such modulation can also be achieved by increasing the expression of the acetate kinase gene. In a particular embodiment, the modulation can be achieved by altering the expression of both the phosphotransacetylase and acetate kinase genes. The modulation can also be achieved by decreasing, attenuating, or deleting the expression of a phosphotransacetylase gene and/or an acetate kinase gene. One way of achieving attenuation is by deleting the phosphotransacetylase (pta) and/or acetate kinase (ackA) genes. This can be accomplished by replacing one or both genes with a chloramphenicol cassette followed by looping out of the cassette. Without being bound by theory, deleting these genes could increase the yield of mevalonate, isoprene or isoprenoids by diverting more carbon into the mevalonate pathway and away from production of acetate.

Alternatively, without being bound by theory, increasing the expression or activity of ackA can increase the production of acetate to be used to synthesize acetyl-CoA.

Alternatively, without being bound by theory, increasing the expression or activity of pta can increase the production of acetyl-CoA.

Further, modulation of the expression of pta and/or an ackA gene can be performed in combination with modulation of the activity of one or more acetylating proteins (such as, but not limited to YfiQ and/or CobB, as described above). In some embodiments, the activity of an acetyltransferase is modulated by deleting or attenuating the expression of the acetyltransferase polypeptide or the acetyltransferase gene. In exemplary embodiments, the activity of YfiQ is modulated by deleting or attenuating the expression of the YfiQ polypeptide or the yfiQ gene. In other embodiments, the activity of a deacetylase is modulated by increasing the expression or activity of the deacetylase polypeptide or the deacetylase gene. In exemplary embodiments, the activity of CobB is modulated by increasing the expression or activity of the CobB polypeptide or the cobB gene.

Another protein involved in acetate production and acetate cycling in microorganisms is AMP-forming acetyl-coenzyme A synthetase (Acs), which is a ubiquitous enzyme responsible for the conversion of acetate to the high energy intermediate acetyl-CoA, a keystone molecule of central metabolism (Cerezo et al., 2011, *Molec. Microb.*, 82(5): 1110-28). Without being bound to theory, cells engineered to increase the expression of Acs could be expected to produce higher amounts of acetyl-CoA. Additional, Acs is a substrate for acetyltransferases and deacetylases. By way of example only, the deacetylase activity of CobB has been demonstrated on Acs in vitro (Zhao et al., 2004, *J. Mol. Biol.*, 337:731-41). Without being bound to theory, since acetylation of Acs can results in its enzymatic inactivation, cells engineered to decrease the amount of Acs acetylation could be expected to produce higher amounts of acetyl-CoA. Further, modulation of the expression of the Acs gene can be performed in combination with modulation of the activity of one or more acetylating proteins (such as, but not limited to YfiQ and/or CobB, as described above). In some embodiments, the activity of an acetyltransferase is modulated by deleting or attenuating the expression of the acetyltransferase polypeptide or the acetyltransferase gene. In exemplary embodiments, the activity of YfiQ is modulated by deleting or attenuating the expression of the YfiQ polypeptide or the yfiQ gene. In other embodiments, the activity of a deacetylase is modulated by increasing the expression or activity of the deacetylase polypeptide or the deacetylase gene. In exemplary embodiments, the activity of CobB is modulated by increasing the expression or activity of the CobB polypeptide or the cobB gene.

Another protein involved in acetate production and acetate handling in microorganisms is the acetate transporter/acetate pump (actP). actP activity can be decreased or attenuated to minimize transport of acetate across the membrane. Without being bound to theory, it is believed that if acetate production is coupled with transport across the membrane, this could result in energy loss due to decoupling of the proton gradient. In some aspects, decreased activity of actP or lack of actP can be used to improve production of mevalonate, isoprene, isoprenoid precursors, and isoprenoids. A modified actP gene may be introduced using chromosomal integration or extra-chromosomal vehicles, such as plasmids. In yet other aspects, actP may be deleted from the genome of cells (for example, microorganisms, such as various *E. coli* strains) which express a actP to improve production of mevalonate and/or isoprene. In another aspect, a heterologous nucleic acid encoding a actP polypeptide can be expressed in a cell which does not endogenously express actP. Further, modulation of the expression of the actP gene can be performed in combination with modulation of the activity of one or more acetylating proteins (such as, but not limited to YfiQ and/or CobB, as described above). In some embodiments, the activity of an acetyltransferase is modulated by deleting or attenuating the expression of the acetyltransferase polypeptide or the acetyltransferase gene. In exemplary embodiments, the activity of YfiQ is modulated by deleting or attenuating the expression of the YfiQ polypeptide or the yfiQ gene. In other embodiments, the activity of a deacetylase is modulated by increasing the expression or activity of the deacetylase polypeptide or the deacetylase gene. In exemplary embodiments, the activity of CobB is modulated by increasing the expression or activity of the CobB polypeptide or the cobB gene.

In some aspects, deletion or attenuation of actP, ackA, and/or pta results in any of about 10%, 20%, 30%, 40%, 50%, 60%, 70%, 80%, 90%, or 100%, inclusive, such as any values in between these percentages, higher percent yield of isoprene in comparison to microorganisms that express actP, ackA, and/or pta. In other aspects, deletion of actP, ackA, or pta results in any of about 10%, 20%, 30%, 40%, 50%, 60%, 70%, 80%, 90%, or 100%, inclusive, including any values in between these percentages, higher instantaneous percent yield of isoprene in comparison to microorganisms that express actP, ackA, and/or pta. In other aspects, deletion of actP, ackA, and/or pta results in any of about 10%, 20%, 30%, 40%, 50%, 60%, 70%, 80%, 90%, or 100%, inclusive, including any values in between these percentages, higher cell productivity index for isoprene in comparison to microorganisms that express actP, ackA, and/or pta. In other aspects, deletion of actP, ackA, and/or pta results in any of about 10%, 20%, 30%, 40%, 50%, 60%, 70%, 80%, 90%, or 100%, inclusive, including any values in between these percentages, higher volumetric productivity of isoprene in comparison to microorganisms that express actP, ackA, and/or pta. In other aspects, deletion of actP, ackA, and/or pta results in any of about 10%, 20%, 30%, 40%, 50%, 60%, 70%, 80%, 90%, or 100%, inclusive, including any values in between these percentages, higher peak specific productivity of isoprene in comparison to microorganisms that express actP, ackA, and/or pta. In some aspects the deletion of actP, ackA, and/or pta results in peak specific productivity being maintained for a longer period of time in comparison to microorganisms that express actP, ackA, and/or pta.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of actP, ackA, and/or pta can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

In some embodiments, the activity of AMP-forming acetyl-coenzyme A synthetase (Acs), phosphotransacetylase (pta) and/or acetate kinase (ackA) can be increased. The increase of these enzymes' activity can be any amount of increase of specific activity or total activity as compared to when no manipulation has been effectuated. In some instances, the increase of enzyme activity is increased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

Citrate Synthase Pathway

Citrate synthase catalyzes the condensation of oxaloacetate and acetyl-CoA to form citrate, a metabolite of the Tricarboxylic acid (TCA) cycle (Ner, S. et al. 1983. *Biochemistry*, 22: 5243-5249; Bhayana, V. and Duckworth, H. 1984. *Biochemistry* 23: 2900-2905). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. *Annual Rev. Biophysics Biophys. Chem.* 15: 97-117; Duckworth et al. 1987. *Biochem Soc Symp.* 54:83-92; Stockell, D. et al. 2003. *J. Biol. Chem.* 278: 35435-43; Maurus, R. et al. 2003. *Biochemistry*. 42:5555-5565). To avoid allosteric inhibition by NADH, replacement by or supplementation with the *Bacillus subtilis* NADH-insensitive citrate synthase has been considered (Underwood et al. 2002. *Appl. Environ. Microbiol.* 68:1071-1081; Sanchez et al. 2005. *Met. Eng.* 7:229-239).

The reaction catalyzed by citrate synthase directly competes with the thiolase catalyzing the first step of the mevalonate pathway, as they both have acetyl-CoA as a substrate (Hedl et al. 2002. *J. Bact.* 184:2116-2122). Therefore, one of skill in the art can modulate citrate synthase expression (e.g., decrease enzyme activity) to allow more carbon to flux into the mevalonate pathway, thereby increasing the eventual production of mevalonate, isoprene and isoprenoids. Decreased citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Lactate Dehydrogenase

In *E. coli*, D-Lactate is produced from pyruvate through the enzyme lactate dehydrogenase (LdhA) (Bunch, P. et al. 1997. *Microbiol.* 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene, isoprenoid precursor and isoprenoids production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used.

By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in *E. coli*, encoded by the sfcA and maeB genes) is an anaplerotic enzyme that catalyzes the conversion of malate into pyruvate (using NAD+ or NADP+) by the following equation:

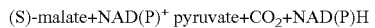

(S)-malate+NAD(P)$^+$ pyruvate+CO$_2$+NAD(P)H

Thus, the two substrates of this enzyme are (S)-malate and NAD(P)$^+$, whereas its 3 products are pyruvate, $CO_2$, and NADPH.

Expression of the NADP-dependent malic enzyme (MaeB) (Iwikura, M. et al. 1979. *J. Biochem.* 85: 1355-1365) can help increase mevalonate, isoprene, isoprenoid precursors and isoprenoids yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) *J. Bact.* 189:5937-5946).

As such, more starting substrate (pyruvate or acetyl-CoA) for the downstream production of mevalonate, isoprene, isoprenoid precursors and isoprenoids can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataaccatctgcggtgataaattatctctggcggtgttgacataaataccactggcggtgatactgagcac atcagcaggacgcactgaccaccatgaaggtg (SEQ ID NO:113), lambda promoter, GenBank NC_001416), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl-CoA in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Exemplary Combinations of Mutations

It is understood that for any of the enzymes and/or enzyme pathways described herein, molecular manipulations that modulate any combination (two, three, four, five, six, or more) of the enzymes and/or enzyme pathways described herein is expressly contemplated.

In one embodiment, for exemplary representation only, and for ease of the recitation of the combinations, citrate synthase (gltA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, pyruvate decarboxylase (aceE, aceF, and/or lpdA) is designated as F, 6-phosphogluconolactonase (ybhE) is designated as G, phosphoenolpyruvate carboxylase (ppl) is designated as H, acetyltransferase (such as YfiQ) is designated as I, and deacetylase (such as CobB) is designated as J. As discussed above, aceE, aceF, and/or lpdA enzymes of the pyruvate decarboxylase complex can be used singly, or two of three enzymes, or three of three enzymes for increasing pyruvate decarboxylase activity. Accordingly, in this exemplary embodiment, for combinations of any two of the enzymes A-J, non-limiting combinations that can be used are: AB, AC, AD, AE, AF, AG, AH, AI, AJ, BC, BD, BE, BF, BG, BH, BI, BJ, CD, CE, CF, CG, CH, CI, CJ, DE, DF, DG, DH, DI, DJ, EF, EG, EH, EI, EJ, GH, GI, GJ, HI, HJ, and IJ. For combinations of any three of the enzymes A-J, non-limiting combinations that can be used are: ABC, ABD, ABE, ABF, ABG, ABH, ABI, ABJ, BCD, BCE, BCF, BCG, BCH, BCI, BCJ, CDE, CDF, CDG, CDH, CDI, CDJ, DEF, DEG, DEH, DEI, DEJ, ACD, ACE, ACF, ACG, ACH, ACI, ACJ, ADE, ADF, ADG, ADH, ADI, ADJ, AEF, AEG, AEH, AEI, AEJ, BDE, BDF, BDG, BDH, BDI, BDJ, BEF, BEG, BEH, BEI, BEJ, CEF, CEG, CEH, CEI, CEJ, CFG, CFH, CFI, CFJ, CGH, CGI, and CGJ. For combinations of any four of the enzymes A-J, non-limiting combinations that can be used are: ABCD, ABCE, ABCF, ABCG, ABCH, ABCI, ABCJ, ABDE, ABDF, ABDG, ABDH, ABDI, ABDJ, ABEF, ABEG, ABEH, ABEI, ABEJ, BCDE, BCDF, BCDG, BCDH, BCDI, BCDJ, CDEF, CDEG, CDEH, CDEI, CDEJ, ACDE, ACDF, ACDG, ACDH, ACDI, ACDJ, ACEF, ACEG, ACEH, ACEI, ACEJ, BCEF, BDEF, BGEF, BHEF, BIEF, BJEF, and ADEF. For combinations of any five of the enzymes A-J, non-limiting combinations that can be used are: ABCDE, ABCDF, ABCDG, ABCDH, ABCDI, ABCDJ, ABDEF, ABDEG, ABDEH, ABDEI, ABDEJ, BCDEF, BCDEG, BCDEH, BCDEI, BCDEJ, ACDEF, ACDEG, ACEDH, ACEDI, ACEDJ, ABCEF, ABCEG, ABCEH, ABCEI, and ABCEJ. For combinations of any six of the enzymes A-J, non-limiting combinations that can be used are: ABCDEF, ABCDEG, ABCDEH, ABCDEI, ABCDEJ, BCDEFG, BCDEFH, BCDEFI, BCDEFJ, CDEFGH, CDEFGI, and CDEFGJ. For combinations of any seven of the enzymes A-J, non-limiting combinations that can be used are: ABCDEFG, ABCDEFH, ABCDEFI, ABCDEFJ, BCDEFGH, BCDEFGI, and BCDEFGJ. For combinations of any eight of the enzymes A-J, non-limiting combinations that can be used are: ABCDEFGH, ABCDEFGI, and ABCDEFGJ. For combinations of any nine of the enzymes A-J, non-limiting combinations that can be used are: ABCDEFGHI and ABCDEFGHJ. In another aspect, all ten enzyme combinations are used ABCDEFGHIJ.

In other embodiments, any of the mutations described herein can be combined and expressed in recombinant cells for use in effectuating the improved/enhanced/increased production of mevalonate, isoprene, isoprenoids, isoprenoid precursors, and/or acetyl-CoA-derived products.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, (e) pyruvate decarboxylase complex (f) acetyltransferases (such as YfiQ), and (g) deacetylases (such as CobB).

Other Regulators and Factors for Increased Production

Other molecular manipulations can be used to increase the flow of carbon towards mevalonate production. One method is to reduce, decrease or eliminate the effects of negative regulators for pathways that feed into the mevalonate pathway. For example, in some cases, the genes aceEF-lpdA are in an operon, with a fourth gene upstream pdhR. PdhR is a negative regulator of the transcription of its operon. In the absence of pyruvate, it binds its target promoter and represses transcription. It also regulates ndh and cyoABCD in the same way (Ogasawara, H. et al. 2007. *J. Bact.* 189:5534-5541). In one aspect, deletion of pdhR regulator can improve the supply of pyruvate, and hence the production of mevalonate, isoprene, isoprenoid precursors, and isoprenoids.

In other aspects, the introduction of 6-phosphogluconolactonase (PGL) into microorganisms (such as various *E. coli* strains) which have decreased PGL or lack PGL can be used to improve production of acetyl-CoA-derived products, mevalonate, isoprene, isoprenoid precursors, and isoprenoids. PGL may be introduced using chromosomal integration or extra-chromosomal vehicles, such as plasmids. In yet other aspects, PGL may be deleted from the genome of cells (for example, microorganisms, such as various *E. coli* strains) which express a PGL to improve production of mevalonate and/or isoprene. In another aspect, a heterologous nucleic acid encoding a PGL polypeptide can be expressed in a cell which does not endogenously express PGL. In some aspects, deletion of PGL results in any of about 10%, 20%, 30%, 40%, 50%, 60%, 70%, 80%, 90%, or 100%, inclusive, such as any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

In another aspect, modulation of phosphoenolpyruvate carboxylase (ppc in *E. coli*) gene expression can be used to improve production of mevalonate, isoprene, isoprenoid precursor molecules, isoprenoids, and/or acetyl-CoA derived products in any of the cells disclosed herein. In one aspect, the gene expression of phosphoenolpyruvate carboxylase can be decreased by replacing the promoter sequence of the ppc gene with another promoter that results in decreased ppc gene expression in comparison to wild type cells. In some aspects, ppc gene expression can be decreased by any of about 10%, 20%, 30%, 40%, 50%, 60%, 70%, 80%, 90%, or 100%, inclusive, including any values in between these percentages, in comparison to wild type cells. In some aspects, decreased expression of phosphoenolpyruvate carboxylase results in any of about 10%, 20%, 30%, 40%, 50%, 60%, 70%, 80%, 90%, or 100%, inclusive, such as any values in between these percentages, higher percent yield of isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher instantaneous percent yield of isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher cell productivity index for isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher volumetric productivity of isoprene in comparison to microorganisms that express phosphoenolpyruvate carboxylase at wild type levels. In other aspects, decreased expression of phosphoenolpyruvate carboxylase results in any of about 10%, 20%, 30%, 40%, 50%, 60%, 70%, 80%, 90%, or 100%, inclusive, including any values in between these percentages, higher peak specific productivity of isoprene in comparison to microorganisms that express phosphoenolpyruvate carboxylase at wild type levels. In some aspects decreased expression of phosphoenolpyruvate carboxylase results in peak specific productivity being maintained for a longer period of time in comparison to microorganisms that express phosphoenolpyruvate carboxylase at wild type levels.

In another aspect, modulation of the inhibitor of RssB activity during magnesium starvation (iraM in *E. coli*) gene expression can be used to improve production of mevalonate, isoprene, isoprenoid precursor molecules, isoprenoids, and/or acetyl-CoA derived products can used in any of the cells disclosed herein. In one aspect, the gene expression of iraM can be increased by replacing the promoter sequence of the iraM gene with another promoter that results in increased iraM gene expression in comparison to wild type cells. In some aspects, iraM gene expression can be increased by any of about 10%, 20%, 30%, 40%, 50%, 60%, 70%, 80%, 90%, or 100%, inclusive, including any values in between these percentages, in comparison to wild type cells. In some aspects, increased expression of the iraM gene results in any of about 10%, 20%, 30%, 40%, 50%, 60%, 70%, 80%, 90%, or 100%, inclusive, such as any values in between these percentages, higher percent yield of isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher instantaneous percent yield of isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher cell productivity index for isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher volumetric productivity of isoprene in comparison to microorganisms that express the iraM gene at wild type levels. In other aspects, increased expression of the iraM gene results in any of about 10%, 20%, 30%, 40%, 50%, 60%, 70%, 80%, 90%, or 100%, inclusive, including any values in between these percentages, higher peak specific productivity of isoprene in comparison to microorganisms that express the iraM gene at wild type levels. In some aspects increased expression of the iraM gene results in peak specific productivity being maintained for a longer period of time in comparison to microorganisms that express the iraM gene at wild type levels.

In another aspect, modulation of the AcrA component of the multidrug efflux pump acrAB-TolC (the acrA gene in *E. coli*) gene expression can be used to improve production of mevalonate, isoprene, isoprenoid precursor molecules, isoprenoids, and/or acetyl-CoA derived products in any of the cells disclosed herein. In one aspect, the gene expression of acrA can be decreased by replacing the promoter sequence of the acrA gene with another promoter that results in decreased acrA gene expression in comparison to wild type cells. In some aspects, acrA gene expression can be decreased by any of about 10%, 20%, 30%, 40%, 50%, 60%, 70%, 80%, 90%, or 100%, inclusive, including any values in between these percentages, in comparison to wild type cells. In another aspect, expression of acrA can be completely abolished, such as by deleting, the acrA gene in the genome of the cell, so that it no longer produces a functional acrA protein. In some aspects, deletion or decreased expression of the acrA gene results in any of about 10%, 20%, 30%, 40%, 50%, 60%, 70%, 80%, 90%, or 100%, inclusive, such as any values in between these percentages, higher percent yield of isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher instantaneous percent yield of isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher cell productivity index for isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher volumetric productivity of isoprene in comparison to microorganisms that express the acrA gene at wild type levels. In other aspects, deletion or decreased expression of the acrA gene results in any of about 10%, 20%, 30%, 40%, 50%, 60%, 70%, 80%, 90%, or 100%, inclusive, including any values in between these percentages, higher peak specific productivity of isoprene in comparison to microorganisms that express the acrA gene at wild type levels. In some aspects deletion or decreased expression of the acrA gene results in peak specific productivity being maintained for a longer period of time in comparison to microorganisms that express the acrA gene at wild type levels.

In another aspect, modulation of FNR DNA binding transcriptional regulator (FNR) gene expression can be used to improve production of mevalonate, isoprene, isoprenoid precursor molecules, isoprenoids, and/or acetyl-CoA derived products in any of the cells disclosed herein. In one aspect, the gene expression of FNR can be increased by replacing the promoter sequence of the gene which encodes FNR with another promoter that results in increased FNR expression in comparison to wild type cells. In other aspects, a heterologous nucleic acid encoding FNR can be expressed in a cell that does not endogenously express FNR. In some aspects, FNR expression can be increased by any of about 10%, 20%, 30%, 40%, 50%, 60%, 70%, 80%, 90%, or 100%, inclusive, including any values in between these percentages, in comparison to wild type cells or cells that do not endogenously express FNR. In some aspects, increased FNR expression results in any of about 10%, 20%, 30%, 40%, 50%, 60%, 70%, 80%, 90%, or 100%, inclusive, such as any values in between these percentages, higher percent yield of isoprene in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher instantaneous percent yield of isoprene in comparison to in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher cell productivity index for isoprene in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher volumetric productivity of isoprene in comparison to wild type cells or cells that do not endogenously express FNR. In other aspects, increased FNR expression results in any of about 10%, 20%, 30%, 40%, 50%, 60%, 70%, 80%, 90%, or 100%, inclusive, including any values in between these percentages, higher peak specific productivity of isoprene in comparison to wild type cells or cells that do not endogenously express FNR. In some aspects increased FNR expression results in peak specific productivity being maintained for a longer period of time in comparison to wild type cells or cells that do not endogenously express FNR.

Exemplary Host Cells

Any microorganism or progeny thereof that can be used to heterologously express one or more genes (e.g., recombinant host cell) and can be engineered such that the expression of the nucleic acids and/or activity of the acetylating protein(s) produced by said cell is modulated, can be used as described herein for increased production of mevalonate, isoprene, isoprenoid precursor molecules, isoprenoids, and/or acetyl-CoA derived products.

Bacteria cells, including gram positive or gram negative bacteria can be used to express any of the nucleic acids described above. In particular, nucleic acids can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the host cell can be a *Lactobacilis* spp., such as *Lactobacillus lactis* or a *Lactobacillus plantarum*.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprene, isoprenoid precursor molecules, isoprenoids, and/or acetyl-CoA derived products can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprene, isoprenoid precursor molecules, isoprenoids, and/or acetyl-CoA derived products. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans,* or *A. awamori, Fusarium* sp., such as *F. roseum, F. graminum F. cerealis, F. oxysporuim,* or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum,* or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6): 423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast*," (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: Chlorococcales, Pleurocapsales, Oscillatoriales, Nostocales, or Stigonematales (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

*E. coli* host cells that comprise one or more nucleic acids encoding one or more acetylating proteins, wherein said cells have been engineered such that the expression of the nucleic acids and/or activity of the acetylating protein(s) is modulated can be used to express one or more upper MVA pathway polypeptides, such as any of the upper MVA pathway polypeptides described herein. In some aspects, *E. coli* host cells can be used to express one or more mvaE and MvaS polypeptides in the compositions and methods described herein. In one aspect, the host cell is a recombinant cell of an *Escherichia coli* (*E. coli*) strain, or progeny thereof, capable of producing mevalonate that expresses one or more nucleic acids encoding upper MVA pathway polypeptides. The *E. coli* host cells (such as those cells that have been engineered as described herein) can produce mevalonate in amounts, peak titers, and cell productivities greater than that of the same cells lacking one or more heterologously expressed nucleic acids encoding upper MVA pathway polypeptides and which do not comprise one or more nucleic acids encoding one or more acetylating proteins, wherein said cells have been engineered such that the expression of the nucleic acids and/or activity of the acetylating protein(s) is modulated. In addition, the one or more heterologously expressed nucleic acids encoding upper MVA pathway polypeptides in E. coli can be chromosomal copies (e.g., integrated into the E. coli chromosome). In another aspect, the one or more heterologously expressed nucleic acids encoding mvaE and MvaS polypeptides in E. coli can be chromosomal copies (e.g., integrated into the E. coli chromosome). In other aspects, the E. coli cells are in culture.

Exemplary Vectors

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Suitable vectors can be used for any of the compositions and methods described herein. For example, suitable vectors can be used to optimize the expression of one or more copies of a gene encoding an MVA pathway polypeptide, an isoprene synthase, and/or a polyprenyl pyrophosphate synthase in anaerobes. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of an upper MVA pathway polypeptide, an isoprene synthase, a polyprenyl pyrophosphate synthase, and/or one or more MVA pathway polypeptide nucleic acid(s) integrate into the genome of host cells without a selective marker.

Any one of the vectors characterized herein or used in the Examples of the present disclosure can be used.

Exemplary Transformation Methods

Nucleic acids encoding one or more copies of an upper MVA pathway polypeptide, isoprene synthase, lower MVA pathway polypeptides, and/or phosphoketolase can be inserted into a microorganism using suitable techniques. Additionally, isoprene synthase, IDI, DXP pathway, and/or polyprenyl pyrophosphate synthase nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 2$^{nd}$ ed., Cold Spring Harbor, 1989; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716, the disclosures of which are incorporated by reference herein.

Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for microorganism (e.g., bacterial, algal, or fungal cell) growth; (2) various salts, which can vary among microorganism (e.g., bacterial, algal, or fungal) species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 mL sterile M9 salts (64 g $Na_2HPO_4$-$7H_2O$, 15 g $KH_2PO_4$, 2.5 g NaCl, and 5.0 g $NH_4Cl$ per liter); (2) 2 mL of 1 M $MgSO_4$ (sterile); (3) 20 mL of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 mL of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4) 1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 mL All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of cell (e.g. bacterial, fungal, algal) cultures are well known in the art. Exemplary techniques can be found in International Publication No. WO 2009/076676, U.S. Publ. No. 2009/0203102, WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the cells (e.g., bacterial cells, such as *E. coli* cells, fungal cells, algal cells) can express one or more heterologous nucleic acids under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the cells (such as bacterial, fungal, or algal cells) are grown in batch culture. The cells (such as bacterial, fungal, or algal cells) can also be grown in fed-batch culture or in continuous culture. Additionally, the cells (such as bacterial, fungal, or algal cells) can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (See, e.g., US Appl. Pub. No. US 2011/0178261 A1, the disclosure of which is incorporated by reference herein). In some aspects, any of the methods described herein further include a step of recovering an isoprenoid. In some aspects, any of the methods described herein further include a step of recovering the terpenoid or carotenoid.

Suitable purification methods are described in more detail in U.S. Patent Application Publication US2010/0196977 A1, the disclosure of which is incorporated by reference herein.

Exemplary In Vitro Protein Acetylation and Deacetylation Assays

Exemplary acetylation assays are carried out in the presence of buffer and Acetyl-CoA. For example the assay can be carried out in 20 mM buffer, 100 mM NaCl, 100 µM acetyl-CoA, 20 µM USP in the presence and absence of 200 µM cAMP. Reactions can initiated by the addition of 20 µM Mt-PatA, incubated for 10 min at 22° C., and quenched by boiling in SDS loading dye. Exemplary buffers are provided as follows: sodium acetate (pH 4.0-5.0), MES (pH 6.0), HEPES (pH 7.0), Tris (pH 7.5-8.0), BisTrisPropane (pH 9.0), and Glycine (pH 10.0). Reactions can be analyzed in parallel with SDS-PAGE and Western blotting with anti-AcLys antibody (Cell Signaling Technology) detected quantitatively by chemiluminescence (LI-COR Biosciences).

Deacetylation assays can be carried out at 22° C. in 20 mM Tris-HCl, pH 7.5, 100 mM NaCl, 1 mM β-Nicotinamide adenine dinucleotide (NAD$^+$), 20 µM auto-acetylated Mt-PatA H173K mutant in the presence and absence of 200 µM cAMP. Reactions can be initiated by addition of 5 µM Rv1151c and terminated at various time points by boiling in SDS loading dye. Samples can be analyzed in parallel using SDS-PAGE and Western blotting using SDS-PAGE and Western blotting with anti-Ac-Lys antibodies.

Methods described here are used for monitoring acetylation and deacetylation of all proteins in bacteria, fungal cells, and algal cells.

The invention can be further understood by reference to the following examples, which are provided by way of illustration and are not meant to be limiting.

EXAMPLES

Example 1: Construction of Reference and Acetylation Modulatory Strains

This Example describes the construction of reference strains as well as strains containing mutations in genes responsible for modulating intracellular protein acetylation.

Figure 15:
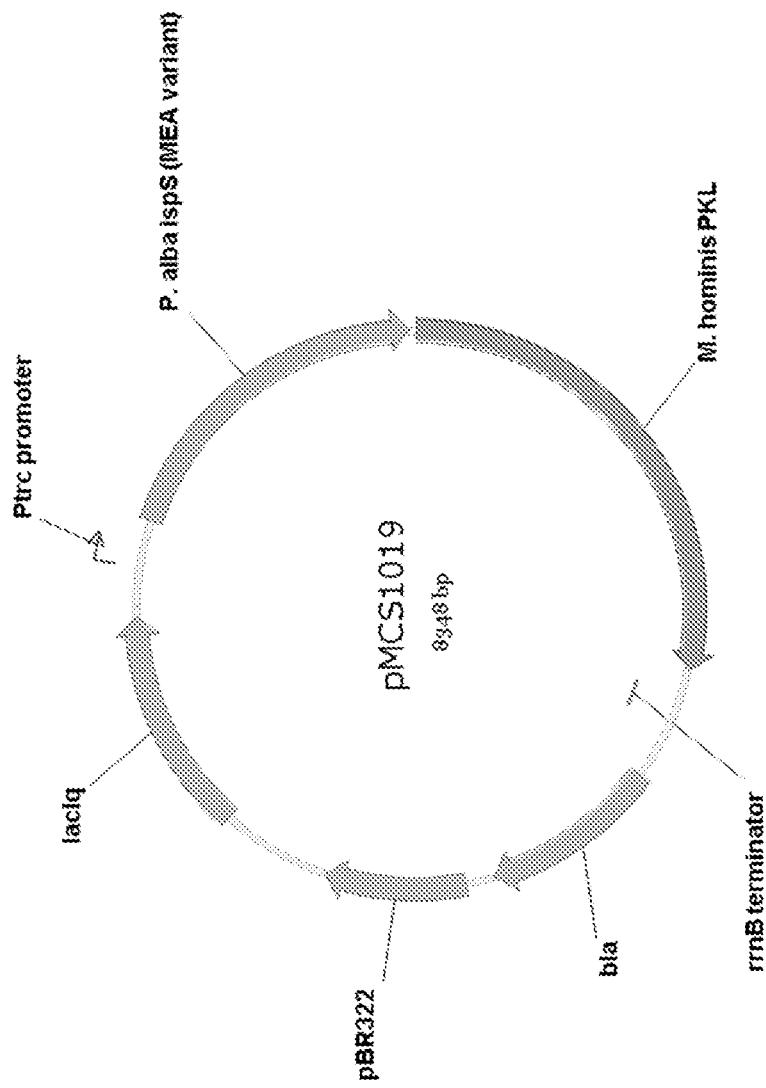
FIG. 15 depicts a map of plasmid pMCS1019.

TACGCGTAACCCCAAGGACGGTAAAatgattagcaaaatc-tatgatgataaaaagt atctgg) (SEQ ID NO:37). The resulting PCR product was purified and self-ligated using standard techniques to form plasmid pMCS1019 (FIG. 15).

A DNA cassette was created by PCR in a 2-stage process. A ~1.8 kb product was amplified by PCR using primers MCS504 and MCS516 from the FRT-gb2-CM-FRT template (Genebridges). This PCR product was then used as template for a second round of amplification by PCR using primers MCS516 and MCS545. This PCR product was integrated into the chromosome of strain MD891 (BL21 wt, pgl+t PL.2-mKKDyI::FRT, Gi1.2gltA yhfSFRTPyddVIspAyhfS thiFRTtruncIspA pgl ML, FRT-PL.2-2cis-RBS10000-MVK (burtonii) clone A+t ackA::FRT) using the Genebridges Red/ET Recombination Quick and Easy E. coli gene deletion Kit, according to manufacturer's instruction. Hereafter, Gi1.2gltA yhfSFRTPyddVIspAyhfS thiFRTtruncIspA and CTO are used interchangeably and pgl ML and pgl- are used interchangeably. The resulting strain was designated MCS1015 (MD891+ackA::Cm_pL.2_pta). Sequence analysis of strain MCS1015 revealed the insertion of the chloramphenicol antibiotic marker and pL.2 promoter upstream of the phosphotransacetylase (pta) gene. The chloramphenicol antibiotic marker was removed from strain MCS1015 by FLP expression according to manufacturer's instruction to create strain MCS1016 (MD891+FRT::ackA::FRT_pL.2_pta). Strain MCS1016 was transformed with plasmids pMCS1019 (SEQ ID NO:30) and pMCM1225 (SEQ ID NO:27) to create isogenic strains MCS1227 (pMCS1019 (pTrc_IspS_RBS3_PKL16 [M. hominis]), pMCM1225) and MCS1316 (pMCS1019 (pTrc_IspS_RBS3_PKL16 [M. hominis]), pMCM1225). The sequences of the primers used are shown in Table 1-1.

TABLE 1-1

Primer Sequences

| | | |
|---|---|---|
| MCS504 | tgtttttttacctcctttgcagtgcgtcctgctgatgtgctcagtatcaccgccagtggtatttac gtcaacaccgccagagataatttatcaccgcagatggttatcttaatacgactcactatagggctc | SEQ ID NO: 38 |
| MCS516 | gactcaagatatttcttccatcatgcaaaaaaaatttgcagtgcatgatgttaatcaaattaac cctcactaaagggcg | SEQ ID NO: 39 |
| MCS545 | gctggtcagaccgacgctggttccggtagggatcagcataataatacgggacatgttttttta cctcctttgcagtg | SEQ ID NO: 40 |

I. Construction of Reference Strains

Figure 13:
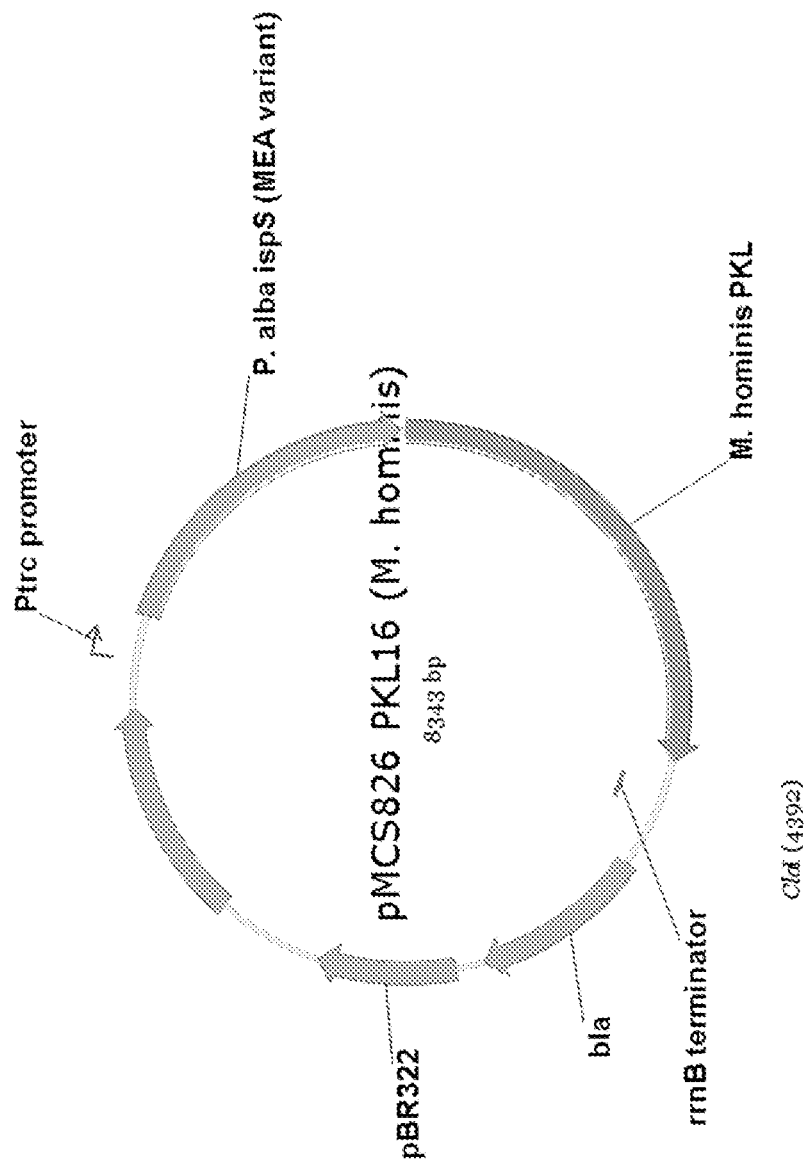
FIG. 13 depicts a map of plasmid pMCS826 PKL16 (*M. hommis*).
Figure 14:
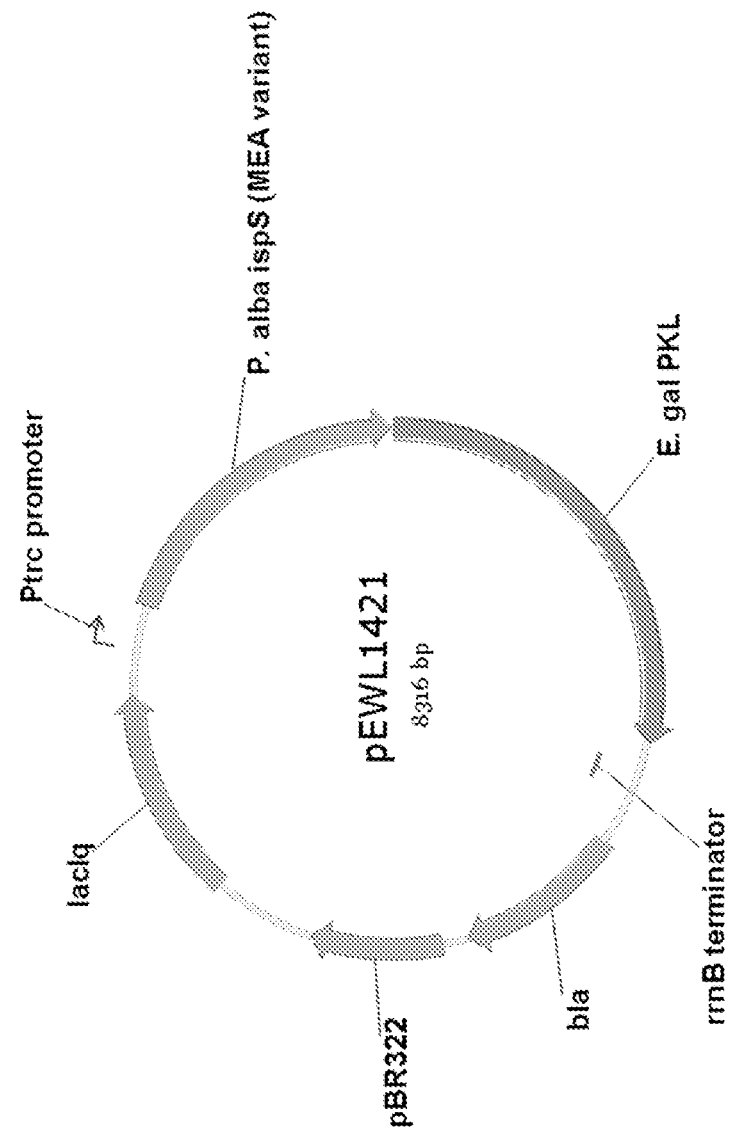
FIG. 14 depicts a map of plasmid pEWL1421.

The DNA sequence for the phosphoketolase (PKL) enzyme from Mycoplasma hominis (strain ATCC 23114) (SEQ ID NO:28) was codon optimized for expression in E. coli (SEQ ID NO:29) and synthesized by Life Technologies. The M. hominis phosphoketolase was subcloned into plasmid pEWL1421 (pTrc P. alba ispS (MEA variant)-E. gallinarum phosphoketolase) using the GENEART Seamless Cloning and Assembly Kit (Life Technologies) according to manufacturer's protocol, to yield plasmid pMCS826 (FIG. 13). Primers used were MCS534 (cgctaactgcataaaggagg-taaaaaaac)(SEQ ID NO:32) and MCS535 (gctggagaccgtt-taaactttaactagactta) (SEQ ID NO:33) for the phosphoketolase, and MCS536 (taaagtctagttaaagtttaaacggtctccagc) (SEQ ID NO:34) and MCS537 (gtttttttacctccttatgcagttagcg) (SEQ ID NO:35) for the plasmid pEWL1421 (FIG. 14). The sequence of the DNA between the IspS and phosphoketolase open reading frames on plasmid pMCS826 was altered by PCR using primers MCS488 (ttagcgttcaaacggcagaatcgg) (SEQ ID NO:36) and MCS562 (ccgtttgaacgctaaAGA- II. Construction of Acetylation Chromosome Mutation Strains Constructs for deletion of yfiQ and cobB were amplified by colony PCR from Keio library clones (Baba et al., Molecular Systems Biology 2 Article number: 2006.0008 doi:10.1038/msb4100050). The yfiQ deletion construct was amplified from JW2568 (plate 21, G12) using primers MCM1038 and MCM1039. The cobB deletion construct was amplified from JW1106 (plate 21, A2) using primers MCM1033 and MCM1035. 50 uL reactions (Agilent Herculase II kit; Catalog 600679) were performed according to the manufacturer's protocol with the following conditions for yfiQ: 95° C., 20 min; (95° C., 20 sec; 55° C., 20 sec; 72° C., 1.5 min)×30; 72° C., 3 min; 4° C. hold and the following conditions for cobB: 95° C., 20 min; (95° C., 20 sec; 55° C., 20 sec; 72° C., 1.25 min)×30; 72° C., 3 min; 4° C. hold. PCR products were purified according to the manufacturer's protocol (Qiagen QIAquick PCR Purification Kit, Catalog 28104) and eluted in 30 uL EB. Primer sequences are shown in Table 1-2.

TABLE 1-2

| | Primer Sequences | |
|---|---|---|
| MCM1033 | aggctgcctcgtcatctctt | SEQ ID NO: 41 |
| MCM1035 | cagaatatcgccactctggg | SEQ ID NO: 42 |
| MCM1038 | acacgctatctggcaggaaa | SEQ ID NO: 43 |
| MCM1039 | tttgacaacatcacagtgca | SEQ ID NO: 44 |

Constructs for insertion of constitutive promoters at yfiQ and cobB were created in a two-step PCR process. The construct designated KanR_gi1.6 was amplified by PCR using primers MCS580 and MCS584 from the FRT-PGK-gb2-neo-FRT template (Genebridges). The PCR product was purified using the QIAquick PCR Purification Kit (Qiagen) and used as a template (10 ng per reaction) in further PCRs. The FRT-kan-FRT-gi1.6-YfiQ construct was amplified using primers MCM1042 and MCM1043. The FRT-kan-FRT-gi1.6-CobB construct was amplified using primers MCM1046 and MCM1048. 50 uL reactions (Agilent Herculase II kit; Catalog 600679) were performed according to the manufacturer's protocol with the following conditions: 95° C., 20 min; (95° C., 20 sec; 55° C., 20 sec; 72° C., 1.25 min)×30; 72° C., 3 min; 4° C. hold. PCR products were purified according to the manufacturer's protocol (Qiagen QIAquick PCR Purification Kit, Catalog 28104) and eluted in 30 uL EB. Primer sequences are shown in Table 1-3.

TABLE 1-3

| | Primer Sequences | |
|---|---|---|
| MCS580 | aattaaccctcactaaagggcggc | SEQ ID NO: 45 |
| MCS584 | atattccaccagctatttgttagtgaataaaagtggttgaattattt-gctca ggatgtggcattgtcaagggctaatacgactcactatagggctcgaggaag | SEQ ID NO: 46 |
| MCM1042 | tcacagcagaacagttagaaagcgtttaaaatcattcggtcacttct gcgggagaccggtaattaaccctcactaaagggcggc | SEQ ID NO: 47 |
| MCM1043 | cgcgccaattaccgctatcgattttggtcgcagtagtgcttccagtcc tcgctgactcatatattccaccagctatttgttagtg | SEQ ID NO: 48 |
| MCM1046 | gcgggaggaatgcgtggtgcggccttcctacatctaaccgattaaa caacagaggttgctaattaaccctcactaaagggcggc | SEQ ID NO: 49 |
| MCM1048 | gcgcaggcggcgtttattttacgaaaacgacttaaccgatgaccc cgacgcgacagcatatattccaccagctatttgttagtg | SEQ ID NO: 50 |

Constructs were introduced into strain DW853, which is strain MD891 carrying pRedET-carb. Using standard molecular biology procedures, DW853 was generated by electroporation of the pRED/ET plasmid (GeneBridges) into MD891, and subsequent propagation of transformants on solid LB medium plates containing carbenicillin at a concentration of 50 μg/mL at 30° Celsius. Cells containing pRedET-carb were grown in LB+carb50 at 30° C. overnight and then diluted 1:100 into fresh LB+carb50 and cultured at 30° C. for 2 hr. 130 uL 10% arabinose was added and cells were cultured at 37° C. for approximately 2 hours. Cells were prepared for electroporation by washing 3× in one half culture volume iced ddH$_2$O and resuspended in one tenth culture volume of the same. 100 uL of cell suspension was combined with 3 uL DNA in a 2 mm electroporation cuvette, electroporated at 25uFD, 200 ohms, 2.5 kV, and immediately quenched with 500 uL LB. Cells were recovered shaking at 37° C. for 3 hrs and then transformants selected overnight on LB/kan10 plates at 37° C. Transformants were restreaked and then grown in liquid LB/kan10 and frozen in 30% glycerol. Descriptions of strains are shown in Table 1-4.

TABLE 1-4

Descriptions of Strains

| Strain | Genotype |
|---|---|
| MCM2721 | MD891 + YfiQ::FRT-kan-FRT |
| MCM2736 | MD891 + CobB::FRT-kan-FRT |
| MCM2740 | MD891 + FRT-kan-FRT-gi1.6-YfiQ |
| MCM2742 | MD891 + FRT-kan-FRT-gi1.6-CobB (BL21 ATG) |

III. Transduction of PL.2-Pta

The FRT-cmR-FRT-PL.2-pta locus was moved from strain MCS1015 into strain MCM2721 by transduction, retaining the deletion of ackA. A P1 lysate of MG1655 was used to create a lysate of MCS1015. 100 uL of this lysate was mixed with 100 uL of an overnight culture of MCM2721 that had resuspended in half the culture volume of 10 mM MgCl$_2$ and 5 mM CaCl$_2$. The reaction was incubated at 30° C., still for 30 minutes and then quenched with 100 uL 1M sodium citrate. 500 uL LB was added and the culture shaken at 37° C. for 1 hr before selecting on LB/cmp5 plates overnight at 37° C. A single colony was restreaked on LB/kan10cmp10. A colony was grown and frozen as MCM2725 (MD891+FRT-kan-FRT::yfiQ FRT-cmp-FRT::PL.2-pta).

IV. Loopouts

The antibiotic markers from the above strains were removed by transient expression of the FLP recombinase. Plasmid pCP20 (see worldwide web cgsc.biology.yale.edu/Site.php?ID=64621) was electroporated and transformants selected on LB/carb50 at 30° C. A transformant colony was grown in LB/carb50 broth at 30° C. until turbid, then cultured at 37 for several hours. Culture was then streaked to LB plates and grown at 37° C. overnight. Single colonies were patched to LB, LB/carb50, LB/kan10 and LB/cmp5 (for MCM2725 loopouts). Streaks from LB for colonies sensitive to each antibiotic were grown and frozen in 30% glycerol. Loopout strains are shown in Table 1-5.

TABLE 1-5

| Loopout strains | |
|---|---|
| Parent strain (markers) | Looped out strain |
| MCM2721 (kan) | MCM2722 |
| MCM2736 (kan) | MCM2754 |
| MCM2740 (kan) | MCM2760 |
| MCM2742 (kan) | MCM2764 |

V. Isoprene Producing Cells

Plasmids pMCS1019 and pMCM1225 were co-electroporated into above hosts to create isoprene-producing cells. Transformants were selected on LB/carb50spec50 and a single colony was grown in liquid LB/carb50spec50 and frozen in 30% glycerol. Isoprene producing cells are shown in Table 1-6.

TABLE 1-6

| Isoprene Producing Cells | | |
|---|---|---|
| Host | Isoprene Producing Cell | Selection Temperature (degrees centigrade) |
| MCM2722 | MCM2728 | 37 |
| MCM2725 | MCM2732 | 37 |
| MCM2754 | MCM2771 | 30 |
| MCM2760 | MCM2773 | 30 |
| MCM2764 | MCM2775 | 30 |

Example 2: Evaluation of yfiQ Deletion in the Small Scale Assay for Growth Rate and Isoprene Specific Productivity This example measured isoprene production and growth rate in strains carrying a deletion of the yfiQ gene.

I. Materials and Methods

LB media, TM3 media without Yeast extract and MgSO$_4$, 10% Yeast extract, 1M MgSO$_4$, 50% Glucose, 200 mM IPTG, 50 mg/mL Spectinomycin, 50 mg/mL Carbenicillin, Aluminum foil seal, 48-well sterile 5 mL block, breathe easier sealing membrane, aluminum foil seal, 96-well micro titer plates, 96-well glass block purchased from Zinsser Analytic. Agilent 6890 GC equipped with a 5973N Mass spectrometer.

Supplemented TM3 media was prepared by combining TM media, (without MgSO$_4$ and Yeast extract) 1% Glucose, 8 mM MgSO$_4$, 0.02% Yeast extract and appropriate antibiotics. 2 mL of day culture was started in 48-well sterile block by inoculating overnight culture in supplemented TM3 media at 0.2 optical density (OD). Blocks were sealed with breathe easier membrane and incubated for 2 hours at 34° C., 600 rpm. After 2 hours of growth, OD was measured at 600 nm in the micro titer plate and cells were induced with 200 µM IPTG. OD reading was taken every hour after the IPTG induction for 4 hours to determine growth rate. OD was measurement was done in the micro titer plate at appropriate dilution in the TM3 media at 600 nm using a SpectraMax Plus190 (Molecular Devices).

100 µL of isoprene samples were collected in a 96 well glass block at 2, 3 and 4 hours after IPTG induction. Glass block was sealed with aluminum foil and incubated at 34° C. while shaking at 450 rpm, for 30 minutes on the thermomixer. After 30 minutes, the block was kept in 70° C. water bath for 2 minutes and isoprene headspace measurement was done in GC/MS to determine specific productivity.

II. Results

Figure 2:
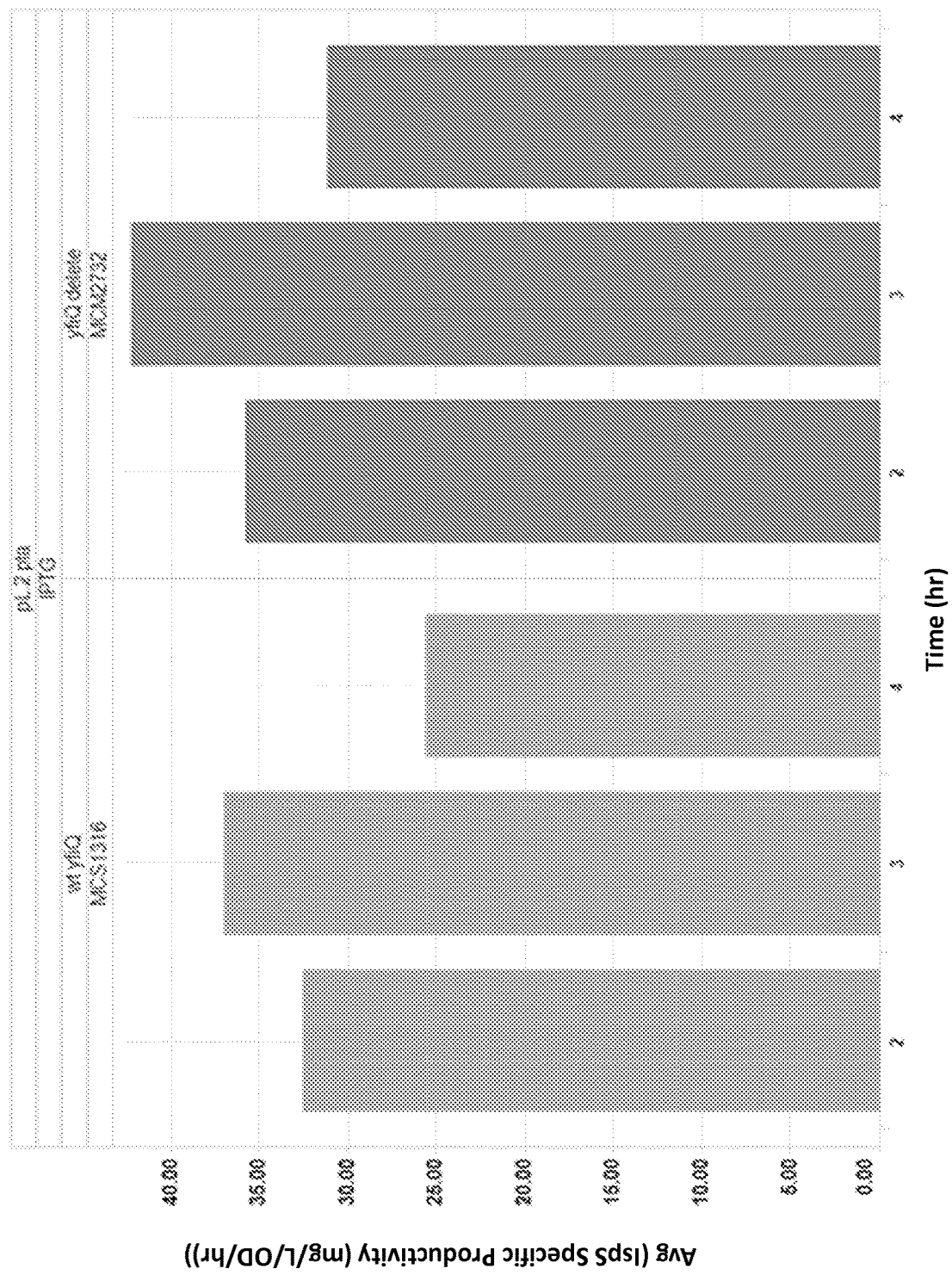
FIG. 2 depicts isoprene specific productivity for control wild type YfiQ cells versus cells carrying a deletion in the YfiQ gene over four hours.

FIG. 1A shows growth (OD600) for control wild type yfiQ cells versus yfiQ delete cells over 4 hours while FIG. 1B shows overnight growth (OD600). FIG. 2 shows isoprene specific productivity for control wild type yfiQ cells versus yfiQ delete cells over 4 hours.

Example 3: Effects of yfiQ Gene Deletion on Isoprene Production in Strains Expressing the Mevalonate Pathway and Isoprene Synthase This example was performed to evaluate isoprene production using a modified *E. coli* host (BL21 derived production host MD891) which expresses introduced genes from the mevalonate pathway and isoprene synthase and is grown in fed-batch culture at the 15-L scale. Both host strains in this experiment carry a deletion in the gene encoding the acetate kinase (AckA) polypeptide and express an *M. hominis* phosphoketolase. Additionally, both over express phosphotransacetylase (pta).

These isoprene producing cells were run in the same process. The performance metrics of control cells, MCS1227 are compared here to those of experimental cells that has been deleted for yfiQ, a lysine acetyltransferase (cell details provided in Table 3-1). The relevant performance metrics are cumulative isoprene yield on glucose, volumetric productivity of isoprene and CPI.

TABLE 3-1

| Cells used in this example | | | |
|---|---|---|---|
| Cell Name | Host | Upper pathway plasmid | Isoprene synthase/ Phosphoketolase plasmid |
| MCS1227 (Control) | CTO pgl- PL.2-2cis- RBS 10000- bKKDyI, ackA::FRT_ pL.2_pta | IPTG inducible P$_{trc}$ expressing *E. gallinarum* mvaE, mvaS (pMCM1225 Spec 50) | IPTG inducible (pTrc_IspS_RBS3_ PKL16 [*M. hominis*]) (pMCS1019, Carb 50) |
| MCM2732 (Experimental- YfiQ deletion) | MD891 + FRT-kan- FRT::YfiQ FRT-cmp- FRT::PL.2- pta | IPTG inducible P$_{trc}$ expressing *E. gallinarum* mvaE, mvaS (pMCM1225 Spec 50) | IPTG inducible (pTrc_IspS_RBS3_ PKL16 [*M. hominis*]) (pMCS1019, Carb 50) |

I. Materials and Methods

Medium Recipe (Per Liter Fermentation Medium):

K$_2$HPO$_4$ 7.5 g, MgSO$_4$*7H$_2$O 2 g, citric acid monohydrate 2 g, ferric ammonium citrate 0.3 g, yeast extract 0.5 g, 50% sulfuric acid 1.6 mL, 1000× Modified Trace Metal Solution 1 mL. All of the components were added together and dissolved in Di H$_2$O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H$_2$O 40 g, MnSO$_4$*H$_2$O 30 g, NaCl 10 g, FeSO$_4$*7H$_2$O 1 g, CoCl$_2$*6H$_2$O 1 g, ZnSO*7H$_2$O 1 g, CuSO$_4$*5H$_2$O 100 mg, H$_3$BO$_3$ 100 mg, NaMoO$_4$*2H$_2$O 100 mg. Each component was dissolved one at a time in Di H$_2$O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H₂O, pH was adjusted to 3.0 with HCl/NaOH, and then the solution was q.s. to volume and filter sterilized with 0.22 micron filter.

Macro Salt Solution (Per Liter):

MgSO$_4$*7H$_2$O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H₂O 0.393 kg, K$_2$HPO$_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 mL, Vitamin Solution 6.55 mL, 1000× Modified Trace Metal Solution 0.82 mL. For a target of 100 µM IPTG: 1.87 mL of a sterile 10 mg/mL solution is added per kilogram of feed.

This experiment was carried out to monitor isoprene production from glucose at the desired fermentation pH (7.0) and temperature (34° C.). To start each experiment, the appropriate frozen vial of the *E. coli* production strain was thawed and inoculated into a flask with tryptone-yeast extract (LB) medium and the appropriate antibiotics. After the inoculum grew to an optical density of approximately 1.0, measured at 550 nm (OD$_{550}$), 500 mL was used to inoculate a 15-L bioreactor and bring the initial tank volume to 5 L.

The inlet gas using to maintain bioreactor backpressure at 0.7 bar gauge and to provide the oxygen to the production organisms was supplied by in house facilities that dilute the inlet gas to a known concentration (7.3 to 8.3 vol % oxygen).

TABLE 3-2

| | Process Conditions | | |
|---|---|---|---|
| Strain Used | Batched [IPTG] (µM) | Target [IPTG] after bolus addition at ~EFT 8 hrs (µM) | Target [IPTG] in Feed Bottle (µM) |
| MC5922 | 1.4 | 100 | 100 |
| MCM2732 | 1.4 | 100 | 100 |

Isoprene, Oxygen, Nitrogen, and Carbon Dioxide levels in the off-gas were determined independently by a Hiden HPR20 (Hiden Analytical) mass spectrometer.

Dissolved Oxygen in the fermentation broth is measured by sanitary, sterilizable probe with an optical sensor provided Hamilton Company.

The citrate, glucose, acetate, and mevalonate concentrations in the fermenter broth was determined in broth samples taken at 4 hour intervals by an HPLC analysis. Concentration in broth samples were determined by comparison of the refractive index response versus a previously generated calibration curve using standard of a known concentration.\

HPLC information was as follows: System: Waters Alliance 2695; Column: BioRad—Aminex HPX-87H Ion Exclusion Column 300 mm×7.8 mm Catalog #125-0140; Column Temperature: 50° C.; Guard column: BioRad—Microguard Cation H refill 30 mm×4.6 mm Catalog #125-0129; Running buffer: 0.01N H$_2$SO$_4$; Running buffer flow rate: 0.6 mL/min; Approximate running pressure: ~1100-1200 psi; Injection volume: 20 microliters; Detector: Refractive Index (Knauer K-2301;) Runtime: 26 minutes.

II. Results

Isoprene Productivity Metrics (and EFT when the value was taken) are shown in Table 3-3.

TABLE 3-3

| | Isoprene Productivity | | | | | | |
|---|---|---|---|---|---|---|---|
| Strain Name | Cumulative % Yield of isoprene on glucose (g/g %) | Overall Isoprene Volumetric Productivity at time of max overall isoprene yield (g/L/hr) | Max Optical Density (A550) | CPI (Total g isoprene/ total gDCW) at time of max overall isoprene yield | Peak Specific Productivity (mg isoprene/ L/hr/OD) | Peak Instantaneous yield of isoprene on glucose (g/g %) | Isoprene Titer (gram isoprene/average volume of tank broth in Liters) |
| MCS 1227 | 18.61 (60 hrs) | 2.00 (60 hrs) | 113.9 (32 hrs) | 3.03 (60 hrs) | 37.2 (28 hrs) | 22.6 (40.4 hrs) | 120.1 (60 hrs) |
| MCM 2732 | 19.64 (60 hrs) | 2.34 (60 hrs) | 99.6 (24 hrs) | 3.53 (60 hrs) | 47.0 (28 hrs) | 23.8 (48 hrs) | 140.3 (60 hrs) |

The batched media had glucose batched in at 9.7 g/L. Induction was achieved by adding isopropyl-beta-D-1-thiogalactopyranoside (IPTG). A syringe containing a sterile solution of IPTG was added to bring the IPTG concentration to 100 µM when the cells were at an OD$_{550}$ of 6. Once the glucose was consumed by the culture, as signaled by a rise in pH, the glucose feed solution was fed to meet metabolic demands at rates less than or equal to 10 g/min. At a fixed time after dissolved oxygen limitation was established, the temperature was raised from 34° C. to 37° C. over the course of one hour. The fermentation was run long enough to determine the maximum cumulative isoprene mass yield on glucose, typically a total of 64 hrs elapsed fermentation time (EFT). Table 3-2 shows process conditions.

Figure 3:
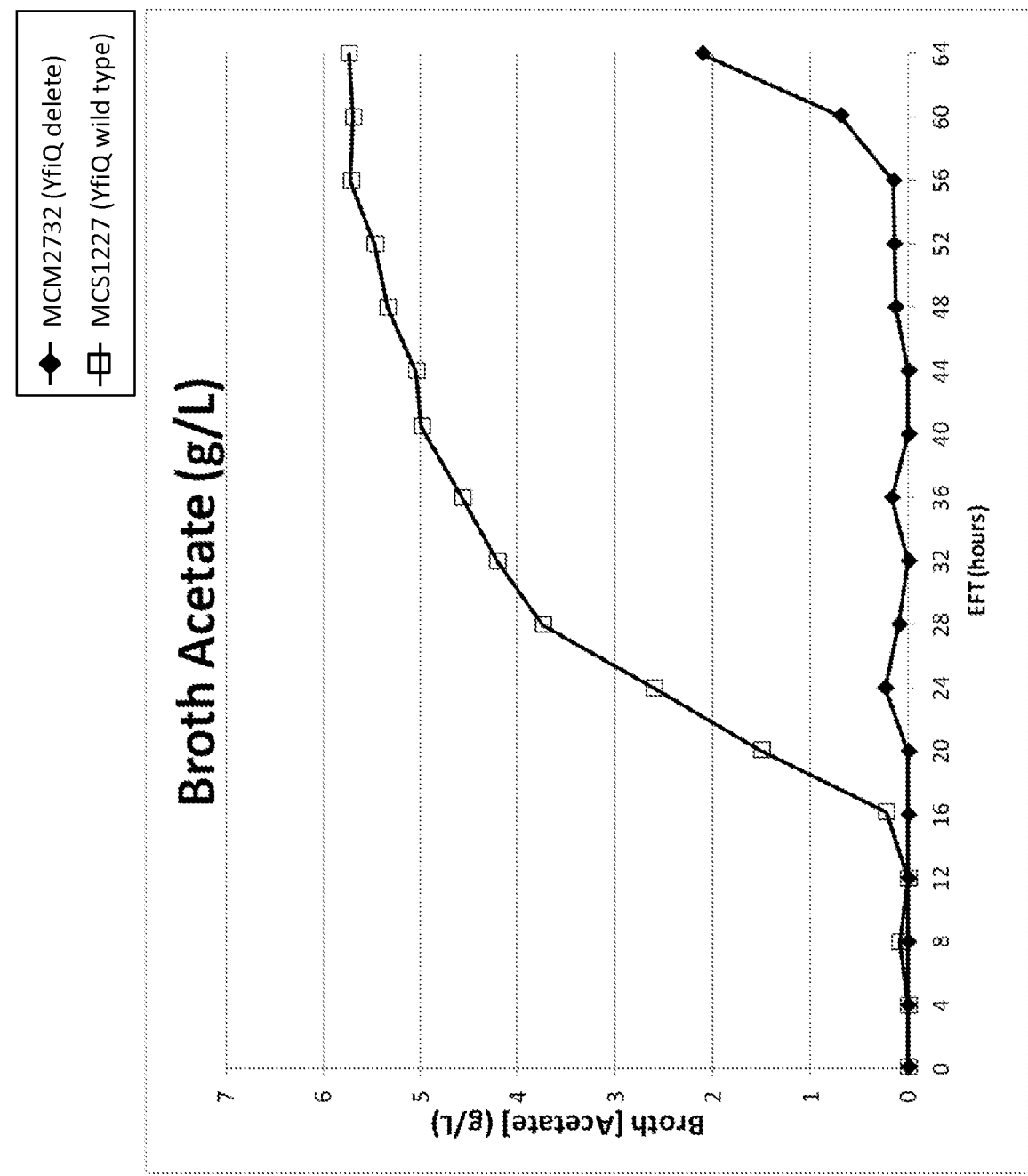
FIG. 3 depicts broth concentration of acetate measured in each 15-L fermentation over time. MCM2732 (YfiQ delete) (closed diamonds); MCS1227 (YfiQ wild type) (open squares).

Broth concentration of acetate measured in each 15-L fermentation over time is shown in FIG. 3. The experimental cells that are deleted for yfiQ (MCM2732) finishes with a lower broth concentration of acetate than the control cells that are wild type for yfiQ. The broth concentration of acetate was determined by HPLC.

Figure 4:
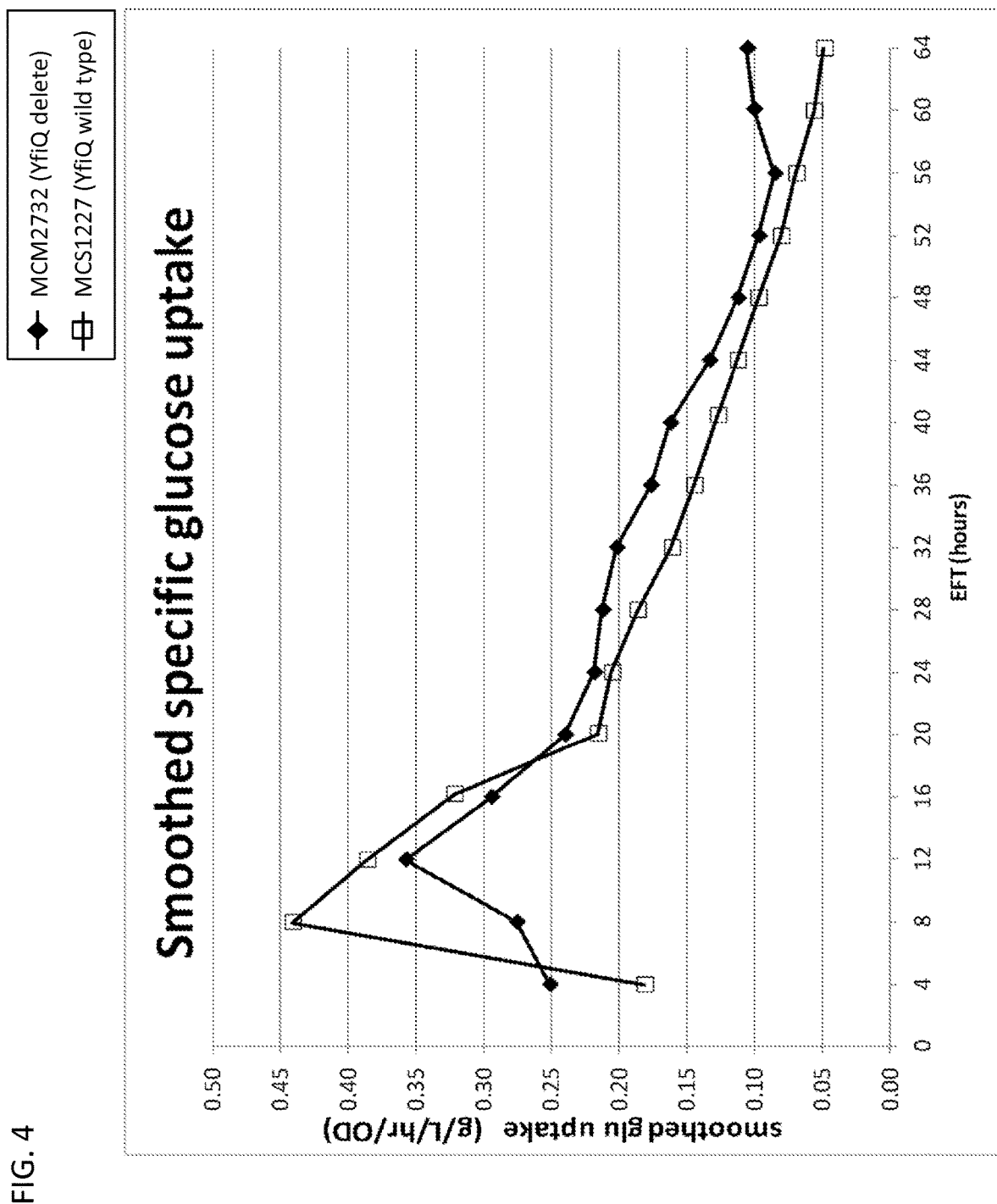
FIG. 4 depicts specific Glucose Uptake Rate measured in each 15-L fermentation over time. MCM2732 (yfiQ delete) (closed diamonds); MCS1227 (yfiQ wild type) (open squares).
Figure 5:
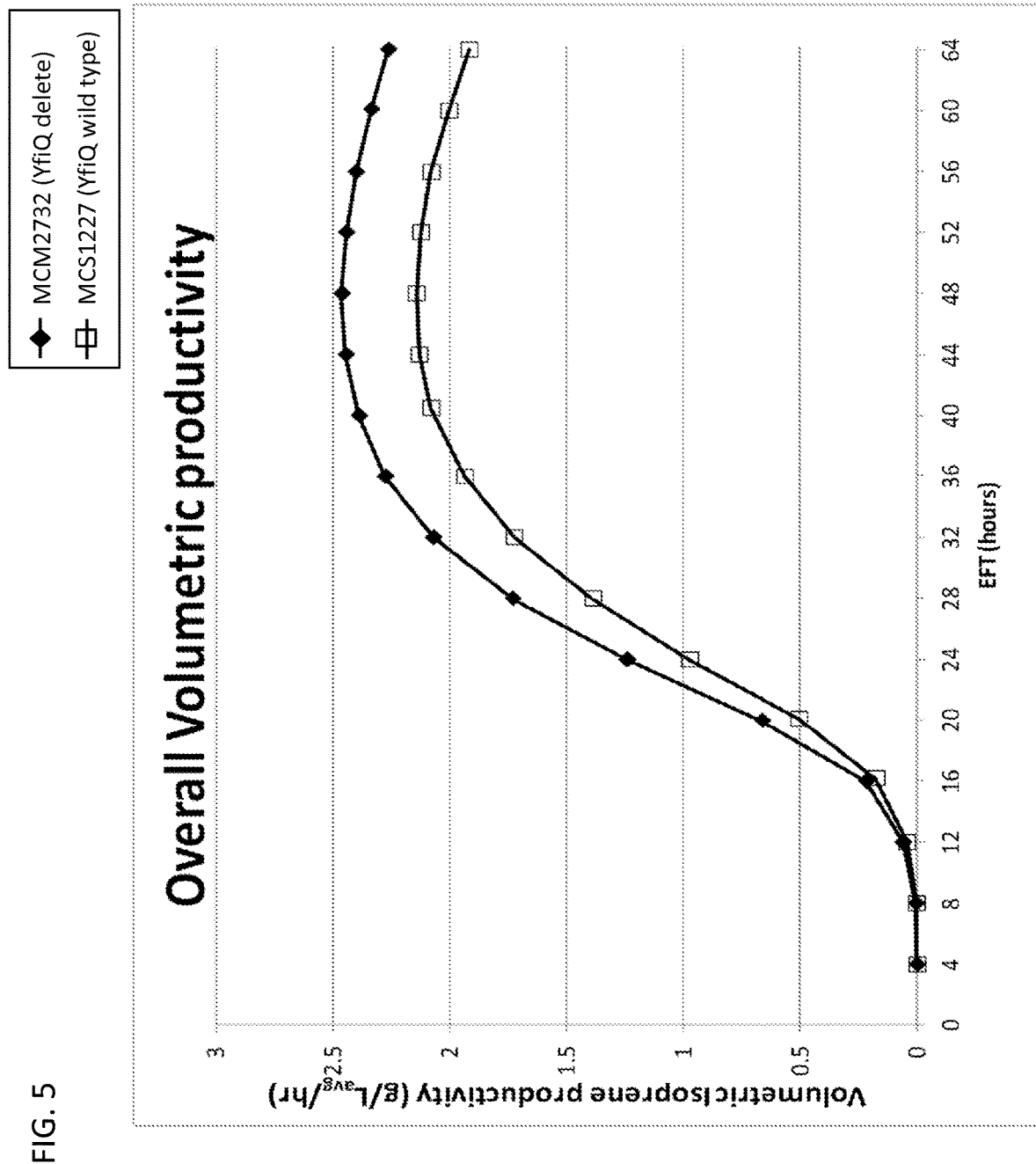
FIG. 5 depicts volumetric isoprene productivity achieved in each 15-L fermentation over time. MCM2732 (yfiQ delete) (closed diamonds); MCS1227 (yfiQ wild type) (open squares).

Specific Glucose Uptake Rate measured in each 15-L fermentation over time is shown in FIG. 4. The experimental cells carrying the yfiQ deletion (MCM2732) consistently shows a higher specific glucose uptake rate than the control cells that are wild type for yfiQ. The lower concentration of acetate in the broth is presumably the driver for the higher specific glucose uptake rate, which in turn drives a higher volumetric productivity (shown in FIG. 5). Smoothed specific glucose uptake rate was calculated using the following formula:

Specific Glucose Uptake Rate (g/L/hr/OD)=slope of grams glucose consumed per hour (averaged over 8 hour interval)/broth volume*OD Volumetric productivity achieved in each 15-L fermentation over time is shown in FIG. 5. The experimental cells carrying the yfiQ deletion (MCM2732) finishes with a higher volumetric productivity of isoprene on glucose than the control cells that are wild type for yfiQ. The 64 hr points were used to populate Table 3-3 above. Volumetric Productivity was calculated using the following formula:

Volumetric productivity (g/L/hr)=[Σ(IspER($t$)/1000*68.117)]/[$t-t_0$], where the summation is from $t_0$ to $t$ and where IspER is the isoprene evolution rate. Tank turnaround time is not factored in.

Figure 6:
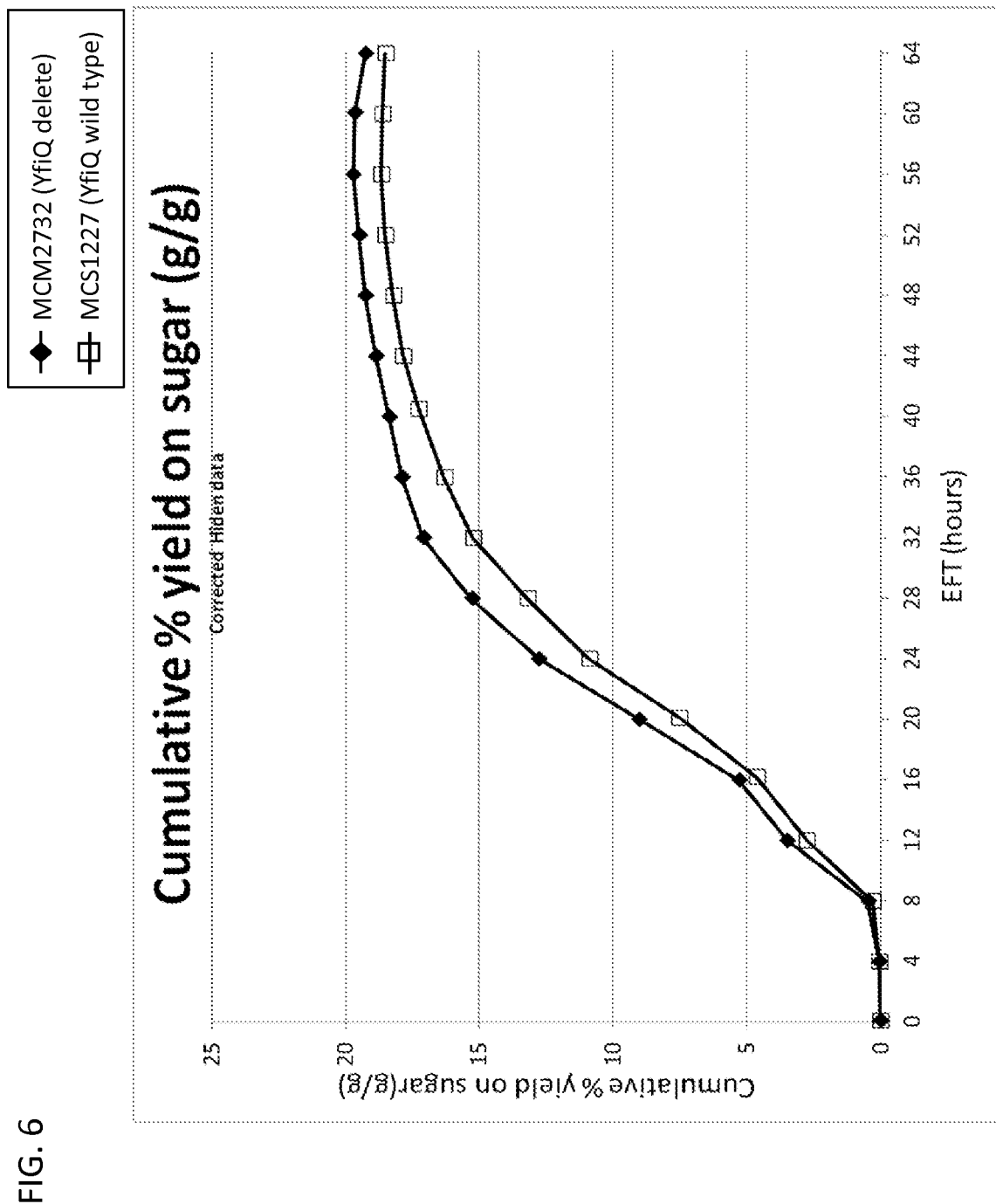
FIG. 6 depicts cumulative yield of isoprene on glucose achieved in each 15-L fermentation over time. MCM2732 (yfiQ delete) (closed diamonds); MCS1227 (yfiQ wild type) (open squares).

Cumulative yield of isoprene on glucose achieved in each 15-L fermentation over time is shown in FIG. 6. The experimental cells carrying the yfiQ deletion (MCM2732) finishes with a higher cumulative yield of isoprene on glucose than the control cells that are wild type for yfiQ. The lower broth acetate in for MCM2732 represents less lost carbon but efficiency gain is more than can be explained by the recapture of the lost acetate carbon. The 64 hr points were used to populate Table 3-3 above. Overall yield was calculated using the following formula:

% wt Yield on glucose=Isoprene total ($t$)/[(Feed Wt(0)−Feed Wt($t$)+83.5)*0.59)], where 0.59 is the wt % of glucose in the glucose feed solution and 83.5 is the grams of this feed batched into the fermenter at t=0. Each feed had its weight % measured independently.

Figure 7:
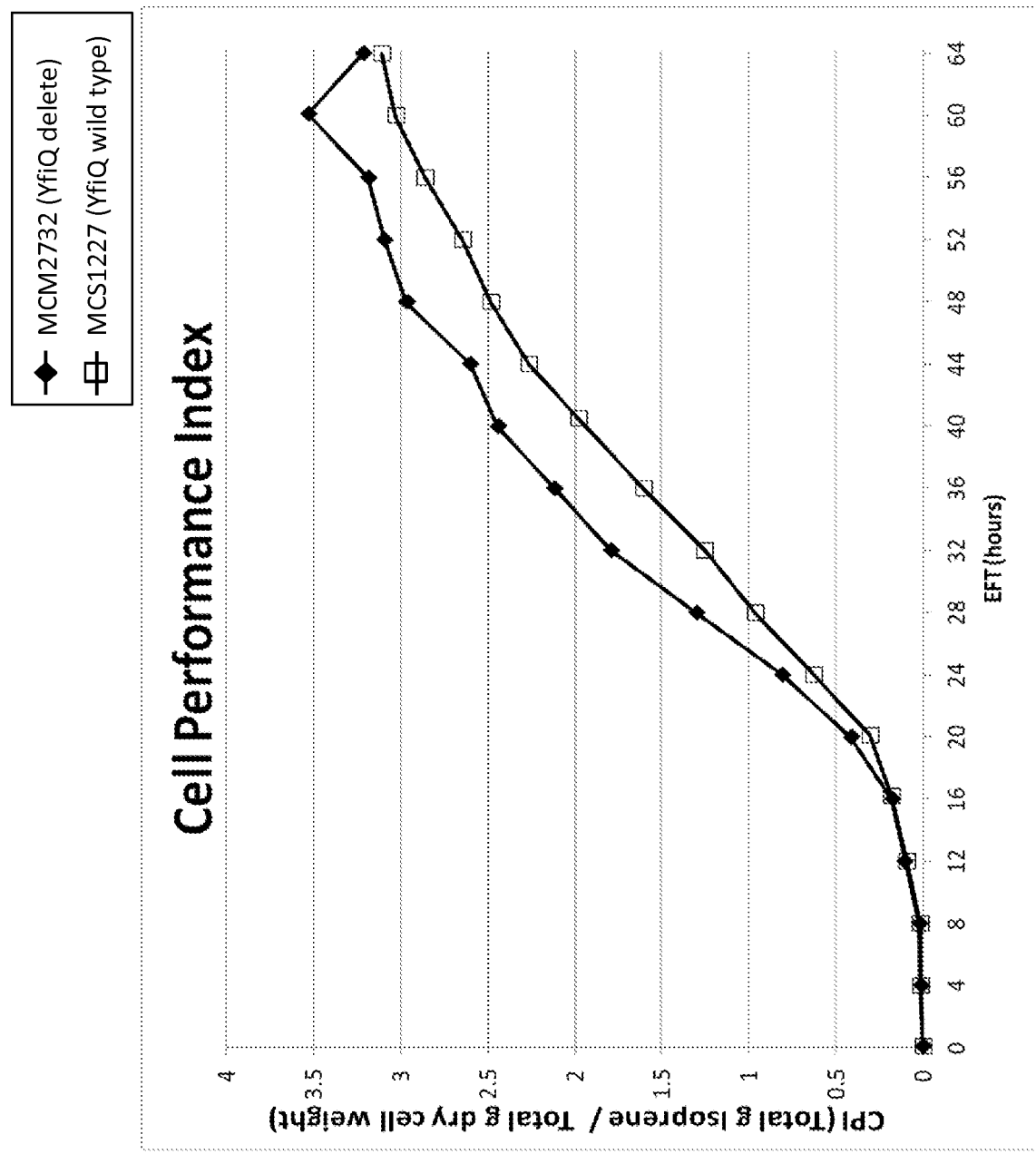
FIG. 7 depicts Cell Performance Index (CPI) achieved in each 15-L fermentation over time. MCM2732 (yfiQ delete) (closed diamonds); MCS1227 (yfiQ wild type) (open squares).

Cell Performance Index (CPI) achieved in each 15-L fermentation over time is shown in FIG. 7. The experimental cells carrying the yfiQ deletion (MCM2732) finishes with a higher cell performance index than the control cells that are wild type for yfiQ. The 64 hr points were used to populate Table 3-3 above. CPI was calculated using the following formula:

CPI=total grams Isoprene/total grams dry cell weight

Figure 8:
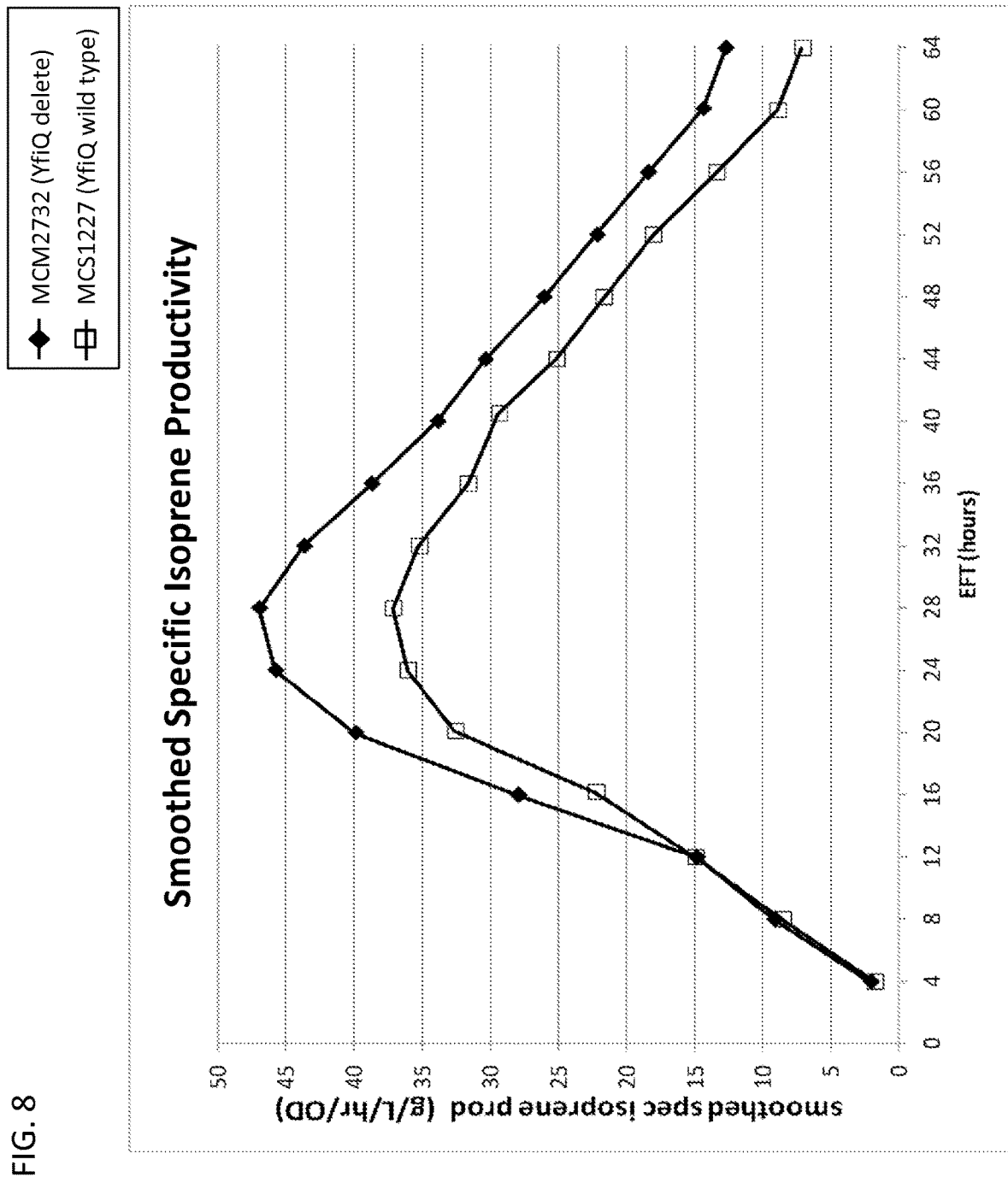
FIG. 8 depicts smoothed specific isoprene productivity achieved in each 15-L fermentation over time. MCM2732 (yfiQ delete) (closed diamonds); MCS1227 (yfiQ wild type) (open squares).

Smoothed specific isoprene productivity achieved in each 15-L fermentation over time is shown in FIG. 8. The experimental cells carrying the yfiQ deletion (MCM2732) shows a higher peak specific productivity than the control cells that are wild type for yfiQ. Presumably this is driven by the higher specific glucose uptake rate. The 64 hr points were used to populate Table 3-3 above. Smoothed specific isoprene productivity was calculated using the following formula:

Specific productivity (mg/L/hr/OD)=IspER*68.117 g/mol/OD. IspER is the isoprene Evolution Rate in (mmol/L/hr). OD=optical density=Absorbance at 550 nm*dilution factor in water.

Smoothed Specific productivity (mg/L/hr/OD)=slope of milligrams isoprene produced per hour (averaged over 8 hour interval)/broth volume*OD The results of these assays suggest that the yfiQ deletion results in a strain (MCM2732) that does not accumulate acetate in the broth during this isoprene production process (FIG. 3). MCM2732 kept a consistently low broth concentration of acetate throughout the fermentation run. Presumably, and without being bound to theory, this is because the gene encoding yfiQ has been deleted leading to decreased acetylation of acetyl-CoA synthetase. Decreased acetylation of acetyl-CoA synthetase remains active and free to take up acetate from the broth. In contrast, control cells MCS1227 accumulated about 6 g/L of acetate and this is typical of what occurs is isoprene producing cells carrying a deletion for ackA. Presumably, and without being bound to theory, this is due to the fact that once acetate gets out of the cell, it cannot again be taken up by acetate kinase, since the gene encoding this polypeptide has been deleted. In conclusion, the yfiQ deletion (MCM2732 stain) results in a higher specific glucose uptake rate (FIG. 4) which in turn has a number of beneficial effects on isoprene performance (FIG. 5).

Example 4: Effect of yfiQ Deletion on Growth Rate and Isoprene Production in Cells Grown with Acetate The example explores the effect of deletion of yfiQ on cellular growth rate and isoprene production when cells are cultured in the presence of acetate.

I. Materials and Methods

LB media, TM3 media without yeast extract and MgSO$_4$, 10% yeast extract, 1M MgSO$_4$, 50% glucose, 200 mM IPTG, 50 mg/mL spectinomycin, 50 mg/mL carbenicillin, 10% sulfuric acid and 100 mM Tris, 100 mM NaCl pH 7.6 buffer were prepared in-house. Aluminum foil seal, 48-well sterile 5 mL block, Breathe Easier sealing membrane, 96-well micro titer plates were purchased from VWR. 96-well glass block was purchased from Zinsser Analytical. Sodium acetate was purchased from Sigma. Agilent 6890 GC was equipped with a 5973N Mass spectrometer. A summary of the isoprene-producing cells used in the example is in Table 4-1.

TABLE 4-1

Summary of Isoprene-Producing Cells

| Strain Name | Genotype |
| --- | --- |
| MCM2732 | MD891 + FRT-kan-FRT::YfiQ FRT-cmp-FRT::PL.2-pta pMCS1019 pMCM1225 |
| MCS1316 | MD891 + FRT::PL.2-pta pMCS1019 pMCM1225 |

Overnight cultures were prepared directly from glycerol culture stocks in 3 mL of LB media with appropriate antibiotics in 10 mL plastic test tubes. Overnight cultures were grown at 30° C., 220 rpm.

Supplemented TM3 media was prepared by combining TM media, (without MgSO$_4$ and yeast extract) 1% glucose or various concentrations of sodium acetate, 8 mM MgSO$_4$, 0.02% yeast extract and appropriate antibiotics. 2 mL of day cultures were prepared in 48-well sterile block by inoculating overnight culture in supplemented TM3 media at 0.2 optical density (OD). Blocks were sealed with Breathe Easier membranes and incubated for 2 hours at 34° C., 600 rpm. After 2 hours of growth, OD was measured at 600 nm in the micro-titer plate and cells were induced with 200 µM of IPTG. OD reading and isoprene specific productivity samples were taken from 2-6 hours post induction. OD measurement was done in the micro-titer plate at appropriate dilution in the TM3 media at 600 nm using a SpectraMax Plus190 (Molecular Devices).

100 µl of isoprene samples were collected in a 96 well glass block every hour after IPTG induction for 4 hours.

Glass block was sealed with aluminum foil and incubated at 34° C. while shaking at 450 rpm, for 30 minutes on the thermomixer. After 30 minutes, the block was kept at 70° C. water bath for 2 minutes and isoprene headspace measurement was done in GC/MS.

II. Results

Figure 9:
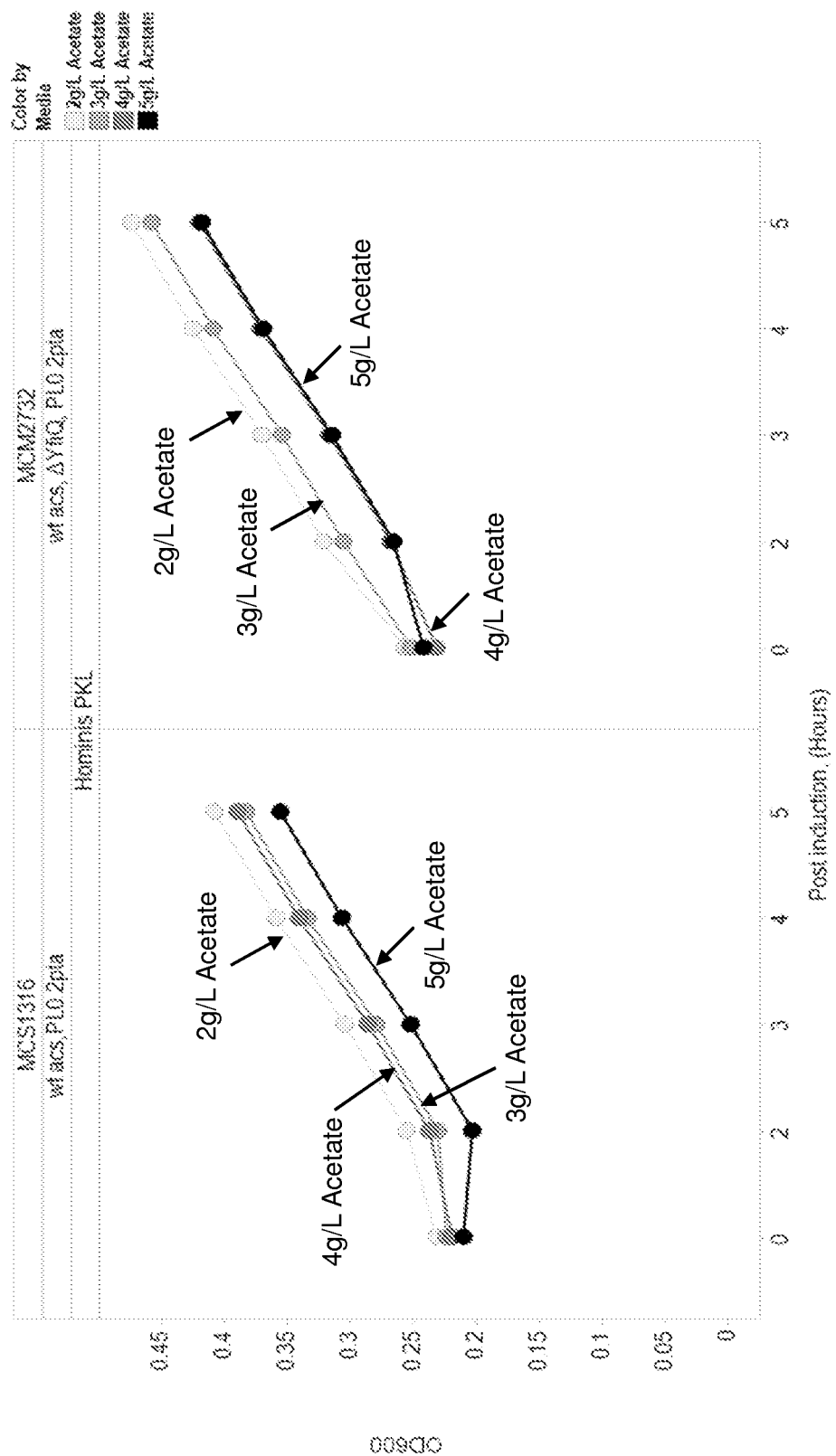
FIG. 9 depicts growth rates of yfiQ wild type and yfiQ deletion isoprene-producing cells grown on various concentrations of acetate as a sole carbon source.
Figure 10:
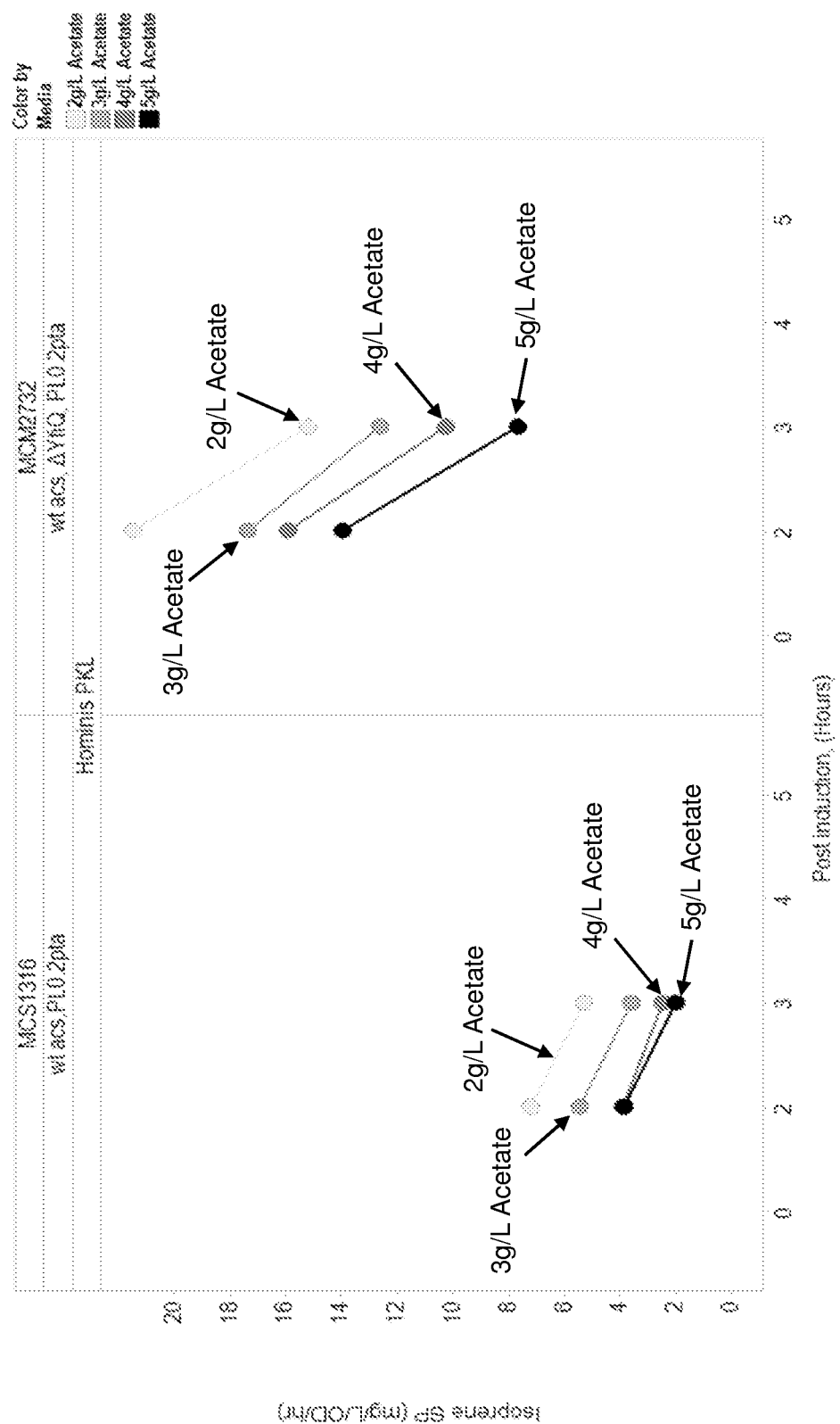
FIG. 10 depicts specific isoprene productivity of yfiQ wild type and yfiQ deletion isoprene producing cells grown on various concentrations of acetate as a sole carbon source.
Figure 11:
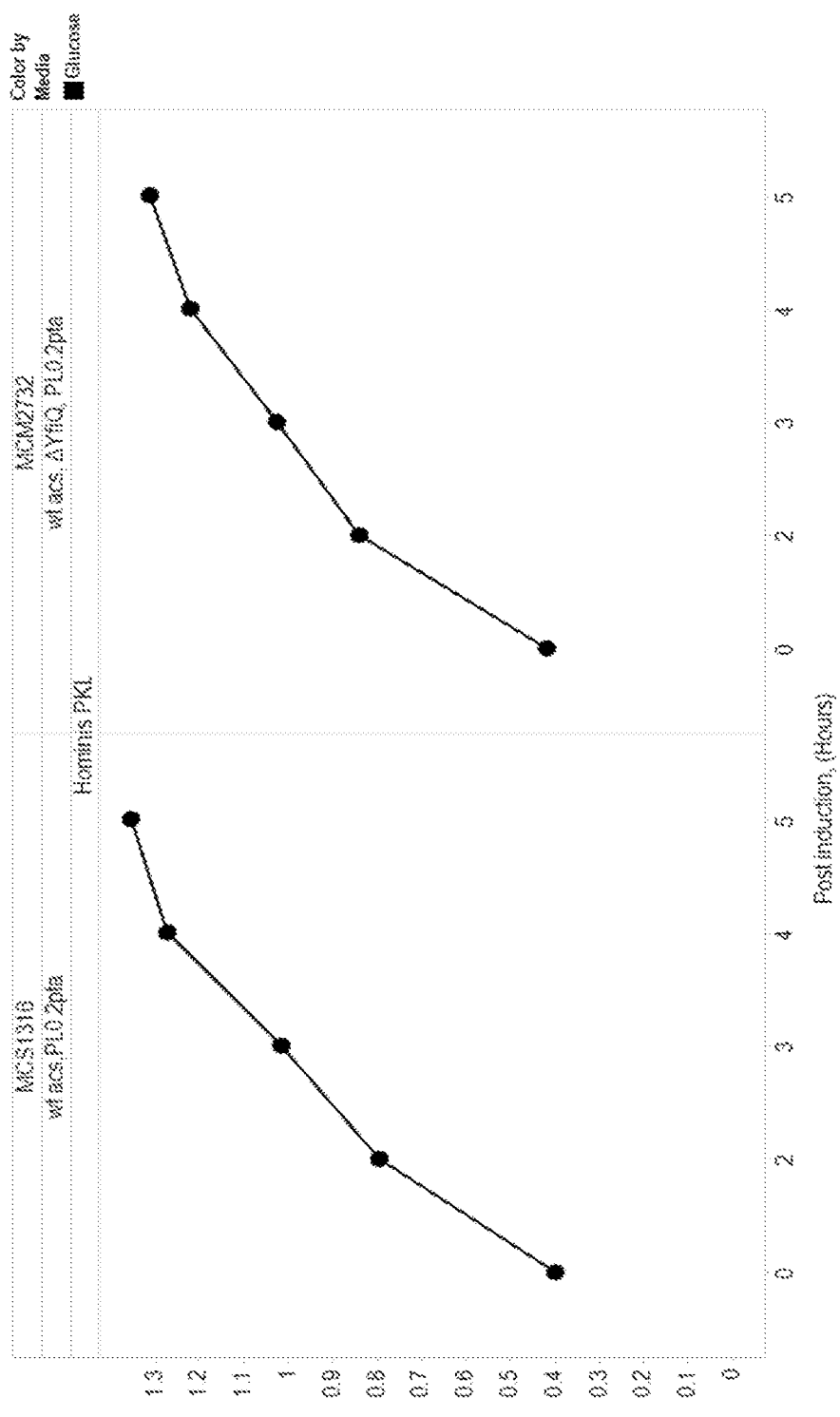
FIG. 11 depicts growth rates of yfiQ wild type and yfiQ deletion isoprene-producing cells grown on glucose as a sole carbon source.
Figure 12:
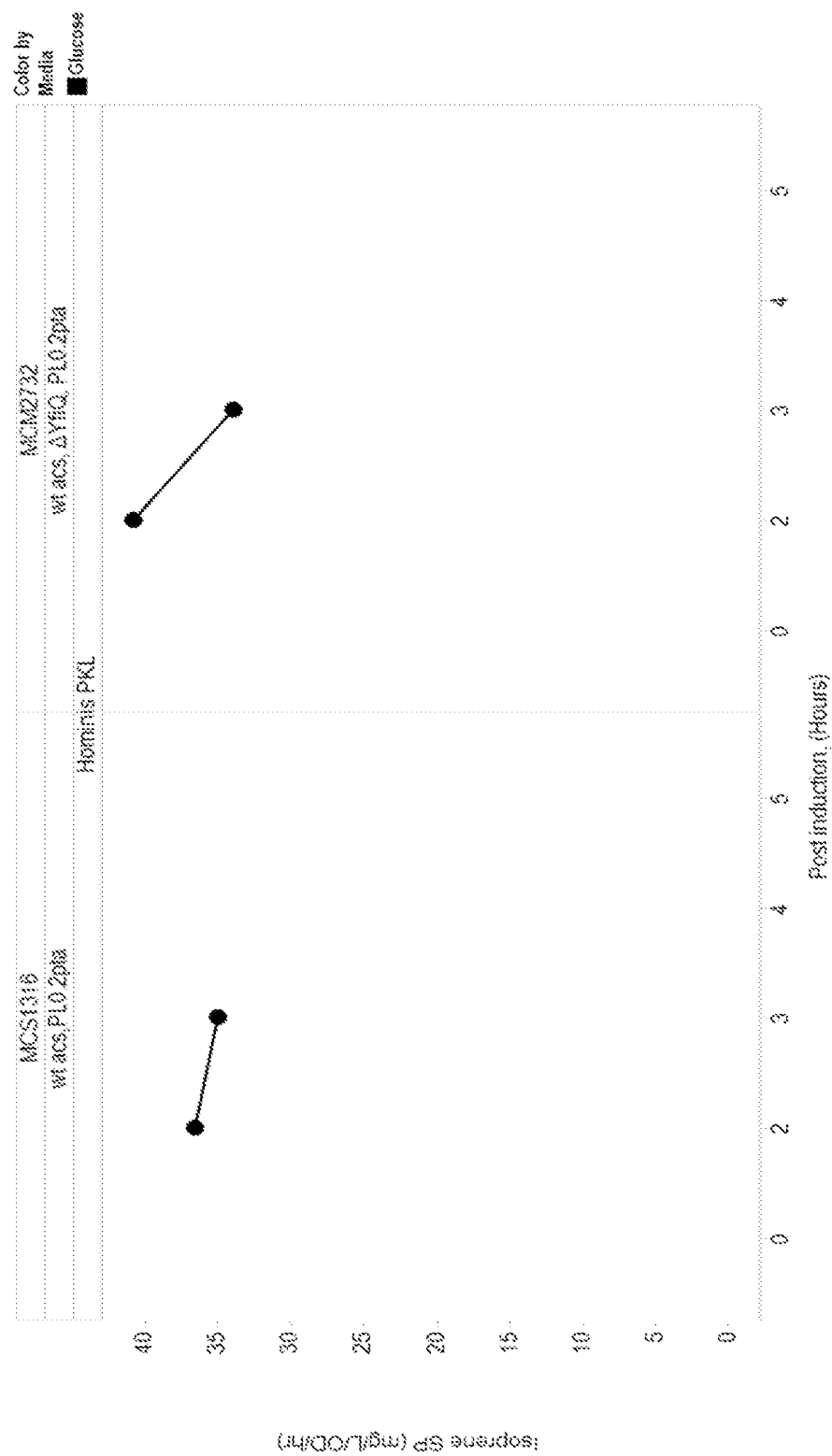
FIG. 12 depicts specific isoprene productivity of yfiQ wild type and yfiQ deletion isoprene-producing cells grown on glucose as a sole carbon source.

The growth rates of wild type and delta yfiQ isoprene producing cells grown on various concentrations of acetate as a sole carbon source are shown in FIG. 9 while isoprene specific productivity is shown in FIG. 10. In contrast, growth rates of wild type and delta yfiQ isoprene producing cells grown using glucose as a sole carbon source are shown in FIG. 11 while isoprene specific productivity is shown in FIG. 12 for this set of conditions.

Example 5: Effects of yfiQ Gene Deletion on Isoprenoid Production in Cells

This example is performed to evaluate isoprenoid production using modified *E. coli* cells which express introduced genes from the mevalonate pathway and farnesyl pyrophosphate (FPP) synthase (e.g. farnesene synthase codon-optimized for *E. coli* (SEQ ID NO:26) or amorphadiene synthase codon-optimized for *E. coli* (SEQ ID NO:25)); geranyl pyrophosphate synthase; or geranylgeranyl pyrophosphate synthase; and are grown in fed-batch culture at the 15-L scale. The cell lines in this experiment carry a deletion in the gene encoding the acetate kinase (AckA) polypeptide and express an *M. hominis* phosphoketolase. Additionally, both over express phosphotransacetylase (pta).

These isoprenoid producing cells are run in the same process. The performance metrics of a control cells are compared to experimental cells that has been deleted for yfiQ, a lysine acetyltransferase or have increased expression of cobB, a deacetylase. The relevant performance metrics are cumulative isoprenoid yield on glucose, volumetric productivity of isoprenoid and cell performance index.

I. Construction of Isoprenoid Producing Cells

Using standard techniques, an farnesyl pyrophosphate (FPP) synthase (e.g. farnesene synthase codon-optimized for *E. coli* (SEQ ID NO:26) or amorphadiene synthase codon-optimized for *E. coli* (SEQ ID NO:25)); geranyl pyrophosphate synthase; or geranylgeranyl pyrophosphate synthase gene is cloned in place of ispS in either pMCS1019 or pEWL1421. The resulting plasmid is co-transformed with pMCM1225 into a host strain. A partial list of host strains are described in Table 5.

TABLE 5

Summary of Host Strains

| Host Strain | Genotype |
| --- | --- |
| MCM2721 | MD891 + YfiQ::FRT-kan-FRT |
| MCM2722 | MCM2721 with kan looped out |
| MCM2736 | MD891 + CobB::FRT-kan-FRT |
| MCM2740 | MD891 + FRT-kan-FRT-gi1.6-YfiQ |
| MCM2742 | MD891 + FRT-kan-FRT-gi1.6-CobB (BL21 ATG) |
| MCM2754 | MCM2736 with kan looped out |
| MCM2760 | MCM2740 with kan looped out |
| MCM2764 | MCM2742 with kan looped out |
| MCM2801 | CTO pgl-FRT-PL.2-2cis-RBS10000-MVK(*burtonii*) yfiQ::FRT-kan-FRT clone A |
| MCM2804 | CTO pgl-FRT-PL.2-2cis-RBS10000-MVK(*burtonii*) yfiQ::FRT clone 1 |
| MCM3083 | CTO pgl-FRT-PL.2-2cis-RBS10000-MVK(*burtonii*) yfiQ::FRT pta::FRT-kanR-FRT clone A |
| MCM3139 | CTO pgl-FRT-PL.2-2cis-RBS10000-MVK(*burtonii*) yfiQ::FRT pta::FRT-kanR-FRT clone A FRT-cmp5-FRT::gi1.6-acs |
| MD1243 | CTO pgl-FRT-PL.2-2cis-RBS10000-MVK(*burtonii*) yfiQ::FRT pta::FRT clone A, FRT::gi1.6-acs, i actP::ML |
| DW1242 | CTO pgl-FRT-PL.2-2cis-RBS10000-MVK(*burtonii*) yfiQ::FRT pta::FRT clone A, FRT::gi1.6-acs, i gi1.6ackA |
| MD1280 | CTO pgl-FRT-PL.2-2cis-RBS10000-MVK(*burtonii*) pta::FRT clone A, FRT::Gi1.6-acs, i yfiQ::Gi1.2-rpe_tktA_rpiA_talB ML |
| MD1281 | CTO pgl-FRT-PL.2-2cis-RBS10000-MVK(*burtonii*) pta::FRT clone A, FRT::Gi1.6-acs, i pfkA_tag T ML, i yfiQ::Gi1.2-rpe_tktA_rpiA_talB ML |
| MD1282 | CTO pgl-FRT-PL.2-2cis-RBS10000-MVK(*burtonii*) pta::FRT clone A, FRT::Gi1.6-acs, i pfkA_tag I ML, i yfiQ::Gi1.2-rpe_tktA_rpiA_talB ML |
| MD1283 | CTO pgl-FRT-PL.2-2cis-RBS10000-MVK(*burtonii*) pta::FRT clone A, FRT::Gi1.6-acs, i pfkA_tag R ML, i yfiQ::Gi1.2-rpe_tktA_rpiA_talB ML |

II. Materials and Methods

Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 50% sulfuric acid 1.6 mL, 1000× Modified Trace Metal Solution 1 mL. All of the components are added together and dissolved in Di $H_2O$. This solution is heat sterilized (123° C. for 20 minutes). The pH is adjusted to 7.0 with ammonium hydroxide (28%) and q.s. to volume. Glucose 10 g, Vitamin Solution 8 mL, and antibiotics are added after sterilization and pH adjustment.

1000× Modified Trace Metal Solution (Per Liter):

Citric Acids*$H_2O$ 40 g, $MnSO_4*H_2O$ 30 g, NaCl, 10 g, $FeSO_4*7H_2O$, 1 g, $CoCl_2*6H_2O$ 1 g, $ZnSO*7H_2O$ 1 g, $CuSO_4*5H_2O$, 100 mg, $H_3BO_3$ 100 mg, $NaMoO_4*2H_2O$ 100 mg. Each component is dissolved one at a time in Di $H_2O$, pH are adjusted to 3.0 with HCl/NaOH, and then the solution is q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component is dissolved one at a time in Di $H_2O$, pH are adjusted to 3.0 with HCl/NaOH, and then the solution is q.s. to volume and filter sterilized with 0.22 micron filter.

Macro Salt Solution (Per Liter):

$MgSO_4*7H_2O$ 296 g, citric acid monohydrate 296 g, ferric ammonium citrate 49.6 g. All components are dissolved in water, q.s. to volume and filter sterilized with 0.22 micron filter.

Feed Solution (Per Kilogram):

Glucose 0.590 kg, Di $H_2O$ 0.393 kg, $K_2HPO_4$ 7.4 g, and 100% Foamblast882 8.9 g. All components are mixed together and autoclaved. After autoclaving the feed solution, nutrient supplements are added to the feed bottle in a sterile hood. Post sterilization additions to the feed are (per kilogram of feed solution), Macro Salt Solution 5.54 mL, Vitamin Solution 6.55 mL, 1000× Modified Trace Metal Solution 0.82 mL. For a target of 100 µM IPTG: 1.87 mL of a sterile 10 mg/mL solution is added per kilogram of feed.

This experiment is carried out to monitor isoprenoid production from glucose at the desired fermentation pH (7.0) and temperature (34° C.). To start each experiment, the appropriate frozen vial of the *E. coli* isoprenoid producing cells is thawed and inoculated into a flask with tryptone-yeast extract (LB) medium and the appropriate antibiotics. After growing to an optical density of approximately 1.0, measured at 550 nm ($OD_{550}$), 500 mL is used to inoculate a 15-L bioreactor and bring the initial tank volume to 5 L.

The inlet gas using to maintain bioreactor backpressure at 0.7 bar gauge and to provide the oxygen to the cells is supplied by in house facilities that dilute the inlet gas to a known concentration (7.3 to 8.3 vol % oxygen).

primers acsAUppKD3 and acsADnGI1.6pKD3R. The resulting PCR product, FRT-cmp-FRT::gi.6-acs, was transformed into strain HMB carrying the pRedET plasmid following the GeneBridges protocol and recombinants were selected at 37° C. on LB cmp5 plates. The HMB genotype is: BL21 wt, pgl+t PL.2-mKKDyI::FRT. A colony was confirmed to be cmpR and carbS and then frozen as CMP400.

TABLE 6-1

Primer Sequences

| acsAUppKD3 | tcacgacagtaaccgcacctacactgtcatgacattgctcgcccctatgtgtaacaaa taaccacactgcccatggtccatatgaatatcctcc | SEQ ID NO: 59 |
|---|---|---|
| acsADnGI1.6pKD3R | caacggtctgcgatgttggcaggaatggtgtgtttgtgaatttggctcatatataattcc tcctgctatttgttagtgaataaaagtggttgaattatttgctcaggatgtggcattgtca agggcgtgtaggctggagctgcttcg | SEQ ID NO: 60 |

The batched media has glucose batched in at 9.7 g/L. Induction is achieved by adding isopropyl-beta-D-1-thiogalactopyranoside (IPTG). A syringe containing a sterile solution of IPTG is added to bring the IPTG concentration to 100 µM when the cells are at an $OD_{550}$ of 6. Once the glucose is consumed by the culture, as signaled by a rise in pH, the glucose feed solution is fed to meet metabolic demands at rates less than or equal to 10 g/min. At a fixed time after dissolved oxygen limitation is established, the temperature is raised from 34° C. to 37° C. over the course of one hour. The fermentation is run long enough to determine the maximum cumulative isoprenoid mass yield on glucose, typically a total of 64 hrs elapsed fermentation time (EFT).

Isoprenoid, Oxygen, Nitrogen, and Carbon Dioxide levels in the off-gas are determined independently by a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermenter broth is determined in broth samples taken at 4 hour intervals by an HPLC analysis. Concentration in broth samples are determined by comparison of the refractive index response versus a previously generated calibration curve using standard of a known concentration.

HPLC information is as follows: System: Waters Alliance 2695; Column: BioRad—Aminex HPX-87H Ion Exclusion Column 300 mm×7.8 mm Catalog #125-0140; Column Temperature: 50° C.; Guard column: BioRad—Microguard Cation H refill 30 mm×4.6 mm Catalog #125-0129; Running buffer: 0.01N $H_2SO_4$; Running buffer flow rate: 0.6 mL/min; Approximate running pressure: ~1100-1200 psi; Injection volume: 20 microliters; Detector: Refractive Index (Knauer K-2301;) Runtime: 26 minutes.

Example 6: Construction of Acetate Cycling Strains

This Example describes the construction of strains containing additional mutations in genes responsible for the modulation of acetate cycling, acetate production, and acetyl-CoA production. This examples describes the construction of strains carrying a deletion of phosphotransacetylase (pta) and a deletion of the yfiQ gene.

I. Construction of CMP400
A chloramphenicol resistance-marked constitutive gi1.6 promoter was inserted in front of the acs gene using GeneBridges protocols. The FRT-gb2-cm-FRT cassette was PCR amplified from plasmid supplied by GeneBridges using II. Construction of MD803
A 4.429 kb PCR fragment, Pta::Kan, was amplified from Keio Collection using primers CMP534 and CMP535. Approximately ~300 ng of this PCR product was used to integrate into the host strain CMP1141 (HMB Gi1.2gltA yhfSFRTPyddVIspAyhfS thiFRTtruncIspA pgl ML (pgl (-))+pRedETAmp). The transformants were selected at 37° C. on LA+Kan10 plates. The mutants were later verified with the same set of primers. The resulting strain was named MD803 (CMP1141+i pta::Kan).

TABLE 6-2

Primer Sequences

| CMP534 | ackACF | gtgcaaattcacaactcagcgg | SEQ ID NO: 61 |
|---|---|---|---|
| CMP535 | PtaCR | caccaacgtatcgggcattgc | SEQ ID NO: 62 |

III. Construction of MCM3151
Strain MCM2065 (BL21, Δpgl PL.2mKKDyI, GI1.2gltA, yhfSFRTPyddVIspAyhfS, thiFRTtruncIspA, bMVK) was transduced with a P1 lysate of MCM2722 (Example 1) using standard methods, with yfiQ::kanR transductants selected on LB kan10 plates at 37° C. overnight. Transductants were restreaked and confirmed by PCR. This strain was grown in LB kan10 and frozen as MCM2801. The kanR marker was looped out by transformation of plasmid pCP20 (see worldwide web cgsc.biology.yale.edu/Site.php?ID=64621), selection on LB carb50 at 30° C. overnight followed by passage of a single colony at 37° C. in liquid LB carb50 until visibly turbid. Culture was streaked on LB without antibiotics and grown at 37° C. overnight. Single colonies were patched to plates with and without antibiotics and a carbS, kanS colony was identified. PCR was used to confirm the presence of a wildtype ackA locus and an unmarked ΔyfiQ locus. This colony was grown in LB at 37° C. and frozen as MCM2804. A P1 lysate from MD803 was used to transduce MCM2804 with pta::FRT-kan-FRT, with transductants selected on LB kan10 plates at 37° C. overnight. A colony was restreaked on LB kan10, grown in liquid broth and frozen as MCM3803. A P1 lysate grown on MCS1388, a subclone of CMP400, was used to transduce MCM3803 with FRT-cmp-FRT::gi.6-acs. Transductants were selected on LB cmp5 plates at 37° C. overnight. A colony was streaked on LB cmp5, grown overnight, and then a resulting single colony was used to inoculate a liquid culture. This culture was frozen as MCM3139. Plasmids pMCM1225 and pMCS1019 were co-electroporated into MCM3139 and transformants selected on a LB carb50 spec50 plate incubated at 37° C. overnight. A single colony was grown in liquid LB carb50 spec50 at 37° C. and frozen as MCM3151.

TABLE 6-3

Descriptions of Cells

| MCM # | Genotype | Parent |
|---|---|---|
| MCM2801 | CTO pgl-FRT-PL.2-2cis-RBS10000-MVK(*burtonii*) yfiQ::FRT-kan-FRT clone A | MCM2065 |
| MCM2804 | CTO pgl-FRT-PL.2-2cis-RBS10000-MVK(*burtonii*) yfiQ::FRT clone 1 | MCM2801 |
| MCM3083 | CTO pgl-FRT-PL.2-2cis-RBS10000-MVK(*burtonii*) yfiQ::FRT pta::FRT-kanR-FRT clone A | MCM2804 |
| MCM3139 | CTO pgl-FRT-PL.2-2cis-RBS10000-MVK(*burtonii*) yfiQ::FRT pta::FRT-kanR-FRT clone A FRT-cmp5-FRT::gi1.6-acs | MCM3083 |
| MCM3151 | CTO pgl-FRT-PL.2-2cis-RBS10000-MVK(*burtonii*) yfiQ::FRT pta::FRT-kanR-FRT clone A FRT-cmp5-FRT::gi1.6-acs + pMCS1019 + pMCM1225 | MCM3139 |

IV. Construction of Isoprene Producing Cells MD1206 (*M. hominis* Phosphoketolase) and MD1207 (*E. gal* Phosphoketolase)

MCM3139 was inoculated and grown overnight. The culture was diluted and grown to OD 0.8-1.0, then were washed and electroporated with plasmid pCP20 (see worldwide web cgsc.biology.yale.edu/Site.php?ID=64621). The culture was recovered for 1 hour at 30° C. Transformants were selected on LA+Carb50 plates and incubated overnight at 30° C. The resulting CmR marker-less strain was named MD1205 (CTO pgl-FRT-PL.2-2cis-RBS10000-MVK(*burtonii*) yfiQ::FRT pta::FRT clone A, FRT::gi1.6-acs).

MD1205 was co-transformed with pMCM1225 and pMCS1019 to generate MD1206 or pMCM1225 and pEWL1421 to generate MD1207. Transformants were selected on LA+Spec50+Carb50 plates.

TABLE 6-4

Descriptions of Cells

| MCM3139 | CTO pgl-FRT-PL.2-2cis-RBS10000-MVK(*burtonii*) yfiQ::FRT pta::FRT-kanR-FRT clone A FRT-cmp5-FRT::gi1.6-acs |
|---|---|
| MD1205 | CTO pgl-FRT-PL.2-2cis-RBS10000-MVK(*burtonii*) yfiQ::FRT pta::FRT clone A, FRT::gi1.6-acs |
| MD1206 | CTO pgl-FRT-PL.2-2cis-RBS10000-MVK(*burtonii*) yfiQ::FRT pta::FRT clone A, FRT::gi1.6-acs + pMCM1225 + pMCS1019 |
| MD1207 | CTO pgl-FRT-PL.2-2cis-RBS10000-MVK(*burtonii*) yfiQ::FRT pta::FRT clone A, FRT::gi1.6-acs + pMCM1225 + pEWL1421 |

Example 7: Effects of Example 6 Strains on Isoprene Yield

This example measures isoprene production in cells carrying a deletion of phosphotransacetylase (pta) and a deletion of the yfiQ gene. Cell details are provided in Table 7-1.

Figure 28:
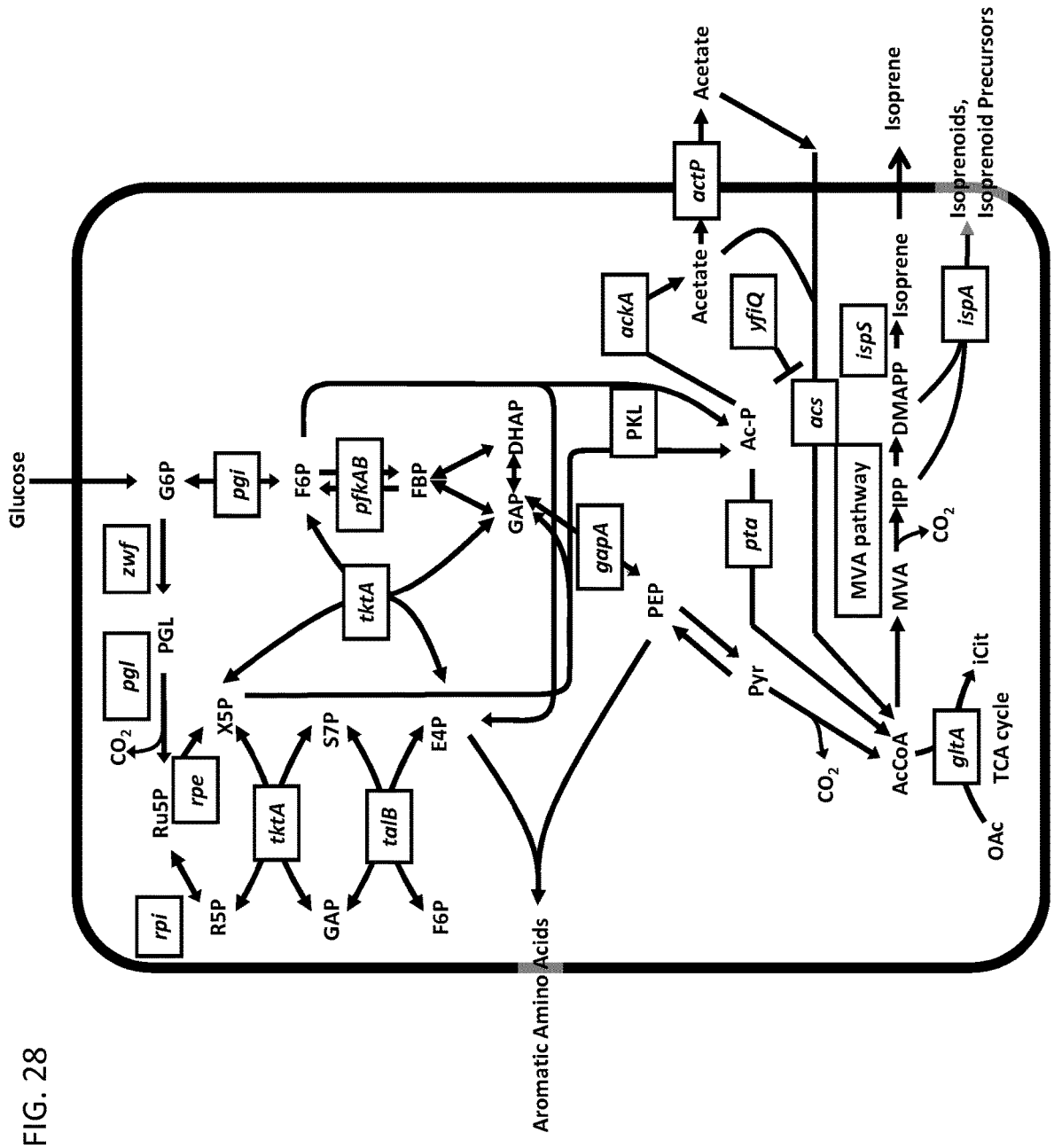
FIG. 28 depicts metabolism in a cell producing mevalonate, isoprene, isoprenoids, isoprenoid precursors, and/or acetyl-CoA-derived products.

Strain MCM2732 with the deletion of yfiQ and acs constitutively active displayed improved acetate reuptake and isoprene production. The improved reuptake of acetate significantly lowered acetate accumulation associated with ackA minus strains, as well as increased isoprene specific productivity, and improved viability, extending the productive portion of the run, which increased isoprene titer. This example uses MCM3151, MD1206, and MD1207 which enhance the acetate reuptake by deleting pta and thereby increasing phosphoketolase flux (AcP to isoprene) (FIG. 28).

TABLE 7-1

Cells Used in the Example

| Host | Upper pathway plasmid | Isoprene synthase/Phosphoketolase plasmid |
|---|---|---|
| MD1207 | CTO pgl bLP GI1.6acsA pta- | IPTG inducible Ptrc expressing *E. gallinarum* mvaE, mvaS (pMCM1225 Spec 50) | IPTG inducible (pTrc IspS *E. gal* PKL) (Carb 50) |
| MD1206 | CTO pgl bLP GI1.6acsA pta- | IPTG inducible Ptrc expressing *E. gallinarum* mvaE, mvaS (pMCM1225 Spec 50) | IPTG inducible (pTrc IspS *M. hominis* PKL) (Carb 50) |
| MCM3151 | CTO pgl bLP GI1.6acsA:: Chlor pta::Kan | IPTG inducible Ptrc expressing *E. gallinarum* mvaE, mvaS (pMCM1225 Spec 50) | IPTG inducible (pTrc IspS *M. hominis* PKL) (Carb 50) |
| MCM2732 (Control cells) | MD891 + FRT-kan- FRT::yfiQ FRT-cmp- FRT::PL.2- pta | IPTG inducible Ptrc expressing *E. gallinarum* mvaE, mvaS (pMCM1225 Spec 50) | IPTG inducible (pTrc_IspS_RBS3_PKL16 [*M. hominis*]) (pMCS1019, Carb 50) |

I. Materials and Methods

Medium Recipe (Per Liter Fermentation Medium):

$K_2HPO_4$ 7.5 g, $MgSO_4*7H_2O$ 2 g, citric acid monohydrate 2 g, ferric ammonium citrate 0.3 g, yeast extract 0.5 g, 50% sulfuric acid 1.6 mL, 1000× Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO*7H_2O$ 1 g, $CuSO_4*5H_2O$ 100 mg, $H_3BO_3$ 100 mg, $NaMoO_4*2H_2O$ 100 mg. Each component was dissolved one at a time in Di $H_2O$, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (Per Liter):

$MgSO_4*7H_2O$ 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di $H_2O$ 0.393 kg, $K_2HPO_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml. For a target of 100 µM IPTG: 1.87 ml of a sterile 10 mg/ml solution is added per kilogram of feed.

This experiment was carried out to monitor isoprene production from glucose at the desired fermentation pH (7.0) and temperature (34° C.). To start each experiment, the appropriate frozen vial of the *E. coli* isoprene producing cells was thawed and inoculated into a flask with tryptone-yeast extract (LB) medium and the appropriate antibiotics. After the inoculum grew to an optical density of approximately 1.0, measured at 550 nm ($OD_{550}$), 500 mL was used to inoculate a 15-L bioreactor and bring the initial tank volume to 5 L.

The inlet gas using to maintain bioreactor backpressure at 0.7 bar gauge and to provide the oxygen to the cells was supplied by in house facilities that dilute the inlet gas to a known concentration (7.3 to 8.3 vol % oxygen).

The batched media had glucose batched in at 9.7 g/L. Induction was achieved by adding isopropyl-beta-D-1-thiogalactopyranoside (IPTG). A syringe containing a sterile solution of IPTG was added to bring the IPTG concentration to 100 µM when the cells were at an $OD_{550}$ of 6. Once the glucose was consumed by the culture, as signaled by a rise in pH, the glucose feed solution was fed to meet metabolic demands at rates less than or equal to 10 g/min. At a fixed time after dissolved oxygen limitation was established, the temperature was raised from 34° C. to 37° C. over the course of one hour. The fermentation was run long enough to determine the maximum cumulative isoprene mass yield on glucose, typically a total of 64 hrs elapsed fermentation time (EFT). Table 7-2 shows process conditions.

TABLE 7-2

| | Process Conditions | | |
|---|---|---|---|
| Strain Used | Batched [IPTG] (µM) | Target [IPTG] after bolus addition at ~EFT 6-8 hrs (µM) | Target [IPTG] in Feed Bottle (µM) |
| MCS922 | 1.4 | 100 | 100 |
| MCM2732 | 1.4 | 100 | 100 |

Isoprene, Oxygen, Nitrogen, and Carbon Dioxide levels in the off-gas were determined independently by a Hiden HPR20 (Hiden Analytical) mass spectrometer.

Dissolved Oxygen in the fermentation broth is measured by sanitary, sterilizable probe with an optical sensor provided Hamilton Company.

The citrate, glucose, acetate, and mevalonate concentrations in the fermenter broth was determined in broth samples taken at 4 hour intervals by an HPLC analysis. Concentration in broth samples were determined by comparison of the refractive index response versus a previously generated calibration curve using standard of a known concentration.

HPLC Information was as follows: System: Waters Alliance 2695; Column: BioRad—Aminex HPX-87H Ion Exclusion Column 300 mm×7.8 mm Catalog #125-0140; Column Temperature: 50° C.; Guard column: BioRad—Microguard Cation H refill 30 mm×4.6 mm Catalog #125-0129; Running buffer: 0.01N $H_2SO_4$; Running buffer flow rate: 0.6 ml/min; Approximate running pressure: ~1100-1200 psi; Injection volume: 20 microliters; Detector: Refractive Index (Knauer K-2301); Runtime: 26 minutes II. Results Isoprene Productivity Metrics (and EFT when the value was taken) are shown in Table 7-3.

Acetate concentration was kept low, even though pta was deleted in the experimental strains, so it would appear that acs overexpression, coupled with yfiQ deletion was sufficient to route the acetyl phosphate (from the phosphoketolase pathway) to acetyl-CoA (and onto the mevalonate pathway, producing isoprene).

The MD1207 strain did not perform as well as the other new strains. It is interesting that this strain is expressing the *E. gallinarum* phosphoketolase which typically shows a higher expression level compared to the *M. hominis* phosphoketolase. The increased lag after induction resulted in a slower growth rate, and longer time to reach DO % limitation, thereby shortening the peak productivity and the high yielding phases of the run.

TABLE 7-3

| | | | | | | | Isoprene |
| | | Overall Isoprene | | | | | Titer (gram |
| | | Volumetric | | CPI (Total g | Peak | Peak | isoprene/ |
| | Cumulative | Productivity | | isoprene/ | Specific | Instantaneous | isoprene/ |
| | % Yield of | at time of | Max | total gDCW) | Productivity | yield of | average |
| | isoprene on | max overall | Optical | at time of | (mg | isoprene | volume of |
| | glucose | isoprene yield | Density | max overall | isoprene/L/ | on glucose | tank broth |
| Strain Name | (g/g %) | (g/L/hr) | (A550) | isoprene yield | hr/OD) | (g/g %) | in Liters) |
|---|---|---|---|---|---|---|---|
| MD1207 | 19.40 | 2.04 | 106.7 | 3.36 | 43.1 | 24.5 | 122.5 |
| | (60 hrs) | (60 hrs) | (32 hrs) | (60 hrs) | (32 hrs) | (52.4 hrs) | (60 hrs) |
| MD1206 | 20.45 | 2.55 | 93.9 | 3.27 | 53.4 | 24.0 | 153.1 |
| | (60 hrs) | (60 hrs) | (28 hrs) | (60 hrs) | (28 hrs) | (48 hrs) | (60 hrs) |
| MCM3151 | 19.24 | 2.37 | 96.6 | 2.73 | 50.1 | 22.8 | 142.3 |
| | (60 hrs) | (60 hrs) | (36 hrs) | (60 hrs) | (28 hrs) | (40 hrs) | (60 hrs) |
| MCM2732 | 19.64 | 2.34 | 99.6 | 3.53 | 47.0 | 23.8 | 140.3 |
| | (60 hrs) | (60 hrs) | (24 hrs) | (60 hrs) | (28 hrs) | (48 hrs) | (60 hrs) |

Figure 16:
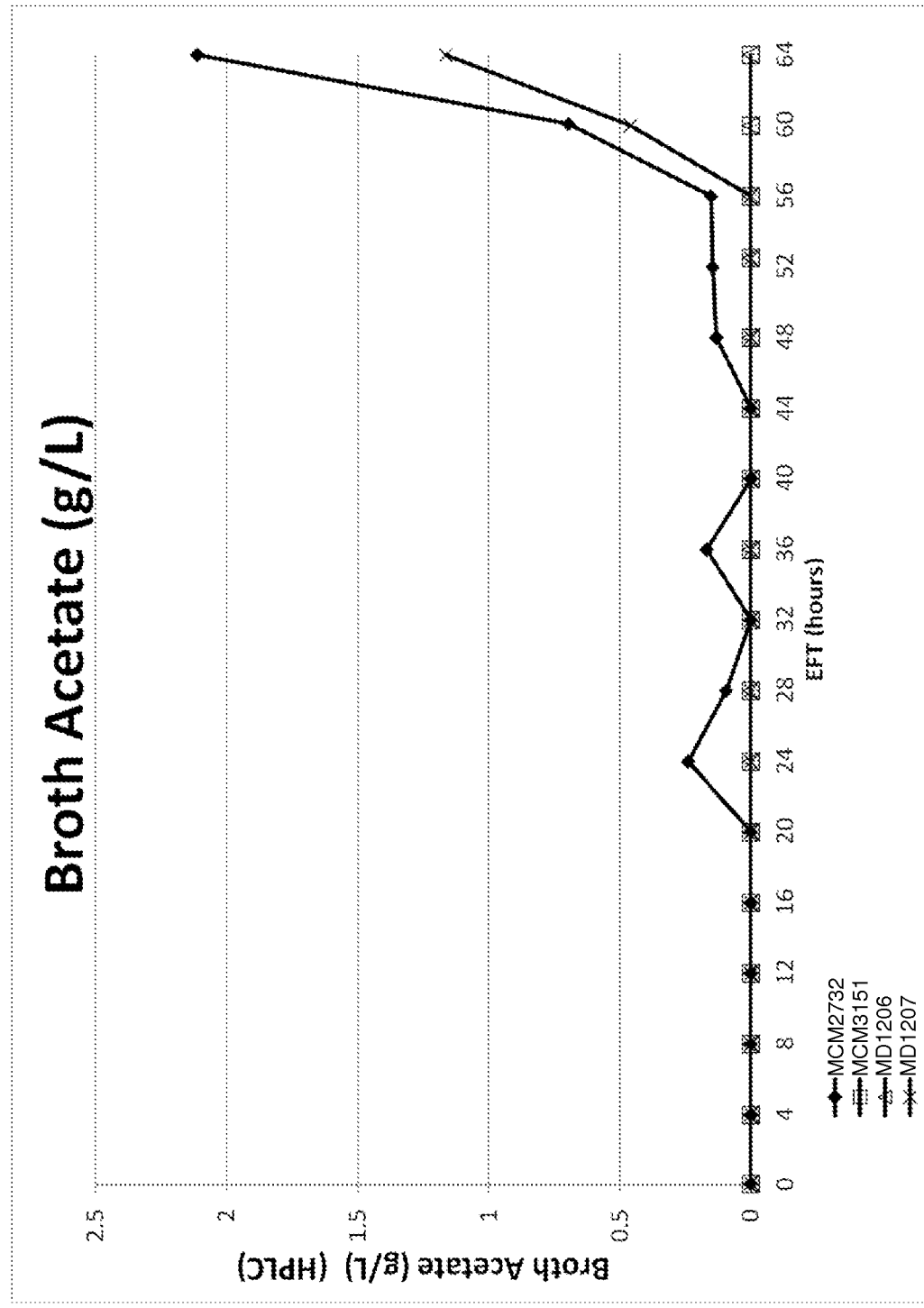
FIG. 16 depicts broth concentration of acetate measured in each 15-L fermentation over time. All cells have yfiQ deleted. MCM2732 control cells (*M. hominis* phosphoketolase heterologously express and pta overexpress) (closed diamond); MCM3151 (*M. hominis* phosphoketolase heterologously express and pta delete) (open squares); MD1206 (*M. hominis* phosphoketolase heterologously express and pta delete) (open triangles); MD1207 (*E. gallinarum* phosphoketolase heterologously express and pta delete) (lines marked with an 'x').

Broth concentration of acetate measured in each 15-L fermentation over time is shown in FIG. 16. In all cases, control and experimental, the broth concentration of acetate was very low. The experimental strains had a slightly lower acetate concentration at the end of fermentation.

Figure 17:
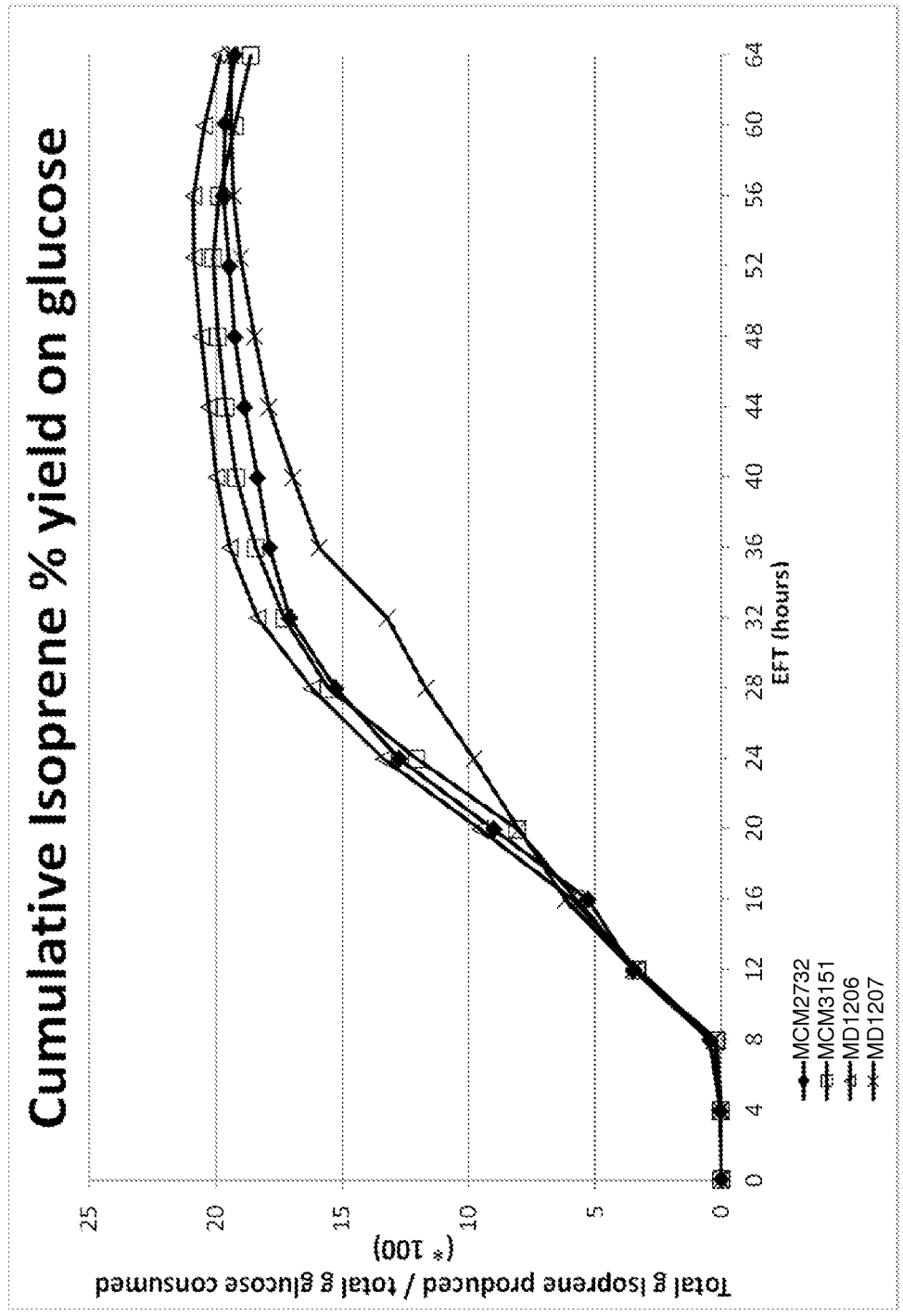
FIG. 17 depicts the cumulative yield of isoprene on glucose achieved in each 15-L fermentation over time. All cells have yfiQ deleted. MCM2732 control cells (*M. hominis* phosphoketolase heterologously express and pta overexpress) (closed diamond); MCM3151 (*M. hominis* phosphoketolase heterologously express and pta delete) (open squares); MD1206 (*M. hominis* phosphoketolase heterologously express and pta delete) (open triangles); MD1207 (*E. gallinarum* phosphoketolase heterologously express and pta delete) (lines marked with an 'x')

Cumulative yield of isoprene on glucose achieved in each 15-L fermentation over time is shown in FIG. 17. The experimental cells that are deleted for pta (MD1206) finishes with a higher cumulative yield of isoprene on glucose than the control cells that overexpresses pta (MCM2732). The 60 hr points were used to populate Table 7-3 above. Overall yield was calculated using the following formula:

% wt Yield on glucose=Isoprene total $(t)$/[(Feed Wt(0)−Feed Wt$(t)$+83.5)*0.59)], where 0.59 is the wt % of glucose in the glucose feed solution and 83.5 is the grams of this feed batched into the fermenter at t=0. Each feed had its weight % measured independently.

Figure 18:
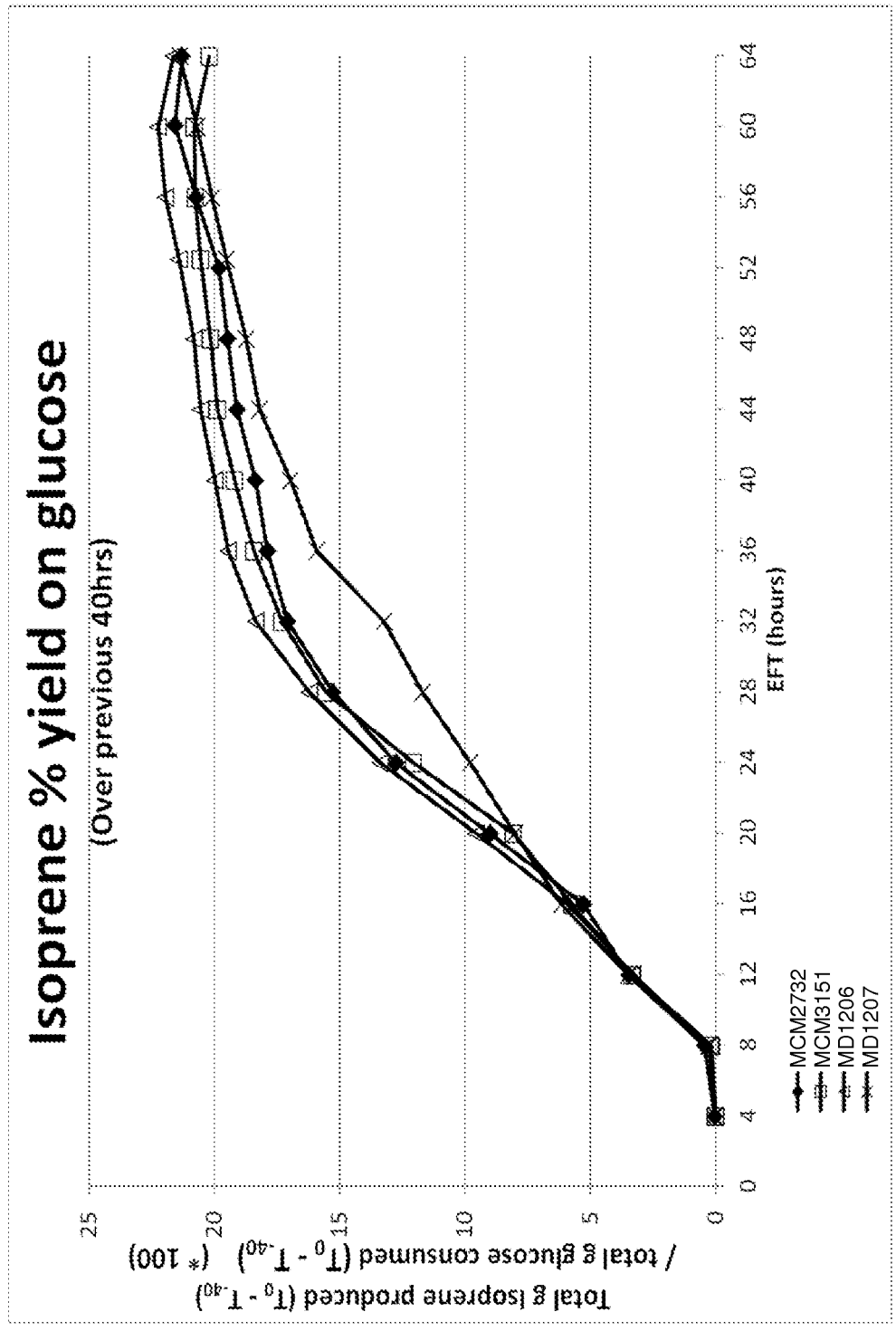
FIG. 18 depicts isoprene yield on glucose (over previous 40 hr period) achieved in each 15-L fermentation over time. All cells have yfiQ deleted. MCM2732 control cells (*M. hominis* phosphoketolase heterologously express and pta overexpress) (closed diamond); MCM3151 (*M. hominis* phosphoketolase heterologously express and pta delete) (open squares); MD1206 (*M. hominis* phosphoketolase heterologously express and pta delete) (open triangles); MD1207 (*E. gallinarum* phosphoketolase heterologously express and pta delete) (lines marked with an 'x')

Yield of Isoprene on glucose (over previous 40 hr period) achieved in each 15-L fermentation over time is shown in FIG. 18. The experimental cells that is deleted for pta (MD1206) finishes with a higher peak "40 hr" yield of isoprene on glucose than the control cells that overexpresses pta (MCM2732). "40 hr" yield was calculated using the following formula:

% wt Yield on glucose=Isoprene total $(t_{initial}-t_{-40})$/ [(Feed Wt $(t_{initial}-t_{-40})$*0.59)], where 0.59 is the wt % of glucose in the glucose feed solution. Each feed had its weight % measured independently.

Example 8: Construction of Additional Acetate Cycling Strains

This Example describes the construction of additional strains containing mutations in genes responsible for acetate production, acetate cycling, and acetyl-CoA production. The ackA gene was overexpressed to drive the conversion of acetate to acetyl-CoA. In another strain, actP was deleted to minimize transport of acetate across the membrane. Without being bound to theory, it is believed that if acetate production is coupled with transport across the membrane, this could result in energy loss due to decoupling of the proton gradient.

Figure 19:
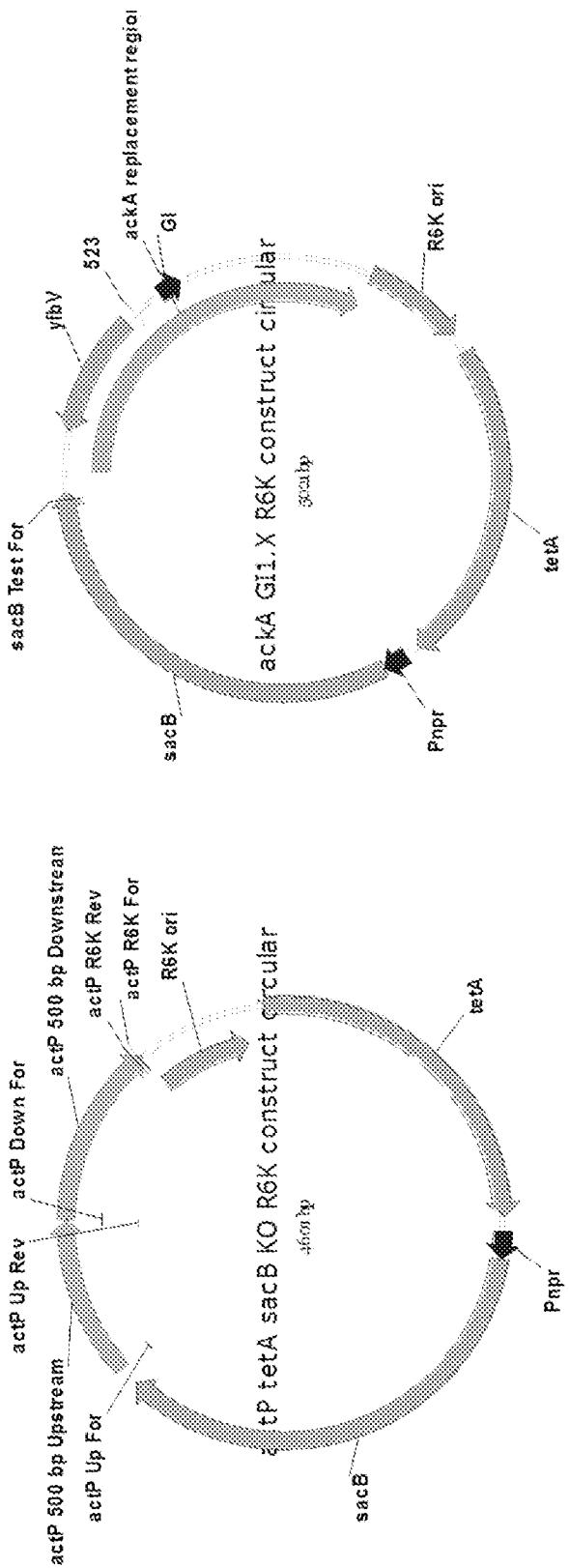
FIG. 19 depicts maps of the actP deletion and ackA overexpression allelic exchanges vectors.
Figure 20A:
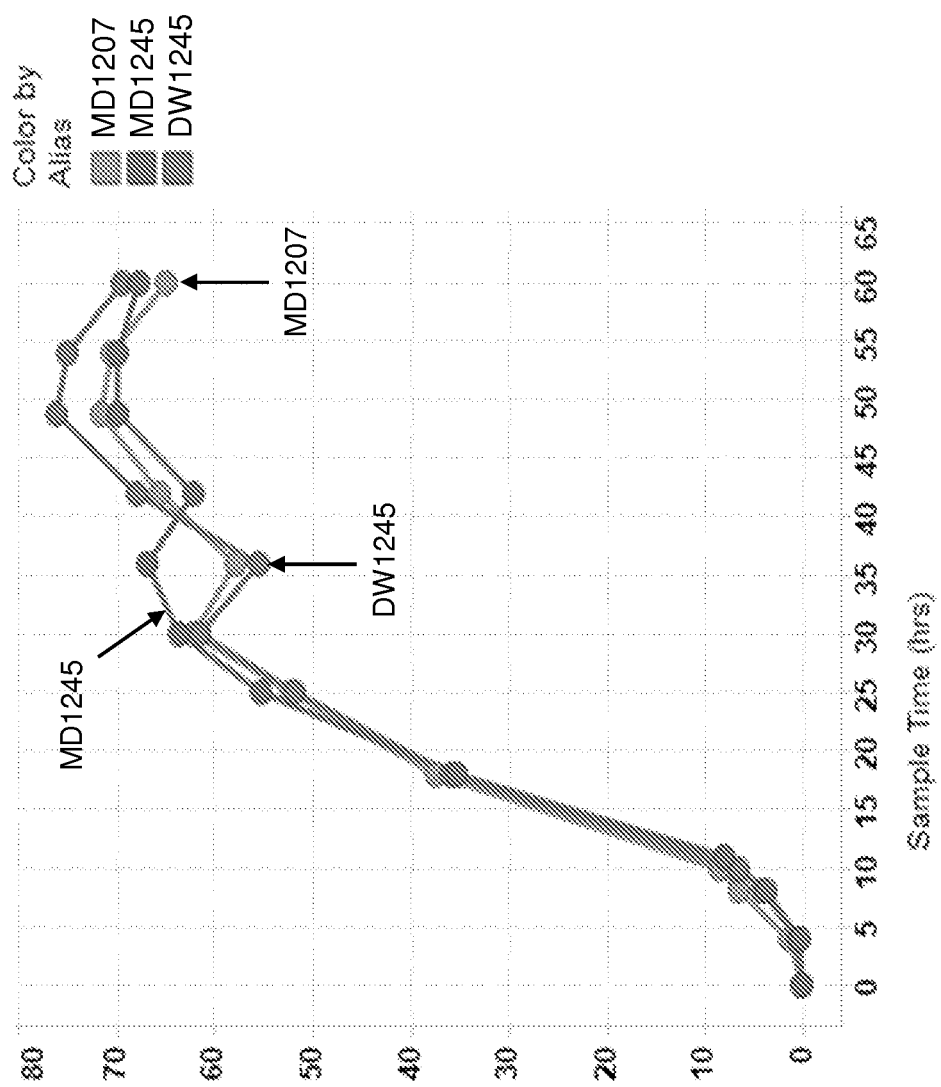
FIG. 20A-D depict the growth rate (FIG. 20A), carbon dioxide evolution rates (CER) over time (FIG. 20B), broth acetate over time (FIG. 20C), and broth MVA over time (FIG. 20D) of MD1207 (control), MD1245 (actP delete), and DW1245 (ackA overexpress). All cells are yfiQ and pta deleted with *E. gallinarum* phosphoketolase heterologous expression.
Figure 20B:
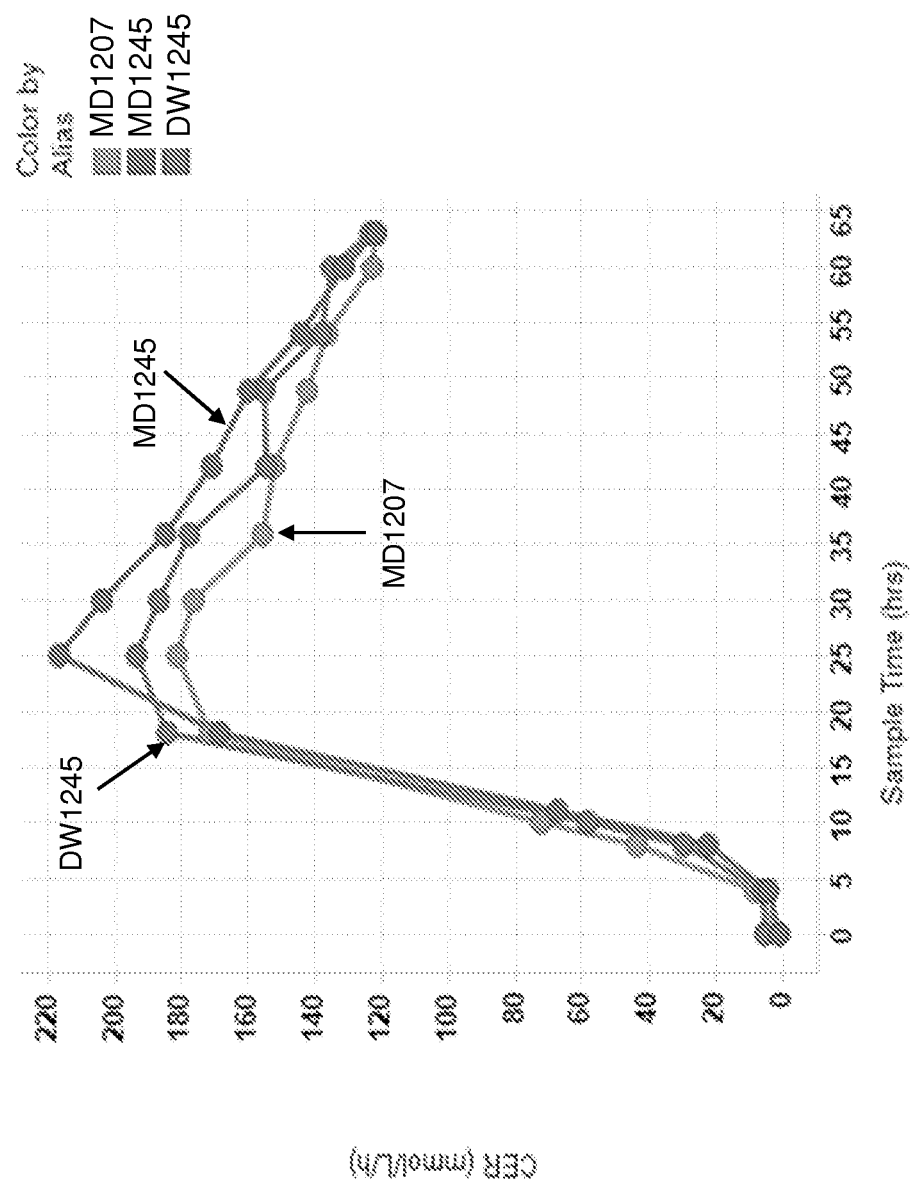
Figure 20C:
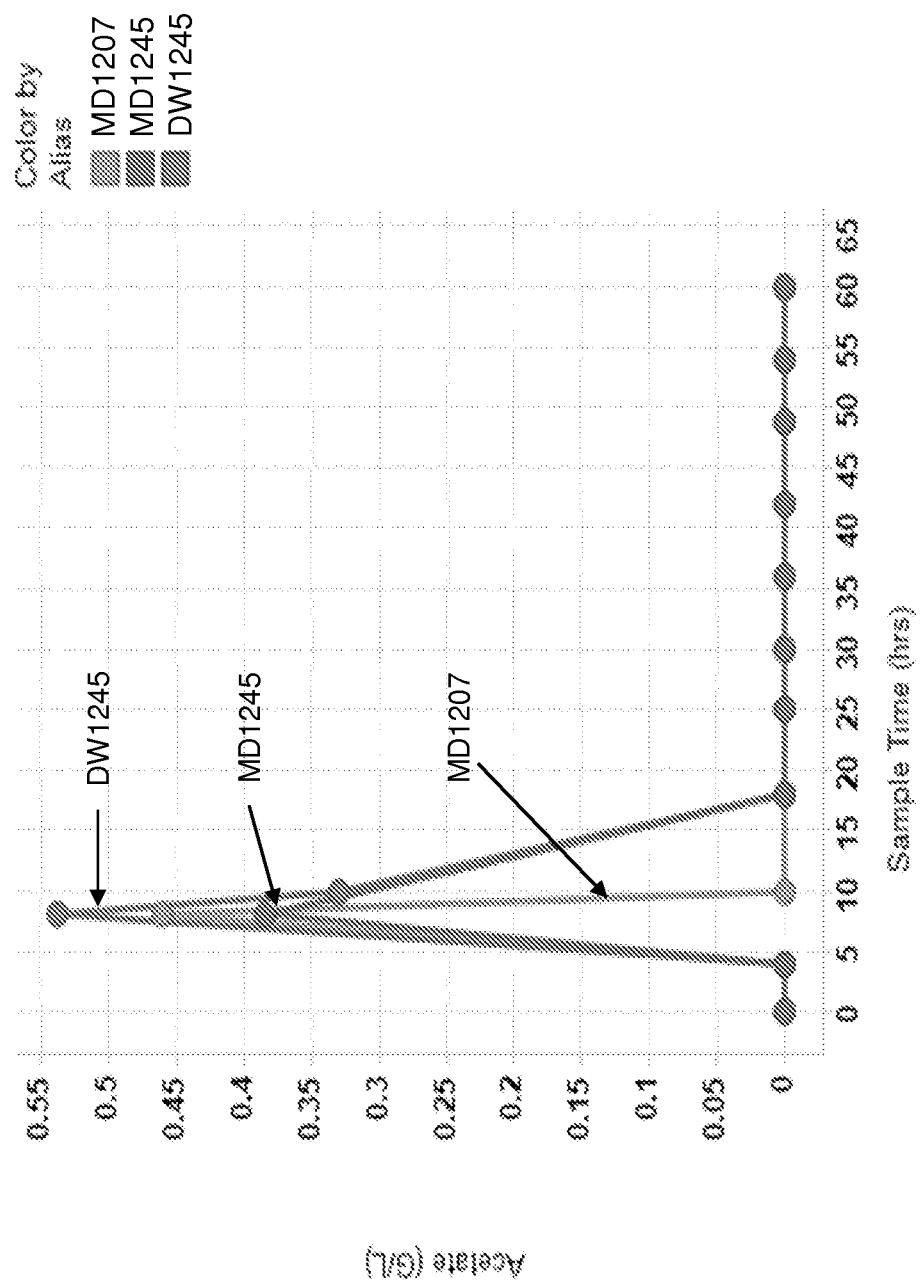
Figure 20D:
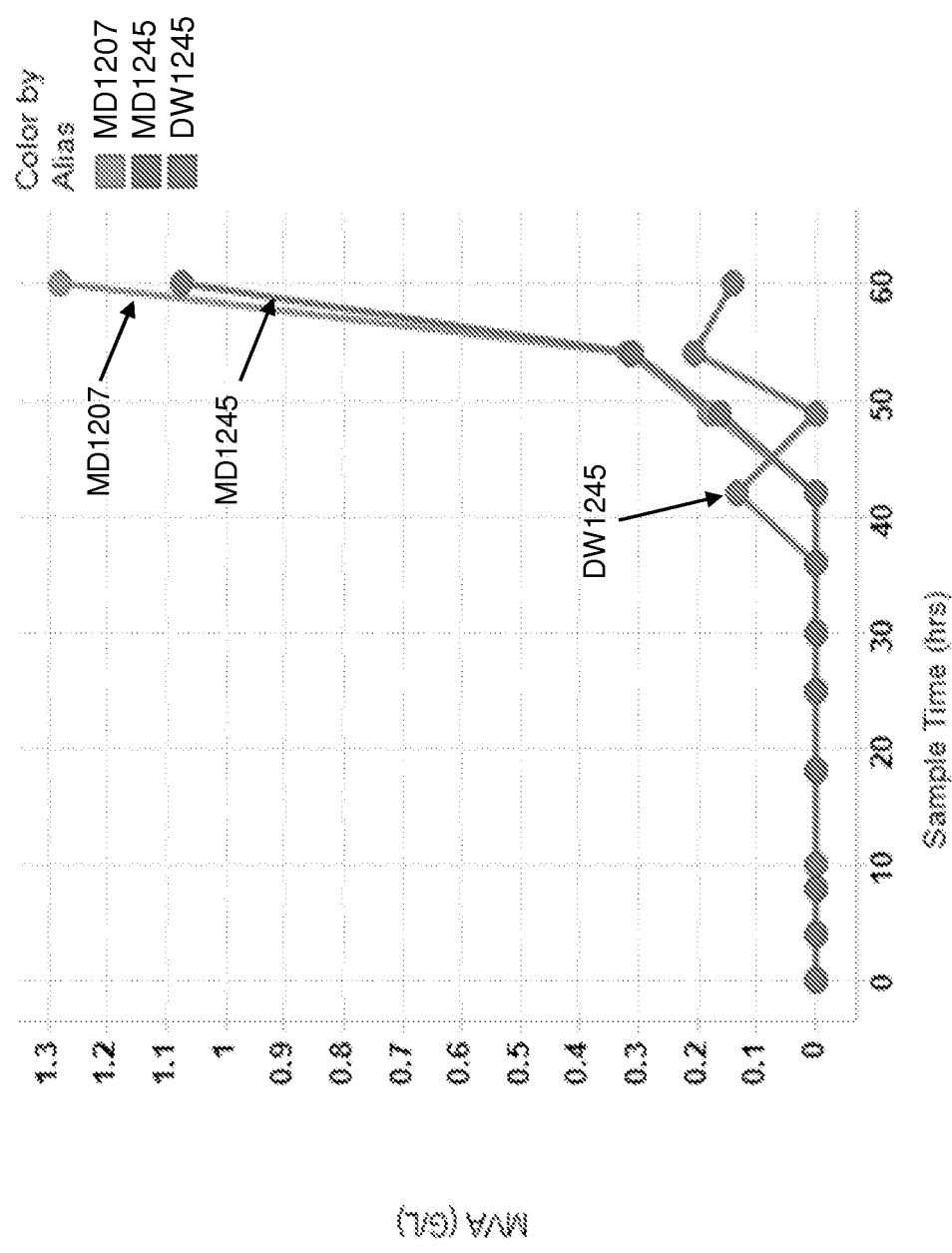
Figure 21A:
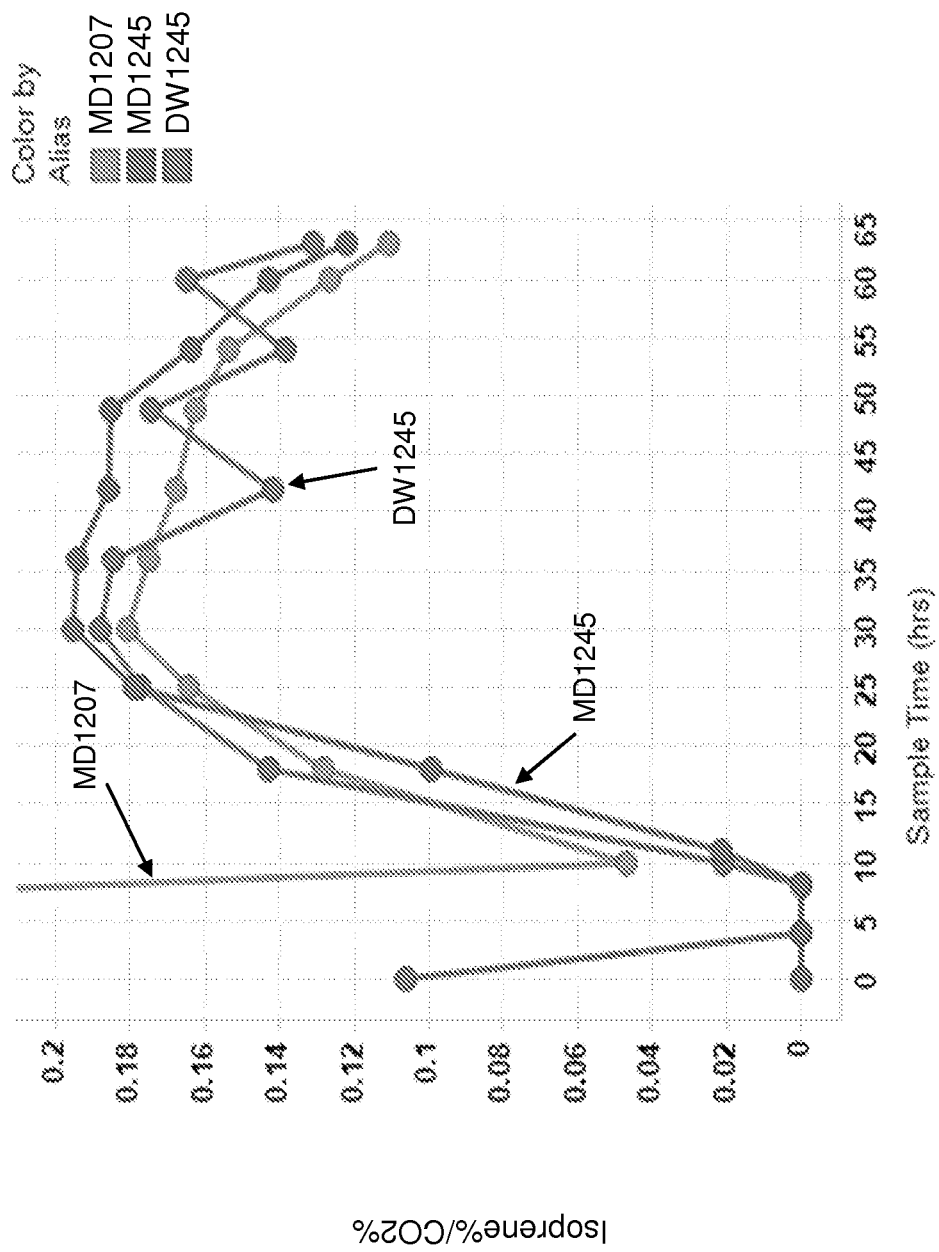
FIG. 21A-D depict the instantaneous isoprene/$CO_2$ production (FIG. 21A), isoprene titer produced over time (FIG. 21B), % yield of isoprene produced over time (FIG. 21C), and isoprene specific productivity over time (FIG. 21D) of MD1207 (control), MD1245 (actP delete), and DW1245 (ackA overexpress). All cells are yfiQ and pta deleted with *E. gallinarum* phosphoketolase heterologous expression.
Figure 21B:
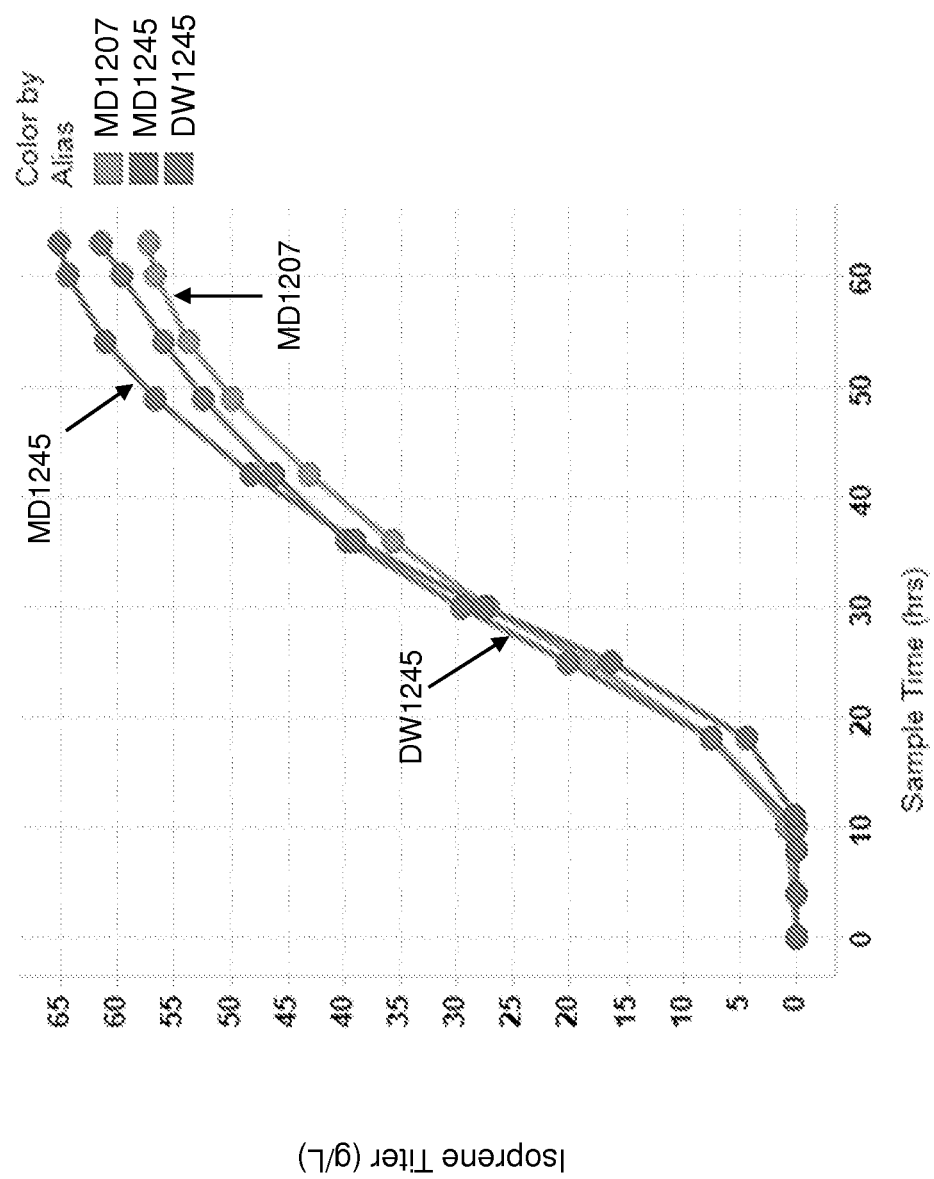
Figure 21C:
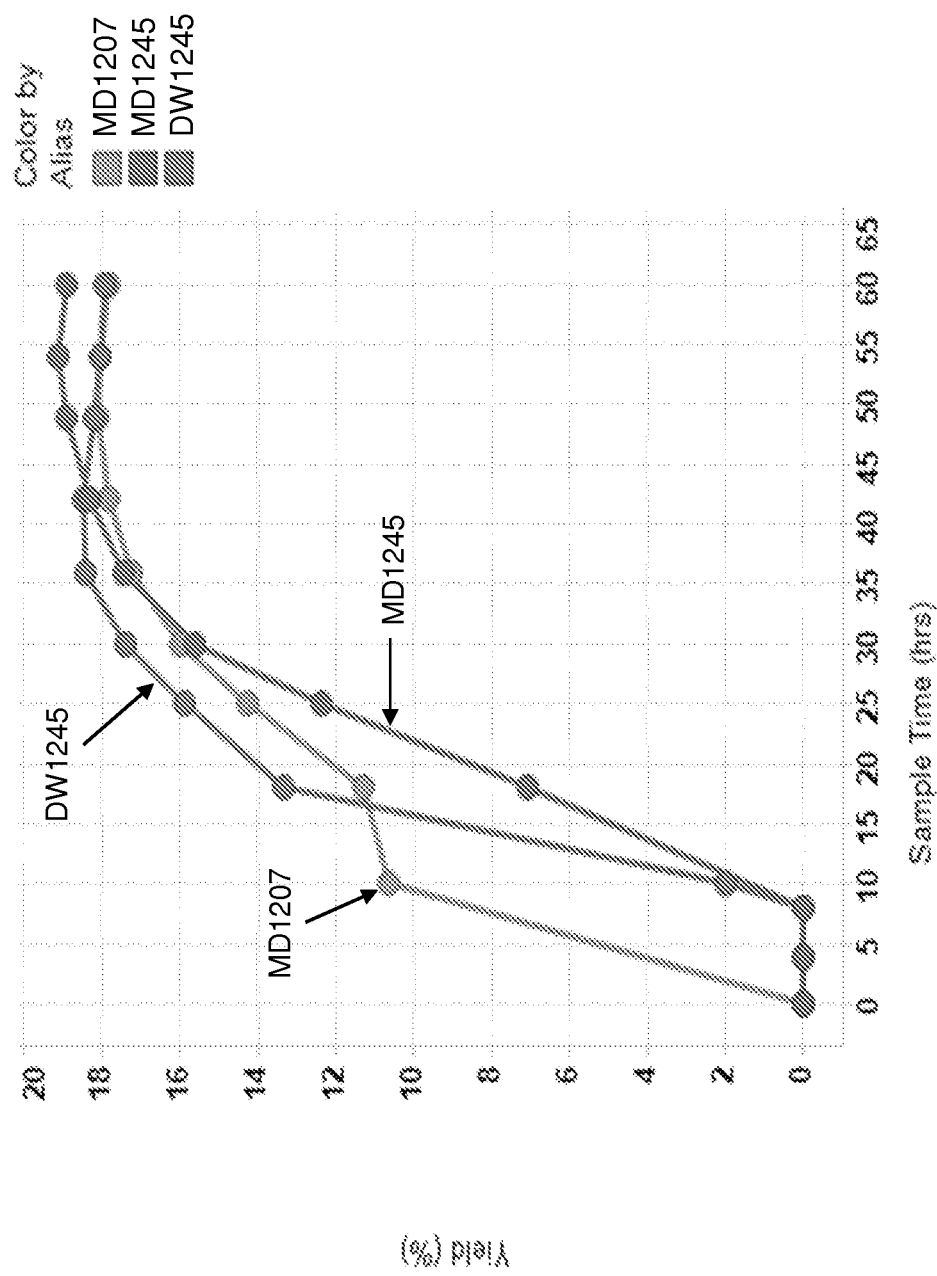
Figure 21D:
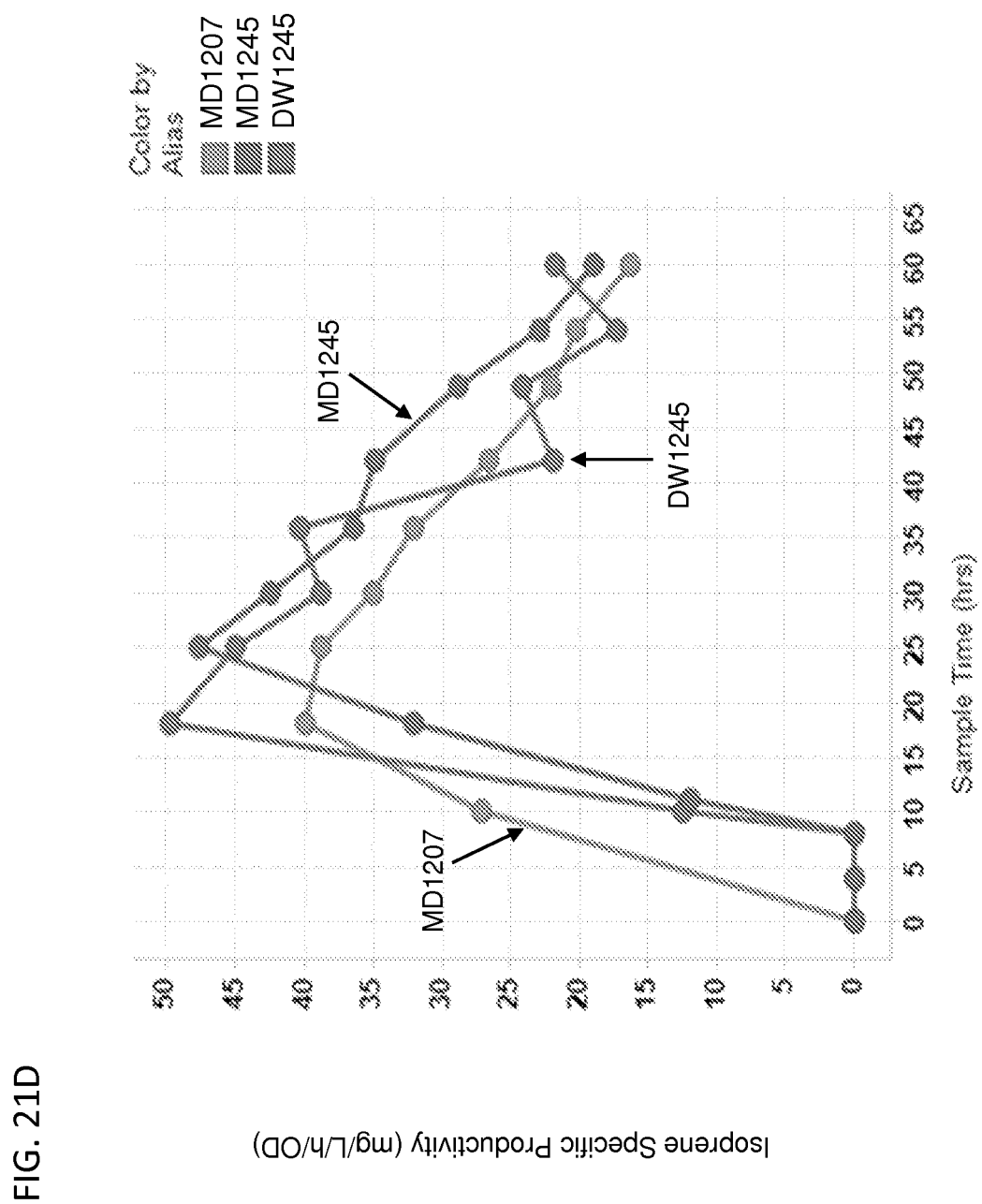

The construct for overexpression of ackA was constructed using standard molecular biology techniques (SEQ ID NO:109). Briefly, flanking regions of ackA were fused to a heterologous promoter (GI1.2) in an allelic exchange cassette by seamless cloning and assembly (Life Technologies). The actP deletion construct was also generated by fusing homologous flanking regions to the allelic exchange cassette (SEQ ID NO:110). The ackA and actP vectors (FIG. 19) were isolated and then transformed into MD1205 to generate DW1242 and MD1243 respectively. Positive integrants were selected for resistance to tetracycline and markerless deletion strains were identified by passaging on 5% sucrose. Final mutant strains were confirmed by PCR and sequencing. Co-transformation of pMCM1225 and pEWL1421 into DW1242 generated DW1245 and into MD1243 generated MD1245.

TABLE 8-1

Primer Sequences

| Primer Name | Sequence | SEQ ID NO |
|---|---|---|
| TS For | tcctaatttttgttgacactctatcattg | SEQ ID NO: 63 |
| TS Rev | ccatcttgttgagaaataaaagaaaatgcca | SEQ ID NO: 64 |
| actP Up For | tttatttctcaacaagatgggcaggctatcgcgatgccatcgtaac | SEQ ID NO: 65 |
| actP Up Rev | ggagagattacatgatgcttgtacctcatgcagga | SEQ ID NO: 66 |
| actP Down For | aagcatcatgtaatctctcccttccccggtcgcctga | SEQ ID NO: 67 |
| actP Down Rev | agtgtcaacaaaaattaggacgtaaccaccatttactgtctgtgga | SEQ ID NO: 68 |
| actP Test For | ctggcgtagtcgagaagctgcttga | SEQ ID NO: 69 |

TABLE 8-1-continued

Primer Sequences

| Primer Name | Sequence | SEQ ID NO |
|---|---|---|
| actP Test Rev | gcatagcggaacatgaatttagagt | SEQ ID NO: 70 |
| ackA Up For | tttatttctcaacaagatggcggatcgagcatagtcatcatcttgtact | SEQ ID NO: 71 |
| ackA Up GI Rev | cggttgatttgtttagtggttgaattatttgctcaggatgtggcatngtcaagg gcgaatttgacgactcaatgaatatgtact | SEQ ID NO: 72 |
| ackA Down GI For | accactaaacaaatcaaccgcgtttcccggaggtaacctaaaggaggtaaa aaaacatgtcgagtaagttagtactggttctga | SEQ ID NO: 73 |
| ackA Down Rev | agtgtcaacaaaaattaggagtacccatgaccagaccttccagc | SEQ ID NO: 74 |
| ackA Up PL Rev | atcaccgccagtggtatttangtcaacaccgccagagataatttatcaccgc agatggttatctgaatttgacgactcaatgaatatgtact | SEQ ID NO: 75 |
| ackA Down PL For | taaataccactggcggtgatactgagcacatcagcaggacgcactgcaaa ggaggtaaaaaaacatgtcgagtaagttagtactggttctga | SEQ ID NO: 76 |
| ackA EX Test For | tgcaggcgacggtaacgttcagcat | SEQ ID NO: 77 |
| ackA EX Test Rev | gtggaagatgatcgccggatcgata | SEQ ID NO: 78 |
| R6K TS Rev | agtgtcaacaaaaattaggactgtcagccgttaagtgttcctgtgt | SEQ ID NO: 79 |
| actP R6K For | ggtggttacgcagttcaacctgttgatagtacgta | SEQ ID NO: 80 |
| actP R6K Rev | ggttgaactgcgtaaccaccatttactgtctgtgga | SEQ ID NO: 81 |

TABLE 8-2

Strain Descriptions

| Strain | Description |
|---|---|
| MD1243 | CTO pgl-FRT-PL.2-2cis-RBS10000-MVK(burtonii) yfiQ:: FRT pta::FRT clone A, FRT::gi1.6-acs, i actP::ML |
| MD1245 | CTO pgl-FRT-PL.2-2cis-RBS10000-MVK(burtonii) yfiQ:: FRT pta::FRT clone A, FRT::gi1.6-acs, i actP::ML + pMCM1225 + pEWL1421 |
| DW1242 | CTO pgl-FRT-PL.2-2cis-RBS10000-MVK(burtonii) yfiQ:: FRT pta::FRT clone A, FRT::gi1.6-acs, i gi1.6ackA |
| DW1245 | CTO pgl-FRT-PL.2-2cis-RBS10000-MVK(burtonii) yfiQ:: FRT pta::FRT clone A, FRT::gi1.6-acs, i gi1.6ackA + pMCM1225 + pEWL1421 |

Example 9: Effect of Example 8 Strains on Isoprene Yield and Growth Rate

This example measured isoprene production and growth rate in cells carrying a deletion of the yfiQ gene and either an actP deletion or an ackA overexpression.

I. Materials and Methods

LB media, TM3 media without Yeast extract and MgSO$_4$, 10% Yeast extract, 1M MgSO$_4$, 50% Glucose, 200 mM IPTG, 50 mg/mL Spectinomycin, 50 mg/mL Carbenicillin, Aluminum foil seal, 48-well sterile 5 mL block, breathe easier sealing membrane, aluminum foil seal, 96-well micro titer plates, 96-well glass block purchased from Zinsser Analytic. Agilent 6890 GC equipped with a 5973N Mass spectrometer.

Supplemented TM3 media was prepared by combining TM media, (without MgSO$_4$ and Yeast extract) 1% Glucose, 8 mM MgSO$_4$, 0.02% Yeast extract and appropriate antibiotics. 2 mL of day culture was started in 48-well sterile block by inoculating overnight culture in supplemented TM3 media at 0.2 optical density (OD). Blocks were sealed with breathe easier membrane and incubated for 2 hours at 34° C., 600 rpm. After 2 hours of growth, OD was measured at 600 nm in the micro titer plate and cells were induced with 200 µM IPTG. OD reading was taken every hour after the IPTG induction for 4 hours to determine growth rate. OD was measurement was done in the micro titer plate at appropriate dilution in the TM3 media at 600 nm using a SpectraMax Plus190 (Molecular Devices).

100 µL of isoprene samples were collected in a 96 well glass block at 2, 3 and 4 hours after IPTG induction. Glass block was sealed with aluminum foil and incubated at 34° C. while shaking at 450 rpm, for 30 minutes on the thermo-mixer. After 30 minutes, the block was kept in 70° C. water bath for 2 minutes and isoprene headspace measurement was done in GC/MS to determine specific productivity.

II. Results

Both the actP deletion (MD1245) and the ackA overexpression (DW1245) cells displayed higher carbon dioxide evolution rates (CER), indicating improved respiration rates compared to the control cells (FIG. 20A-D). Both cells displayed improved isoprene titer and specific productivity as compared to the control, and the actP cells displayed an improvement in isoprene yield (FIG. 21A-D). These results show that improvements around acetate production and/or acetate cycling have a beneficial effect on several different parameters of isoprene production. Without being bound by theory, it is possible that this effect is achieved by optimizing the fluxes through glycolysis and phosphoketolase.

Example 10: Construction of Pentose Phosphate Pathway Modulation Strains

This Example describes the construction of strains containing mutations in genes responsible for modulating the Pentose Phosphate Pathway (PPP).

Without being bound by theory, it is believed that the four genes in the pentose phosphate pathway critical for balancing carbon flux in a phosphoketolase-expressing host are tktA, talB, rpe, and rpiA. Maximizing the cycling of carbon towards X5P could optimize the split between fluxes through glycolysis, the pentose phosphate pathway, and phosphoketolase. The construct described below was designed to overexpress and integrate all four non-oxidative pentose phosphate genes in the yfiQ locus in the chromosome. This construct represents only one attempt at improving the routing of carbon through PPP, and it is very likely that refinement of this construct, by the addition of more promoters, terminators, rearranging the genes, etc., will help to determine what is the optimum expression level to balance flux through phosphoketolase.

In addition to four genes of the PPP discussed above, modulation of the pentose phosphate pathway can be achieved by modulating PfkA. Without being bound by theory, it is believed that PfkA controls a major entry point and regulated node in glycolysis, and it is likely that for phosphoketolase (PKL) to function properly, phosphofructokinase activity must be decreased. This would increase available fructose 6-phosphate (F6P) and drive carbon flux through pentose phosphate towards xylulose 5-phosphate (X5P), the other substrate of phosphoketolase.

I. Construction of tktA, talB, Rpe, and rpiA Mutant Strains

Figure 22:
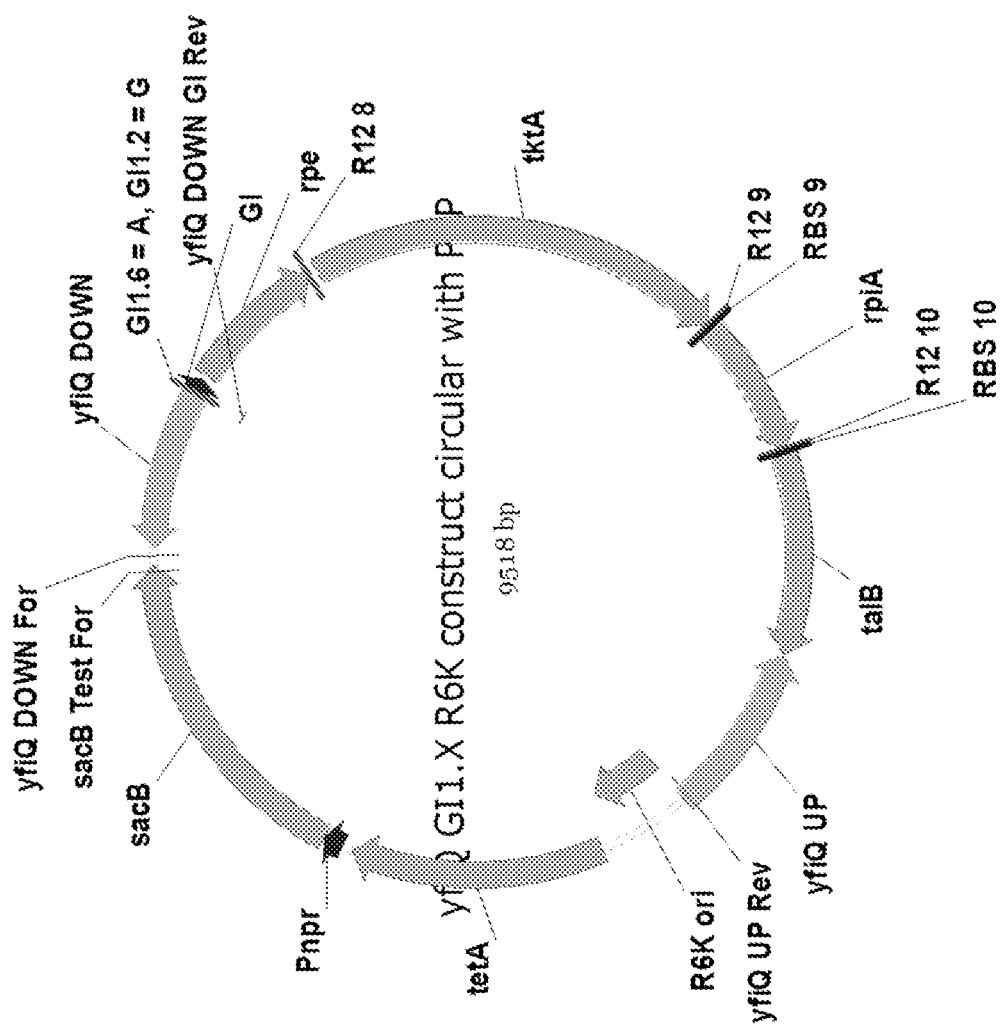
FIG. 22 depicts a map of the pentose phosphate pathway upregulation allelic exchange vector.

PPP genes were optimized and ordered from IDT as gBlocks double stranded gene fragments. All four genes were TOPO cloned into the pCR2.1 vector (Life Technologies) and sequenced prior to subsequent cloning. Initial vectors were built by seamless assembly (Life Technologies) with either the GI1.2 or GI1.6 promoters and flanking sites for homologous recombination. The final vector with all four PPP genes in a single operon were also built by seamless cloning (Life Technologies) (FIG. 22) (SEQ ID NO:111). This plasmid was transformed into MD1205 for allelic exchange, and strains were isolated by resistance to tetracycline. Independent strains were selected by resistance to 5% sucrose, and the presence of the insertion in the proper genomic locus was verified by PCR. This cell was frozen as MD1280. MD1280 was co-transfected with pMCM1225 and pEWL1421 to generate MD1284.

TABLE 10-1

Primers Sequences

| Primer Name | sequence | SEQ ID NO |
| --- | --- | --- |
| yfiQ DOWN For | tttatttctcaacaagatggggccgattaacatcatccagacgat | SEQ ID NO: 82 |
| yfiQ DOWN GI1.6 Rev | cggttgatttgtttagtggttgaattatttgctcaggatgtggcattgt caagggctcttgcccaacgcgaggaatcatgagta | SEQ ID NO: 83 |
| yfiQ DOWN GI1.2 Rev | cggttgatttgtttagtggttgaattatttgctcaggatgtggcatcgt caagggctcttgcccaacgcgaggaatcatgagta | SEQ ID NO: 84 |
| yfiQ UP GI For | accactaaacaaatcaaccgcgtttcccggaggtaacctaaagga ggtaaaaaaacaccggtctcccgcagaagtgaccga | SEQ ID NO: 85 |
| yfiQ UP Rev | actatcaacaggttgaactgcgccgttcgatagctggctgaacga | SEQ ID NO: 86 |
| yfiQ Test For | gcatcacgcagctcctggcggaaca | SEQ ID NO: 87 |
| yfiQ Test Rev | gctgaacgtgaattgagcagtcgct | SEQ ID NO: 88 |
| rpe R6K For | tacacacataaggaggttcccaatgaaacagtatctgatcgcacctagca | SEQ ID NO: 89 |
| rpe R6K Rev | tattcgaatgtatgctagtggacgtcaatcattactcgtggctcacttt cgccagttca | SEQ ID NO: 90 |
| tkt R6K For | cactagcatacattcgaataaggaggaatactatgtcatctcgtaa ggaactggcgaa | SEQ ID NO: 91 |
| tkt R6K Rev | tatctccttcttgagccgattatcattacagcagctctttggctttcgcgaca | SEQ ID NO: 92 |
| rpi R6K For | atcggctcaagaaggagatatacatatgacgcaggacgaactga aaaaagcggt | SEQ ID NO: 93 |
| rpi R6K Rev | tattcctccttcaggacctttcattatttaacgatcgttttgacgccatc | SEQ ID NO: 94 |
| tal R6K For | aaggtcctgaaggaggaataaaccatgaccgataaactgaccagcctgcgt | SEQ ID NO: 95 |
| tal R6K Rev | gaccggttcattacagcaggtcgccgatcattttctcca | SEQ ID NO: 96 |
| R6K Plasmid For | cctgctgtaatgaaccggtctcccgcagaagtgaccgaatga | SEQ ID NO: 97 |
| R6K Plasmid Rev | ggaacctccttatgtgtgtaaacctttaggttacctccgggaaacgc ggttga | SEQ ID NO: 98 |

TABLE 10-2

Strain Descriptions

| Strain | Description |
|---|---|
| MD1280 | CTO pgl-FRT-PL.2-2cis-RBS10000-MVK(*burtonii*) pta::FRT clone A, FRT::Gi1.6-acs, i yfiQ::Gi1.2-rpe_tktA_rpiA_talB ML |
| MD1281 | CTO pgl-FRT-PL.2-2cis-RBS10000-MVK(*burtonii*) pta::FRT clone A, FRT::Gi1.6-acs, i pfkA_tag T ML, i yfiQ::Gi1.2-rpe_tktA_rpiA_talB ML |
| MD1282 | CTO pgl-FRT-PL.2-2cis-RBS10000-MVK(*burtonii*) pta::FRT clone A, FRT::Gi1.6-acs, i pfkA_tag I ML, i yfiQ::Gi1.2-rpe_tktA_rpiA_talB ML |
| MD1283 | CTO pgl-FRT-PL.2-2cis-RBS10000-MVK(*burtonii*) pta::FRT clone A, FRT::Gi1.6-acs, i pfkA_tag R ML, i yfiQ::Gi1.2-rpe_tktA_rpiA_talB ML |
| MD1284 | CTO pgl-FRT-PL.2-2cis-RBS10000-MVK(*burtonii*) pta::FRT clone A, FRT::Gi1.6-acs, i yfiQ::Gi1.2-rpe_tktA_rpiA_talB ML + pMCM1225 + pEWL1421 |
| MD1285 | CTO pgl-FRT-PL.2-2cis-RBS10000-MVK(*burtonii*) pta::FRT clone A, FRT::Gi1.6-acs, i pfkA_tag T ML, i yfiQ::Gi1.2-rpe_tktA_rpiA_talB ML + pMCM1225 + pEWL1421 |
| MD1286 | CTO pgl-FRT-PL.2-2cis-RBS10000-MVK(*burtonii*) pta::FRT clone A, FRT::Gi1.6-acs, i pfkA_tag I ML, i yfiQ::Gi1.2-rpe_tktA_rpiA_talB ML + pMCM1225 + pEWL1421 |
| MD1287 | CTO pgl-FRT-PL.2-2cis-RBS10000-MVK(*burtonii*) pta::FRT clone A, FRT::Gi1.6-acs, i pfkA_tag R ML, i yfiQ::Gi1.2-rpe_tktA_rpiA_talB ML + pMCM1225 + pEWL1421 |

II. Construction of pfkA Mutant Strains

Figure 23:
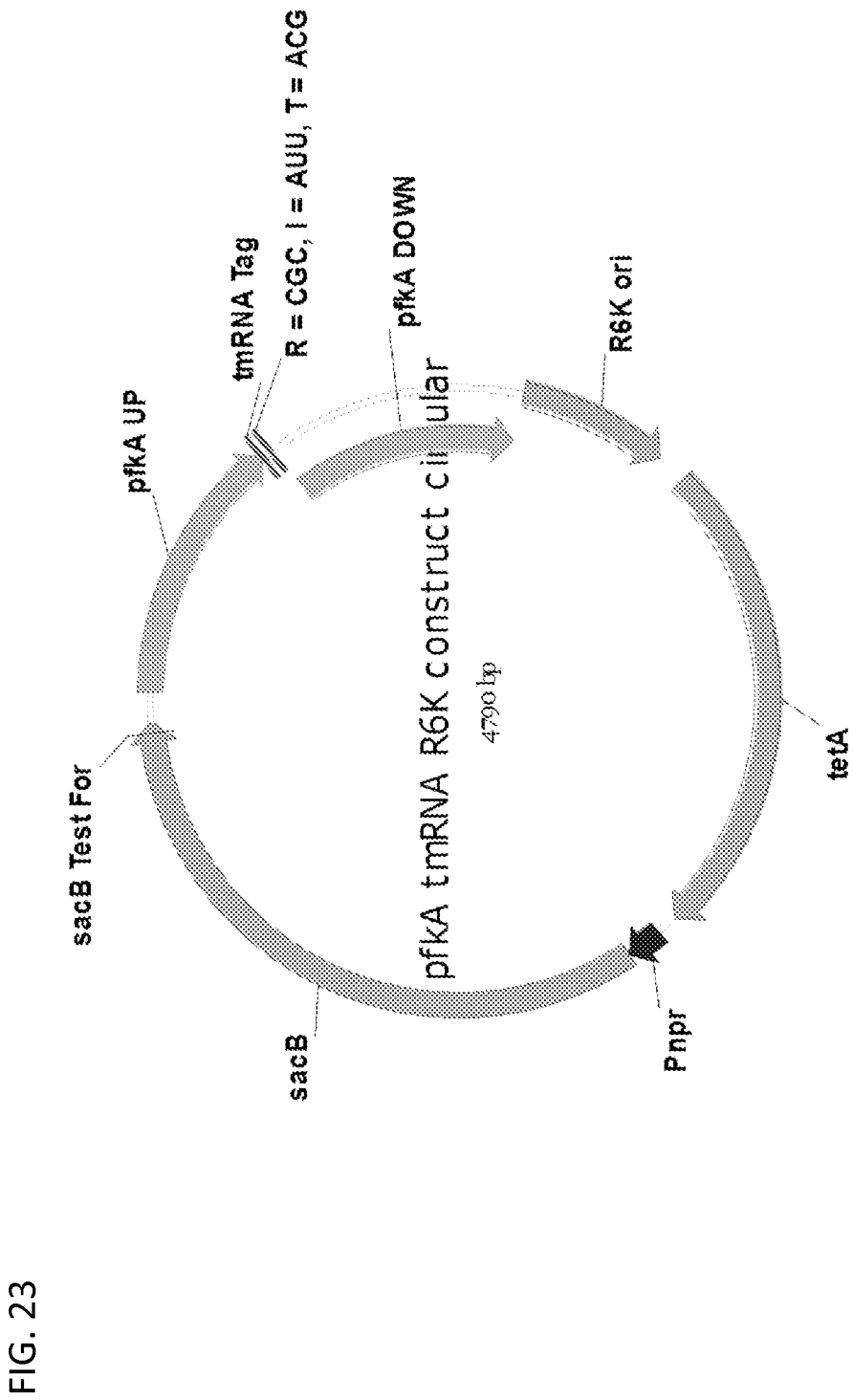
FIG. 23 depicts a map of the pfkA downregulation allelic exchange vector.
Figure 24:
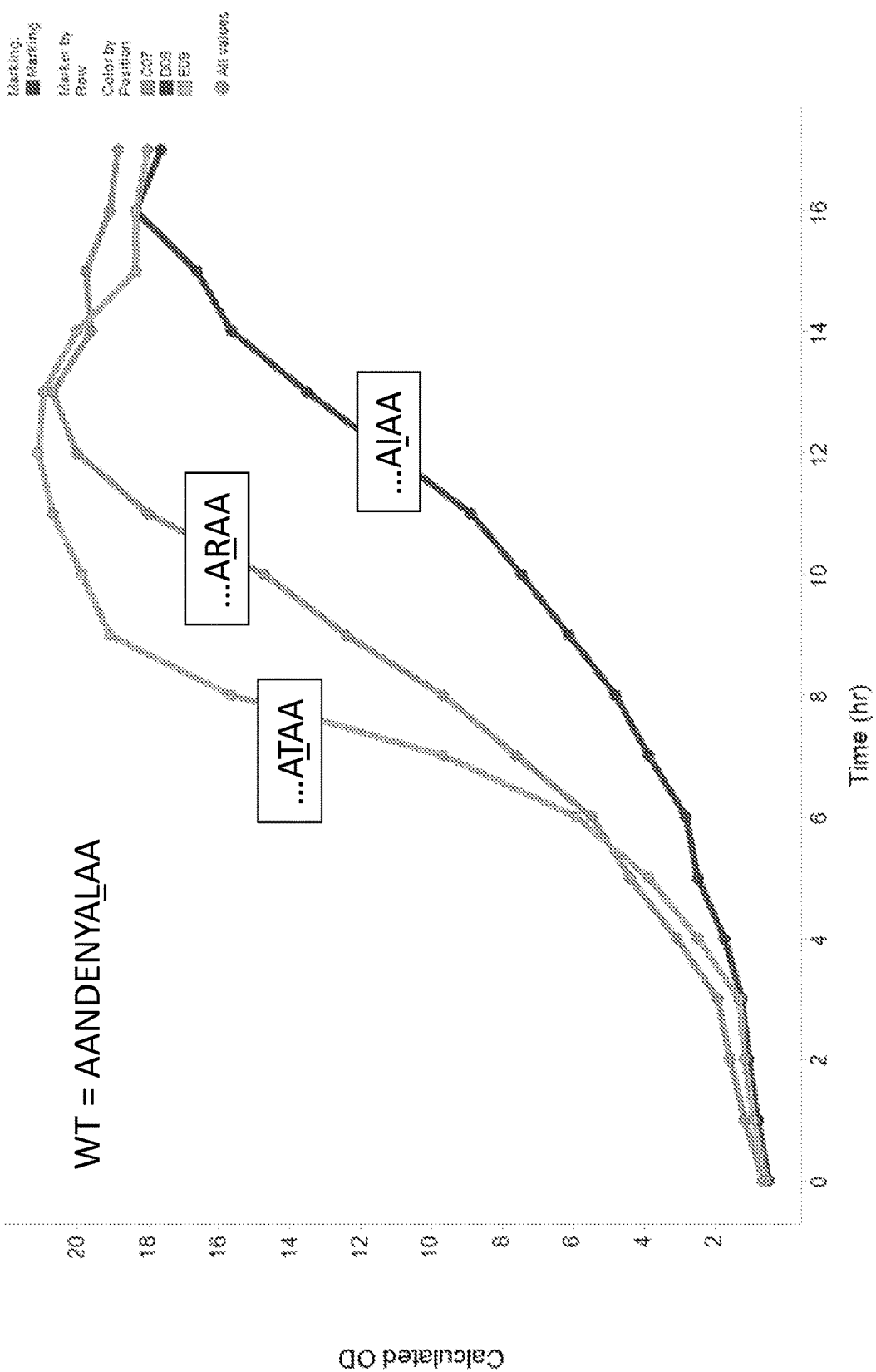
FIG. 24 depicts the growth rate of cells expressing PfkA::TmRNA proteolytic tags with isoleucine (I), arginine (R), or threonine (T) mutations in the third to last amino acid position.
Figure 25A:
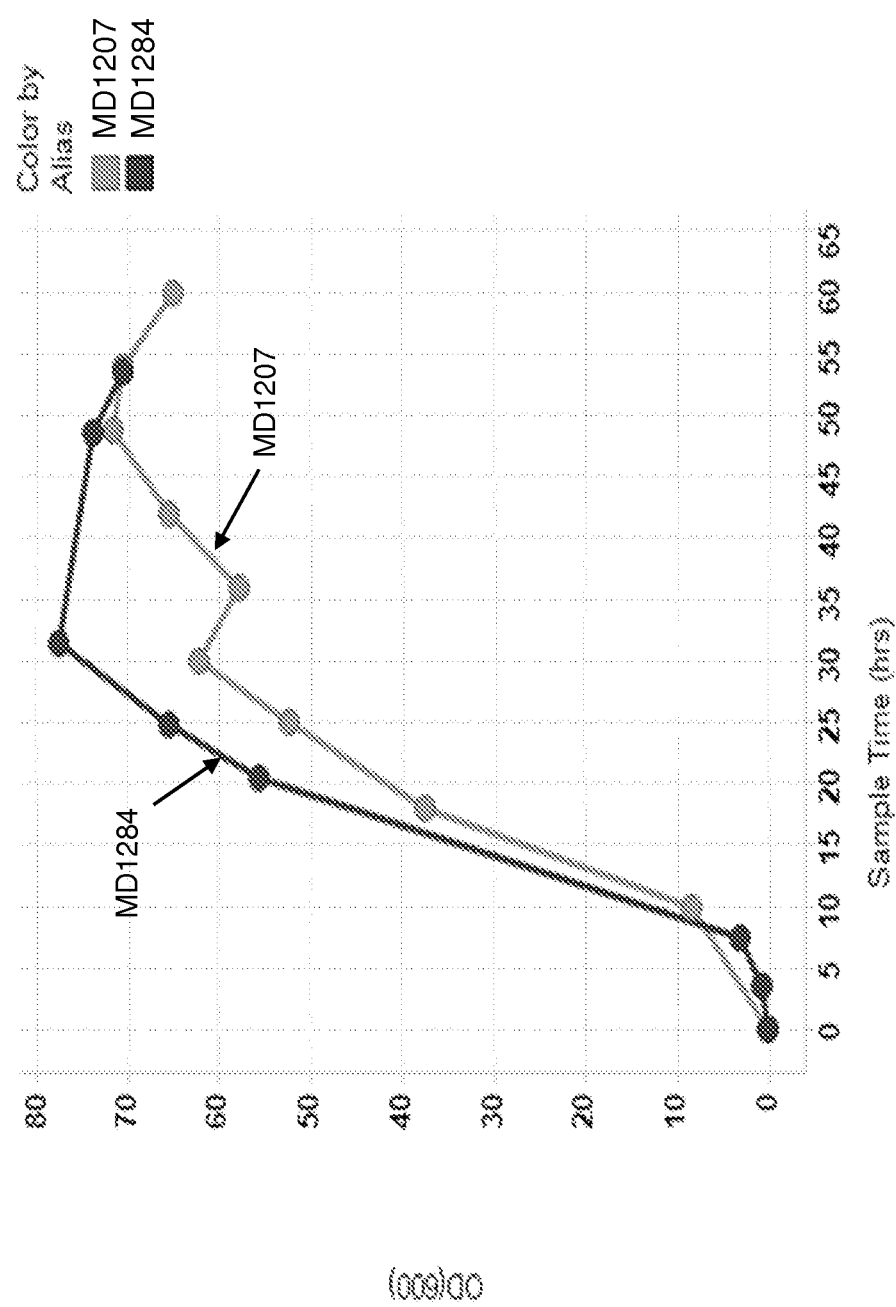
FIG. 25A-D depict the growth rate (FIG. 25A), carbon dioxide evolution rates (CER) over time (FIG. 25B), broth acetate over time (FIG. 25C), and broth MVA over time (FIG. 25D) of MD1207 (control) and MD1284 (PPP overexpression). All cells are yfiQ and pta deleted with *E. gallinarum* phosphoketolase heterologous expression.
Figure 25B:
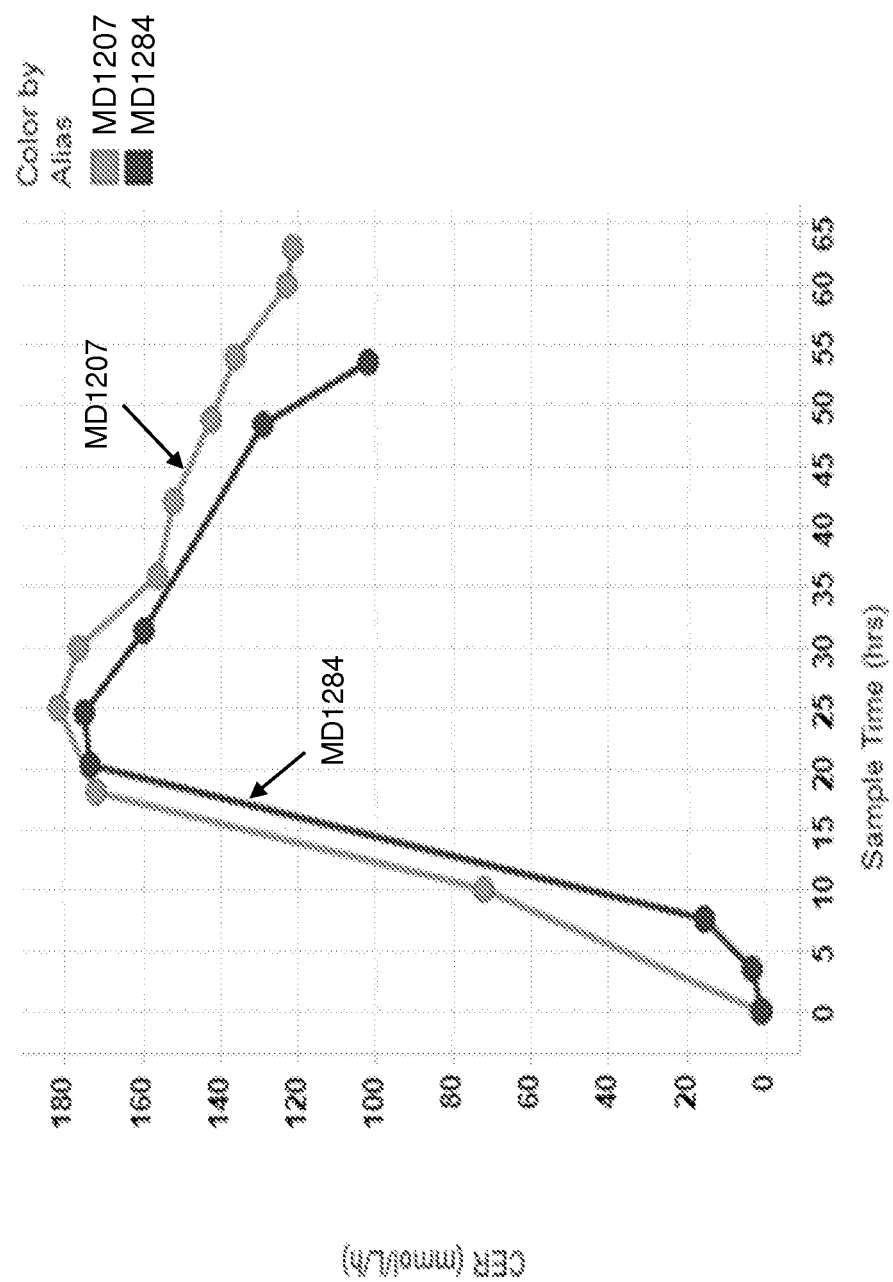
Figure 25C:
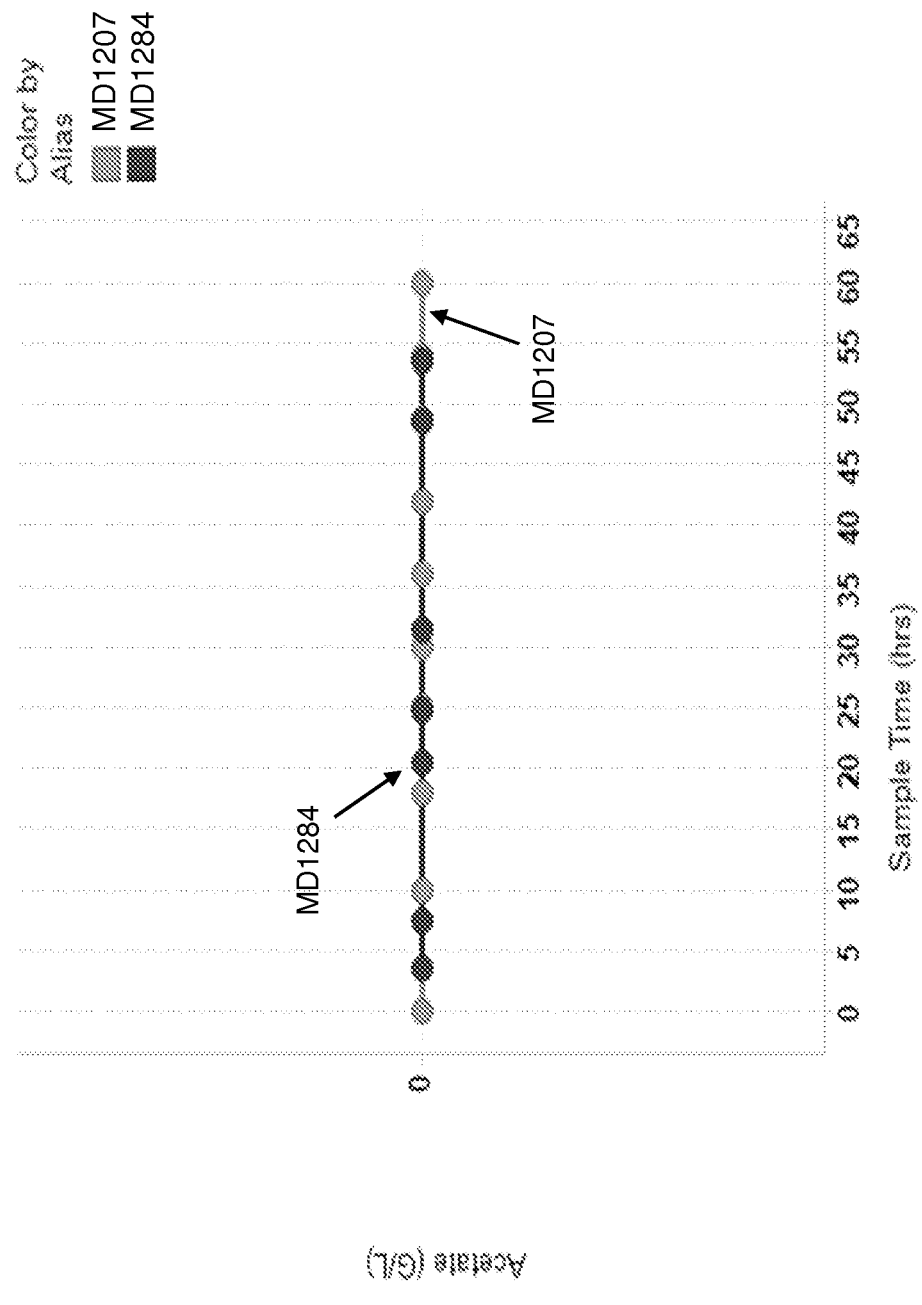
Figure 25D:
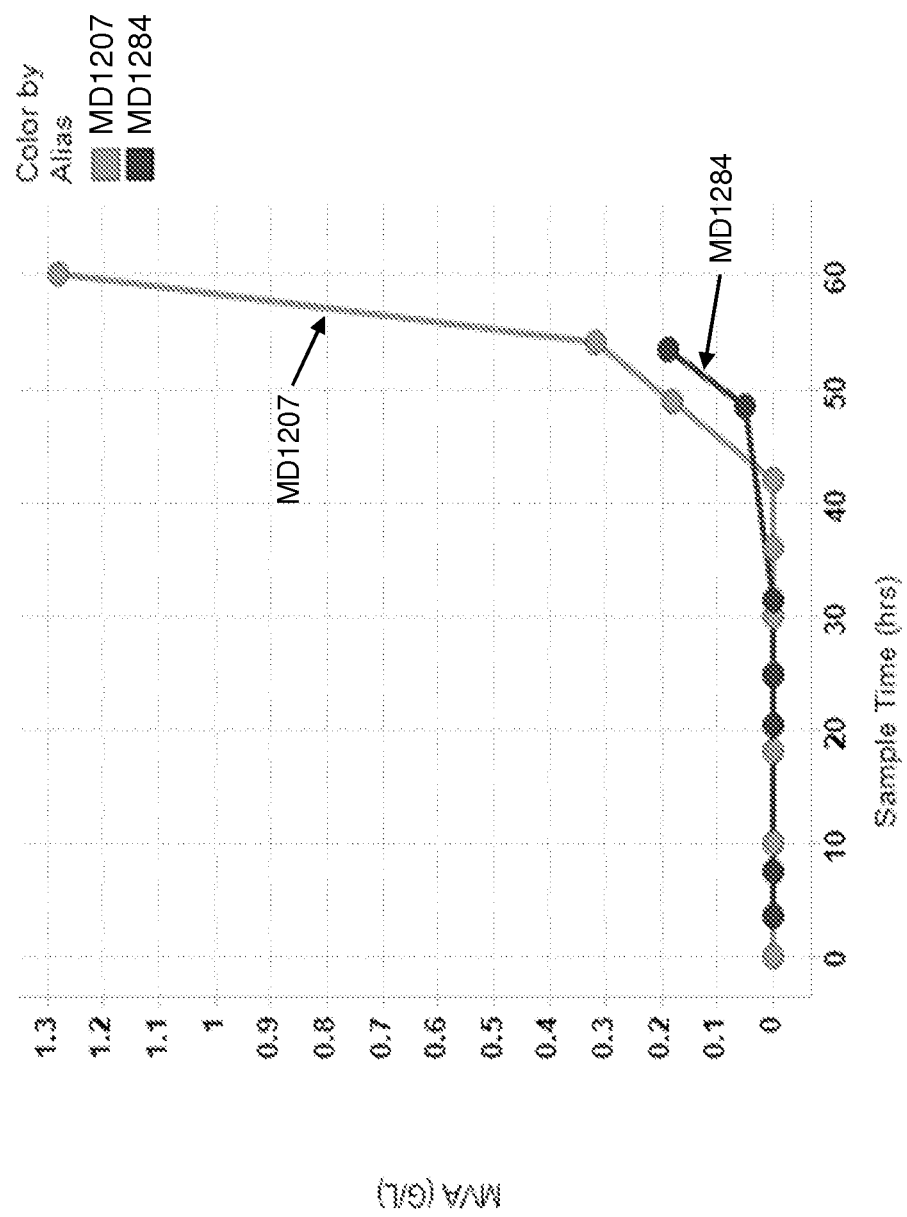
Figure 26A:
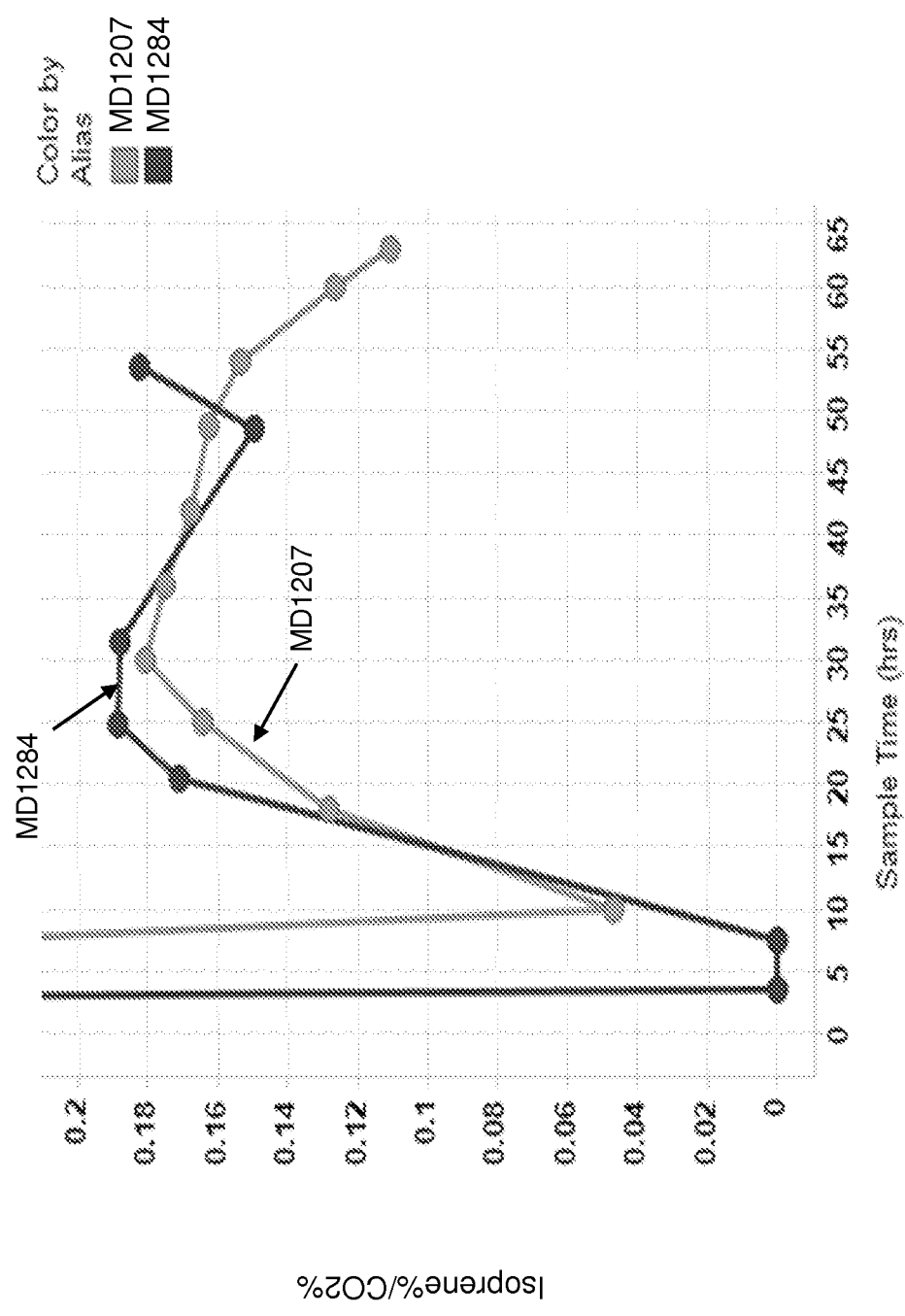
FIG. 26A-D depicts the instantaneous isoprene/$CO_2$ production (FIG. 26A), isoprene titer produced over time (FIG. 26B), % yield of isoprene produced over time (FIG. 26C), and isoprene specific productivity over time (FIG. 26D) of MD1207 (control) and MD1284 (PPP overexpression). All cells are yfiQ and pta deleted with *E. gallinarum* phosphoketolase heterologous expression.
Figure 26B:
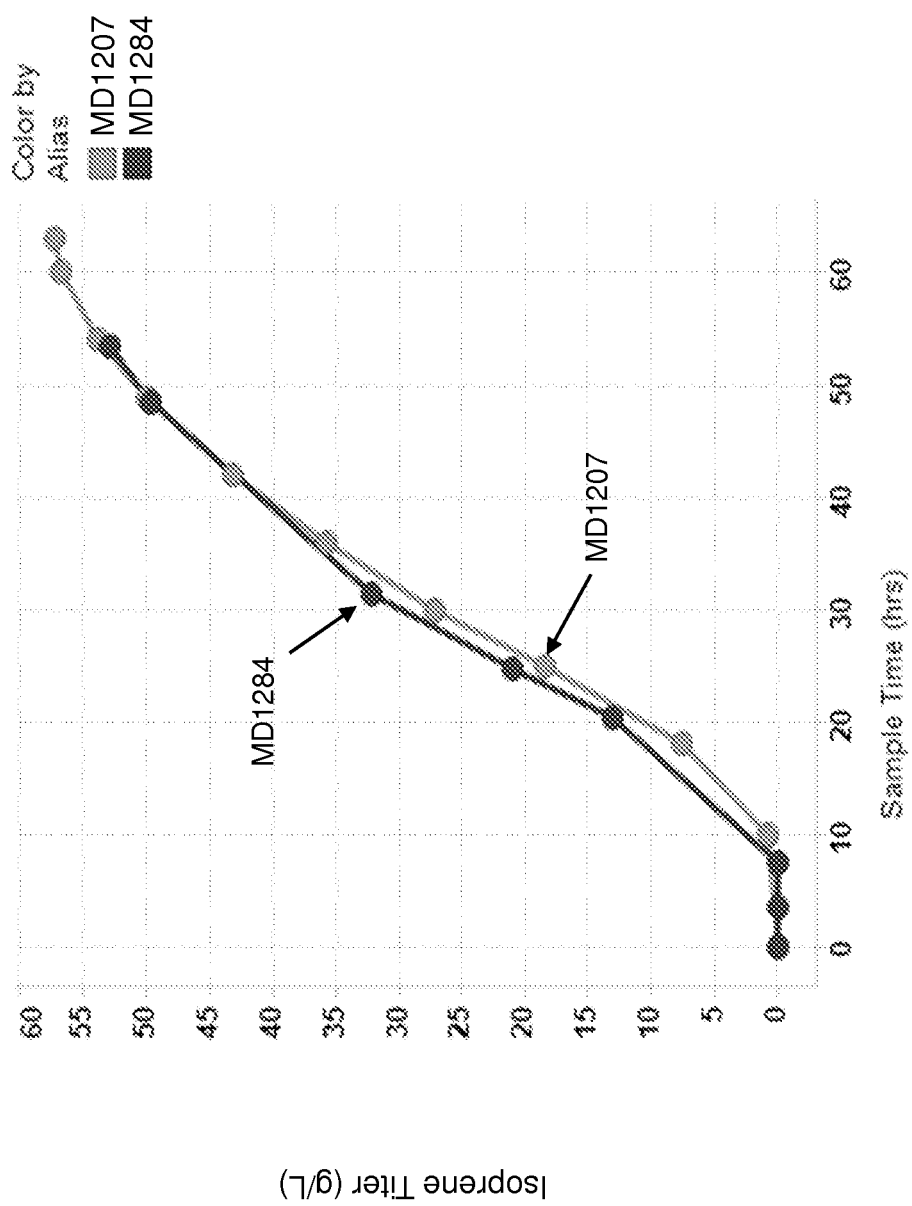
Figure 26C:
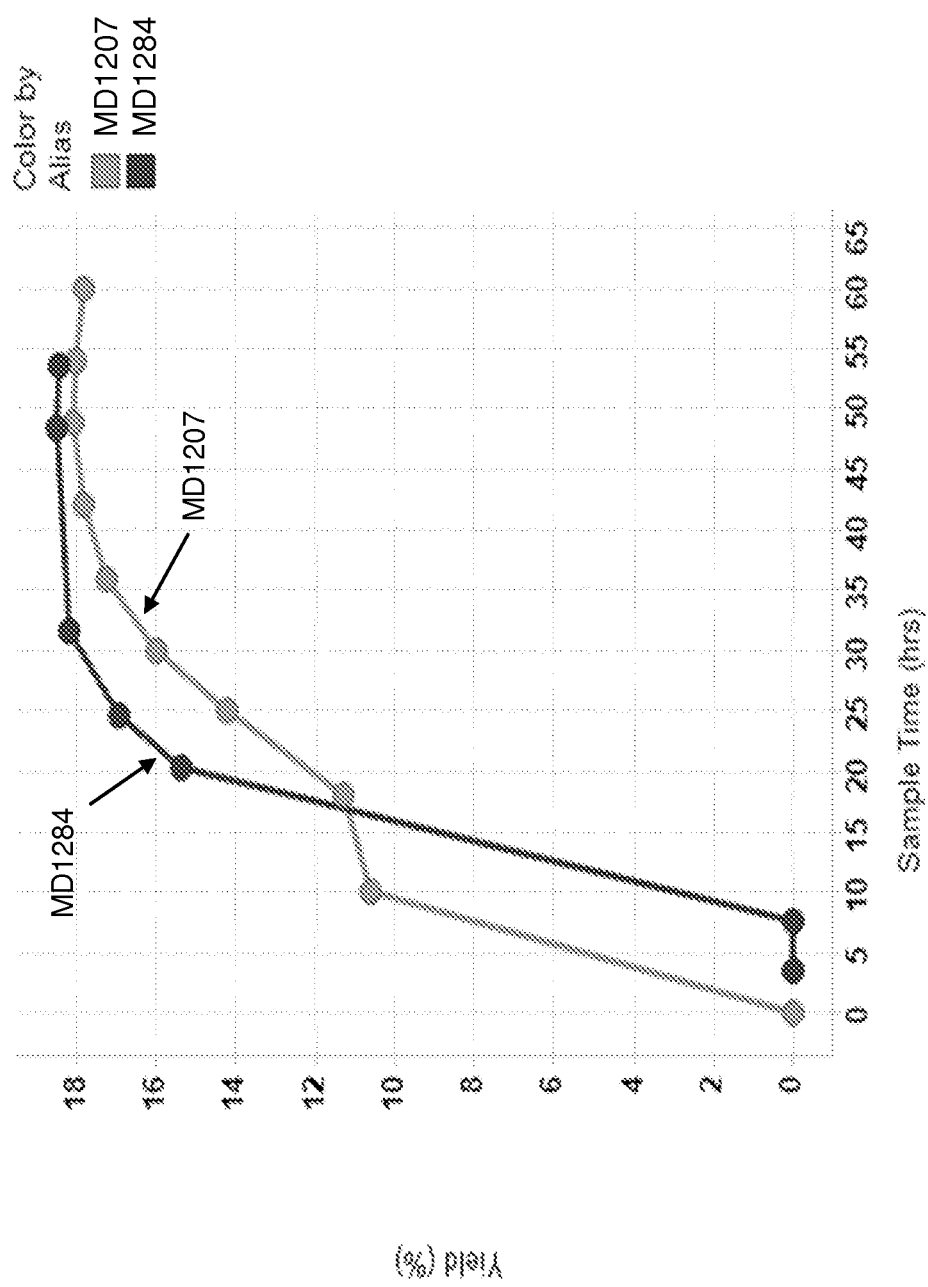
Figure 26D:
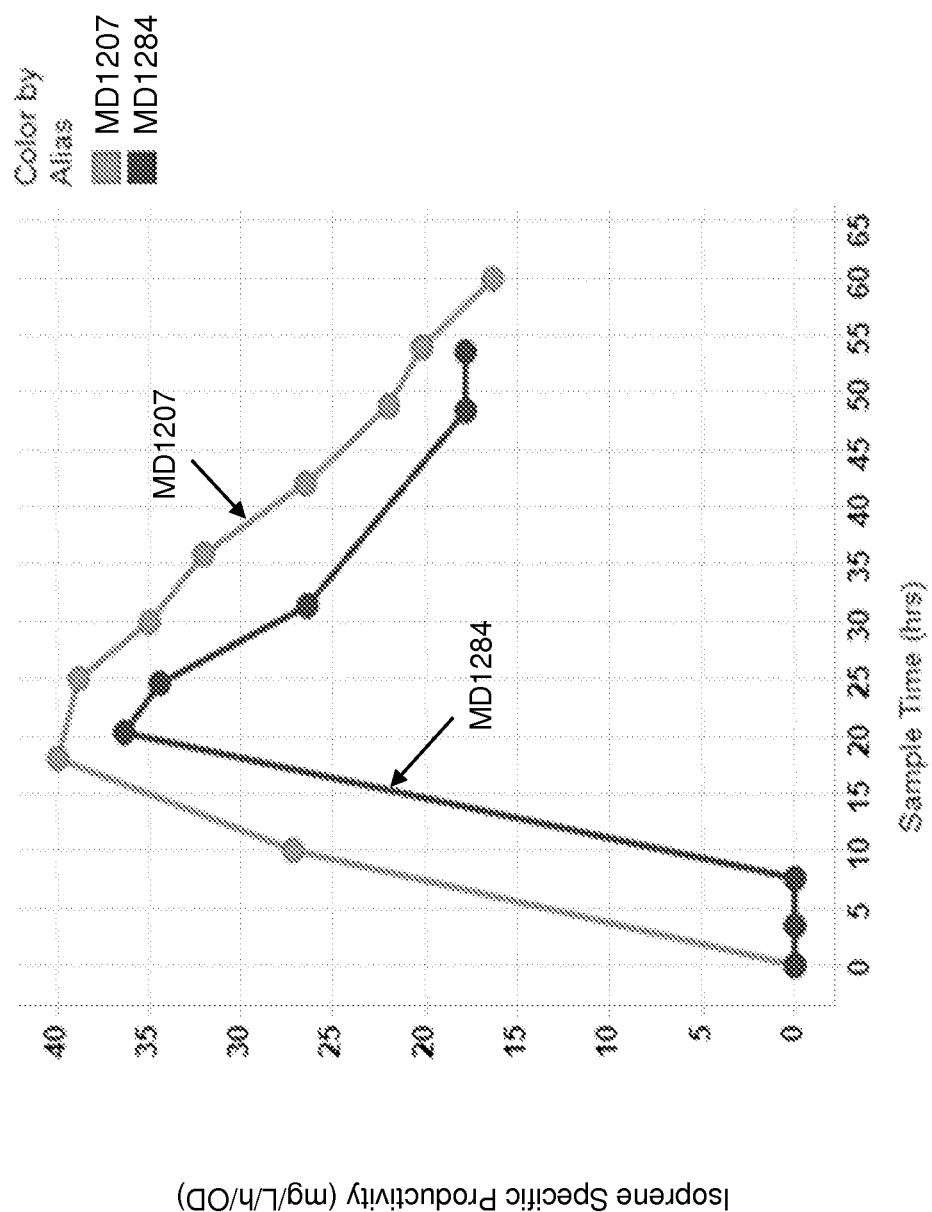

Partially functional proteolytic tags were generated to downregulate pfkA. Random mutations at the third to last amino acid position in tmRNA were fused to the C-terminus of PfkA using GeneBridges recombineering (following the manufacturer's recommended protocol) in a WT BL21 background (FIG. 23). Mutants were then screened for growth in TM3 glucose in the growth profiler (FIG. 24). The variant with isoleucine (I) in the $3^{rd}$ to last position is likely very similar to leucine (L), the native amino acid. This accordingly grew the slowest due to the high protein degradation rate of a "WT" tag. The variant with arginine (R) displayed a more modest effect, and threonine (T) was the least impaired. These three variants were selected and moved into MD1205 or MD1280 using the R6K allelic exchange method. Briefly, PCR fragments generated from primers listed below were used with tet-sac (TS) and R6K fragments in seamless cloning reactions (Life Technologies) to yield the plasmids for allelic exchange (SEQ ID NO:112). These plasmids were then introduced into MD1205 or MD1280 by selection for tetracycline resistance, and then counter selected by subsequent plating onto medium containing 5% sucrose. Strains harboring the individual proteolytic tag mutations in pfkA were identified by PCR and sequencing. pMCM1225 and pEWL1421 transfected into each cell using standard molecular biology techniques. See Table 10-2 for strain details.

TABLE 10-3

Primer Sequences

| Primer Name | sequence | SEQ ID NO |
|---|---|---|
| pfkA tmRNA XAA For | tgaagcgtccgttcaaaggcgactggctagactgcgcgaaaaaactgtatgctg ctaacgatgaaaattatgctnnngctgcataaaattaaccctcactaaagggcg | SEQ ID NO: 99 |
| pfkA tmRNA Rev | gcttctgtcatcggtttcaggctaaaggaatctgccttttccgaaatcataat acgactcactatagggctc | SEQ ID NO: 100 |
| pfkA UP For | tttatttctcaacaagatgggttatcggcggtgacggttcctacat | SEQ ID NO: 101 |
| pfkA UP Rev | agcataattttcatcgttagcagcatacagttttttcgcgcagtctagccagtc gcct | SEQ ID NO: 102 |
| pfkA DOWN R For | ctaacgatgaaaattatgctcgcgctgcataatgatttcggaaaaaggcag attcct | SEQ ID NO: 103 |
| pfkA DOWN I For | ctaacgatgaaaattatgctattgctgcataatgatttcggaaaaaggcaga ttcct | SEQ ID NO: 104 |
| pfkA DOWN T For | ctaacgatgaaaattatgctacggctgcataatgatttcggaaaaaggcag attcct | SEQ ID NO: 105 |
| pfkA DOWN Rev | actatcaacaggttgaactgcggtgcggagttatccggcagacgt | SEQ ID NO: 106 |
| pfkA Test For | ctgacatgatcaaccgtggcggta | SEQ ID NO: 107 |
| pfkA Test Rev | gatcgttccagtcatggatctgct | SEQ ID NO: 108 |

Example 11: Effects of the Modulation of the Pentose Phosphate Pathway on Isoprene Yield I. Materials and Methods LB media, TM3 media without Yeast extract and $MgSO_4$, 10% Yeast extract, 1M $MgSO_4$, 50% Glucose, 200 mM IPTG, 50 mg/mL Spectinomycin, 50 mg/mL Carbenicillin, Aluminum foil seal, 48-well sterile 5 mL block, breathe easier sealing membrane, aluminum foil seal, 96-well micro titer plates, 96-well glass block purchased from Zinsser Analytic. Agilent 6890 GC equipped with a 5973N Mass spectrometer.

Supplemented TM3 media was prepared by combining TM media, (without $MgSO_4$ and Yeast extract) 1% Glucose, 8 mM $MgSO_4$, 0.02% Yeast extract and appropriate antibiotics. 2 mL of day culture was started in 48-well sterile block by inoculating overnight culture in supplemented TM3 media at 0.2 optical density (OD). Blocks were sealed with breathe easier membrane and incubated for 2 hours at 34° C., 600 rpm. After 2 hours of growth, OD was measured at 600 nm in the micro titer plate and cells were induced with 200 µM IPTG. OD reading was taken every hour after the IPTG induction for 4 hours to determine growth rate. OD was measurement was done in the micro titer plate at appropriate dilution in the TM3 media at 600 nm using a SpectraMax Plus190 (Molecular Devices).

100 µL of isoprene samples were collected in a 96 well glass block at 2, 3 and 4 hours after IPTG induction. Glass block was sealed with aluminum foil and incubated at 34° C. while shaking at 450 rpm, for 30 minutes on the thermomixer. After 30 minutes, the block was kept in 70° C. water bath for 2 minutes and isoprene headspace measurement was done in GC/MS to determine specific productivity.

II. Results

Figure 27A:
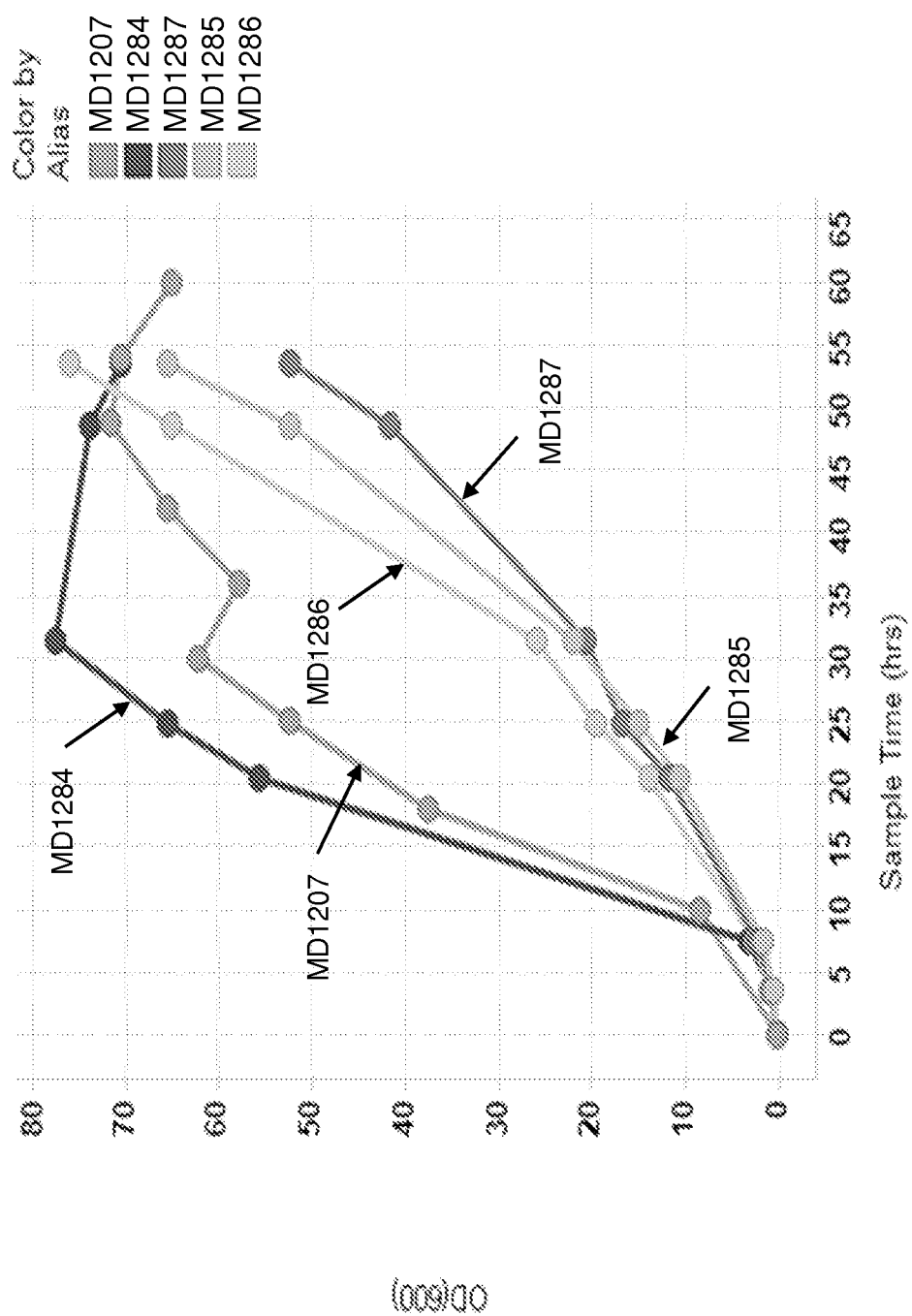
FIG. 27A-B depicts the growth rate (FIG. 27A) and isoprene titer produced over time (FIG. 27B) of MD1207 (control), MD1284 (PPP overexpression), MD1286 (PPP overexpression and PfkA I tag), MD1285 (PPP overexpression and PfkA T tag), MD1287 ((PPP overexpression and PfkA R tag)). All cells are yfiQ and pta deleted with *E. gallinarum* phosphoketolase heterologous expression.
Figure 27B:
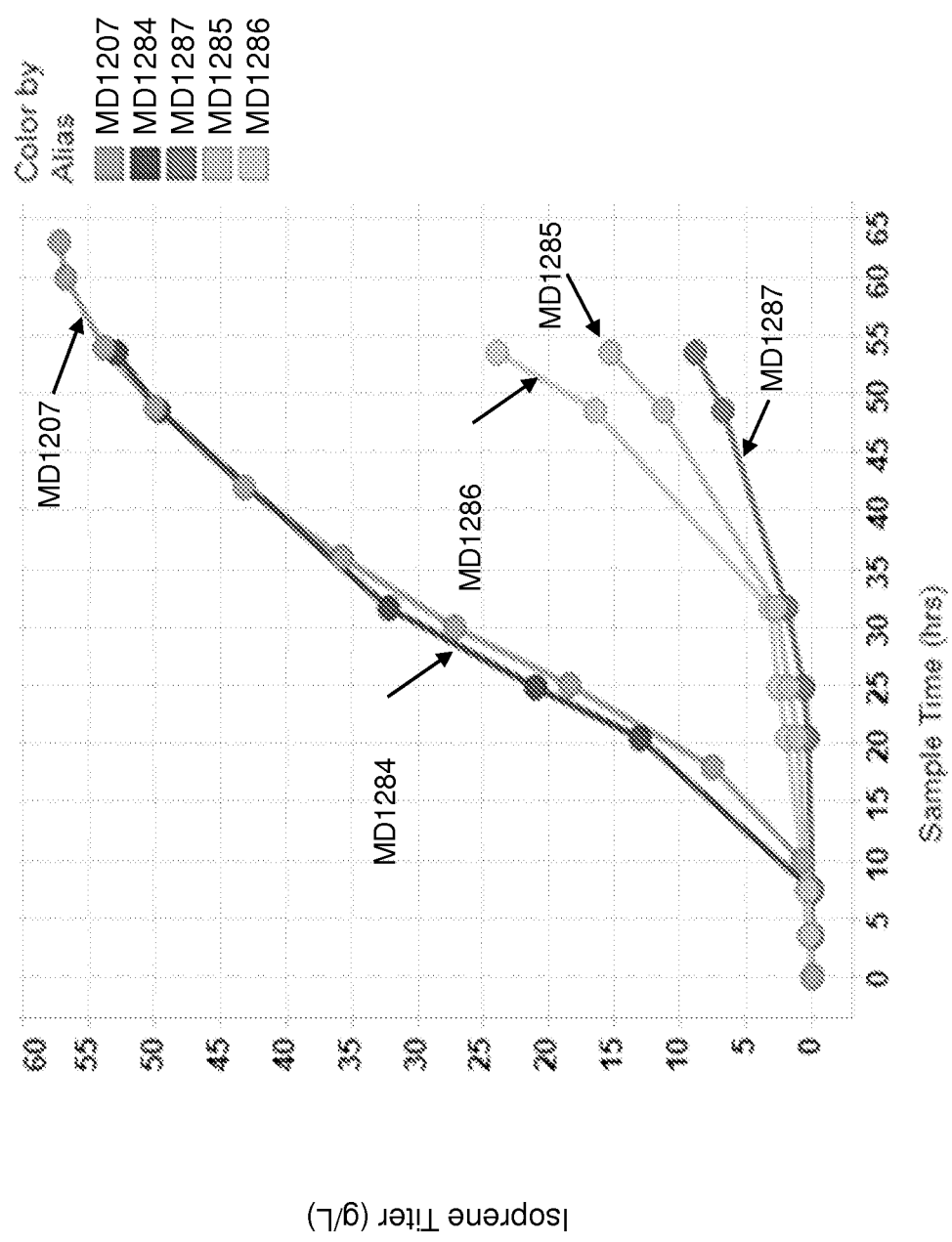

Cells with both the pentose phosphate pathway upregulated and pfkA downregulated were assayed under fed batch conditions. The cells with only the pentose phosphate pathway upregulated (MD1284), performed well compared to the control MD1207 cells (FIGS. 25A-D and 26A-D). The PPP upregulated cells displayed improved growth over the control, and additionally displayed faster instantaneous isoprene/$CO_2$ production and higher yield. Upregulation of the pentose phosphate pathway using a combination of the four non-oxidative genes is therefore beneficial for isoprene production. This could be due to an increase in available substrate for PKL (xylulose-5-phosphate), or more effective balancing of pentose phosphate intermediates (such as glyceraldehyde-3-phosphate or sedoheptulose-7-phosphate) that could benefit the overall flux through the pathway. All cells with pfkA downregulated by proteolytic tag grew poorly and underperformed compared to the control cells (FIG. 27A-B). This was likely due to too high of a degradation rate for all three tags, despite the broad effect on growth in Example 10. Additional mutations in pfkA tags would likely allow for improved growth rates while still driving the proper flux partition between glycolysis and phosphoketolase.

Example 12: Construction of Saccharomyces cerevisiae Reference and Acetylation Modulatory Strains This example describes the construction of reference strains and strains containing mutations in genes responsible for modulating intracellular protein acetylation. This example also describes measuring the effects of an acetyltransferase gene deletion on isoprene production in Saccharomyces cerevisiae strains expressing the mevalonate pathway and isoprene synthase I. Construction of Reference Strains with Constructs for Expression of the P. tremuloides Isoprene Synthase and Phosphoketolase Pathway in Saccharomyces cerevisiae The Saccharomyces cerevisiae codon-optimized P. tremuloides isoprene synthase and E. gallinarum phosphoketolase genes are synthesized by DNA 2.0. Using molecular biology techniques, the genes are PCR amplified and cloned into a construct suitable for insertion into a Saccharomyces cerevisiae 2 micron plasmid or chromosome. The construct has then the following structure: Upper homology-Promoter-Gene-Terminator-marker-Lower homology). The yeast cells are transformed and transformants are selected. Several colonies are picked and inoculated into YPD medium (Yeast extract 10 g/L, Bacto peptone 20 g/L, glucose 20 g/L) and grown. DNA is isolated from the cultures and purified. Constructs are PCR-amplified with error-proof DNA polymerase and are sequenced to verify that the DNA sequence is correct. In addition, in some strains, one or more MVA pathway polypeptides are similarly expressed in the yeast host cells.

II. Construction of Reference Strains Containing a Deletion of a Saccharomyces cerevisiae Acetyltransferase Gene Strains as described above containing also a deletion of a Saccharomyces cerevisiae acetyltransferase are generated using standard molecular biology protocols.

III. Production of Isoprene in Recombinant Strains of Saccharomyces cerevisiae

One ml of 15 and 36 hour old cultures of isoprene synthase transformants described above are transferred to head space vials. The vials are sealed and incubated for 5 hours at 30° C. Head space gas is measured and isoprene is identified by the methods described above.

Example 13: Construction of Saccharomyces cerevisiae Acetylation Modulatory Strains that Further Contain Mutations in Genes Responsible for Either Modulating the Pentose Phosphate Pathway (PPP) or Acetate Cycling This Example describes the construction of yeast strains from Example 12 further containing mutations in genes responsible for modulating the Pentose Phosphate Pathway (PPP) or acetate cycling. This Example also describes measuring the effects these mutations on isoprene production.

I. Construction of Reference Strains Containing Overexpression of One or More Saccharomyces cerevisiae PPP Genes, or Expression or Overexpression of Acetate Cycling Genes Strains created in Example 12 above (containing mutated acetylation proteins, isoprene synthase, phosphoketolase and MVA pathway polypeptides) are further engineered to create strains containing mutations of Saccharomyces cerevisiae PPP genes. These are generated using standard molecular biology protocols. TKL1, TAL1, RPE1 and RKI1 genes in the yeast pentose phosphate pathway involved in balancing carbon flux in a phosphoketolase-expressing host are optimized for expression in yeast. The genes are cloned and assembled to express different amount of the 4 activities of the PPP pathway using standard molecular biology techniques. These plasmids are transformed into yeast cells, and strains are isolated, and frozen down. Independent strains are verified by PCR. Alternatively, or additionally, strains created in Example 12 above are further engineered to contain mutations in the acetate cycling genes. One set of constructs expresses the *E. coli* phosphotransacetylase (codon-optimized for *Saccharomyces cerevisiae* and synthesized by DNA2.0), and yet another series expresses *E. coli* acetate kinase (codon-optimized for *Saccharomyces cerevisiae* and synthesized by DNA2.0) with or without overexpression of *Saccharomyces cerevisiae* acetyl-CoA synthase. Further genes for acetate kinase and acetyl-CoA synthase are introduced.

II. Production of Isoprene in Recombinant Strains of *Saccharomyces cerevisiae*

One ml of 15 and 36 hour old cultures of isoprene synthase transformants described above are transferred to head space vials. The vials are sealed and incubated for 5 hours at 30° C. Head space gas is measured and isoprene is identified by the methods described above.

Example 14: Construction of *Trichoderma reesei* Reference and Acetylation Modulatory Strains This Example describes the construction of reference strains and strains containing mutations in genes responsible for modulating intracellular protein acetylation in *Trichoderma reesei*. This Example also describes measuring the effects of an acetyltransferase gene deletion on isoprene production in *Trichoderma reesei* strains expressing the mevalonate pathway and isoprene synthase I. Construction of *Trichoderma reesei* Strains Expressing Isoprene Synthase, MVA Pathway and PKL Genes encoding *Trichoderma reesei* codon-optimized *P. alba* or *P. tremuloides* isoprene synthase, *E. gallinarum* PKL and *E. gallinarum* mvaE and mvaS are synthesized by DNA 2.0. Using standard molecular biology techniques, the genes are cloned into a vector such as pTrex3g under the control of sophorose-inducible promoters. pyr2 *Trichoderma reesei* protoplasts are transformed with a mixture of the above constructs and transformants are selected on amdS selection plates supplemented with uradine. Stable transformants are grown in media containing a glucose-sophorose carbon source and screened for expression of IspS, PKL and the MVA pathway proteins by immunoblot. Strains expressing all proteins are screened for isoprene production. Isoprene producers are selected for spore purification and further manipulation.

II. Construction Strains Containing a Deletion of a *Trichoderma reesei* Acetyltransferase Gene Isoprene-producing strains containing a deletion of a *Trichoderma reesei* acetyltransferase are generated using standard molecular biology protocols. Briefly, a cassette containing a loxP-flanked the hph gene is inserted within 2-4 kb of chromosomal DNA within or flanking the targeted acetyltransferase gene. This cassette is transformed into *T. reesei* protoplasts and hygromycin-resistant transformants are selected on Vogel's plates. Stable transformants are screened by PCR for insertion of the cassette to confirm disruption of the targeted locus and subsequently spore-purified. The resulting strain is confirmed to produce isoprene and be deleted for the acetyltransferase gene.

III. Construction of Strains for Acetate Cycling Via Pta

A gene encoding *Trichoderma reesei* codon-optimized *E. coli* pta is synthesized by DNA 2.0. Using standard molecular biology techniques, the gene is cloned under the control of a sophorose-inducible promoter such as from cbh1 on a hph-marked telomeric vector. This DNA is used to transform protoplasts of isoprene-producing *Trichoderma reesei* with and without the lysine acetyltransferase gene deleted. Transformants are selected on Vogel's plates containing hygromycin.

IV. Construction of Strains for Acetate Cycling Via *T. reesei* Acs1

A gene encoding *Trichoderma reesei* codon-optimized *E. coli* ackA is synthesized by DNA 2.0. Using standard molecular biology techniques, the gene is cloned under the control of a sophorose-inducible promoter such as from cbh1 on a hph-marked telomeric vector. A second cassette expressing the *T. reesei* acs1 gene from a sophorose-inducible promoter is cloned onto this vector. This DNA is used to transform protoplasts of isoprene-producing *Trichoderma reesei* with and without the lysine acetyltransferase gene deleted. Transformants are selected on Vogel's plates containing hygromycin.

V. Production of Isoprene in Recombinant Strains of *Trichoderma reesei*

Cultures of strains indicated in Table 11 are induced with glucose-sophorose and at 15 and 36 hours one mL from each culture is transferred to head space vials. The vials are sealed and incubated for 5 hours at 32° C. Head space gas is measured and isoprene is identified by the methods described above. Broth is clarified and MVA is identified by HPLC.

TABLE 11

Relevant genotypes of *T. reesei* strains for acetate recycle with and without deletion of acetyltransferase

| *E. gallinarum* mvaE and mvaS | P. albaispS | *E. gallinarum* PKL | *T. reesei* lysine acetyltransferase | *E. coli* pta | *E. coli* ackA | *T. reesei* acs1 |
|---|---|---|---|---|---|---|
| + | + | + | + | − | − | wt |
| + | + | + | − | − | − | wt |
| + | + | + | + | + | − | wt |
| + | + | + | − | + | − | wt |
| + | + | + | + | − | + | overexpressed |
| + | + | + | − | − | + | overexpressed |

SEQUENCES

*L. grayi* mvaE
```
atggttaaagacattgtaataattgatgccctccgtactcccatcggtaagtaccgcggtcagctctcaaagatgacggcggtggaattggga
accgcagttacaaaggctctgttcgagaagaacgaccaggtcaaagaccatgtagaacaagtcatttttggcaacgttttacaggcaggga
acggccagaatcccgcccgtcagatcgcccttaattctggcctgtccgcagagataccggcttcgactattaaccaggtgtgtggttctggc
ctgaaagcaataagcatggcgcgccaacagatcctactcggagaagcggaagtaatagtagcaggaggtatcgaatccatgacgaatgc
```

SEQUENCES

```
gccgagtattacatattataataaagaagaagacaccctctcaaagcctgttcctacgatgaccttcgatggtctgaccgacgcgtttagcgg
aaagattatgggtttaacagccgaaaatgttgccgaacagtacggcgtatcacgtgaggcccaggacgcctttgcgtatggatcgcagatg
aaagcagcaaaggcccaagaacagggcattttcgcagctgaaatactgcctcttgaaatagggggacgaagttattactcaggacgagggg
gttcgtcaagagaccaccctcgaaaaattaagtctgcttcggaccattttaaagaagatggtactgttacagcgggcaacgcctcaacgatc
aatgatggcgcctcagccgtgatcattgcatcaaaggagtttgctgagacaaaccagattccctaccttgcgatcgtacatgatattacagag
ataggcattgatccatcaataatgggcattgctcccgtgagtgcgatcaataaactgatcgatcgtaaccaaattagcatggaagaaatcgat
ctctttgaaattaatgaggcattgcagcatcctcggtggtagttcaaaaagagttaagcattcccgatgaaaagatcaatattggcggttccg
gtattgcactaggccatcctcttggcgccacaggagcgcgcattgtaaccaccctagcgcaccagttgaaacgtacacacggacgctatgg
tattgcctccctgtgcattggcggtggccttggcctagcaatattaatagaagtgcctcaggaagatcagccggttaaaaaattttatcaattgg
cccgtgaggaccgtctggctagacttcaggagcaagccgtgatcagcccagctacaaaacatgtactggcagaaatgacacttcctgaag
atattgccgacaatctgatcgaaaatcaaatatctgaaatggaaatccctcttggtgtggctttgaatctgagggtcaatgataagagttatacc
atcccactagcaactgaggaaccgagtgtaatcgctgcctgtgtaataatggtgcaaaaatggcaaaccacctgggcggttttcagtcagaatt
aaaagatggtttcctgcgtgggcaaattgtacttatgaacgtcaaagaacccgcaactatcgagcatacgatcacggcagagaaagcggca
atttttcgtgccgcagcgcagtcacatccatcgattgtgaaacgaggtgggggtctaaaagagatagtagtgcgtacgttcgatgatgatccg
acgttcctgtctattgatctgatagttgatactaaagacgcaatgggcgctaacatcattaacaccattctcgagggtgtagccggctttctgag
ggaaatccttaccgaagaaattctgttctctattttatctaattacgcaaccaaatcaattgtgaccgccagctgtcgcataccttacgaagcact
gagtaaaaaaggtgatggtaaacgaatcgctgaaaaagtggctgctgcatctaaatttgcccagttagatccttatcgagctgcaacccaca
acaaaggtattatgaatggtattgaggccgtcgtttggcctcaggaaatgacacacgggcggtcgcggcagccgcacatgcgtatgcttc
acgcgatcagcactatcggggcttaagccagtggcaggttgcagaaggcgcgttacacggggagatcagtctaccacttgcactcggca
gcgttggcggtgcaattgaggtcttgcctaaagcgaaggcggcattcgaaatcattggggatcacagaggcgaaggagctggcagaagtc
acagctgcggtagggctggcgcaaaacctggcggcgttaagagcgctcgttgttagtgaaggaatacagcaaggtcacatgtcgctccaggct
cgctctcttgcattatcggtaggtgctacaggcaaggaagttgaaatcctggccgaaaaattacagggctctcgtatgaatcaggcgaacgc
tcagaccatactcgcagagatcagatcgcaaaaagttgaattgtga                                    SEQ ID NO: 1
```

*L. grayi* mvaS

```
atgaccatgaacgttggaatcgataaaatgtcattctttgttccaccttactttgtggacatgactgatctggcagtagcacgggatgtcgatcc
caataagtttctgattggtattggccaggaccagatggcagttaatccgaaaacgcaggatattgtgacatttgccacaaatgctgccaaaaa
catactgtcagctgaggaccttgataaaattgatatggtcagtatcggcaccgagatggaaggtgaatccaaagcgagtgccgtagtgc
ttcacaggttgctcggtatccagaagtttgctcgctccttgaaatcaaagaagcctgttatgggggtaccgcggctttacagttcgctgtaaac
cacattaggaatcatcctgaatcaaaggttcttgtagttgcatcagatatcgcgaaatacggcctggcttctggaggtgaaccaacgcaaggt
gcaggcgctgtggctatgctcgtctcaactgaccctaagatcattgctttcaacgacgatagcctcgcgcttacacaagatatctatgacttct
ggcgaccagttggacatgactatcctatggtcgacgggcctcttagtacagaaccatacatccagtcattttcagaccgtatgcgcaggaatac
acaaaacggtcgcagcatgcactgcactgacactttgctgccttagctttcatatcccgtatcataaaatgggcaaaaaggcgctgcttgcaatc
cttgaaggcgaatcagaggaggctcagaaccgtatactagcaaaatatgaaaagagtatagcctactccagaaaggcgggtaacctgtata
ccggtagcctgtatctaggacttatttcacttctggaaaatgcagaagaccttaaagctggtgatttaataggcctcttttcttacggttccggtg
ctgttgcggagtttttctcaggaaggctggttgaggactatcaggaacagctacttaaaacaaaacatgccgaacagctggcccatagaaag
caactgacaatcgaggagtacgaaacgatgttctccgatcgcttggacgtggacaaagacgccgaatacgaagacacattagcttatagca
tttcgtcagtccgaaacaccgtacgtgagtacaggagttga                                         SEQ ID NO: 2
```

*E. faecium* mvaE

```
atgaaagaagtggttatgattgatgcggctcgcacacccattgggaaatacagaggtagtcttagtcctttttacagcggtgtggagctgggac
actggtcacgaaagggctgctggataaaacaaagcttaagaaagacaagatagaccaagtcgatattcggcaatgtgcttcaggcaggaaa
cggacaaaacgttgcaagacaaatagccctgaacagtggcttaccagttgacgtgccggcgatgactattaacgaagtttgcgggtccgga
atgaaagcggtgattttagccccgccagttaatacagttaggggaggcagagttggtcattgcaggggtacggagtcaatgtcacaagcac
ccatgctgaaacctaccagtcagagaccaacgaataacggaagacgcgatatcatcaatgcttaatgacgggctgacggtgcgttttccaat
gctcacatgggtcttactgccgaaaaggtggcgaccccagtttcagtgtcgcgcgaggaacaagaccgtacgcattgtccagccaattga
aagcagcgcacgcggttgaagccggggtgttctcagaagagattattccggttaagattagcgacgaggatgtcttgagtgaagacgagg
cagtaagaggcaacagcactttggaaaaactgggcaccttgcggacggtgttttctgaagagggcacggttaccgctggcaatgcttcacc
gctgaatgacgcgctagtgtcgtgattcttgcatcaaaagaatacggcgaaaacaatcaattgtgcctttacctggcgacgataaaggaggttg
cggaagttggtatcgatcctcctatcatgggtattgcccaataaaggccattcaaaagttaacagatcggtcgggcatgaacctgtccacga
ttgatctgttcgaaattaatgaagcattcgcggcatctagcattgttgtttctcaagagctgcaattggacaagaaaaagtgaatatctatggc
ggggcgatagctttaggccatccaatcggcgcaagcggagccccggatactgacaaccttagcatacggcctcctgcgtgagcaaaagcg
ttatggtattgcgtcattatgtatcggcggtggtcttggtctggccgtgctgttagaagcagaccccacaaagacgttcagaag
aaaaagttttaccagcttaccccctccgagcggagatcgcagcttatcgagaagaacggttctgactcaagaaacggcacttatttttccagga
gcagacgttgtccgaagaactgtccgatcacatgattgagaatcaggtcctccgaagtggaaattccaatgggaattgcacaaaattttcagat
taatggcaagaaaaatggattcctatggcgactgaagaaccttcagtaatagcggcagcatcgaacggcgccaaaatctgcgggaacatt
tgcgcggaaacgcctcagcggcttatgcgcgggcagttgtcctgtctggcaaatcagaatatcaagccgtgataaatgccgtgaatcatc
gcaaagaagaactgattcttttgcgcaaacgagtcgtaccccgagtattgttaaacgcggggaggtgttcaggatatttctacgcgggagttta
tgggttcttttcacgcgtatttatcaatcgactttctggtggacgtcaaggacgcaatggggcaaacatgatcaactctattctcgaaagcgtt
gcaaataaactgcgtgaatggttcccggaagaggaaatactgttctccatcctgtcaaacttcgctacggagtccctggcatctgcatgttgc
gagattccttttgaaagacttggtcgtaacaaagaaattggtgaacagatcgccaagaaaattcaacaggcagggggaatatgctaagcttga
cccttaccgcgcggcaacccataacaagggattatgaacgtatcgaagccgtcgttgccgcaacgggaaacgacacaggctgttttc
cgcttctattcacgcatacgccgccctaatggcttgtaccaaggtttaacggattggcagatcaaggggcataaactggttggtaaattaac
agtcccactggctgtggcgactgtcggtggcgtcgaacatattaccaaaagcaaagcttccctcgccatgctggatattgattccgcaa
aagaactggcccaagtgatcgccgcggtaggtttagcacagaatctggcggcgttacgtgcattagtgacagaaggcattcagaaaggac
acatgggcttgcaagcacgttcttagcgatttcgataggtgccatcggtgaggagatagagcaagtcgcgaaaaaactgcgtgaagctga
aaaaatgaatcagcaaacgcaatacagatttagaaaaaattcgcgagaaatga                             SEQ ID NO: 3
```

*E. faecium* mvaS

```
atgaaaatcggtattgaccgtctgtccttcttcatcccgaatttgtatttggacatgactgagctggcagaatcacgcggggatgatccagcta
aatatcatattggaatcggacaagatcagatggcagtgaatcgcgcaaacgaggacatcataacactggggtgcaaacgctgcgagtaaga
tcgtgacagagaaagaccgcagttgatttgattgatatggtgcgacgaatcaggaattgaccactccaaagcaagtgcgtgattatt
caccatctccttaaaattcagtcgttcgcccgttctttcgaggtaaaagaagcttgctatgggcgaactgctgccctgcacatggcgaaggag
tatgtcaaaaatcatccggagcgtaaggtcttggtaattgcgtcagacatcgcgcgttatggttccagcggaggagaagttactcaagg
cgtggggcgtagccatgatgattacacaaaaccccgattcttcgattgaagacgatagtgttttctcacagaggatatctatgatttct
ggcggcctgattactccgagttccctgtagtggacggccccttcaaactcaacgtatatagagagttttcagaaagtttggaaccggcaca
aggaattgtccggaagagggctggaagattatcaagctattgcttttcacataccctatacgaagatgggtaagaaagcgctccagagtgttt
```

-continued

SEQUENCES tagaccaaaccgatgaagataaccaggagcgcttaatggctagatatgaggagtctattcgctatagccggagaattggtaacctgtacaca
ggcagcttgtaccttggtcttacaagcttgttggaaaactctaaaagtttacaaccgggagatcggatcggcctcttttcctatggcagtggtg
cggtgtccgagttctttaccgggtatttagaagaaaattaccaagagtacctgttcgctcaaagccatcaagaaatgctggatagccggactc
ggattacggtcgatgaatacgagaccatcttttcagagactctgccagaacatgtgaatgcgccgaatatacgagcgacgtccccttttcta
taaccaagattgagaacgacattcgttattataaaatctga SEQ ID NO: 4

E. gallinarum mvaE
atggaagaagtggtaattatagatgcacgtcggactccgattggtaaatatcacgggtcgttgaagaagttttcagcggtggcgctgggac
ggccgtggctaaagacatgttcgaacgcaaccagaaaatcaaagaggagatcgcgcaggtcataattggtaatgtcttgcaggcaggaaa
tggccagaacccgcgcggcaagttgctcttcaatcagggttgtccgttgacattccgcttctacaattaacgaggtttgtgggtctggtttg
aaagctatcttgatgggcatggaacaaatccaactcggcaaagcgcaagtagtgctggcaggcggcattgaatcaatgacaaatgcgcca
agcctgtcccactataacaaggcggaggatacgtatagtcccagtgtcgagcatgacactggatggtctgacagacgcattttctagtaa
acctatgggattaacagcggaaaacgtcgcacagcgctacgtatctcccgtgaggcgcaagatcaattcgcatatcaatctcagatgaaa
gcagcaaaagcgcaggcagaaaacaaattcgctaaggaaattgtgccactggcgggtgaaactaaaaccatcacagctgacgaagggat
cagatccccaaacaacgatggagaaactggcaagtctcaaacctgttttaaaaccgatggcactgtaaccgcagggaatgctagcaccatt
aatgacggggccgcccttgtgctgcttgctagcaaaacttactgcgaaactaatgacataccgtaccttgcgacaatcaaagaaattgttgaa
gttggaatcgatccggagattatgggcatctctccgataaaagcgatacaaacattgttacaaaatcaaaaagttagcctcgaagatattgga
gttttgaaataaatgaagcctttgccgcaagtagcatagtggttgaatctgagttgggattagatccggctaaagttaaccgttatgggggtg
gtatatccttaggtcatgcaatgggggcaaccggcgctcgcctggccacttcactggtgtatcaaatgcaggagatacaagcacgttatggta
ttgcgagcctgtgcgttggtggtggacttggactggcaatgcttttagaacgtccaactattgagaaggctaaaccgacagacaaaagttct
atgaattgtcaccagctgaacggttgcaagagctggaaaatcaacagaaaatcagttctgaaactaaacagcagttatctcagatgatgcttg
ccgaggacactgcaaaccatttgatagaaaatcaaatatcagagatttgaactcccaatgggcgtcggggtgaacctgaaggttgatgggaa
agcctatgttgtgccaatggcgacggaagagccgtccgtcatcgcggcgcatgtctaatggtgccaaaatggccggcgaaattcacactcag
tcgaaagaacggctgctcagaggtcagattgtttttcagcgcgaagaatccgaatgaaatcgaacagagaatagctgagaaccaagctttga
ttttcgaacgtgccgaacagtcctatccttccattgtgaaaagagagggaggctccgccgcattgcacttcgtcattttcctgccgattctcag
caggagtctgcggaccagtccacattttttatcagtggacctttttgtagatgtgaaagacgcgatgggggcaaatatcataaatgcaatacttg
agggcgtcgcagccctgtttcgcgaatggttccccaatggaaattcttttttctattctctcgaacttggctacggagagcttagtcacggct
gtttgtgaagtcccatttagtgcacttagcaaggaggtggtgcaacggtggcccagaaaattgtgcaggcgtcgctcttcgcaaagacag
acccataccgcagtgacccacaacaaagggattatgaacggtgtagaggcgttatgcttgccacaggcaacgacacgcgcagtct
cagccgcttgtcatggatacgcagcgcgcaccggtagctatcagggtctgactaactggacgattgagtcggatcgcctggtaggcagaga
taacactgccgctggccatcgctacagttggaggcgctaccaaagtgttgcccaaagctcaagcggcactggagattagtgatgttcactct
tctcaagagcttgcagcctagcggcgtcagtaggtttagtacaaaatctgcgggccctgcgcgcactggtttccgaaggtatacaaaaagg
gcacatgtccatgcaagcccggtctctcgcaatcgcggtcggtgctgaaaaagccgagatcgagcaggtcgccgaaaagttgcggcaga
acccgccaatgaatcagcagcaggcgctccgttttcttggcgagatccgcgaacaatga SEQ ID NO: 5

E. gallinarum mvaS
atgaacgtcggcattgacaaaattaattttttcgttccaccgtattatctggatatggtcgacctggcccacgcacgcgaagtggaccgaac
aaatttcaattggaattggacaggatcagatggctgtgagcaaaaagacgcacgatatcgtaacattcgcggctagtgccgcgaaggaaa
ttttagaacctgaggacttgcaagctatagacatggttatagttggtaccgaatcgggcattgacgagagcaaagcatccgcggtcgttttac
atcgtttgttgggcgtacaacccttcgctcgcagttttgaaattaaagaagcctgttacggggcaaccgcaggcattcagtttgccaagactca
tatacaagcgaacccggagagcaaggtcctggtaattgcaagcgatatagctcggtatggtcttcggtcaggtggagagcccacacaagg
cgcagggcagttgctatgcttctcacggcaaatcccagaatcctgaccttcgaaaacgacaatctgatgttaacgcaggatatttatgacttc
tggagaccacttggtcacgcttacccctatggtagatgaggccactttccaatcaagtctatattgacagtttttaagcaaggctcggcaagcacattg
cgaacgcaatcaagcttctatatccgactatgccgcgattcagttttttcatatttccgtatacaaaatgggtaagaaagcccgtgctcgctgttttgc
agatgaagtggaaactgaacaggaacgcgttatgcacgtatgaagagtctatcgtatattcacgccggatcggcaacttgtatacggat
cattgtacctggggctgatatccttattggaaaacagttctcacctgtcggcgggcgaccggataggattgtttagttatgggagtggcgctgt
cagcgaattttctccggtcgtttagtggcaggctatgaaaatcaattgaacaaagaggcgcatacccagctcctggatcagcgtcagaagc
tttccatcgaagagtatgaggcgatttttacagattccttagaaattgatcaggatgcagcgttctcggatgacctgccatattccatccgcgag
ataaaaaacacgattcggtactataaggagagctga SEQ ID NO: 6

E. casseliflavus mvaE
atggaagaagttgtcatcattgacgcactgcgtactccaataggaaagtaccacggttcgctgaaagattacacagctgttgaactggggac
agtagcaaaggcgttgctggcacgaaatcagcaagcaaaagaacacatagcgcaagttattattggcaacgtcctgcaagccggaa
gtgggcagaatccaggccgacaagtcagtttacagtcaggattgtcttctgatatcccgctagcacgatcaatgaagtgtggctcgggt
atgaaagcgattctgatgggtatggagcaaattcagtcgaacaaaagcctctgtggtcttaacaggcggaattgaaagcatgaccaacgcgc
cgctgtttagttattacaacaaggctgaggatcaatattcggcgccggttagcacaatgatgcacgatggtctaacagatgctttcagttccaa
accaatgggcttaaccgcagagaccgtcgctgagagatatggaattacgcgtaaggaacaagatgaatttgcttatcactctcaaatgaagg
cggccaaagcccaggcggcgaaaaagtttgatcaggaaatttgtaccctgcaggaaaatcggaacggttctccaggacgaaggcatc
agagccgcgacaacagtcgagaagctagctgagcttaaaacggtgttcaaaaaagacggaacagttacagcgggtaaccgcctctacgat
aaatgatggcgctgctatggtattaatagcatcaaaatcttattgcgaagaacaccagattcctatctggccgttataaaggagatcgttgag
gtggggtttgccccgaaataatgggtatttccccccattaaggctatagacaccctgctgaaaaatcaagcactgaccatagaggatataggag
atatttgagattaatgaagcctttgctgcgagttcgattgtggtagaacgcgagttgggcctggaccccaaaaagttaatcgctatggcggt
ggtatatcactcggccacgcaattgggcgacgggagctcgcattgcgacgaccgttgctatcagctgaaagatacccaggagcgctac
ggtagcttccttgccgttggtgggtcttggtgcgatgcttctgaaaacgccctcagcgtttttggaagcccaaggcgctattaccg
ctgctgaaacctggtcttccaggagatgaccttaaacaaagagacagccaatcacttaatcgaaaaccaaatcagcgaagttgaaattcctt
taggcgtgggcctgaacttacaggtgaatgggaaagcgtataatgttcctctggccacggaggaaccgtccgttatcgctgcgatgtcgaat
ggcgccaaaatggctggtcctattacaacaacaagtcaggagaggctgttacgggtcagattgtcttcatggacgtacaggacccagaa
gcaatattagcgaaagttgaatccggagcataccttttcgcggtgaaataaccgtctcatcgtgaaaagaggaggctct
gcgtagagtcattggcaggaatttcagtccgccaaagtgacttagccacggcatgtatcaattgacctgatggtagatgtttaaggatgc
aatgggtgctaatatcatcaatagtatcctagaaggtgttcggaattgtttagaaaatggttcccagaagaagaaatcctgttctcaattctctc
caatctcgcgacagaaagtctggtaacggcgacgtgctcagttccgtttgataaattgtccaaaactgggaatggtcgacaagtagctggta
aaatagtgcacgcggggactttgctaagatagatccatacagagctgccacacacaataaaggtattatgaatggcgttgaagcgttaatct
tagccaccggtaatgacacccgtcggtgtcggctgcatgccacggttacgcggcacgcaatgggcgaatgcaagggcttacctcttgga -continued

| SEQUENCES |
|---|
| cgattatcgaagatcggctgataggctctatcacattacctttggctattgcgacagtggggggtgccacaaaaatcttgccaaaagcacag |
| gccgcctggcgctaactggcgttgagacggcgtcggaactggccagcctggcggcgagtgtgggattagttcaaaatttggccgctttac |
| gagcactagtgagcgagggcattcagcaagggcacatgagtatgcaagctagatccctggccattagcgtaggtgcgaaaggtactgaa |
| atagagcaactagctgcgaagctgagggcagcgacgcaaatgaatcaggagcaggctcgtaaatttctgaccgaaataagaaattaa |

SEQ ID NO: 7

*E. casseliflavus mvaS* atgaacgttggaattgataaaatcaatttttcgttccgccctatttcattgatatggtggatctcgctcatgcaagagaagttgaccccaacaag
ttcactataggaataggccaagatcagatggcagtaaacaagaaaacgcaagatatcgtaacgttcgcgatgcacgcgcgaaggatattc
tgactaaggaagatttacaggccatagatatggtaatagtggggactgagtctgggatcgacgagagcaaggcaagtgctgtcgtattgcat
cggcttttaggtattcagccttttgcgcgctcctttgaaattaaggaggcatgctatgggccactgccggccttcagtttgcaaaagctcatgt
gcaggctaatccccagagcaaggtcctggtggtagcttccgatatcagcacgtacggactggcatccggaggagaaccgactcaaggtgt
aggtgctgtggcaatgttgatttccgctgatccagctatctgcagttagaaaatgataatctcatgttgacccaagatatacgattttggcg
cccggtcgggcatcaatatcctatggtagacggccatctgtctaatgccgtctatatagacagctttaaacaagtctggcaagcacattgcga
gaaaaaccaacggactgctaaagattatgctgcattgtcgttccatattccgtcacacgaaatgggtaagaaagctctgttagcggttttttgcg
gaggaagatgagacagaacaaaagcggttaatggcacgttatgaagaatcaattgtatacagtcgtcggaatgctgaaatctgtatactggctc
actctatctgggcctgatttccttactggagaatagtagcagtttacaggcgaacgatcgcataggtctgtttagctatggttcaggggccgttg
cggaatttttcagtggcctcttggtaccgggtacgagaaacaattagcgcaagctgcccatcaagtcttctggacgaccggcaaaactg
actatcgcagagtacgaagccatgtttaatgaaaccattgatattgatcaggaccagtcatttgaggatgacttactgtactccatcagagaga
tcaaaaacactattcgctactataacgaggagaatgaataa SEQ ID NO: 8

*E. gallinarum EG2 (mvaE)*

MEEVVIIDARRTPIGKYHGSLKKFSAVALGTAVAKDMFERNQKIKEEIAQVIIGNVLQAGNGQNPARQVALQSGLSVDIPASTINEVCGSGLKAILM
GMEQIQLGKAQVVLAGGIESMTNAPSLSHYNKAEDTYSVPVSSMTLDGLTDAFSSKPMGLTAENVAQRYGISREAQDQFAYQSQMKAAKA
QAENKFAKEIVPLAGETKTITADEGIRSQTTMEKLASLKPVFKTDGTVTAGNASTINDGAALVLLASKTYCETNDIPYLATIKEIVEVGI
DPEIMGISPIKAIQTLLQNQKVSLEDIGVFEINEAFAASSIVVESELGLDPAKVNRYGGGISLGHAIGATGARLATSLVYQMQEIQARYGIAS
LCVGGGLGLAMLLERPTIEKAKPTDKKFYELSPAERLQELENQQKISSETKQQLSQMMLAEDTANHLIENQISEIELPMGVGMNLKVDGKAYVVPMA
TEEPSVIAAMSNGAKMAGEIHTQSKERLLRGQIVFSAKNPNEIEQRIAENQALIFERAEQSYPSIVKREGGLRRIALRHFPADSQQESADQSTFLSVD
LFVDVKDAMGANIINAILEGVAALFREWFPNEEILFSILSNLATESLVTAVCEVPFSALSKRGGATVAQKIVQASLFAKTDPYRAVTHNKGIMNGVEA
VMLATGNDTRAVSAACHGYAARTGSYQGLTNWTIESDRLVGEITLPLAIATVGGATKVLPKAQAALEISDVHSSQELAALAASVGLVQNLAALRALV
SEGIQKGHMSMQARSLAIAVGAEKAEIEQVAEKLRQNPPMNQQQALRFLGEIREQ SEQ ID NO: 9

*E. gallinarum EG2 (mvaS)*

MNVGIDKINFFVPPYYLDMVDLAHAREVDPNKFTIGIGQDQMAVSKKTHDIVTFAASAAKEILEPEDLQAIDMVIVGTESGIDESKASAVVLHRLLG
VQPFARSFEIKEACYGATAGIQFAKTHIQANPESKVLVIASDIARYGLRSGGEPTQGAGAVAMLLTANPRILTFENDNLMLTQDIYDFWRPLGHAY
PMVDGHLSNQVYIDSFKKVWQAHCERNQASISDYAAISFHIPYTKMGKKALLAVFADEVETEQERVMARYEESIVYSRRIGNLYTGSLYLGLISLLENSS
HLSAGDRIGLFSYGSGAVSEFFSGRLVAGYENQLNKEAHTQLLDQRQKLSIEEYEAIFTDSLEIDQDAAFSDDLPYSIREIKNTIRYYKES
SEQ ID NO: 10

*L. grayi (mvaE)*

MVKDIVIIDALRTPIGKYRGQLSKMTAVELGTAVTKALFEKNDQVKDHVEQVIFGNVLQAGNGQNPARQIALNSGLSAEIPASTINQVCGSGLKAISMA
RQQILLGEAEVIVAGGIESMTNAPSITYYNKEEDTLSKPVPTMTFDGLTDAFSGKIMGLTAENVAEQYGVSREAQDAFAYGSQMKAAKAQEQGI
FAAEILPLEIGDEVITQDEGVRQETTLEKLSLLRTIFKEDGTVTAGNASTINDGASAVIIASKEFAETNQIPYLAIVHDITEIGIDPSIMGIA
PVSSAINKLIDRNQISMEEIDLFEINEAFAASSVVVQKELSIPDEKINIGGSSIALGHPLGATGARIVTTLAHQLKRTHGRYGIASLCIGGGLGLAIL
IEVPQEDQPVKKFYQLAREDRLARLQEQAVISPATKHVLAEMTLPEDIADNLIENQISEMEIPLGVALNLRVNDKSYTIPLATEEPSVIAACNNGAKM
ANHLGGFQSELKDGFLRGQIVLMNVKEPATIEHTITAEKAAIFRAAAQSHPSIVKRGGGLKEIVVRTFDDDPTFLSIDLIVDTKDAMGANIINTILEGV
AGFLREILTEEILFSILSNYATESIVTASCRIPYEALSKKGDGKRIAEKVAAASKFAQLDPYRAATHNKGIMNGIEAVVLASGNDTRAVAAAAHAYASR
DQHYRGLSQWQVAEGALHGEISLPLALGSVGGAIEVLPKAKAAFEIMGITEAKELAEVTAAVGLAQNLAALRALVSEGIQQGHMSLQARSLALSVGATG
KEVEILAEKLQGSRMNQANAQTILAEIRSQKVEL SEQ ID NO: 11

*L. grayi (mvaS)*

MTMNVGIDKMSFFVPPYFVDMTDLAVARDVDPNKFLIGIGQDQMAVNPKTQDIVFATNAAKNILSAEDLDKIDMVIVGTESGIDESKASAV
VLHRLLGIQKFARSFEIKEACYGGTAALQFAVNHIRNHPESKVLVVASDIAKYGLASGGEPTQGAGAVAMLVSTDPKIIAFNDDSLALTQDIYDFWRP
VGHDYPMVDGPLSTETYIQSFQTVWQEYTKRSQHALADFAALSFHIPYTKMGKKALLAILEGESEEAQNRILAKYEKSIAYSRKAGNLYTGSLYLGLISL
LENAEDLKAGDLIGLFSYGSGAVAEFFSGRLVEDYQEQLLKTKHAEQLAHRKQLTIEEYETMFSDRLDVDKDAEYEDTLAYSISSVRNTVREYRS
SEQ ID NO: 12

*E. faecium (mvaE)*

MKEVVMIDAARTPIGKYRGSLSPFTAVELGTLVTKGLLDKTKLKKDKIDQVIFGNVLQAGNGQNVARQIALNSGLPVDVPAMTINEVCGSGMKAVIL
ARQIQLGEAELVIAGGTESMSQAPMLKPYQSETNEYGEPISSMVNDGLTDAFSNAHMGLTAEKVATQFSVSREEQDRYALSSQLKAAHAVEAGVFSEE
IIPVKISDEDVLSEDEAVRGNSTLEKLGTLRTVFSEEGTVTAGNASPLNDGASVVILASKEYAENNNLPYLATIKEVAEVGIDPSIMGIAPIKAIQKLTD

RSGMNLSTIDLFEINEAFAASSIVVSQELQLDEEKVNIYGGAIALGHPIGASGARILTTLAYGLLREQKRYGIASLCIGGGLGLAVLLEANMEQTH
KDVQKKKFYQLTPSERRSQLIEKNVLTQETALIFQEQTLSEELSDHMIENQVSEVEIPMGIAQNFQINGKKKWIPMATEEPSVIAAASNGAKICGNI
CAETPQRLMRGQIVLSGKSEYQAVIVANVNHRKEELILCANESYPSIVKRGGVQDISTREFMGSFHAYLSIDFLVDVKDAMGANMINSILESVANKLR
EWFPEEEIILFSILSNFATESLASACCEIPFERLGRNKEIGEQIAKKIQQAGEYAKLDPYRAATHNKGIMNGIEAVVAATGNDTRAVSASIHAYAARNG
LYQGLTDWQIKGDKLVGKLTVPLAVATVGGASNILPKAKASLAMLDIDSAKELAQVIAAVGLAQNLAALRALVTEGIQKGHMGLQARSL
AISIGAIGEEIEQVAKKLREAEKMNQQTAIQILEKIREK SEQ ID NO: 13

*E. faecium (mvaS)*

MKIGIDRLSFFIPNLYLDMTELAESRGDDPAKYHIGIGQDQMAVNRANEDIITLGANAASKIVTEKDRELIDMVIVGTESGIDHSKASAVIIHHLLKIQ
SFARSFEVKEACYGGTAALHMAKEYVKNHPERKVLVIASDIARYGLASGGEVTQGVGAVAMMITQNPRILSEDDSVFLTEDIYDFWRPDYSEFPVVD
GPLSNSTYIESPQKVWNRHKELSGRGLEDYQAIAFHIPYTKMGKKALQSVLDQTDEDNQERLMARYEESIRYSRRIGNLYTGSLYLGLTSLLENSKSLQP
GDRIGLFSYGSGAVSEFFTGYLEENYQEYLFAQSHQEMLDSRTRITVDEYETIFSETLPEHGECAEYTSDVPFSITKIENDIRYYKI
SEQ ID NO: 14

SEQUENCES

*E. casseliflavus* (mvaE)
MEEVVIIDALRTPIGKYHGSLKDYTAVELGTVAAKALLARNQQAKEHIAQVIIGNVLQAGSGQNPGRQVSLQSGLSSDIPASTINEVCGSGMKAI
LMGMEQIQLNKASVVLTGGIESMTNAPLFSYYNKAEDQYSAPVSTMMHDGLTDAFSSKPMGLTAETVAERYGITRKEQDEFAYHSQMKAAKAQAAKK
FDQEIVPLTEKSGTVLQDEGIRAATTVEKLAELKTVFKKDGTVTAGNASTINDGAAMVLIASKSYCEEHQIPYLAVIKEIVEVGFAPEIMGISPIKAIDT LLKNQALTIEDIGIFEINEAFAASSIVVERELGLDPKKVNRYGGGISLGHAIGATGARIATTVAYQLKDTQERYGIASLCVGGGLGL
AMLLENPSATASQTNFDEESASEKTEKKKFYALAPNERLAFLEAQGAITAAETLVFQEMTLNKETANHLIENQISEVEIPLGVGLNLQVNGKAYNV
PLATEEPSVIAAMSNGAKMAGPITTTSQERLLRGQIVFMDVQDPEAILAKVESEQATIFAVANETYPSIVKRGGGLRRVIGRNFSPAESDLATAYVSID
LMVDVKDAMGANIINSILEGVAELFRKWFPEEEILFSILSNLATESLVTATCSVPFDKLSKTGNGRQVAGKIVHAADFAKIDPYRAATHNKGIMNGVEAL
ILATGNDTRAVSAACHGYAARNGRMQGLTSWTIIEDRLIGSITLPLAIATVGGATKILPKAQAALALTGVETASELASLAASVGLVQNLAALRALVS
EGIQQGHMSMQARSLAISVGAKGTEIEQLAAKLRAATQMNQEQARKFLTEIRN SEQ ID NO: 15

*E. casseliflavus* (mvaS)
AKDILTKEDLQAIDMVIVGTESGIDESKASAVVLHRLLGIQPFARSFEIKEACYGATAGLQFAKAHVQANPQSKVLVVASDIARYGLASGGEPTQGVGA
VAMLISADPAILQLENDNLMLTQDIYDFWRPVGHQYPMVDGHLSNAVYIDSFKQVWQAHCEKNQRTAKDYAALSFHIPYTKMGKKALLAVFAEEDE
TEQKRLMARYEESIVYSRRTGNLYTGSLYLGLISLLENSSSLQANDRIGLFSYGSGAVAEFFSGLLVPGYEKQLAQAAHQALLDDRQKLTIAEYEAM
FNETIDIDQDQSFEDDLLYSIREIKNTIRYYNEENE SEQ ID NO: 16

Acetoactyl-CoA-synthase
MTDVRFRIIGTGAYVPERIVSNDEVGAPAGVDDDWITRKTGIRQRRWAADDQATSDLATAAGRAALKAAGITPEQLTVIAVATSTPDRPQPPTA
AYVQHHLGATGTAAFDVNAVCSGTVFALSSVAGTLVYRGGYALVIGADLYSRILNPADRKTVVLFGDGAGAMVLGPTSTGTGPIVRRVALHTFGGLTDL
IRVPAGGSRQPLDTDGLDAGLQYFAMDGREVRRFVTEHLPQLIKGFLHEAGVDAADISHFVPHQANGVMLDEVFGELHLPRATMHRTVETYGNTGAAS
IPITMDAAVRAGSFRPGELVLLAGFGGGMAASFALIEW SEQ ID NO: 17

*E. faecalis* mvaE
atgaaaacagtagttattattgatgcattacgaacaccaattggaaaatataaaggcagcttaagtcaagtaagtgccgtagacttaggaaca
catgttacaacacaacttttaaaaagacattccactattctgaagaaattgatcaagtaatctttggaaatgttttacaagctggaaatggccaa
aatcccgcacgacaaatagcaatcaaacagcggttgtctcatgaaattcccgcaactgacggttaatgaggtctgcggatcaggaatgaagg
ccgttattttggcgaaacaattgattcaattaggagaagcggaagttttaattgctggcgggattgagaatatgtcccaagcacctaaattaca
acgttttaattacgaaacagaaagctacgatgcgcctttttctagtatgatgtatgatggattaacggatgcctttagtggtcaggcaatgggcctt
aactgctgaaaatgtggccgaaaagtatcatgtaactagagaagagcaagatcaattttctgtacattcacaattaaaagcagctcaagcaca
agcagaaggatattcgctgacgaaatagccccattagaagtatcaggaacgcttgtggagaaagatgaaggattcgccctaattcgagc
gttgagaacgctaaaacagttttttaaagaacgttactgtaacgcaggggaatgcatcaaccattaatgatggggcttctgct
ttgattattgcttcacaagaatatgccgaagcacacggtcttcctatttagctattattcgagacagtgttggaagtcggtattgatccagcctata
tgggaaattcgccgattaaagccattcaaaaactgttagcgcgcaataacttactacgaagaaattgatctgtatgaaatcaacgaagcatt
tgcagcaacttcaatcgtggtccaaagagaactggcttttaccagaggaaaaggtcaacatttatggtggcggtattcattaggtcatgcgatt
ggtgccacaggtgctcgttttattaacgagttttaagttatcaattaaatcaaagaaaaaataaagtggagtggctttcttttatgtatcggcggtgg
cttaggactcgctatgctactagagagacctcagcaaaaaaaaacagccgattttatcaaatgagtcctgaggaacgcctggcttctcttctt
aatgaaggccagatttctgctgatacaaaaaaagaatttgaaaatacggctttatcttcgcagattgccaatcatatgattgaaaatcaaatcag
tgaaacagaagtgccgatgggcgttggcttacatttaacagtggacgaaactgattatttggtaccaatggcgacagaagagccctcagttat
tgcggctttgagtaatggtgcaaaaatagcacaaggatttaaaacagttaaccaagcttaatcgtgcgacaaatcagtcgttttttacgatgtt
gcagatcccgagtcattgattgataaactacaagtaagaagcggaagtttttcaacaagcagagttaagtatccatctatcgttaaacgg
ggcggcggcttaagagatttgcaatatcgtacttttttgatgaatcattcgtatctgtcgactttttagtagatgttaaggatgcaatggggcaaat
atcgttaacgctatgttggaagtgtggccgagttgttccgtgaatggtttgcgagcaaaagattttattcagtattttaagtaattatgccacg
gagtcggttgttacgatgaaaacgctattccagtttcacgttttaagtaaggggacaattggcgggaaattgctgaaaaaattgttttagctt
cacgctatgcttcattagatcctatcggccagtcacgcataacaaaggaatcatgaatggcattgaagctgtagttttagctacaggaaatga
tacacgcgctgttagcgcttcttgtcatgcttttgcggtgaaggaaggtcgctaccaaggctgactagttggacgctggatggcgaacaact
aattggtgaaatttcagttccgcttgctttagccacggttggcggtgccacaaaagtcttacctaaatctcaagcagctgctgatttgttagcagt
gacggatgcaaaagaactaagtcgagtagtagcgtcgtgttggtttggcacaaaatttagcggcgttacgggccttagtctctgaaggaattc
aaaaaggacacatggctctacaagcacgttcttagcgatgacggtcggagctactggtaaagaagttgaggcgagctcgctcaacaattaaa
acgtcaaaaaacgatgaaccaagacggagccatggctattttaaatgatttaagaaaacaataa SEQ ID NO: 18

*E. faecalis* mvaS
Atgacaattgggattgataaaattagtttttttgtgcccccttattatattgatatgacggcactggctgaagcccagaaatgtagaccctggaaaa
atttcatattggtattgggcaagaccaaatggcggtgaacccaatcagccaagatattgtgacatttgcagccaatgccgcagaagcgatctt
gaccaaagaagataaagaggccattgatatggtgattgtcgggactgagtccagtatcgatgagtcaaaagcggccgcagttgtcttacatc
gtttaatggggattcaaccttttcgctcgctctttcgaaatcaaggaagcttgttacggagaacagcaggcttacagttagctaagaatcacgt
agccttacatccagataaaaaatcttggtcgtagcggcagatattgcaaaatatggcttaaattctggcggtgagcctcacacaaggagctg
gggcggttgcaatgttagttgctagtgaacgcgcattttggcttaaaagaggataatgtgatgctgacgcaagatatctatgactttttggcgt
ccaacaggcacccgtatcctatggtcgatggtcctttgtcaaacgaaacctacatccaatcttttgcccaagtctgggatgaacataaaaaaa
cgaaccggtcttgattttgcagattatgatgctttagcgttccatattccttacacaaaaatgggcaaaaaagccttattagcaaaaatctccgac
caaactgaagcagaacaggacgaatttttagccgtgatgaagaaagtatcgtctatagtcgtcgcgtaggaaaccttgtatacgggttcacttt
atctgggactcatttccctttagaaaatgcaacgactttaaccgcaggcaatcaaattggtttattcagttatgtgtctggtgctgtcgctgaatt
ttcactggtgaattagtagctggttatcaaatcattacaaaaagaaactcatttagcactgctggataatcggacagaactttctatcgctgaa
tatgaagccatgtttgcagaaactttagacacagacattgatcaaacgttagaagatgaattaaaaatatgtatttctgctattaataataccgttc
gttcttatcgaaactaa SEQ ID NO: 19

*E. faecalis* (mvaE)
MKTVVIIDALRTPIGKYKGSLS QVSAVDLGTHVTTQLLKRHSTISEEIDQVIFGNVLQAGNGQNPARQIAINSGLSHEIPAMTVNEVCGSGMKAVILA
KQLIQLGEAEVLIAGGIENMSQAPKLQRFNYETESYDAPFSSMMYDGLTDAFSGQAMGLTAENVAEKYHVTREEQDQFSVHSQLKAAQAQAEGIFADEI
APLEVSGTLVEKDEGIRPNSSVEKLGTLKTVFKEDGTVTAGNASTINDGASALIIASQEYAEAHGLPYLAIIRDSVEVGIDPAYMGISPIKAIQKLLARN
QLTTEEIDLYEINEAFAATSIVVQRELALPEEKVNIYGGGISLGHAIGATGARLLTSLSYQLNQKEKKYGVASLCIGGGLGLAMLLERPQQKKNSRFYQM
SPEERLASLLNEGQISADTKKEFENTALSSQIANHMIENQISETEVPMGVGLHLTVDETDYLVPMATEEPSVIAALSNGAKIAQGFKTVNQQRLMRGQI
VPFYDVADPESLIDKLQVREAEVFQQAELSYPSIVKRGGGLRDLQYRTFDESFVSVDPLVDVKDAMGANIVNAMLEGVAELFREWFAEQKILFSILSNY
ATESVVTMKTAIPVSRLSKGSNGREIAEKIVLASRYASLDPYRAVTHNKGIMNGIEAVVLATGNDTRAVSASCHAFAVKEGRYQGLTSWTLDGEQL
IGEISVPLALATVGGATKVLPKSQAADDLLAVTDAKELSRVVAAVGLAQNLAALRALVSEGIQKGHMALQARSLAMTVGATGKEVEAVAQQLKRQ
KTMNQDRAMAILNDLRKQ SEQ ID NO: 20

SEQUENCES

*E. faecalis* (mvaS)
MTIGIDKISFFVPPYYIDMTALAEEARNVDPGKFHIGIGQDQMAVNPISQDIVTFAANAAEAILTKEDKEAIDMVIVGTESSIDESKAAAVVLHRLMG
IQPFARSFEIKEACYGATAGLQLAKNHVALHPDKKVLVVAADIAKYGLNSGGEPTQGAGAVAMLVASEPRILALKEDNVMLTQDIYDFWRPTGHPYPM
VDGPLSNETYIQSFAQVWDEHKKRTGLDFADYDALAFHIPYTKMGKKALLAKISDQTEAEQERILARYEESIVYSRRVGNLYTGSLYLGLISLLENATTL
TAGNQIGLFSYGSGAVAEFFTGELVAGYQNHLQKETHLALLDNRTELSIAEYEAMFAETLDTDIDQTLEDELKYSISAINNTVRSYRN
SEQ ID NO: 21

MEA P. alba Isoprene synthase
atggaagctcgtcgttctgcgaactacgaacctaacagctgggactatgattacctgctgtcctccgacacggacgagtccatcgaagtata
caaagacaaagcgaaaaagctggaagccgaagttcgtcgcgagattaataacgaaaagcagaatttctgaccctgctggaactgattga
caacgtccagcgcctgggcctgggttaccgtttcgagtctgatatccgtggtgcgctggatcgcttcgtttcctccggcggcttcgatgcggt
aaccaagacttccctgcacggtacggcactgtctttccgtctgctgcgtcaacacggttttgaggtttctcaggaagcgttcagcggcttcaaa
gaccaaaacggcaacttcctggagaacctgaaggaagatatcaaagctatcctgagcctgtacgaggcagttcctggctctggaaggc
gaaaacatcctggacgaggcgaaggttttcgcaatctctcatctgaaagaactgtctgaagaaaagatcggtaaagagctggcagaacag
gtgaaccatgcactggaactgccactgcacgcctactcacgtactacggtatggtctatcgaggctaccgtaaaaaggaggac
gcgaatcaggttctgctggagctggcaattctggattacaacatgatccagtctgtataccagcgtgatctgcgtgaaacgtcccgttggtgg
cgtcgtgtgggtctggccgaccaaactgcactttgctcgtgaccgcctgattgagagcttctactgggccgtgggtgtagcattcgaaccgca
atactccgactgccgtaactccgtcgcaaaatgttttcttcgtaaccattatcgacgatatctacgatgtatacggcaccctggacgaactgg
agctgttactgatgcagttgagcgtgggacgtaaacgccatcaacgctgccggatttacatgaaactgtgcttttctggctctgtataacac
tattaacgaaatcgcctacgacaaacctgaaagataaaggtgagaacatcctgccgtatctgaccaaagctgggctgacctgtgcaacgctt
tcctgcaagaagccaagtggctgtacaacaaatctactccgaccttgacgactacttcggcaacgcatggaaatcctcttctggcccgctgc
aactggtgttcgcttacttcgctgtcgtcagaacattaaaaagaagagatcgaaaaactgcaaaaataccatgacaccatctctcgtcctc
ccatatcttccgtctgtgcaatgaccggctagcgcgtctgcggaaattgcgcgtggtgaaacgcaaatagcgtttcttgttacatgcgcact
aaaggtatctccgaagaactggctaccgaaagcgtgatgaatctgatcgatgaaacctggaaaaagatgaacaaggaaaaactgggtggt
agcctgttcgcgaaaccgttcgtgaaaccgcgatcaacctggcacgtcaatctcactgcacttatcataacggcgacgcgcataccctctcc
ggatgagctgacccgcaaacgcgttctgtctgtaatcactgaaccgattctgccgtttgaacgctaa SEQ ID NO: 22 ispA
tggactttccgcagcaactcgaagcctgcgttaagcaggccaaccaggcgctgagccgttttatcgccccactgcccttcagaacactccc
gtggtcgaaaccatgcagtatggcgcattattaggtggtaagcgcctgcgacctttcctggtttatgccaccggtcatatgtttggcgttagca
caaacacgctggacgccaccgctgctgccgtagagtgtatccacgcttactcattaatcatgatgatttaccggcgatggatgatgacgatc
tgcgccgcgctttgccgaccgccatgtgaagtttggcgaagcaaacgcgattctcgctggcgacgctttacaaacgctggcgttctcgatt
ctaagcgatgccgatatgccggaagtgtcggatcgcgacagaatttcgatgatttctgaactggcgagcgccagcggtattgccggaatgt
gcggtggtcaggcactagatttagacgcggaaggcaaacacgtacctctggacgcgcttgagcgtattcatcgtcataaaaccggcgcatt
gattcgcgccgccgttcgccttggtgcattaagcgccggagataaagggcgtcgtgctctgccagtactcgacaagtacgcagagagcat
cggccttgccttccaggttcaagatgacatcctggatgtggtaggagatactgcaagtctgggaaaacgccagggtgccgaccagcaactt
ggtaaaagtacctacctgcacttctgggtcttgagcaagccccggaaagaagccccgggatctgatcgacgatgccgtcagtcgctgaaa
caactggctgaacagtcactcgataccctcggcactggaagcgctagcggactacatcatcagcgtaataaataa SEQ ID NO: 23

MEA P. alba isoprene synthase
MEARRSANYEPNSWDYDYLLSSDTDESIEVYKDKAKKLEAEVRREINNEKAEFLTLLELIDNVQRLGLGYRFESDIRGALDRFVSSGGFDAVTKTSLHG
TALSFRLLRQHGFEVSQEAFSGFKDQNGNFLENLKEDIKAILSLYEASFLALEGENILDEAKVFAISHLKELSEEKIGKELAEQVNHALELPLHRRTQR DVYGTLDELELFTDAVERWDVNAINDLPDYMKLCFLALYNTINEIAYDNLKDKGENILPYLTKAWADLCNAFLQEAKWLYNKSTPTFDDYFGNAWKS
SSGPLQLVFAYFAVVQNIKKEEIENLQKYHDTISRPSHIFRLCNDLASASAEIARGETANSVSCYMRTKGISEELATESVMNLIDETWKKMNKEKLGGSL
FAKPFVETAINLARQSHCTYHNGDAHTSPDELTRKRVLSVITEPILPFER SEQ ID NO: 24

Amorphadiene synthase codon-optimized for *E. coli*
ATGAGCCTGACCGAAGAAAAACCGATTCGTCCGATTGCAAATTTTCCGCCTAGCATTTGGGGTGATCAGTTTCTGATTTATGAGAAACAGGTTGAA
CAGGGCGTTGAGCAGATTGTTAATGATCTGAAAAAAGAAGTTCGCCAGCTGCTGAAAGAAGCACTGGATATTCCGATGAAACATGCCAATCTGCTGA
AACTGATTGATGAAATTCAGCGTCTGGGTATCCCGTATCATTTTGAACGTGAAATTGATCATGCCCTGCAGTGCATTTATGAAACCTATGGTGATAAT
TGGAATGGTGATCGTAGCAGCCTGTGGTTTCGTCTGCTGCGTCAAAGCGGGTTATTATGTTAACAACTATAAAGATAAAAACGGTG
CCTTTAAACAGAGCCTGGCAAATGATGTTGAAGGTCTGCTGGAACTGTATGAAGCAACCAGCATGCGTGTTCCGGGTGAAATTATTCTGGAAGATGCAC
TGGGTTTTACCCGTAGCCGTCTGAGCATGATGACCAAAGATGCATTTAGCACCAATCCGGCACTGTTTACCGAAATCCAGCGTGCACTGAAACAGCCGC
TGTGGAAACGTCTGCCTCGTATTGAAGCAGCACAGTATATTCCGTTTTATCAGCAGCAGGATAGCCATAACAAAACCCTGCTGAAACTGGCAAAACTGGA
ATTTAATCTGCTGCAGAGCCTGCATAAAGAAGAACTGAGCCACGTCTTTGAAATGGTGGAAAGCCTTCGACATCAAAAAAAACGCACCGTGTCTGCGTGAT
CGTATTGTTGAATGTTATTTTTGGGGTCTGGGTAGCGGTTTTGAACCGCAGTATAGCCTGAAATCTTTACCGAAGCGTTGGTGCACGTGTGTTTTTA
CCAAAGCAGTTGCAGTTATTACCCTGATCGATGATACCTATGACGCATATGGCACCTATGAGGAACAACGTTGGAGCATTACCTGTCTGGATACCCTGCC
GGAATATATGAAACCGATCTATAAACTGTTCATGGACACCTATACCGAGATGGAAGAATTTCTGGCAAAAGAAGGTCGTACCGACCTGTTTAATTGCGGT
AAGAAATTTGTGAAGAATTCGTGCGTAACCTGATGGTTGAAGCAAATGGGCCAATGAAGGTCATATTCCGACCACCGAAGACATGATCCGGTTGTGA
TTATTACCGGTGGTGCAAACCTGCTGACCACCACCTGTTATCTGGGTATGAGCGATATTTTCACCAAAGAAAGCGTTGAATGGGCAGTTAGCGCACCGCC
TCTGTTTCGTTATAGCGGTATTCTGGGTCGTCGTCTGAACGATCTGATGACCCATAAAGCAGAACAAGAACGTAAACATAGCAGCAGCAGCCTGGAAAGC
TATATGAAAGAATATAACGTGAACGAAGAGTATGCACAGACCCTGATTTACAAAGAAGTTGAGGACGTTTGGAAAGATATCAACCGTGAATATCTGACCA
CGAAAACATTCCGCGTTCCGCTGCTGATGGCAGTTATTTATCTGTGTCAGTTCCTGGAAGTTCAGTATGCAGGTAAAGATAACTTTA
CGCGTATGGGCGACGAATATAAACATCTGATTAAAAGCCTGCTGGTGTATCCGATGAGCATTTAA SEQ ID NO: 25

Farnesene synthase codon-optimized for *E. coli*
ATGAGCACCCTGCCGATTAGCAGCGTTAGCTTTAGCAGCAGCACCAGTCCGCTGGTTGTTGATGATAAAGTTAGCACCAAACCGGATGTTATTCGTCACA CCATGAACTTTAATGCAAGCATTTGGGGTGATCAGTTTCTGACCTATGATGAACCGGAAGATCTGGTGATGAAAAACAGCTGGTTGAAGAACTGAAAGA AGAAGTTAAAAAAGCTGATCACCGAATCAAAGGTAGCAATGAACCGATGCAGCATGTTAAACTGATTGAACTGATCGATGCCGTTCAGCGTCTGGGTATT GCATATCATTTTGAAGAAGAAATCGAAGAAGCCCTGCAGCATATTCATGTTACCTATGGTGAACAGTGGGGTGATAAAGAAAATCTGCAGAGCATTAGCC TGTGGTTTCGTCTGCTGCGTCAGCAGGGTTTTAATGTTAGCAGCGGTGTGTTTAAAGATTTTATGGACGAGAAAGGCAAATTCAAAGAAGCCTGTGTAA

| SEQUENCES |
| --- |
| TGATGCACAGGGTATTCTGGCACTGTATGAAGCAGCATTTATGCGTGTTGAAGATGAAACCATTCTGGATAATGCACTGGAATTTACCAAAGTGCACCTG<br>GATATCATTGCAAAAGATCCGAGCTGTGATAGCAGCCTGCGTACCCAGATTCATCAGGCACTGAAACAGCCGCTGCGTCGTCGTCTGGCACGCATTGAAG<br>CACTGCATTATATGCCGATTTATCAGCAAGAAACCAGCCATAATGAAGATCTGCTGAAACTGGCAAAACTGGATTTTAGCGTTCTGCAGTCCATGCACAA<br>AAAAGAACTGAGCCATATTTGTAAATGGTGGAAAGATCTGGATCTGCAGAATAAACTGCCGTATGTTCGTGATCGTGTTGTGGAAGGTTATTTTTGGATT<br>CTGAGCATCTATTATGAACCGCAGCATGCACGTACCCGTATGTTTCTGATGAAAACCTGTATGTGGCTGGTTGTGCTGGATGATACGTTTGATAATTATG<br>GCACCTACGAGGAACTGGAAATCTTTACCCAGGCAGTTGAACGTTGGAGCATTAGTTGTCTGGATATGCTGCCGGAATACATGAAACTGATTTATCAAGA<br>ACTGGTGAACCTGCACGTTGAAATGGAAGAAAGTCTGGGCAAAGGTGGTAAAAACATTAGCAATAGTCTGTGTCAGGGTCGTTGGCAGAAGAACTGGGT<br>AGTCAGATTACCCTGGTTGAAACCAAAATGGCAAAACGTGGTGTTCATGCCCAGCCGCTGGAAGAGTATATGAGCGTTAGCATGGTTACCGGCACCTATG<br>GTCTGATGATTGCACGTAGCTATGTTGGTCGTGGTGATATTGTTACCGAAGATACCTTTAAATGGGTGAGCAGCTATCCGCCTATTATCAAAGCAAGCTG<br>TGTTATTGTTCGCCTGATGGATGATATTGTGAGCCACAAAGAAGAACAAGAACGCGGTCATGTTGCCAGCAGCATTGAATGTTATAGCAAAGAAAGTGGT<br>GCAAGCGAAGAAGAAGCCTGCGAATATATCGCGTAAAGTGGAAGATGCCTGGAAAGTTATTAATCGTGAAAGCCTGCGTCCGACCGCAGTTCCGTTTC<br>CGCTGCTGATGCCTGCAATTAACCTGGCACGTATGTGTGAAGTTCTGTATAGCGTTAATGATGGTTTTACCCATGCCGAAGGTGATATGAAATCCTATAT<br>GAAAAGCTTCTTCGTGCATCCGATGGTTGTTTAA SEQ ID NO: 26 | pMCM1225 - pCL-Ptrc-Upper_GcMM_163 (*Enterococcus gallinarum* EG2)
cccgtcttactgtcgggaattcgcgttggccgattcattaatgcagattctgaaatgagctgttgacaattaatcatccggctcgtataatgtgtg
gaattgtgagcggataacaatttcacacaggaaacagccgccgctgagaaaaagcgaagcggcactgctctttaacaatttatcagacaatct
gtgtgggcactcgaccggaattatcgattaacttttattattaaaaattaaagaggtatatattaatgtatcgattaaataaggaggaataaaccat
ggaagaagtggtaattatagatgcacgtcggactccgattggtaaatatcacgggtcgttgaagaagttttcagcggtggcgctgggacg
gccgtggctaaagacatgttcgaacgcaaccagaaaatcaaagaggagatcgcgcaggtcataattggtaatgtcttgcaggcaggaaat
ggccagaaccccgcgcggcaagttgctcttcaatcagggttgtccgttgacattcccgcttctacaattaacgaggtttgtgggtctggtttga
aagctatcttgatgggcatggaacaaatccaactcggcaaagcgcaagtagtgctggcaggcggcattgaatcaatgacaaatgcgccaa
gcctgtcccactataacaaggcggaggatacgtatagtgtcccagtgtcgagcatgacactggatggtctgacagacgcatttctagtaaa
cctatgggattaacagcggaaaacgtcgcacagcgctacggtatctcccgtgaggcgaagatcaattcgcatatcaattctcagatgaaag
cagcaaaagcgcaggcagaaaacaaattcgctaaggaaattgtgccactggcgggtgaaactaaaaccatcacagctgacgaagggatc
agatcccaaacaacgatggagaaactggcaagtctcaaacctgttttaaaaccgatggcactgtaaccgcaggggatgctagcaccatta
atgacggggccgccttgtgctgcttgctagcaaaacttactgcgaaactaatgacataccgtaccttgcgacaatcaaagaaattgttgaag
ttggaatcgatccggagattatgggcatctctccgataaaaagcagatacaaacattgttacaaaatcaaaaagttagcctcgaagatattggagt
ttttgaaataaatgaagccttttgccgcaagtgcatagtggttgaatctgagttgggattagatccggctaaagttaaccgttatgggggtggt
atatccttaggtcatgcaattggggcaaccggcgctcgcctggccacttcactggtgtatcaaatgcaggagatacaagcacgttatggtatt
gcgagcctgtgcgttggtggtggacttggactggcaatgcttttagaacgtccaactattgagaggctaaaccgacagacaaaagttcta
tgaattgtcaccagctgaacggttgcaaggctggaaatcaacagaaatcagttctgaaactaaacagcagttatctcagatgatgcttgc
cgaggacactgcaaaccatttgataagaaaatcaaatatcagagattgaactcccaatgggcgtcgggatgaactcgaaggttgatgggaaa
gcctatgttgtgccaatggcgacggaagagccgtccgtcatcgcggccatgtctaatggtgccaaaatggccggcgaaattcacactcagt
cgaaagaacggctgctcagaggtcagattgttttcagcgcgaagaatccgaatgaaatcgaacagagaatagctgagaaccaagctttgat
tttcgaacgtgccgaacagtcctatccttccattgtgaaaagagagggaggtctccgccgcattgcacttcgtcattttcctgccgattctcagc
aggagtctgcggaccagtccacattttatcagtggaccttttgtagtcggcgcactagggggcaaatatcataaatgcaatacttga
gggcgtcgcagccctgtttcgcgaatggttccccaatgaggaaattcttttttctattctctcgaacttggctacggagagcttagtcacggctg
tttgtgaagtcccatttagtgcacttagcaagagaggtggtgcaacggtggcccagaaaattgtgcaggcgtcgctcttcgcaaagacagac
ccataccgcgcagtgacccacaacaaagggattatgaacggtgtagaggctgttatgcttgccacaggcaacgacacgcgcgcagtctca
gccgcttgtcatggatacgcagcgcgcaccggtagctatcaggtctgactaactggacgattgagctggacgatgcctggtaggcgagata
acactgccgctggccatcgctacagttggaggcgctaccaaagtgttgcccaaagctcaagcggcactggagattagtgatgttcactcttc
tcaagagcttgcagcctagcggcgtcagtaggtttagtacaaaatctcgcggccctgcgcgcactggtttccgaaggtatacaaaaaggg
cacatgtccatgcaagcccggtctctcgcaatcgcggtcggtgctgaaaaagccgagatcgagcaggtcgccgaaaagttgcggcagaa
cccgccaatgaatcagcagcaggcgctccgtttttcttggcgagatccgcaacaatgatctagacgcactaggaggatataccaatgaacg
tcggcattgacaaaatttaatttttttcgttccaccgtattatctggatatggtcgacctggcccacgcacgcgaagtggacccgaacaaatttac
aattggaattggacaggatcagatggctgtgagcaaaaagacgcacgatatcgtaacattcgcggctagtgccgcgaaggaaattttagaa
cctgaggacttgcaagctatagacatggttatagttggtaccgaatcgggcattgacgagagcaaagcatccgcggtcgttttacatcgtttgt
tgggcgtacaaccttttcgctcgcagttttttgaaattaaagaaagctgttaccggggcaaccgcaggcattcagtttgccaagactcatatacaag
cgaaccccggagagcaaggtcctggtaattgcaagcgatatagctcggtatggtcttcggtcaggtggagagcccacacaaggcgcaggg
gcagttgctatgcttctcacggcaaatcccagaatcctgaccttcgaaaacgacaatctgatgttaacgcaggatatttatgacttctggagac
cacttggtcacgcttacccatggtagatggccacctttccaatcaagtctatattgacagttttaaggaggtctggcaagcacattgcgaacg
caatcaagcttctatatccgactatgcgcgattagttttcatattccgtatacaaaaatgggtaagaaagccgtgctgctgttttttgcagatga
agtggaaactgaacaggaacgcgttatggcacgtatgaagagtctatcgtatattcacgccggatcggcaacttgtatacgggatcattgt
acctggggctgatatccttattggaaaacagttctcacctgtcggcgggcgaccggataggattgttagttatgggagtgcgctgtcagcg
aatttttctccggtcgtttagtggcaggctatgaaaatcaattgaacaaagaggcgcataccagctcctggatcagcgtcagaagcttccat
cgaagagtatgaggcgatttttacagattccttagaaattgatcaggatgcagcgttctcggatgacctgccatattccatccgcgagataaaa
aacacgattcggtactataaggagagctgactgcagctgtaccatatgggaattcgaagcttgggcccgaacaaaactcatctcagaag
aggatctgaatagcgccgtcgaccatcatcatcatcatcattgagtttaaacggtctccagcttggctgttttggcggatgagaagattttca
gcctgatacagattaaatcagaacgcagaagcggtctgataaaacagaatttgcctggcggcagtagcgcggtggtcccacctgaccccca
tgccgaactcagaagtgaaacgccgtagcgccgatggtagtgtggggtctccccatgcgagagtagggaactgccaggcatcaaataaa
acgaaaggctcagtcgaaagactgggcctttcgttttatctgttgtttgtcggtgaacgctctcctgagtaggacaaatccgccgggagcgga
tttgaacgttgcgaagcaacggcccggagggtggcgggcaggacgcccgccataaactgccaggcatcaaattaagcagaaggccatc
ctgacggatggcctttttgcgtttctacaaactcttttgtttatttttctaaatacattcaaatatgtatccgctcatgagacaataaccctgataaa
tgcttcaataatctggcgtaatagcgaagaggcccgcaccgatcgcccttcccaacagttgcgcagcctgaatggcgaatggcgcctgatg
cggtattttctccttacgcatctgtgcggtatttcacaccgcatatggtgcactctcagtacaatctgctctgatgccgcatagttaagcagccc
cgacacccgccaacacccgctgacgagcttagtaaagccctcgctagattttaatgcggatgttgcgattacttcgccaactattgcgataac
aagaaaaagccagcctttcatgatatatctcccaatttgtgtagggcttattatgcacgcttaaaaataataaaagcagacttgacctgatagttt
ggctgtgagcaattatgtgcttagtgcatctaacgcttgagttaagccgcgccgcgaagcggcgtcggcttgaacgaattgttagacattattt
gccgactaccttggtgatctcgcctttcacgtagtggacaaattcttccaactgatctgcgcgcgaggccaagcgatcttcttcttgtccaagat
aagcctgtctagcttcaagtatgacgggctgatactgggccggcaggcgctccattgcccagtcggcagcgacatccttcggcgcgattt
gccggttactgcgctgtaccaaatgcgggacaacgtaagcactacatttcgctcgcgccccagtcgggcggcgacatgccttcatagcgtt
aaggtttcatttagcgcctcaaatagatcctgttcaggaaccggatcaaagagttcctccgccgctggacctaccaaggcaacgctatgttct
cttgcttttgtcagcaagatagccagatcaatgtcgatcgtggctggctcgaagatacctgcaagaatgtcattgcgctgccattctccaaatt
gcagttcgcgcttagctggataacgccacggaatgatgtcgtcgtgcacaacaatggtgacttctacagcgcggagaatctcgctctctcca
ggggaagccgaagtttccaaaaggtcgttgatcaaagctcgccgcgttgtttcatcaagccttacggtcaccgtaaccagcaaatcaatatc
actgtgtggcttcaggccgccatccactgcggagccgtacaaatgtacggccagcaacgtcggttcgagatggcgctcgatgacgccaac -continued

SEQUENCES

```
tacctctgatagttgagtcgatacttcggcgatcaccgcttccctcatgatgtttaactttgttttagggcgactgccctgctgcgtaacatcgttg
ctgctccataacatcaaacatcgacccacggcgtaacgcgcttgctgcttggatgcccgaggcatagactgtacccaaaaaaacagtcat
aacaagccatgaaaaccgccactgcgccgttaccaccgctgcgttcggtcaagttctggaccagttgcgtgagcgcatacgctacttgca
ttacagettacgaaccgaacaggettatgtccactgggttcgtgccttcatccgtttccacggtgtgcgtcaccccggcaaccttgggcagcag
cgaagtcgaggcatttctgtcctggctggcgaacgagcgcaaggtttcggtctccacgcatcgtcaggcattggcggccttgctgttcttcta
cggcaaggtgctgtgcacggatctgccctggcttcaggagatcggaagacctcggccgtcgcggcgcttgccggtggtgctgaccccgg
atgaagtggttcgcatcctcggttttctggaaggcgagcatcgtttgttcgcccagcttctgtatggaacgggcatgcggatcagtgagggttt
gcaactgcgggtcaaggatctggattttcgatcacggcacgatcatcgtgcgggagggcaaggctccaaggatcgggccttgatgttacc
cgagagctggcacccagcctgcgcgagcagggaattaattccccacgggttttgctgcccgcaaacgggctgttctggtgttgctagtttg
ttatcagaatcgcagatccggcttcagccggtttgccggctgaaagcgctattctccagaattgccatgattttttccccacgggaggcgtc
actggctcccgtgttgtcggcagctttgattcgataagcagcatcgcctgtttcaggctgtctatgtgtgactgttgagctgtaacaagttgtctc
aggtgttcaatttcatgttcagttgctttgttttactggtttcacctgttcattaggtgttacatgctgttcatctgttcattgtcgatctgttca
tggtgaacagctttgaatgcaccaaaaactcgtaaaagctctgatgtatctatctttttacaccgttttcatctgtgcatatggacagttttcccttt
gatatgtaacggtgaacagttgttctacttttgtttgttagtcttgatgcttcactgatagatcaagagccataagaacctcagatcctccgtattt
agccagtatgttctctagtgtggttcgttgttttttgcgtgagccatgagaacgaaccattgagatcatacttactttgcatgtcactcaaaaattttgcc
tcaaaactggtgagctgaatttttgcagttaaagcatcgtgatggtgttttttcttagtccgttatgtaggtaggaatctgatgtaatggttgttggtattt
tgtcaccattcattttttatctggttgttctcaagttcggttacgagatccatttgtctatctagttcaacttggaaaatcaacgtatcagtcgggcgg
cctgcttatcaaccaccaatttcatattgctgtaagtgtttaaatcttttacttattggtttcaaaacccattggttaagccttttaaactcatggtagt
tattttcaagcattaacatgaacttaaattcatcaaggctaatctctatatttgccttgtgagttttctttttgtgttagttcttttaataaccactcata
aatcctcatagagtatttgttttcaaaagacttaacatgttccagatttatatttttatgaattttttaactggaaaagataaggcaatatctcttcacta
aaaactaattctaattttttcgcttgagaacttgcatagtttgtccactggaaaatctcaaagccttaaccaaaggattcctgatttccacagttctcg
tcatcagctctctggttgctttagctaatacaccataagcattttccctactgatgttcatcatctgagcgtattggttataagtgaacgataccgtc
cgttcttttccttgtagggttttcaatcgtggggttgagtagtgccacacagcataaaattagcttggtttcatgctccgttaagtcatagcgactaa
tcgctagttcatttgctttgaaaacaactaattcagacatacatctcaattggtctaggtgattttaatcactatacccaattggaagtgggctagtca
atgataattactagtccttttccttttgagttgtgggtatctgtaaattctgctagaccttttgctggaaaacttgtaaattctgctagaccctctgtaaa
ttccgctagacctttgtgtgttttttttgtttatattcaagtggttataatttatagaataaaagaaagaataaaaaagataaaagaatagatccca
gccctgtgtataactcactactttagtcagttccgcagtattacaaaaggatgtcgcaaacgctgtttgctcctctacaaaacagaccttaaaac
cctaaaggcttaagtagcacctcgcaagctcgggcaaatcgctgaatattccttttgtcctccgaccatcaggcacctgagtcgctgtcttttc
gtgacattcagttcgctgcgctcacggctctggcagtgaatggggtaaatgcactacaggcgcctttatggattcatgcaaggaaacta
cccataatacaagaaaagcccgtcacgggcttctcagggcgttttatggcgggtctgctatgtggtgctatctgacttttttgctgttcagcagtt
cctgccctctgattttccagtctgaccacttcggattatcccgtgacaggtcattcgactggctaatgcacccagtaaggcagcgggtatcatc
aacaggctta SEQ ID NO: 27
```

Amino acid sequence for phosphoketolase from Mycoplasma hominis ATCC 23114
MISKIYDDKKYLEKMDKWFRAANYLGVCQMYLRDNPLLKKPLTSNDIKLYPIGHWGTVPGQNFIYTHLNRVIKKYDLNMFYIEGPGHGGQVMISNSYLDG
SYSEIYPEISQDEAGLAKMFKRFSFPGGTASHAAPETPGSIHEGGELGYSISHGTGAILDNPDVICAAVVGDGEAETGPLATSWFSNAFINPVNDGAILP
ILHLNGGKISNPTLLSRKPKEEIKKYFEGLGWNPIFVEWSEDKSNLDMHELMAKSLDKAIESIKEIQAEARKKPAEEATRPTWPMIVLRTPKGWTGPKQW
NNEAIEGSFRAHQVPIPVSAFKMEKIADLEKWLKSYKPEELFDENGTIIKEIRDLAPEGLKRMAVNPITNGGIDSKPLKLQDWKKYALKIDYPGEIKAQD
MAEMKAFAADIMKDNPSSFRVFGPDETKSNRMFALFNVTNRQWLEPVSKKYDEWISPAGRIIDSQLSEHQCEGFLEGYVLTGRHGFFASYEAFLRVVDSM
LTQHMKWIKKASELSWRKTYPSLNIIATSNAFQQDHNGYTHQDPGLLGHLADKRPEIIREYLPADTNSLLAVMNKALTERNVINLIVASKQPREQFFTVE
DAEELLEKGYKVVPWASNISENEEPDIVFASSGVEPNIESLAAISLINQEYPHLKIRYVYVLDLLKLRSRKIDPRGISDEEFDKVFTKNKPIIFAFHGFE
GLLRDIFFTRSNHNLIAHGYRENGDITTSFDIRQLSEMDRYHIAKDAAEAVYGKDAKAFMNKLDQKLEYHRNYIDEYGYDMPEVVEWKWKNINKEN SEQ
ID NO: 28

Codon optimized DNA sequence for phosphoketolase from Mycoplasma hominis ATCC 23114
```
atgattagcaaaatctatgatgataaaaagtatctggaaaaaatggacaaatggtttcgcgcagcaaattatctgggtgtttgtcagatgtatctg
cgtgataatccgctgctgaaaaaaccgctgaccagcaatgatatcaaactgtatccgattggtcattggggcaccgttccgggtcagaatttt
atctatacccatctgaatcgcgtgatcaagaaatatgatctgaatatgttctacatcgaaggtcctggtcatggtggtcaggttatgattagtaat
agctatctggatggcagctatagcgaaatttatccggaaattagccaggatgaagcaggtctggccaaatgtttaaacgttttagctttccgg
gtggcaccgcaagcatgcagcaccggaaaccaccgggtagcattcatgaaggtggtgaactggttatagcattagcatggcaccggt
gcaattctggataacccggatgttatttgtgcagcagttgttggtgatggtgaagcagaaaccggtccgctggcgaccagctggtttagcaat
gcctttattaacccggttaatgatggtgccattctgccgattctgcatctgaacggtggtaaaattagcaatccgacccgtgagccgtaaac
cgaaagaagaaatcaaaaaatactttgaaggcctgggctggaatccgatttttgttgaatggtcagaagataagagcaacctggatatgcat
gaactgatggcaaaaagcctggataaagccattgaaagcatcaaagaaattcaggcagaagcacgtaaaaaacctgcagaagaagcaac
ccgtccgacctggccgatgattgttctgcgtaccccgaaaggttggacaggtccgaaacagtggaataatgaagcaattgaaggtagctttc
gtgcacatcaggttccgattccggttagcgcctttaaaatggaaaagattgccgatctggaaaaatggctgaaaagctacaaaccggaagaa
ctgtttgatgaaaatggcacgatcataaaagaaatccgtgatctggctccggaaggtctgaaacgtatggcagttaacccgattaccaatggt
ggtattgatagcaaacctctgaaactgcaggattggaaaaagtacgcactgaaaattgatatccggggtgaaattaaagcacaggatatggc
cgaaatggccaaatttgcagcagatatcatgaaagataacccgagcagcttcgcgttttcgtggtccggatgaaaccaaaagcaatcgtatgtt
tgcctgtttaatgtgaccaatcgtcagtggctggaaccggttagtaagaaatacgatgaatggattagtccggcaggtcgcattattgattcac
agctgagcgaacatcagtgtgaaggttttctggaaggttatgttctgaccggtcgtcatggtttttttgcaagctatgaagcatttctgcgtgttgt
ggatagcatgctgacccaacatatgaaatggatcaaaaaggcaagcgaactgagctggcgtaaaacctatccgagcctgaacattattgca
accagtaatgcattttcagcaggatcaataatggttatacgcatcaggatccgggtctgctgggtcatctggcagataaacgtccagaaattatc
cgtgaatatctgcctgcagataccaatagcctgctggcggttatgaataaagcactgaccgaacgtaatgtgattaatctgattgttgcaagca
aacagcctcgcgaacagttttttaccgttgaagatgcagaggaactgctggaaaagggttataaagttgttccgtgggcaagcaatattagc
gaaaatgaagaaccggatattgtgtttgccagcagcggtgttgaaccgaatatcgaagtctggcagcaattagcctgatcaatcaagaata
tcctcatctgaaaatccgctatgtgtatgtgctggatctgctgaagctgcgtagtcgtaaaatcgatccgcgtggtattagtgatgaagagtttg
ataaagtgtttaccaaaaacaaaccgattatcttttgctttcatggctttgagggactgctgcgcgatatttttcaccgtagcaaccataacct
gattgcacatggttatcgtgaaaacggtgatatcacaaccagctttgatattcgtcagctgagtgagatggatcgttatcatattgcaaaagatg
ctgccgaagccgtgtatggtaaagatgcaaaagcatttatgaacaaactggatcagaaactggaataccaccgcaactatatcgatgagtat
ggctatgatatgccggaagttgtggaatgaaatggaagaacatcaataaagaaattaa SEQ ID NO: 29
```

Sequence of pMCS1019
```
gtttgacagcttatcatcgactgcacggtgcaccaatgcttctggcgtcaggcagcagcatcggaagctgtggtatggctgtgcaggtcgtaaat
cactgcataattcgtgtcgctcaaggcgcactcccgttctggataatgttttttgcgccgacatcataacggttctggcaaatattctgaaatga
gctgttgacaattaatcatccggctcgtataatgtgtggaattgtgagcggataacaatttcacacaggaaacagcgccgctgagaaaaagc
gaagcggcactgctctttaacaatttatcagacaatctgtgtgggcactcgaccggaattatcgattaactttattattaaaaattaaagaggtat
atattaatgtatcgattaaataaggaggaataaaccatggaaacgcgtcgttctgcgaactacgaacctaacagctgggactatgattacctg
```

| SEQUENCES |
|---|
| ctgtcctccgacacggacgagtccatcgaagtatacaaagacaaagcgaaaagctggaagccgaagttcgtcgcgagattaataacgaa |
| aaagcagaatttctgaccctgctggaactgattgacaacgtccagcgcctgggcctgggttaccgtttcgagtctgatatccgtggtgcgctg |
| gatcgcttcgtttcctccggcggcttcgatgcggtaaccaagacttccctgcacggtacggcactgtctttccgtctgctgcgtcaacacggtt |
| ttgagggtttctcaggaagcgttcagcggcttcaaagaccaaaacggcaacttcctggagaacctgaaggaagatatcaaagctatcctgag |
| cctgtacgaggccagcttcctggctctggaaggcgaaaacatcctggacgaggcgaaggttttcgcaatctctcatctgaaagaactgtctg |
| aagaaaagatcggtaaagagctggcagaacaggtgaaccatgcactggaactgccactgcatcgccgtactcagcgtctggaagcagtat |
| ggtctatcgaggcctaccgtaaaaaggaggacgcgaatcaggttctgctggagctggcaattctggattacaacatgatccagtctgtatac |
| cagcgtgatctgcgtgaaacgtcccgttggtggcgtcgtgtgggtctggcgaccaaactgcactttgctcgtgaccgcctgattgagagctt |
| ctactgggccgtgggtgtagcattcgaaccgcaatactccgactgccgtaactccgtcgcaaaaatgttttgtttcgtaaccattatcgacgat |
| atctacgatgtatacggcaccctggacgaactggagctgtttactgatgcagttgagcgttgggacgtaaacgccatcaacgacctgccgg |
| attacatgaaactgtgctttctggctctgtataacactattaacgaaatcgcctacgacaacctgaaagataaaggtgagaacatcctgccgta |
| tctgaccaaagcctgggctgacctgtgcaacgctttcctgcaagaagccaagtggctgtacaacaaatctactccgacctttgacgactactt |
| cggcaacgcatggaaatcctcttctgccccgtcgaactggtgttcgcttactcgctgtcgtcagaacattaaaaaggaagagatcgaaa |
| acctgcaaaaataccatgacaccatctctcgtccttcccatatcttccgtctgtgcaatgacctggctagcgcgtctgcggaaattgcgcgtgg |
| tgaaaccgcaaatagcgtttcttgttacatgcgcactaaaggtatctccgaagaactggctaccgaaagcgtgatgaatctgatcgatgaata |
| ttggaaaaaagatgaacaaggaaaaaactgggtggtagcctgttcgcgaaaccgtcgtggaaaccggcgatcaacctggcacgtcaatctca |
| ctgcacttatcataacggcgacgcgcataccctccggatgagctgaccgcaaacgcgttctgtctgtaatcactgaaccgattctgccgttt |
| gaacgctaaagatacgcgtaaccccaaggacggtaaaatgattagcaaaatctatgatgataaaaagtatctggaaaaaatggataaatggt |
| ttcgcgcagcaaattatctgggtgtttgtcagatgtatctgcgtgataatccgctgctgaaaaaaccgctgaccagcaatgatatcaaactgtat |
| ccgattggtcattggggcaccgttccgggtcagaattttatctatacccatctgaatcgcgtgatcaagaaatatgatctgaatatgttctacatc |
| gaaggtcctggtcatggtggtcaggttatgattagtaatagctatctgggatggcagctatagcgaaatttatccggaaattagccaggatgaa |
| gcaggtctggccaaaatgtttaaacgttttagctttccgggtggcaccgcaagccatgcagcaccggaaacaccgggtagcattcatgaag |
| gtggtgaactgggtatagcattagccatggcaccggtgcaattctggataacccggatgtatttgtgcagcagttgttggtgatggtgaagc |
| agaaaccggtccgctggcgaccagctggtttagcaatgcctttattaaacccggttaatgatggtgccattctgccgattctgcatctgaacggt |
| ggtaaaattagcaatccgaccctgctgagccgtaaaccgaaagaagaaatcaaaaaatacttttgaaggcctgggctggaatccgattttgtt |
| gaatggtcagaagataagagcaacctggatatgcatgaactgatggcaaaaagcctggataaagccattgaaagcatcaaagaaattcag |
| gcagaagcacgtaaaaaacctgcagaagaagcaacccgtccgacctggccgatgattgttctgcgtaccccgaaaggttggacaggtcc |
| gaaacagtggaataatgaagcaattgaaggtagctttcgtgcacatcaggttccgattccggttgccgcctttaaaatggaaaagattgccga |
| tcttgagaaatggctgaaaagctacaaaaccggaagaactgtttgatgaaaatggcacgtcataaaagaaatccgtgatctggctccggaa |
| ggtctgaaacgtatggcagttaacccgattaccaatggtggtattgatagcaaacctctgaaactgcaggattgaaaaagtacgcactgaa |
| aattgattatccgggtgaaattaaagcacaggatatggccgaaatggccaaatttgcagcagatatcatgaaagataaccctagcagctttcg |
| cgttttttggtccggatgaaaccaaaagcaatcgtatgtttgccctgtttaatgtgaccaatcgtcagtggctgtggaaccggttagtaagaaatac |
| gatgaatggattagtccggcaggtcgcattattgattcacagctgagcgaacatcagtgtgaaggtttctggaaggttatgttctgaccgggtc |
| gtcatggtttttttgcaagctatgaagcatttctgcgtgttgtggatagcatgctgaccaacatatgaaatggatcaaaaaggcaagcgaact |
| gagctggcgtaaaacctatccgagcctgaacattattgcaaccagtaatgcatttcagcaggatcataatggttatacgcatcaggatccggg |
| tctgctgggtcatctggcagataaacgtccagaaattatccgtgaatatctgcctgcagataccaatagcctgctggcggttatgaataaagc |
| actgaccgaacgtaatgtgattaatctgattgttgcaagcaaacagcctcgcgaaacgctttttttaccgttgaagatgcagaggaactgctgga |
| aaagggttataaagttgttccgtgggcaagcaatattagcgaaaatgaagaaccggatattgtgtttgccagcagcggtgttgaaccgaatat |
| cgaaagtctggcagcaattagcctgatcaatcaagaatatcctcatctgaaaatccgctatgtgtatgtgctggatctgctgaagctgcgtagt |
| cgtaaaatcgatccgcgtggtattagtgatgaagagtttgataaagtgtttaccaaaaacaaaccgattatctttgcctttcatggctttgaggga |
| ctgctgcgcgatatttttcttaccgtagcaaccataaccgattgcacatggttatcgtgaaaacggcttatcgtgaaaacggtgatatcacaaccagctttgatattcgt |
| cagctgagtgagatggatcgttatcatattgcaaaagatgctgccgaagccgtatggtaaagatgcaaaagcatttatgaacaaactggat |
| cagaaactggaataccaccgcaactatatcgatgagtatggctatgatatgccggaagttgtggaatggaaatgaagaacatcaataaag |
| aaaattaaagtctagttaaagtttaaacggtctccagcttggctgtttggcggatgagagaagattttcagcctgatacagattaaatcagaac |
| gcagaagcggtctgataaaacgaaatttgcctggcggcagtagcgcggtggtcccacctgaccccatgccgaactcagaagtgaaacgc |
| cgtagcgccgatggtagtgtggggtctccccatgcgagagtagggaactgccaggcatcaaatcaaaacgaaaggctcagtcgaaagact |
| gggcctttcgttttatctgttgtttgtcggtgaacgctctcctgagtaggacaaatccgccgggagcggatttgaacgttgcgaagcaacggc |
| ccggagggtggcgggcaggacgcccgccataaactgccaggcatcaaattaagcagaaggccatcctgacggatggcctttttgcgtttc |
| tacaaactcttttgttatttttctaaatacattcaaatatgtatccgctcatgagacaataaccctgataaatgcttcaataatattgaaaaaggaa |
| gagtatgagtattcaacatttccgtgtcgcccttattccctttttgcggcattttgccttcctgtttttgctcacccagaaacgctggtgaaagtaa |
| aagatgctgaagatcagttgggtgcacgagtgggttacatcgaactggatctcaacagcggtaagatccttgagagttttcgccccgaagaa |
| cgttttccaatgatgagcacttttaaagttctgctatgtggcgcggtattatcccgtgttgacgccgggcaagagcaactcggtcgccgcatac |
| actattctcagaatgacttggttgagtactcaccagtcacagaaaagcatcttacggatggcatgacagtaagagaattatgcagtgctgcca |
| taaccatgagtgataacactgcggccaacttacttctgacaacgatcggaggaccgaaggagctaaccgcttttttgcacaacatgggggat |
| catgtaactcgccttgatcgttgggaaccggagctgaatgaagccataccaaacgacgagcgtgacaccacgatgcctgtagcaatggca |
| acaacgttgcgcaaactattaactggcgaactacttactctagcttcccggcaacaattaatagactggatggaggcggataaagttgcagg |
| accacttctgcgctcggcccttccggctggctggtttattgctgataaatctggagccggtgagcgtgggtctcgcggtatcattgcagcact |
| ggggccagatggtaagccctcccgtatcgtagttatctacacgacggggagtcaggcaactatggatgaacgaaatagacagatcgctga |
| gataggtgcctcactgattaagcattggtaactgtcagaccaagtttactcatatatactttagattgatttaaaacttcatttttaatttaaaaggat |
| ctaggtgaagatcctttttgataatctcatgaccaaaatcccttaacgtgagttttcgttccactgagcgtcagaccccgtagaaaagatcaaag |
| gatcttcttgagatcctttttttctgcgcgtaatctgctgcttgcaaacaaaaaaaccaccgctaccagcggtggtttgtttgccggatcaagag |
| ctaccaactctttttccgaaggtaactggcttcagcagagcgcagataccaaatactgtccttctagtgtagccgtagttaggccaccacttca |
| agaactctgtagcaccgcctacatacctcgctctgctaatcctgttaccagtggctgctgccagtggcgataagtcgtgtcttaccgggttgg |
| actcaagacgatagttaccggataaggcgcagcggtcgggctgaacggggggttcgtgcacacagcccagcttggagcgaacgaccta |
| caccgaactgagatacctacagcgtgagctatgagaaagcgccacgcttcccgaagggagaaaggcggacaggtatccggtaagcggc |
| agggtcggaacaggagagcgcacgagggagcttccagggggaaacgcctggtatctttatagtcctgtcgggtttcgccacctctgacttg |
| agcgtcgatttttgtgatgctcgtcaggggggcggagcctatggaaaaacgccagcaacgcggcctttttacggttcctggccttttgctggc |
| cttttgctcacatgttctttcctgcgttatcccctgattctgtggataaccgtattaccgcctttgagtgagctgataccgctcgccgcagccga |
| acgaccgagcgcagcgagtcagtgagcgaggaagcggaagagcgcctgatgcggtattttctccttacgcatctgtgcggtatttcacaccg |
| catatggtgcactctcagtacaatctgctctgatgccgcatagttaagccagtatacactccgctatcgctacgtgactgggtcatggctgcgc |
| cccgacacccgccaacacccgctgacgcgccctgacgggcttgtctgctcccggcatccgcttacagacaagctgtgaccgtctccggg |
| agctgcatgtgtcagaggttttcaccgtcatcaccgaaacgcgcgaggcagctgcggtaaagctcatcagcgtggtcgtgaagcgattcac |
| agatgtctgcctgttcatccgcgtccagctcgttgagtttctccagaagcgttaatgtctggcttctgataaagcgggccatgttaagggcggt |
| tttttcctgtttggtcactgatgcctccgtgtaagggggatttctgttcatgggggtaatgataccgatgaaacgagagaggatgctcacgat |
| acgtgtgacaccatcgaatggtgcaaaacctttcgcggtatggcatgatagcgcccggaagagagtcaattcagggtggtgaatgtgaaacc |
| agtaacgttatacgatgtcgcagagtatgccggtgtctcttatcagaccgtttcccgcgtggtgaaccaggccagccacgtttctgcgaaaac |
| gcgggaaaaagtggaagcggcgatggcggagctgaattacattcccaaccgcgtggcacaacaactggcgggcaaacagtcgttgctg |
| attggcgttgccacctccagtctggccctgcacgcgccgtcgcaaattgtcgcggcgattaaatctcgcgccgatcaactgggtgccagcg |
| tggtggtgtcgatggtagaacgaagcggcgtcgaagcctgtaaagcggcggtgcacaatcttctcgcgcaacgcgtcagtgggctgatca |

-continued

SEQUENCES ttaactatccgctggatgaccaggatgccattgctgtggaagctgcctgcactaatgttccggcgttatttcttgatgtctctgaccagacaccc
atcaacagtattattttctcccatgaagacggtacgcgactgggcgtggagcatctggtcgcattgggtcaccagcaaatcgcgctgttagc
gggcccttaagttctgtctcggcgcgtctgcgtctggctggctggcataaatatctcactcgcaatcaaattcagccgatagcggaacggg
aaggcgactggagtgccatgtccggttttcaacaaaccatgcaaatgctgaatgagggcatcgttcccactgcgatgctggttgccaacgat
cagatgcgctgggcgcaatgcgcgccattaccgagtccgggctgcgcgttggtgcggatatctcggtagtgggatacgacgataccga
agacagctcatgttatatcccgccgtcaaccaccatcaaacaggattttcgcctgctggggcaaaccagcgtggaccgcttgctgcaactct
ctcagggccaggcggtgaagggcaatcagctgttgcccgtctcactggtgaaaagaaaaaccaccctggcgcccaatacgcaaaccgcc
tctccccgcgcgttggccgattcattaatgcagctggcacgacaggtttcccgactggaaagcgggcagtgagcgcaacgcaattaatgtg
agttagcgcgaattgatcctg SEQ ID NO: 30

DNA sequence of plasmid pMCS826
gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatga
gctgttgacaattaatcatccggctcgtataatgtgtggaattgtgagcggataacaatttcacacaggaaacagcgccgctgagaaaaagc
gaagcggcactgctcttaacaatttatcagacaatctgtgtgggcactcgaccggaattatcgattaactttattattaaaaattaaagaggtat
atattaatgtatcgattaaataaggaggaataaaccatggaaacgcgtcgttctgcgaactacgaacctaacagctgggactatgattacctg
ctgtcctccgacacggacgagtccatcgaagtatacaaagacaaagcgaaaaagctggaagcgaagttcgtcgcgagattaataacgaa
aaagcagaatttctgaccctgctggaactgattgacaacgtccagcgcctgggcctgggttaccgtttcgagtctgatatccgtggtgcgctg
gatcgcttcgttcctccggcggcttcgatgcggtaaccaagacttccctgcacggtacggcactgtctttccgtctgctgcgtcaacacggtt
ttgaggtttctcaggaagcgttcagcggcttcaaagaccaaaacggcaacttcctggagaacctgaaggaagatatcaaagctatcctgag
cctgtacgaggccagcttcctggctctggaaggcgaaaacatcctggacgaggcgaaggttttcgcaatctctcatctgaaagaactgtctg
aagaaaagatcggtaaagagctggcagaacaggtgaaccatgcactggaactgccactgcatcgccgtactcagcgtctggaagcagtat
ggtctatcgaggcctaccgtaaaaaggaggacgcgaatcaggttctgctggagctggcaattctggattacaacatgatccagtctgtatac
cagcgtgatctgcgtgaaacgtcccgttggtggcgtcgtgttggctggcgaccaaactcctttgctcgtgaccgcctgattgagagctt
ctactgggccgtgggtgtagcattcgaaccgcaatactccgactgccgtaactccgtcgcaaaaatgttttgtttcgtaaccattatcgacgat
atctacgatgtatacggcaccctggacgaactggagctgtttactgatgcagttgagcgttgggacgtaaacgccatcaacgacctgccgg
attacatgaaactgtgctttctggctctgtataacactattaacgaaatcgcctacgacaacctgaaagataaaggtgagaacatcctgccgta
tctgaccaaagcctgggctgcaactgtgcaacgctttcctgcaagaagccaagtggctgtacaacaaatctactccgaccttgacgactactt
cggcaacgcatggaaatcctcttctggcccgctgcaactggtgttcgcttacttcgctgtcgtgcagaacattaaaaaggaagagatcgaaa
acctgcaaaaataccatgacaccatctctcgtccttcccatatcttccgtctgtgcaatgacctggctagcgcgtctgcggaaattgcgcgtgg
tgaaaccgcaaatagcgtttcttgttacatgcgcactaaaggtatctccgaagaactggctaccgaaagcgtgatgaatctgatcgatgaata
ttggaaaagatgaacaaggaaaaaactgggtggtagccgttcgcgaaaccgtcgtggaaaccgcgatcaacctggcacgtcaatctca
ctgcacttatcataacggcgacgcgcataacctctccggatgagctgaccgcaaacgcgttctgtctgtaatcactgaaccgattctgccgttt
gaacgctaactgcataaaggaggtaaaaaaacatgattagcaaaatctatgatgataaaaagtatctggaaaaaatggataaatggtttcgc
gcagcaaattatctgggtgtttgtcagatgtatctgcgtgataatccgctgctgaaaaaaccgctgaccagcaatgatatcaaactgtatccga
ttggtcattggggcaccgttccgggtcagaattttatctatacccatctgaatcgcgtgatcaagaaatatgatctgaatatgttctacatcgaag
gtcctggtcatggtggtcaggttatgattagtaatagctatctctggattgcgcagcatatagcgaaatttatccggaaattagccaggatgaagcag
gtctggccaaaatgttttaaacgttttagctttccgggtggcaccgcaagccatgcagcaccgggaaacacccgggtagcattcatgaaggtgt
gaactggggttatagcattagccatggcaccggtgcaattctggataaccccggatgttatttgtgcagcagttgttggtgatggtgaagcagaa
accggtccgctggcgaccagctggtttagcaatgcctttattaacccggttaatgatggtgccattctgccgattctgcatctgaacggtggta
aaattagcaatcgaccctgctgagccgtaaaccgaaagaagaaattactttgaaggcctggcgtggaaatccgattttttgttgaat
ggtcagaagataagcaacctggatatgcatgaactgatggcaaaaagcctggataaagcattgaaagcatcaaagaaattcaggcag
aagcacgtaaaaaaacctgcagaagaagcaacccgtccgacctggccgatgattgttctgcgtaccccgaaaggttggacaggtccgaaa
cagtggaataatgaagcaattgaaggtagctttcgtgcacatcaggttccgattccggttagcgcctttaaaatggaaaagattgccgatcttg
agaaatggctgaaaagctacaaaaccggaagaactgtttgatgaaaatgcgaacaatcataaaagaaatccgtgatctggctcggaaggtct
gaaacgtatggcagttaacccgattaccaatggtggtattagcaaacctctgaaactgcaggattggaaaaagtacgcactgaaaattg
attatccgggtgaaattaaagcacaggatatggccgaaatggccaaatttgcagcagatatcatgaaagataacctagcagctttcgcgttt
ttggtccggatgaaaccaaaagcaatcgtatgtttgcctgtttaatgtgaccaatcgtcagtggctggaaccggttagtaagaaatacgatg
aatggattagtccggcaggtcgcattattgattcacagctgagcgaacatcagtgtgaaggttttttcctggaaggttttatgttctgaccgtcgtcat
ggttttttttgcaagctatgaagcatttctcgcgtgttgtggatagcatgctgacccaacatatgaaatggatcaaaaaggcaagcgaactgagct
ggcgtaaaacctatccgagcctgaacattattgcaaccagtaatgcatttcagcaggatcataatggttatacgcatcaggatccgggtctgc
tgggtcatctgcagatataacgtccagaaattatccgtgaatatctgcctgcagataccaatagcctgctggcggttatgaataaagcactga
ccgaacgtaatgtgattaatcctgattgttgcaagcaaacagcctcgcgaacagcctgcagatggcagaggaactgctggaaaagg
gttataaagttgttccgtgggcaagcaatattagcgaaaatgaagaaccggatattgtggccagcagcggtgttgaaccgaatatcgaaa
gtctggcagcaattagcctgatcaatcaagaatatcctcatctgaaaatccgctatgtgtatgtgctggatctgctgaagctgcgtagtcgtaa
aatcgatccgcgtggtattagtgatgaagagtttgataaagtgtttaccaaaaacaaaccgattatctttgcctttcatggctttgagggactgct
gcgcgatatttttcttaccccgtagcaaccataacctgattgcacatggttatcgtgaaaacggtgatatcacaaccagctttgatattcgtcagct
gagtgagatgcgttatcatattgtcaaaagatgctgccgaagccgtgtatgtgaaggtgcaaaagcatttatgaacaaactggatcaga
aactggaataccaccgcaactatatcgatgagtatgcctatgatatgccggaagtgtgaatgaaatgtaagaacatcaataaagaaat
taaagtctagttaaagtttaaacggtctccagcttggctgttttggcggatgagagaagattttcagcctgatacagattaaatcagaacgcag
aagcggtctgataaaacagaatttgcctggcggcagtagcgcggtggtcccacctgacccctgccgaactcagaagtgaaacgccgta
gcgccgatggtagtgtggggtctccccatgcgagagtagggaactgccaggcatcaaaacaagcggcagctcagtgaaaagactgggc
ctttcgttttatctgttgtttgtcggtgaacgctctcctgagtaggacaaatccgccgggagcggatttgaacgttgcgaagcaacggcccgg
agggtggcgggcaggacgcccgccataaactgccaggcatcaaattaagcagaaggccatcctgacggatggcctttttgcgtttctacaa
actcttttgtttatttttctaaatacattcaaatatgtatccgctcatgagacaataaccctgataaatgcttcaataatattgaaaaaggaagagta
tgagtattcaacatttccgtgtcgcccttattcccttttttgcggcattttgccttcctgtttttgctcacccagaaacgctggtgaaagtaaaagat
gctgaagatcagttgggtgcacgagtgggttacatcgaactggatctcaacagcggtaagatccttgagagttttcgccccgaagaacgttt
ccaatgatgagcacttttaaagttctgctatgtggcgcggtattatcccgtgttgacgccgggcaagagcaactcggtcgccgcatacactat
tctcagaatgacttggttgagtactcaccagtcacagaaaagcatcttacggatggcatgacagtaagagaattatgcagtgctgccataacc
atgagtgataacactgcggccaacttacttctgacaacgatcggaggaccgaaggagctaaccgcttttttgcacaacatgggggatcatgt
aactcgccttgatcgttgggaaccggagctgaatgaagccataccaaacgacgagcgtgacaccacgatgcctgtagcaatggcaacaa
cgttgcgcaaactattaactggcgaactacttactctagcttcccggcaacaattaatagactggatggaggcggataaagttgcaggacca
cttctgcgctcggcccttccggctggctggtttattgctgataaatctggagccggtgagcgtgggtctcgcggtatcattgcagcactgggg
ccagatggtaagccctcccgtatcgtagttatctacacgacggggagtcaggcaactatggatgaacgaaatagacagatcgctgagatag
gtgcctcactgattaagcattggtaactgtcagaccaagtttactcatatatactttagattgatttaaaacttcatttttaatttaaaaggatctagg
tgaagatcctttttgataatctcatgaccaaaatcccttaacgtgagttttcgttccactgagcgtcagaccccgtagaaaagatcaaaggatct
tcttgagatcctttttttctgcgcgtaatctgctgcttgcaaacaaaaaaaccaccgctaccagcggtggtttgtttgccggatcaagagctacc

| SEQUENCES |
|---|
| aactctttttccgaaggtaactggcttcagcagagcgcagataccaaatactgtccttctagtgtagccgtagttaggccaccacttcaagaac
tctgtagcaccgcctacatacctcgctctgctaatcctgttaccagtggctgctgccagtggcgataagtcgtgtcttaccgggttggactcaa
gacgatagttaccggataaggcgcagcggtcgggctgaacgggggggttcgtgcacacagcccagcttggagcgaacgacctacaccga
actgagatacctacagcgtgagctatgagaaagcgccacgcttcccgaagggagaaaggcggacaggtatccggtaagcggcagggtc
ggaacaggagagcgcacgagggagcttccaggggggaaacgcctggtatctttatagtcctgtcgggtttcgccacctctgacttgagcgtc
gattttttgtgatgctcgtcaggggggcggagcctatggaaaaacgccagcaacgcggccttttttacggttcctggccttttgctggccttttgc
tcacatgttctttcctgcgttatccccctgattctgtggataaccgtattaccgcctttgagtgagctgataccgctcgccgcagccgaacgaccg
agcgcagcgagtcagtgagcgaggaagcggaagagcgcctgatgcggtattttctccttacgcatctgtgcggtatttcacaccgcatatg
gtgcactctcagtacaatctgctctgatgccgcatagttaagccagtatacactccgctatcgctacgtgactgggtcatggctgcgccccga
cacccgccaacacccgctgacgcgccctgacgggcttgtctgctcccggcatccgcttacagacaagctgtgaccgtctccgggagctgc
atgtgtcagaggttttcaccgtcatcaccgaaacgcgcgaggcagcagatcaattcgcgcgcgaaggcgaagcggcatgcatttacgttg
acaccatcgaatggtgcaaaaccttcgcggtatggcatgatagcgcccggaagagagtcaattcagggtggtgaatgtgaaaccagtaac
gttatacgatgtcgcagagtatgccggtgtctcttatcagaccgtttcccgcgtggtgaaccaggccagccacgtttctgcgaaaacgcggg
aaaaagtggaagcggcgatggcggagctgaattacattcccaaccgcgtggcacaacaactggcgggcaaacagtcgttgctgattggc
gttgccacctccagtctggccctgcacgcgccgtcgcaaattgtcgcggcgattaaatctcgcgccgatcaactgggtgccagcgtggtgg
tgtcgatggtagaacgaagcggcgtcgaagcctgtaaagcggcggtgcacaatcttctcgcgcaacgcgtcagtgggctgatcattaacta
tccgctggatgaccaggatgccattgctgtggaagctgcctgcactaatgttccggcgttatttcttgatgtctctgaccagacacccatcaac
agtattattttctcccatgaagacggtacggactgggcgtggagcatctggtcgcattgggtcaccagcaaatcgcgctgttagcgggccc
attaagttctgtctcggcgcgtctgcgtctggctggctggcataaatatctcactcgcaatcaaattcagccgatagcggaacgggaaggcg
actggagtgccatgtccggttttcaacaaaccatgcaaatgctgaatgcccggaagagattccactgcgatgctggttgccaacgatcagatg
gcgctgggcgcaatgcgcgccattaccgagtccgggctgcgcgttggtgcggatatctcggtagtgggatacgacgataccgaagacag
ctcatgttatatcccgccgtcaaccaccatcaaacaggattttcgcctgctggggcaaaccagcgtggaccgcttgctgcaactctctcagg
gccaggcggtgaagggcaatcagctgttgcccgtctcactggtgaaaagaaaaaccaccctggcgcccaatacgcaaaccgcctctccc
cgcgcgttggccgattcattaatgcagctggcacgacaggtttcccgactggaaagcgggcagtgagcgcaacgcaattaatgtgagttag
cgcgaattgatctg SEQ ID NO: 31 |

MCS534
cgctaactgcataaaggaggtaaaaaaac SEQ ID NO: 32

MCS535
gctggagaccgtttaaactttaactagacttta SEQ ID NO: 33 oMCS536
taaagtctagttaaagtttaaacggtctccagc SEQ ID NO: 34

MCS537
gttttttttacctcctttatgcagttagcg SEQ ID NO: 35

MCS488
ttagcgttcaaacggcagaatcgg SEQ ID NO: 36

MCS562
ccgtttgaacgctaaAGATACGCGTAACCCCAAGGACGGTAAAatgattagcaaaatctatgatgataaaaagtatctgg SEQ ID NO: 37

MCS504
tgttttttttacctcctttgcagtgcgtcctgctgatgtgctcagtatcaccgccagtggtatttacgtcaacaccgccagagataatttatcaccgc
agatggttatcttaatacgactcactatagggctc SEQ ID NO: 38

MCS516
gactcaagatatttcttccatcatgcaaaaaaaaatttgcagtgcatgatgttaatcaaattaaccctcactaaagggcg SEQ ID NO: 39

MCS545
gctggtcagaccgacgctggttccggtagggatcagcataataatacgggacatGTTTTTTTACCTCCTTTGCAGTG SEQ ID NO: 40

MCM1033
AGGCTGCCTCGTCATCTCTT SEQ ID NO: 41

MCM1035
CAGAATATCGCCACTCTGGG SEQ ID NO: 42

MCM1038
ACACGCTATCTGGCAGGAAA SEQ ID NO: 43

MCM1039
TTTGACAACATCACAGTGCA SEQ ID NO: 44

MCS580
aattaaccctcactaaagggcggc SEQ ID NO: 45

MCS584
atattccaccagctatttgttagtgaataaaagtggttgaattatttgctcaggatgtggcattgtcaagggctaatacgactcactatagggctc
gaggaag SEQ ID NO: 46

MCM1042
tcacagcagaacagttagaaagcgtttaaaatcattcggtcacttctgcgggagaccggtaattaaccctcactaaagggcggc SEQ ID NO: 47

SEQUENCES

MCM1043
CGCGCCAATTACCGCTATCGATTTTGGTCGCAGTAGTGCTTCCAGTCCTCGCTGACTCATATATTCCACCAGCTATTTGTTAGTG SEQ ID NO: 48

MCM1046
gcgggaggaatgcgtggtgcggccttcctacatctaaccgattaaacaacagaggttgctaattaaccctcactaaagggcggc SEQ ID NO: 49

MCM1048
GCGCAGGCGGCGTTTATTTTTACGAAAACGACTTAACCGATGACCCCGACGCGACAGCATATATTCCACCAGCTATTTGTTAGTG SEQ ID NO: 50

*Salmonella enterica* acetyltransferase gi|16503810|emb|CAD05835.1|
MSQQGLEALLRPKSIAVIGASMKPHRAGYLMMRNLLAGGFNGPVLPVTPAWKAVLGVMAWPDIASLPFTPDLAILCTNASRNLALLDALGAKGCKTCII
LSAPTSQHEELLASARHYKMRLLGPNSLGLLAPWQGLNASFSPVPIKQGKLAFISQSAAVSNTILDWAQQREMGFSYFIALGDSLDIDVDELLDYLARD
SKTSAILLYLEQLSDARRFVSAARSASRNKPILVIKSGRSPAAQRLLNTSAGMDPAWDAAIQRAGLLRVQDTHELFSAVETLSHMRPLHGDRLMIIS
NGAAPAALALDELWSRNGKLATLSEETCLQLRQTLPAHIDIANPLDLCDDASSEHYVKTLDILLASQDFDALMVIHSPSAAAPGTESAHALIETIKRHPR
GKFVTLLTNWCGEFSSQEARRLFSEAGLPTYRTPEGTITAFMHMVEYRRNQKQLRETPALPSNLTSNTAEAHNLLQRAIAEGATSLDTHEVQPILHAYG
LHTLPTWIASDSAEAVHIAEQIGYPVALKLRSPDIPHKSEVQGVMLYLRTASEVQQAANAIFDRVKMAWPQARIHGLLVQSMANRAGAQELRVVVEHDP
VFGPLIMLGEGGVEWRPEEQAVVALPPLNMMNLARYLVIQGIKQRKIRARSALRPLDIVGLSQLLVQVSNLIVDCPEIQRLDIHPLLASASEFTALDVTL
DIAPFDGDNESRLAVRPYPHQLEEWVEMKNGDRCLFRPILPEDEPQLRQFIAQVTKEDLYYRYFSEINEFTHEDLANMTQIDYDREMAFVAVRRMDNAE
EILGVTRAISDPDNVDAEFAVLVRSDLKGLGLGRRLMEKLIAYTRDHGLKRLNGITMPNNRGMVALARKLGFQVDIQLDEGIVGLTLNLAKCDES SEQ
ID NO: 51

*Rhodopseudomonas palustris* GCN5 family N-acetyltransferase
gi|499473135|ref|WP_011159775.1|
MSTYRLSTLLSPGAVAVVGASPRPASLGRAVLTNLREAGFKGQIGVVNPRYPEIGGFKTVGSLAELSFVPDLIVITAPPRSVAKVVAEAGE
LGVAGAIIISSEMGRGKGSYAEAANRAARKSGIRLIGPNCLGIIVIIPGVNLNASFAAHMPRRGNLALISQSGAIAAGMVDWAAVKEIG
FSGIVSIGDQLDVDIADMLDFYAADLDTRAILLYIEAVTDARKFMSAARAAARVKPVVVVKSGRMAHGAKAAATHTGAFAGADAVYEAAFRRAGMLRVYD
LRELFDCAETLGRVS
APRGKRVAILTNGGGIGILAVDRLVELGGEPATLSADLHKKLDAILPTSWSGFNPIDITGDADAERYSATLSMLLADPDNDAILVMNVQTAVASPRDI
AREVIRVVGEERVRRT
LFKPVFAVWVGAEEAVTHAFDAASIPNYPTEDDAVRSIMNMVRYREAVQLLTEVPPSLPKDFDPDTETARAIVEKALREGRTWLDPLEISGLFAAYQIPM
IPTLAATNAEEAVSWASSFLSQGVTVVVKVLSRDIPHKSDIGGVVLNLTSVEAVRVAVNEIMARAAKLRPNARLEGVMVQPMILRPKARELTIGIAD
DPTFGPVIAFGQGGTGVELIDDRSLALPPLDLPLAESLIARTRVSKLLCAYRDVPEVKRSAVALTLVKLSQMAADLPEIRELDVNPLLADESGVVAIDAR
VVV
RPPERKFAGLGNSHFAVKPYPTEWERHLTVKDGWRVLARPIRPDDEPAIHEFLKHVTPEDLRLRFFAAMKEFSHAFIARLSQIDYARAMAFVAFDEIT
GEMLGVVRIHSDSIYES
GEYAILLRSDLKGKGLGWALMKLIIEYARSEGLHYVCGQVLRENTAMLRMCRDLGFETKTDASEPDILNVRLPLTEEAARAAGSA SEQ ID NO:52

*Streptomyces lividans* protein acetyl transferase EFD66247
MSYASRTLGPMQTSSDRHEYPAHWEADVVLRDGGTARVRPITVDDAERLVSFYEQVSDESKYYRFFAPYPRLSAKDVHRFTHHDFVDRVGLAATIGGEFI
ATVRYDRIGAGGTPATAPADEAEVAFLVQDAHQGRGVASALLEHIAAVARERGIRRFAAEVLPANNKMIKVFMDAGYTQKRSFEDGVVRLE
FDLEPTDRSLAVQYAREHRAEARSVQRLLQPGSVAVVGAGRTPGGVGRSILGNIRDAGYTGRLYAVNRAFPEDMKELDGVPACRSVGDIDGPVDLAVVT
VPAEHVPDVVTACGEHGVQGLVVISAGYADSGPEGRERQRALVRHARTYGMRIIGPNAFGIINTSPDVRLNASLAPEMPRAGRIGLFAQSGAIGIALLSR
LHRRGGGVTGVTGVSTFVSSGNRADVSGNDVLQYWYDDPQTDVALMYLESIGNPRKFTRLARRTAAAKPLVVVQGARHGGVAPQGHAVRATRLPHATVSA
LLRQAGVIRVDTITDLVDAGLLLARQPLPAGPRVAILGNSESLGLLTYDACLSEGLRPQPPLDLTTAASADDFHAALARALADDTCDAVVVTAIPTLGE
GAAGDAVARGGPALGGGRGPHQARPRGPRGAGRPGGGPVRGGEHGSPDGSGHRGHHRPGG SEQ ID NO: 53

*Mycobacterium tuberculosis* acetyltransferase gi|15608138|ref|NP_215513.1|
MDGIAELTGARVEDLAGMDVFQGCPAEGLVSLAASVQPLRAAAGQVLLRQGEPAVSFLLISSGSAEVSHVGDDGVAIIARALPGMIVGEIALLRDSPRSA
TVTTIEPLTGWTGGRGAFATMVHIPGVGERLLRTARQRLAAFVSPIPVRLADGTQLMLRPVLPGDRERTVHGHIQFSGETLYRRFMSARVPSPALMHY
LSEVDYVDHFVWVTDGSDPVADARFVRDETDPTVAEIAFTVADAYQGRGIGSFLIGALSVAARVDGVERFAARMLSDNVPMRTIIVIDRYGAVWQR
EDVGVITTMIDVPGPGELSLGREMVDQINRVARQVIEAVG SEQ ID NO: 54

*Mycobacterium smegmatis* acetyl transferase gi|118468187|ref|YP_889697.1|
MAELTEVRAADLAALEFFTGCRPSALEPLATQLRPLKAEPGQVLIRQGDPALTFMLIESGRVQVSHAVADGPPIVLDIEPGLIIGEIALLRDA
PRTATVVAAEPVIGWVGDRDAFDTILHLPGMFDRLVRIARQRLAAFITPIPVQVRTGEWFYLRPVLPGDVERTLNGPVEFSSETLYRR
FQSVRKPTRALLEYLFEVDYADHFVWVMTEGALGPVIADARFVREGHNATMAEVAFTVGDDYQGRGIGSFLMGALIVSANYVGVQRF
NARVLTDNMAMRKIMDRLGAVWVREDLGVVMTEVDVPPVDTVPFEPELIDQIRDATRKVIRAVSQ SEQ ID NO: 55

*Salmonella enterica* NAD-dependent deacetylase gi|16764576|ref|NP_460191.1|
MQSRRFPHRLSRFRKNKRLLRERLRQRIFFRDRVVPEMMENPRVLVLTGAGISAESGIRTFRAADGLWEEHRVEDVATPEGFARNPGLV
QTFYNARRQQLQQPEIQPNAAHLALAKLEEALGDRFLLVTQNIDNLHERAGNRNIIHMGELLKVRCSQSGQILEWNGDVMPEDKCHC
CQFPAPLRPHVVWFGEMPLGMDEIYMALSMADIFIAIGTSGHVYPAAGFVHEAKLHGAHTVELNLEPSQVGSEFEEKHYGPASQVVPEFVDKFLKGL
SEQ ID NO:56

*Rhodopseudomonas palustris* NAD-dependent deacetylase
gi|499471434|ref|WP_011158074.1|
MIAPSLSSGVEQLGDMIAHASSIVPFTGAGISTESGIPDFRSPGGLWSRNQPIPFDEFVARQDARDEAWRRFAMEQTFAKARPARGHRALAS
LYKAGKVPAIITQNIDNLHQVSGFAEHDVVELHGNTTYARCIGCGKRHELDWVREWFFRTGHAPHCTACDEPVKTATVSFGQSM
PSDAMRRATELAQHCDLFIAIGSSLVVWPAAGFPMLAKECGAKLVIINREPTEQDEIADLVIRHDIGETLGPFVGN SEQ ID NO: 57

*Mycobacterium tuberculosis* NAD-dependent protein deacylase
gi|614103494|sp|P9WGG3.1|NPD_MYCTU
MRVAVLSGAGISAESGVPTFRDDKNGLWARFDPYELSSTQGWLRNPERVWGWYLWRHYLVANVEPNDGHRAIAAWQDHAEVSITQNVD
DLHERAGSGAVHHLHGSLFEFRCARCGVPYTDALPEMPEPAIEVEPPVCDCGGLIRPDIVWFGEPLPEEPWRSAVEATGSADV
MVVVGTSAIVYPAAGLPDLALARGTAVIEVNPEPTPLSGSATISIRESASQALPGLLERLPALLK SEQ ID NO: 58

| SEQUENCES |
|---|
| acsAUppKD3<br>tcacgacagtaaccgcacctacactgtcatgacattgctcgccctatgtgtaacaaataaccacactgcccatggtccatatgaatatcctcc<br>SEQ ID NO: 59 |
| acsADnGI1.6pKD3R<br>caacggtctgcgatgttggcaggaatggtgtgtttgtgaatttggctcatatataattcctcctgctatttgttagtgaataaaagtggttgaattat<br>ttgctcaggatgtggcattgtcaagggcgtgtaggctggagctgcttcg SEQ ID NO: 60 |
| CMP534<br>gtgcaaattcacaactcagcgg SEQ ID NO: 61 |
| CMP535<br>caccaacgtatcgggcattgc SEQ ID NO: 62 |
| TS For<br>tcctaattttttgttgacactctatcattg SEQ ID NO: 63 |
| TS Rev<br>ccatcttgttgagaaataaaagaaaatgcca SEQ ID NO: 64 |
| actP Up For<br>tttatttctcaacaagatgggcaggctatcgcgatgccatcgtaac SEQ ID NO: 65 |
| actP Up Rev<br>ggagagattacatgatgcttgtacctcatgcagga SEQ ID NO: 66 |
| actP Down For<br>aagcatcatgtaatctctccccttccccggtcgcctga SEQ ID NO: 67 |
| actP Down Rev<br>agtgtcaacaaaaattaggacgtaaccaccatttactgtctgtgga SEQ ID NO: 68 |
| actP Test For<br>ctggcgtagtcgagaagctgcttga SEQ ID NO: 69 |
| actP Test Rev<br>gcatagcggaacatgaatttagagt SEQ ID NO: 70 |
| ackA Up For<br>tttatttctcaacaagatggcggatcgagcatagtcatcatcttgtact SEQ ID NO: 71 |
| ackA Up GI Rev<br>cggttgatttgtttagtggttgaattatttgctcaggatgtggcatngtcaagggcgaatttgacgactcaatgaatatgtact SEQ ID NO: 72 |
| ackA Down GI For<br>accactaaacaaatcaaccgcgtttcccggaggtaacctaaaggaggtaaaaaaacatgtcgagtaagttagtactggttctga SEQ ID NO: 73 |
| ackA Down Rev<br>agtgtcaacaaaaattaggagtacccatgaccagaccttccagc SEQ ID NO: 74 |
| ackA Up PL Rev<br>atcaccgccagtggtatttangtcaacaccgccagagataatttatcaccgcagatggttatctgaatttgacgactcaatgaatatgtact<br>SEQ ID NO: 75 |
| ackA Down PL For<br>taaataccactggeggtgatactgagcacatcagcaggacgcactgcaaaggaggtaaaaaaacatgtcgagtaagttagtactggttctg<br>a SEQ ID NO: 76 |
| ackA EX Test For<br>tgcaggcgacggtaacgttcagcat SEQ ID NO: 77 |
| ackA EX Test Rev<br>gtggaagatgatcgccggatcgata SEQ ID NO: 78 |
| R6K TS Rev<br>agtgtcaacaaaaattaggactgtcagccgttaagtgttcctgtgt SEQ ID NO: 79 |
| actP R6K For<br>ggtggttacgcagttcaacctgttgatagtacgta SEQ ID NO: 80 |
| actP R6K Rev<br>ggttgaactgcgtaaccaccatttactgtctgtgga SEQ ID NO: 81 |
| yfiQ DOWN For<br>TTTATTTCTCAACAAGATGGGGCCGATTAACATCATCCAGACGAT SEQ ID NO: 82 |

| SEQUENCES |
|---|
| yfiQ DOWN GI1.6 Rev<br>CGGTTGATTTGTTTAGTGGTTGAATTATTTGCTCAGGATGTGGCATTGTCAAGGGCTCTTGCCCAACGCGAGGAATCATGAGTA SEQ ID NO: 83 |
| yfiQ DOWN GI1.2 Rev<br>CGGTTGATTTGTTTAGTGGTTGAATTATTTGCTCAGGATGTGGCATCGTCAAGGGCTCTTGCCCAACGCGAGGAATCATGAGTA SEQ ID NO: 84 |
| yfiQ UP GI For<br>ACCACTAAACAAATCAACCGCGTTTCCCGGAGGTAACCTAAAGGAGGTAAAAAAACACCGGTCTCCCGCAGAAGTGACCGA SEQ ID NO: 85 |
| yfiQ UP Rev<br>ACTATCAACAGGTTGAACTGCGCCGTTCGATAGCTGGCTGAACGA SEQ ID NO: 86 |
| yfiQ Test For<br>GCATCACGCAGCTCCTGGCGGAACA SEQ ID NO: 87 |
| yfiQ Test Rev<br>GCTGAACGTGAATTGAGCAGTCGCT SEQ ID NO: 88 |
| rpe R6K For<br>TACACACATAAGGAGGTTCCCAATGAAACAGTATCTGATCGCACCTAGCA SEQ ID NO: 89 |
| rpe R6K Rev<br>TATTCGAATGTATGCTAGTGGACGTCAATCATTACTCGTGGCTCACTTTCGCCAGTTCA SEQ ID NO: 90 |
| tkt R6K For<br>CACTAGCATACATTCGAATAAGGAGGAATACTATGTCATCTCGTAAGGAACTGGCGAA SEQ ID NO: 91 |
| tkt R6K Rev<br>TATCTCCTTCTTGAGCCGATTATCATTACAGCAGCTCTTTGGCTTTCGCGACA SEQ ID NO: 92 |
| rpi R6K For<br>ATCGGCTCAAGAAGGAGATATACATATGACGCAGGACGAACTGAAAAAAGCGGT SEQ ID NO: 93 |
| rpi R6K Rev<br>TATTCCTCCTTCAGGACCTTTCATTATTTAACGATCGTTTTGACGCCATC SEQ ID NO: 94 |
| tal R6K For<br>AAGGTCCTGAAGGAGGAATAAACCATGACCGATAAACTGACCAGCCTGCGT SEQ<br>ID NO: 95 |
| tal R6K Rev<br>GACCGGTTCATTACAGCAGGTCGCCGATCATTTTCTCCA SEQ ID NO: 96 |
| R6K Plasmid For<br>CCTGCTGTAATGAACCGGTCTCCCGCAGAAGTGACCGAATGA SEQ ID NO: 97 |
| R6K Plasmid Rev<br>GGAACCTCCTTATGTGTGTAAACCTTTAGGTTACCTCCGGGAAACGCGGTTGA SEQ ID NO: 98 |
| pfkA tmRNA XAA For<br>TGAAGCGTCCGTTCAAAGGCGACTGGCTAGACTGCGCGAAAAAACTGTATGCTGCTAACGATGAAAATTATGCTNNNGCTGCATAAAATTAACCCTCACT<br>AAAGGGCG SEQ ID NO: 99 |
| pfkA tmRNA Rev<br>GCTTCTGTCATCGGTTTCAGGCTAAAGGAATCTGCCTTTTTCCGAAATCATAATACGACTCACTATAGGGCTC SEQ ID NO: 100 |
| pfkA UP For<br>TTTATTTCTCAACAAGATGGGTTATCGGCGGTGACGGTTCCTACAT SEQ ID NO: 101 |
| pfkA UP Rev<br>AGCATAATTTTCATCGTTAGCAGCATACAGTTTTTTCGCGCAGTCTAGCCAGTCGCCT SEQ ID NO: 102 |
| pfkA DOWN R For<br>CTAACGATGAAAATTATGCTCGCGCTGCATAATGATTTCGGAAAAAGGCAGATTCCT SEQ ID NO: 103 |
| pfkA DOWN I For<br>CTAACGATGAAAATTATGCTATTGCTGCATAATGATTTCGGAAAAAGGCAGATTCCT SEQ ID NO: 104 |
| pfkA DOWN T For<br>CTAACGATGAAAATTATGCTACGGCTGCATAATGATTTCGGAAAAAGGCAGATTCCT SEQ ID NO: 105 |
| pfkA DOWN Rev<br>ACTATCAACAGGTTGAACTGCGGTGCGGAGTTATCCGGCAGACGT SEQ ID NO: 106 |

-continued

SEQUENCES pfkA Test For
CTGACATGATCAACCGTGGCGGTA SEQ ID NO: 107 pfkA Test Rev
GATCGTTCCAGTCATGGATCTGCT SEQ ID NO: 108 ackA overexpression plasmid
cggatcgagcatagtcatcatcttgtactgattagacaaaataagacgttgcgcgttggtcatttccattgttgactcctgtatcactctactacg
gtgaaaaaaagaaggctgagtatgccttcttttatatgcgtaatcaggggtcaattacaaatcatcaaggaaagttttatccagttgtttgaag
gcgcgcttaagcgtgtcagctaatgcctggtaatcaggcttgccttcaacgggtgccaacacctgtccagactcctgcaatttaccgcgaact
tcataaaaccagttgaggatagcaggggtaatggcgttacagaacgcttgcccagccaccacaatccctgcatgggtaaacttaaggcg
aacagcgcagtggcaactgccggcccaagctgaccgcccagggcaatctgccagcagagagtaaatacggcgatcggcggcataaaa
cggatcgcataacgcgtcatcttgataacgcgattttcgacaaagaccggggcaaggcgttttccagcggccacgtctttgagtaatgctgt
ccccggcgaaacaagctaaaaaattaacagaacgattatccggcgttgacatgcttcacctcaacttcacatataaagattcaaaaatttgtg
caaattcacaactcagcgggacaacgttcaaaacattttgtcttccatacccactatcaggtatccttttagcagcctgaaggcctaagtagtac
atattcattgagtcgtcaaattcgcccttgacnatgccacatcctgagcaaataattcaaccactaaacaaatcaaccgcgtttcccggaggta
acctaaaggaggtaaaaaaacatgtcgagtaagttagtactggttctgaactgcggtagtcttcactgaaatttgccatcatcgatgcagtaa
atggtgaagagtaccttctggtttagccgaatgtttccacctgcctgaagcacgtatcaaatggaaaatggacggcaataaacaggaagcg
gctttaggtgcaggcgccgctcacagcgaagcgctcaacttttatcgttaatactattctggcacaaaaaccagaactgtctgcgcagctgact
gctatcggtcaccgtatcgtacacggcggcgaaaagtataccagctccgtagtgatcgatgagtctgttattcagggtatcaaagatgcagct
tcttttgcaccgctgcacaacccggctcacctgatcggtatcgaagaagctctgaaatctttcccacagctgaaagacaaaaacgttgctgta
tttgacaccgcgttccaccagactatgccggaagagtcttacctctacgccctgccttacaacctgtacaaagagcacggcatccgtcgttac
ggcgcgcacggcaccagccacttctatgtaacccaggaagcggcaaaaatgctgaacaaaccggtagaagaactgaacatcatcacctg
ccacctgggcaacggtggttccgtttctgctatccgcaacgtaaatgcgttgacacctctatgggcctgaccccgtcggaaggtctggtca
tgggtaccagttcaacctgttgatagtacgtactaagctctcatgtttcacgtactaagctctcatgtttaacgtactaagctctcatgtttaacga
actaaaccctcatggctaacgtactaagctctcatggctaacgtactaagctctcatgtttcacgtactaagctctcatgtttgaacaataaaatt
aatataaatcagcaacttaaatagcctctaaggttttaagttttataagaaaaaaagataataaggttttaaagcttttaaggtttaacggttg
tggacaacaagccagggatgtaacgcactgagaagcccttagagcctctcaaagcaattttcagtgacacaggaacacttaacggctgac
agtcctaatttttgttgacactctatcattgatagagttattttaccactccctatcagtgatagagaaagtgaaatgaatagttcgacaaagatc
gcattggtaattacgttactcgatgccatggggattggccttatcatgccagtcttgccaacgttattacgtgaatttattgcttcggaagatatcg
ctaaccactttggcgtattgettgcacttttatgcgttaatgcaggttatctttgctccttggcttggaaaaatgtctgaccgatttggtcggcgcc
agtgctgttgttgtcattaatagggcgcatcgctggattacttattgctggcttttcaagtgcgctttggatgctgtatttaggccgtttgctttcagg
gatcacaggagctactgggggctgtcgcggcatcggtcattgccgataccacctcagctctcaacgcgtgaagtggttcggttggttaggg
gcaagttgggcttggttaatagcggggcctattattggtggttgcaggagagatttcaccgcatagtcccttttttatcgctgcgttgctaa
atattgtcactttccttgtggttatgttttggttccgtgaaaccaaaatacacgtgataatacagataccgaagtaggggttgagacgcaatcg
aattcggtatacatcactttattaaacgatgccattttgttgatattttattttttcagcgcaattgataggccaaattcccgcaacggtgggt
gctatttaccgaaaatcgttttggatggaatagcatgatggttggcttttcattagcgggtcttggtcttttacactcagtattccaagcctttgtgg
caggaagaatagccactaaatggggcgaaaaacggcagtactgctcgaatttattgcagatagtagtgcatttgccttttagcgtttatatct
gaaggttggttagatttccctgtttaattttattggctggtggtgggatcgcttacctgcattacagggagtgatgtctatccaaacaaagagtc
atgagcaaggtgctttacagggattattggtgagccttaccaatgcaaccggtgtctgccattactgttactgttatttataatcattcacta
ccaattttgggatggctggatttggattattggtttagcgttttactgtattattatcctgctatcgatgacctcatgttaacccctcaagctcaggg
gagtaaacaggagacaagtgcttagttatttcgtcaccaaatgatgttattccgcgaaatataatgaccctcttggatcttaacatttttccctat
cattttttccgtcttcatttgtcatttttccagaaaaatcgcgtcattcgactcatgtctaatccaacacgtgtctctcggcttatccctgacaccg
cccgccgacagcccgcatgggacgattctatcaattcagccgcggagtctagttttataattgcagaatgcgaagtctgggttgaagtttattataacaa
tataagttttcattattttcaaaaagggggattttattgtggggtttaggtaagaaattgtctgttgctgtcgccgcttccttttatgagtttaaccatcagt
ctgccgggtgttcaggccgctgaggatatcaataaccaaaagcatacaaagaaacgtacggcgtctctcatattacacgccatgatatgct
gcagatccctaaacagcagcaaaacgaaaaataccaagtgcctcaattcgatcaatcaacgattaaaaatattgagtctgcaaaaggacttg
atgtgtccgacagctggccgctgcaaaacgctgacggaacagtagcagaatacaacggctatcacgttgtgttgctcttgcgggaagccc
gaaagacgctgatgacacatcaatctacatgtttttatcaaaaggtcggcgacaactcaatcgacagctggaaaaacgcgggccgtgtcttta
aagacagcgataagttcgacgccaacgatccgatcctgaaagatcagacgcaagaatggtccggttctgcaacctttacatctgacggaaa
aatccgtttattctacactgactattccggtaaacattacggcaaacaaagcctgacaacagcgcaggtaaatgtgtcaaatctgatgacac
actcaaaatcaacggagtggaagatcacaaaacgattttttgacggagacggaaaaacatatcagaacgctcagcagtttcagcagtttatcgatgaaggc
aattatacatccgccgacaaccatacgctgagagaccctcactacgttgaagacaaaaggccataaataccttgtattcgaagcgaacacgg
gaacagaaaacggataccaaggcgaagaatctttatttaacaaagcgtactacggcggcggcacgaacttcttccgtaaagaaagccaga
agcttcagcagagcgctaaaaaacgcgatgctgagttagcgaacggcgccctcggtatcatagagttaaataatgattacacattgaaaaaa
gtaatgaagcgcgctgatcacttcaaaacacggtaactgatgaaatcgagcgcgcgaatgttttcaaaatgaacggcaaatggtacttgttcact
gattcacgcggttcaaaaatgacgatcgatggtattaactcaaacgatatttcacgttgtatcaaactctttaaccggccgcccttacaag
ccgctgaacaaaacagggcttgtgctgcaaatgggtcttgatccaaacgatgtgacattcacttactctcacttcgcagtgccgcaagccaa
aggcaacaatgtggttatcacaagctacatgacaaacagaggcttcttcgaggataaaaaggcaacatttggcccaagcttcttaatcaacat
caaaggcaataaaacatccgttgtcaaaaacagcatcctggagcaaggacagctgacagtcaactaataacagcaaaaagaaaatgccg
atacttcattggcattttctttttatttctcaacaagatgg SEQ ID NO: 109 actP deletion plasmid
taatctctcccccttccccggtcgcctgaccggggaatactcttcctctccagcatgcatcaccttttcccaaaatatttaaacaaataaactcatta
aaaaatgagcgattttttgacagtcgtagaaaatgataatgcagagaatatgccttttctttcttgttaattataaggatattttatgtgctacaatggt
ttaaataatatgttttttccctctttgccagattaacgataaccactctgtcacaagtccatcacatacaaagaaacaaaatcagataattacaga
aaacatcataaaagcacgttaattgacaatcaaagcccctctctctttttcaagatggatgatcatgaaaaagtgataggcttgattcagaaaatga
aaagaatttatgatagtttaccatcaggaaaaatcacgaaggaaacggacaggaaatacataaacattttatagatatagctttatatgcaaat
aataaatgtgacgatagaattacgagaagagttttacctttagtaaagaaaggaagtatccattaaggtggtatattattataaataatgtcgcca
tccataataatactatcgaaattccacagacagtaaatggtggttacgcagttcaacctgttgatagtacgtactaagctctcatgtttcacgtac
taagctctcatgtttaacgtactaagctctcatgtttcacgtactaagctctcatgttgaacaataaaattaataaatcagcacttaaatagcctctaaggttttaagttttataagaaaaaaa
agaatatataaggcttttaaagcttttaaggtttaacggttgtggacaacaagccagggatgtaacgcactgagaagcccttagagcctctca
aagcaattttcagtgacacaggaacacttaacggctgacagtcctaattttttgttgacactctatcattgatagagttattttaccactccctatca
gtgatagagaaagtgaaatgaatagttcgacaaagatcgcattggtaattacgttactcgatgccatggggattggccttatcatgccagtct
tgccaacgttattacgtgaatttattgcttcggaagatatcgctaaccactttggcgtattgcttgcactttatgcgttaatgcaggttatctttgctc

SEQUENCES cttggcttggaaaaatgtctgaccgatttggtcggcgcccagtgctgttgttgtcattaataggcgcatcgctggattacttattgctggcttttc
aagtgcgctttggatgctgtatttaggccgtttgctttcagggatcacaggagctactggggctgtcgcggcatcggtcattgccgataccac
ctcagcttctcaacgcgtgaagtggttcggttggttaggggcaagttttgggcttggtttaatagcggggcctattattggtggttttgcaggag
agatttcaccgcatagtcccttttttatcgctgcgttgctaaatattgtcacttttccttgtggttatgttttggttccgtgaaaccaaaaatacacgtg
ataatacagataccgaagtaggggttgagacgcaatcgaattcggtatacatcactttatttaaaacgatgcccatttttgttgattatttatttttca
gcgcaattgataggccaaattcccgcaacggtgtgggtgctatttaccgaaaatcgttttggatggaatagcatgatggttggcttttcattagc
gggtcttggtcttttacactcagtattccaagccttttgtggcaggaagaatagccactaaatggggcgaaaaaacggcagtactgctcgaatt
tattgcagatagtagtgcatttgccttttttagcgtttatatctgaaggttggttagatttccctgtttttaatttttattggctggtggtgggatcgcttta
cctgcattacagggagtgatgtctatccaaacaaagagtcatgagcaaggtgctttacagggattattggtgagccttaccaatgcaaccggtg
ttattggcccattactgtttactgttatttataatcattcactaccaatttgggatggctggatttggattattggtttagcgttttactgtattattat
cctgcatcgatgaccttcatgttaacccctcaagctcagggagtaaacaggagacaagtgcttagttatttcgtcaccaaatgatgttattccgc
gaaatataatgaccctcttggatcttaacattttccctatcattttccgtcttcattttgtcattttttccagaaaaaatcgcgtcattcgactcatg
tctaatccaacacgtgtctctcggcttatccctgacaccgcccgccgacgcccgcatgggacgattctatcaattcagccgcggagtctag
ttttatattgcagaatgcgagatgctggtttattataacaatataagttttcattattttcaaaaaggggggatttattgtgggtttaggtaagaaattg
tctgttgctgtcgccgcttccttatgagtttaaccatcagtctgccgggtgttcaggccgctgaggatatcaataaccaaaaagcatacaaag
aaacgtacggcgtctctcatattacacgccatgatatgctgcagatccctaaacagcagcaaaacgaaaaataccaagtgcctcaattcgat
caatcaacgattaaaaatattgagtctgcaaaaggacttgatgtgtccgacagctggccgctgcaaaacgctgacggaacagtagcagaat
acaacggctatacgttgtgtttgctcttgcgggaagcccgaaagacgctgatgacacatcaatctacatgttttatcaaaaggtcggcgaca
actcaatcgacagctggaaaaacgcgggccgtgtctttaaagacagcgataagttcgacgccaacgatccgatcctgaaagatcagacgc
aagaatggtccggttctgcaacctttacatctgacggaaaaatccgtttattctacactgactattccggtaaacattacggcaaacaaagcct
gacaacagcgcaggtaaatgtgtcaaaatctgatgacacactcaaaatcaacggagtggaagatcacaaaacgattttttgacggagacgg
aaaaacatatcagaacgttcagcagtttatcgatgaaggcaattatacatccgccgacaaccatacgctgagagaccctcactacgttgaag
acaaaggccataaataccttgtattcgaagccaacacgggaacagaaaacggataccaaggcgaagaatctttatttaacaaagcgtacta
cggcggcggcacgaacttcttccgtaaagaaaagccagaagcttcagcagagcgctaaaaaacgcgatgctgagttagcgaacggcgcc
ctcggtatcatagagttaaataatgattacacattgaaaaaagtaatgaagccgctgatcacttcaaacacggtaactgatgaaatcgagcgc
gcgaatgtttttcaaaatgaacggcaaatggtacttgttcactgattcacgcggttcaaaaatgacgatcgatggtattaactcaaacgatattta
catgcttggttatgtatcaaactctttaaccggccttacaagccgctgaacaaaacagggcttgtgctgcaaatgggtcttgatccaaacgat
gtgacattcacttactctcacttcgcagtgccgcaagccaaaggcaacaatgtggttatcacaagctacatgacaaaacagaggcttcttcgag
gataaaaaggcaacatttggcccaagcttcttaatcaacatcaaaggcaataaaaacatccgttgtcaaaaacagcatcctggagcaaggac
agctgacagtcaactaataacagcaaaaagaaaatgccgatacttcattggcattttcttttatttctcaacaagatgggcaggctatcgcgatg
ccatcgtaacccacaattgccggatgcgagtcggtaacggtttgtaggcctgataagacgcgacagcgtcgcatcaggcattgattgccgg
atgcggcgtataacgccttatccggcctacattcggcaagggttaccgagcgttaacctctcccataagggagcgggaattaaaaacaatc
cctacattacctctggagaatctgtgatgaatggtacgattttatcagcggatagaagacaatgcgcatttcagggagttagtcgaaaaacggc
aacggtttgccaccatcctgtcgattattatgctggcagtttatatcggcttttattttactgatcgccttcgcgcccggctggctgggcacccg
ctgaatccgaacaccagcgtcacacgcggtattccgattggtgttggagtgattgtgatctcctttgttctcaccggtatctacatctggcggg
cgaacggcgaattcgaccgtcttaataacgaagtcctgcatgaggtacaagcatcatg SEQ ID NO: 110

Pentose Phosphate Pathway Upregulation Plasmid
ggccgattaacatcatccagacgattaacgccgcggccattcataatattctgtgtaacccattcaaacataatgtctgacatcttacggttacg
gataagatgataacggtcgtagcgatatttatcgtgctgatgcaggtaaacatcgttcaggctggcaccgctataaagtacgctatcgtcgat
gataaagcctttaaagtgcagaacaccaagggcttcacgggtattgattggaacgccataaaccggaacatctacgcccggatttttcctgcg
ccatgcggcagtaccagtcagcgttagtgttagatgccgcagcgccaatgcgtccacgttgtgcacgatgccagtcgaccagcacccgca
catccagttccggacgctgccttttagcttcatacaacgcgttcagaatgcctttgccaccgtcatcctgttcgagatacagggcgacaatgca
aatgcgctgcttcgcgctggctatttttccagcagcgtctcccggaagtcggcgggagcgtaaaagaaatcgacatcatcaactgattgag
aaatcttgggtagttgggcaaggtgttgttgatgtttatcacgcttaaattttgacaacatcacagtgcatttcttctctgtcattgaagggtcctct
gtgcaatgcagacgacataagcgggcaataataacaccagtcccgattaagtggtcaacattccagtaccttactcatgattcctcgcgttg
ggcaagagccctgacnatgccacatcctgagcaaataattcaaccactaaacaaatcaaccgcgtttcccggaggtaacctaaaggtttac
acacataaggaggttcccaatgaaacagtatctgatcgcacctagcatcctgtctgcagacttcgcccgtctgggcgaggacaccgctaaa
gcactggcgggcgggcggatgtagttcatttcgacgtgatggataatacctaccgaacctgactatcggcccgatggtactgaaatc
tctgcgtaactacggcatcaccgccgatcgatgttcacctgatggttaaaccggtggatcgtatcgtgccggatttcgccgcggctggtg
catccattatcaccttccacccctgaagcttccgaacacgttgaccgcaccctgcagctgattaaagaaaacggctgtaaggctggtctggtgt
tcaacccagctacgccgctgtcttatctggattatgttatggataagctggacgtaatcctgctgatgagcgtcaacccgggtttcggtggtca
gagcttcattccgcagaccctggacaaactgcgcgaaagtgcgtcgtgatgaatcgatgattcggctttcgatatccgtctggagggtgatggcg
gcgtgaaagttaacaacatcggcgagatcgccgcggcaggtgcggacatgttcgtcgcaggttctctgcaattcttcgatcagcggactataa
aaaagtgattgacgaaatgcgttctgaactggcgaaagtgagccacgagtaatgattgacgtccactagcatacattcgaataaggaggaat
actatgtcatctcgtaaggaactggcgaatgccatccgtgctctgtctatggacgccgtgcagaaagccaaatctggtcaccctggcgcacc
gatgggcatggcagacatcgccgaagtactgtggcgcgacttcctgaaacataaccccgcagaaccgcgtcttgggctgaccgtgatcgtttc
gtgctgagcaacgccgcacgtagcatgctgatttattccctgctgactggttttacgacggttgacgaagagctgaagaacttcg
ccagctgcactccaaaaccccgggtcacccagaagtgggctataccgccggtgtcgagactaccaccggtccactgggcagggcatc
gccaacgctgtgggtatggcgattgcagaagaaccctggcagcccagttcaaccgtccgggtcacgatatcgttgaccactatacctacg
cctttatgggtgacggctgcatgatggaaggtattagccacgaagtttgctctctggctggcactctgaaactgggtaaactgatcgcattcta
cgacgacaatggcattagcatcgacggccacgtggaaggttggttcaccgacgacactgcgcagctgttcgaagcttacggtggcacgtg
attcgtgacattgatggtcacgacgcagcgtctatcaaacgtcggttgaagaggcacgtgccgtaaccgataaagccttctctgctgatgtg
caaaacgattatcggtttcggcagcccgaacaaagcggcacccacgacagccatgcgcgcctctgggcgatgccgaaatcgctctga
cccgtgagcaactggggtggaaatacgcgccgttcgaaatcccatctgaaatttatgctcagtgggacgcaaaggaagcgggtcaagcaa
aggaatctgcatggaacgaaaaatttgctgcttatgctcaaggcgtacccgcaggaagcagctgaatttacccgtcgtatgaaaggtgaaatg
ccgtctgattttgacgcgaaacgcaaggaatttattgcgaaactgcaggcaaaccgcaaaaatcctcccgtaaagcgtccagaac
gcgatcgaggcattcggcccgtgctgccgaattcctgggtggttctgccgacctggcgcctagcaacctgaccctgtggtctggttcca
aagcaattaatgaagatgctgccggtaactacatccactacggcgtccgcgaatttggtatgaccgcaatcgctaacggtatcagcctgcat
ggcggttttctgccgtacaccagcacctttctgatgttcgtagaatacgcacgtaacgcggttcgcatgccgcactgatgaaacagcgcca
ggtgatggtatatactcacgacagcatcggtctgggtgaagacggtccgacccaccagccggttgaacaagttgcgagcctgcgcgtaac
tccaaacatgtccacggcgtcctgcaggttaaagcgcgttgaagcttgaaatgcggtggacagcaggacggtccgaccg
cactgatcctgtcccgtcagaatctggctcagcaggagcgtaccgaggcagctgtcaaactcgcacgtggcggttacgtctgaaag
attgcgctggccagccggaactgattttcatcgcaacggctctgaagtcgagctggcagtcgcagcgtatgagaaactgaccgcggaag
gtgttaaagcgcgtgttgtcagcatgccgagcaccgacgcattcgacaaacaggatgcagcatatcgcgagagcgttctgcctaaagctgt
tactgctcgtgtcgcggttgaggctggtatcgcggactactggtataaatatgtaggtctgaacggtgcgattgttggtatgacgaccttcggt
gaatccgctcctgcggaactgctgttcgaagaattcggcttcaccgtagacaacgttgtcgcgaaagccaaagagctgctgtaatgataatc

| SEQUENCES |
|---|
| ggctcaagaaggagatatacatatgacgcaggacgaactgaaaaaagcggttggttgggcagccctgcagtatgtgcaaccgggtactat
tgttggtgttggcaccggctccaccgccgcccactttattgatgcgctgggcaccatgaagggtcagatcgaaggtgctgtgtctagctctg
acgcgtctactgaaaaactgaagtccctgggcatccacgtgttcgatctgaacgaagttgactctctgggcatctatgtggacggcgcagac
gaaattaacggtcacatgcagatgatcaaaggcggtggcgcggccctgacccgcgagaaaatcatcgcatccgttgcagaaaaattcatct
gtatcgctgacgcgtctaaacaggtagacattctgggtaaattccctctgccagttgaagtgatccctatggcccgtccgccgtggcccgtc
agctggtaaagctgggtggtcgtcctgaatatcgccagggcgttgttactgataacggcaatgtgatcctggacgtgcacgtatggaaatc
ctggacccgattgcaatggaaaacgcgatcaacgcgattccgggcgttgtaacggtgggcctgttcgcgaatcgcggtgcggacgttgca
ctgatcggtaccccggatggcgtcaaaacgatcgttaaataatgaaaggtcctgaaggaggaataaaccatgaccgataaactgaccagc
ctgcgtcagtacaccaccgtagttgcggataccggtgacatcgctgcgatgaaactgtatcaaccgcaggatgcaaccactaacccgtccc
tgattctgaacgcggcacagatcccggaatatcgtaaactgatcgatgacgcagttgcatgggcaaaacaacagagcaatgatcgcgccc
aacagattgtagacgctaccgatgtaaactggccgtaaacatcggcctggagattctgaaactggttccgggtcgtatcagcactgaagttgat
gctcgtctgagctatgacacggaagcgagcattgccaaagctaaacgtctgatcaaactgtacaacgacgcggtgtatcgccggccatgaccgt
attctgattaaactggcttctacctggcagggcattcgcgcggccgaacagctggagaaagaaggcatcaactgcaacctgaccctgctgtt
ctcttttgctcaggcccgtgcctgcgctgaagccggtgttttttctgatctctcctttcgtgggccgtattctggattggtacaaagccaacacgg
ataaaaaggagtacgctccggctgaagatccgggtgtggtgagcgtttccgaaatttaccagtactacaaagaacatggttacgaaaccgtt
gttatgggtgcctcttttcgtaacatcggtgaaatcctggaacctggcaggctgcgaccgcctgaccatcgcgccgacccctgctgaaagaact
ggcggagtctgaaggtgccatcgaacgtaaactgtcctacaccggtgaagtgaaagcacgcccggcacgcattaccgaatctgagttcct
gtggcaacacaaccaggatccgatggcagtcgataaactggctgaaggtatccgcaaattcgcaatcgaccaggagaaactggagaaaa
tgatcggcgacctgctgtaatgaaccggtctcccgcagaagtgaccgaatgattttaaacgctttctaactgttctgctgtgatgctacccaga
tgttgcgttttcctgccagatagcgtgttttaaagcgggtaaaatgctcgcctaaccctgctgccgccccggtatcgccggccatatctaaca
gtgcgatggctacctcggcagtacaatattggccttcagcctggcttcacgcaggcgataggcagaaagccgggaaagatcgacggaa
atgacggaagattatccagatacggacttttacgaaacatcttgcgagcttccggccaggtaccatcgagcatgataaacagcggtggctt
accggcaggtggtgtgaagatcactteccgttgctcatcagcatacgaggcgggaaagaccaccattggctgataatacgggttttgtacca
gatccagcaaatcctgcgagggttcggtacgcgaccattgaaacgcaacgcctgaccaaatatcagcaatcagacgcccggtattact
gggcttcattggctcggtgtcgaacatcagcaaacagaagcgacttttttgcttgtgctggggtaattgtcgaacagagacataatttctctggc
aaaagacagcgttggcagcgacgaacgcgattaccgcgggcaagaaaagacgtgttgcgcgcgcaatacgctcggcgcgtaactgg
agaacagcgttttcggtcataagagagcgtcgaaaaaacgccattgtcgcagaggagaaaacggggcacaagatgcgccccggtaagat
taaagagattcgttcagccagctatcgaacggcgcagttcaacctgttgatagtacgtactaagctctcacgtactaagctctcatgtt
taacgtactaagctctcatgtttaacgaactaaaccctcatgctaacgtactaagctctcatggctaacgtactaagctctcatgtttcacgtac
taagctctcatgtttgaacaataaaattaatataaatcagcaacttaaatagcctctaaggttttaagttttataagaaaaaaagaatatataagg
cttttaaagcttttaaggtttaacggttgtggacaacaagccaggatgtaacgcactgagaagcccttagagcctctcaaagcaattttcagt
gacacaggaacacttaacggctgacagtcctaattttttgttgacactctatcattgatagagttattttaccactccctatcagtgatagagaaaa
gtgaaatgaatagttcgacaaagatcgcattggtaattacgttactcgatgccatgggggattggcttatcatgccagtcttgccaacgttatta
cgtgaatttattgcttcggaagatatcgctaaccactttggcgtattgcttgcacttttatgcgttaatgcaggttatctttgctccttggcttggaaa
aatgtctgaccgatttggtcggcgcccagtgctgttgttgtcattaataggcgcatcgctcgattacttattgctggcttttttcaagtgcgctttgg
atgctgtatttaggccgtttgctttcagggatcacaggagctactggggctgtcgcggcatcggtcattgccgataccacctcagcttctcaac
gcgtgaagtggttcggttggtttagggcgcaagttttgggcttggttttaatagcggggcctattattggttggttttgcaggagagatttcaccgcat
agtccctttttatcgctgcgttgctaaatattgtcacttttccttgtatgtttttggttccgtgaaacccaaaatacacgtgataatacagatacc
gaagtaggggttgagacgcaatcgaattcggtatacatcactttatttaaaacgatgccattgttgattatttattttcagcgcaattgatagg
ccaaattcccgcaacggtgtgggtgctatttaccgaaaatcgttttggatggaatagcatgatggttggcttttcattagcgggtcttggtcttta
cactcagtattccaagccttttggcaggaagaatagccacataaatgggcgcgaaaaacggcagtactgctcgaatttattgcagatagtag
tgcatttgcctttttagcgtttatatctgaaggttggttagatttccctgtttaatttattggctggtggtgggatcgcttacctgcattacaggga
gtgatgtctatccaaacaaagagtcatgagcaagtggctttacagggatatttggtgagccttaccaatgcaaccggtgttattggcccattac
tgtttactgttatttataatcattcactaccaatttgggatggctggatttggattattggtttagcgttttactgtattattatcctgctatcgatgac
cttcatgtaaccctcaagctcagggggataaacaggacaagtgcttagttattttcgtcaccaaatgatgttattccgcgaatataatgacc
ctcttggatcttaacattttttccctatcatttttccgtcttcatttgtcatttttccagaaaaatcgcgtcattcgactcatgtctaatccaacacg
tgtctctcggcttatccctgacaccgccgccgacagcccgcatgggacgattctatcaattcagccgcggagtctagttttatattgcagaa
tgcgagattgctggtttattataacaatataagttttcattattttcaaaaaggggggattattgtgggtttaggtaagaaattgtctgttgctgtcgc
cgcttcctttatgagttaaccatcagtctgccgggtgttcaggccgctgaggatatcaattaaccaaaaagcatacaaaagaaacgtacggcgt
ctctcatattacagccatgatatgctgcagatccctaaacagcagcaaaacgaaaaataccaagtgcctcaattcgatcaatcaacgattaa
aaatattgagtctgcaaaaggacttgatgtgtccgacagctggccgctgcaaaacgctgacggaacagtagcagaatacaacggctatcac
gttgtgtttgctcttgcgggaagcccgaaagacgctgatgacacatcaatctacatgttttatcaaaaggtcggcgacaactcaatcgacagc
tggaaaaacgcgggccgtgtcttaaagacagcgataagttgcgcgcaacgcaatgtcgaggatatcaattacaaagaatggtccggt
tctgcaaccttacatctgacggaaaaatccgtttattctacactgactattccggtaaacattacggcaaacaaagcctgacaacagcgcag
gtaaatgtgtcaaaatctgatgacacactcaaaatcaacggagtggaagatcacaaaacgatttttgacggagacgaaaaacatatcaga
acgttcagcagtttatcgatgaaggcaattatacatccgccgacaaccatacgctgagagaccctcactacgttgaagacaaaggccataaa
taccttgtattcgaagccaacacgggaacagaaaacgatggatccaaggcgaagactttatttaacaaagctactacggcggcggcacg
aacttcttccgtaaagaaagccaagagcttcagcagagcgctcaaaaaacgcgatgctgagttagcgaacggcgccctcggtatcatagagt
taaataatgattacacattgaaaaagtaatgaagcgcgtgatcacttcaaacacgtaactgatgaaatcgagcgcgcgaatgttttcaaaat
gaacggcaaatggtacttgttcactgattcacgcggttcaaaaatgacgatcgatggtattaactcaaacgatatttacatgcttggttatgtatc
aaactcttttaaccggccttacaagccgctgaacaaaacaggcttgtgctgcaaatgggtcttgatccaaacgatgtgacattcacttactct
cacttcgcagtgcccaagccaacaatgtggtttatcacaacgacattcgagggtcaagacaaacaaaaggcaacat
ttggcccaagcttcttaatcaacatcaaaggcaataaaacatccgttgtcaaaaacagcatcctggagcaaggacagctgacagtcaactaa
taacagcaaaaagaaaatgccgatacttcattggcattttctttttatttctcaacaagatgg SEQ ID NO: 111 | pfkA tmRNA allelic exchange vector
gttatcggcggtgacggttcctacatgggtgcaatgcgtctgaccgaaatgggcttcccgtgcatcggcctgccgggcactatcgacaacg
acatcaaaggcactgactacactatcggtttcttcactgcgctgagcaccgttgtagaagcgatcgaccgtctgcgtgacacctcttcttctca
ccagcgtatttccgtggtggaagtgatgggccgttattgtggcgatctgacgttggctgcggccattgccggtggctgtgaattcgttgtggtt
ccggaagttgaattcagccgtgaagacctggtaaacgaaatcaaagcgggtatcgcgaaaggtaaaaaacacgcgatcgtggcgattacc
gaacatatgtgtgatgttgacgaactggcgcatttcatcgagaagaaaccggtcgtgaaacccgcgaactgtgctgggccacatccagc
gcggtggttctccggtgccttacgaccgtattctggctccgtatgggcgctacgctatcgtcgctgctggccaggttacggcggtcgttg
cgtaggtatccagaacgaacagctggttcaccacgacatcatcgacgctatcgaaaacatgaagcgttccgttcaaaggcgactggctaga
ctgcgcgaaaaaactgtatgctgctaacgatgaaaattatgctnnngctgcataatgatttcggaaaaaggcagattccttttagcctgaaacc
gatgacagaagcaaaaatgcctgatgcgcttcgcttatcaggcctacgtgaattctgcaatttattgaatttacaaattttttgtaggtcggataag
gcgttcgcgccgcatccggcatcgataaagcgcactttgtcagcaatatgaggcggatttcttccgccttttttaattcctcaacatataccgc
aagtctatagccaatctttttttattctttaatgtttggttaaccttctggcacgctttgctcatcacaacacaacataagagagtcgggcgatgaac

| SEQUENCES |
|---|
| aagtgggcgtagggttaacattttttgctggcggcaaccagcgttatggcaaaggatattcagcttcttaacgtttcatatgatccaacgcgcg<br>aattgtacgaacagtacaacaaggcattcagcgcccactggaaacagcaaactggcgataacgtggtgatccgtcagtcccacggtggttc<br>aggcaaacaagcgacgtcggtaatcaacggtattgaagctgatgttgtcacgctggctctggcctatgacgtggacgcaattgcggaacgc<br>gggcggattgataaagagtggatcaaacgtctgccggataactccgcaccgcagttcaacctgttgatagtacgtactaagctctcatgtttc<br>acgtactaagctctcatgtttaacgtactaagctctcatgtttaacgaactaaaccctcatggctaacgtactaagctctcatggctaacgtacta<br>agctctcatgtttcacgtactaagctctcatgtttgaacaataaaattaatataaatcagcaacttaaatagcctctaaggttttaagttttataaga<br>aaaaaaagaatatataaggcttttaaagcttttaacggttgtggacaacaagccaggggatgtaacgcactgagaagcccttagagc<br>ctctcaaagcaattttcagtgacacaggaacacttaacggctgacagtcctaattttttgttgacactctatcattgatagagttatttaccactcc<br>ctatcagtgatagagaaaagtgaaatgaatagttcgacaaagatcgcattggtaattacgttactcgatgccatgggattggccttatcatgc<br>cagtcttgccaacgttattacgtgaatttattgcttcggaagatatcgctaaccactttggcgtattgcttgcactttatgcgttaatgcaggttatc<br>tttgctccttggcttggaaaatgtctgaccgatttggtcggcgcccagtgctgttgttgtcattaataggcgcatcgctggattacttattgctg<br>gctttttcaagtgcgctttggatgctgtatttaggccgttttgctttcagggatcacaggagctactggggctgtcgcggcatcggtcattgccga<br>taccacctcagcttctcaacgcgtgaagtggtcggttggttagggggcaagttttgggcttggtttaatagcggggcctattattggtggttttg<br>caggagagatttcaccgcatagtcccttttttatcgctgcgttgctaaatattgtcacttttccttgtggttatgttttggttccgtgaaaccaaaaata<br>cacgtgataatacagataccgaagtaggggttgagacgcaatcgaattcggtatacatcactttatttaaaacgatgcccattttgttgattattt<br>atttttcagcgcaattgataggccaaattcccgcaacggtgtgggtgctatttaccgaaaatcgttttggatggaatagcatgatggttggcttt<br>cattagcgggtcttggtctttttacactcagtattccaagccttgtggcaggaagaataagccactaaatggggcgaaaaaacgcagtactgc<br>tcgaatttattgcagatagtagtgcatttgccttttttagcgtttatatctgaaggttggttagatttccctgttttaattttattggctggtggtgggat<br>cgcttttacctgcattacagggagtgatgtctatccaaacaaagagtcatgagcaaggtgcttttacagggattattggtgagccttaccaatgcaa<br>ccggtgttattggccattactgtttactgttatttataatcattcactaccaatttggatggctggattttggattattggtttagcgttttactgtat<br>tattatcctgctatcgatgaccttcatgttaaccctcaagctcagggtgagtaaacaggagacaagtgcttagttatttcgtcaccaaatgatgtt<br>attccgcgaaatataatgaccctcttggatcttaacattttttcccctatcatttttccgtcttcatttgtcatttttttccagaaaaaatcgcgtcattcg<br>actcatgtctaatccaacacgtgtctctcggcttatccctgacaccgcccgccgacagcccgcatgggacgattctatcaattcagccgcgg<br>agtctagttttatattgcagaatgcgagattgcgtttattataacaatataagttttcattatttttcaaaaagggggattttattgtgggtttaggtaa<br>gaaattgtctgttgctgtcgccgcttccttttatgagtttaaccatcagtctgccgggtgttcaggccgctgaggatatcaataaccaaaaagcat<br>acaaagaaacgtacggcgtctctcatattacacgccatgatatgctgcagatcccctaaacagcagcaaaacgaaaaataccaagtgcctca<br>attcgatcaatcaacgattaaaaatattgagtctgcaaaaggacttgatgtgtccgacagctggccgctgcaaaacgctgacggaacagtag<br>cagaatacaacggctatcacgttgtgttgctcttgcgggaaagcccgaaagacgctgatgacacatcaatctacatgttttatcaaaaggtcg<br>gcgacaactcaatcgacagctggaaaaacgcgggccgtgtctttaaagacagcgataagttcgacgccaacgatccgatcctgaaagatc<br>agacgcaagaatggtccggttctgcaacctttacatctgacggaaaaatccgttattctacactgactattccggtaaacattacggcaaaca<br>aagcctgacaacagcgcaggtaaatgtgtcaaaatctgatgacacactcaaaatcaacggagtggaagatcacaaaacgatttttgacgga<br>gacggaaaaacatatcagaacgttcagcagtttatcgatgaaggcaattcgccgcacaaccatacgctgagagaccctcactacgt<br>tgaagacaaaggccataaaatccttgtattcgaagccaacacgggaacagaaaacgggtcaccaaggcgaagaatctttatttaacaaagcg<br>tactacggcggcggcacgaacttcttccgtaaagaaaagccagaagcttcagcagagcgctaaaaaacgcgatgctgagttagcgaacgg<br>cgccctcggtatcatagagttaaataatgattacacattgaaaaaagtaatgaagccgctgatcacttcaaacacggtaactgatgaaatcga<br>gcgcgcgaatgttttcaaaatgaacggcaaatggtacttgttcactgattcacgcggttcaaaaatgacgatcgatggtattaactcaaacgat<br>atttacatgcttggttatgtatcaaactctttaaccggccttaaccgaacaaaaacagggcttgtgctgcaaatgggtcttgatccaaa<br>cgatgtgacattcacttactctcacttcgcagtgccgcaagccaaaggcaacaatgtggttatcacaagctacatgacaaacagaggcttctt<br>cgaggataaaaaggcaacatttggcccaagcttcttaatcaacatcaaaggcaataaaacatccgttgtcaaaaacagcatcctggagcaa<br>ggacagctgacagtcaactaataacagcaaaaagaaaatgccgatacttcattggcattttcttttatttctcaacaagatgg SEQ ID<br>NO: 112 |
| PL.6 constitutive promoter - lambda promoter, GenBank NC_001416<br>aattcatataaaaaacatacagataaccatctgcggtgataaattatctctggcggtgttgacataaataccactggcggtgatactgagcaca<br>tcagcaggacgcactgaccaccatgaaggtg SEQ ID NO: 113 |

What is claimed is:

1. Recombinant cells capable of producing isoprene, wherein the cells:
   (i) (a) have been modified such that the activity of a YfiQ polypeptide is modulated by decreasing, attenuating, or deleting the expression of a nucleic acid encoding the YfiQ polypeptide;
   (b) comprise a nucleic acid encoding a CobB polypeptide, wherein the cells have been modified such that the activity of the CobB polypeptide is modulated by increasing the expression of the nucleic acid encoding the CobB polypeptide;
   (ii) comprise one or more nucleic acids encoding one or more polypeptides of a mevalonate (MVA) pathway: and
   (iii) comprise a heterologous nucleic acid encoding a polypeptide having isoprene synthase activity, wherein culturing of the recombinant cells in a suitable media provides for the production of isoprene.

2. The recombinant cells of claim 1, wherein the recombinant cells further comprise:
   (iv) one or more nucleic acids encoding one or more acetyltransferases selected from the group consisting of a protein acetyltransferase (Pat) polypeptide and an acetoin utilization protein AcuA (AcuA) polypeptide, wherein the activity of the one or more acetyltransferases is modulated by decreasing, attenuating, or deleting the expression of the one or more nucleic acids encoding the one or more acetyltransferases; and/or
   (v) a nucleic acid encoding a sirtuin NAD-dependent deacetylase (SrtN) polypeptide, wherein the activity of the SrtN polypeptide is modulated by increasing the expression of the nucleic acid encoding the SrtN polypeptide.

3. The recombinant cells of claim 1, wherein the heterologous nucleic acid encoding a polypeptide having isoprene synthase activity is a plant isoprene synthase polypeptide.

4. The recombinant cells of claim 3, wherein the polypeptide having isoprene synthase activity is from *Pueraria montana, Pueraria lobata, Populus tremuloides, Populus alba, Populus nigra,* or *Populus trichocarpa.*

5. The recombinant cells of claim 1, wherein the one or more polypeptides of the MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA; (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate.

6. The recombinant cells of claim 1, wherein the recombinant cells further comprise (iv) one or more heterologous nucleic acids encoding a polypeptide having phosphoketolase activity.

7. The recombinant cells of claim 1, wherein the recombinant cells further comprise (iv) one or more nucleic acids encoding one or more pentose phosphate pathway proteins, wherein the cells have been modified such that the expression of the nucleic acids encoding the pentose phosphate pathway proteins and/or the activity of the pentose phosphate pathway proteins is modulated.

8. The recombinant cells of claim 7, wherein the one or more nucleic acids encoding the pentose phosphate pathway proteins is selected from the group consisting of transketolase (tktA), transaldolase (talB), ribulose-5-phosphate-epimerase (rpe), ribose-5-phosphate epimerase (rpiA), and phosphofructokinase (pfkA).

9. The recombinant cells of claim 1, wherein the recombinant cells further comprise (iv) one or more nucleic acids encoding one or more acetate cycling proteins, wherein the cells have been modified such that the expression of the nucleic acids encoding the acetate cycling proteins and/or activity of the acetate cycling proteins is modulated.

10. The recombinant cells of claim 9, wherein the one or more nucleic acids encoding the acetate cycling proteins is selected from the group consisting of acetyl-coenzyme A synthetase (acs), acetate kinase (ackA), acetate transporter/acetate pump (actP) and phosphotransacetylase (pta).

11. The recombinant cells of claim 1, wherein the recombinant cells further comprise one or more nucleic acids encoding one or more proteins selected from the group consisting of: malic enzyme (sfcA), malic enzyme (maeB), pyruvate dehydrogenase complex repressor (pdhR), pyruvate decarboxylase (aceE), pyruvate decarboxylase (aceF), pyruvate decarboxylase (lpdA), citrate synthase (glta), acs, pta, ackA, actP, pfkA, rpe, rpiA, tkta, talB, 6-phosphogluconolactonase (pgl), phosphogluconate dehydratase (edd), and 2-keto-3-deoxygluconate 6-phosphate aldolase (eda), and wherein the cells have been modified such that the expression of the nucleic acids and/or activity of the proteins is modulated.

12. The recombinant cells of claim 1, wherein the recombinant cells are gram-positive bacterial cells, gram-negative bacterial cells, fungal cells, filamentous fungal cells, algal cells or yeast cells.

13. The recombinant cells of claim 12, wherein the recombinant cells are selected from the group consisting of *Bacillus subtilis, Streptomyces lividans, Streptomyces coelicolor, Streptomyces griseus, Escherichia coli,* and *Pantoea citrea.*

14. The recombinant cells of claim 12, wherein the recombinant cells are selected from the group consisting of *Trichoderma reesei, Aspergillus oryzae, Aspergillus niger, Saccharomyces cerevisieae* and *Yarrowia lipolytica.*

15. The recombinant cells of claim 1, wherein the isoprene production is increased relative to recombinant cells that have not been modified as in (i) (a) and (i) (b).

16. The recombinant cells of claim 15, wherein the isoprene production is increased by at least 5%, wherein the increased production of isoprene comprises an increase in: (i) titer, (ii) instantaneous yield, (iii) cumulative yield, (iv) ratio of isoprene to carbon dioxide, (v) specific productivity, or (vi) cell productivity index.

17. Recombinant cells capable of producing an isoprenoid precursor, wherein the cells:
  (i) (a) have been modified such that the activity of a YfiQ polypeptide is modulated by decreasing, attenuating, or deleting the expression of a nucleic acid encoding the YfiQ polypeptide; and
  (b) comprise a nucleic acid encoding a CobB polypeptide, wherein the cells have been modified such that the activity of the CobB polypeptide is modulated by increasing the expression of the nucleic acid encoding the CobB polypeptide; and
  (ii) comprise one or more nucleic acids encoding one or more polypeptides of a MVA pathway, wherein culturing of the recombinant cells in a suitable media provides for the production of the isoprenoid precursor.

18. Recombinant cells capable of producing an isoprenoid, wherein the cells:
  (i) (a) have been modified such that the activity of a YfiQ polypeptide is modulated by decreasing, attenuating, or deleting the expression of a nucleic acid encoding the YfiQ polypeptide; and
  (b) comprise a nucleic acid encoding a CobB polypeptide, wherein the cells have been modified such that the activity of the CobB polypeptide is modulated by increasing the expression of the nucleic acid encoding the CobB polypeptide;
  (ii) comprise one or more nucleic acids encoding one or more polypeptides of a MVA pathway; and
  (iii) comprise a heterologous nucleic acid encoding a polyprenyl pyrophosphate synthase polypeptide, wherein culturing of the recombinant cells in a suitable media provides for production of the isoprenoid.

19. A method of producing isoprene comprising: (a) culturing the recombinant cell of claim 1 under conditions suitable for producing isoprene and (b) producing isoprene.

20. The method of claim 19, further comprising (c) recovering the isoprene.

* * * * *

SEQUENCE LISTING

<160> NUMBER OF SEQ ID NOS: 113

<210> SEQ ID NO 1
<211> LENGTH: 2439
<212> TYPE: DNA
<213> ORGANISM: L. grayi

<400> SEQUENCE: 1

```
atggttaaag acattgtaat aattgatgcc ctccgtactc ccatcggtaa gtaccgcggt      60
cagctctcaa agatgacggc ggtggaattg gaaccgcag  ttacaaaggc tctgttcgag     120
aagaacgacc aggtcaaaga ccatgtagaa caagtcattt ttggcaacgt tttacaggca     180
gggaacggcc agaatcccgc ccgtcagatc gcccttaatt ctggcctgtc cgcagagata     240
ccggcttcga ctattaacca ggtgtgtggt tctggcctga agcaataag  catggcgcgc     300 caacagatcc tactcggaga agcggaagta atagtagcag gaggtatcga atccatgacg     360
aatgcgccga ttattacata tttataataaa gaagaagaca ccctctcaa  gcctgttcct     420 acgatgacct tcgatggtct gaccgacgcg tttagcggaa agattatggg tttaacagcc     480
```

-continued

| | |
|---|---|
| gaaaatgttg ccgaacagta cggcgtatca cgtgaggccc aggacgcctt tgcgtatgga | 540 |
| tcgcagatga aagcagcaaa ggcccaagaa cagggcattt tcgcagctga aatactgcct | 600 |
| cttgaaatag gggacgaagt tattactcag gacgagggg ttcgtcaaga gaccaccctc | 660 |
| gaaaaattaa gtctgcttcg gaccattttt aaagaagatg gtactgttac agcgggcaac | 720 |
| gcctcaacga tcaatgatgg cgcctcagcc gtgatcattg catcaaagga gtttgctgag | 780 |
| acaaaccaga ttccctacct tgcgatcgta catgatatta cagagatagg cattgatcca | 840 |
| tcaataatgg gcattgctcc cgtgagtgcg atcaataaac tgatcgatcg taaccaaatt | 900 |
| agcatggaag aaatcgatct ctttgaaatt aatgaggcat ttgcagcatc ctcggtggta | 960 |
| gttcaaaaag agttaagcat tcccgatgaa aagatcaata ttggcggttc cggtattgca | 1020 |
| ctaggccatc ctcttggcgc cacaggagcg cgcattgtaa ccaccctagc gcaccagttg | 1080 |
| aaacgtacac acggacgcta tggtattgcc tccctgtgca ttggcggtgg ccttggccta | 1140 |
| gcaatattaa tagaagtgcc tcaggaagat cagccggtta aaaattttta tcaattggcc | 1200 |
| cgtgaggacc gtctggctag acttcaggag caagccgtga tcagcccagc tacaaaacat | 1260 |
| gtactggcag aaatgacact tcctgaagat attgccgaca atctgatcga aaatcaaata | 1320 |
| tctgaaatgg aaatccctct tggtgtggct ttgaatctga gggtcaatga taagagttat | 1380 |
| accatcccac tagcaactga ggaaccgagt gtaatcgctg cctgtaataa tggtgcaaaa | 1440 |
| atggcaaacc acctgggcgg ttttcagtca gaattaaaag atggtttcct gcgtgggcaa | 1500 |
| attgtactta tgaacgtcaa agaacccgca actatcgagc atacgatcac ggcagagaaa | 1560 |
| gcggcaattt ttcgtgccgc agcgcagtca catccatcga ttgtgaaacg aggtgggggt | 1620 |
| ctaaaagaga tagtagtgcg tacgttcgat gatgatccga cgttcctgtc tattgatctg | 1680 |
| atagttgata ctaaagacgc aatgggcgct aacatcatta acaccattct cgagggtgta | 1740 |
| gccggctttc tgagggaaat ccttaccgaa gaaattctgt tctctatttt atctaattac | 1800 |
| gcaaccgaat caattgtgac cgccagctgt cgcataccct acgaagcact gagtaaaaaa | 1860 |
| ggtgatggta aacgaatcgc tgaaaaagtg gctgctgcat ctaaatttgc ccagttagat | 1920 |
| ccttatcgag ctgcaaccca caacaaaggt attatgaatg gtattgaggc cgtcgttttg | 1980 |
| gcctcaggaa atgacacacg ggcggtcgcg gcagccgcac atgcgtatgc ttcacgcgat | 2040 |
| cagcactatc ggggcttaag ccagtggcag gttcagaag gcgcgttaca cggggagatc | 2100 |
| agtctaccac ttgcactcgg cagcgttggc ggtgcaattg aggtcttgcc taaagcgaag | 2160 |
| gcggcattcg aaatcatggg gatcacagag gcgaaggagc tggcagaagt cacagctgcg | 2220 |
| gtagggctgg cgcaaaacct ggcggcgtta agagcgcttg ttagtgaagg aatacagcaa | 2280 |
| ggtcacatgt cgctccaggc tcgctctctt gcattatcgg taggtgctac aggcaaggaa | 2340 |
| gttgaaatcc tggccgaaaa attacagggc tctcgtatga tcaggcgaa cgctcagacc | 2400 |
| atactcgcag agatcagatc gcaaaaagtt gaattgtga | 2439 |

<210> SEQ ID NO 2
<211> LENGTH: 1158
<212> TYPE: DNA
<213> ORGANISM: L. grayi

<400> SEQUENCE: 2

| | |
|---|---|
| atgaccatga acgttggaat cgataaaatg tcattctttg ttccacctta ctttgtggac | 60 |
| atgactgatc tggcagtagc acgggatgtc gatcccaata agtttctgat tggtattggc | 120 |
| caggaccaga tggcagttaa tccgaaaacg caggatattg tgacatttgc cacaaatgct | 180 |

```
gccaaaaaca tactgtcagc tgaggacctt gataaaattg atatggtcat agtcggcacc      240
gagagtggaa tcgatgaatc caaagcgagt gccgtagtgc ttcacaggtt gctcggtatc      300
cagaagtttg ctcgctcctt tgaaatcaaa gaagcctgtt atgggggtac cgcggcttta      360
cagttcgctg taaaccacat taggaatcat cctgaatcaa aggttcttgt agttgcatca      420
gatatcgcga aatacggcct ggcttctgga ggtgaaccaa cgcaaggtgc aggcgctgtg      480
gctatgctcg tctcaactga ccctaagatc attgctttca cgacgatag cctcgcgctt      540 acacaagata tctatgactt ctggcgacca gttggacatg actatcctat ggtcgacggg      600
cctcttagta cagagaccta catccagtca tttcagaccg tatggcagga atacacaaaa      660
cggtcgcagc atgcactggc agactttgct gcccttagct ttcatatccc gtatactaaa      720
atgggcaaaa aggcgctgct tgcaatcctt gaaggcgaat cagaggaggc tcagaaccgt      780
atactagcaa aatatgaaaa agtatagcc tactccagaa aggcgggtaa cctgtatacc      840
ggtagcctgt atctaggact tatttcactt ctggaaaatg cagaagacct aaagctggt      900 gatttaatag gcctctttc ttacggttcc ggtgctgttg cggagttttt ctcaggaagg      960
ctggttgagg actatcagga acagctactt aaaacaaaac atgccgaaca gctggcccat     1020
agaaagcaac tgacaatcga ggagtacgaa acgatgttct ccgatcgctt ggacgtggac     1080
aaagacgccg aatacgaaga cacattagct tatagcattt cgtcagtccg aaacaccgta     1140
cgtgagtaca ggagttga                                                   1158

<210> SEQ ID NO 3
<211> LENGTH: 2442
<212> TYPE: DNA
<213> ORGANISM: E. faecium

<400> SEQUENCE: 3
atgaaagaag tggttatgat tgatgcggct cgcacaccca ttgggaaata cagaggtagt       60
cttagtcctt ttacagcggt ggagctgggg acactggtca cgaaagggct gctggataaa      120
acaaagctta agaaagacaa gatagaccaa gtgatattcg gcaatgtgct tcaggcagga      180
aacggacaaa acgttgcaag acaaatagcc ctgaacagtg gcttaccagt tgacgtgccg      240
gcgatgacta ttaacgaagt ttgcgggtcc ggaatgaaag cggtgatttt agcccgccag      300
ttaatacagt taggggaggc agagttggtc attgcagggg gtacggagtc aatgtcacaa      360
gcacccatgc tgaaacctta ccagtcagag accaacgaat acggagagcc gatatcatca      420
atggttaatg acgggctgac ggatgcgttt tccaatgctc acatgggtct tactgccgaa      480
aaggtggcga cccagttttc agtgtcgcgc gaggaacaag accggtacgc attgtccagc      540
caattgaaag cagcgcacgc ggttgaagcc ggggtgttct cagaagagat tattccggtt      600
aagattagcg acgaggatgt cttgagtgaa gacgaggcag taagaggcaa cagcactttg      660
gaaaaactgg gcaccttgcg gacggtgttt tctgaagagg gcacggttac cgctggcaat      720
gcttcaccgc tgaatgacgg cgctagtgtc gtgattcttg catcaaaaga atacgcggaa      780
aacaataatc tgccttacct ggcgacgata aaggaggttg cggaagttgg tatcgatcct      840
tctatcatgg gtattgcccc aataaaggcc attcaaaagt aacagatcg gtcgggcatg      900 aacctgtcca cgattgatct gttcgaaatt aatgaagcat tcgcggcatc tagcattgtt      960
gtttctcaag agctgcaatt ggacgaagaa aaagtgaata tctatggcgg ggcgatagct     1020
ttaggccatc caatcggcgc aagcggagcc cggatactga caaccttagc atacggcctc     1080
```

```
ctgcgtgagc aaaagcgtta tggtattgcg tcattatgta tcggcggtgg tcttggtctg   1140
gccgtgctgt tagaagctaa tatggagcag acccacaaag acgttcagaa gaaaaagttt   1200
taccagctta ccccctccga gcggagatcg cagcttatcg agaagaacgt tctgactcaa   1260
gaaacggcac ttattttcca ggagcagacg ttgtccgaag aactgtccga tcacatgatt   1320
gagaatcagg tctccgaagt ggaaattcca atgggaattg cacaaaattt tcagattaat   1380
ggcaagaaaa aatggattcc tatggcgact gaagaacctt cagtaatagc ggcagcatcg   1440
aacggcgcca aaatctgcgg gaacatttgc gcggaaacgc ctcagcggct tatgcgcggg   1500
cagattgtcc tgtctggcaa atcagaatat caagccgtga taaatgccgt gaatcatcgc   1560
aaagaagaac tgattctttg cgcaaacgag tcgtacccga gtattgttaa acgcggggga   1620
ggtgttcagg atatttctac gcgggagttt atgggttctt ttcacgcgta tttatcaatc   1680
gactttctgg tggacgtcaa ggacgcaatg ggggcaaaca tgatcaactc tattctcgaa   1740
agcgttgcaa ataaactgcg tgaatggttc ccggaagagg aaatactgtt ctccatcctg   1800
tcaaacttcg ctacggagtc cctggcatct gcatgttgcg agattccttt tgaaagactt   1860
ggtcgtaaca agaaaattgg tgaacagatc gccaagaaaa ttcaacaggc aggggaatat   1920
gctaagcttg acccttaccg cgcggcaacc ataacaagg ggattatgaa cggtatcgaa   1980
gccgtcgttg ccgcaacggg aaacgacaca cgggctgttt ccgcttctat tcacgcatac   2040
gccgcccgta tggcttgta ccaaggttta acggattggc agatcaaggg cgataaactg   2100
gttggtaaat taacagtccc actggctgtg gcgactgtcg gtggcgcgtc gaacatatta   2160
ccaaaagcca aagcttccct cgccatgctg gatattgatt ccgcaaaaga actggcccaa   2220
gtgatcgccg cggtaggttt agcacagaat ctggcggcgt tacgtgcatt agtgacagaa   2280
ggcattcaga aaggacacat gggcttgcaa gcacgttctt tagcgatttc gataggtgcc   2340
atcggtgagg agatagagca agtcgcgaaa aaactgcgtg aagctgaaaa aatgaatcag   2400
caaacggcaa tacagatttt agaaaaaatt cgcgagaaat ga                     2442
```

<210> SEQ ID NO 4
<211> LENGTH: 1155
<212> TYPE: DNA
<213> ORGANISM: E. faecium

<400> SEQUENCE: 4

```
atgaaaatcg gtattgaccg tctgtccttc ttcatcccga atttgtattt ggacatgact     60
gagctggcag aatcacgcgg ggatgatcca gctaaatatc atattggaat cggacaagat   120
cagatggcag tgaatcgcgc aaacgaggac atcataacac tgggtgcaaa cgctgcgagt   180
aagatcgtga cagagaaaga ccgcgagttg attgatatgg taatcgttgg cacggaatca   240
ggaattgacc actccaaagc aagcgccgtg attattcacc atctccttaa aattcagtcg   300
ttcgcccgtt ctttcgaggt aaaagaagct tgctatggcg gaactgctgc cctgcacatg   360
gcgaaggagt atgtcaaaaa tcatccggag cgtaaggtct tggtaattgc gtcagacatc   420
gcgcgttatg gtttggccag cggaggagaa gttactcaag gcgtgggggc gtagccatg   480 atgattacac aaaaccccg gattctttcg attgaagacg atagtgtttt ctctcacagag   540 gatatctatg atttctggcg gcctgattac tccgagttcc ctgtagtgga cgggcccctt   600
tcaaactcaa cgtatataga gagttttcag aaagtttgga accggcacaa ggaattgtcc   660
ggaagagggc tggaagatta tcaagctatt gcttttcaca tacccatac gaagatgggt   720 aagaaagcgc tccagagtgt tttagaccaa accgatgaag ataaccagga gcgcttaatg   780
```

```
gctagatatg aggagtctat tcgctatagc cggagaattg gtaacctgta cacaggcagc      840
ttgtaccttg gtcttacaag cttgttggaa aactctaaaa gtttacaacc gggagatcgg      900
atcggcctct tttcctatgg cagtggtgcg gtgtccgagt tctttaccgg gtatttagaa      960
gaaaattacc aagagtacct gttcgctcaa agccatcaag aaatgctgga tagccggact     1020
cggattacgg tcgatgaata cgagaccatc ttttcagaga ctctgccaga acatggtgaa     1080
tgcgccgaat atacgagcga cgtccccttt tctataacca agattgagaa cgacattcgt     1140
tattataaaa tctga                                                      1155

<210> SEQ ID NO 5
<211> LENGTH: 2448
<212> TYPE: DNA
<213> ORGANISM: E. gallinarum

<400> SEQUENCE: 5
atggaagaag tggtaattat agatgcacgt cggactccga ttggtaaaata tcacgggtcg       60 ttgaagaagt tttcagcggt ggcgctgggg acggccgtgg ctaaagacat gttcgaacgc      120
aaccagaaaa tcaaagagga gatcgcgcag gtcataattg gtaatgtctt gcaggcagga      180
aatggccaga accccgcgcg gcaagttgct cttcaatcag ggttgtccgt tgacattccc      240
gcttctacaa ttaacgaggt ttgtgggtct ggtttgaaag ctatcttgat gggcatggaa      300
caaatccaac tcggcaaagc gcaagtagtg ctggcaggcg gcattgaatc aatgacaaat      360
gcgccaagcc tgtcccacta taacaaggcg gaggatacgt atagtgtccc agtgtcgagc      420
atgacactgg atggtctgac agacgcattt tctagtaaac ctatgggatt aacagcggaa      480
aacgtcgcac agcgctacgg tatctcccgt gaggcgcaag atcaattcgc atatcaatct      540
cagatgaaag cagcaaaagc gcaggcagaa acaaaattcg ctaaggaaat tgtgccactg      600
gcgggtgaaa ctaaaaccat cacagctgac gaagggatca gatcccaaac aacgatggag      660
aaactggcaa gtctcaaacc tgttttttaaa accgatggca ctgtaaccgc agggaatgct      720
agcaccatta atgacggggc cgcccttgtg ctgcttgcta gcaaaactta ctgcgaaact      780
aatgacatac cgtaccttgc gacaatcaaa gaaattgttg aagttggaat cgatccggag      840
attatgggca tctctccgat aaaagcgata caaacattgt tacaaaatca aaaagttagc      900
ctcgaagata ttggagtttt tgaaataaat gaagcctttg ccgcaagtag catagtggtt      960
gaatctgagt tgggattaga tccggctaaa gttaaccgtt atgggggtgg tatatcctta     1020
ggtcatgcaa ttgggggcaac cggcgctcgc ctggccactt cactggtgta tcaaatgcag     1080
gagatacaag cacgttatgg tattgcgagc ctgtgcgttg gtggtggact tggactggca     1140
atgcttttag aacgtccaac tattgagaag gctaaaccga cagacaaaaa gttctatgaa     1200
ttgtcaccag ctgaacggtt gcaagagctg gaaaatcaac agaaaatcag ttctgaaact     1260
aaacagcagt tatctcagat gatgcttgcc gaggacactg caaaccattt gatagaaaat     1320
caaatatcag agattgaact cccaatgggc gtcgggatga acctgaaggt tgatgggaaa     1380
gcctatgttg tgccaatggc gacggaagag ccgtccgtca tcgcggccat gtctaatggt     1440
gccaaaatgg ccggcgaaat tcacactcag tcgaaagaac ggctgctcag aggtcagatt     1500
gttttcagcg cgaagaatcc gaatgaaatc gaacagagaa tagctgagaa ccaagctttg     1560
attttcgaac gtgccgaaca gtcctatcct tccattgtga aaagagaggg aggtctccgc     1620
cgcattgcac ttcgtcattt tcctgccgat tctcagcagg agtctgcgga ccagtccaca     1680
```

```
tttttatcag tggacctttt tgtagatgtg aaagacgcga tgggggcaaa tatcataaat    1740
gcaatacttg agggcgtcgc agccctgttt cgcgaatggt tccccaatga ggaaattctt    1800
ttttctattc tctcgaactt ggctacggag agcttagtca cggctgtttg tgaagtccca    1860
tttagtgcac ttagcaagag aggtggtgca acggtggccc agaaaattgt gcaggcgtcg    1920
ctcttcgcaa agacagaccc ataccgcgca gtgacccaca caaagggat tatgaacggt     1980 gtagaggctg ttatgcttgc cacaggcaac gacacgcgcg cagtctcagc cgcttgtcat    2040
ggatacgcag cgcgcaccgg tagctatcag ggtctgacta actggacgat tgagtcggat    2100
cgcctggtag cgagataac actgccgctg ccatcgcta cagttggagg cgctaccaaa      2160
gtgttgccca agctcaagc ggcactggag attagtgatg ttcactcttc tcaagagctt     2220
gcagccttag cggcgtcagt aggtttagta caaaatctcg cggccctgcg cgcactggtt    2280
tccgaaggta tacaaaaagg gcacatgtcc atgcaagccc ggtctctcgc aatcgcggtc    2340
ggtgctgaaa aagccgagat cgagcaggtc gccgaaaagt tgcggcagaa cccgccaatg    2400
aatcagcagc aggcgctccg ttttcttggc gagatccgcg aacaatga               2448
```

<210> SEQ ID NO 6
<211> LENGTH: 1155
<212> TYPE: DNA
<213> ORGANISM: E. gallinarum
<400> SEQUENCE: 6

```
atgaacgtcg gcattgacaa aattaatttt ttcgttccac cgtattatct ggatatggtc     60
gacctggccc acgcacgcga agtggacccg aacaaattta caattggaat tggacaggat   120
cagatggctg tgagcaaaaa gacgcacgat atcgtaacat tcgcggctag tgccgcgaag   180
gaaattttag aacctgagga cttgcaagct atagacatgg ttatagttgg taccgaatcg   240
ggcattgacg agagcaaagc atccgcggtc gttttacatc gtttgttggg cgtacaacct   300
ttcgctcgca gttttgaaat taagaagcc tgttacgggg caaccgcagg cattcagttt   360
gccaagactc atatacaagc gaacccggag agcaaggtcc tggtaattgc aagcgatata   420
gctcggtatg tcttcggtc aggtggagag cccacacaag gcgcagggc agttgctatg    480 cttctcacgg caaatcccag aatcctgacc ttcgaaaacg acaatctgat gttaacgcag   540 gatatttat acttctggag accacttggt cacgcttacc ctatggtaga tggccacctt   600
tccaatcaag tctatattga cagttttaag aaggtctggc aagcacattg cgaacgcaat   660
caagcttcta tatccgacta tgccgcgatt agttttcata ttccgtatac aaaaatgggt   720
aagaaagccc tgctcgctgt ttttgcagat gaagtggaaa ctgaacagga acgcgttatg   780
gcacggtatg aagagtctat cgtatattca cgccggatcg gcaacttgta tacgggatca   840
ttgtacctgg ggctgatatc cttattggaa acagttctc acctgtcggc gggcgaccgg   900
ataggattgt ttagttatgg gagtggcgct gtcagcgaat ttttctccgg tcgtttagtg   960
gcaggctatg aaaatcaatt gaacaaagag gcgcatacc agctcctgga tcagcgtcag  1020
aagctttcca tcgaagagta tgaggcgatt tttacagatt ccttagaaat tgatcaggat  1080
gcagcgttct cggatgacct gccatattcc atccgcgaga taaaaaacac gattcggtac  1140
tataaggaga gctga                                                    1155
```

<210> SEQ ID NO 7
<211> LENGTH: 2475
<212> TYPE: DNA
<213> ORGANISM: E. casseliflavus

<400> SEQUENCE: 7

```
atggaagaag ttgtcatcat tgacgcactg cgtactccaa taggaaagta ccacggttcg      60
ctgaaagatt acacagctgt tgaactgggg acagtagcag caaaggcgtt gctggcacga     120
aatcagcaag caaaagaaca catagcgcaa gttattattg caacgtcct gcaagccgga      180
agtgggcaga atccaggccg acaagtcagt ttacagtcag gattgtcttc tgatatcccc     240
gctagcacga tcaatgaagt gtgtggctcg ggtatgaaag cgattctgat gggtatggag     300
caaattcagc tgaacaaagc ctctgtggtc ttaacaggcg gaattgaaag catgaccaac     360
gcgccgctgt ttagttatta acaaggct gaggatcaat attcggcgcc ggttagcaca       420
atgatgcacg atggtctaac agatgctttc agttccaaac caatgggctt aaccgcagag     480
accgtcgctg agagatatgg aattacgcgt aaggaacaag atgaatttgc ttatcactct     540
caaatgaagg cggccaaagc ccaggcggcg aaaaagtttg atcaggaaat tgtaccctg      600
acggaaaaat ccggaacggt tctccaggac gaaggcatca gagccgcgac aacagtcgag     660
aagctagctg agcttaaaac ggtgttcaaa aagacggaa cagttacagc gggtaacgcc      720
tctacgataa atgatggcgc tgctatggta ttaatagcat caaaatctta ttgcgaagaa     780
caccagattc cttatctggc cgttataaag gagatcgttg aggtgggttt tgccccccgaa    840
ataatgggta tttcccccat taaggctata gacaccctgc tgaaaaatca agcactgacc     900
atagaggata taggaatatt tgagattaat gaagcctttg ctgcgagttc gattgtggta     960
gaacgcgagt tgggcctgga ccccaaaaaa gttaatcgct atggcggtgg tatatcactc    1020
ggccacgcaa ttggggcgac gggagctcgc attgcgacga ccgttgctta tcagctgaaa    1080
gatacccagg agcgctacgg tatagcttcc ttatgcgttg gtgggggtct tggattggcg    1140
atgcttctgg aaaacccatc ggccactgcc tcacaaacta attttgatga ggaatctgct    1200
tccgaaaaaa ctgagaagaa gaagttttat gcgctagctc ctaacgaacg cttagcgttt    1260
ttggaagccc aaggcgctat taccgctgct gaaaaccctgg tcttccagga gatgaccta    1320
aacaaagaga cagccaatca cttaatcgaa aaccaaatca gcgaagttga aattccttta    1380
ggcgtgggcc tgaacttaca ggtgaatggg aaagcgtata atgttcctct ggccacggag    1440
gaaccgtccg ttatcgctgc gatgtcgaat ggcgccaaaa tggctggtcc tattacaaca    1500
acaagtcagg agaggctgtt acggggtcag attgtcttca tggacgtaca ggacccagaa    1560
gcaatattag cgaaagttga atccgagcaa gctaccattt tcgcggtggc aaatgaaaca    1620
tacccgtcta tcgtgaaaag aggaggaggt ctgcgtagag tcattggcag gaatttcagt    1680
ccggccgaaa gtgacttagc cacggcgtat gtatcaattg acctgatggt agatgttaag    1740
gatgcaatgg gtgctaatat catcaatagt atcctagaag gtgttgcgga attgtttaga    1800
aaatggttcc agaagaaga aatcctgttc tcaattctct ccaatctcgc gacagaaagt     1860
ctggtaacgg cgacgtgctc agttccgttt gataaattgt ccaaaactgg gaatggtcga    1920
caagtagctg gtaaaatagt gcacgcggcg gactttgcta agatagatcc atacagagct    1980
gccacacaca ataaaggtat tatgaatggc gttgaagcgt taatcttagc caccggtaat    2040
gacacccgtg cggtgtcggc tgcatgccac ggttacgcgg cacgcaatgg gcgaatgcaa    2100
gggcttacct cttggacgat tatcgaagat cggctgatag gctctatcac attaccttg    2160
gctattgcga cagtgggggg tgccacaaaa atcttgccaa agcacaggc cgccctggcg    2220
ctaactggcg ttgagacggc gtcggaactg gccagcctgg cggcgagtgt gggattagtt    2280
```

| | |
|---|---|
| caaaatttgg ccgctttacg agcactagtg agcgagggca ttcagcaagg gcacatgagt | 2340 |
| atgcaagcta gatccctggc cattagcgta ggtgcgaaag gtactgaaat agagcaacta | 2400 |
| gctgcgaagc tgagggcagc gacgcaaatg aatcaggagc aggctcgtaa atttctgacc | 2460 |
| gaaataagaa attaa | 2475 |

<210> SEQ ID NO 8
<211> LENGTH: 1161
<212> TYPE: DNA
<213> ORGANISM: E. casseliflavus

<400> SEQUENCE: 8

| | |
|---|---|
| atgaacgttg gaattgataa atcaattttt ttcgttccgc cctatttcat tgatatggtg | 60 |
| gatctcgctc atgcaagaga agttgacccc aacaagttca ctataggaat aggccaagat | 120 |
| cagatggcag taaacaagaa aacgcaagat atcgtaacgt tcgcgatgca cgccgcgaag | 180 |
| gatattctga ctaaggaaga tttacaggcc atagatatgg taatagtggg gactgagtct | 240 |
| gggatcgacg agagcaaggc aagtgctgtc gtattgcatc ggcttttagg tattcagcct | 300 |
| tttgcgcgct cctttgaaat taaggaggca tgctatgggg ccactgccgg ccttcagttt | 360 |
| gcaaaagctc atgtgcaggc taatccccag agcaaggtcc tggtggtagc ttccgatata | 420 |
| gcacgctacg gactggcatc cggaggagaa ccgactcaag gtgtaggtgc tgtggcaatg | 480 |
| ttgatttccg ctgatccagc tatcttgcag ttagaaaatg ataatctcat gttgacccaa | 540 |
| gatatatacg attttggcg cccggtcggg catcaatatc ctatggtaga cggccatctg | 600 |
| tctaatgccg tctatataga cagctttaaa caagtctggc aagcacattg cgagaaaaac | 660 |
| caacggactg ctaaagatta tgctgcattg tcgttccata ttccgtacac gaaaatgggt | 720 |
| aagaaagctc tgttagcggt ttttgcggag gaagatgaga cagaacaaaa gcggttaatg | 780 |
| gcacgttatg aagaatcaat tgtatacagt cgtcggactg gaaatctgta tactggctca | 840 |
| ctctatctgg gcctgatttc cttactggag aatagtagca gtttacaggc gaacgatcgc | 900 |
| ataggtctgt ttagctatgg ttcaggggcc gttgcggaat ttttcagtgg cctcttggta | 960 |
| ccgggttacg agaaacaatt agcgcaagct gcccatcaag ctcttctgga cgaccggcaa | 1020 |
| aaactgacta tcgcagagta cgaagccatg tttaatgaaa ccattgatat tgatcaggac | 1080 |
| cagtcatttg aggatgactt actgtactcc atcagagaga tcaaaaacac tattcgctac | 1140 |
| tataacgagg agaatgaata a | 1161 |

<210> SEQ ID NO 9
<211> LENGTH: 815
<212> TYPE: PRT
<213> ORGANISM: E. gallinarum

<400> SEQUENCE: 9

Met Glu Glu Val Val Ile Ile Asp Ala Arg Arg Thr Pro Ile Gly Lys
1               5                   10                  15

Tyr His Gly Ser Leu Lys Lys Phe Ser Ala Val Ala Leu Gly Thr Ala
            20                  25                  30

Val Ala Lys Asp Met Phe Glu Arg Asn Gln Lys Ile Lys Glu Glu Ile
        35                  40                  45

Ala Gln Val Ile Ile Gly Asn Val Leu Gln Ala Gly Asn Gly Gln Asn
    50                  55                  60

Pro Ala Arg Gln Val Ala Leu Gln Ser Gly Leu Ser Val Asp Ile Pro
65                  70                  75                  80

```
Ala Ser Thr Ile Asn Glu Val Cys Gly Ser Gly Leu Lys Ala Ile Leu
                85                  90                  95

Met Gly Met Glu Gln Ile Gln Leu Gly Lys Ala Gln Val Val Leu Ala
        100                 105                 110

Gly Gly Ile Glu Ser Met Thr Asn Ala Pro Ser Leu Ser His Tyr Asn
        115                 120                 125

Lys Ala Glu Asp Thr Tyr Ser Val Pro Val Ser Ser Met Thr Leu Asp
    130                 135                 140

Gly Leu Thr Asp Ala Phe Ser Ser Lys Pro Met Gly Leu Thr Ala Glu
145                 150                 155                 160

Asn Val Ala Gln Arg Tyr Gly Ile Ser Arg Glu Ala Gln Asp Gln Phe
                165                 170                 175

Ala Tyr Gln Ser Gln Met Lys Ala Ala Lys Ala Gln Ala Glu Asn Lys
            180                 185                 190

Phe Ala Lys Glu Ile Val Pro Leu Ala Gly Glu Thr Lys Thr Ile Thr
        195                 200                 205

Ala Asp Glu Gly Ile Arg Ser Gln Thr Thr Met Glu Lys Leu Ala Ser
    210                 215                 220

Leu Lys Pro Val Phe Lys Thr Asp Gly Thr Val Thr Ala Gly Asn Ala
225                 230                 235                 240

Ser Thr Ile Asn Asp Gly Ala Ala Leu Val Leu Leu Ala Ser Lys Thr
                245                 250                 255

Tyr Cys Glu Thr Asn Asp Ile Pro Tyr Leu Ala Thr Ile Lys Glu Ile
            260                 265                 270

Val Glu Val Gly Ile Asp Pro Glu Ile Met Gly Ile Ser Pro Ile Lys
        275                 280                 285

Ala Ile Gln Thr Leu Leu Gln Asn Gln Lys Val Ser Leu Glu Asp Ile
    290                 295                 300

Gly Val Phe Glu Ile Asn Glu Ala Phe Ala Ala Ser Ser Ile Val Val
305                 310                 315                 320

Glu Ser Glu Leu Gly Leu Asp Pro Ala Lys Val Asn Arg Tyr Gly Gly
                325                 330                 335

Gly Ile Ser Leu Gly His Ala Ile Gly Ala Thr Gly Ala Arg Leu Ala
            340                 345                 350

Thr Ser Leu Val Tyr Gln Met Gln Glu Ile Gln Ala Arg Tyr Gly Ile
        355                 360                 365

Ala Ser Leu Cys Val Gly Gly Gly Leu Gly Leu Ala Met Leu Leu Glu
    370                 375                 380

Arg Pro Thr Ile Glu Lys Ala Lys Pro Thr Asp Lys Lys Phe Tyr Glu
385                 390                 395                 400

Leu Ser Pro Ala Glu Arg Leu Gln Glu Leu Glu Asn Gln Gln Lys Ile
                405                 410                 415

Ser Ser Glu Thr Lys Gln Gln Leu Ser Gln Met Met Leu Ala Glu Asp
            420                 425                 430

Thr Ala Asn His Leu Ile Glu Asn Gln Ile Ser Glu Ile Glu Leu Pro
        435                 440                 445

Met Gly Val Gly Met Asn Leu Lys Val Asp Gly Lys Ala Tyr Val Val
    450                 455                 460

Pro Met Ala Thr Glu Glu Pro Ser Val Ile Ala Met Ser Asn Gly
465                 470                 475                 480

Ala Lys Met Ala Gly Glu Ile His Thr Gln Ser Lys Glu Arg Leu Leu
                485                 490                 495

Arg Gly Gln Ile Val Phe Ser Ala Lys Asn Pro Asn Glu Ile Glu Gln
```

```
                   500                 505                 510
Arg Ile Ala Glu Asn Gln Ala Leu Ile Phe Glu Arg Ala Glu Gln Ser
            515                 520                 525

Tyr Pro Ser Ile Val Lys Arg Glu Gly Gly Leu Arg Arg Ile Ala Leu
            530                 535                 540

Arg His Phe Pro Ala Asp Ser Gln Gln Glu Ser Ala Asp Gln Ser Thr
545                 550                 555                 560

Phe Leu Ser Val Asp Leu Phe Val Asp Val Lys Asp Ala Met Gly Ala
                565                 570                 575

Asn Ile Ile Asn Ala Ile Leu Glu Gly Val Ala Ala Leu Phe Arg Glu
                580                 585                 590

Trp Phe Pro Asn Glu Glu Ile Leu Phe Ser Ile Leu Ser Asn Leu Ala
            595                 600                 605

Thr Glu Ser Leu Val Thr Ala Val Cys Glu Val Pro Phe Ser Ala Leu
            610                 615                 620

Ser Lys Arg Gly Gly Ala Thr Val Ala Gln Lys Ile Val Gln Ala Ser
625                 630                 635                 640

Leu Phe Ala Lys Thr Asp Pro Tyr Arg Ala Val Thr His Asn Lys Gly
                645                 650                 655

Ile Met Asn Gly Val Glu Ala Val Met Leu Ala Thr Gly Asn Asp Thr
                660                 665                 670

Arg Ala Val Ser Ala Ala Cys His Gly Tyr Ala Ala Arg Thr Gly Ser
            675                 680                 685

Tyr Gln Gly Leu Thr Asn Trp Thr Ile Glu Ser Asp Arg Leu Val Gly
            690                 695                 700

Glu Ile Thr Leu Pro Leu Ala Ile Ala Thr Val Gly Gly Ala Thr Lys
705                 710                 715                 720

Val Leu Pro Lys Ala Gln Ala Ala Leu Glu Ile Ser Asp Val His Ser
                725                 730                 735

Ser Gln Glu Leu Ala Ala Leu Ala Ala Ser Val Gly Leu Val Gln Asn
                740                 745                 750

Leu Ala Ala Leu Arg Ala Leu Val Ser Glu Gly Ile Gln Lys Gly His
            755                 760                 765

Met Ser Met Gln Ala Arg Ser Leu Ala Ile Ala Val Gly Ala Glu Lys
            770                 775                 780

Ala Glu Ile Glu Gln Val Ala Glu Lys Leu Arg Gln Asn Pro Pro Met
785                 790                 795                 800

Asn Gln Gln Gln Ala Leu Arg Phe Leu Gly Glu Ile Arg Glu Gln
                805                 810                 815

<210> SEQ ID NO 10
<211> LENGTH: 384
<212> TYPE: PRT
<213> ORGANISM: E. gallinarum

<400> SEQUENCE: 10

Met Asn Val Gly Ile Asp Lys Ile Asn Phe Phe Val Pro Pro Tyr Tyr
1               5                   10                  15

Leu Asp Met Val Asp Leu Ala His Ala Arg Glu Val Asp Pro Asn Lys
            20                  25                  30

Phe Thr Ile Gly Ile Gly Gln Asp Gln Met Ala Val Ser Lys Lys Thr
        35                  40                  45

His Asp Ile Val Thr Phe Ala Ala Ser Ala Ala Lys Glu Ile Leu Glu
    50                  55                  60
```

Pro Glu Asp Leu Gln Ala Ile Asp Met Val Ile Val Gly Thr Glu Ser
 65                  70                  75                  80

Gly Ile Asp Glu Ser Lys Ala Ser Ala Val Val Leu His Arg Leu Leu
             85                  90                  95

Gly Val Gln Pro Phe Ala Arg Ser Phe Glu Ile Lys Glu Ala Cys Tyr
        100                 105                 110

Gly Ala Thr Ala Gly Ile Gln Phe Ala Lys Thr His Ile Gln Ala Asn
    115                 120                 125

Pro Glu Ser Lys Val Leu Val Ile Ala Ser Asp Ile Ala Arg Tyr Gly
130                 135                 140

Leu Arg Ser Gly Gly Glu Pro Thr Gln Gly Ala Gly Ala Val Ala Met
145                 150                 155                 160

Leu Leu Thr Ala Asn Pro Arg Ile Leu Thr Phe Glu Asn Asp Asn Leu
                165                 170                 175

Met Leu Thr Gln Asp Ile Tyr Asp Phe Trp Arg Pro Leu Gly His Ala
            180                 185                 190

Tyr Pro Met Val Asp Gly His Leu Ser Asn Gln Val Tyr Ile Asp Ser
        195                 200                 205

Phe Lys Lys Val Trp Gln Ala His Cys Glu Arg Asn Gln Ala Ser Ile
210                 215                 220

Ser Asp Tyr Ala Ala Ile Ser Phe His Ile Pro Tyr Thr Lys Met Gly
225                 230                 235                 240

Lys Lys Ala Leu Leu Ala Val Phe Ala Asp Glu Val Glu Thr Glu Gln
                245                 250                 255

Glu Arg Val Met Ala Arg Tyr Glu Glu Ser Ile Val Tyr Ser Arg Arg
            260                 265                 270

Ile Gly Asn Leu Tyr Thr Gly Ser Leu Tyr Leu Gly Leu Ile Ser Leu
        275                 280                 285

Leu Glu Asn Ser Ser His Leu Ser Ala Gly Asp Arg Ile Gly Leu Phe
290                 295                 300

Ser Tyr Gly Ser Gly Ala Val Ser Glu Phe Phe Ser Gly Arg Leu Val
305                 310                 315                 320

Ala Gly Tyr Glu Asn Gln Leu Asn Lys Glu Ala His Thr Gln Leu Leu
                325                 330                 335

Asp Gln Arg Gln Lys Leu Ser Ile Glu Glu Tyr Glu Ala Ile Phe Thr
            340                 345                 350

Asp Ser Leu Glu Ile Asp Gln Asp Ala Ala Phe Ser Asp Asp Leu Pro
        355                 360                 365

Tyr Ser Ile Arg Glu Ile Lys Asn Thr Ile Arg Tyr Tyr Lys Glu Ser
370                 375                 380

<210> SEQ ID NO 11
<211> LENGTH: 812
<212> TYPE: PRT
<213> ORGANISM: L. grayi

<400> SEQUENCE: 11

Met Val Lys Asp Ile Val Ile Ile Asp Ala Leu Arg Thr Pro Ile Gly
1               5                   10                  15

Lys Tyr Arg Gly Gln Leu Ser Lys Met Thr Ala Val Glu Leu Gly Thr
            20                  25                  30

Ala Val Thr Lys Ala Leu Phe Glu Lys Asn Asp Gln Val Lys Asp His
        35                  40                  45

Val Glu Gln Val Ile Phe Gly Asn Val Leu Gln Ala Gly Asn Gly Gln
    50                  55                  60

Asn Pro Ala Arg Gln Ile Ala Leu Asn Ser Gly Leu Ser Ala Glu Ile
 65                  70                  75                  80

Pro Ala Ser Thr Ile Asn Gln Val Cys Gly Ser Gly Leu Lys Ala Ile
                 85                  90                  95

Ser Met Ala Arg Gln Gln Ile Leu Leu Gly Glu Ala Glu Val Ile Val
            100                 105                 110

Ala Gly Gly Ile Glu Ser Met Thr Asn Ala Pro Ser Ile Thr Tyr Tyr
            115                 120                 125

Asn Lys Glu Glu Asp Thr Leu Ser Lys Pro Val Pro Thr Met Thr Phe
            130                 135                 140

Asp Gly Leu Thr Asp Ala Phe Ser Gly Lys Ile Met Gly Leu Thr Ala
145                 150                 155                 160

Glu Asn Val Ala Glu Gln Tyr Gly Val Ser Arg Glu Ala Gln Asp Ala
                165                 170                 175

Phe Ala Tyr Gly Ser Gln Met Lys Ala Ala Lys Ala Gln Glu Gln Gly
            180                 185                 190

Ile Phe Ala Ala Glu Ile Leu Pro Leu Glu Ile Gly Asp Glu Val Ile
            195                 200                 205

Thr Gln Asp Glu Gly Val Arg Gln Glu Thr Thr Leu Glu Lys Leu Ser
210                 215                 220

Leu Leu Arg Thr Ile Phe Lys Glu Asp Gly Thr Val Thr Ala Gly Asn
225                 230                 235                 240

Ala Ser Thr Ile Asn Asp Gly Ala Ser Ala Val Ile Ile Ala Ser Lys
                245                 250                 255

Glu Phe Ala Glu Thr Asn Gln Ile Pro Tyr Leu Ala Ile His Asp
            260                 265                 270

Ile Thr Glu Ile Gly Ile Asp Pro Ser Ile Met Gly Ile Ala Pro Val
            275                 280                 285

Ser Ala Ile Asn Lys Leu Ile Asp Arg Asn Gln Ile Ser Met Glu Glu
290                 295                 300

Ile Asp Leu Phe Glu Ile Asn Glu Ala Phe Ala Ala Ser Ser Val Val
305                 310                 315                 320

Val Gln Lys Glu Leu Ser Ile Pro Asp Glu Lys Ile Asn Ile Gly Gly
                325                 330                 335

Ser Gly Ile Ala Leu Gly His Pro Leu Gly Ala Thr Gly Ala Arg Ile
            340                 345                 350

Val Thr Thr Leu Ala His Gln Leu Lys Arg Thr His Gly Arg Tyr Gly
            355                 360                 365

Ile Ala Ser Leu Cys Ile Gly Gly Gly Leu Gly Leu Ala Ile Leu Ile
            370                 375                 380

Glu Val Pro Gln Glu Asp Gln Pro Val Lys Lys Phe Tyr Gln Leu Ala
385                 390                 395                 400

Arg Glu Asp Arg Leu Ala Arg Leu Gln Glu Gln Ala Val Ile Ser Pro
                405                 410                 415

Ala Thr Lys His Val Leu Ala Glu Met Thr Leu Pro Glu Asp Ile Ala
            420                 425                 430

Asp Asn Leu Ile Glu Asn Gln Ile Ser Glu Met Glu Ile Pro Leu Gly
            435                 440                 445

Val Ala Leu Asn Leu Arg Val Asn Asp Lys Ser Tyr Thr Ile Pro Leu
            450                 455                 460

Ala Thr Glu Glu Pro Ser Val Ile Ala Ala Cys Asn Asn Gly Ala Lys
465                 470                 475                 480

Met Ala Asn His Leu Gly Gly Phe Gln Ser Glu Leu Lys Asp Gly Phe
            485                 490                 495

Leu Arg Gly Gln Ile Val Leu Met Asn Val Lys Glu Pro Ala Thr Ile
            500                 505                 510

Glu His Thr Ile Thr Ala Glu Lys Ala Ala Ile Phe Arg Ala Ala Ala
            515                 520                 525

Gln Ser His Pro Ser Ile Val Lys Arg Gly Gly Leu Lys Glu Ile
            530                 535                 540

Val Val Arg Thr Phe Asp Asp Pro Thr Phe Leu Ser Ile Asp Leu
545                 550                 555                 560

Ile Val Asp Thr Lys Asp Ala Met Gly Ala Asn Ile Ile Asn Thr Ile
            565                 570                 575

Leu Glu Gly Val Ala Gly Phe Leu Arg Glu Ile Leu Thr Glu Glu Ile
            580                 585                 590

Leu Phe Ser Ile Leu Ser Asn Tyr Ala Thr Glu Ser Ile Val Thr Ala
            595                 600                 605

Ser Cys Arg Ile Pro Tyr Glu Ala Leu Ser Lys Lys Gly Asp Gly Lys
            610                 615                 620

Arg Ile Ala Glu Lys Val Ala Ala Ser Lys Phe Ala Gln Leu Asp
625                 630                 635                 640

Pro Tyr Arg Ala Ala Thr His Asn Lys Gly Ile Met Asn Gly Ile Glu
            645                 650                 655

Ala Val Val Leu Ala Ser Gly Asn Asp Thr Arg Ala Val Ala Ala Ala
            660                 665                 670

Ala His Ala Tyr Ala Ser Arg Asp Gln His Tyr Arg Gly Leu Ser Gln
            675                 680                 685

Trp Gln Val Ala Glu Gly Ala Leu His Gly Glu Ile Ser Leu Pro Leu
            690                 695                 700

Ala Leu Gly Ser Val Gly Gly Ala Ile Glu Val Leu Pro Lys Ala Lys
705                 710                 715                 720

Ala Ala Phe Glu Ile Met Gly Ile Thr Glu Ala Lys Glu Leu Ala Glu
            725                 730                 735

Val Thr Ala Ala Val Gly Leu Ala Gln Asn Leu Ala Ala Leu Arg Ala
            740                 745                 750

Leu Val Ser Glu Gly Ile Gln Gln Gly His Met Ser Leu Gln Ala Arg
            755                 760                 765

Ser Leu Ala Leu Ser Val Gly Ala Thr Gly Lys Glu Val Glu Ile Leu
            770                 775                 780

Ala Glu Lys Leu Gln Gly Ser Arg Met Asn Gln Ala Asn Ala Gln Thr
785                 790                 795                 800

Ile Leu Ala Glu Ile Arg Ser Gln Lys Val Glu Leu
            805                 810

<210> SEQ ID NO 12
<211> LENGTH: 385
<212> TYPE: PRT
<213> ORGANISM: L. grayi

<400> SEQUENCE: 12

Met Thr Met Asn Val Gly Ile Asp Lys Met Ser Phe Phe Val Pro Pro
1               5                   10                  15

Tyr Phe Val Asp Met Thr Asp Leu Ala Val Ala Arg Asp Val Asp Pro
            20                  25                  30

Asn Lys Phe Leu Ile Gly Ile Gly Gln Asp Gln Met Ala Val Asn Pro
            35                  40                  45

Lys Thr Gln Asp Ile Val Thr Phe Ala Thr Asn Ala Ala Lys Asn Ile
 50                  55                  60

Leu Ser Ala Glu Asp Leu Asp Lys Ile Asp Met Val Ile Val Gly Thr
 65                  70                  75                  80

Glu Ser Gly Ile Asp Glu Ser Lys Ala Ser Ala Val Val Leu His Arg
                 85                  90                  95

Leu Leu Gly Ile Gln Lys Phe Ala Arg Ser Phe Glu Ile Lys Glu Ala
                100                 105                 110

Cys Tyr Gly Gly Thr Ala Ala Leu Gln Phe Ala Val Asn His Ile Arg
                115                 120                 125

Asn His Pro Glu Ser Lys Val Leu Val Val Ala Ser Asp Ile Ala Lys
                130                 135                 140

Tyr Gly Leu Ala Ser Gly Gly Glu Pro Thr Gln Gly Ala Gly Ala Val
145                 150                 155                 160

Ala Met Leu Val Ser Thr Asp Pro Lys Ile Ile Ala Phe Asn Asp Asp
                165                 170                 175

Ser Leu Ala Leu Thr Gln Asp Ile Tyr Asp Phe Trp Arg Pro Val Gly
                180                 185                 190

His Asp Tyr Pro Met Val Asp Gly Pro Leu Ser Thr Glu Thr Tyr Ile
                195                 200                 205

Gln Ser Phe Gln Thr Val Trp Gln Glu Tyr Thr Lys Arg Ser Gln His
                210                 215                 220

Ala Leu Ala Asp Phe Ala Ala Leu Ser Phe His Ile Pro Tyr Thr Lys
225                 230                 235                 240

Met Gly Lys Lys Ala Leu Leu Ala Ile Leu Glu Gly Glu Ser Glu Glu
                245                 250                 255

Ala Gln Asn Arg Ile Leu Ala Lys Tyr Glu Lys Ser Ile Ala Tyr Ser
                260                 265                 270

Arg Lys Ala Gly Asn Leu Tyr Thr Gly Ser Leu Tyr Leu Gly Leu Ile
                275                 280                 285

Ser Leu Leu Glu Asn Ala Glu Asp Leu Lys Ala Gly Asp Leu Ile Gly
290                 295                 300

Leu Phe Ser Tyr Gly Ser Gly Ala Val Ala Glu Phe Phe Ser Gly Arg
305                 310                 315                 320

Leu Val Glu Asp Tyr Gln Glu Gln Leu Leu Lys Thr Lys His Ala Glu
                325                 330                 335

Gln Leu Ala His Arg Lys Gln Leu Thr Ile Glu Glu Tyr Glu Thr Met
                340                 345                 350

Phe Ser Asp Arg Leu Asp Val Asp Lys Asp Ala Glu Tyr Glu Asp Thr
                355                 360                 365

Leu Ala Tyr Ser Ile Ser Ser Val Arg Asn Thr Val Arg Glu Tyr Arg
                370                 375                 380

Ser
385

<210> SEQ ID NO 13
<211> LENGTH: 813
<212> TYPE: PRT
<213> ORGANISM: E. faecium

<400> SEQUENCE: 13

Met Lys Glu Val Val Met Ile Asp Ala Ala Arg Thr Pro Ile Gly Lys
1                   5                   10                  15

Tyr Arg Gly Ser Leu Ser Pro Phe Thr Ala Val Glu Leu Gly Thr Leu

-continued

```
                20                  25                  30
Val Thr Lys Gly Leu Leu Asp Lys Thr Lys Leu Lys Lys Asp Lys Ile
            35                  40                  45
Asp Gln Val Ile Phe Gly Asn Val Leu Gln Ala Gly Asn Gly Gln Asn
        50                  55                  60
Val Ala Arg Gln Ile Ala Leu Asn Ser Gly Leu Pro Val Asp Val Pro
 65                 70                  75                  80
Ala Met Thr Ile Asn Glu Val Cys Gly Ser Gly Met Lys Ala Val Ile
                85                  90                  95
Leu Ala Arg Gln Leu Ile Gln Leu Gly Glu Ala Glu Leu Val Ile Ala
            100                 105                 110
Gly Gly Thr Glu Ser Met Ser Gln Ala Pro Met Leu Lys Pro Tyr Gln
        115                 120                 125
Ser Glu Thr Asn Glu Tyr Gly Glu Pro Ile Ser Ser Met Val Asn Asp
        130                 135                 140
Gly Leu Thr Asp Ala Phe Ser Asn Ala His Met Gly Leu Thr Ala Glu
145                 150                 155                 160
Lys Val Ala Thr Gln Phe Ser Val Ser Arg Glu Glu Gln Asp Arg Tyr
                165                 170                 175
Ala Leu Ser Ser Gln Leu Lys Ala Ala His Ala Val Glu Ala Gly Val
            180                 185                 190
Phe Ser Glu Glu Ile Ile Pro Val Lys Ile Ser Asp Glu Asp Val Leu
        195                 200                 205
Ser Glu Asp Glu Ala Val Arg Gly Asn Ser Thr Leu Glu Lys Leu Gly
        210                 215                 220
Thr Leu Arg Thr Val Phe Ser Glu Glu Gly Thr Val Thr Ala Gly Asn
225                 230                 235                 240
Ala Ser Pro Leu Asn Asp Gly Ala Ser Val Val Ile Leu Ala Ser Lys
                245                 250                 255
Glu Tyr Ala Glu Asn Asn Asn Leu Pro Tyr Leu Ala Thr Ile Lys Glu
            260                 265                 270
Val Ala Glu Val Gly Ile Asp Pro Ser Ile Met Gly Ile Ala Pro Ile
        275                 280                 285
Lys Ala Ile Gln Lys Leu Thr Asp Arg Ser Gly Met Asn Leu Ser Thr
        290                 295                 300
Ile Asp Leu Phe Glu Ile Asn Glu Ala Phe Ala Ala Ser Ser Ile Val
305                 310                 315                 320
Val Ser Gln Glu Leu Gln Leu Asp Glu Glu Lys Val Asn Ile Tyr Gly
                325                 330                 335
Gly Ala Ile Ala Leu Gly His Pro Ile Gly Ala Ser Gly Ala Arg Ile
            340                 345                 350
Leu Thr Thr Leu Ala Tyr Gly Leu Arg Glu Gln Lys Arg Tyr Gly
        355                 360                 365
Ile Ala Ser Leu Cys Ile Gly Gly Leu Gly Leu Ala Val Leu Leu
        370                 375                 380
Glu Ala Asn Met Glu Gln Thr His Lys Asp Val Gln Lys Lys Lys Phe
385                 390                 395                 400
Tyr Gln Leu Thr Pro Ser Glu Arg Arg Ser Gln Leu Ile Glu Lys Asn
                405                 410                 415
Val Leu Thr Gln Glu Thr Ala Leu Ile Phe Gln Glu Gln Thr Leu Ser
            420                 425                 430
Glu Glu Leu Ser Asp His Met Ile Glu Asn Gln Val Ser Glu Val Glu
        435                 440                 445
```

```
Ile Pro Met Gly Ile Ala Gln Asn Phe Gln Ile Asn Gly Lys Lys Lys
    450                 455                 460

Trp Ile Pro Met Ala Thr Glu Glu Pro Ser Val Ile Ala Ala Ala Ser
465                 470                 475                 480

Asn Gly Ala Lys Ile Cys Gly Asn Ile Cys Ala Glu Thr Pro Gln Arg
                485                 490                 495

Leu Met Arg Gly Gln Ile Val Leu Ser Gly Lys Ser Glu Tyr Gln Ala
            500                 505                 510

Val Ile Asn Ala Val Asn His Arg Lys Glu Glu Leu Ile Leu Cys Ala
            515                 520                 525

Asn Glu Ser Tyr Pro Ser Ile Val Lys Arg Gly Gly Val Gln Asp
530                 535                 540

Ile Ser Thr Arg Glu Phe Met Gly Ser Phe His Ala Tyr Leu Ser Ile
545                 550                 555                 560

Asp Phe Leu Val Asp Val Lys Asp Ala Met Gly Ala Asn Met Ile Asn
                565                 570                 575

Ser Ile Leu Glu Ser Val Ala Asn Lys Leu Arg Glu Trp Phe Pro Glu
            580                 585                 590

Glu Glu Ile Leu Phe Ser Ile Leu Ser Asn Phe Ala Thr Glu Ser Leu
        595                 600                 605

Ala Ser Ala Cys Cys Glu Ile Pro Phe Glu Arg Leu Gly Arg Asn Lys
610                 615                 620

Glu Ile Gly Glu Gln Ile Ala Lys Lys Ile Gln Gln Ala Gly Glu Tyr
625                 630                 635                 640

Ala Lys Leu Asp Pro Tyr Arg Ala Ala Thr His Asn Lys Gly Ile Met
                645                 650                 655

Asn Gly Ile Glu Ala Val Val Ala Thr Gly Asn Asp Thr Arg Ala
            660                 665                 670

Val Ser Ala Ser Ile His Ala Tyr Ala Ala Arg Asn Gly Leu Tyr Gln
            675                 680                 685

Gly Leu Thr Asp Trp Gln Ile Lys Gly Asp Lys Leu Val Gly Lys Leu
        690                 695                 700

Thr Val Pro Leu Ala Val Ala Thr Val Gly Gly Ala Ser Asn Ile Leu
705                 710                 715                 720

Pro Lys Ala Lys Ala Ser Leu Ala Met Leu Asp Ile Asp Ser Ala Lys
                725                 730                 735

Glu Leu Ala Gln Val Ile Ala Val Gly Leu Ala Gln Asn Leu Ala
            740                 745                 750

Ala Leu Arg Ala Leu Val Thr Glu Gly Ile Gln Lys Gly His Met Gly
            755                 760                 765

Leu Gln Ala Arg Ser Leu Ala Ile Ser Ile Gly Ala Ile Gly Glu Glu
        770                 775                 780

Ile Glu Gln Val Ala Lys Lys Leu Arg Glu Ala Glu Lys Met Asn Gln
785                 790                 795                 800

Gln Thr Ala Ile Gln Ile Leu Glu Lys Ile Arg Glu Lys
                805                 810
```

<210> SEQ ID NO 14
<211> LENGTH: 384
<212> TYPE: PRT
<213> ORGANISM: E. faecium

<400> SEQUENCE: 14

Met Lys Ile Gly Ile Asp Arg Leu Ser Phe Phe Ile Pro Asn Leu Tyr

```
  1               5                  10                 15
Leu Asp Met Thr Glu Leu Ala Glu Ser Arg Gly Asp Pro Ala Lys
             20                 25                 30

Tyr His Ile Gly Ile Gly Gln Asp Gln Met Ala Val Asn Arg Ala Asn
             35                 40                 45

Glu Asp Ile Ile Thr Leu Gly Ala Asn Ala Ala Ser Lys Ile Val Thr
 50                 55                 60

Glu Lys Asp Arg Glu Leu Ile Asp Met Val Ile Val Gly Thr Glu Ser
 65                 70                 75                 80

Gly Ile Asp His Ser Lys Ala Ser Ala Val Ile Ile His His Leu Leu
                 85                 90                 95

Lys Ile Gln Ser Phe Ala Arg Ser Phe Glu Val Lys Glu Ala Cys Tyr
                100                105                110

Gly Gly Thr Ala Ala Leu His Met Ala Lys Glu Tyr Val Lys Asn His
                115                120                125

Pro Glu Arg Lys Val Leu Val Ile Ala Ser Asp Ile Ala Arg Tyr Gly
                130                135                140

Leu Ala Ser Gly Gly Glu Val Thr Gln Gly Val Gly Ala Val Ala Met
145                150                155                160

Met Ile Thr Gln Asn Pro Arg Ile Leu Ser Ile Glu Asp Asp Ser Val
                165                170                175

Phe Leu Thr Glu Asp Ile Tyr Asp Phe Trp Arg Pro Asp Tyr Ser Glu
                180                185                190

Phe Pro Val Val Asp Gly Pro Leu Ser Asn Ser Thr Tyr Ile Glu Ser
                195                200                205

Phe Gln Lys Val Trp Asn Arg His Lys Glu Leu Ser Gly Arg Gly Leu
                210                215                220

Glu Asp Tyr Gln Ala Ile Ala Phe His Ile Pro Tyr Thr Lys Met Gly
225                230                235                240

Lys Lys Ala Leu Gln Ser Val Leu Asp Gln Thr Asp Glu Asp Asn Gln
                245                250                255

Glu Arg Leu Met Ala Arg Tyr Glu Glu Ser Ile Arg Tyr Ser Arg Arg
                260                265                270

Ile Gly Asn Leu Tyr Thr Gly Ser Leu Tyr Leu Gly Leu Thr Ser Leu
                275                280                285

Leu Glu Asn Ser Lys Ser Leu Gln Pro Gly Asp Arg Ile Gly Leu Phe
                290                295                300

Ser Tyr Gly Ser Gly Ala Val Ser Glu Phe Phe Thr Gly Tyr Leu Glu
305                310                315                320

Glu Asn Tyr Gln Glu Tyr Leu Phe Ala Gln Ser His Gln Glu Met Leu
                325                330                335

Asp Ser Arg Thr Arg Ile Thr Val Asp Glu Tyr Glu Thr Ile Phe Ser
                340                345                350

Glu Thr Leu Pro Glu His Gly Glu Cys Ala Glu Tyr Thr Ser Asp Val
                355                360                365

Pro Phe Ser Ile Thr Lys Ile Glu Asn Asp Ile Arg Tyr Tyr Lys Ile
                370                375                380
```

<210> SEQ ID NO 15
<211> LENGTH: 824
<212> TYPE: PRT
<213> ORGANISM: E. casseliflavus

<400> SEQUENCE: 15

```
Met Glu Glu Val Val Ile Ile Asp Ala Leu Arg Thr Pro Ile Gly Lys
1               5                   10                  15

Tyr His Gly Ser Leu Lys Asp Tyr Thr Ala Val Glu Leu Gly Thr Val
                20                  25                  30

Ala Ala Lys Ala Leu Leu Ala Arg Asn Gln Gln Ala Lys Glu His Ile
                35                  40                  45

Ala Gln Val Ile Ile Gly Asn Val Leu Gln Ala Gly Ser Gly Gln Asn
        50                  55                  60

Pro Gly Arg Gln Val Ser Leu Gln Ser Gly Leu Ser Ser Asp Ile Pro
65                  70                  75                  80

Ala Ser Thr Ile Asn Glu Val Cys Gly Ser Gly Met Lys Ala Ile Leu
                85                  90                  95

Met Gly Met Glu Gln Ile Gln Leu Asn Lys Ala Ser Val Val Leu Thr
                100                 105                 110

Gly Gly Ile Glu Ser Met Thr Asn Ala Pro Leu Phe Ser Tyr Tyr Asn
                115                 120                 125

Lys Ala Glu Asp Gln Tyr Ser Ala Pro Val Ser Thr Met Met His Asp
        130                 135                 140

Gly Leu Thr Asp Ala Phe Ser Ser Lys Pro Met Gly Leu Thr Ala Glu
145                 150                 155                 160

Thr Val Ala Glu Arg Tyr Gly Ile Thr Arg Lys Glu Gln Asp Glu Phe
                165                 170                 175

Ala Tyr His Ser Gln Met Lys Ala Ala Lys Ala Gln Ala Ala Lys Lys
                180                 185                 190

Phe Asp Gln Glu Ile Val Pro Leu Thr Glu Lys Ser Gly Thr Val Leu
                195                 200                 205

Gln Asp Glu Gly Ile Arg Ala Ala Thr Val Glu Lys Leu Ala Glu
        210                 215                 220

Leu Lys Thr Val Phe Lys Lys Asp Gly Thr Val Thr Ala Gly Asn Ala
225                 230                 235                 240

Ser Thr Ile Asn Asp Gly Ala Ala Met Val Leu Ile Ala Ser Lys Ser
                245                 250                 255

Tyr Cys Glu Glu His Gln Ile Pro Tyr Leu Ala Val Ile Lys Glu Ile
                260                 265                 270

Val Glu Val Gly Phe Ala Pro Glu Ile Met Gly Ile Ser Pro Ile Lys
                275                 280                 285

Ala Ile Asp Thr Leu Leu Lys Asn Gln Ala Leu Thr Ile Glu Asp Ile
        290                 295                 300

Gly Ile Phe Glu Ile Asn Glu Ala Phe Ala Ala Ser Ser Ile Val Val
305                 310                 315                 320

Glu Arg Glu Leu Gly Leu Asp Pro Lys Lys Val Asn Arg Tyr Gly Gly
                325                 330                 335

Gly Ile Ser Leu Gly His Ala Ile Gly Ala Thr Gly Ala Arg Ile Ala
                340                 345                 350

Thr Thr Val Ala Tyr Gln Leu Lys Asp Thr Gln Glu Arg Tyr Gly Ile
                355                 360                 365

Ala Ser Leu Cys Val Gly Gly Gly Leu Gly Leu Ala Met Leu Leu Glu
                370                 375                 380

Asn Pro Ser Ala Thr Ala Ser Gln Thr Asn Phe Asp Glu Glu Ser Ala
385                 390                 395                 400

Ser Glu Lys Thr Glu Lys Lys Lys Phe Tyr Ala Leu Ala Pro Asn Glu
                405                 410                 415

Arg Leu Ala Phe Leu Glu Ala Gln Gly Ala Ile Thr Ala Ala Glu Thr
```

```
            420                 425                 430
Leu Val Phe Gln Glu Met Thr Leu Asn Lys Glu Thr Ala Asn His Leu
            435                 440                 445
Ile Glu Asn Gln Ile Ser Glu Val Glu Ile Pro Leu Gly Val Gly Leu
        450                 455                 460
Asn Leu Gln Val Asn Gly Lys Ala Tyr Asn Val Pro Leu Ala Thr Glu
465                 470                 475                 480
Glu Pro Ser Val Ile Ala Ala Met Ser Asn Gly Ala Lys Met Ala Gly
                485                 490                 495
Pro Ile Thr Thr Thr Ser Gln Glu Arg Leu Leu Arg Gly Gln Ile Val
            500                 505                 510
Phe Met Asp Val Gln Asp Pro Glu Ala Ile Leu Ala Lys Val Glu Ser
            515                 520                 525
Glu Gln Ala Thr Ile Phe Ala Val Ala Asn Glu Thr Tyr Pro Ser Ile
        530                 535                 540
Val Lys Arg Gly Gly Gly Leu Arg Arg Val Ile Gly Arg Asn Phe Ser
545                 550                 555                 560
Pro Ala Glu Ser Asp Leu Ala Thr Ala Tyr Val Ser Ile Asp Leu Met
                565                 570                 575
Val Asp Val Lys Asp Ala Met Gly Ala Asn Ile Ile Asn Ser Ile Leu
            580                 585                 590
Glu Gly Val Ala Glu Leu Phe Arg Lys Trp Phe Pro Glu Glu Glu Ile
            595                 600                 605
Leu Phe Ser Ile Leu Ser Asn Leu Ala Thr Glu Ser Leu Val Thr Ala
        610                 615                 620
Thr Cys Ser Val Pro Phe Asp Lys Leu Ser Lys Thr Gly Asn Gly Arg
625                 630                 635                 640
Gln Val Ala Gly Lys Ile Val His Ala Ala Asp Phe Ala Lys Ile Asp
                645                 650                 655
Pro Tyr Arg Ala Ala Thr His Asn Lys Gly Ile Met Asn Gly Val Glu
            660                 665                 670
Ala Leu Ile Leu Ala Thr Gly Asn Asp Thr Arg Ala Val Ser Ala Ala
        675                 680                 685
Cys His Gly Tyr Ala Ala Arg Asn Gly Arg Met Gln Gly Leu Thr Ser
        690                 695                 700
Trp Thr Ile Ile Glu Asp Arg Leu Ile Gly Ser Ile Thr Leu Pro Leu
705                 710                 715                 720
Ala Ile Ala Thr Val Gly Gly Ala Thr Lys Ile Leu Pro Lys Ala Gln
                725                 730                 735
Ala Ala Leu Ala Leu Thr Gly Val Glu Thr Ala Ser Glu Leu Ala Ser
            740                 745                 750
Leu Ala Ala Ser Val Gly Leu Val Gln Asn Leu Ala Ala Leu Arg Ala
        755                 760                 765
Leu Val Ser Glu Gly Ile Gln Gln Gly His Met Ser Met Gln Ala Arg
        770                 775                 780
Ser Leu Ala Ile Ser Val Gly Ala Lys Gly Thr Glu Ile Glu Gln Leu
785                 790                 795                 800
Ala Ala Lys Leu Arg Ala Ala Thr Gln Met Asn Gln Glu Gln Ala Arg
                805                 810                 815
Lys Phe Leu Thr Glu Ile Arg Asn
            820

<210> SEQ ID NO 16
```

```
<211> LENGTH: 386
<212> TYPE: PRT
<213> ORGANISM: E. casseliflavus

<400> SEQUENCE: 16

Met Asn Val Gly Ile Asp Lys Ile Asn Phe Phe Val Pro Pro Tyr Phe
1               5                   10                  15

Ile Asp Met Val Asp Leu Ala His Ala Arg Glu Val Asp Pro Asn Lys
            20                  25                  30

Phe Thr Ile Gly Ile Gly Gln Asp Gln Met Ala Val Asn Lys Lys Thr
        35                  40                  45

Gln Asp Ile Val Thr Phe Ala Met His Ala Ala Lys Asp Ile Leu Thr
50                  55                  60

Lys Glu Asp Leu Gln Ala Ile Asp Met Val Ile Val Gly Thr Glu Ser
65                  70                  75                  80

Gly Ile Asp Glu Ser Lys Ala Ser Ala Val Val Leu His Arg Leu Leu
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Phe Ala Lys Ala His Val Gln Ala Asn
        115                 120                 125

Pro Gln Ser Lys Val Leu Val Val Ala Ser Asp Ile Ala Arg Tyr Gly
130                 135                 140

Leu Ala Ser Gly Gly Glu Pro Thr Gln Gly Val Gly Ala Val Ala Met
145                 150                 155                 160

Leu Ile Ser Ala Asp Pro Ala Ile Leu Gln Leu Glu Asn Asp Asn Leu
                165                 170                 175

Met Leu Thr Gln Asp Ile Tyr Asp Phe Trp Arg Pro Val Gly His Gln
            180                 185                 190

Tyr Pro Met Val Asp Gly His Leu Ser Asn Ala Val Tyr Ile Asp Ser
        195                 200                 205

Phe Lys Gln Val Trp Gln Ala His Cys Glu Lys Asn Gln Arg Thr Ala
210                 215                 220

Lys Asp Tyr Ala Ala Leu Ser Phe His Ile Pro Tyr Thr Lys Met Gly
225                 230                 235                 240

Lys Lys Ala Leu Leu Ala Val Phe Ala Glu Glu Asp Glu Thr Glu Gln
                245                 250                 255

Lys Arg Leu Met Ala Arg Tyr Glu Glu Ser Ile Val Tyr Ser Arg Arg
            260                 265                 270

Thr Gly Asn Leu Tyr Thr Gly Ser Leu Tyr Leu Gly Leu Ile Ser Leu
        275                 280                 285

Leu Glu Asn Ser Ser Ser Leu Gln Ala Asn Asp Arg Ile Gly Leu Phe
290                 295                 300

Ser Tyr Gly Ser Gly Ala Val Ala Glu Phe Phe Ser Gly Leu Leu Val
305                 310                 315                 320

Pro Gly Tyr Glu Lys Gln Leu Ala Gln Ala Ala His Gln Ala Leu Leu
                325                 330                 335

Asp Asp Arg Gln Lys Leu Thr Ile Ala Glu Tyr Glu Ala Met Phe Asn
            340                 345                 350

Glu Thr Ile Asp Ile Asp Gln Asp Gln Ser Phe Glu Asp Asp Leu Leu
        355                 360                 365

Tyr Ser Ile Arg Glu Ile Lys Asn Thr Ile Arg Tyr Tyr Asn Glu Glu
370                 375                 380

Asn Glu
```

<210> SEQ ID NO 17
<211> LENGTH: 329
<212> TYPE: PRT
<213> ORGANISM: Unknown
<220> FEATURE:
<223> OTHER INFORMATION: Streptomyces sp.

<400> SEQUENCE: 17

| Met | Thr | Asp | Val | Arg | Phe | Arg | Ile | Ile | Gly | Thr | Gly | Ala | Tyr | Val | Pro |
|---|---|---|---|---|---|---|---|---|---|---|---|---|---|---|---|
| 1 | | | | 5 | | | | | 10 | | | | | 15 | |

| Glu | Arg | Ile | Val | Ser | Asn | Asp | Glu | Val | Gly | Ala | Pro | Ala | Gly | Val | Asp |
| | | | 20 | | | | | 25 | | | | | 30 | | |

| Asp | Asp | Trp | Ile | Thr | Arg | Lys | Thr | Gly | Ile | Arg | Gln | Arg | Arg | Trp | Ala |
| | | | 35 | | | | 40 | | | | | 45 | | | |

| Ala | Asp | Asp | Gln | Ala | Thr | Ser | Asp | Leu | Ala | Thr | Ala | Ala | Gly | Arg | Ala |
| | 50 | | | | | 55 | | | | | 60 | | | | |

| Ala | Leu | Lys | Ala | Ala | Gly | Ile | Thr | Pro | Glu | Gln | Leu | Thr | Val | Ile | Ala |
| 65 | | | | | 70 | | | | | 75 | | | | | 80 |

| Val | Ala | Thr | Ser | Thr | Pro | Asp | Arg | Pro | Gln | Pro | Pro | Thr | Ala | Ala | Tyr |
| | | | | 85 | | | | | 90 | | | | | 95 | |

| Val | Gln | His | His | Leu | Gly | Ala | Thr | Gly | Thr | Ala | Ala | Phe | Asp | Val | Asn |
| | | | | 100 | | | | | 105 | | | | | 110 | |

| Ala | Val | Cys | Ser | Gly | Thr | Val | Phe | Ala | Leu | Ser | Ser | Val | Ala | Gly | Thr |
| | | | 115 | | | | | 120 | | | | | 125 | | |

| Leu | Val | Tyr | Arg | Gly | Gly | Tyr | Ala | Leu | Val | Ile | Gly | Ala | Asp | Leu | Tyr |
| | 130 | | | | | 135 | | | | | 140 | | | | |

| Ser | Arg | Ile | Leu | Asn | Pro | Ala | Asp | Arg | Lys | Thr | Val | Leu | Phe | Gly |
| 145 | | | | | 150 | | | | | 155 | | | | | 160 |

| Asp | Gly | Ala | Gly | Ala | Met | Val | Leu | Gly | Pro | Thr | Ser | Thr | Gly | Thr | Gly |
| | | | | 165 | | | | | 170 | | | | | 175 | |

| Pro | Ile | Val | Arg | Arg | Val | Ala | Leu | His | Thr | Phe | Gly | Gly | Leu | Thr | Asp |
| | | | | 180 | | | | | 185 | | | | | 190 | |

| Leu | Ile | Arg | Val | Pro | Ala | Gly | Gly | Ser | Arg | Gln | Pro | Leu | Asp | Thr | Asp |
| | | | 195 | | | | | 200 | | | | | 205 | | |

| Gly | Leu | Asp | Ala | Gly | Leu | Gln | Tyr | Phe | Ala | Met | Asp | Gly | Arg | Glu | Val |
| | 210 | | | | | 215 | | | | | 220 | | | | |

| Arg | Arg | Phe | Val | Thr | Glu | His | Leu | Pro | Gln | Leu | Ile | Lys | Gly | Phe | Leu |
| 225 | | | | | 230 | | | | | 235 | | | | | 240 |

| His | Glu | Ala | Gly | Val | Asp | Ala | Ala | Asp | Ile | Ser | His | Phe | Val | Pro | His |
| | | | | 245 | | | | | 250 | | | | | 255 | |

| Gln | Ala | Asn | Gly | Val | Met | Leu | Asp | Glu | Val | Phe | Gly | Glu | Leu | His | Leu |
| | | | 260 | | | | | 265 | | | | | 270 | | |

| Pro | Arg | Ala | Thr | Met | His | Arg | Thr | Val | Glu | Thr | Tyr | Gly | Asn | Thr | Gly |
| | | 275 | | | | | 280 | | | | | 285 | | | |

| Ala | Ala | Ser | Ile | Pro | Ile | Thr | Met | Asp | Ala | Ala | Val | Arg | Ala | Gly | Ser |
| | 290 | | | | | 295 | | | | | 300 | | | | |

| Phe | Arg | Pro | Gly | Glu | Leu | Val | Leu | Leu | Ala | Gly | Phe | Gly | Gly | Gly | Met |
| 305 | | | | | 310 | | | | | 315 | | | | | 320 |

| Ala | Ala | Ser | Phe | Ala | Leu | Ile | Glu | Trp |
| | | | 325 | | | | | |

<210> SEQ ID NO 18
<211> LENGTH: 2412
<212> TYPE: DNA

<213> ORGANISM: E. faecalis

<400> SEQUENCE: 18

| | |
|---|---|
| atgaaaacag tagttattat tgatgcatta cgaacaccaa ttggaaaata taaaggcagc | 60 |
| ttaagtcaag taagtgccgt agacttagga acacatgtta caacacaact tttaaaaaga | 120 |
| cattccacta tttctgaaga aattgatcaa gtaatctttg gaatgttttt acaagctgga | 180 |
| aatggccaaa atcccgcacg acaaatagca ataaacagcg gtttgtctca tgaaattccc | 240 |
| gcaatgacgg ttaatgaggt ctgcggatca ggaatgaagg ccgttatttt ggcgaaacaa | 300 |
| ttgattcaat taggagaagc ggaagtttta attgctggcg ggattgagaa tatgtcccaa | 360 |
| gcacctaaat tacaacgttt taattacgaa acagaaagct acgatgcgcc ttttttctagt | 420 |
| atgatgtatg atggattaac ggatgccttt agtggtcagg caatgggctt aactgctgaa | 480 |
| aatgtggccg aaaagtatca tgtaactaga gaagagcaag atcaattttc tgtacattca | 540 |
| caattaaaag cagctcaagc acaagcgaaa gggatattcg ctgacgaaat agccccatta | 600 |
| gaagtatcag gaacgcttgt ggagaaagat aagggattc gccctaattc gagcgttgag | 660 |
| aagctaggaa cgcttaaaac agttttttaaa gaagacggta ctgtaacagc agggaatgca | 720 |
| tcaaccatta tgatggggc ttctgctttg attattgctt cacaagaata tgccgaagca | 780 |
| cacggtcttc cttatttagc tattattcga gacagtgtgg aagtcggtat tgatccagcc | 840 |
| tatatgggaa tttcgccgat taaagccatt caaaaactgt tagcgcgcaa tcaacttact | 900 |
| acggaagaaa ttgatctgta tgaaatcaac gaagcatttg cagcaacttc aatcgtggtc | 960 |
| caaagagaac tggcttttacc agaggaaaag gtcaacattt atggtggcgg tatttcatta | 1020 |
| ggtcatgcga ttggtgccac aggtgctcgt ttattaacga gtttaagtta tcaattaaat | 1080 |
| caaaaagaaa agaaatatgg agtggcttct ttatgtatcg gcggtggctt aggactcgct | 1140 |
| atgctactag agagacctca gcaaaaaaaa aacagccgat tttatcaaat gagtcctgag | 1200 |
| gaacgcctgg cttctcttct taatgaaggc cagatttctg ctgatacaaa aaagaatttt | 1260 |
| gaaaatacgg ctttatcttc gcagattgcc aatcatatga ttgaaaatca atcagtgaa | 1320 |
| acagaagtgc cgatgggcgt tggcttacat ttaacagtgg acgaaactga ttatttggta | 1380 |
| ccaatggcga cagaagagcc ctcagttatt gcggctttga gtaatggtgc aaaaatagca | 1440 |
| caaggattta aaacagtgaa tcaacaacgc ttaatgcgtg gacaaatcgt tttttacgat | 1500 |
| gttgcagatc ccgagtcatt gattgataaa ctacaagtaa gagaagcgga gttttttcaa | 1560 |
| caagcagagt taagttatcc atctatcgtt aaacggggcg gcggcttaag agatttgcaa | 1620 |
| tatcgtactt ttgatgaatc atttgtatct gtcgactttt tagtagatgt taaggatgca | 1680 |
| atgggggcaa atatcgttaa cgctatgttg aaggtgtgg ccgagttgtt ccgtgaatgg | 1740 |
| tttgcggagc aaaagatttt attcagtatt ttaagtaatt atgccacgga gtcggttgtt | 1800 |
| acgatgaaaa cggctattcc agtttcacgt ttaagtaagg ggagcaatgg ccgggaaatt | 1860 |
| gctgaaaaaa ttgtttttagc ttcacgctat gcttcattag atccttatcg ggcagtcacg | 1920 |
| cataacaaag gaatcatgaa tggcattgaa gctgtagttt tagctacagg aaatgataca | 1980 |
| cgcgctgtta gcgcttcttg tcatgctttt gcggtgaagg aaggtcgcta ccaaggcttg | 2040 |
| actagttgga cgctggatgg cgaacaacta attggtgaaa tttcagttcc gcttgcttta | 2100 |
| gccacggttg gcggtgccac aaaagtctta cctaaatctc aagcagctgc tgatttgtta | 2160 |
| gcagtgacgg atgcaaaaga actaagtcga gtagtagcgg ctgttggttt ggcacaaaat | 2220 |
| ttagcggcgt tacgggcctt agtctctgaa ggaattcaaa aaggacacat ggctctacaa | 2280 |

```
gcacgttctt tagcgatgac ggtcggagct actggtaaag aagttgaggc agtcgctcaa    2340
caattaaaac gtcaaaaaac gatgaaccaa gaccgagcca tggctatttt aaatgattta    2400
agaaaacaat aa                                                        2412
```

<210> SEQ ID NO 19
<211> LENGTH: 1152
<212> TYPE: DNA
<213> ORGANISM: E. faecalis

<400> SEQUENCE: 19

```
atgacaattg ggattgataa aattagtttt tttgtgcccc cttattatat tgatatgacg      60
gcactggctg aagccagaaa tgtagaccct ggaaaatttc atattggtat tgggcaagac    120
caaatggcgg tgaacccaat cagccaagat attgtgacat ttgcagccaa tgccgcagaa    180
gcgatcttga ccaagaagat aaagaggcc attgatatgg tgattgtcgg gactgagtcc     240
agtatcgatg agtcaaaagc ggccgcagtt gtcttacatc gtttaatggg gattcaacct    300
ttcgctcgct ctttcgaaat caaggaagct tgttacggag caacagcagg cttacagtta    360
gctaagaatc acgtagcctt acatccagat aaaaaagtct tggtcgtagc ggcagatatt    420
gcaaaatatg gcttaaattc tggcggtgag cctacacaag gagctggggc ggttgcaatg    480
ttagttgcta gtgaaccgcg catttttggct ttaaaagagg ataatgtgat gctgacgcaa    540
gatatctatg acttttggcg tccaacaggc cacccgtatc ctatggtcga tggtcctttg    600
tcaaacgaaa cctacatcca atcttttgcc caagtctggg atgaacataa aaaacgaacc    660
ggtcttgatt ttgcagatta tgatgcttta gcgttccata ttccttacac aaaaatgggc    720
aaaaaagcct tattagcaaa aatctccgac caaactgaag cagaacagga acgaatttta    780
gcccgttatg aagaaagtat cgtctatagt cgtcgcgtag aaacttgta tacgggttca     840 ctttatctgg gactcatttc ccttttagaa aatgcaacga ctttaaccgc aggcaatcaa    900
attggtttat tcagttatgg ttctggtgct gtcgctgaat ttttcactgg tgaattagta    960
gctggttatc aaaatcattt acaaaaagaa actcatttag cactgctgga taatcggaca   1020
gaactttcta tcgctgaata tgaagccatg tttgcagaaa ctttagacac agacattgat   1080
caaacgttag aagatgaatt aaaatatagt atttctgcta ttaataatac cgttcgttct   1140
tatcgaaact aa                                                        1152
```

<210> SEQ ID NO 20
<211> LENGTH: 803
<212> TYPE: PRT
<213> ORGANISM: E. faecalis

<400> SEQUENCE: 20

```
Met Lys Thr Val Val Ile Ile Asp Ala Leu Arg Thr Pro Ile Gly Lys
1               5                   10                  15

Tyr Lys Gly Ser Leu Ser Gln Val Ser Ala Val Asp Leu Gly Thr His
            20                  25                  30

Val Thr Thr Gln Leu Leu Lys Arg His Ser Thr Ile Ser Glu Glu Ile
        35                  40                  45

Asp Gln Val Ile Phe Gly Asn Val Leu Gln Ala Gly Asn Gly Gln Asn
    50                  55                  60

Pro Ala Arg Gln Ile Ala Ile Asn Ser Gly Leu Ser His Glu Ile Pro
65                  70                  75                  80

Ala Met Thr Val Asn Glu Val Cys Gly Ser Gly Met Lys Ala Val Ile
```

```
                         85                  90                  95
Leu Ala Lys Gln Leu Ile Gln Leu Gly Glu Ala Glu Val Leu Ile Ala
                100                 105                 110
Gly Gly Ile Glu Asn Met Ser Gln Ala Pro Lys Leu Gln Arg Phe Asn
                115                 120                 125
Tyr Glu Thr Glu Ser Tyr Asp Ala Pro Phe Ser Ser Met Met Tyr Asp
            130                 135                 140
Gly Leu Thr Asp Ala Phe Ser Gly Gln Ala Met Gly Leu Thr Ala Glu
145                 150                 155                 160
Asn Val Ala Glu Lys Tyr His Val Thr Arg Glu Glu Gln Asp Gln Phe
                165                 170                 175
Ser Val His Ser Gln Leu Lys Ala Ala Gln Ala Gln Ala Glu Gly Ile
                180                 185                 190
Phe Ala Asp Glu Ile Ala Pro Leu Glu Val Ser Gly Thr Leu Val Glu
                195                 200                 205
Lys Asp Glu Gly Ile Arg Pro Asn Ser Ser Val Glu Lys Leu Gly Thr
            210                 215                 220
Leu Lys Thr Val Phe Lys Glu Asp Gly Thr Val Thr Ala Gly Asn Ala
225                 230                 235                 240
Ser Thr Ile Asn Asp Gly Ala Ser Ala Leu Ile Ile Ala Ser Gln Glu
                245                 250                 255
Tyr Ala Glu Ala His Gly Leu Pro Tyr Leu Ala Ile Ile Arg Asp Ser
            260                 265                 270
Val Glu Val Gly Ile Asp Pro Ala Tyr Met Gly Ile Ser Pro Ile Lys
            275                 280                 285
Ala Ile Gln Lys Leu Leu Ala Arg Asn Gln Leu Thr Thr Glu Glu Ile
            290                 295                 300
Asp Leu Tyr Glu Ile Asn Glu Ala Phe Ala Ala Thr Ser Ile Val Val
305                 310                 315                 320
Gln Arg Glu Leu Ala Leu Pro Glu Glu Lys Val Asn Ile Tyr Gly Gly
                325                 330                 335
Gly Ile Ser Leu Gly His Ala Ile Gly Ala Thr Gly Ala Arg Leu Leu
            340                 345                 350
Thr Ser Leu Ser Tyr Gln Leu Asn Gln Lys Glu Lys Lys Tyr Gly Val
            355                 360                 365
Ala Ser Leu Cys Ile Gly Gly Gly Leu Gly Leu Ala Met Leu Leu Glu
            370                 375                 380
Arg Pro Gln Gln Lys Lys Asn Ser Arg Phe Tyr Gln Met Ser Pro Glu
385                 390                 395                 400
Glu Arg Leu Ala Ser Leu Leu Asn Glu Gly Gln Ile Ser Ala Asp Thr
                405                 410                 415
Lys Lys Glu Phe Glu Asn Thr Ala Leu Ser Ser Gln Ile Ala Asn His
                420                 425                 430
Met Ile Glu Asn Gln Ile Ser Glu Thr Glu Val Pro Met Gly Val Gly
            435                 440                 445
Leu His Leu Thr Val Asp Glu Thr Asp Tyr Leu Val Pro Met Ala Thr
450                 455                 460
Glu Glu Pro Ser Val Ile Ala Ala Leu Ser Asn Gly Ala Lys Ile Ala
465                 470                 475                 480
Gln Gly Phe Lys Thr Val Asn Gln Gln Arg Leu Met Arg Gly Gln Ile
                485                 490                 495
Val Phe Tyr Asp Val Ala Asp Pro Glu Ser Leu Ile Asp Lys Leu Gln
            500                 505                 510
```

```
Val Arg Glu Ala Glu Val Phe Gln Gln Ala Glu Leu Ser Tyr Pro Ser
        515                 520                 525

Ile Val Lys Arg Gly Gly Leu Arg Asp Leu Gln Tyr Arg Thr Phe
        530                 535                 540

Asp Glu Ser Phe Val Ser Val Asp Phe Leu Val Asp Val Lys Asp Ala
545                 550                 555                 560

Met Gly Ala Asn Ile Val Asn Ala Met Leu Glu Gly Val Ala Glu Leu
                565                 570                 575

Phe Arg Glu Trp Phe Ala Glu Gln Lys Ile Leu Phe Ser Ile Leu Ser
                580                 585                 590

Asn Tyr Ala Thr Glu Ser Val Val Thr Met Lys Thr Ala Ile Pro Val
                595                 600                 605

Ser Arg Leu Ser Lys Gly Ser Asn Gly Arg Glu Ile Ala Glu Lys Ile
                610                 615                 620

Val Leu Ala Ser Arg Tyr Ala Ser Leu Asp Pro Tyr Arg Ala Val Thr
625                 630                 635                 640

His Asn Lys Gly Ile Met Asn Gly Ile Glu Ala Val Leu Ala Thr
                645                 650                 655

Gly Asn Asp Thr Arg Ala Val Ser Ala Ser Cys His Ala Phe Ala Val
                660                 665                 670

Lys Glu Gly Arg Tyr Gln Gly Leu Thr Ser Trp Thr Leu Asp Gly Glu
                675                 680                 685

Gln Leu Ile Gly Glu Ile Ser Val Pro Leu Ala Leu Ala Thr Val Gly
                690                 695                 700

Gly Ala Thr Lys Val Leu Pro Lys Ser Gln Ala Ala Asp Leu Leu
705                 710                 715                 720

Ala Val Thr Asp Ala Lys Glu Leu Ser Arg Val Val Ala Val Gly
                725                 730                 735

Leu Ala Gln Asn Leu Ala Ala Leu Arg Ala Leu Val Ser Glu Gly Ile
                740                 745                 750

Gln Lys Gly His Met Ala Leu Gln Ala Arg Ser Leu Ala Met Thr Val
                755                 760                 765

Gly Ala Thr Gly Lys Glu Val Glu Ala Val Ala Gln Gln Leu Lys Arg
                770                 775                 780

Gln Lys Thr Met Asn Gln Asp Arg Ala Met Ala Ile Leu Asn Asp Leu
785                 790                 795                 800

Arg Lys Gln

<210> SEQ ID NO 21
<211> LENGTH: 383
<212> TYPE: PRT
<213> ORGANISM: E. faecalis

<400> SEQUENCE: 21

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
                20                  25                  30

Phe His Ile Gly Ile Gly Gln Asp Gln Met Ala Val Asn Pro Ile Ser
                35                  40                  45

Gln Asp Ile Val Thr Phe Ala Ala Asn Ala Ala Glu Ala Ile Leu Thr
                50                  55                  60

Lys Glu Asp Lys Glu Ala Ile Asp Met Val Ile Val Gly Thr Glu Ser
65                  70                  75                  80
```

Ser Ile Asp Glu Ser Lys Ala Ala Val Val Leu His Arg Leu Met
            85                  90                  95

Gly Ile Gln Pro Phe Ala Arg Ser Phe Glu Ile Lys Glu Ala Cys Tyr
                100                 105                 110

Gly Ala Thr Ala Gly Leu Gln Leu Ala Lys Asn His Val Ala Leu His
            115                 120                 125

Pro Asp Lys Lys Val Leu Val Val Ala Ala Asp Ile Ala Lys Tyr Gly
130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
            165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
            195                 200                 205

Phe Ala Gln Val Trp Asp Glu His Lys Lys Arg Thr Gly Leu Asp Phe
210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
            245                 250                 255

Glu Arg Ile Leu Ala Arg Tyr Glu Glu Ser Ile Val Tyr Ser Arg Arg
            260                 265                 270

Val Gly Asn Leu Tyr Thr Gly Ser Leu Tyr Leu Gly Leu Ile Ser Leu
            275                 280                 285

Leu Glu Asn Ala Thr Thr Leu Thr Ala Gly Asn Gln Ile Gly Leu Phe
            290                 295                 300

Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
            325                 330                 335

Asp Asn Arg Thr Glu Leu Ser Ile Ala Glu Tyr Glu Ala Met Phe Ala
            340                 345                 350

Glu Thr Leu Asp Thr Asp Ile Asp Gln Thr Leu Glu Asp Glu Leu Lys
            355                 360                 365

Tyr Ser Ile Ser Ala Ile Asn Asn Thr Val Arg Ser Tyr Arg Asn
            370                 375                 380

<210> SEQ ID NO 22
<211> LENGTH: 1635
<212> TYPE: DNA
<213> ORGANISM: P. alba

<400> SEQUENCE: 22

```
atggaagctc gtcgttctgc gaactacgaa cctaacagct gggactatga ttacctgctg      60
tcctccgaca cggacgagtc catcgaagta tacaaagaca aagcgaaaaa gctggaagcc     120
gaagttcgtc gcgagattaa taacgaaaaa gcagaatttc tgaccctgct ggaactgatt     180
gacaacgtcc agcgcctggg cctgggttac cgtttcgagt ctgatatccg tggtgcgctg     240
gatcgcttcg tttcctccgg cggcttcgat gcggtaacca agacttccct gcacggtacg     300
gcactgtctt tccgtctgct gcgtcaacac ggttttgagg tttctcagga agcgttcagc     360
ggcttcaaag accaaaacgg caacttcctg gagaacctga aggaagatat caaagctatc     420
```

-continued

```
ctgagcctgt acgaggccag cttcctggct ctggaaggcg aaaacatcct ggacgaggcg      480
aaggttttcg caatctctca tctgaaagaa ctgtctgaag aaaagatcgg taaagagctg      540
gcagaacagg tgaaccatgc actggaactg ccactgcatc gccgtactca gcgtctggaa      600
gcagtatggt ctatcgaggc ctaccgtaaa aaggaggacg cgaatcaggt tctgctggag      660
ctggcaattc tggattacaa catgatccag tctgtatacc agcgtgatct gcgtgaaacg      720
tcccgttggt ggcgtcgtgt gggtctggcg accaaactgc actttgctcg tgaccgcctg      780
attgagagct tctactgggc cgtgggtgta gcattcgaac cgcaatactc cgactgccgt      840
aactccgtcg caaaaatgtt ttctttcgta accattatcg acgatatcta cgatgtatac      900
ggcaccctgg acgaactgga gctgtttact gatgcagttg agcgttggga cgtaaacgcc      960
atcaacgacc tgccggatta catgaaactg tgctttctgg ctctgtataa cactattaac     1020
gaaatcgcct acgacaacct gaaagataaa ggtgagaaca tcctgccgta tctgaccaaa     1080
gcctgggctg acctgtgcaa cgcttttcct caagaagcca gtggctgta  caacaaatct     1140 actccgacct ttgacgacta cttcggcaac gcatggaaat cctcttctgg cccgctgcaa     1200
ctggtgttcg cttacttcgc tgtcgtgcag aacattaaaa aggaagagat cgaaaacctg     1260
caaaaatacc atgacaccat ctctcgtcct tcccatatct tccgtctgtg caatgacctg     1320
gctagcgcgt ctgcggaaat tgcgcgtggt gaaaccgcaa atagcgtttc ttgttacatg     1380
cgcactaaag gtatctccga agaactggct accgaaagcg tgatgaatct gatcgatgaa     1440
acctggaaaa agatgaacaa ggaaaaactg ggtggtagcc tgttcgcgaa accgttcgtg     1500
gaaaccgcga tcaacctggc acgtcaatct cactgcactt atcataacgg cgacgcgcat     1560
acctctccgg atgagctgac ccgcaaacgc gttctgtctg taatcactga accgattctg     1620
ccgtttgaac gctaa                                                      1635
```

<210> SEQ ID NO 23
<211> LENGTH: 899
<212> TYPE: DNA
<213> ORGANISM: E. coli

<400> SEQUENCE: 23

```
tggactttcc gcagcaactc gaagcctgcg ttaagcaggc caaccaggcg ctgagccgtt       60
ttatcgcccc actgcccttt cagaacactc ccgtggtcga aaccatgcag tatggcgcat      120
tattaggtgg taagcgcctg cgaccttttcc tggtttatgc caccggtcat atgtttggcg     180
ttagcacaaa cacgctggac gcaccgctg ctgccgtaga gtgtatccac gcttactcat       240
taattcatga tgatttaccg gcgatggatg atgacgatct cgccgcggt ttgccgacct       300 gccatgtgaa gtttggcgaa gcaaacgcga ttctcgctgg cgacgcttta caaacgctgg     360
cgttctcgat tctaagcgat gccgatatgc cggaagtgtc ggatcgcgac agaatttcga     420
tgatttctga actggcgagc gccagcgta  ttgccggaat gtgcggtggt caggcactag     480
atttagacgc ggaaggcaaa cacgtacctc tggacgcgct tgagcgtatt catcgtcata     540
aaaccggcgc attgattcgc gccgccgttc gccttggtgc attaagcgcc ggagataaag     600
ggcgtcgtgc tctgccagta ctcgacaagt acgcagagag catcggcctt gccttccagg     660
ttcaagatga catcctggat gtggtaggag atactgcaac gttgggaaaa cgccagggtg     720
ccgaccagca acttggtaaa agtacctacc ctgcacttct gggtcttgag caagcccgga     780
agaaagcccg ggatctgatc gacgatgccc gtcagtcgct gaaacaactg gctgaacagt     840
```
cactcgatac ctcggcactg gaagcgctag cggactacat catccagcgt aataaataa    899

<210> SEQ ID NO 24
<211> LENGTH: 544
<212> TYPE: PRT
<213> ORGANISM: P. alba

<400> SEQUENCE: 24

```
Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

Leu His Gly Thr Ala Leu Ser Phe Arg Leu Leu Arg Gln His Gly Phe
            100                 105                 110

Glu Val Ser Gln Glu Ala Phe Ser Gly Phe Lys Asp Gln Asn Gly Asn
        115                 120                 125

Phe Leu Glu Asn Leu Lys Glu Asp Ile Lys Ala Ile Leu Ser Leu Tyr
    130                 135                 140

Glu Ala Ser Phe Leu Ala Leu Glu Gly Glu Asn Ile Leu Asp Glu Ala
145                 150                 155                 160

Lys Val Phe Ala Ile Ser His Leu Lys Glu Leu Ser Glu Glu Lys Ile
                165                 170                 175

Gly Lys Glu Leu Ala Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Gln Val Leu Leu Glu Leu Ala Ile Leu
    210                 215                 220

Asp Tyr Asn Met Ile Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Asn Ser Val Ala Lys Met Phe Ser
        275                 280                 285

Phe Val Thr Ile Ile Asp Asp Ile Tyr Asp Val Tyr Gly Thr Leu Asp
    290                 295                 300

Glu Leu Glu Leu Phe Thr Asp Ala Val Glu Arg Trp Asp Val Asn Ala
305                 310                 315                 320

Ile Asn Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Asp Lys Gly Glu
            340                 345                 350

Asn Ile Leu Pro Tyr Leu Thr Lys Ala Trp Ala Asp Leu Cys Asn Ala
        355                 360                 365
```

```
Phe Leu Gln Glu Ala Lys Trp Leu Tyr Asn Lys Ser Thr Pro Thr Phe
    370                 375                 380

Asp Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415

Ile Glu Asn Leu Gln Lys Tyr His Asp Thr Ile Ser Arg Pro Ser His
                420                 425                 430

Ile Phe Arg Leu Cys Asn Asp Leu Ala Ser Ala Ser Ala Glu Ile Ala
            435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Gly Ser Leu Phe Ala
                485                 490                 495

Lys Pro Phe Val Glu Thr Ala Ile Asn Leu Ala Arg Gln Ser His Cys
                500                 505                 510

Thr Tyr His Asn Gly Asp Ala His Thr Ser Pro Asp Glu Leu Thr Arg
            515                 520                 525

Lys Arg Val Leu Ser Val Ile Thr Glu Pro Ile Leu Pro Phe Glu Arg
    530                 535                 540

<210> SEQ ID NO 25
<211> LENGTH: 1641
<212> TYPE: DNA
<213> ORGANISM: Artificial sequence
<220> FEATURE:
<223> OTHER INFORMATION: Synthetic construct

<400> SEQUENCE: 25
atgagcctga ccgaagaaaa accgattcgt ccgattgcaa attttccgcc tagcatttgg      60
ggtgatcagt ttctgattta tgagaaacag gttgaacagg gcgttgagca gattgttaat     120
gatctgaaaa agaagttcg ccagctgctg aaagaagcac tggatattcc gatgaaacat      180
gccaatctgc tgaaactgat tgatgaaatt cagcgtctgg gtatcccgta tcatttgaa     240 cgtgaaattg atcatgccct gcagtgcatt tatgaaacct atggtgataa ttggaatggt     300
gatcgtagca gcctgtggtt tcgtctgatg cgtaaacagg ttattatgt tacctgcgac     360 gtgtttaaca actataaaga taaaaacggt gcctttaaac agagcctggc aaatgatgtt     420
gaaggtctgc tggaactgta tgaagcaacc agcatgcgtg ttccgggtga attattctg     480 gaagatgcac tgggttttac ccgtagccgt ctgagcatga tgaccaaaga tgcatttagc     540
accaatccgg cactgtttac cgaaatccag cgtgcactga acagccgct gtggaaacgt     600 ctgcctcgta ttgaagcagc acagtatatt ccgttttatc agcagcagga tagccataac     660
aaaaccctgc tgaaactggc aaaactggaa tttaatctgc tgcagagcct gcataaagaa     720
gaactgagcc acgtttgtaa atggtggaaa gccttcgaca tcaaaaaaaa cgcaccgtgt     780
ctgcgtgatc gtattgttga atgttatttt tggggtctgg gtagcggttt tgaaccgcag     840
tatagccgtg cacgtgtgtt ttttaccaaa gcagttgcag ttattaccct gatcgatgat     900
acctatgacg catatggcac ctatgaggaa ctgaaaatct ttaccgaagc cgttgaacgt     960
tggagcatta cctgtctgga tacccctgccg gaatatatga aaccgatcta taaactgttc    1020
atggacacct ataccgagat ggaagaattt ctggcaaaag aaggtcgtac cgacctgttt    1080
```

```
aattgcggta aagaatttgt gaaagaattc gtgcgtaacc tgatggttga agcaaaatgg   1140
gccaatgaag gtcatattcc gaccaccgaa gaacatgatc cggttgtgat tattaccggt   1200
ggtgcaaacc tgctgaccac cacctgttat ctgggtatga gcgatatttt caccaaagaa   1260
agcgttgaat gggcagttag cgcaccgcct ctgtttcgtt atagcggtat tctgggtcgt   1320
cgtctgaacg atctgatgac ccataaagca gaacaagaac gtaaacatag cagcagcagc   1380
ctggaaagct atatgaaaga atataacgtg aacgaagagt atgcacagac cctgatttac   1440
aaagaagttg aggacgtttg gaaagatatc aaccgtgaat atctgaccac gaaaaacatt   1500
ccgcgtccgc tgctgatggc agttatttat ctgtgtcagt tcctggaagt tcagtatgca   1560
ggtaaagata actttacgcg tatgggcgac gaatataaac atctgattaa aagcctgctg   1620
gtgtatccga tgagcattta a                                             1641
```

```
<210> SEQ ID NO 26
<211> LENGTH: 1734
<212> TYPE: DNA
<213> ORGANISM: Artificial sequence
<220> FEATURE:
<223> OTHER INFORMATION: Synthetic construct

<400> SEQUENCE: 26
atgagcaccc tgccgattag cagcgttagc tttagcagca gcaccagtcc gctggttgtt     60
gatgataaag ttagcaccaa accggatgtt attcgtcaca ccatgaactt taatgcaagc    120
atttggggtg atcagtttct gacctatgat gaaccggaag atctggtgat gaaaaaacag    180
ctggttgaag aactgaaaga agaagttaaa aaagagctga tcaccatcaa aggtagcaat    240
gaaccgatgc agcatgttaa actgattgaa ctgatcgatg ccgttcagcg tctgggtatt    300
gcatatcatt ttgaagaaga atcgaagaa gccctgcagc atattcatgt tacctatggt    360
gaacagtggg tggataaaga aaatctgcag agcattagcc tgtggtttcg tctgctgcgt    420
cagcagggtt ttaatgttag cagcggtgtg tttaaagatt ttatggacga gaaaggcaaa    480
ttcaaagaaa gcctgtgtaa tgatgcacag ggtattctgg cactgtatga agcagcattt    540
atgcgtgttg aagatgaaac cattctggat aatgcactgg aatttaccaa agtgcacctg    600
gatatcattg caaaagatcc gagctgtgat agcagcctgc gtacccagat tcatcaggca    660
ctgaaacagc cgctgcgtcg tcgtctggca cgcattgaag cactgcatta tgccgatt     720 tatcagcaag aaaccagcca taatgaagat ctgctgaaac tggcaaaact ggatttagc    780 gttctgcagt ccatgcacaa aaaagaactg agccatattt gtaaatggtg aaagatctg    840 gatctgcaga ataaactgcc gtatgttcgt gatcgtgttg tggaaggtta ttttttggatt   900 ctgagcatct attatgaacc gcagcatgca cgtacccgta tgtttctgat gaaaccctgt    960
atgtggctgg ttgtgctgga tgatacgttt gataattatg gcacctacga ggaactggaa   1020
atctttaccc aggcagttga acgttggagc attagttgtc tggatatgct gccggaatac   1080
atgaaactga tttatcaaga actggtgaac ctgcacgttg aaatggaaga agtctgggc    1140 aaaggtggta aaacattag caatagtctg tgtcagggtc gttggcagaa agaactgggt   1200
agtcagatta ccctggttga aaccaaaatg gcaaaacgtg tgttcatgc ccagccgctg    1260 gaagagtata tgagcgttag catggttacc ggcacctatg gtctgatgat tgcacgtagc   1320
tatgttggtc gtggtgatat tgttaccgaa gatacccttta aatgggtgag cagctatccg   1380
cctattatca aagcaagctg tgttattgtt cgcctgatgg atgatattgt gagccacaaa   1440
gaagaacaag aacgcggtca tgttgccagc agcattgaat gttatagcaa agaaagtggt   1500
```

```
gcaagcgaag aagaagcctg cgaatatatc agccgtaaag tggaagatgc ctggaaagtt    1560
attaatcgtg aaagcctgcg tccgaccgca gttccgtttc cgctgctgat gcctgcaatt    1620
aacctggcac gtatgtgtga agttctgtat agcgttaatg atggttttac ccatgccgaa    1680
ggtgatatga atcctatat gaaaagcttc ttcgtgcatc cgatggttgt ttaa           1734
```

<210> SEQ ID NO 27
<211> LENGTH: 8719
<212> TYPE: DNA
<213> ORGANISM: Artificial sequence
<220> FEATURE:
<223> OTHER INFORMATION: Synthetic construct

<400> SEQUENCE: 27

```
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttaa caatttatca     180
gacaatctgt gtgggcactc gaccggaatt atcgattaac tttattatta aaaattaaag     240
aggtatatat taatgtatcg attaaataag gaggaataaa ccatggaaga gtggtaatt      300 atagatgcac gtcggactcc gattggtaaa tatcacgggt cgttgaagaa gttttcagcg     360
gtggcgctgg ggacggccgt ggctaaagac atgttcgaac gcaaccagaa atcaaagag      420 gagatcgcgc aggtcataat tggtaatgtc ttgcaggcag gaaatggcca gaaccccgcg     480
cggcaagttg ctcttcaatc agggttgtcc gttgacattc ccgcttctac aattaacgag     540
gtttgtgggt ctggtttgaa agctatcttg atgggcatgg aacaaatcca actcggcaaa     600
gcgcaagtag tgctggcagg cggcattgaa tcaatgacaa atgcgccaag cctgtcccac     660
tataacaagg cggaggatac gtatagtgtc ccagtgtcga gcatgacact ggatggtctg     720
acagacgcat tttctagtaa acctatggga ttaacagcgg aaaacgtcgc acagcgctac     780
ggtatctccc gtgaggcgca agatcaattc gcatatcaat ctcagatgaa agcagcaaaa     840
gcgcaggcag aaaacaaatt cgctaaggaa attgtgccac tggcgggtga aactaaaaacc    900 atcacagctg acgaagggat cagatcccaa acaacgatgg agaaactggc aagtctcaaa     960
cctgttttta aaaccgatgg cactgtaacc gcagggaatg ctagcaccat taatgacggg    1020
gccgcccttg tgctgcttgc tagcaaaact tactgcgaaa ctaatgacat accgtacctt    1080
gcgacaatca agaaattgt tgaagttgga atcgatccgg agattatggg catctctccg     1140
ataaaagcga tacaaacatt gttacaaaat caaaagttta gcctcgaaga tattggagtt    1200
tttgaaataa atgaagcctt tgccgcaagt agcatagtgg ttgaatctga gttgggatta    1260
gatccggcta aagttaaccg ttatgggggt ggtatatcct taggtcatgc aattgggca     1320 accggcgctc gcctggccac ttcactggtg tatcaaatgc aggagataca agcacgttat    1380
ggtattgcga gcctgtgcgt tggtggtgga cttggactgg caatgcttt tagaacgtcca    1440 actattgaga aggctaaacc gacagacaaa aagttctatg aattgtcacc agctgaacgg    1500
ttgcaagagc tggaaaatca acagaaaatc agttctgaaa ctaaacagca gttatctcag    1560
atgatgcttg ccgaggacac tgcaaaccat ttgatagaaa atcaaatatc agagattgaa    1620
ctcccaatgg gcgtcgggat gaacctgaag gttgatggga agcctatgt tgtgccaatg    1680 gcgacggaag agccgtccgt catcgcggcc atgtctaatg gtgccaaaat ggccggcgaa    1740
attcacactc agtcgaaaga acggctgctc agaggtcaga ttgttttcag cgcgaagaat   1800
```

```
ccgaatgaaa tcgaacagag aatagctgag aaccaagctt tgattttcga acgtgccgaa   1860
cagtcctatc cttccattgt gaaaagagag ggaggtctcc gccgcattgc acttcgtcat   1920
tttcctgccg attctcagca ggagtctgcg gaccagtcca cattttatc agtggacctt    1980 tttgtagatg tgaaagacgc gatggggggca aatatcataa atgcaatact tgagggcgtc  2040
gcagccctgt ttcgcgaatg gttccccaat gaggaaattc ttttttctat tctctcgaac   2100
ttggctacgg agagcttagt cacggctgtt tgtgaagtcc catttagtgc acttagcaag   2160
agaggtggtg caacggtggc ccagaaaatt gtgcaggcgt cgctcttcgc aaagacagac   2220
ccataccgcg cagtgaccca caacaaaggg attatgaacg gtgtagaggc tgttatgctt   2280
gccacaggca acgacacgcg cgcagtctca gccgcttgtc atggatacgc agcgcgcacc   2340
ggtagctatc agggtctgac taactggacg attgagtcgg atcgcctggt aggcgagata   2400
acactgccgc tggccatcgc tacagttgga ggcgctacca aagtgttgcc caaagctcaa   2460
gcggcactgg agattagtga tgttcactct tctcaagagc ttgcagcctt agcggcgtca   2520
gtaggtttag tacaaaatct cgcggccctg cgcgcactgg tttccgaagg tatacaaaaa   2580
gggcacatgt ccatgcaagc ccggtctctc gcaatcgcgg tcggtgctga aaaagccgag   2640
atcgagcagg tcgccgaaaa gttgcggcag aacccgccaa tgaatcagca gcaggcgctc   2700
cgttttcttg gcgagatccg cgaacaatga tctagacgca ctaggaggat ataccaatga   2760
acgtcggcat tgacaaaatt aatttttcg ttccaccgta ttatctggat atggtcgacc    2820
tggcccacgc acgcgaagtg gacccgaaca aatttacaat tggaattgga caggatcaga   2880
tggctgtgag caaaaagacg cacgatatcg taacattcgc ggctagtgcc gcgaaggaaa   2940
ttttagaacc tgaggacttg caagctatag acatggttat agttggtacc gaatcgggca   3000
ttgacgagag caaagcatcc gcggtcgttt tacatcgttt gttgggcgta caaccttcg    3060 ctcgcagttt tgaaattaaa gaagcctgtt acggggcaac cgcaggcatt cagtttgcca   3120
agactcatat acaagcgaac ccggagagca aggtcctggt aattgcaagc gatatagctc   3180
ggtatggtct tcggtcaggt ggagagccca cacaaggcgc aggggcagtt gctatgcttc   3240
tcacggcaaa tcccagaatc ctgaccttcg aaaacgacaa tctgatgtta acgcaggata   3300
tttatgactt ctggagacca cttggtcacg cttaccctat ggtagatggc cacctttcca   3360
atcaagtcta tattgacagt tttaagaagg tctggcaagc acattgcgaa cgcaatcaag   3420
cttctatatc cgactatgcc gcgattagtt ttcatattcc gtatacaaaa atgggtaaga   3480
aagccctgct cgctgttttt gcagatgaag tggaaactga acaggaacgc gttatggcac   3540
ggtatgaaga gtctatcgta tattcacgcc ggatcggcaa cttgtatacg ggatcattgt   3600
acctggggct gatatcctta ttggaaaaca gttctcacct gtcggcgggc gaccggatag   3660
gattgtttag ttatgggagt ggcgctgtca gcgaattttt ctccggtcgt ttagtggcag   3720
gctatgaaaa tcaattgaac aaagaggcgc atacccagct cctggatcag cgtcagaagc   3780
tttccatcga agagtatgag gcgatttta cagattcctt agaaattgat caggatgcag    3840
cgttctcgga tgacctgcca tattccatcc gcgagataaa aaacacgatt cggtactata   3900
aggagagctg actgcagctg gtaccatatg ggaattcgaa gctgggccc gaacaaaaac    3960 tcatctcaga agaggatctg aatagcgccg tcgaccatca tcatcatcat cattgagttt   4020
aaacggtctc cagcttggct gttttggcgg atgagagaag attttcagcc tgatacagat   4080
taaatcagaa cgcagaagcg gtctgataaa acagaatttg cctggcggca gtagcgcggt   4140
ggtcccacct gacccccatgc cgaactcaga agtgaaacgc cgtagcgccg atggtagtgt   4200
```

-continued

```
ggggtctccc catgcgagag tagggaactg ccaggcatca aataaaacga aaggctcagt    4260
cgaaagactg ggcctttcgt tttatctgtt gtttgtcggt gaacgctctc ctgagtagga    4320
caaatccgcc gggagcggat ttgaacgttg cgaagcaacg gcccggaggg tggcgggcag    4380
gacgcccgcc ataaactgcc aggcatcaaa ttaagcagaa ggccatcctg acggatggcc    4440 ttttgcgtt tctacaaact cttttttgttt attttctaa atacattcaa atatgtatcc    4500
gctcatgaga caataaccct gataaatgct tcaataatct ggcgtaatag cgaagaggcc    4560
cgcaccgatc gcccttccca acagttgcgc agcctgaatg gcgaatggcg cctgatgcgg    4620
tattttctcc ttacgcatct gtgcggtatt tcacaccgca tatggtgcac tctcagtaca    4680
atctgctctg atgccgcata gttaagccag ccccgacacc cgccaacacc cgctgacgag    4740
cttagtaaag ccctcgctag attttaatgc ggatgttgcg attacttcgc caactattgc    4800
gataacaaga aaaagccagc ctttcatgat atatctccca atttgtgtag ggcttattat    4860
gcacgcttaa aaataataaa agcagacttg acctgatagt ttggctgtga caattatgt     4920 gcttagtgca tctaacgctt gagttaagcc gcgccgcgaa gcggcgtcgg cttgaacgaa    4980
ttgttagaca ttatttgccg actaccttgg tgatctcgcc tttcacgtag tggacaaatt    5040
cttccaactg atctgcgcgc gaggccaagc gatcttcttc ttgtccaaga taagcctgtc    5100
tagcttcaag tatgacgggc tgatactggg ccggcaggcg ctccattgcc cagtcggcag    5160
cgacatcctt cggcgcgatt ttgccggtta ctgcgctgta ccaaatgcgg gacaacgtaa    5220
gcactacatt tcgctcatcg ccagcccagt cgggcggcga gttccatagc gttaaggttt    5280
catttagcgc ctcaaataga tcctgttcag gaaccggatc aaagagttcc tccgccgctg    5340
gacctaccaa ggcaacgcta tgttctcttg cttttgtcag caagatagcc agatcaatgt    5400
cgatcgtggc tggctcgaag atacctgcaa gaatgtcatt gcgctgccat tctccaaatt    5460
gcagttcgcg cttagctgga taacgccacg gaatgatgtc gtcgtgcaca acaatggtga    5520
cttctacagc gcggagaatc tcgctctctc caggggaagc cgaagtttcc aaaaggtcgt    5580
tgatcaaagc tcgccgcgtt gtttcatcaa gccttacggt caccgtaacc agcaaatcaa    5640
tatcactgtg tggcttcagg ccgccatcca ctgcggagcg tacaaatgt acggccagca     5700 acgtcggttc gagatggcgc tcgatgacgc caactacctc tgatagttga gtcgatactt    5760
cggcgatcac cgcttccctc atgatgttta actttgtttt agggcgactg ccctgctgcg    5820
taacatcgtt gctgctccat aacatcaaac atcgacccac ggcgtaacgc gcttgctgct    5880
tggatgcccg aggcatagac tgtacccaa aaaacagtc ataacaagcc atgaaaaccg      5940
ccactgcgcc gttaccaccg ctgcgttcgg tcaaggttct ggaccagttg cgtgagcgca    6000
tacgctactt gcattacagc ttacgaaccg aacaggctta tgtccactgg gttcgtgcct    6060
tcatccgttt ccacggtgtg cgtcacccgg caaccttggg cagcagcgaa gtcgaggcat    6120
ttctgtcctg gctggcgaac gagcgcaagg tttcggtctc cacgcatcgt caggcattgg    6180
cggccttgct gttcttctac ggcaaggtgc tgtgcacgga tctgccctgg cttcaggaga    6240
tcggaagacc tcggccgtcg cggcgcttgc cggtggtgct gaccccggat gaagtggttc    6300
gcatcctcgg ttttctggaa ggcgagcatc gtttgttcgc ccagcttctg tatgaacgg     6360 gcatgcggat cagtgagggt ttgcaactgc gggtcaagga tctggatttc gatcacggca    6420
cgatcatcgt gcgggagggc aagggctcca aggatcgggc cttgatgtta cccgagagct    6480
tggcacccag cctgcgcgag caggggaatt aattcccacg ggttttgctg cccgcaaacg    6540
```

```
ggctgttctg gtgttgctag tttgttatca gaatcgcaga tccggcttca gccggtttgc    6600
cggctgaaag cgctatttct tccagaattg ccatgatttt ttccccacgg gaggcgtcac    6660
tggctcccgt gttgtcggca gctttgattc gataagcagc atcgcctgtt tcaggctgtc    6720
tatgtgtgac tgttgagctg taacaagttg tctcaggtgt tcaatttcat gttctagttg    6780
ctttgtttta ctggtttcac ctgttctatt aggtgttaca tgctgttcat ctgttacatt    6840
gtcgatctgt tcatggtgaa cagctttgaa tgcaccaaaa actcgtaaaa gctctgatgt    6900
atctatcttt tttacaccgt tttcatctgt gcatatggac agttttccct ttgatatgta    6960
acggtgaaca gttgttctac ttttgtttgt tagtcttgat gcttcactga tagatacaag    7020
agccataaga acctcagatc cttccgtatt tagccagtat gttctctagt gtggttcgtt    7080 gttttttgcgt gagccatgag aacgaaccat tgagatcata cttactttgc atgtcactca    7140
aaaattttgc ctcaaaactg gtgagctgaa ttttgcagt taaagcatcg tgtagtgttt    7200
ttcttagtcc gttatgtagg taggaatctg atgtaatggt tgttggtatt ttgtcaccat    7260 tcattttat ctggttgttc tcaagttcgg ttacgagatc catttgtcta tctagttcaa    7320
cttggaaaat caacgtatca gtcgggcggc ctcgcttatc aaccaccaat ttcatattgc    7380
tgtaagtgtt taaatcttta cttattggtt tcaaaaccca ttggttaagc ttttaaact    7440 catggtagtt attttcaagc attaacatga acttaaattc atcaaggcta atctctatat    7500
ttgccttgtg agttttcttt tgtgttagtt cttttaataa ccactcataa atcctcatag    7560
agtatttgtt ttcaaaagac ttaacatgtt ccagattata ttttatgaat tttttaact    7620 ggaaagata aggcaatatc tcttcactaa aaactaattc taattttcg cttgagaact    7680 tggcatagtt tgtccactgg aaaatctcaa agcctttaac caaggattc ctgatttcca    7740 cagttctcgt catcagctct ctggttgctt tagctaatac accataagca ttttccctac    7800
tgatgttcat catctgagcg tattggttat aagtgaacga taccgtccgt tctttccttg    7860
tagggttttc aatcgtgggg ttgagtagtg ccacacagca taaaattagc ttggtttcat    7920
gctccgttaa gtcatagcga ctaatcgcta gttcatttgc tttgaaaaca actaattcag    7980
acatacatct caattggtct aggtgatttt aatcactata ccaattgaga tgggctagtc    8040
aatgataatt actagtcctt ttcctttgag ttgtgggtat ctgtaaattc tgctagacct    8100
ttgctggaaa acttgtaaat tctgctagac cctctgtaaa ttccgctaga cctttgtgtg    8160 tttttttttgt ttatattcaa gtggttataa tttatagaat aaagaaagaa taaaaaaaga    8220 taaaagaat agatcccagc cctgtgtata actcactact ttagtcagtt ccgcagtatt    8280
acaaaaggat gtcgcaaacg ctgtttgctc ctctacaaaa cagaccttaa aaccctaaag    8340
gcttaagtag caccctcgca agctcgggca aatcgctgaa tattccttt gtctccgacc    8400 atcaggcacc tgagtcgctg tcttttttcgt gacattcagt tcgctgcgct cacggctctg    8460
gcagtgaatg ggggtaaatg gcactacagg cgccttttat ggattcatgc aaggaaacta    8520
cccataatac aagaaaagcc cgtcacgggc ttctcagggc gttttatggc gggtctgcta    8580
tgtggtgcta tctgactttt tgctgttcag cagttcctgc cctctgattt tccagtctga    8640
ccacttcgga ttatcccgtg acaggtcatt cagactggct aatgcaccca gtaaggcagc    8700
ggtatcatca acaggctta                                                 8719
```

<210> SEQ ID NO 28
<211> LENGTH: 796
<212> TYPE: PRT
<213> ORGANISM: Mycoplasma hominis

<400> SEQUENCE: 28

Met Ile Ser Lys Ile Tyr Asp Asp Lys Lys Tyr Leu Glu Lys Met Asp
1               5                   10                  15

Lys Trp Phe Arg Ala Ala Asn Tyr Leu Gly Val Cys Gln Met Tyr Leu
            20                  25                  30

Arg Asp Asn Pro Leu Leu Lys Lys Pro Leu Thr Ser Asn Asp Ile Lys
                35                  40                  45

Leu Tyr Pro Ile Gly His Trp Gly Thr Val Pro Gly Gln Asn Phe Ile
    50                  55                  60

Tyr Thr His Leu Asn Arg Val Ile Lys Lys Tyr Asp Leu Asn Met Phe
65                  70                  75                  80

Tyr Ile Glu Gly Pro Gly His Gly Gly Gln Val Met Ile Ser Asn Ser
                85                  90                  95

Tyr Leu Asp Gly Ser Tyr Ser Glu Ile Tyr Pro Glu Ile Ser Gln Asp
                100                 105                 110

Glu Ala Gly Leu Ala Lys Met Phe Lys Arg Phe Ser Phe Pro Gly Gly
            115                 120                 125

Thr Ala Ser His Ala Ala Pro Glu Thr Pro Gly Ser Ile His Glu Gly
130                 135                 140

Gly Glu Leu Gly Tyr Ser Ile Ser His Gly Thr Gly Ala Ile Leu Asp
145                 150                 155                 160

Asn Pro Asp Val Ile Cys Ala Ala Val Val Gly Asp Gly Glu Ala Glu
                165                 170                 175

Thr Gly Pro Leu Ala Thr Ser Trp Phe Ser Asn Ala Phe Ile Asn Pro
            180                 185                 190

Val Asn Asp Gly Ala Ile Leu Pro Ile Leu His Leu Asn Gly Gly Lys
        195                 200                 205

Ile Ser Asn Pro Thr Leu Leu Ser Arg Lys Pro Lys Glu Glu Ile Lys
210                 215                 220

Lys Tyr Phe Glu Gly Leu Gly Trp Asn Pro Ile Phe Val Glu Trp Ser
225                 230                 235                 240

Glu Asp Lys Ser Asn Leu Asp Met His Glu Leu Met Ala Lys Ser Leu
                245                 250                 255

Asp Lys Ala Ile Glu Ser Ile Lys Glu Ile Gln Ala Glu Ala Arg Lys
            260                 265                 270

Lys Pro Ala Glu Glu Ala Thr Arg Pro Thr Trp Pro Met Ile Val Leu
        275                 280                 285

Arg Thr Pro Lys Gly Trp Thr Gly Pro Lys Gln Trp Asn Asn Glu Ala
    290                 295                 300

Ile Glu Gly Ser Phe Arg Ala His Gln Val Pro Ile Pro Val Ser Ala
305                 310                 315                 320

Phe Lys Met Glu Lys Ile Ala Asp Leu Glu Lys Trp Leu Lys Ser Tyr
                325                 330                 335

Lys Pro Glu Glu Leu Phe Asp Glu Asn Gly Thr Ile Ile Lys Glu Ile
            340                 345                 350

Arg Asp Leu Ala Pro Glu Gly Leu Lys Arg Met Ala Val Asn Pro Ile
        355                 360                 365

Thr Asn Gly Gly Ile Asp Ser Lys Pro Leu Lys Leu Gln Asp Trp Lys
    370                 375                 380

Lys Tyr Ala Leu Lys Ile Asp Tyr Pro Gly Glu Ile Lys Ala Gln Asp
385                 390                 395                 400

Met Ala Glu Met Ala Lys Phe Ala Ala Asp Ile Met Lys Asp Asn Pro 405                 410                 415

Ser Ser Phe Arg Val Phe Gly Pro Asp Glu Thr Lys Ser Asn Arg Met
            420                 425                 430

Phe Ala Leu Phe Asn Val Thr Asn Arg Gln Trp Leu Glu Pro Val Ser
            435                 440                 445

Lys Lys Tyr Asp Glu Trp Ile Ser Pro Ala Gly Arg Ile Ile Asp Ser
        450                 455                 460

Gln Leu Ser Glu His Gln Cys Glu Gly Phe Leu Glu Gly Tyr Val Leu
465                 470                 475                 480

Thr Gly Arg His Gly Phe Phe Ala Ser Tyr Glu Ala Phe Leu Arg Val
                485                 490                 495

Val Asp Ser Met Leu Thr Gln His Met Lys Trp Ile Lys Lys Ala Ser
            500                 505                 510

Glu Leu Ser Trp Arg Lys Thr Tyr Pro Ser Leu Asn Ile Ile Ala Thr
            515                 520                 525

Ser Asn Ala Phe Gln Gln Asp His Asn Gly Tyr Thr His Gln Asp Pro
        530                 535                 540

Gly Leu Leu Gly His Leu Ala Asp Lys Arg Pro Glu Ile Ile Arg Glu
545                 550                 555                 560

Tyr Leu Pro Ala Asp Thr Asn Ser Leu Leu Ala Val Met Asn Lys Ala
                565                 570                 575

Leu Thr Glu Arg Asn Val Ile Asn Leu Ile Val Ala Ser Lys Gln Pro
            580                 585                 590

Arg Glu Gln Phe Phe Thr Val Glu Asp Ala Glu Glu Leu Leu Glu Lys
            595                 600                 605

Gly Tyr Lys Val Val Pro Trp Ala Ser Asn Ile Ser Glu Asn Glu Glu
        610                 615                 620

Pro Asp Ile Val Phe Ala Ser Ser Gly Val Pro Asn Ile Glu Ser
625                 630                 635                 640

Leu Ala Ala Ile Ser Leu Ile Asn Gln Glu Tyr Pro His Leu Lys Ile
                645                 650                 655

Arg Tyr Val Tyr Val Leu Asp Leu Leu Lys Leu Arg Ser Arg Lys Ile
            660                 665                 670

Asp Pro Arg Gly Ile Ser Asp Glu Glu Phe Asp Lys Val Phe Thr Lys
            675                 680                 685

Asn Lys Pro Ile Ile Phe Ala Phe His Gly Phe Glu Gly Leu Leu Arg
        690                 695                 700

Asp Ile Phe Phe Thr Arg Ser Asn His Asn Leu Ile Ala His Gly Tyr
705                 710                 715                 720

Arg Glu Asn Gly Asp Ile Thr Thr Ser Phe Asp Ile Arg Gln Leu Ser
                725                 730                 735

Glu Met Asp Arg Tyr His Ile Ala Lys Asp Ala Glu Ala Val Tyr
            740                 745                 750

Gly Lys Asp Ala Lys Ala Phe Met Asn Lys Leu Asp Gln Lys Leu Glu
        755                 760                 765

Tyr His Arg Asn Tyr Ile Asp Glu Tyr Gly Tyr Asp Met Pro Glu Val
770                 775                 780

Val Glu Trp Lys Trp Lys Asn Ile Asn Lys Glu Asn
785                 790                 795

<210> SEQ ID NO 29
<211> LENGTH: 2391
<212> TYPE: DNA
<213> ORGANISM: Artificial sequence
<220> FEATURE:
<223> OTHER INFORMATION: Synthetic construct

<400> SEQUENCE: 29

| | | | | |
|---|---|---|---|---|
| atgattagca | aaatctatga | tgataaaaag | tatctggaaa | aaatggataa | atggtttcgc | 60 |
| gcagcaaatt | atctgggtgt | ttgtcagatg | tatctgcgtg | ataatccgct | gctgaaaaaa | 120 |
| ccgctgacca | gcaatgatat | caaactgtat | ccgattggtc | attggggcac | cgttccgggt | 180 |
| cagaatttta | tctatacccca | tctgaatcgc | gtgatcaaga | aatatgatct | gaatatgttc | 240 |
| tacatcgaag | gtcctggtca | tggtggtcag | gttatgatta | gtaatagcta | tctggatggc | 300 |
| agctatagcg | aaatttatcc | ggaaattagc | caggatgaag | caggtctggc | caaaatgttt | 360 |
| aaacgtttta | gctttccggg | tggcaccgca | agccatgcag | caccggaaac | accgggtagc | 420 |
| attcatgaag | tggtgaact | gggttatagc | attagccatg | gcaccggtgc | aattctggat | 480 |
| aacccggatg | ttatttgtgc | agcagttgtt | ggtgatggtg | aagcagaaac | cggtccgctg | 540 |
| gcgaccagct | ggtttagcaa | tgcctttatt | aacccggtta | atgatggtgc | cattctgccg | 600 |
| attctgcatc | tgaacggtgg | taaaattagc | aatccgaccc | tgctgagccg | taaaccgaaa | 660 |
| gaagaaatca | aaaatactt | tgaaggcctg | gctggaatc | cgattttgt | tgaatggtca | 720 |
| gaagataaga | gcaacctgga | tatgcatgaa | ctgatggcaa | aaagcctgga | taaagccatt | 780 |
| gaaagcatca | agaaattca | ggcagaagca | cgtaaaaaac | tgcagaagaa | agcaacccgt | 840 |
| ccgacctggc | cgatgattgt | tctgcgtacc | ccgaaaggtt | ggacaggtcc | gaaacagtgg | 900 |
| aataatgaag | caattgaagg | tagctttcgt | gcacatcagg | ttccgattcc | ggttagcgcc | 960 |
| tttaaaatgg | aaaagattgc | cgatcttgag | aaatggctga | aaagctacaa | accggaagaa | 1020 |
| ctgtttgatg | aaaatggcac | gatcataaaa | gaaatccgtg | atctggctcc | ggaaggtctg | 1080 |
| aaacgtatgg | cagttaaccc | gattaccaat | ggtggtattg | atagcaaaacc | tctgaaactg | 1140 |
| caggattgga | aaaagtacgc | actgaaaaatt | gattatccgg | gtgaaattaa | agcacaggat | 1200 |
| atggccgaaa | tggccaaatt | tgcagcagat | atcatgaaag | ataaccctag | cagctttcgc | 1260 |
| gttttggtc | cggatgaaac | caaaagcaat | cgtatgtttg | ccctgtttaa | tgtgaccaat | 1320 |
| cgtcagtggc | tggaaccggt | tagtaagaaa | tacgatgaat | ggattagtcc | ggcaggtcgc | 1380 |
| attattgatt | cacagctgag | cgaacatcag | tgtgaaggtt | ttctggaagg | ttatgttctg | 1440 |
| accggtcgtc | atggttttttt | tgcaagctat | gaagcatttc | tgcgtgttgt | ggatagcatg | 1500 |
| ctgacccaac | atatgaaatg | gatcaaaaag | gcaagcgaac | tgagctggcg | taaaacctat | 1560 |
| ccgagcctga | acattattgc | aaccagtaat | gcatttcagc | aggatcataa | tggttatacg | 1620 |
| catcaggatc | cgggtctgct | gggtcatctg | gcagataaac | gtccagaaat | tatccgtgaa | 1680 |
| tatctgcctg | cagataccaa | tagcctgctg | gcggttatga | ataaagcact | gaccgaacgt | 1740 |
| aatgtgatta | atctgattgt | tgcaagcaaa | cagcctcgcg | aacagttttt | taccgttgaa | 1800 |
| gatgcagaga | aactgctgga | aagggttat | aaagttgttc | cgtgggcaag | caatattagc | 1860 |
| gaaaatgaag | aaccggatat | tgtgtttgcc | agcagcggtg | ttgaaccgaa | tatcgaaagt | 1920 |
| ctggcagcaa | ttagcctgat | caatcaagaa | tatcctcatc | tgaaaatccg | ctatgtgtat | 1980 |
| gtgctggatc | tgctgaagct | gcgtagtcgt | aaaatcgatc | cgcgtggtat | tagtgatgaa | 2040 |
| gagtttgata | agtgtttac | caaaaacaaa | ccgattatct | ttgcctttca | tggctttgag | 2100 |
| ggactgctgc | gcgatatttt | ctttacccgt | agcaaccata | acctgattgc | acatggttat | 2160 |
| cgtgaaaacg | gtgatatcac | aaccagcttt | gatattcgtc | agctgagtga | gatggatcgt | 2220 |

-continued

| | |
|---|---|
| tatcatattg caaaagatgc tgccgaagcc gtgtatggta agatgcaaa agcatttatg | 2280 |
| aacaaactgg atcagaaact ggaataccac cgcaactata tcgatgagta tggctatgat | 2340 |
| atgccggaag ttgtggaatg gaaatggaag aacatcaata agaaaatta a | 2391 |

<210> SEQ ID NO 30
<211> LENGTH: 8348
<212> TYPE: DNA
<213> ORGANISM: Artificial sequence
<220> FEATURE:
<223> OTHER INFORMATION: Synthetic construct

<400> SEQUENCE: 30

| | |
|---|---|
| gtttgacagc ttatcatcga ctgcacggtg caccaatgct tctggcgtca ggcagccatc | 60 |
| ggaagctgtg gtatggctgt gcaggtcgta aatcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagcgccgct gagaaaaagc gaagcggcac tgctctttaa | 300 |
| caatttatca gacaatctgt gtgggcactc gaccggaatt atcgattaac tttattatta | 360 |
| aaaattaaag aggtatatat taatgtatcg attaaataag gaggaataaa ccatggaaac | 420 |
| gcgtcgttct gcgaactacg aacctaacag ctgggactat gattacctgc tgtcctccga | 480 |
| cacggacgag tccatcgaag tatacaaaga caaagcgaaa agctggaagc cgaagttcg | 540 |
| tcgcgagatt aataacgaaa agcagaatt tctgaccctg ctggaactga ttgacaacgt | 600 |
| ccagcgcctg ggcctgggtt accgtttcga gtctgatatc cgtggtgcgc tggatcgctt | 660 |
| cgtttcctcc ggcggcttcg atgcggtaac caagacttcc ctgcacggta cggcactgtc | 720 |
| tttccgtctg ctgcgtcaac acggttttga ggtttctcag gaagcgttca gcggcttcaa | 780 |
| agaccaaaac ggcaacttcc tggagaacct gaaggaagat atcaaagcta tcctgagcct | 840 |
| gtacgaggcc agcttcctgg ctctggaagg cgaaaacatc ctggacgagg cgaaggtttt | 900 |
| cgcaatctct catctgaaag aactgtctga agaaagatc ggtaaagagc tggcagaaca | 960 |
| ggtgaaccat gcactggaac tgccactgca tcgccgtact cagcgtctgg aagcagtatg | 1020 |
| gtctatcgag gcctaccgta aaaggagga cgcgaatcag gttctgctgg agctggcaat | 1080 |
| tctggattac aacatgatcc agtctgtata ccagcgtgat ctgcgtgaaa cgtcccgttg | 1140 |
| gtggcgtcgt gtgggtctgg cgaccaaact gcactttgct cgtgaccgcc tgattgagag | 1200 |
| cttctactgg gccgtgggtg tagcattcga accgcaatac tccgactgcc gtaactccgt | 1260 |
| cgcaaaaatg ttttgtttcg taaccattat cgacgatatc tacgatgtat acggcaccct | 1320 |
| ggacgaactg gagctgtttta ctgatgcagt tgagcgttgg gacgtaaacg ccatcaacga | 1380 |
| cctgccggat tacatgaaac tgtgctttct ggctctgtat aacactatta cgaaatcgc | 1440 |
| ctacgacaac ctgaaagata aggtgagaa catcctgccg tatctgacca agcctgggc | 1500 |
| tgacctgtgc aacgctttcc tgcaagaagc caagtggctg tacaacaaat ctactccgac | 1560 |
| ctttgacgac tacttcggca acgcatggaa atcctcttct ggcccgctgc aactggtgtt | 1620 |
| cgcttacttc gctgtcgtgc agaacattaa aaaggaagag atcgaaaacc tgcaaaaata | 1680 |
| ccatgacacc atctctcgtc cttcccatat cttccgtctg tgcaatgacc tggctagcgc | 1740 |
| gtctgcggaa attgcgcgtg gtgaaaccgc aaatagcgtt tcttgttaca tgcgcactaa | 1800 |
| aggtatctcc gaagaactgg ctaccgaaag cgtgatgaat ctgatcgatg aatattggaa | 1860 |
| aaagatgaac aaggaaaaac tgggtggtag cctgttcgcg aaaccgttcg tggaaaccgc | 1920 |

```
gatcaacctg gcacgtcaat ctcactgcac ttatcataac ggcgacgcgc atacctctcc   1980
ggatgagctg acccgcaaac gcgttctgtc tgtaatcact gaaccgattc tgccgtttga   2040
acgctaaaga tacgcgtaac cccaaggacg gtaaaatgat tagcaaaatc tatgatgata   2100
aaaagtatct ggaaaaaatg gataaatggt ttcgcgcagc aaattatctg ggtgtttgtc   2160
agatgtatct gcgtgataat ccgctgctga aaaaaccgct gaccagcaat gatatcaaac   2220
tgtatccgat tggtcattgg ggcaccgttc cgggtcagaa ttttatctat acccatctga   2280
atcgcgtgat caagaaatat gatctgaata tgttctacat cgaaggtcct ggtcatggtg   2340
gtcaggttat gattagtaat agctatctgg atggcagcta tagcgaaatt tatccggaaa   2400
ttagccagga tgaagcaggt ctggccaaaa tgtttaaacg ttttagcttt ccgggtggca   2460
ccgcaagcca tgcagcaccg aaacaccggg tagcattca tgaaggtggt gaactgggtt   2520
atagcattag ccatggcacc ggtgcaattc tggataaccc ggatgttatt tgtgcagcag   2580
ttgttggtga tggtgaagca gaaaccggtc cgctggcgac cagctggttt agcaatgcct   2640
ttattaaccc ggttaatgat ggtgccattc tgccgattct gcatctgaac ggtggtaaaa   2700
ttagcaatcc gaccctgctg agccgtaaac cgaaagaaga aatcaaaaaa tactttgaag   2760
gcctgggctg gaatccgatt tttgttgaat ggtcagaaga taagagcaac ctggatatgc   2820
atgaactgat ggcaaaaagc ctggataaag ccattgaaag catcaaagaa attcaggcag   2880
aagcacgtaa aaaacctgca gaagaagcaa cccgtccgac ctggccgatg attgttctgc   2940
gtaccccgaa aggttggaca ggtccgaaac agtggaataa tgaagcaatt gaaggtagct   3000
ttcgtgcaca tcaggttccg attccggtta gcgccttta aatggaaaag attgccgatc   3060
ttgagaaatg gctgaaaagc tacaaaccgg aagaactgtt tgatgaaaat ggcacgatca   3120
taaaagaaat ccgtgatctg ctccggaag gtctgaaacg tatggcagtt aacccgatta   3180
ccaatggtgg tattgatagc aaacctctga aactgcagga ttggaaaaag tacgcactga   3240
aaattgatta tccgggtgaa attaaagcac aggatatggc cgaaatggcc aaatttgcag   3300
cagatatcat gaaagataac cctagcagct ttcgcgtttt tggtccggat gaaaccaaaa   3360
gcaatcgtat gtttgccctg tttaatgtga ccaatcgtca gtggctggaa ccggttagta   3420
agaaatacga tgaatggatt agtccggcag gtcgcattat tgattcacag ctgagcgaac   3480
atcagtgtga aggttttctg gaaggttatg ttctgaccgg tcgtcatggt ttttttgcaa   3540
gctatgaagc atttctgcgt gttgtggata gcatgctgac ccaacatatg aaatggatca   3600
aaaaggcaag cgaactgagc tggcgtaaaa cctatccgag cctgaacatt attgcaacca   3660
gtaatgcatt tcagcaggat cataatggtt atacgcatca ggatccgggt ctgctgggtc   3720
atctggcaga taaacgtcca gaaattatcc gtgaatatct gcctgcagat accaatagcc   3780
tgctggcggt tatgaataaa gcactgaccg aacgtaatgt gattaatctg attgttgcaa   3840
gcaaacagcc tcgcgaacag ttttttaccg ttgaagatgc agaggaactg ctggaaaagg   3900
gttataaagt tgttccgtgg gcaagcaata ttagcgaaaa tgaagaaccg atattgtgt   3960
ttgccagcag cggtgttgaa ccgaatatcg aaagtctggc agcaattagc ctgatcaatc   4020
aagaatatcc tcatctgaaa atccgctatg tgtatgtgct ggatctgctg aagctgcgta   4080
gtcgtaaaat cgatccgcgt ggtattagtg atgaagagtt tgataaagtg tttaccaaaa   4140
acaaaccgat tatctttgcc tttcatggct ttgagggact gctgcgcgat attttctta   4200
cccgtagcaa ccataacctg attgcacatg gttatcgtga aaacggtgat atcacaacca   4260
```

```
gctttgatat tcgtcagctg agtgagatgg atcgttatca tattgcaaaa gatgctgccg    4320
aagccgtgta tggtaaagat gcaaaagcat ttatgaacaa actggatcag aaactggaat    4380
accaccgcaa ctatatcgat gagtatggct atgatatgcc ggaagttgtg aatggaaat    4440 ggaagaacat caataaagaa aattaaagtc tagttaaagt ttaaacggtc tccagcttgg    4500
ctgttttggc ggatgagaga agattttcag cctgatacag attaaatcag aacgcagaag    4560
cggtctgata aaacagaatt tgcctggcgg cagtagcgcg gtggtcccac ctgaccccat    4620
gccgaactca gaagtgaaac gccgtagcgc cgatggtagt gtggggtctc cccatgcgag    4680
agtagggaac tgccaggcat caaataaaac gaaaggctca gtcgaaagac tgggcctttc    4740
gttttatctg ttgtttgtcg gtgaacgctc tcctgagtag acaaatccg ccgggagcgg    4800 atttgaacgt tgcgaagcaa cggcccggag ggtggcgggc aggacgcccg ccataaactg    4860
ccaggcatca aattaagcag aaggccatcc tgacggatgg ccttttttgcg tttctacaaa    4920 ctcttttttgt ttattttct aaatacattc aaatatgtat ccgctcatga gacaataacc    4980
ctgataaatg cttcaataat attgaaaaag gaagagtatg agtattcaac atttccgtgt    5040
cgcccttatt cccttttttg cggcattttg ccttcctgtt tttgctcacc cagaaacgct    5100
ggtgaaagta aaagatgctg aagatcagtt gggtgcacga gtgggttaca tcgaactgga    5160
tctcaacagc ggtaagatcc ttgagagttt tcgccccgaa gaacgttttc caatgatgag    5220
cacttttaaa gttctgctat gtggcgcggt attatcccgt gttgacgccg ggcaagagca    5280
actcggtcgc cgcatacact attctcagaa tgacttggtt gagtactcac cagtcacaga    5340
aaagcatctt acggatggca tgacagtaag agaattatgc agtgctgcca taaccatgag    5400
tgataacact gcggccaact tacttctgac aacgatcgga ggaccgaagg agctaaccgc    5460
ttttttgcac aacatgggg atcatgtaac tcgccttgat cgttgggaac cggagctgaa    5520
tgaagccata ccaaacgacg agcgtgacac cacgatgcct gtagcaatgg caacaacgtt    5580
gcgcaaacta ttaactggcg aactacttac tctagcttcc cggcaacaat taatagactg    5640
gatggaggcg gataaagttg caggaccact tctgcgctcg gcccttccgg ctggctggtt    5700
tattgctgat aaatctggag ccggtgagcg tgggtctcgc ggtatcattg cagcactggg    5760
gccagatggt aagccctccc gtatcgtagt tatctacacg acggggagtc aggcaactat    5820
ggatgaacga aatagacaga tcgctgagat aggtgcctca ctgattaagc attggtaact    5880
gtcagaccaa gtttactcat atatacttta gattgattta aaacttcatt tttaatttaa    5940
aaggatctag gtgaagatcc ttttttgataa tctcatgacc aaaatccctt aacgtgagtt    6000
ttcgttccac tgagcgtcag accccgtaga aaagatcaaa ggatcttctt gagatccttt    6060
ttttctgcgc gtaatctgct gcttgcaaac aaaaaaacca ccgctaccag cggtggtttg    6120
tttgccggat caagagctac caactctttt tccgaaggta actggcttca gcagagcgca    6180
gataccaaat actgtccttc tagtgtagcc gtagttaggc caccacttca gaactctgt    6240 agcaccgcct acatacctcg ctctgctaat cctgttacca gtggctgctg ccagtggcga    6300
taagtcgtgt cttaccgggt tggactcaag acgatagtta ccggataagg cgcagcggtc    6360
gggctgaacg ggggttcgt gcacacagcc cagcttggag cgaacgacct acaccgaact    6420
gagataccta cagcgtgagc tatgagaaag cgccacgctt cccgaaggga aaaggcgga    6480 caggtatccg gtaagcggca gggtcggaac aggagagcgc acgagggagc ttccaggggg    6540
aaacgcctgg tatctttata gtcctgtcgg gtttcgccac ctctgacttg agcgtcgatt    6600
tttgtgatgc tcgtcagggg ggcggagcct atggaaaaac gccagcaacg cggccttttt    6660
```

```
acggttcctg gccttttgct ggccttttgc tcacatgttc tttcctgcgt tatcccctga   6720
ttctgtggat aaccgtatta ccgcctttga gtgagctgat accgctcgcc gcagccgaac   6780
gaccgagcgc agcgagtcag tgagcgagga agcggaagag cgcctgatgc ggtattttct   6840
ccttacgcat ctgtgcggta tttcacaccg catatggtgc actctcagta caatctgctc   6900
tgatgccgca tagttaagcc agtatacact ccgctatcgc tacgtgactg gtcatggct    6960 gcgccccgac acccgccaac acccgctgac gcgccctgac gggcttgtct gctcccggca   7020
tccgcttaca gacaagctgt gaccgtctcc gggagctgca tgtgtcagag gttttcaccg   7080
tcatcaccga aacgcgcgag gcagcagatc aattcgcgcg cgaaggcgaa gcggcatgca   7140
tttacgttga caccatcgaa tggtgcaaaa cctttcgcgg tatggcatga tagcgcccgg   7200
aagagagtca attcagggtg gtgaatgtga accagtaac gttatacgat gtcgcagagt    7260
atgccggtgt ctcttatcag accgtttccc gcgtggtgaa ccaggccagc cacgtttctg   7320
cgaaaacgcg ggaaaaagtg gaagcggcga tggcggagct gaattacatt cccaaccgcg   7380
tggcacaaca actggcgggc aaacagtcgt tgctgattgg cgttgccacc tccagtctgg   7440
ccctgcacgc gccgtcgcaa attgtcgcgg cgattaaatc tcgcgccgat caactgggtg   7500
ccagcgtggt ggtgtcgatg gtagaacgaa gcggcgtcga agcctgtaaa gcggcggtgc   7560
acaatcttct cgcgcaacgc gtcagtgggc tgatcattaa ctatccgctg gatgaccagg   7620
atgccattgc tgtggaagct gcctgcacta atgttccggc gttatttctt gatgtctctg   7680
accagacacc catcaacagt attatttctt cccatgaaga cggtacgcga ctgggcgtgg   7740
agcatctggt cgcattgggt caccagcaaa tcgcgctgtt agcgggccca ttaagttctg   7800
tctcggcgcg tctgcgtctg gctggctggc ataaatatct cactcgcaat caaattcagc   7860
cgatagcgga acgggaaggc gactggagtg ccatgtccgg ttttcaacaa accatgcaaa   7920
tgctgaatga gggcatcgtt cccactgcga tgctggttgc caacgatcag atggcgctgg   7980
gcgcaatgcg cgccattacc gagtccgggc tgcgcgttgg tgcggatatc tcggtagtgg   8040
gatacgacga taccgaagac agctcatgtt atatcccgcc gtcaaccacc atcaaacagg   8100 atttcgcct gctggggcaa accagcgtgg accgcttgct gcaactctct cagggccagg    8160
cggtgaaggg caatcagctg ttgcccgtct cactggtgaa agaaaaaacc accctggcgc   8220
ccaatacgca aaccgcctct ccccgcgcgt tggccgattc attaatgcag ctggcacgac   8280
aggtttcccg actggaaagc gggcagtgag cgcaacgcaa ttaatgtgag ttagcgcgaa   8340
ttgatctg                                                           8348

<210> SEQ ID NO 31
<211> LENGTH: 8343
<212> TYPE: DNA
<213> ORGANISM: Artificial sequence
<220> FEATURE:
<223> OTHER INFORMATION: Synthetic construct

<400> SEQUENCE: 31
gtttgacagc ttatcatcga ctgcacggtg caccaatgct tctggcgtca ggcagccatc     60
ggaagctgtg gtatggctgt gcaggtcgta atcactgca taattcgtgt cgctcaaggc     120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
```

```
caatttatca gacaatctgt gtgggcactc gaccggaatt atcgattaac tttattatta    360
aaaattaaag aggtatatat taatgtatcg attaaataag gaggaataaa ccatggaaac    420
gcgtcgttct gcgaactacg aacctaacag ctgggactat gattacctgc tgtcctccga    480
cacggacgag tccatcgaag tatacaaaga caaagcgaaa aagctggaag ccgaagttcg    540
tcgcgagatt aataacgaaa aagcagaatt tctgaccctg ctggaactga ttgacaacgt    600
ccagcgcctg ggcctgggtt accgtttcga gtctgatatc cgtggtgcgc tggatcgctt    660
cgtttcctcc ggcggcttcg atgcggtaac caagacttcc ctgcacggta cggcactgtc    720
tttccgtctg ctgcgtcaac acggttttga ggtttctcag gaagcgttca gcggcttcaa    780
agaccaaaac ggcaacttcc tggagaacct gaaggaagat atcaaagcta tcctgagcct    840
gtacgaggcc agcttcctgg ctctggaagg cgaaaacatc ctggacgagg cgaaggtttt    900
cgcaatctct catctgaaag aactgtctga agaaaagatc ggtaaagagc tggcagaaca    960
ggtgaaccat gcactggaac tgccactgca tcgccgtact cagcgtctgg aagcagtatg   1020
gtctatcgag gcctaccgta aaaggagga cgcgaatcag gttctgctgg agctggcaat   1080
tctggattac aacatgatcc agtctgtata ccagcgtgat ctgcgtgaaa cgtcccgttg   1140
gtggcgtcgt gtgggtctgg cgaccaaact gcactttgct cgtgaccgcc tgattgagag   1200
cttctactgg gccgtgggtg tagcattcga accgcaatac tccgactgcc gtaactccgt   1260
cgcaaaaatg ttttgtttcg taaccattat cgacgatatc tacgatgtat acggcaccct   1320
ggacgaactg gagctgttta ctgatgcagt tgagcgttgg gacgtaaacg ccatcaacga   1380
cctgccggat tacatgaaac tgtgctttct ggctctgtat aacactatta acgaaatcgc   1440
ctacgacaac ctgaaagata aggtgagaa catcctgccg tatctgacca agcctgggc    1500 tgacctgtgc aacgctttcc tgcaagaagc caagtggctg tacaacaaat ctactccgac   1560
ctttgacgac tacttcggca acgcatggaa atcctcttct ggcccgctgc aactggtgtt   1620
cgcttacttc gctgtcgtgc agaacattaa aaaggaagag atcgaaaacc tgcaaaaata   1680
ccatgacacc atctctcgtc cttcccatat cttccgtctg tgcaatgacc tggctagcgc   1740
gtctgcggaa attgcgcgtg tgaaaccgc aaatagcgtt tcttgttaca tgcgcactaa   1800
aggtatctcc gaagaactgg ctaccgaaag cgtgatgaat ctgatcgatg aatattggaa   1860
aaagatgaac aaggaaaaac tggggtggtag cctgttcgcg aaaccgttcg tggaaaccgc   1920
gatcaacctg gcacgtcaat ctcactgcac ttatcataac ggcgacgcgc atacctctcc   1980
ggatgagctg acccgcaaac gcgttctgtc tgtaatcact gaaccgattc tgccgtttga   2040
acgctaactg cataaaggag gtaaaaaaac atgattagca aaatctatga tgataaaaag   2100
tatctggaaa aaatggataa atggtttcgc gcagcaaatt atctgggtgt ttgtcagatg   2160
tatctgcgtg ataatccgct gctgaaaaaa ccgctgacca gcaatgatat caaactgtat   2220
ccgattggtc attggggcac cgttccgggt cagaatttta tctatacccc tctgaatcgc   2280
gtgatcaaga aatatgatct gaatatgttc tacatcgaag gtcctggtca tggtggtcag   2340
gttatgatta gtaatagcta tctggatggc agctatagcg aaatttatcc ggaaattagc   2400
caggatgaag caggtctggc caaaatgttt aaacgtttta gctttccggg tggcaccgca   2460
agccatgcag caccggaaac accgggtagc attcatgaag tggtgaact gggttatagc   2520 attagccatg gcaccggtgc aattctggat aacccggatg ttatttgtgc agcagttgtt   2580
ggtgatggta agcagaaaac cggtccgctg gcgaccagct ggtttagcaa tgccttatt   2640 aacccggtta tgatggtgc cattctgccg attctgcatc tgaacggtgg taaaattagc   2700
```

```
aatccgaccc tgctgagccg taaaccgaaa gaagaaatca aaaatactt tgaaggcctg    2760 ggctggaatc cgattttgt tgaatggtca aagataaga gcaacctgga tatgcatgaa     2820
ctgatggcaa aaagcctgga taaagccatt gaaagcatca agaaattca ggcagaagca    2880 cgtaaaaaac ctgcagaaga agcaacccgt ccgacctggc cgatgattgt tctgcgtacc   2940
ccgaaaggtt ggacaggtcc gaaacagtgg aataatgaag caattgaagg tagctttcgt   3000
gcacatcagg ttccgattcc ggttagcgcc tttaaaatgg aaaagattgc cgatcttgag   3060
aaatggctga aagctacaa accggaagaa ctgtttgatg aaaatggcac gatcataaaa    3120
gaaatccgtg atctggctcc ggaaggtctg aaacgtatgg cagttaaccc gattaccaat   3180
ggtggtattg atagcaaacc tctgaaactg caggattgga aaaagtacgc actgaaaatt   3240
gattatccgg gtgaaattaa agcacaggat atggccgaaa tggccaaatt tgcagcagat   3300
atcatgaaag ataaccctag cagctttcgc gttttggtc cggatgaaac caaaagcaat    3360
cgtatgtttg ccctgtttaa tgtgaccaat cgtcagtggc tggaaccggt tagtaagaaa   3420
tacgatgaat ggattagtcc ggcaggtcgc attattgatt cacagctgag cgaacatcag   3480
tgtgaaggtt ttctggaagg ttatgttctg accggtcgtc atggtttttt tgcaagctat   3540
gaagcatttc tgcgtgttgt ggatagcatg ctgacccaac atatgaaatg gatcaaaaag   3600
gcaagcgaac tgagctggcg taaaacctat ccgagcctga acattattgc aaccagtaat   3660
gcatttcagc aggatcataa tggttatacg catcaggatc cgggtctgct gggtcatctg   3720
gcagataaac gtccagaaat tatccgtgaa tatctgcctg cagataccaa tagcctgctg   3780
gcggttatga ataaagcact gaccgaacgt aatgtgatta atctgattgt tgcaagcaaa   3840
cagcctcgcg aacagttttt taccgttgaa gatgcagagg aactgctgga aaagggttat   3900
aaagttgttc cgtgggcaag caatattagc gaaaatgaag aaccggatat tgtgtttgcc   3960
agcagcggtg ttgaaccgaa tatcgaaagt ctggcagcaa ttagcctgat caatcaagaa   4020
tatcctcatc tgaaaatccg ctatgtgtat gtgctggatc tgctgaagct gcgtagtcgt   4080
aaaatcgatc cgcgtggtat tagtgatgaa gagtttgata agtgtttac caaaaacaaa    4140 ccgattatct ttgcctttca tggctttgag ggactgctgc gcgatatttt ctttacccgt   4200
agcaaccata acctgattgc acatggttat cgtgaaaacg gtgatatcac aaccagcttt   4260
gatattcgtc agctgagtga gatggatcgt tatcatattg caaagatgc tgccgaagcc    4320 gtgtatggta agatgcaaa agcatttatg aacaaactgg atcagaaact ggaataccac    4380
cgcaactata tcgatgagta tggctatgat atgccggaag ttgtggaatg gaatggaag    4440 aacatcaata agaaaattaa agtctagtt aaagtttaaa cggtctccag cttggctgtt    4500
ttggcggatg agagaagatt ttcagcctga tacagattaa atcagaacgc agaagcggtc   4560
tgataaaaca gaatttgcct ggcggcagta gcgcggtggt cccacctgac cccatgccga   4620
actcagaagt gaaacgccgt agcgccgatg gtagtgtggg gtctccccat gcgagagtag   4680
ggaactgcca ggcatcaaat aaaacgaaag gctcagtcga agactgggc ctttcgtttt    4740 atctgttgtt tgtcggtgaa cgctctcctg agtaggacaa atccgccggg agcggatttg   4800
aacgttgcga agcaacggcc cggagggtgg cgggcaggac gcccgccata aactgccagg   4860
catcaaatta agcagaaggc catcctgacg gatggccttt ttgcgtttct acaaactctt   4920
tttgtttatt tttctaaata cattcaaata tgtatccgct catgagacaa taaccctgat   4980
aaatgcttca ataatattga aaaaggaaga gtatgagtat tcaacatttc cgtgtcgccc   5040
```

```
ttattccctt ttttgcggca ttttgccttc ctgttttgc tcacccagaa acgctggtga      5100
aagtaaaaga tgctgaagat cagttgggtg cacgagtggg ttacatcgaa ctggatctca      5160
acagcggtaa gatccttgag agttttcgcc ccgaagaacg ttttccaatg atgagcactt      5220
ttaaagttct gctatgtggc gcggtattat cccgtgttga cgccgggcaa gagcaactcg      5280
gtcgccgcat acactattct cagaatgact tggttgagta ctcaccagtc acagaaaagc      5340
atcttacgga tggcatgaca gtaagagaat tatgcagtgc tgccataacc atgagtgata      5400
acactgcggc caacttactt ctgacaacga tcggaggacc gaaggagcta accgcttttt      5460
tgcacaacat gggggatcat gtaactcgcc ttgatcgttg ggaaccggag ctgaatgaag      5520
ccataccaaa cgacgagcgt gacaccacga tgcctgtagc aatggcaaca acgttgcgca      5580
aactattaac tggcgaacta cttactctag cttcccggca acaattaata gactggatgg      5640
aggcggataa agttgcagga ccacttctgc gctcggccct tccggctggc tggtttattg      5700
ctgataaatc tggagccggt gagcgtgggt ctcgcggtat cattgcagca ctggggccag      5760
atggtaagcc ctcccgtatc gtagttatct acacgacggg gagtcaggca actatggatg      5820
aacgaaatag acagatcgct gagataggtg cctcactgat taagcattgg taactgtcag      5880
accaagttta ctcatatata ctttagattg atttaaaact tcatttttaa tttaaaagga      5940
tctaggtgaa gatcctttt gataatctca tgaccaaaat cccttaacgt gagttttcgt      6000
tccactgagc gtcagacccc gtagaaaaga tcaaaggatc ttcttgagat cctttttttc      6060
tgcgcgtaat ctgctgcttg caaacaaaaa accaccgct accagcggtg tttgtttgc      6120
cggatcaaga gctaccaact cttttccga aggtaactgg cttcagcaga gcgcagatac      6180
caaatactgt ccttctagtg tagccgtagt taggccacca cttcaagaac tctgtagcac      6240
cgcctacata cctcgctctg ctaatcctgt taccagtggc tgctgccagt ggcgataagt      6300
cgtgtcttac cgggttggac tcaagacgat agttaccgga taaggcgcag cggtcgggct      6360
gaacggggg ttcgtgcaca cagcccagct tggagcgaac gacctacacc gaactgagat      6420
acctacagcg tgagctatga gaaagcgcca cgcttcccga agggagaaag gcggacaggt      6480
atccggtaag cggcagggtc ggaacaggag agcgcacgag ggagcttcca gggggaaacg      6540
cctggtatct ttatagtcct gtcgggtttc gccacctctg acttgagcgt cgatttttgt      6600
gatgctcgtc agggggggcgg agcctatgga aaaacgccag caacgcggcc ttttacggt      6660
tcctggcctt ttgctggcct tttgctcaca tgttctttcc tgcgttatcc cctgattctg      6720
tggataaccg tattaccgcc tttgagtgag ctgataccgc tcgccgcagc cgaacgaccg      6780
agcgcagcga gtcagtgagc gaggaagcgg aagagcgcct gatgcggtat tttctcctta      6840
cgcatctgtg cggtatttca caccgcatat ggtgcactct cagtacaatc tgctctgatg      6900
ccgcatagtt aagccagtat acactccgct atcgctacgt gactgggtca tggctgcgcc      6960
ccgacacccg ccaacacccg ctgacgcgcc ctgacgggct tgtctgctcc cggcatccgc      7020
ttacagacaa gctgtgaccg tctccgggag ctgcatgtgt cagaggtttt caccgtcatc      7080
accgaaacgc gcgaggcagc agatcaattc gcgcgcgaag gcgaagcggc atgcatttac      7140
gttgacacca tcgaatggtg caaaacctt cgcggtatgg catgatagcg cccggaagag      7200
agtcaattca gggtggtgaa tgtgaaacca gtaacgttat acgatgtcgc agagtatgcc      7260
ggtgtctctt atcagaccgt ttcccgcgtg gtgaaccagg ccagccacgt ttctgcgaaa      7320
acgcgggaaa aagtggaagc ggcgatgcg gagctgaatt acattcccaa ccgcgtggca      7380
caacaactgg cgggcaaaca gtcgttgctg attggcgttg ccacctccag tctggccctg      7440
```

```
cacgcgccgt cgcaaattgt cgcggcgatt aaatctcgcg ccgatcaact gggtgccagc    7500
gtggtggtgt cgatggtaga acgaagcggc gtcgaagcct gtaaagcggc ggtgcacaat    7560
cttctcgcgc aacgcgtcag tgggctgatc attaactatc cgctggatga ccaggatgcc    7620
attgctgtgg aagctgcctg cactaatgtt ccggcgttat ttcttgatgt ctctgaccag    7680
acacccatca acagtattat tttctcccat gaagacggta cgcgactggg cgtggagcat    7740
ctggtcgcat tgggtcacca gcaaatcgcg ctgttagcgg gcccattaag ttctgtctcg    7800
gcgcgtctgc gtctggctgg ctggcataaa tatctcactc gcaatcaaat tcagccgata    7860
gcggaacggg aaggcgactg gagtgccatg tccggttttc aacaaaccat gcaaatgctg    7920
aatgagggca tcgttcccac tgcgatgctg gttgccaacg atcagatggc gctgggcgca    7980
atgcgcgcca ttaccgagtc cgggctgcgc gttggtgcgg atatctcggt agtgggatac    8040
gacgataccg aagacagctc atgttatatc ccgccgtcaa ccaccatcaa acaggatttt    8100
cgcctgctgg ggcaaaccag cgtggaccgc ttgctgcaac tctctcaggg ccaggcggtg    8160
aagggcaatc agctgttgcc cgtctcactg gtgaaaagaa aaaccaccct ggcgcccaat    8220
acgcaaaccg cctctccccg cgcgttggcc gattcattaa tgcagctggc acgacaggtt    8280
tcccgactgg aaagcgggca gtgagcgcaa cgcaattaat gtgagttagc gcgaattgat    8340
ctg                                                                  8343

<210> SEQ ID NO 32
<211> LENGTH: 29
<212> TYPE: DNA
<213> ORGANISM: Artificial sequence
<220> FEATURE:
<223> OTHER INFORMATION: Synthetic construct

<400> SEQUENCE: 32
cgctaactgc ataaaggagg taaaaaaac                                       29

<210> SEQ ID NO 33
<211> LENGTH: 33
<212> TYPE: DNA
<213> ORGANISM: Artificial sequence
<220> FEATURE:
<223> OTHER INFORMATION: Synthetic construct

<400> SEQUENCE: 33
gctggagacc gtttaaactt taactagact tta                                  33

<210> SEQ ID NO 34
<211> LENGTH: 33
<212> TYPE: DNA
<213> ORGANISM: Artificial sequence
<220> FEATURE:
<223> OTHER INFORMATION: Synthetic construct

<400> SEQUENCE: 34
taaagtctag ttaaagttta aacggtctcc agc                                  33

<210> SEQ ID NO 35
<211> LENGTH: 29
<212> TYPE: DNA
<213> ORGANISM: Artificial sequence
<220> FEATURE:
<223> OTHER INFORMATION: Synthetic construct

<400> SEQUENCE: 35
```
gtttttttac ctcctttatg cagttagcg         29

<210> SEQ ID NO 36
<211> LENGTH: 24
<212> TYPE: DNA
<213> ORGANISM: Artificial sequence
<220> FEATURE:
<223> OTHER INFORMATION: Synthetic construct

<400> SEQUENCE: 36
ttagcgttca aacggcagaa tcgg              24

<210> SEQ ID NO 37
<211> LENGTH: 80
<212> TYPE: DNA
<213> ORGANISM: Artificial sequence
<220> FEATURE:
<223> OTHER INFORMATION: Synthetic construct

<400> SEQUENCE: 37
ccgtttgaac gctaaagata cgcgtaaccc caaggacggt aaaatgatta gcaaaatcta         60
tgatgataaa aagtatctgg                   80

<210> SEQ ID NO 38
<211> LENGTH: 132
<212> TYPE: DNA
<213> ORGANISM: Artificial sequence
<220> FEATURE:
<223> OTHER INFORMATION: Synthetic construct

<400> SEQUENCE: 38
tgttttttta cctcctttgc agtgcgtcct gctgatgtgc tcagtatcac cgccagtggt         60
atttacgtca acaccgccag agataattta tcaccgcaga tggttatctt aatacgactc        120
actatagggc tc                          132

<210> SEQ ID NO 39
<211> LENGTH: 80
<212> TYPE: DNA
<213> ORGANISM: Artificial sequence
<220> FEATURE:
<223> OTHER INFORMATION: Synthetic construct

<400> SEQUENCE: 39
gactcaagat atttcttcca tcatgcaaaa aaaaatttgc agtgcatgat gttaatcaaa         60
ttaaccctca ctaaagggcg                   80

<210> SEQ ID NO 40
<211> LENGTH: 77
<212> TYPE: DNA
<213> ORGANISM: Artificial sequence
<220> FEATURE:
<223> OTHER INFORMATION: Synthetic construct

<400> SEQUENCE: 40
gctggtcaga ccgacgctgg ttccggtagg gatcagcata ataatacggg acatgttttt         60
ttacctcctt tgcagtg                      77

<210> SEQ ID NO 41
<211> LENGTH: 20
<212> TYPE: DNA
<213> ORGANISM: Artificial sequence
<220> FEATURE:
<223> OTHER INFORMATION: Synthetic construct

```
<400> SEQUENCE: 41
aggctgcctc gtcatctctt                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic construct

<400> SEQUENCE: 42
cagaatatcg ccactctggg                                                  20

<210> SEQ ID NO 43
<211> LENGTH: 20
<212> TYPE: DNA
<213> ORGANISM: Artificial sequence
<220> FEATURE:
<223> OTHER INFORMATION: Synthetic construct

<400> SEQUENCE: 43
acacgctatc tggcaggaaa                                                  20

<210> SEQ ID NO 44
<211> LENGTH: 20
<212> TYPE: DNA
<213> ORGANISM: Artificial sequence
<220> FEATURE:
<223> OTHER INFORMATION: Synthetic construct

<400> SEQUENCE: 44
tttgacaaca tcacagtgca                                                  20

<210> SEQ ID NO 45
<211> LENGTH: 24
<212> TYPE: DNA
<213> ORGANISM: Artificial sequence
<220> FEATURE:
<223> OTHER INFORMATION: Synthetic construct

<400> SEQUENCE: 45
aattaaccct cactaaaggg cggc                                             24

<210> SEQ ID NO 46
<211> LENGTH: 103
<212> TYPE: DNA
<213> ORGANISM: Artificial sequence
<220> FEATURE:
<223> OTHER INFORMATION: Synthetic construct

<400> SEQUENCE: 46
atattccacc agctatttgt tagtgaataa aagtggttga attatttgct caggatgtgg      60
cattgtcaag ggctaatacg actcactata gggctcgagg aag                       103

<210> SEQ ID NO 47
<211> LENGTH: 84
<212> TYPE: DNA
<213> ORGANISM: Artificial sequence
<220> FEATURE:
<223> OTHER INFORMATION: Synthetic construct

<400> SEQUENCE: 47
tcacagcaga acagttagaa agcgtttaaa atcattcggt cacttctgcg ggagaccggt      60
```
aattaaccct cactaaaggg cggc                                          84

<210> SEQ ID NO 48
<211> LENGTH: 85
<212> TYPE: DNA
<213> ORGANISM: Artificial sequence
<220> FEATURE:
<223> OTHER INFORMATION: Synthetic construct

<400> SEQUENCE: 48
cgcgccaatt accgctatcg attttggtcg cagtagtgct tccagtcctc gctgactcat    60
atattccacc agctatttgt tagtg                                         85

<210> SEQ ID NO 49
<211> LENGTH: 84
<212> TYPE: DNA
<213> ORGANISM: Artificial sequence
<220> FEATURE:
<223> OTHER INFORMATION: Synthetic construct

<400> SEQUENCE: 49
gcgggaggaa tgcgtggtgc ggccttccta catctaaccg attaaacaac agaggttgct    60
aattaaccct cactaaaggg cggc                                          84

<210> SEQ ID NO 50
<211> LENGTH: 85
<212> TYPE: DNA
<213> ORGANISM: Artificial sequence
<220> FEATURE:
<223> OTHER INFORMATION: Synthetic construct

<400> SEQUENCE: 50
gcgcaggcgg cgtttatttt tacgaaaacg acttaaccga tgaccccgac gcgacagcat    60
atattccacc agctatttgt tagtg                                         85

<210> SEQ ID NO 51
<211> LENGTH: 886
<212> TYPE: PRT
<213> ORGANISM: Salmonella enterica

<400> SEQUENCE: 51

Met Ser Gln Gln Gly Leu Glu Ala Leu Leu Arg Pro Lys Ser Ile Ala
1               5                   10                  15

Val Ile Gly Ala Ser Met Lys Pro His Arg Ala Gly Tyr Leu Met Met
            20                  25                  30

Arg Asn Leu Leu Ala Gly Gly Phe Asn Gly Pro Val Leu Pro Val Thr
        35                  40                  45

Pro Ala Trp Lys Ala Val Leu Gly Val Met Ala Trp Pro Asp Ile Ala
    50                  55                  60

Ser Leu Pro Phe Thr Pro Asp Leu Ala Ile Leu Cys Thr Asn Ala Ser
65                  70                  75                  80

Arg Asn Leu Ala Leu Leu Asp Ala Leu Gly Ala Lys Gly Cys Lys Thr
                85                  90                  95

Cys Ile Ile Leu Ser Ala Pro Thr Ser Gln His Glu Glu Leu Leu Ala
            100                 105                 110

Ser Ala Arg His Tyr Lys Met Arg Leu Leu Gly Pro Asn Ser Leu Gly
        115                 120                 125

Leu Leu Ala Pro Trp Gln Gly Leu Asn Ala Ser Phe Ser Pro Val Pro
    130                 135                 140

```
Ile Lys Gln Gly Lys Leu Ala Phe Ile Ser Gln Ser Ala Val Ser
145                 150                 155                 160

Asn Thr Ile Leu Asp Trp Ala Gln Gln Arg Glu Met Gly Phe Ser Tyr
            165                 170                 175

Phe Ile Ala Leu Gly Asp Ser Leu Asp Ile Asp Val Asp Glu Leu Leu
        180                 185                 190

Asp Tyr Leu Ala Arg Asp Ser Lys Thr Ser Ala Ile Leu Leu Tyr Leu
    195                 200                 205

Glu Gln Leu Ser Asp Ala Arg Arg Phe Val Ser Ala Ala Arg Ser Ala
    210                 215                 220

Ser Arg Asn Lys Pro Ile Leu Val Ile Lys Ser Gly Arg Ser Pro Ala
225                 230                 235                 240

Ala Gln Arg Leu Leu Asn Thr Ser Ala Gly Met Asp Pro Ala Trp Asp
            245                 250                 255

Ala Ala Ile Gln Arg Ala Gly Leu Leu Arg Val Gln Asp Thr His Glu
            260                 265                 270

Leu Phe Ser Ala Val Glu Thr Leu Ser His Met Arg Pro Leu His Gly
        275                 280                 285

Asp Arg Leu Met Ile Ile Ser Asn Gly Ala Ala Pro Ala Ala Leu Ala
    290                 295                 300

Leu Asp Glu Leu Trp Ser Arg Asn Gly Lys Leu Ala Thr Leu Ser Glu
305                 310                 315                 320

Glu Thr Cys Leu Gln Leu Arg Gln Thr Leu Pro Ala His Ile Asp Ile
            325                 330                 335

Ala Asn Pro Leu Asp Leu Cys Asp Asp Ala Ser Ser Glu His Tyr Val
            340                 345                 350

Lys Thr Leu Asp Ile Leu Leu Ala Ser Gln Asp Phe Asp Ala Leu Met
        355                 360                 365

Val Ile His Ser Pro Ser Ala Ala Pro Gly Thr Glu Ser Ala His
        370                 375                 380

Ala Leu Ile Glu Thr Ile Lys Arg His Pro Arg Gly Lys Phe Val Thr
385                 390                 395                 400

Leu Leu Thr Asn Trp Cys Gly Glu Phe Ser Ser Gln Glu Ala Arg Arg
            405                 410                 415

Leu Phe Ser Glu Ala Gly Leu Pro Thr Tyr Arg Thr Pro Glu Gly Thr
        420                 425                 430

Ile Thr Ala Phe Met His Met Val Glu Tyr Arg Arg Asn Gln Lys Gln
        435                 440                 445

Leu Arg Glu Thr Pro Ala Leu Pro Ser Asn Leu Thr Ser Asn Thr Ala
    450                 455                 460

Glu Ala His Asn Leu Leu Gln Arg Ala Ile Ala Glu Gly Ala Thr Ser
465                 470                 475                 480

Leu Asp Thr His Glu Val Gln Pro Ile Leu His Ala Tyr Gly Leu His
            485                 490                 495

Thr Leu Pro Thr Trp Ile Ala Ser Asp Ser Ala Glu Ala Val His Ile
        500                 505                 510

Ala Glu Gln Ile Gly Tyr Pro Val Ala Leu Lys Leu Arg Ser Pro Asp
        515                 520                 525

Ile Pro His Lys Ser Glu Val Gln Gly Val Met Leu Tyr Leu Arg Thr
        530                 535                 540

Ala Ser Glu Val Gln Gln Ala Asn Ala Ile Phe Asp Arg Val Lys
545                 550                 555                 560

Met Ala Trp Pro Gln Ala Arg Ile His Gly Leu Leu Val Gln Ser Met
```

Ala Asn Arg Ala Gly Ala Gln Glu Leu Arg Val Val Glu His Asp
                580                 585                 590

Pro Val Phe Gly Pro Leu Ile Met Leu Gly Glu Gly Val Glu Trp
            595                 600                 605

Arg Pro Glu Glu Gln Ala Val Val Ala Leu Pro Leu Asn Met Asn
610                 615                 620

Leu Ala Arg Tyr Leu Val Ile Gln Gly Ile Lys Gln Arg Lys Ile Arg
625                 630                 635                 640

Ala Arg Ser Ala Leu Arg Pro Leu Asp Ile Val Gly Leu Ser Gln Leu
                645                 650                 655

Leu Val Gln Val Ser Asn Leu Ile Val Asp Cys Pro Glu Ile Gln Arg
            660                 665                 670

Leu Asp Ile His Pro Leu Leu Ala Ser Ala Ser Glu Phe Thr Ala Leu
        675                 680                 685

Asp Val Thr Leu Asp Ile Ala Pro Phe Asp Gly Asp Asn Glu Ser Arg
    690                 695                 700

Leu Ala Val Arg Pro Tyr Pro His Gln Leu Glu Glu Trp Val Glu Met
705                 710                 715                 720

Lys Asn Gly Asp Arg Cys Leu Phe Arg Pro Ile Leu Pro Glu Asp Glu
                725                 730                 735

Pro Gln Leu Arg Gln Phe Ile Ala Gln Val Thr Lys Glu Asp Leu Tyr
            740                 745                 750

Tyr Arg Tyr Phe Ser Glu Ile Asn Glu Phe Thr His Glu Asp Leu Ala
        755                 760                 765

Asn Met Thr Gln Ile Asp Tyr Asp Arg Glu Met Ala Phe Val Ala Val
    770                 775                 780

Arg Arg Met Asp Asn Ala Glu Glu Ile Leu Gly Val Thr Arg Ala Ile
785                 790                 795                 800

Ser Asp Pro Asp Asn Val Asp Ala Glu Phe Ala Val Leu Val Arg Ser
                805                 810                 815

Asp Leu Lys Gly Leu Gly Leu Gly Arg Arg Leu Met Glu Lys Leu Ile
            820                 825                 830

Ala Tyr Thr Arg Asp His Gly Leu Lys Arg Leu Asn Gly Ile Thr Met
        835                 840                 845

Pro Asn Asn Arg Gly Met Val Ala Leu Ala Arg Lys Leu Gly Phe Gln
    850                 855                 860

Val Asp Ile Gln Leu Asp Glu Gly Ile Val Gly Leu Thr Leu Asn Leu
865                 870                 875                 880

Ala Lys Cys Asp Glu Ser
                885

<210> SEQ ID NO 52
<211> LENGTH: 907
<212> TYPE: PRT
<213> ORGANISM: Rhodopseudomonas palustris

<400> SEQUENCE: 52

Met Ser Thr Tyr Arg Leu Ser Thr Leu Leu Ser Pro Gly Ala Ala
1               5                   10                  15

Val Val Gly Ala Ser Pro Arg Pro Ala Ser Leu Gly Arg Ala Val Leu
                20                  25                  30

Thr Asn Leu Arg Glu Ala Gly Phe Lys Gly Gln Ile Gly Val Val Asn
            35                  40                  45

```
Pro Arg Tyr Pro Glu Ile Gly Gly Phe Lys Thr Val Gly Ser Leu Ala
 50              55                  60

Glu Leu Ser Phe Val Pro Asp Leu Ile Val Ile Thr Ala Pro Pro Arg
 65              70                  75                  80

Ser Val Ala Lys Val Val Ala Glu Ala Gly Glu Leu Gly Val Ala Gly
             85                  90                  95

Ala Ile Ile Ile Ser Ser Glu Met Gly Arg Gly Lys Gly Ser Tyr Ala
             100                 105                 110

Glu Ala Ala Asn Arg Ala Ala Arg Lys Ser Gly Ile Arg Leu Ile Gly
             115                 120                 125

Pro Asn Cys Leu Gly Ile Met Ile Pro Gly Val Asn Leu Asn Ala Ser
130                 135                 140

Phe Ala Ala His Met Pro Arg Arg Gly Asn Leu Ala Leu Ile Ser Gln
145                 150                 155                 160

Ser Gly Ala Ile Ala Ala Gly Met Val Asp Trp Ala Val Lys Glu
             165                 170                 175

Ile Gly Phe Ser Gly Ile Val Ser Ile Gly Asp Gln Leu Asp Val Asp
             180                 185                 190

Ile Ala Asp Met Leu Asp Phe Tyr Ala Ala Asp Leu Asp Thr Arg Ala
             195                 200                 205

Ile Leu Leu Tyr Ile Glu Ala Val Thr Asp Ala Arg Lys Phe Met Ser
             210                 215                 220

Ala Ala Arg Ala Ala Ala Arg Val Lys Pro Val Val Val Lys Ser
225                 230                 235                 240

Gly Arg Met Ala His Gly Ala Lys Ala Ala Thr His Thr Gly Ala
             245                 250                 255

Phe Ala Gly Ala Asp Ala Val Tyr Glu Ala Ala Phe Arg Arg Ala Gly
             260                 265                 270

Met Leu Arg Val Tyr Asp Leu Arg Glu Leu Phe Asp Cys Ala Glu Thr
             275                 280                 285

Leu Gly Arg Val Ser Ala Pro Arg Gly Lys Arg Val Ala Ile Leu Thr
             290                 295                 300

Asn Gly Gly Gly Ile Gly Ile Leu Ala Val Asp Arg Leu Val Glu Leu
305                 310                 315                 320

Gly Gly Glu Pro Ala Thr Leu Ser Ala Asp Leu His Lys Lys Leu Asp
             325                 330                 335

Ala Ile Leu Pro Thr Ser Trp Ser Gly Phe Asn Pro Ile Asp Ile Thr
             340                 345                 350

Gly Asp Ala Asp Ala Glu Arg Tyr Ser Ala Thr Leu Ser Met Leu Leu
             355                 360                 365

Ala Asp Pro Asp Asn Asp Ala Ile Leu Val Met Asn Val Gln Thr Ala
370                 375                 380

Val Ala Ser Pro Arg Asp Ile Ala Arg Glu Val Ile Arg Val Gly
385                 390                 395                 400

Glu Glu Arg Val Arg Arg Thr Leu Phe Lys Pro Val Phe Ala Val Trp
             405                 410                 415

Val Gly Ala Glu Glu Ala Val Thr His Ala Phe Asp Ala Ala Ser Ile
             420                 425                 430

Pro Asn Tyr Pro Thr Glu Asp Asp Ala Val Arg Ser Ile Met Asn Met
             435                 440                 445

Val Arg Tyr Arg Glu Ala Val Gln Leu Leu Thr Glu Val Pro Pro Ser
450                 455                 460

Leu Pro Lys Asp Phe Asp Pro Asp Thr Glu Thr Ala Arg Ala Ile Val
```

-continued

```
            465                 470                 475                 480
        Glu Lys Ala Leu Arg Glu Gly Arg Thr Trp Leu Asp Pro Leu Glu Ile
                            485                 490                 495
        Ser Gly Leu Phe Ala Ala Tyr Gln Ile Pro Met Ile Pro Thr Leu Ala
                        500                 505                 510
        Ala Thr Asn Ala Glu Glu Ala Val Ser Trp Ala Ser Ser Phe Leu Ser
                    515                 520                 525
        Gln Gly Val Thr Val Val Lys Val Leu Ser Arg Asp Ile Pro His
                530                 535                 540
        Lys Ser Asp Ile Gly Gly Val Leu Asn Leu Thr Ser Val Glu Ala
        545                 550                 555                 560
        Val Arg Val Ala Val Asn Glu Ile Met Ala Arg Ala Lys Leu Arg
                            565                 570                 575
        Pro Asn Ala Arg Leu Glu Gly Val Met Val Gln Pro Met Ile Leu Arg
                        580                 585                 590
        Pro Lys Ala Arg Glu Leu Thr Ile Gly Ile Ala Asp Asp Pro Thr Phe
                    595                 600                 605
        Gly Pro Val Ile Ala Phe Gly Gln Gly Gly Thr Gly Val Glu Leu Ile
                610                 615                 620
        Asp Asp Arg Ser Leu Ala Leu Pro Pro Leu Asp Leu Pro Leu Ala Glu
        625                 630                 635                 640
        Ser Leu Ile Ala Arg Thr Arg Val Ser Lys Leu Leu Cys Ala Tyr Arg
                            645                 650                 655
        Asp Val Pro Glu Val Lys Arg Ser Ala Val Ala Leu Thr Leu Val Lys
                        660                 665                 670
        Leu Ser Gln Met Ala Ala Asp Leu Pro Glu Ile Arg Glu Leu Asp Val
                    675                 680                 685
        Asn Pro Leu Leu Ala Asp Glu Ser Gly Val Val Ala Ile Asp Ala Arg
                690                 695                 700
        Val Val Arg Pro Pro Glu Arg Lys Phe Ala Gly Leu Gly Asn Ser
        705                 710                 715                 720
        His Phe Ala Val Lys Pro Tyr Pro Thr Glu Trp Glu Arg His Leu Thr
                            725                 730                 735
        Val Lys Asp Gly Trp Arg Val Leu Ala Arg Pro Ile Arg Pro Asp Asp
                        740                 745                 750
        Glu Pro Ala Ile His Glu Phe Leu Lys His Val Thr Pro Glu Asp Leu
                    755                 760                 765
        Arg Leu Arg Phe Phe Ala Ala Met Lys Glu Phe Ser His Ala Phe Ile
                770                 775                 780
        Ala Arg Leu Ser Gln Ile Asp Tyr Ala Arg Ala Met Ala Phe Val Ala
        785                 790                 795                 800
        Phe Asp Glu Ile Thr Gly Glu Met Leu Gly Val Val Arg Ile His Ser
                            805                 810                 815
        Asp Ser Ile Tyr Glu Ser Gly Glu Tyr Ala Ile Leu Leu Arg Ser Asp
                        820                 825                 830
        Leu Lys Gly Lys Gly Leu Gly Trp Ala Leu Met Lys Leu Ile Ile Glu
                    835                 840                 845
        Tyr Ala Arg Ser Glu Gly Leu His Tyr Val Cys Gly Gln Val Leu Arg
                850                 855                 860
        Glu Asn Thr Ala Met Leu Arg Met Cys Arg Asp Leu Gly Phe Glu Thr
        865                 870                 875                 880
        Lys Thr Asp Ala Ser Glu Pro Asp Ile Leu Asn Val Arg Leu Pro Leu
                            885                 890                 895
```

Thr Glu Glu Ala Ala Arg Ala Ala Gly Ser Ala
            900                 905

<210> SEQ ID NO 53
<211> LENGTH: 649
<212> TYPE: PRT
<213> ORGANISM: Streptomyces lividans

<400> SEQUENCE: 53

Met Ser Tyr Ala Ser Arg Thr Leu Gly Pro Met Gln Thr Ser Ser Asp
1               5                   10                  15

Arg His Glu Tyr Pro Ala His Trp Glu Ala Asp Val Val Leu Arg Asp
            20                  25                  30

Gly Gly Thr Ala Arg Val Arg Pro Ile Thr Val Asp Asp Ala Glu Arg
        35                  40                  45

Leu Val Ser Phe Tyr Glu Gln Val Ser Asp Glu Ser Lys Tyr Tyr Arg
    50                  55                  60

Phe Phe Ala Pro Tyr Pro Arg Leu Ser Ala Lys Asp Val His Arg Phe
65                  70                  75                  80

Thr His His Asp Phe Val Asp Arg Val Gly Leu Ala Ala Thr Ile Gly
                85                  90                  95

Gly Glu Phe Ile Ala Thr Val Arg Tyr Asp Arg Ile Gly Ala Gly Gly
            100                 105                 110

Thr Pro Ala Thr Ala Pro Ala Asp Glu Ala Glu Val Ala Phe Leu Val
        115                 120                 125

Gln Asp Ala His Gln Gly Arg Gly Val Ala Ser Ala Leu Leu Glu His
130                 135                 140

Ile Ala Ala Val Ala Arg Glu Arg Gly Ile Arg Arg Phe Ala Ala Glu
145                 150                 155                 160

Val Leu Pro Ala Asn Asn Lys Met Ile Lys Val Phe Met Asp Ala Gly
                165                 170                 175

Tyr Thr Gln Lys Arg Ser Phe Glu Asp Gly Val Val Arg Leu Glu Phe
            180                 185                 190

Asp Leu Glu Pro Thr Asp Arg Ser Leu Ala Val Gln Tyr Ala Arg Glu
        195                 200                 205

His Arg Ala Glu Ala Arg Ser Val Gln Arg Leu Leu Gln Pro Gly Ser
    210                 215                 220

Val Ala Val Val Gly Ala Gly Arg Thr Pro Gly Gly Val Gly Arg Ser
225                 230                 235                 240

Ile Leu Gly Asn Ile Arg Asp Ala Gly Tyr Thr Gly Arg Leu Tyr Ala
                245                 250                 255

Val Asn Arg Ala Phe Pro Glu Asp Met Lys Glu Leu Asp Gly Val Pro
            260                 265                 270

Ala Cys Arg Ser Val Gly Asp Ile Asp Gly Pro Val Asp Leu Ala Val
        275                 280                 285

Val Thr Val Pro Ala Glu His Val Pro Asp Val Val Thr Ala Cys Gly
    290                 295                 300

Glu His Gly Val Gln Gly Leu Val Val Ile Ser Ala Gly Tyr Ala Asp
305                 310                 315                 320

Ser Gly Pro Glu Gly Arg Glu Arg Gln Arg Ala Leu Val Arg His Ala
                325                 330                 335

Arg Thr Tyr Gly Met Arg Ile Ile Gly Pro Asn Ala Phe Gly Ile Ile
            340                 345                 350

Asn Thr Ser Pro Asp Val Arg Leu Asn Ala Ser Leu Ala Pro Glu Met

```
              355                 360                 365
Pro Arg Ala Gly Arg Ile Gly Leu Phe Ala Gln Ser Gly Ala Ile Gly
            370                 375                 380
Ile Ala Leu Leu Ser Arg Leu His Arg Gly Gly Gly Val Thr Gly
385                 390                 395                 400
Val Thr Gly Val Ser Thr Phe Val Ser Ser Gly Asn Arg Ala Asp Val
                405                 410                 415
Ser Gly Asn Asp Val Leu Gln Tyr Trp Tyr Asp Asp Pro Gln Thr Asp
            420                 425                 430
Val Ala Leu Met Tyr Leu Glu Ser Ile Gly Asn Pro Arg Lys Phe Thr
            435                 440                 445
Arg Leu Ala Arg Arg Thr Ala Ala Lys Pro Leu Val Val Gln
    450                 455                 460
Gly Ala Arg His Gly Val Ala Pro Gln Gly His Ala Val Arg Ala
465                 470                 475                 480
Thr Arg Leu Pro His Ala Thr Val Ser Ala Leu Leu Arg Gln Ala Gly
                485                 490                 495
Val Ile Arg Val Asp Thr Ile Thr Asp Leu Val Asp Ala Gly Leu Leu
                500                 505                 510
Leu Ala Arg Gln Pro Leu Pro Ala Gly Pro Arg Val Ala Ile Leu Gly
            515                 520                 525
Asn Ser Glu Ser Leu Gly Leu Leu Thr Tyr Asp Ala Cys Leu Ser Glu
530                 535                 540
Gly Leu Arg Pro Gln Pro Pro Leu Asp Leu Thr Thr Ala Ala Ser Ala
545                 550                 555                 560
Asp Asp Phe His Ala Ala Leu Ala Arg Ala Leu Ala Asp Thr Cys
                565                 570                 575
Asp Ala Val Val Val Thr Ala Ile Pro Thr Leu Gly Glu Gly Ala Ala
                580                 585                 590
Gly Asp Ala Val Ala Arg Gly Gly Pro Ala Leu Gly Gly Gly Arg Gly
            595                 600                 605
Pro His Gln Ala Arg Pro Arg Gly Pro Arg Gly Ala Gly Arg Pro Gly
            610                 615                 620
Gly Gly Pro Val Arg Gly Gly Glu His Gly Ser Pro Asp Gly Ser Gly
625                 630                 635                 640
His Arg Gly His His Arg Pro Gly Gly
                645

<210> SEQ ID NO 54
<211> LENGTH: 333
<212> TYPE: PRT
<213> ORGANISM: Mycobacterium tuberculosis

<400> SEQUENCE: 54

Met Asp Gly Ile Ala Glu Leu Thr Gly Ala Arg Val Glu Asp Leu Ala
1               5                   10                  15
Gly Met Asp Val Phe Gln Gly Cys Pro Ala Glu Gly Leu Val Ser Leu
                20                  25                  30
Ala Ala Ser Val Gln Pro Leu Arg Ala Ala Gly Gln Val Leu Leu
            35                  40                  45
Arg Gln Gly Glu Pro Ala Val Ser Phe Leu Leu Ile Ser Ser Gly Ser
        50                  55                  60
Ala Glu Val Ser His Val Gly Asp Asp Gly Val Ala Ile Ile Ala Arg
65                  70                  75                  80
```

Ala Leu Pro Gly Met Ile Val Gly Glu Ile Ala Leu Leu Arg Asp Ser
            85                  90                  95

Pro Arg Ser Ala Thr Val Thr Thr Ile Glu Pro Leu Thr Gly Trp Thr
        100                 105                 110

Gly Gly Arg Gly Ala Phe Ala Thr Met Val His Ile Pro Gly Val Gly
        115                 120                 125

Glu Arg Leu Leu Arg Thr Ala Arg Gln Arg Leu Ala Ala Phe Val Ser
130                 135                 140

Pro Ile Pro Val Arg Leu Ala Asp Gly Thr Gln Leu Met Leu Arg Pro
145                 150                 155                 160

Val Leu Pro Gly Asp Arg Glu Arg Thr Val His Gly His Ile Gln Phe
                165                 170                 175

Ser Gly Glu Thr Leu Tyr Arg Arg Phe Met Ser Ala Arg Val Pro Ser
            180                 185                 190

Pro Ala Leu Met His Tyr Leu Ser Glu Val Asp Tyr Val Asp His Phe
        195                 200                 205

Val Trp Val Val Thr Asp Gly Ser Asp Pro Val Ala Asp Ala Arg Phe
210                 215                 220

Val Arg Asp Glu Thr Asp Pro Thr Val Ala Glu Ile Ala Phe Thr Val
225                 230                 235                 240

Ala Asp Ala Tyr Gln Gly Arg Gly Ile Gly Ser Phe Leu Ile Gly Ala
                245                 250                 255

Leu Ser Val Ala Ala Arg Val Asp Gly Val Glu Arg Phe Ala Ala Arg
            260                 265                 270

Met Leu Ser Asp Asn Val Pro Met Arg Thr Ile Met Asp Arg Tyr Gly
        275                 280                 285

Ala Val Trp Gln Arg Glu Asp Val Gly Val Ile Thr Thr Met Ile Asp
290                 295                 300

Val Pro Gly Pro Gly Glu Leu Ser Leu Gly Arg Glu Met Val Asp Gln
305                 310                 315                 320

Ile Asn Arg Val Ala Arg Gln Val Ile Glu Ala Val Gly
                325                 330

<210> SEQ ID NO 55
<211> LENGTH: 333
<212> TYPE: PRT
<213> ORGANISM: Mycobacterium smegmatis

<400> SEQUENCE: 55

Met Ala Glu Leu Thr Glu Val Arg Ala Ala Asp Leu Ala Ala Leu Glu
1               5                   10                  15

Phe Phe Thr Gly Cys Arg Pro Ser Ala Leu Glu Pro Leu Ala Thr Gln
            20                  25                  30

Leu Arg Pro Leu Lys Ala Glu Pro Gly Gln Val Leu Ile Arg Gln Gly
        35                  40                  45

Asp Pro Ala Leu Thr Phe Met Leu Ile Glu Ser Gly Arg Val Gln Val
    50                  55                  60

Ser His Ala Val Ala Asp Gly Pro Pro Ile Val Leu Asp Ile Glu Pro
65                  70                  75                  80

Gly Leu Ile Ile Gly Glu Ile Ala Leu Leu Arg Asp Ala Pro Arg Thr
                85                  90                  95

Ala Thr Val Val Ala Ala Glu Pro Val Ile Gly Trp Val Gly Asp Arg
            100                 105                 110

Asp Ala Phe Asp Thr Ile Leu His Leu Pro Gly Met Phe Asp Arg Leu
        115                 120                 125

```
Val Arg Ile Ala Arg Gln Arg Leu Ala Ala Phe Ile Thr Pro Ile Pro
    130                 135                 140

Val Gln Val Arg Thr Gly Glu Trp Phe Tyr Leu Arg Pro Val Leu Pro
145                 150                 155                 160

Gly Asp Val Glu Arg Thr Leu Asn Gly Pro Val Glu Phe Ser Ser Glu
                165                 170                 175

Thr Leu Tyr Arg Arg Phe Gln Ser Val Arg Lys Pro Thr Arg Ala Leu
            180                 185                 190

Leu Glu Tyr Leu Phe Glu Val Asp Tyr Ala Asp His Phe Val Trp Val
        195                 200                 205

Met Thr Glu Gly Ala Leu Gly Pro Val Ile Ala Asp Ala Arg Phe Val
    210                 215                 220

Arg Glu Gly His Asn Ala Thr Met Ala Glu Val Ala Phe Thr Val Gly
225                 230                 235                 240

Asp Asp Tyr Gln Gly Arg Gly Ile Gly Ser Phe Leu Met Gly Ala Leu
                245                 250                 255

Ile Val Ser Ala Asn Tyr Val Gly Val Gln Arg Phe Asn Ala Arg Val
            260                 265                 270

Leu Thr Asp Asn Met Ala Met Arg Lys Ile Met Asp Arg Leu Gly Ala
        275                 280                 285

Val Trp Val Arg Glu Asp Leu Gly Val Val Met Thr Glu Val Asp Val
    290                 295                 300

Pro Pro Val Asp Thr Val Pro Phe Glu Pro Glu Leu Ile Asp Gln Ile
305                 310                 315                 320

Arg Asp Ala Thr Arg Lys Val Ile Arg Ala Val Ser Gln
                325                 330

<210> SEQ ID NO 56
<211> LENGTH: 273
<212> TYPE: PRT
<213> ORGANISM: Salmonella enterica

<400> SEQUENCE: 56

Met Gln Ser Arg Arg Phe His Arg Leu Ser Arg Phe Arg Lys Asn Lys
1               5                   10                  15

Arg Leu Leu Arg Glu Arg Leu Arg Gln Arg Ile Phe Phe Arg Asp Arg
            20                  25                  30

Val Val Pro Glu Met Met Glu Asn Pro Arg Val Leu Val Leu Thr Gly
        35                  40                  45

Ala Gly Ile Ser Ala Glu Ser Gly Ile Arg Thr Phe Arg Ala Ala Asp
    50                  55                  60

Gly Leu Trp Glu Glu His Arg Val Glu Asp Val Ala Thr Pro Glu Gly
65                  70                  75                  80

Phe Ala Arg Asn Pro Gly Leu Val Gln Thr Phe Tyr Asn Ala Arg Arg
                85                  90                  95

Gln Gln Leu Gln Gln Pro Glu Ile Gln Pro Asn Ala Ala His Leu Ala
            100                 105                 110

Leu Ala Lys Leu Glu Glu Ala Leu Gly Asp Arg Phe Leu Leu Val Thr
        115                 120                 125

Gln Asn Ile Asp Asn Leu His Glu Arg Ala Gly Asn Arg Asn Ile Ile
    130                 135                 140

His Met His Gly Glu Leu Leu Lys Val Arg Cys Ser Gln Ser Gly Gln
145                 150                 155                 160

Ile Leu Glu Trp Asn Gly Asp Val Met Pro Glu Asp Lys Cys His Cys
```

```
                165                 170                 175
Cys Gln Phe Pro Ala Pro Leu Arg Pro His Val Val Trp Phe Gly Glu
            180                 185                 190
Met Pro Leu Gly Met Asp Glu Ile Tyr Met Ala Leu Ser Met Ala Asp
        195                 200                 205
Ile Phe Ile Ala Ile Gly Thr Ser Gly His Val Tyr Pro Ala Ala Gly
    210                 215                 220
Phe Val His Glu Ala Lys Leu His Gly Ala His Thr Val Glu Leu Asn
225                 230                 235                 240
Leu Glu Pro Ser Gln Val Gly Ser Glu Phe Glu Lys His Tyr Gly
                245                 250                 255
Pro Ala Ser Gln Val Val Pro Glu Phe Val Asp Lys Phe Leu Lys Gly
            260                 265                 270
Leu
```

<210> SEQ ID NO 57
<211> LENGTH: 253
<212> TYPE: PRT
<213> ORGANISM: Rhodopseudomonas palustris

<400> SEQUENCE: 57

```
Met Ile Ala Pro Ser Leu Ser Ser Gly Val Glu Gln Leu Gly Asp Met
1               5                   10                  15
Ile Ala His Ala Ser Ser Ile Val Pro Phe Thr Gly Ala Gly Ile Ser
            20                  25                  30
Thr Glu Ser Gly Ile Pro Asp Phe Arg Ser Pro Gly Gly Leu Trp Ser
        35                  40                  45
Arg Asn Gln Pro Ile Pro Phe Asp Glu Phe Val Ala Arg Gln Asp Ala
    50                  55                  60
Arg Asp Glu Ala Trp Arg Arg Phe Ala Met Glu Gln Thr Phe Ala
65                  70                  75                  80
Lys Ala Arg Pro Ala Arg Gly His Arg Ala Leu Ala Ser Leu Tyr Lys
                85                  90                  95
Ala Gly Lys Val Pro Ala Ile Ile Thr Gln Asn Ile Asp Asn Leu His
            100                 105                 110
Gln Val Ser Gly Phe Ala Glu His Asp Val Val Glu Leu His Gly Asn
        115                 120                 125
Thr Thr Tyr Ala Arg Cys Ile Gly Cys Gly Lys Arg His Glu Leu Asp
    130                 135                 140
Trp Val Arg Glu Trp Phe Phe Arg Thr Gly His Ala Pro His Cys Thr
145                 150                 155                 160
Ala Cys Asp Glu Pro Val Lys Thr Ala Thr Val Ser Phe Gly Gln Ser
                165                 170                 175
Met Pro Ser Asp Ala Met Arg Arg Ala Thr Glu Leu Ala Gln His Cys
            180                 185                 190
Asp Leu Phe Ile Ala Ile Gly Ser Ser Leu Val Val Trp Pro Ala Ala
        195                 200                 205
Gly Phe Pro Met Leu Ala Lys Glu Cys Gly Ala Lys Leu Val Ile Ile
    210                 215                 220
Asn Arg Glu Pro Thr Glu Gln Asp Glu Ile Ala Asp Leu Val Ile Arg
225                 230                 235                 240
His Asp Ile Gly Glu Thr Leu Gly Pro Phe Val Gly Asn
                245                 250
```

-continued

<210> SEQ ID NO 58
<211> LENGTH: 237
<212> TYPE: PRT
<213> ORGANISM: Mycobacterium tuberculosis

<400> SEQUENCE: 58

Met Arg Val Ala Val Leu Ser Gly Ala Gly Ile Ser Ala Glu Ser Gly
1               5                   10                  15

Val Pro Thr Phe Arg Asp Asp Lys Asn Gly Leu Trp Ala Arg Phe Asp
            20                  25                  30

Pro Tyr Glu Leu Ser Ser Thr Gln Gly Trp Leu Arg Asn Pro Glu Arg
        35                  40                  45

Val Trp Gly Trp Tyr Leu Trp Arg His Tyr Leu Val Ala Asn Val Glu
    50                  55                  60

Pro Asn Asp Gly His Arg Ala Ile Ala Ala Trp Gln Asp His Ala Glu
65                  70                  75                  80

Val Ser Val Ile Thr Gln Asn Val Asp Asp Leu His Glu Arg Ala Gly
                85                  90                  95

Ser Gly Ala Val His His Leu His Gly Ser Leu Phe Glu Phe Arg Cys
            100                 105                 110

Ala Arg Cys Gly Val Pro Tyr Thr Asp Ala Leu Pro Glu Met Pro Glu
        115                 120                 125

Pro Ala Ile Glu Val Glu Pro Pro Val Cys Asp Cys Gly Gly Leu Ile
    130                 135                 140

Arg Pro Asp Ile Val Trp Phe Gly Glu Pro Leu Pro Glu Glu Pro Trp
145                 150                 155                 160

Arg Ser Ala Val Glu Ala Thr Gly Ser Ala Asp Val Met Val Val Val
                165                 170                 175

Gly Thr Ser Ala Ile Val Tyr Pro Ala Ala Gly Leu Pro Asp Leu Ala
            180                 185                 190

Leu Ala Arg Gly Thr Ala Val Ile Glu Val Asn Pro Glu Pro Thr Pro
        195                 200                 205

Leu Ser Gly Ser Ala Thr Ile Ser Ile Arg Glu Ser Ala Ser Gln Ala
    210                 215                 220

Leu Pro Gly Leu Leu Glu Arg Leu Pro Ala Leu Leu Lys
225                 230                 235

<210> SEQ ID NO 59
<211> LENGTH: 94
<212> TYPE: DNA
<213> ORGANISM: Artificial sequence
<220> FEATURE:
<223> OTHER INFORMATION: Synthetic construct

<400> SEQUENCE: 59
tcacgacagt aaccgcacct acactgtcat gacattgctc gccctatgt gtaacaaata      60 accacactgc ccatggtcca tatgaatatc ctcc                                 94

<210> SEQ ID NO 60
<211> LENGTH: 147
<212> TYPE: DNA
<213> ORGANISM: Artificial sequence
<220> FEATURE:
<223> OTHER INFORMATION: Synthetic construct

<400> SEQUENCE: 60
caacggtctg cgatgttggc aggaatggtg tgtttgtgaa tttggctcat atataattcc      60
tcctgctatt tgttagtgaa taaaagtggt tgaattattt gctcaggatg tggcattgtc     120
aagggcgtgt aggctggagc tgcttcg                                    147

<210> SEQ ID NO 61
<211> LENGTH: 22
<212> TYPE: DNA
<213> ORGANISM: Artificial sequence
<220> FEATURE:
<223> OTHER INFORMATION: Synthetic construct

<400> SEQUENCE: 61
gtgcaaattc acaactcagc gg                                          22

<210> SEQ ID NO 62
<211> LENGTH: 21
<212> TYPE: DNA
<213> ORGANISM: Artificial sequence
<220> FEATURE:
<223> OTHER INFORMATION: Synthetic construct

<400> SEQUENCE: 62
caccaacgta tcgggcattg c                                           21

<210> SEQ ID NO 63
<211> LENGTH: 29
<212> TYPE: DNA
<213> ORGANISM: Artificial sequence
<220> FEATURE:
<223> OTHER INFORMATION: Synthetic construct

<400> SEQUENCE: 63 tcctaattt tgttgacact ctatcattg                                    29

<210> SEQ ID NO 64
<211> LENGTH: 31
<212> TYPE: DNA
<213> ORGANISM: Artificial sequence
<220> FEATURE:
<223> OTHER INFORMATION: Synthetic construct

<400> SEQUENCE: 64
ccatcttgtt gagaaataaa agaaaatgcc a                                31

<210> SEQ ID NO 65
<211> LENGTH: 46
<212> TYPE: DNA
<213> ORGANISM: Artificial sequence
<220> FEATURE:
<223> OTHER INFORMATION: Synthetic construct

<400> SEQUENCE: 65
tttatttctc aacaagatgg gcaggctatc gcgatgccat cgtaac                46

<210> SEQ ID NO 66
<211> LENGTH: 35
<212> TYPE: DNA
<213> ORGANISM: Artificial sequence
<220> FEATURE:
<223> OTHER INFORMATION: Synthetic construct

<400> SEQUENCE: 66
ggagagatta catgatgctt gtacctcatg cagga                            35

<210> SEQ ID NO 67
<211> LENGTH: 38
<212> TYPE: DNA

```
<213> ORGANISM: Artificial sequence
<220> FEATURE:
<223> OTHER INFORMATION: Synthetic construct

<400> SEQUENCE: 67
aagcatcatg taatctctcc ccttccccgg tcgcctga                              38

<210> SEQ ID NO 68
<211> LENGTH: 46
<212> TYPE: DNA
<213> ORGANISM: Artificial sequence
<220> FEATURE:
<223> OTHER INFORMATION: Synthetic construct

<400> SEQUENCE: 68
agtgtcaaca aaattagga cgtaaccacc atttactgtc tgtgga                      46

<210> SEQ ID NO 69
<211> LENGTH: 25
<212> TYPE: DNA
<213> ORGANISM: Artificial sequence
<220> FEATURE:
<223> OTHER INFORMATION: Synthetic construct

<400> SEQUENCE: 69
ctggcgtagt cgagaagctg cttga                                            25

<210> SEQ ID NO 70
<211> LENGTH: 25
<212> TYPE: DNA
<213> ORGANISM: Artificial sequence
<220> FEATURE:
<223> OTHER INFORMATION: Synthetic construct

<400> SEQUENCE: 70
gcatagcgga acatgaattt agagt                                            25

<210> SEQ ID NO 71
<211> LENGTH: 49
<212> TYPE: DNA
<213> ORGANISM: Artificial sequence
<220> FEATURE:
<223> OTHER INFORMATION: Synthetic construct

<400> SEQUENCE: 71
tttatttctc aacaagatgg cggatcgagc atagtcatca tcttgtact                  49

<210> SEQ ID NO 72
<211> LENGTH: 84
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (47)..(47)
<223> OTHER INFORMATION: n is a, c, g, or t

<400> SEQUENCE: 72
cggttgattt gtttagtggt tgaattattt gctcaggatg tggcatngtc aagggcgaat      60
ttgacgactc aatgaatatg tact                                             84

<210> SEQ ID NO 73
<211> LENGTH: 84
<212> TYPE: DNA
<213> ORGANISM: Artificial sequence
```

<220> FEATURE:
<223> OTHER INFORMATION: Synthetic construct

<400> SEQUENCE: 73
accactaaac aaatcaaccg cgtttcccgg aggtaaccta aaggaggtaa aaaaacatgt    60
cgagtaagtt agtactggtt ctga    84

<210> SEQ ID NO 74
<211> LENGTH: 44
<212> TYPE: DNA
<213> ORGANISM: Artificial sequence
<220> FEATURE:
<223> OTHER INFORMATION: Synthetic construct

<400> SEQUENCE: 74
agtgtcaaca aaaattagga gtacccatga ccagaccttc cagc    44

<210> SEQ ID NO 75
<211> LENGTH: 92
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (21)..(21)
<223> OTHER INFORMATION: n is a, c, g, or t

<400> SEQUENCE: 75
atcaccgcca gtggtattta ngtcaacacc gccagagata atttatcacc gcagatggtt    60
atctgaattt gacgactcaa tgaatatgta ct    92

<210> SEQ ID NO 76
<211> LENGTH: 92
<212> TYPE: DNA
<213> ORGANISM: Artificial sequence
<220> FEATURE:
<223> OTHER INFORMATION: Synthetic construct

<400> SEQUENCE: 76
taaataccac tggcggtgat actgagcaca tcagcaggac gcactgcaaa ggaggtaaaa    60
aaacatgtcg agtaagttag tactggttct ga    92

<210> SEQ ID NO 77
<211> LENGTH: 25
<212> TYPE: DNA
<213> ORGANISM: Artificial sequence
<220> FEATURE:
<223> OTHER INFORMATION: Synthetic construct

<400> SEQUENCE: 77
tgcaggcgac ggtaacgttc agcat    25

<210> SEQ ID NO 78
<211> LENGTH: 25
<212> TYPE: DNA
<213> ORGANISM: Artificial sequence
<220> FEATURE:
<223> OTHER INFORMATION: Synthetic construct

<400> SEQUENCE: 78
gtggaagatg atcgccggat cgata    25

<210> SEQ ID NO 79

```
<211> LENGTH: 46
<212> TYPE: DNA
<213> ORGANISM: Artificial sequence
<220> FEATURE:
<223> OTHER INFORMATION: Synthetic construct

<400> SEQUENCE: 79
agtgtcaaca aaaattagga ctgtcagccg ttaagtgttc ctgtgt            46

<210> SEQ ID NO 80
<211> LENGTH: 35
<212> TYPE: DNA
<213> ORGANISM: Artificial sequence
<220> FEATURE:
<223> OTHER INFORMATION: Synthetic construct

<400> SEQUENCE: 80
ggtggttacg cagttcaacc tgttgatagt acgta                        35

<210> SEQ ID NO 81
<211> LENGTH: 36
<212> TYPE: DNA
<213> ORGANISM: Artificial sequence
<220> FEATURE:
<223> OTHER INFORMATION: Synthetic construct

<400> SEQUENCE: 81
ggttgaactg cgtaaccacc atttactgtc tgtgga                       36

<210> SEQ ID NO 82
<211> LENGTH: 45
<212> TYPE: DNA
<213> ORGANISM: Artificial sequence
<220> FEATURE:
<223> OTHER INFORMATION: Synthetic construct

<400> SEQUENCE: 82
tttatttctc aacaagatgg ggccgattaa catcatccag acgat             45

<210> SEQ ID NO 83
<211> LENGTH: 84
<212> TYPE: DNA
<213> ORGANISM: Artificial sequence
<220> FEATURE:
<223> OTHER INFORMATION: Synthetic construct

<400> SEQUENCE: 83
cggttgattt gtttagtggt tgaattattt gctcaggatg tggcattgtc aagggctctt   60
gcccaacgcg aggaatcatg agta                                         84

<210> SEQ ID NO 84
<211> LENGTH: 84
<212> TYPE: DNA
<213> ORGANISM: Artificial sequence
<220> FEATURE:
<223> OTHER INFORMATION: Synthetic construct

<400> SEQUENCE: 84
cggttgattt gtttagtggt tgaattattt gctcaggatg tggcatcgtc aagggctctt   60
gcccaacgcg aggaatcatg agta                                         84

<210> SEQ ID NO 85
<211> LENGTH: 81
<212> TYPE: DNA
<213> ORGANISM: Artificial sequence
```

<220> FEATURE:
<223> OTHER INFORMATION: Synthetic construct

<400> SEQUENCE: 85
accactaaac aaatcaaccg cgtttcccgg aggtaaccta aaggaggtaa aaaaacaccg    60
gtctcccgca gaagtgaccg a                                              81

<210> SEQ ID NO 86
<211> LENGTH: 45
<212> TYPE: DNA
<213> ORGANISM: Artificial sequence
<220> FEATURE:
<223> OTHER INFORMATION: Synthetic construct

<400> SEQUENCE: 86
actatcaaca ggttgaactg cgccgttcga tagctggctg aacga                    45

<210> SEQ ID NO 87
<211> LENGTH: 25
<212> TYPE: DNA
<213> ORGANISM: Artificial sequence
<220> FEATURE:
<223> OTHER INFORMATION: Synthetic construct

<400> SEQUENCE: 87
gcatcacgca gctcctggcg gaaca                                          25

<210> SEQ ID NO 88
<211> LENGTH: 25
<212> TYPE: DNA
<213> ORGANISM: Artificial sequence
<220> FEATURE:
<223> OTHER INFORMATION: Synthetic construct

<400> SEQUENCE: 88
gctgaacgtg aattgagcag tcgct                                          25

<210> SEQ ID NO 89
<211> LENGTH: 50
<212> TYPE: DNA
<213> ORGANISM: Artificial sequence
<220> FEATURE:
<223> OTHER INFORMATION: Synthetic construct

<400> SEQUENCE: 89
tacacacata aggaggttcc caatgaaaca gtatctgatc gcacctagca                50

<210> SEQ ID NO 90
<211> LENGTH: 59
<212> TYPE: DNA
<213> ORGANISM: Artificial sequence
<220> FEATURE:
<223> OTHER INFORMATION: Synthetic construct

<400> SEQUENCE: 90
tattcgaatg tatgctagtg gacgtcaatc attactcgtg gctcactttc gccagttca     59

<210> SEQ ID NO 91
<211> LENGTH: 58
<212> TYPE: DNA
<213> ORGANISM: Artificial sequence
<220> FEATURE:
<223> OTHER INFORMATION: Synthetic construct

<400> SEQUENCE: 91

```
cactagcata cattcgaata aggaggaata ctatgtcatc tcgtaaggaa ctggcgaa        58

<210> SEQ ID NO 92
<211> LENGTH: 53
<212> TYPE: DNA
<213> ORGANISM: Artificial sequence
<220> FEATURE:
<223> OTHER INFORMATION: Synthetic construct

<400> SEQUENCE: 92
tatctccttc ttgagccgat tatcattaca gcagctcttt ggctttcgcg aca            53

<210> SEQ ID NO 93
<211> LENGTH: 54
<212> TYPE: DNA
<213> ORGANISM: Artificial sequence
<220> FEATURE:
<223> OTHER INFORMATION: Synthetic construct

<400> SEQUENCE: 93
atcggctcaa gaaggagata tacatatgac gcaggacgaa ctgaaaaaag cggt           54

<210> SEQ ID NO 94
<211> LENGTH: 50
<212> TYPE: DNA
<213> ORGANISM: Artificial sequence
<220> FEATURE:
<223> OTHER INFORMATION: Synthetic construct

<400> SEQUENCE: 94
tattcctcct tcaggacctt tcattattta acgatcgttt tgacgccatc                50

<210> SEQ ID NO 95
<211> LENGTH: 51
<212> TYPE: DNA
<213> ORGANISM: Artificial sequence
<220> FEATURE:
<223> OTHER INFORMATION: Synthetic construct

<400> SEQUENCE: 95
aaggtcctga aggaggaata aaccatgacc gataaactga ccagcctgcg t              51

<210> SEQ ID NO 96
<211> LENGTH: 39
<212> TYPE: DNA
<213> ORGANISM: Artificial sequence
<220> FEATURE:
<223> OTHER INFORMATION: Synthetic construct

<400> SEQUENCE: 96
gaccggttca ttacagcagg tcgccgatca ttttctcca                            39

<210> SEQ ID NO 97
<211> LENGTH: 42
<212> TYPE: DNA
<213> ORGANISM: Artificial sequence
<220> FEATURE:
<223> OTHER INFORMATION: Synthetic construct

<400> SEQUENCE: 97
cctgctgtaa tgaaccggtc tcccgcagaa gtgaccgaat ga                        42

<210> SEQ ID NO 98
<211> LENGTH: 53
<212> TYPE: DNA
<213> ORGANISM: Artificial sequence
```

<220> FEATURE:
<223> OTHER INFORMATION: Synthetic construct

<400> SEQUENCE: 98
ggaacctcct tatgtgtgta aacctttagg ttacctccgg gaaacgcggt tga            53

<210> SEQ ID NO 99
<211> LENGTH: 108
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (75)..(77)
<223> OTHER INFORMATION: n is a, c, g, or t

<400> SEQUENCE: 99
tgaagcgtcc gttcaaaggc gactggctag actgcgcgaa aaaactgtat gctgctaacg     60
atgaaaatta tgctnnngct gcataaaatt aaccctcact aaagggcg                 108

<210> SEQ ID NO 100
<211> LENGTH: 73
<212> TYPE: DNA
<213> ORGANISM: Artificial sequence
<220> FEATURE:
<223> OTHER INFORMATION: Synthetic construct

<400> SEQUENCE: 100
gcttctgtca tcggtttcag gctaaaggaa tctgcctttt tccgaaatca taatacgact     60
cactataggg ctc                                                       73

<210> SEQ ID NO 101
<211> LENGTH: 46
<212> TYPE: DNA
<213> ORGANISM: Artificial sequence
<220> FEATURE:
<223> OTHER INFORMATION: Synthetic construct

<400> SEQUENCE: 101
tttatttctc aacaagatgg gttatcggcg gtgacggttc ctacat                    46

<210> SEQ ID NO 102
<211> LENGTH: 58
<212> TYPE: DNA
<213> ORGANISM: Artificial sequence
<220> FEATURE:
<223> OTHER INFORMATION: Synthetic construct

<400> SEQUENCE: 102
agcataattt tcatcgttag cagcatacag ttttttcgcg cagtctagcc agtcgcct       58

<210> SEQ ID NO 103
<211> LENGTH: 57
<212> TYPE: DNA
<213> ORGANISM: Artificial sequence
<220> FEATURE:
<223> OTHER INFORMATION: Synthetic construct

<400> SEQUENCE: 103
ctaacgatga aaattatgct cgcgctgcat aatgatttcg gaaaaaggca gattcct        57

<210> SEQ ID NO 104
<211> LENGTH: 57
<212> TYPE: DNA

```
<213> ORGANISM: Artificial sequence
<220> FEATURE:
<223> OTHER INFORMATION: Synthetic construct

<400> SEQUENCE: 104
ctaacgatga aaattatgct attgctgcat aatgatttcg gaaaaaggca gattcct        57

<210> SEQ ID NO 105
<211> LENGTH: 57
<212> TYPE: DNA
<213> ORGANISM: Artificial sequence
<220> FEATURE:
<223> OTHER INFORMATION: Synthetic construct

<400> SEQUENCE: 105
ctaacgatga aaattatgct acggctgcat aatgatttcg gaaaaaggca gattcct        57

<210> SEQ ID NO 106
<211> LENGTH: 45
<212> TYPE: DNA
<213> ORGANISM: Artificial sequence
<220> FEATURE:
<223> OTHER INFORMATION: Synthetic construct

<400> SEQUENCE: 106
actatcaaca ggttgaactg cggtgcggag ttatccggca gacgt                     45

<210> SEQ ID NO 107
<211> LENGTH: 24
<212> TYPE: DNA
<213> ORGANISM: Artificial sequence
<220> FEATURE:
<223> OTHER INFORMATION: Synthetic construct

<400> SEQUENCE: 107
ctgacatgat caaccgtggc ggta                                            24

<210> SEQ ID NO 108
<211> LENGTH: 24
<212> TYPE: DNA
<213> ORGANISM: Artificial sequence
<220> FEATURE:
<223> OTHER INFORMATION: Synthetic construct

<400> SEQUENCE: 108
gatcgttcca gtcatggatc tgct                                            24

<210> SEQ ID NO 109
<211> LENGTH: 5021
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (775)..(775)
<223> OTHER INFORMATION: n is a, c, g, or t

<400> SEQUENCE: 109
cggatcgagc atagtcatca tcttgtactg attagacaaa ataagacgtt gcgcgttggt     60
catttccatt gttgactcct gtatcactct actacggtga aaaaaagaa ggctgagtat     120 gccttctttt atatgcgtaa tcaggggtca attacaaatc atcaaggaaa gttttatcca    180
gttgtttgaa ggcgcgctta agcgtgtcag ctaatgcctg gtaatcaggc ttgccttcaa    240
cgggtgccaa cacctgtcca gactcctgca atttaccgcg aacttcataa aaccagttga    300
```

```
ggatagcagg gggtaatggc gttacagaac gcttgcccag ccaccacaat ccctgcatgg    360
gtaaacttaa ggcgaacagc gcagtggcaa ctgccggccc aagctgaccg cccagggcaa    420
tctgccagca gagagtaaat acggcgatcg gcggcataaa acggatcgca taacgcgtca    480
tcttgataac gcgattttcg acaaagaccg gggcaaggcg ttttccagc ggccacgtct    540 ttgagtaatg ctgtccccgg cgaaacaagc taaaaaaatt aacagaacga ttatccggcg    600
ttgacatgct tcacctcaac ttcacatata aagattcaaa aatttgtgca aattcacaac    660
tcagcgggac aacgttcaaa acattttgtc ttccatalccc actatcaggt atcctttagc    720
agcctgaagg cctaagtagt acatattcat tgagtcgtca aattcgccct tgacnatgcc    780
acatcctgag caaataattc aaccactaaa caaatcaacc gcgtttcccg gaggtaacct    840
aaaggaggta aaaaaacatg tcgagtaagt tagtactggt tctgaactgc ggtagttctt    900
cactgaaatt tgccatcatc gatgcagtaa atggtgaaga gtaccttcct ggtttagccg    960
aatgtttcca cctgcctgaa gcacgtatca aatggaaaat ggacggcaat aaacaggaag   1020
cggctttagg tgcaggcgcc gctcacagcg aagcgctcaa ctttatcgtt aatactattc   1080
tggcacaaaa accagaactg tctgcgcagc tgactgctat cggtcaccgt atcgtacacg   1140
gcggcgaaaa gtataccagc tccgtagtga tcgatgagtc tgttattcag ggtatcaaag   1200
atgcagcttc ttttgcaccg ctgcacaacc cggctcacct gatcggtatc gaagaagctc   1260
tgaaatcttt cccacagctg aaagacaaaa acgttgctgt atttgacacc gcgttccacc   1320
agactatgcc ggaagagtct tacctctacg ccctgcctta caacctgtac aaagagcacg   1380
gcatccgtcg ttacggcgcg cacggcacca gccacttcta tgtaacccag gaagcggcaa   1440
aaatgctgaa caaaccggta gaagaactga acatcatcac ctgccacctg ggcaacggtg   1500
gttccgtttc tgctatccgc aacggtaaat gcgttgacac ctctatgggc ctgacccgc   1560 tggaaggtct ggtcatgggt accagttcaa cctgttgata gtacgtacta agctctcatg   1620
tttcacgtac taagctctca tgtttaacgt actaagctct catgtttaac gaactaaacc   1680
ctcatggcta acgtactaag ctctcatggc taacgtacta agctctcatg tttcacgtac   1740
taagctctca tgtttgaaca ataaaattaa tataaatcag caacttaaat agcctctaag   1800
gttttaagtt ttataagaaa aaaaagaata tataaggctt ttaaagcttt aaggtttaa    1860 cggttgtgga caacaagcca gggatgtaac gcactgagaa gcccttagag cctctcaaag   1920
caattttcag tgacacagga acacttaacg gctgacagtc ctaattttg ttgacactct   1980 atcattgata gagttatttt accactccct atcagtgata gagaaaagtg aaatgaatag   2040
ttcgacaaag atcgcattgg taattacgtt actcgatgcc atggggattg ccttatcat   2100 gccagtcttg ccaacgttat tacgtgaatt tattgcttcg gaagatatcg ctaaccactt   2160
tggcgtattg cttgcacttt atgcgttaat gcaggttatc tttgctcctt ggcttggaaa   2220
aatgtctgac cgatttggtc ggcgcccagt gctgttgttg tcattaatag gcgcatcgct   2280
ggattactta ttgctggctt tttcaagtgc gctttggatg ctgtatttag gccgtttgct   2340
ttcagggatc acaggagcta ctggggctgt cgcggcatcg gtcattgccg ataccacctc   2400
agcttctcaa cgcgtgaagt ggttcggttg gttaggggca agttttgggc ttggtttaat   2460
agcggggcct attattggtg gttttgcagg agagatttca ccgcatagtc cctttttat   2520 cgctgcgttg ctaaatattg tcactttcct tgtggttatg ttttggttcc gtgaaccaa   2580 aaatacacgt gataatacag ataccgaagt aggggttgag acgcaatcga attcggtata   2640
```

```
catcacttta tttaaaacga tgcccatttt gttgattatt tattttttcag cgcaattgat    2700
aggccaaatt cccgcaacgg tgtgggtgct atttaccgaa aatcgttttg gatggaatag    2760
catgatggtt ggcttttcat tagcgggtct tggtctttta cactcagtat tccaagcctt    2820
tgtggcagga agaatagcca ctaaatgggg cgaaaaaacg gcagtactgc tcgaatttat    2880
tgcagatagt agtgcatttg ccttttttagc gtttatatct gaaggttggt tagatttccc    2940
tgttttaatt ttattggctg gtggtgggat cgctttacct gcattacagg gagtgatgtc    3000
tatccaaaca aagagtcatg agcaaggtgc tttacaggga ttattggtga gccttaccaa    3060
tgcaaccggt gttattggcc cattactgtt tactgttatt tataatcatt cactaccaat    3120
ttgggatggc tggatttgga ttattggttt agcgttttac tgtattatta tcctgctatc    3180
gatgaccttc atgttaaccc ctcaagctca ggggagtaaa caggagacaa gtgcttagtt    3240
atttcgtcac caaatgatgt tattccgcga aatataatga ccctcttgga tcttaacatt    3300
tttcccctat catttttccg tcttcatttg tcatttttc cagaaaaaat cgcgtcattc    3360
gactcatgtc taatccaaca cgtgtctctc ggcttatccc ctgacaccgc ccgccgacag    3420
cccgcatggg acgattctat caattcagcc gcggagtcta gttttatatt gcagaatgcg    3480
agattgctgg tttattataa caatataagt tttcattatt ttcaaaaagg gggatttatt    3540
gtgggtttag gtaagaaatt gtctgttgct gtcgccgctt cctttatgag tttaaccatc    3600
agtctgccgg gtgttcaggc cgctgaggat atcaataacc aaaaagcata caagaaaacg    3660
tacggcgtct ctcatattac acgccatgat atgctgcaga tccctaaaca gcagcaaaac    3720
gaaaaatacc aagtgcctca attcgatcaa tcaacgatta aaaatattga gtctgcaaaa    3780
ggacttgatg tgtccgacag ctggccgctg caaaacgctg acggaacagt agcagaatac    3840
aacggctatc acgttgtgtt tgctcttgcg ggaagcccga agacgctga tgacacatca    3900
atctacatgt tttatcaaaa ggtcggcgac aactcaatcg acagctggaa aaacgcgggc    3960
cgtgtcttta aagacagcga taagttcgac gccaacgatc cgatcctgaa agatcagacg    4020
caagaatggt ccggttctgc aacctttaca tctgacggaa aaatccgttt attctacact    4080
gactattccg gtaaacatta cggcaaacaa agcctgacaa cagcgcaggt aaatgtgtca    4140
aaatctgatg acacactcaa aatcaacgga gtggaagatc acaaaacgat ttttgacgga    4200
gacggaaaaa catatcagaa cgttcagcag tttatcgatg aaggcaatta tacatccgcc    4260
gacaaccata cgctgagaga ccctcactac gttgaagaca aaggccataa ataccttgta    4320
ttcgaagcca cacgggaac agaaaacgga taccaaggcg aagaatcttt atttaacaaa    4380
gcgtactacg gcggcggcac gaacttcttc cgtaaagaaa gccagaagct tcagcagagc    4440
gctaaaaaac gcgatgctga gttagcgaac ggcgccctcg gtatcataga gttaaataat    4500
gattacacat tgaaaaaagt aatgaagccg ctgatcactt caaacacggt aactgatgaa    4560
atcgagcgcg cgaatgtttt caaaatgaac ggcaaatggt acttgttcac tgattcacgc    4620
ggttcaaaaa tgacgatcga tggtattaac tcaaacgata tttacatgct ggttatgta     4680
tcaaactctt taaccggccc ttacaagccg ctgaacaaaa cagggcttgt gctgcaaatg    4740
ggtcttgatc caaacgatgt gacattcact tactctcact tcgcagtgcc gcaagccaaa    4800
ggcaacaatg tggttatcac aagctacatg acaaacagag gcttcttcga ggataaaaag    4860
gcaacatttg gcccaagctt cttaatcaac atcaaaggca ataaacatc cgttgtcaaa    4920
aacagcatcc tggagcaagg acagctgaca gtcaactaat aacagcaaaa agaaaatgcc    4980
gatacttcat tggcattttc ttttattttct caacaagatg g                      5021
```

<210> SEQ ID NO 110
<211> LENGTH: 4601
<212> TYPE: DNA
<213> ORGANISM: Artificial sequence
<220> FEATURE:
<223> OTHER INFORMATION: Synthetic construct

<400> SEQUENCE: 110

```
taatctctcc ccttccccgg tcgcctgacc ggggaatact cttcctctcc agcatgcatc      60
acctttccc aaaatattaa acaaataaac tcattaaaaa atgagcgatt tttgacagtc     120
gtagaaaatg ataatgcaga gaatatgcct tttctttctt gttaattata aggatatttt     180
atgtgctaca atggtttaaa taatatgttt ttccctcttt gccagattaa cgataaccac     240
tctgtcacaa gtccatcaca tacaaagaaa acaaaatcag ataattacag aaaacatcat     300
aaaagcacgt taattgacaa taaagccctc tctcttttca agatggatga tcatgaaaaa     360
gtgataggct tgattcagaa aatgaaaaga atttatgata gtttaccatc aggaaaaatc     420
acgaaggaaa cggacaggaa aatacataaa cattttatag atatagcttt atatgcaaat     480
aataaatgtg acgatagaat tacgagaaga gtttacctta gtaaagaaaa ggaagtatcc     540
attaaggtgg tatattatta taaataatgt cgccatccat aataatacta tcgaaattcc     600
acagacagta aatggtggtt acgcagttca acctgttgat agtacgtact aagctctcat     660
gtttcacgta ctaagctctc atgtttaacg tactaagctc tcatgtttaa cgaactaaac     720
cctcatggct aacgtactaa gctctcatgg ctaacgtact aagctctcat gtttcacgta     780
ctaagctctc atgtttgaac aataaaatta atataaatca gcaacttaaa tagcctctaa     840
ggttttaagt tttataagaa aaaaagaat atataaggct tttaaagctt ttaaggttta     900
acggttgtgg acaacaagcc agggatgtaa cgcactgaga agcccttaga gcctctcaaa     960
gcaattttca gtgacacagg aacacttaac ggctgacagt cctaattttt gttgacactc    1020
tatcattgat agagttattt taccactccc tatcagtgat agagaaaagt gaaatgaata    1080
gttcgacaaa gatcgcattg gtaattacgt tactcgatgc catggggatt ggccttatca    1140
tgccagtctt gccaacgtta ttacgtgaat ttattgcttc ggaagatatc gctaaccact    1200
ttggcgtatt gcttgcactt tatgcgttaa tgcaggttat cttgctcct tggcttggaa    1260
aaatgtctga ccgatttggt cggcgccag tgctgttgtt gtcattaata ggcgcatcgc    1320
tggattactt attgctggct ttttcaagtg cgctttggat gctgtattta ggccgtttgc    1380
tttcagggat cacaggagct actggggctg tcgcggcatc ggtcattgcc gataccacct    1440
cagcttctca acgcgtgaag tggttcggtt ggttaggggc aagttttggg cttggtttaa    1500
tagcggggcc tattattggt ggttttgcag gagagatttc accgcatagt cccttttta    1560
tcgctgcgtt gctaaatatt gtcactttcc ttgtggttat gttttggttc cgtgaaacca    1620
aaaatacacg tgataataca gataccgaag taggggttga gacgcaatcg aattcggtat    1680
acatcacttt atttaaaacg atgcccattt tgttgattat ttatttttca gcgcaattga    1740
taggccaaat tcccgcaacg gtgtgggtgc tatttaccga aaatcgtttt ggatggaata    1800
gcatgatggt tggcttttca ttagcgggtc ttggtctttt acactcagta ttccaagcct    1860
ttgtggcagg aagaatagcc actaaatggg gcgaaaaaac ggcagtactg ctcgaattta    1920
ttgcagatag tagtgcattt gccttttttag cgtttatatc tgaaggttgg ttagatttcc    1980
ctgttttaat tttattggct ggtggtggga tcgctttacc tgcattacag ggagtgatgt    2040
```

-continued

```
ctatccaaac aaagagtcat gagcaaggtg ctttacaggg attattggtg agccttacca    2100
atgcaaccgg tgttattggc ccattactgt ttactgttat ttataatcat tcactaccaa    2160
tttgggatgg ctggatttgg attattggtt tagcgtttta ctgtattatt atcctgctat    2220
cgatgacctt catgttaacc cctcaagctc aggggagtaa acaggagaca agtgcttagt    2280
tatttcgtca ccaaatgatg ttattccgcg aaatataatg accctcttgg atcttaacat    2340
ttttcccta tcatttttcc gtcttcattt gtcattttt ccagaaaaaa tcgcgtcatt       2400
cgactcatgt ctaatccaac acgtgtctct cggcttatcc cctgacaccg cccgccgaca    2460
gcccgcatgg gacgattcta tcaattcagc cgcggagtct agttttatat tgcagaatgc    2520
gagattgctg gtttattata acaatataag ttttcattat tttcaaaaag ggggatttat    2580
tgtgggttta ggtaagaaat tgtctgttgc tgtcgccgct tcctttatga gtttaaccat    2640
cagtctgccg ggtgttcagg ccgctgagga tatcaataac caaaaagcat acaaagaaac    2700
gtacggcgtc tctcatatta cacgccatga tatgctgcag atccctaaac agcagcaaaa    2760
cgaaaaatac caagtgcctc aattcgatca atcaacgatt aaaaatattg agtctgcaaa    2820
aggacttgat gtgtccgaca gctggccgct gcaaaacgct gacggaacag tagcagaata    2880
caacggctat acgttgtgt ttgctcttgc gggaagcccg aaagacgctg atgacacatc      2940
aatctacatg ttttatcaaa aggtcggcga caactcaatc gacagctgga aaaacgcggg    3000
ccgtgtcttt aaagacagcg ataagttcga cgccaacgat ccgatcctga agatcagac     3060
gcaagaatgg tccggttctg caacctttac atctgacgga aaaatccgtt tattctacac    3120
tgactattcc ggtaaacatt acggcaaaca aagcctgaca acagcgcagg taaatgtgtc    3180
aaaatctgat gacacactca aaatcaacgg agtggaagat cacaaaacga tttttgacgg    3240
agacggaaaa acatatcaga acgttcagca gtttatcgat gaaggcaatt atacatccgc    3300
cgacaaccat acgctgagag accctcacta cgttgaagac aaaggccata atacccttgt    3360
attcgaagcc aacacgggaa cagaaaacg ataccaaggc gaagaatctt tatttaacaa     3420
agcgtactac ggcggcggca cgaacttctt ccgtaaagaa gccagaagc ttcagcagag      3480
cgctaaaaaa cgccgatgctg agttagcgaa cggcgccctc ggtatcatag agttaaataa    3540
tgattacaca ttgaaaaaag taatgaagcc gctgatcact tcaaacacgg taactgatga    3600
aatcgagcgc gcgaatgttt tcaaaatgaa cggcaaatgg tacttgttca ctgattcacg    3660
cggttcaaaa atgacgatcg atggtattaa ctcaaacgat atttacatgc ttggttatgt    3720
atcaaactct ttaaccggcc cttacaagcc gctgaacaaa acagggcttg tgctgcaaat    3780
gggtcttgat ccaaacgatg tgacattcac ttactctcac ttcgcagtgc cgcaagccaa    3840
aggcaacaat gtggttatca caagctacat gacaaacaga ggcttcttcg aggataaaaa    3900
ggcaacattt ggcccaagct tcttaatcaa catcaaaggc aataaaacat ccgttgtcaa    3960
aaacagcatc ctggagcaag acagctgac agtcaactaa taacagcaaa aagaaaatgc     4020
cgatacttca ttggcatttt cttttatttc tcaacaagat gggcaggcta tcgcgatgcc    4080
atcgtaaccc acaattgccg gatgcgagtc ggtaacggtt tgtaggcctg ataagacgcg    4140
acagcgtcgc atcaggcatt gattgccgga tgcggcgtat aacgccttat ccggcctaca    4200
ttcggcaagg gttacccgag cgttaacctt ctcccataag ggagcgggaa ttaaaacaat    4260
ccctacatta cctctggaga atctgtgatg aatggtacga tttatcagcg gatagaagac    4320
aatgcgcatt tcagggagtt agtcgaaaaa cggcaacggt tgccaccat cctgtcgatt      4380
attatgctgg cagtttatat cggctttatt ttactgatcg ccttcgcgcc cggctggctg    4440
```

| | |
|---|---|
| ggcaccccgc tgaatccgaa caccagcgtc acacgcggta ttccgattgg tgttggagtg | 4500 |
| attgtgatct cctttgttct caccggtatc tacatctggc gggcgaacgg cgaattcgac | 4560 |
| cgtcttaata acgaagtcct gcatgaggta caagcatcat g | 4601 |

<210> SEQ ID NO 111
<211> LENGTH: 9518
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (765)..(765)
<223> OTHER INFORMATION: n is a, c, g, or t

<400> SEQUENCE: 111

| | |
|---|---|
| ggccgattaa catcatccag acgattaacg ccgcggccat tcataatatt ctgtgtaacc | 60 |
| cattcaaaca taatgtctga catcttacgg ttacggataa gatgataacg gtcgtagcga | 120 |
| tatttatcgt gctgatgcag gtaaacatcg ttcaggctgg caccgctata agtacgcta | 180 |
| tcgtcgatga taaagccttt aaagtgcaga acaccaaggg cttcacgggt attgattgga | 240 |
| acgccataaa ccggaacatc tacgcccgga ttttcctgcg ccatgcggca gtaccagtca | 300 |
| gcgttagtgt tagatgccgc agcgccaatg cgtccacgtt gtgcacgatg ccagtcgacc | 360 |
| agcacccgca catccagttc cggacgctgc cttttagctt catacaacgc gttcagaatg | 420 |
| cctttgccac cgtcatcctg ttcgagatac agggcgacaa tgcaaatgcg ctgcttcgcg | 480 |
| ctggctattt tttccagcag cgtctcccgg aagtcggcgg gagcgtaaaa gaaatcgaca | 540 |
| tcatcaactg attgagaaat cttgggtagt tgggcaaggt gttgttgatg tttattacgc | 600 |
| ttaaattttg acaacatcac agtgcatttc ttctctgttc attgaagggt cctctgtgca | 660 |
| atgcagacga cataagcggg caataataac accagtcccg attaagtggt caacatttcc | 720 |
| agtaccttac tcatgattcc tcgcgttggg caagagccct tgacnatgcc acatcctgag | 780 |
| caaataattc aaccactaaa caaatcaacc gcgtttcccg gaggtaacct aaaggtttac | 840 |
| acacataagg aggttcccaa tgaaacagta tctgatcgca cctagcatcc tgtctgcaga | 900 |
| cttcgcccgt ctgggcgagg acaccgctaa agcactggcg gcgggcgcgg atgtagttca | 960 |
| tttcgacgtg atggataatc actacgtacc gaacctgact atcggcccga tggtactgaa | 1020 |
| atctctgcgt aactacggca tcaccgcgcc gatcgatgtt cacctgatgg ttaaaccggt | 1080 |
| ggatcgtatc gtgccggatt tcgccgcggc tggtgcatcc attatcacct tccaccctga | 1140 |
| agcttccgaa cacgttgacc gcaccctgca gctgattaaa gaaaacggct gtaaggctgg | 1200 |
| tctggtgttc aacccagcta cgccgctgtc ttatctggat tatgttatgg ataagctgga | 1260 |
| cgtaatcctg ctgatgagcg tcaacccggg tttcggtggt cagagcttca ttccgcagac | 1320 |
| cctggacaaa ctgcgcgaag tgcgtcgtcg tatcgatgaa tctggcttcg atatccgtct | 1380 |
| ggaggtggat ggcggcgtga agttaacaa catcggcgag atcgccgcgg caggtgcgga | 1440 |
| catgttcgtc gcaggttctg caatcttcga tcagccggac tataaaaaag tgattgacga | 1500 |
| aatgcgttct gaactggcga aagtgagcca cgagtaatga ttgacgtcca ctagcataca | 1560 |
| ttcgaataag gaggaatact atgtcatctc gtaaggaact ggcgaatgcc atccgtgctc | 1620 |
| tgtctatgga cgccgtgcag aaagccaaat ctggtcaccc tggcgcaccg atgggcatgg | 1680 |
| cagacatcgc cgaagtactg tggcgcgact tcctgaaaca taacccgcag aacccgtctt | 1740 |

```
gggctgaccg tgatcgtttc gtgctgagca acggccacgg tagcatgctg atttattccc    1800
tgctgcacct gactggttac gacctgccga tggaagagct gaagaacttt cgccagctgc    1860
actccaaaac cccgggtcac ccagaagtgg gctataccgc cggtgtcgag actaccaccg    1920
gtccactggg ccagggcatc gccaacgctg tgggtatggc gattgcagag aagaccctgg    1980
cagcccagtt caaccgtccg ggtcacgata tcgttgacca ctatacctac gcctttatgg    2040
gtgacggctg catgatggaa ggtattagcc acgaagtttg ctctctggct ggcactctga    2100
aactgggtaa actgatcgca ttctacgacg acaatggcat tagcatcgac ggccacgtgg    2160
aaggttggtt caccgacgac actgcgatgc gtttcgaagc ttacggttgg cacgtgattc    2220
gtgacattga tggtcacgac gcagcgtcta tcaaacgtgc ggttgaagag gcacgtgccg    2280
taaccgataa gccttctctg ctgatgtgca aaacgattat cggtttcggc agcccgaaca    2340
aagccggcac ccacgacagc catggcgcgc tctgggcga tgccgaaatc gctctgaccc     2400
gtgagcaact gggttggaaa tacgcgccgt tcgaaatccc atctgaaatt tatgctcagt    2460
gggacgcaaa ggaagcgggt caagcaaagg aatctgcatg gaacgaaaaa tttgctgctt    2520
atgctaaggc gtacccgcag gaagcagctg aatttacccg tcgtatgaaa ggtgaaatgc    2580
cgtctgattt tgacgcgaaa gcgaaggaat ttattgcgaa actgcaggca aacccggcaa    2640
aaatcgcctc ccgtaaagcg tcccagaacg cgatcgaggc attcggcccg ctgctgccgg    2700
aattcctggg tggttctgcc gacctggcgc ctagcaacct gaccctgtgg tctggttcca    2760
aagcaattaa tgaagatgct gccggtaact acatccacta cggcgtccgc gaatttggta    2820
tgaccgcaat cgctaacggt atcagcctgc atggcggttt tctgccgtac accagcacct    2880
ttctgatgtt cgtagaatac gcacgtaacg cggttcgcat ggccgcactg atgaaacagc    2940
gccaggtgat ggtatatact cacgacagca tcggtctggg tgaagacggt ccgacccacc    3000
agccggttga acaagttgcg agcctgcgcg taactccaaa catgtccacg tggcgtccgt    3060
gcgaccaggt tgaaagcgct gtcgcttgga aatatggcgt ggaacgccag gacggtccga    3120
ccgcactgat cctgtcccgt cagaatctgg ctcagcagga gcgtaccgag gagcagctgg    3180
caaacatcgc acgtggcggt tacgttctga aagattgcgc tggccagccg gaactgattt    3240
tcatcgcaac cggctctgaa gtcgagctgg cagtcgcagc gtatgagaaa ctgaccgcgg    3300
aaggtgttaa agcgcgtgtt gtcagcatgc cgagcaccga cgcattcgac aaacaggatg    3360
cagcatatcg cgagagcgtt ctgcctaaag ctgttactgc tcgtgtcgcg gttgaggctg    3420
gtatcgcgga ctactggtat aaatatgtag gtctgaacgg tgcgattgtt ggtatgacga    3480
ccttcggtga atccgctcct gcggaactgc tgttcgaaga attcggcttc accgtagaca    3540
acgttgtcgc gaaagccaaa gagctgctgt aatgataatc ggctcaagaa ggagatatac    3600
atatgacgca ggacgaactg aaaaaagcgg ttggttgggc agccctgcag tatgtgcaac    3660
cgggtactat tgttggtgtt ggcaccggct ccaccgccgc ccactttatt gatgcgctgg    3720
gcaccatgaa gggtcagatc gaaggtgctg tgtctagctc tgacgcgtct actgaaaaac    3780
tgaagtccct gggcatccac gtgttcgatc tgaacgaagt tgactctctg ggcatctatg    3840
tggacgcgc agacgaaatt aacggtcaca tgcagatgat caaaggcggt ggcgcggccc    3900
tgacccgcga gaaatcatc gcatccgttg cagaaaaatt catctgtatc gctgacgcgt    3960
ctaaacaggt agacattctg ggtaaattcc ctctgccagt tgaagtgatc cctatggccc    4020
gctccgccgt ggcccgtcag ctggtaaagc tgggtggtcg tcctgaatat cgccagggcg    4080
ttgttactga taacggcaat gtgatcctgg acgtgcacgg tatggaaatc ctggacccga    4140
```

```
ttgcaatgga aaacgcgatc aacgcgattc cgggcgttgt aacggtgggc ctgttcgcga    4200
atcgcggtgc ggacgttgca ctgatcggta ccccggatgg cgtcaaaacg atcgttaaat    4260
aatgaaaggt cctgaaggag gaataaacca tgaccgataa actgaccagc ctgcgtcagt    4320
acaccaccgt agttgcggat accggtgaca tcgctgcgat gaaactgtat caaccgcagg    4380
atgcaaccac taacccgtcc ctgattctga acgcggcaca gatcccggaa tatcgtaaac    4440
tgatcgatga cgcagttgca tgggcaaaac aacagagcaa tgatcgcgcc caacagattg    4500
tagacgctac cgataaactg gccgtaaaca tcggcctgga gattctgaaa ctggttccgg    4560
gtcgtatcag cactgaagtt gatgctcgtc tgagctatga cacggaagcg agcattgcca    4620
aagctaaacg tctgatcaaa ctgtacaacg acgcgggtat cagcaacgac cgtattctga    4680
ttaaactggc ttctacctgg cagggcattc gcgcggccga acagctggag aaagaaggca    4740
tcaactgcaa cctgaccctg ctgttctctt ttgctcaggc ccgtgcctgc gctgaagccg    4800
gtgtttttct gatctctcct ttcgtgggcc gtattctgga ttggtacaaa gccaacacgg    4860
ataaaaagga gtacgctccg gctgaagatc cgggtgtggt gagcgtttcc gaaatttacc    4920
agtactacaa agaacatggt tacgaaaccg ttgttatggg tgcctctttt cgtaacatcg    4980
gtgaaatcct ggaactggca ggctgcgacc gcctgaccat cgcgccgacc ctgctgaaag    5040
aactggcgga gtctgaaggt gccatcgaac gtaaactgtc ctacaccggt gaagtgaaag    5100
cacgcccggc acgcattacc gaatctgagt tcctgtggca acacaaccag gatccgatgg    5160
cagtcgataa actggctgaa ggtatccgca aattcgcaat cgaccaggag aaactggaga    5220
aaatgatcgg cgacctgctg taatgaaccg gtctcccgca gaagtgaccg aatgatttta    5280
aacgctttct aactgttctg ctgtgatgct acccagatgt tgcgtttttc ctgccagata    5340
gcgtgtttta aagcgggtaa aatgctcgcc taaccctgct gccgcccgg tatcgccggc    5400 catatctaac agtgcgatgg ctacctcggc agtacaatat tggccttcag cctgggcttc    5460
acgcaggcga taggcagaaa gccgggaaag atcgacggaa atgacgggaa gattatccag    5520
atacggactt ttacgaaaca tcttgcgagc ttccggccag gtaccatcga gcatgataaa    5580
cagcggtggc ttaccggcag gtggtgtgaa gatcacttcc cgttgctcat cagcatacga    5640
ggcgggaaag accaccattg gctgataata cgggttttgt accagatcca gcaaatcctg    5700
cgagggttcg gtacgcgacc attgaaacgc aacggtatca ggcaaaatat cagcaatcag    5760
acgcccggta ttactgggct tcattggctc ggtgtcgaac atcagcaaac agaagcgact    5820
ttttgcttgt gctggggtaa ttgtcgaaca gagacataat ttctctggca aaagacagcg    5880
ttggcagcga cgaacgcgat taccgcgggc aagaaaagga cgtgttgcgc gcgcaatacg    5940
ctcggcgcgt aactggagaa cagcgttttc ggtcataaga gagcgtcgaa aaaacgccat    6000
tgtcgcagag gagaaaacgg ggcacaagat gcgccccggt aagattaaag agattcgttc    6060
agccagctat cgaacggcgc agttcaacct gttgatagta cgtactaagc tctcatgttt    6120
cacgtactaa gctctcatgt ttaacgtact aagctctcat gtttaacgaa ctaaaccctc    6180
atggctaacg tactaagctc tcatggctaa cgtactaagc tctcatgttt cacgtactaa    6240
gctctcatgt ttgaacaata aaattaatat aaatcagcaa cttaaatagc ctctaaggtt    6300
ttaagtttta taagaaaaaa agaatatat aaggctttta aagcttttaa ggtttaacgg    6360
ttgtggacaa caagccaggg atgtaacgca ctgagaagcc cttagagcct ctcaaagcaa    6420
ttttcagtga cacaggaaca cttaacggct gacagtccta atttttgttg acactctatc    6480
```

```
attgatagag ttatttttacc actccctatc agtgatagag aaaagtgaaa tgaatagttc      6540
gacaaagatc gcattggtaa ttacgttact cgatgccatg gggattggcc ttatcatgcc      6600
agtcttgcca acgttattac gtgaatttat tgcttcggaa gatatcgcta accactttgg      6660
cgtattgctt gcactttatg cgttaatgca ggttatcttt gctccttggc ttggaaaaat      6720
gtctgaccga tttggtcggc gcccagtgct gttgttgtca ttaataggcg catcgctgga      6780
ttacttattg ctggcttttt caagtgcgct tggatgctg  tatttaggcc gtttgctttc      6840
agggatcaca ggagctactg gggctgtcgc ggcatcggtc attgccgata ccacctcagc      6900
ttctcaacgc gtgaagtggt tcggttggtt aggggcaagt tttgggcttg gtttaatagc      6960
ggggcctatt attggtggtt ttgcaggaga gatttcaccg catagtccct ttttatcgc      7020 tgcgttgcta atattgtca ctttccttgt ggttatgttt tggttccgtg aaaccaaaaa       7080
tacacgtgat aatacagata ccgaagtagg ggttgagacg caatcgaatt cggtatacat      7140
cactttattt aaaacgatgc ccattttgtt gattatttat ttttcagcgc aattgatagg      7200
ccaaattccc gcaacggtgt gggtgctatt taccgaaaat cgttttggat ggaatagcat      7260
gatggttggc ttttcattag cgggtcttgg tcttttacac tcagtattcc aagcctttgt      7320
ggcaggaaga atagccacta aatggggcga aaaaacggca gtactgctcg aatttattgc      7380
agatagtagt gcatttgcct ttttagcgtt tatatctgaa ggttggttag atttccctgt      7440 tttaattta ttggctggtg gtgggatcgc tttacctgca ttacagggag tgatgtctat       7500
ccaaacaaag agtcatgagc aaggtgcttt acagggatta ttggtgagcc ttaccaatgc      7560
aaccggtgtt attggcccat tactgtttac tgttattat aatcattcac taccaatttg       7620
ggatggctgg atttggatta ttggtttagc gttttactgt attattatcc tgctatcgat      7680
gaccttcatg ttaaccccctc aagctcaggg gagtaaacag gagacaagtg cttagttatt     7740
tcgtcaccaa atgatgttat tccgcgaaat ataatgaccc tcttggatct taacattttt      7800
cccctatcat ttttccgtct tcatttgtca tttttccag  aaaaaatcgc gtcattcgac      7860
tcatgtctaa tccaacacgt gtctctcggc ttatcccctg acaccgcccg ccgacagccc      7920
gcatgggacg attctatcaa ttcagccgcg gagtctagtt ttatattgca gaatgcgaga      7980
ttgctggttt attataacaa tataagtttt cattattttc aaaaggggg  atttattgtg       8040 ggtttaggta agaaattgtc tgttgctgtc gccgcttcct ttatgagttt aaccatcagt      8100
ctgccgggtg ttcaggccgc tgaggatatc aataaccaaa aagcatacaa agaaacgtac      8160
ggcgtctctc atattacacg ccatgatatg ctgcagatcc ctaaacagca gcaaaacgaa      8220
aaataccaag tgcctcaatt cgatcaatca acgattaaaa atattgagtc tgcaaaagga      8280
cttgatgtgt ccgacagctg gccgctgcaa aacgctgacg gaacagtagc agaatacaac      8340
ggctatcacg ttgtgtttgc tcttgcggga agcccgaaag acgctgatga cacatcaatc      8400
tacatgtttt atcaaaaggt cggcgacaac tcaatcgaca gctggaaaaa cgcgggccgt      8460
gtctttaaag acagcgataa gttcgacgcc aacgatccga tcctgaaaga tcagacgcaa      8520
gaatggtccg gttctgcaac ctttacatct gacggaaaaa tccgtttatt ctacactgac      8580
tattccggta acattacgg  caaacaaagc ctgacaacag cgcaggtaaa tgtgtcaaaa       8640
tctgatgaca cactcaaaat caacggagtg gaagatcaca aaacgatttt tgacggagac      8700
ggaaaaacat atcagaacgt tcagcagttt atcgatgaag gcaattatac atccgccgac      8760
aaccatacgc tgagagaccc tcactacgtt gaagacaaag gccataaata ccttgtattc      8820
gaagccaaca cgggaacaga aaacggatac caaggcgaag aatctttatt taacaaagcg      8880
```

```
tactacggcg gcggcacgaa cttcttccgt aaagaaagcc agaagcttca gcagagcgct    8940
aaaaaacgcg atgctgagtt agcgaacggc gccctcggta tcatagagtt aaataatgat    9000
tacacattga aaaagtaat  gaagccgctg atcacttcaa acacggtaac tgatgaaatc    9060
gagcgcgcga atgttttcaa aatgaacggc aaatggtact tgttcactga ttcacgcggt    9120
tcaaaaatga cgatcgatgg tattaactca aacgatattt acatgcttgg ttatgtatca    9180
aactctttaa ccggcccttta caagccgctg aacaaaacag gcttgtgct  gcaaatgggt    9240 cttgatccaa acgatgtgac attcacttac tctcacttcg cagtgccgca agccaaaggc    9300
aacaatgtgg ttatcacaag ctacatgaca acagaggct  tcttcgagga taaaaaggca    9360
acatttggcc caagcttctt aatcaacatc aaaggcaata aacatccgt  tgtcaaaaac    9420 agcatcctgg agcaaggaca gctgacagtc aactaataac agcaaaaaga aaatgccgat    9480
acttcattgg cattttcttt tatttctcaa caagatgg                            9518
```

<210> SEQ ID NO 112
<211> LENGTH: 4790
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (688)..(690)
<223> OTHER INFORMATION: n is a, c, g, or t

<400> SEQUENCE: 112

```
gttatcggcg gtgacggttc ctacatgggt gcaatgcgtc tgaccgaaat gggcttcccg      60
tgcatcggcc tgccgggcac tatcgacaac gacatcaaag gcactgacta cactatcggt     120
ttcttcactg cgctgagcac cgttgtagaa gcgatcgacc gtctgcgtga cacctcttct     180
tctcaccagc gtatttccgt ggtggaagtg atgggccgtt attgtggcga tctgacgttg     240
gctgcggcca ttgccggtgg ctgtgaattc gttgtggttc cggaagttga attcagccgt     300
gaagacctgg taaacgaaat caaagcgggt atcgcgaaag gtaaaaaaca cgcgatcgtg     360
gcgattaccg aacatatgtg tgatgttgac gaactggcgc atttcatcga aaagaaacc      420 ggtcgtgaaa cccgcgcaac tgtgctgggc cacatccagc gcggtggttc tccggtgcct     480
tacgaccgta ttctggcttc ccgtatgggc gcttacgcta tcgatctgct gctggcaggt     540
tacggcggtc gttgcgtagg tatccagaac gaacagctgg ttcaccacga catcatcgac     600
gctatcgaaa acatgaagcg tccgttcaaa ggcgactggc tagactgcgc gaaaaaactg     660
tatgctgcta acgatgaaaa ttatgctnnn gctgcataat gatttcggaa aaaggcagat     720
tcctttagcc tgaaaccgat gacagaagca aaaatgcctg atgcgcttcg cttatcaggc     780
ctacgtgaat tctgcaattt attgaattta caaattttg  taggtcggat aaggcgttcg     840
cgccgcatcc ggcatcgata aagcgcactt tgtcagcaat atgaggcgga tttcttccgc     900 cttttttaatt cctcaacata tacccgcaag ttatagccaa tctttttta  ttctttaatg     960 tttggttaac cttctggcac gctttgctca tcacaacaca acataagaga gtcgggcgat    1020
gaacaagtgg ggcgtagggt taacattttt gctggcggca accagcgtta tggcaaagga    1080
tattcagctt cttaacgttt catatgatcc aacgcgcgaa ttgtacgaac agtacaacaa    1140
ggcattcagc gccactgga  aacagcaaac tggcgtaaac gtggtgatcc gtcagtccca    1200
cggtggttca ggcaaacaag cgacgtcggt aatcaacggt attgaagctg atgttgtcac    1260
```

```
gctggctctg gcctatgacg tggacgcaat tgcggaacgc gggcggattg ataaagagtg    1320
gatcaaacgt ctgccggata actccgcacc gcagttcaac ctgttgatag tacgtactaa    1380
gctctcatgt ttcacgtact aagctctcat gtttaacgta ctaagctctc atgtttaacg    1440
aactaaaccc tcatggctaa cgtactaagc tctcatggct aacgtactaa gctctcatgt    1500
ttcacgtact aagctctcat gtttgaacaa taaaattaat ataaatcagc aacttaaata    1560
gcctctaagg ttttaagttt tataagaaaa aaagaatat ataaggcttt taaagctttt    1620
aaggtttaac ggttgtggac aacaagccag ggatgtaacg cactgagaag cccttagagc    1680
ctctcaaagc aattttcagt gacacaggaa cacttaacgg ctgacagtcc taattttgt    1740
tgacactcta tcattgatag agttatttta ccactcccta tcagtgatag agaaaagtga    1800
aatgaatagt tcgacaaaga tcgcattggt aattacgtta ctcgatgcca tgggattgg    1860
ccttatcatg ccagtcttgc aacgttatt acgtgaattt attgcttcgg aagatatcgc    1920
taaccacttt ggcgtattgc ttgcacttta tgcgttaatg caggttatct ttgctccttg    1980
gcttggaaaa atgtctgacc gatttggtcg gcgcccagtg ctgttgttgt cattaatagg    2040
cgcatcgctg gattacttat tgctggcttt ttcaagtgcg cttttggatgc tgtatttagg    2100
ccgtttgctt tcagggatca caggagctac tggggctgtc gcggcatcgg tcattgccga    2160
taccacctca gcttctcaac gcgtgaagtg gttcggttgg ttaggggcaa gttttgggct    2220
tggtttaata gcggggccta ttattggtgg ttttgcagga gagatttcac cgcatagtcc    2280
cttttttatc gctgcgttgc taaatattgt cactttcctt gtggttatgt tttggttccg    2340
tgaaaccaaa aatacacgtg ataatacaga taccgaagta ggggttgaga cgcaatcgaa    2400
ttcggtatac atcactttat ttaaaacgat gcccattttg ttgattattt attttttcagc    2460
gcaattgata ggccaaattc ccgcaacggt gtgggtgcta tttaccgaaa atcgttttgg    2520
atggaatagc atgatggttg cttttcatt agcgggtctt ggtcttttac actcagtatt    2580
ccaagccttt gtgcaggaa gaatagccac taaatgggc gaaaaaacgg cagtactgct    2640
cgaatttatt gcagatagta gtgcatttgc cttttagcg tttatatctg aaggttggtt    2700
agatttccct gttttaattt tattggctgg tgtgtgggatc gctttacctg cattacaggg    2760
agtgatgtct atccaaacaa agagtcatga gcaaggtgct ttacagggat tattggtgag    2820
ccttaccaat gcaaccggtg ttattggccc attactgttt actgttattt ataatcattc    2880
actaccaatt tgggatggct ggatttggat tattggttta gcgttttact gtattattat    2940
cctgctatcg atgaccttca tgttaacccc tcaagctcag gggagtaaac aggagacaag    3000
tgcttagtta tttcgtcacc aaatgatgtt attccgcgaa atataatgac cctcttggat    3060
cttaacattt ttccctatc attttccgt cttcatttgt catttttcc agaaaaaatc    3120
gcgtcattcg actcatgtct aatccaacac gtgtctctcg gcttatcccc tgacaccgcc    3180
cgccgacagc ccgcatggga cgattctatc aattcagccg cggagtctag ttttatattg    3240
cagaatgcga gattgctggt ttattataac aatataagtt ttcattattt tcaaaagggg    3300
ggatttattg tgggtttagg taagaaattg tctgttgctg tcgccgcttc ctttatgagt    3360
ttaaccatca gtctgccggg tgttcaggcc gctgaggata tcaataacca aaaagcatac    3420
aaagaaacgt acggcgtctc tcatattaca cgccatgata tgctgcagat ccctaaacag    3480
cagcaaaacg aaaaatacca agtgcctcaa ttcgatcaat caacgattaa aaatattgag    3540
tctgcaaaag gacttgatgt gtccgacagc tggccgctgc aaaacgctga cggaacagta    3600
gcagaataca acggctatca cgttgtgttt gctcttgcgg gaagcccgaa agacgctgat    3660
```

-continued

```
gacacatcaa tctacatgtt ttatcaaaag gtcggcgaca actcaatcga cagctggaaa      3720
aacgcgggcc gtgtctttaa agacagcgat aagttcgacg ccaacgatcc gatcctgaaa      3780
gatcagacgc aagaatggtc cggttctgca acctttacat ctgacggaaa aatccgttta      3840
ttctacactg actattccgg taaacattac ggcaaacaaa gcctgacaac agcgcaggta      3900
aatgtgtcaa aatctgatga cacactcaaa atcaacggag tggaagatca caaaacgatt     3960
tttgacggag acggaaaaac atatcagaac gttcagcagt ttatcgatga aggcaattat     4020
acatccgccg acaaccatac gctgagagac cctcactacg ttgaagacaa aggccataaa     4080
taccttgtat tcgaagccaa cacgggaaca gaaaacggat accaaggcga agaatcttta     4140
tttaacaaag cgtactacgg cggcggcacg aacttcttcc gtaaagaaag ccagaagctt     4200
cagcagagcg ctaaaaaacg cgatgctgag ttagcgaacg gcgccctcgg tatcatagag     4260
ttaaataatg attacacatt gaaaaaagta atgaagccgc tgatcacttc aaacacggta     4320
actgatgaaa tcgagcgcgc gaatgttttc aaaatgaacg gcaaatggta cttgttcact     4380
gattcacgcg gttcaaaaat gacgatcgat ggtattaact caaacgatat ttacatgctt     4440
ggttatgtat caaactcttt aaccggccct tacaagccgc tgaacaaaac agggcttgtg     4500
ctgcaaatgg gtcttgatcc aaacgatgtg acattcactt actctcactt cgcagtgccg     4560
caagccaaag gcaacaatgt ggttatcaca agctacatga caaacagagg cttcttcgag     4620
gataaaaagg caacatttgg cccaagcttc ttaatcaaca tcaaaggcaa taaaacatcc     4680
gttgtcaaaa acagcatcct ggagcaagga cagctgacag tcaactaata acagcaaaaa     4740
gaaaatgccg atacttcatt ggcattttct tttatttctc aacaagatgg                4790
```

```
<210> SEQ ID NO 113
<211> LENGTH: 125
<212> TYPE: DNA
<213> ORGANISM: Artificial sequence
<220> FEATURE:
<223> OTHER INFORMATION: Synthetic construct

<400> SEQUENCE: 113
aattcatata aaaaacatac agataaccat ctgcggtgat aaattatctc tggcggtgtt       60
gacataaata ccactggcgg tgatactgag cacatcagca ggacgcactg accaccatga      120
aggtg                                                                  125
```